US012440576B2

(12) United States Patent
Duvall et al.

(10) Patent No.: US 12,440,576 B2
(45) Date of Patent: *Oct. 14, 2025

(54) ANTIBODY DRUG CONJUGATES COMPRISING STING AGONISTS

(71) Applicant: Mersana Therapeutics, Inc., Cambridge, MA (US)

(72) Inventors: Jeremy R. Duvall, Topsfield, MA (US); Keith W. Bentley, Boston, MA (US); Raghida A. Bukhalid, Medford, MA (US); Naniye Cetinbas, Somerville, MA (US); Marc I. Damelin, Needham, MA (US); Eugene W. Kelleher, Wellesley, MA (US); Timothy B. Lowinger, Carlisle, MA (US); Joshua D. Thomas, Natick, MA (US); Dorin Toader, Cambridge, MA (US); Ling Xu, Brookline, MA (US); Liping Yang, Arlington, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 290 days.

This patent is subject to a terminal disclaimer.

(21) Appl. No.: 18/068,476

(22) Filed: Dec. 19, 2022

(65) Prior Publication Data

US 2023/0321048 A1 Oct. 12, 2023

Related U.S. Application Data

(63) Continuation of application No. 17/221,341, filed on Apr. 2, 2021.

(60) Provisional application No. 63/111,820, filed on Nov. 10, 2020, provisional application No. 63/040,755, filed on Jun. 18, 2020, provisional application No. 63/004,108, filed on Apr. 2, 2020.

(51) Int. Cl.

| | |
|---|---|
| ***A61K 47/68*** | (2017.01) |
| ***A61K 31/4184*** | (2006.01) |
| ***A61K 31/422*** | (2006.01) |
| ***A61K 31/428*** | (2006.01) |
| ***A61K 31/437*** | (2006.01) |
| ***A61K 45/06*** | (2006.01) |
| ***A61K 47/54*** | (2017.01) |
| ***A61K 47/55*** | (2017.01) |
| ***A61K 47/60*** | (2017.01) |
| ***A61K 47/65*** | (2017.01) |
| ***A61P 35/00*** | (2006.01) |

(52) U.S. Cl.

CPC ...... *A61K 47/6849* (2017.08); *A61K 31/4184* (2013.01); *A61K 31/422* (2013.01); *A61K 31/428* (2013.01); *A61K 31/437* (2013.01); *A61K 45/06* (2013.01); *A61K 47/54* (2017.08); *A61K 47/542* (2017.08); *A61K 47/545* (2017.08); *A61K 47/55* (2017.08); *A61K 47/60* (2017.08); *A61K 47/65* (2017.08); *A61K 47/6803* (2017.08); *A61K 47/6841* (2017.08); *A61P 35/00* (2018.01)

(58) Field of Classification Search

CPC ............ A61K 47/6849; A61K 31/4184; A61K 31/422; A61K 31/428; A61K 31/437; A61K 45/06; A61K 47/54; A61K 47/542; A61K 47/545; A61K 47/55; A61K 47/60; A61K 47/65; A61K 47/6803; A61K 47/6841; A61K 47/6855; A61K 47/6889; A61P 35/00; C07K 2317/52; C07K 2317/71; C07K 16/1027; C07K 16/32

See application file for complete search history.

(56) References Cited

U.S. PATENT DOCUMENTS

| | | | |
|---|---|---|---|
| 7,488,802 B2 | 2/2009 | Collins et al. | |
| 7,521,051 B2 | 4/2009 | Collins et al. | |
| 8,008,449 B2 | 8/2011 | Korman et al. | |
| 8,168,757 B2 | 5/2012 | Finnefrock et al. | |
| 8,354,509 B2 | 1/2013 | Carven et al. | |
| 8,603,474 B2 | 12/2013 | Ritter et al. | |
| 10,189,820 B2 | 1/2019 | Mehlmann et al. | |
| 11,155,567 B2 | 10/2021 | Duvall et al. | |
| 11,596,694 B2 | 3/2023 | Mosher et al. | |
| 11,939,343 B2 | 3/2024 | Duvall et al. | |
| 12,156,870 B2 | 12/2024 | Duvall et al. | |
| 2011/0271358 A1 | 11/2011 | Freeman et al. | |
| 2015/0366987 A1* | 12/2015 | Bodyak | A61K 47/6883 |
| 2017/0298139 A1 | 10/2017 | Thompson et al. | |
| 2018/0105514 A1 | 4/2018 | Mehlmann et al. | |
| 2019/0336615 A1 | 11/2019 | Thompson et al. | |

(Continued)

FOREIGN PATENT DOCUMENTS

| | | |
|---|---|---|
| CN | 110016025 A | 7/2019 |
| CN | 110963997 A | 4/2020 |

(Continued)

OTHER PUBLICATIONS

Banerjee M et al. Abstract LB-061: CRD5500: A versatile small molecule STING agonist amenable to bioconjugation as an ADC (Cancer Res (2019) 79 (13_Supplement): LB-061) (Year: 2019).*

(Continued)

*Primary Examiner* — Karen A. Canella
*Assistant Examiner* — John J Skoko, III
(74) *Attorney, Agent, or Firm* — Fenwick & West LLP

(57) ABSTRACT

The present disclosure provides scaffolds and antibody-drug conjugates (ADCs) comprising a stimulator of interferon genes (STING). The present disclosure also provides uses of the ADCs in treatment, e.g., treatment of cancer.

20 Claims, 38 Drawing Sheets

Specification includes a Sequence Listing.

(56) References Cited

U.S. PATENT DOCUMENTS

| | | | |
|---|---|---|---|
| 2020/0031825 A1 | 1/2020 | Slassi et al. |
| 2020/0113912 A1 | 4/2020 | Odegard et al. |
| 2021/0032269 A1 | 2/2021 | Duvall et al. |
| 2021/0332080 A1 | 10/2021 | Han |
| 2022/0064189 A1 | 3/2022 | Duvall et al. |
| 2022/0233707 A1 | 7/2022 | Lowinger et al. |
| 2022/0378749 A1 | 12/2022 | Duvall et al. |
| 2023/0074558 A1 | 3/2023 | Duvall et al. |
| 2023/0172910 A1 | 6/2023 | Duvall et al. |
| 2023/0398229 A1 | 12/2023 | Bukhalid et al. |
| 2025/0011339 A1 | 1/2025 | Duvall et al. |

FOREIGN PATENT DOCUMENTS

| | | | | |
|---|---|---|---|---|
| CN | 111393404 A | 7/2020 | |
| CN | 111499617 A | 8/2020 | |
| CN | 111848573 A | 10/2020 | |
| CN | 112300227 A | 2/2021 | |
| CN | 112898286 A | 6/2021 | |
| CN | 113248475 A | 8/2021 | |
| EP | 2176293 B1 | 4/2019 | |
| WO | WO-0102369 A2 | 1/2001 | |
| WO | WO-0210192 A2 | 2/2002 | |
| WO | WO-02068470 A2 | 9/2002 | |
| WO | WO-2004004771 A1 | 1/2004 | |
| WO | WO-2004056875 A1 | 7/2004 | |
| WO | WO-2004072286 A1 | 8/2004 | |
| WO | WO-2009097128 A1 | 8/2009 | |
| WO | WO-2010027827 A2 | 3/2010 | |
| WO | WO-2010077634 A1 | 7/2010 | |
| WO | WO-2011066342 A2 | 6/2011 | |
| WO | WO-2013019906 A1 | 2/2013 | |
| WO | WO-2014093936 A1 | 6/2014 | |
| WO | WO-2014189805 A1 | 11/2014 | |
| WO | WO-2014189806 A1 | 11/2014 | |
| WO | WO-2015162291 | 10/2015 | |
| WO | WO-2015185565 A1 | 12/2015 | |
| WO | WO-2015195917 A1 | 12/2015 | |
| WO | WO-2016096174 A1 | 6/2016 | |
| WO | WO-2016096577 A1 | 6/2016 | |
| WO | WO-2016120305 A1 | 8/2016 | |
| WO | WO-2017027645 A1 | 2/2017 | |
| WO | WO-2017027646 A1 | 2/2017 | |
| WO | WO-2017075477 A1 | 5/2017 | |
| WO | WO-2017093933 A1 | 6/2017 | |
| WO | WO-2017100305 A2 | 6/2017 | |
| WO | WO-2017160754 A1 | 9/2017 | |
| WO | WO-2017175147 A1 | 10/2017 | |
| WO | WO-2017175156 A1 | 10/2017 | |
| WO | WO-2018009466 A1 | 1/2018 | |
| WO | WO-2018067423 A1 | 4/2018 | |
| WO | WO-2018098269 A2 | 5/2018 | |
| WO | WO-2018160538 A1 | 9/2018 | |
| WO | WO-2018200812 A1 * | 11/2018 | ............. A61K 47/68 |
| WO | WO-2018227023 A1 | 12/2018 | |
| WO | WO-2019027857 A1 | 2/2019 | |
| WO | WO-2019027858 A1 | 2/2019 | |
| WO | WO-2019069269 A1 | 4/2019 | |
| WO | WO-2019069270 A1 | 4/2019 | |
| WO | WO-2019069275 A1 | 4/2019 | |
| WO | WO-2019084060 A1 | 5/2019 | |
| WO | WO-2019134705 A1 | 7/2019 | |
| WO | WO-2019134707 A1 | 7/2019 | |
| WO | WO-2019195063 A1 | 10/2019 | |
| WO | WO-2019195124 A1 | 10/2019 | |
| WO | WO-2019227007 A1 | 11/2019 | |
| WO | WO-2019236567 A2 | 12/2019 | |
| WO | WO-2019243825 A1 | 12/2019 | |
| WO | WO-2020006432 A1 | 1/2020 | |
| WO | WO-2020010451 A1 | 1/2020 | |
| WO | WO-2020028566 A1 | 2/2020 | |
| WO | WO-2020038387 A1 | 2/2020 | |
| WO | WO-2020042995 A1 | 3/2020 | |
| WO | WO-2020115676 A1 | 6/2020 | |
| WO | WO-2020132549 A1 | 6/2020 | |
| WO | WO-2020132566 A1 | 6/2020 | |
| WO | WO-2020132582 A1 * | 6/2020 | |
| WO | WO-2020140894 A1 | 7/2020 | |
| WO | WO-2020146237 A1 | 7/2020 | |
| WO | WO-2020151682 A1 | 7/2020 | |
| WO | WO-2020156363 A1 | 8/2020 | |
| WO | WO-2020181050 A1 | 9/2020 | |
| WO | WO-2020194160 A1 | 10/2020 | |
| WO | WO-2020202091 A1 | 10/2020 | |
| WO | WO-2020214858 A1 | 10/2020 | |
| WO | WO-2020221038 A1 | 11/2020 | |
| WO | WO-2020227159 A2 | 11/2020 | |
| WO | WO-2021000770 A1 | 1/2021 | |
| WO | WO-2021009365 A1 | 1/2021 | |
| WO | WO-2021013250 A1 | 1/2021 | |
| WO | WO-2021014365 A1 | 1/2021 | |
| WO | WO-2021026009 A1 | 2/2021 | |
| WO | WO-2021113679 A1 | 6/2021 | |
| WO | WO-2021202984 A1 | 10/2021 | |

OTHER PUBLICATIONS

Lee KW et al. Molecular targets of phytochemicals for cancer prevention. (Nature Reviews Cancer 2011 11 211-218). (Year: 2011).*

Hanahan D et al. Hallmarks of Cancer: The Next Generation. (Cell 2011 144(5) 646-674) (Year: 2011).*

Lichtman MA et al. A Bacterial Cause of Cancer: An Historical Essay. (The Oncologist2017; 22(5); 542-548) (Year: 2017).*

Jain et al., "Current ADC linker chemistry". Pharmaceutical research. Nov. 2015; 32(11): 3526-40.

Elemes et al., "Synthesis of enantiopure a-deuteriated Boc-L-amino acids", J. Chem. Soc, Perkin Trans. 1, 1996, vol. 6, p. 537-540.

Francisco et al., "cAC10-vcMMAE, an anti-CD30-monomethyl auristatin E conjugate with potent and selective antitumor activity". Blood. Aug. 15, 2003; 102(4): 1458-65.

Leit De Moradei et al. CAPLUS 2020:1235220, 2020, 4 pages.

Pan et al., "An orally available non-nucleotide STING agonist with antitumor activity", Science, vol. 369, 13 pages, (2020).

Ramanjulu et al., "Design of amidobenzimidazole STING receptor agonists with systemic activity", Nature. Dec. 20, 2018; 564(7736): 439-43.

Slassi et al., CAPLUS 2020:185181,2020,3 pages.

Song et al., "Structure-Activity Relationship Study of Amidobenzimidazole Analogues Leading to Potent and Systemically Administrable Stimulator of Interferon Gene (STING) Agonists", Journal of Medicinal Chemistry. Jan. 20, 2021; 64(3): 1649-69.

CAS Registry No. 2138299-29-1, date entered STN: Nov. 2, 2017; 1H-Benzimidazole-5-carboxamide, 1-[(2E)-4-[5-(aminocarbonyl)-2-[[(1-ethyl-3-methyl-1H-pyrazol-5-yl)carbonyl]amino]-1H-benzimidazol-1-yl]-2-buten-1-yl]-2-[[(1-ethyl-3-methyl-1H-pyrazol-5-yl)carbonyl]amino]-7-(3-hydroxypropoxy), 2 pages.

Enomoto et al., "Synthesis of peptide-grafted comb polypeptides via polymerisation of NCA-peptides." Chemical Communications. 2013; 49(4): 409-411.

Hofland et al. "Preclinical Data Supports the Development of XMT-1536 in a Broad Population of Patients with Ovarian Cancer," ADC Review, News, Oct. 30, 2017, pp. 1-3, Retrieved from: https://www.adcreview.com/news/preclinical-data-supports-development-xmt-1536-broad-population-patients-ovarian-cancer/.

Karaman "The Prodrug Naming Dilemma." Drug Des. 2013; 2: e115, pp. 1-4.

Kim et al., "Antibody-assisted delivery of a peptide-drug conjugate for targeted cancer therapy." Molecular pharmaceutics. Dec. 6, 2018; 16(1): 165-172.

Lowe "Prodrugs: How the Pros Do It?," In the Pipeline: Drug Development. Dec. 1, 2008; 2 pages. Available from: https://www.science.org/content/blog-post/prodrugs-pros-do.

Rautio et al., "The expanding role of prodrugs in contemporary drug design and development." Nature Reviews Drug Discovery. Aug. 2018; 17(8): 559-587.

Stella "Prodrugs: My initial exploration and where it led." Journal of Pharmaceutical Sciences. Dec. 1, 2020; 109(12): 3514-3523.

U.S. Appl. No. 17/469,983, filed Sep. 9, 2021.

(56) References Cited

OTHER PUBLICATIONS

U.S. Appl. No. 17/782,796, filed Jun. 6, 2022.
U.S. Appl. No. 17/221,341, filed Dec. 1, 2022.
U.S. Appl. No. 18/068,936, filed Dec. 20, 2022.

* cited by examiner

VEHICLE Conjugate 8a-1 Conjugate 8c-1

Effect of IFNλ1 (IL29) or IFNλ2(IL28A) neutralizing antibodies in cancer cell and PBMC co-cultures

Individual Plots

ANTIBODY DRUG CONJUGATES COMPRISING STING AGONISTS

RELATED APPLICATIONS

This application is a continuation of U.S. application Ser. No. 17/221,341, filed Apr. 2, 2021, which claims priority to, and the benefit of U.S. Provisional Application No. 63/004,108 filed Apr. 2, 2020, U.S. Provisional Application No. 63/040,755 filed Jun. 18, 2020, and U.S. Provisional Application No. 63/111,820 filed Nov. 10, 2020. The contents of each of these applications are hereby incorporated by reference in their entireties.

INCORPORATION BY REFERENCE OF SEQUENCE LISTING

The Sequence Listing XML associated with this application is provided electronically in XML file format and is hereby incorporated by reference into the specification. The name of the XML file containing the Sequence Listing XML is "MRSN-033_C01US_ST26.xml". The XML file is 34,142 bytes in size, created on Sep. 30, 2022, and is being submitted electronically via USPTO Patent Center.

BACKGROUND

Stimulator of interferon genes (STING) is a receptor in the endoplasmic reticulum that propagates innate immune sensing of cytosolic pathogen derived- and self-DNA. STING is a 378 amino acid protein, which mainly contains three structural domains: (i) N-terminal transmembrane domain (aa 1-154); (ii) central globular domain (aa 155-341); and (iii) C-terminal tail (aa 342-379). STING may form symmetrical dimers combined with its ligands in V-shaped conformation, while not completely covering the bound ligands. A STING agonist can bind into the pocket region of STING. However, the STING activation process is easily inhibited in some severe disease conditions, resulting in the inactivation of the STING pathway. Therefore, screening and designing potent STING agonists is of great importance for cancer immune therapy and other infectious diseases treatments, including, but not limited to, obesity, liver injury, sugar-lipid metabolism, and virus infection. Specific targeting of immune pathways presents opportunities for cancer therapy, potentially offering greater specificity than cell population-based therapeutic approaches.

Antibody-drug conjugates (ADCs) are comprised of a drug like small molecule, covalently linked to an antibody. The antibody represents a targeting mechanism tuned to a specific site of action. Upon reaching the site, the ADC is designed to release a small molecule, the drug, allowing it to perform its designed function in a targeted manner, as opposed to diffusing systemically through the entire body of the subject. This targeted approach allows for treatment with drugs that would otherwise require doses so high as to be toxic when administered systemically.

A key feature of the innate immune system is the recognition and elimination of foreign substances. Identification of these pathogenic invaders occurs through host recognition of evolutionarily conserved microbial structures known as pathogen-associated molecular patterns (PAMPs). Host recognition may occur by multiple pathways, such as activation of pattern recognition receptors (PRRs), which ultimately lead to downstream signaling events and culminate in the mounting of an immune response.

The antibody-drug conjugates of this disclosure modulate the activity of STING, and accordingly, may provide a beneficial therapeutic impact in treatment of diseases, disorders and/or conditions wherein modulation of STING (Stimulator of Interferon Genes) is beneficial, including, but not limited to, inflammation, allergic and autoimmune diseases, infectious diseases, cancer, pre-cancerous syndromes, and as vaccine adjuvants. There remains a need for new immunotherapies for the treatment of diseases, in particular cancer.

SUMMARY

In some aspects, the present disclosure provides a conjugate of Formula (I):

$$\text{PBRM-}[A^1\text{-}(L^C)_{0\ or\ 1}\text{-D}]_{d15} \quad \text{(I)}$$

or a pharmaceutically acceptable salt or solvate thereof, wherein:

PBRM denotes a protein-based recognition-molecule;

$L^C$, when present, is a linker unit;

$A^1$ is a divalent linker moiety connecting the PBRM to $L^C$ when $L^C$ is present, or to D when $L^C$ is absent;

D is a STING agonist drug moiety; and $d_{15}$ is an integer ranging from about 1 to about 20.

In some aspects, the present disclosure provides a scaffold useful for conjugating with a PBRM, wherein the scaffold is of Formula (II):

$$A^{1'}\text{-}(L^C)_{0\ or\ 1}\text{-D} \quad \text{(II)}$$

or a pharmaceutically acceptable salt or solvate thereof, wherein:

PBRM denotes a protein-based recognition-molecule;

$L^C$, when present, is a linker unit;

$A^{1'}$ is a monovalent linker moiety comprising a functional group capable of forming a covalent bond with a functional group of the PBRM;

D is a STING agonist drug moiety; and $d_{15}$ is an integer ranging from about 1 to about 20.

In some aspects, the present disclosure provides a pharmaceutical composition comprising a conjugate described herein and one or more pharmaceutically acceptable carriers or excipients.

In some aspects, the present disclosure provides a method of activating or enhancing an activity of a stimulator of interferon genes (STING) in a subject, comprising administering to the subject a conjugate described herein or a pharmaceutically acceptable salt thereof.

In some aspects, the present disclosure provides a method of preventing or treating a disease or disorder in a subject, comprising administering to the subject a therapeutically effective amount of a conjugate described herein or a pharmaceutically acceptable salt thereof.

In some aspects, the present disclosure provides a conjugate described herein, or a pharmaceutically acceptable salt thereof, for activating or enhancing an activity of STING in a subject.

In some aspects, the present disclosure provides a conjugate described herein, or a pharmaceutically acceptable salt thereof, for preventing or treating a disease or disorder in a subject.

In some aspects, the present disclosure provides a use of a conjugate described herein, or a pharmaceutically acceptable salt thereof, in the manufacture of a medicament for activating or enhancing an activity of STING in a subject.

In some aspects, the present disclosure provides a use of a conjugate described herein, or a pharmaceutically acceptable salt thereof, in the manufacture of a medicament for preventing or treating a disease or disorder in a subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF THE FIGURES

FIG. 7A), IL-6 (FIG. 7B), TNFα (FIG. 7C), IFNγ (FIG. 7D), CXCL1 (KC) (FIG. 7E), MIG (FIG. 7F), MIP-1a (FIG. 7G), and RANTES (FIG. 7H) as a function of time following administration of diABZI STING agonist (0/5 mg/kg), Conjugate 8c-1 (3/0.12 mg/kg) or Conjugate 8a-1 (3/0.09 mg/kg) (all doses are written as antibody/payload) in a SKOV3 mouse model. Inserts in each plot show cytokine levels induced by Conjugate 8a-1 and Conjugate 8c-1 relative to vehicle.

DETAILED DESCRIPTION

Figure 1A:
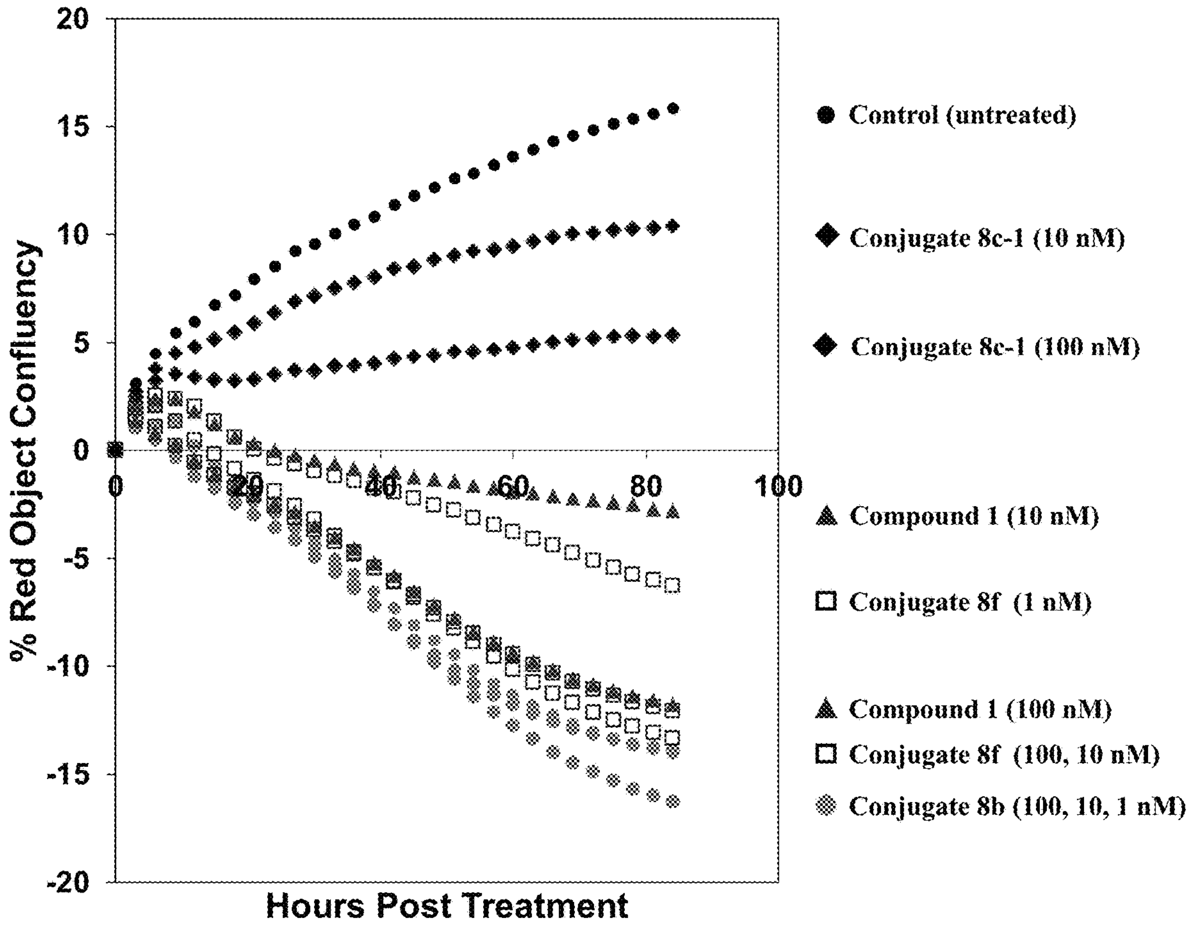
FIG. 1A plots the red object confluency as a function of time for Conjugate 8b-1 and Conjugate 8f (each at 100, 10, and 1 nM) and Conjugate 8c-1 and Compound 1 (each at 100 and 10 nM) (conjugate concentrations were based on the payload).

The present disclosure provides novel antibody-drug conjugates, synthetic methods for making the conjugates or scaffolds, pharmaceutical compositions containing them, and various uses of the conjugates.

Definitions

The chemical names provided for the intermediate compounds and/or the compounds of this disclosure described herein may refer to any one of the tautomeric representations of such compounds (in some instances, such alternate names are provided with the experimental). It is to be understood that any reference to a named compound (an intermediate compound or a compound of the disclosure) or a structurally depicted compound (an intermediate compound or a compound of the disclosure) is intended to encompass all tautomeric forms including zwitterionic forms of such compounds and any mixture thereof.

It is to be understood that the terms "In some embodiments", "In some embodiments of the present disclosure", and "In some embodiments of a compound of the present disclosure" may be used interchangeably where appropriate.

The term "about", "approximately", or "approximate", when used in connection with a numerical value, means that a collection or range of values is included. In some embodiments, "about X" includes a range of values that are ±25%, ±20%, ±15%, ±10%, ±5%, ±2%, ±1%, ±0.5%, ±0.2%, or ±0.1% of X, where X is a numerical value. In some embodiments, the term "about" refers to a range of values which are 5% more or less than the specified value. In some embodiments, the term "about" refers to a range of values which are 2% more or less than the specified value. In some embodiments, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. In some embodiments, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

The term "antibody" as used herein, is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The numbering of the antibody amino acids is according to Kabat EU Index (See Kabat, E. A., et al., Sequences of Protein of immunological interest, Fifth Edition, US Department of Health and Human Services, US Government Printing Office (1991)).

The term "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "antibody that binds to the same epitope" as a reference antibody as used herein, refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgGi, IgG2, IgG3, IgG4, IgAi, and IgA2. The heavy chain constant domains that correspond to the different classes of immunoglobulins are called α, δ, ε, γ, and μ, respectively.

The term "monoclonal antibody" as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "epitope" refers to the particular site on an antigen molecule to which an antibody binds.

The term "Protein-based recognition-molecule" or "PBRM" refers to a molecule that recognizes and binds to a cell surface marker or receptor such as, a transmembrane protein, surface immobilized protein, or proteoglycan. In some embodiments, the PBRM comprises an engineered cysteine. Examples of PBRMs include but are not limited to, antibodies, peptides, lipocalins, proteins, peptides or peptide mimics, and the like. The protein-based recognition molecule, in addition to targeting the conjugate to a specific cell, tissue or location, may also have certain therapeutic effect such as antiproliferative (cytostatic and/or cytotoxic) activity against a target cell or pathway. The protein-based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine. In some embodiments, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. In some embodiments, the ligand can preferentially associate with the cell surface molecule with a Kd of less than about 50 nM, less than about 5 nM, or less than 500 pM. Techniques for measuring binding affinity of a ligand to a cell surface molecule are well-known; for example, one suitable technique, is termed surface plasmon resonance (SPR). In some embodiments, the ligand is used for targeting and has no detectable therapeutic effect as separate from the drug which it delivers. In some embodiments, the ligand functions both as a targeting moiety and as a therapeutic or immunomodulatory agent (e.g., to enhance the activity of the active drug or prodrug). The term "PEG unit" ss used herein refers to a polyethylene glycol subunit having the formula

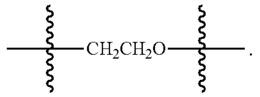

In some embodiments, the PEG unit comprises multiple PEG subunits.

The term "alkyl", as used herein, represents a saturated, straight or branched hydrocarbon group having the specified number of carbon atoms. The term "$C_1$-$C_6$ alkyl" or "$C_{1-6}$ alkyl" refers to a methyl moiety or a straight or branched alkyl moiety comprising from 2 to 6 carbon atoms. Exemplary alkyls include, but are not limited to methyl, ethyl, n-propyl, isopropyl, n-butyl, isobutyl, s-butyl, t-butyl, pentyl and hexyl.

The term "halo(alkyl)", as used herein, represents a saturated, straight or branched hydrocarbon group having the specified number (n) of carbon atoms and one or more (up to 2n+1) halogen atoms. Examples of "halo($C_{1-4}$ alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

The term "alkenyl", as used herein, refers to straight or branched hydrocarbon group having the specified number of carbon atoms and at least 1 and up to 3 carbon-carbon double bonds. Examples include ethenyl and propenyl.

The term "alkynyl", as used herein, refers to straight or branched hydrocarbon group having the specified number of carbon atoms and at least 1 and up to 3 carbon-carbon triple bonds. Examples include ethynyl and propynyl.

The term "alkoxy-" or "(alkyl)oxy-", as used herein, refers to an "alkyl-oxy-" group, comprising an alkyl moiety, having the specified number of carbon atoms, attached through an oxygen linking atom. Exemplary "$C_{1-4}$ alkoxy-"

or "($C_{1-4}$ alkyl)oxy-" groups include, but are not limited to, methoxy, ethoxy, n-propoxy, isopropoxy, n-butoxy, s-butoxy, and t-butoxy.

The term "halo(alkoxy)-", as used herein, represents a saturated, straight or branched hydrocarbon group having the specified number (n) of carbon atoms and one or more (up to 2n+1) halogen atoms, attached through an oxygen linking atom. Exemplary "halo($C_{1-4}$ alkoxy)-" groups include, but are not limited to, $-OCHF_2$ (difluoromethoxy), $-OCF_3$ (trifluoromethoxy), $-OCH_2CF_3$ (trifluoroethoxy), and $-OCH(CF_3)_2$ (hexafluoroisopropoxy).

The term "amino" as used herein refers to a substituent comprising at least one nitrogen atom. Specifically, $-NH_2$, $-NH(C_{1-4}$ alkyl), alkylamino, or ($C_{1-4}$ alkyl)amino- or ($C_{1-4}$ alkyl)($C_{1-4}$ alkyl)amino- or dialkylamino, amide-, carbamide-, urea, and sulfamide substituents are included in the term "amino".

The term "carbocyclic group or moiety" as used herein, refers to a cyclic group or moiety wherein the ring members are carbon atoms, which may be saturated, partially unsaturated (non-aromatic) or fully unsaturated (aromatic).

The term "cycloalkyl", as used herein, refers to a non-aromatic, saturated, hydrocarbon ring group comprising the specified number of carbon atoms in the ring. For example, the term "$C_{3-6}$ cycloalkyl" refers to a cyclic group having from three to six ring carbon atoms. Exemplary "$C_{3-6}$ cycloalkyl" groups include cyclopropyl, cyclobutyl, cyclopentyl, and cyclohexyl.

The term "aryl", as used herein, refers to a group with aromaticity, including "conjugated" or multicyclic systems with one or more aromatic rings, which does not contain any heteroatom in the ring structure. The term aryl includes both monovalent species and divalent species. Examples of aryl groups include, but are not limited to, phenyl, biphenyl, naphthyl and the like. In some embodiments, an aryl is phenyl.

The term "heterocyclic group or moiety", as used herein, refers to a cyclic group or moiety having, as ring members, atoms of at least two different elements, which cyclic group or moiety may be saturated, partially unsaturated (non-aromatic) or fully unsaturated (aromatic).

The term "heteroatom", as used herein, refers to a nitrogen, sulfur, or oxygen atom, for example a nitrogen atom or an oxygen atom.

The term "heterocycloalkyl", as used herein, refers to a non-aromatic, monocyclic or bicyclic group comprising 3-10 ring atoms and comprising one or more (generally one or two) heteroatom ring members independently selected from oxygen, sulfur, and nitrogen. The point of attachment of a heterocycloalkyl group may be by any suitable carbon or nitrogen atom.

The term "heteroaryl", as used herein, refers to an aromatic monocyclic or bicyclic group comprising 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups comprising either a phenyl ring fused to a heterocyclic moiety or a heteroaryl ring moiety fused to a carbocyclic moiety. The point of attachment of a heteroaryl group may be by any suitable carbon or nitrogen atom.

The terms "halogen" and "halo", as used herein, refers to a halogen radical, for example, a fluoro, chloro, bromo, or iodo substituent.

The term "oxo", as used herein, refers to a double-bonded oxygen moiety; for example, if attached directly to a carbon atom forms a carbonyl moiety (C=O).

The term "hydroxy" or "hydroxyl", as used herein, is intended to mean the radical —OH.

The term "cyano", as used herein, refers to a nitrile group, —C≡N.

The term "optionally substituted", as used herein, indicates that a group (such as an alkyl, cycloalkyl, alkoxy, heterocycloalkyl, aryl, or heteroaryl group) or ring or moiety may be unsubstituted, or the group, ring or moiety may be substituted with one or more substituent(s). In the case where groups may be selected from a number of alternative groups, the selected groups may be the same or different. Suitable substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "independently", as used herein, means that where more than one substituent is selected from a number of possible substituents, those substituents may be the same or different.

The term "pharmaceutically acceptable", as used herein, refers to those compounds, conjugates, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "preventing," "prevent," or "protecting against" describes reducing or eliminating the onset of the symptoms or complications of such disease, condition or disorder.

The term "subject" refers to an animal, preferably a mammal, most preferably a human, who has been the object of treatment, observation or experiment.

The term "therapeutically effective amount" refers to an amount of an active compound or pharmaceutical agent, including a conjugate of the disclosure, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

A therapeutically "effective amount" is intended to mean that amount of a conjugate that, when administered to a patient in need of such treatment, is sufficient to effective treat or prevent, as defined herein. The amount of a given conjugate that will correspond to such an amount will vary depending upon factors such as the particular conjugate (e.g., the potency (pICso), efficacy ($EC_{50}$), and the biological half-life of the particular conjugate), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the conjugate will vary according to the identity of the mammal in need of treatment (e.g., weight), the particular conjugate and its properties (e.g., pharmacokinetic properties), disease or disorder and its severity and the specific composition and method being used, but can nevertheless be determined by one of skill in the art.

The term "composition" refers to a product that includes the specified ingredients in therapeutically effective amounts, as well as any product that results, directly, or indirectly, from combinations of the specified ingredients in the specified amounts.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "STING agonist", as used herein, refers to a compound or moiety which is capable of interacting with STING, e.g., by binding to STING and/or inducing downstream signal transduction (e.g., characterized by activation of the molecules associated with STING function). This includes direct phosphorylation of STING, IRF3 and/or NF-kB and could also include STAT6. In some embodiments, STING pathway activation results in increased production of type 1 interferons (mainly IFN-a and IFN-b) and/or expression of interferon-stimulated genes.

The term "STING agonist drug moiety", as used herein, refers to a moiety derived from a STING agonist and capable of interacting with STING. In some embodiments, the STING agonist drug moiety is a moiety derived from a STING agonist to allow the moiety being linked to the rest of a conjugate of the present disclosure.

The conjugates of the disclosure are useful in methods for treating or ameliorating a viral infection, disease, a syndrome, a condition or a disorder that is affected by the agonism of STING. Such methods comprise, consist of and/or consist essentially of administering to a subject, including an animal, a mammal, and a human in need of such treatment, amelioration and/or prevention, a therapeutically effective amount of a conjugate of the disclosure, or an enantiomer, diastereomer, solvate or pharmaceutically acceptable salt thereof.

In some embodiments, conjugates of the disclosure, or an enantiomer, diastereomer, solvate or pharmaceutically acceptable salt form thereof are useful for treating or ameliorating diseases, syndromes, conditions, or disorders such as melanoma, colon cancer, breast cancer, prostate cancer, lung cancer, fibrosarcoma, and hepatitis B.

The terms "conjugate(s) of the disclosure" or "conjugate(s) of the present disclosure", as used herein, mean a conjugate as defined herein, in any form, i.e., any tautomeric form, any isomeric form, any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present disclosure are the conjugates as disclosure herein, in any salt or non-salt form and any physical form thereof, and mixtures of various forms. While such are included within the present disclosure, it will be understood that the conjugates of the present disclosure, in any salt or non-salt form, and in any physical form thereof, may have varying levels of activity, different bioavailabilities and different handling properties for formulation purposes.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Conjugates and Scaffolds of the Present Disclosure

In some aspects, the present disclosure provides a conjugate of Formula (I):

$$\text{PBRM-}[\text{A}^1\text{-}(\text{L}^C)_{or\ 1}\text{-D}]_{d15} \quad \text{(I)}$$

or a pharmaceutically acceptable salt or solvate thereof, wherein:

PBRM denotes a protein-based recognition-molecule;

$L^C$, when present, is a linker unit;

$A^1$ is a divalent linker moiety connecting the PBRM to $L^C$ when $L^C$ is present, or to D when $L^C$ is absent;

D is a STING agonist drug moiety; and $d_{15}$ is an integer ranging from about 1 to about 20.

In some embodiments, the conjugate is of Formula (I-A):

$$\text{PBRM-}[A^1\text{-D}]_{d15} \quad \text{(I-A)}$$

or a pharmaceutically acceptable salt or solvate thereof.

In some embodiments, the conjugate is of Formula (I-B):

$$\text{PBRM-}[A^1\text{-}L^C\text{-D}]_{d15} \quad \text{(I-B)}$$

or a pharmaceutically acceptable salt or solvate thereof.

In some embodiments, the conjugate is of Formula (I-B'):

(I-B')

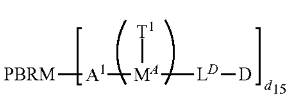

or a pharmaceutically acceptable salt or solvate thereof.

In some aspects, the present disclosure provides a scaffold useful for conjugating with a PBRM, wherein the scaffold is of Formula (II):

$$A^{1'}\text{-}(L^C)_{0\ or\ 1}\text{-D} \quad \text{(II)}$$

or a pharmaceutically acceptable salt or solvate thereof, wherein:

PBRM denotes a protein-based recognition-molecule;

$L^C$, when present, is a linker unit;

$A^{1'}$ is a monovalent linker moiety comprising a functional group capable of forming a covalent bond with a functional group of the PBRM; and D is a STING agonist drug moiety.

In some embodiments, the scaffold is of Formula (II-A):

$$A^{1'}\text{-D} \quad \text{(II-A)}$$

or a pharmaceutically acceptable salt or solvate thereof.

In some embodiments, the scaffold is of Formula (II-B):

$$A^{1'}\text{-}L^C\text{-D} \quad \text{(II-B)}$$

or a pharmaceutically acceptable salt or solvate thereof.

In some embodiments, the scaffold is of Formula (II-B'):

(II-B')

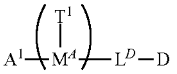

or a pharmaceutically acceptable salt or solvate thereof.

It is understood that, for a conjugate of any one of Formulae (I), (I-A), (I-B), (I-B'), (II), (II-A), (II-B), or (II-B'), or a pharmaceutically acceptable salt or solvate thereof, variables PBRM, $L^C$, $A^1$, $T^1$, $M^A$, $L^D$, D, and $d_{15}$ can each be, where applicable, selected from the groups described herein, and any group described herein for any of variables PBRM, $L^C$, $A^1$, $T^1$, $M^A$, $L^D$, D, and $d_{15}$ can be combined, where applicable, with any group described herein for one or more of the remainder of variables PBRM, $L^C$, $A^1$, $T^1$, $M^A$, $L^D$, D, and $d_{15}$.

Variable $d_{15}$

In some embodiments, $d_{15}$ is an integer ranging from about 2 to about 14, from about 2 to about 12, from about 2 to about 10, from about 2 to about 8, from about 2 to about 6, from about 2 to about 4, from about 4 to about 10, from about 4 to about 8, from about 4 to about 6, from about 6 to about 14, from about 6 to about 12, from about 6 to about 10, from about 6 to about 8, from about 8 to about 14, from about 8 to about 12, or from about 8 to about 10.

In some embodiments, $d_{15}$ is an integer ranging from about 2 to about 8.

In some embodiments, $d_{15}$ is 2, 4, 6, or 8. In some embodiments, $d_{15}$ is 6 or 8.

In some embodiments, $d_{15}$ is 8. In some embodiments, $d_{15}$ is 6.

Variables $A^1$ and $A^{1'}$

In some embodiments, each $A^1$ independently is a divalent linker moiety connecting the PBRM to $L^C$ when $L^C$ is present, or to D when $L^C$ is absent.

In some embodiments, each $A^1$ independently is:

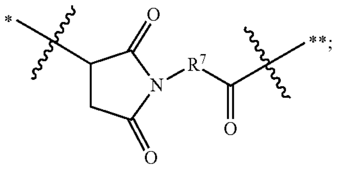

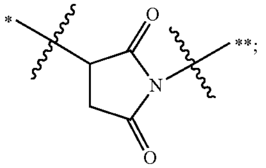

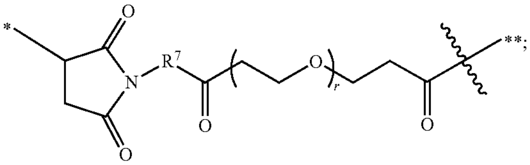 or

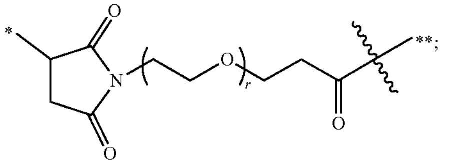

wherein:

$R^7$ is —O—, —$NR^8$, —($C_1$-$C_{10}$ alkyl)-, —($C_1$-$C_{10}$ alkenyl)-, —($C_1$-$C_{10}$ alkynyl)-, —($C_3$-$C_8$ cycloalkyl)-aryl-, —O—($C_1$-$C_8$ alkyl)-, —O—($C_1$-$C_{10}$ alkenyl)-, —O—($C_1$-$C_{10}$ alkynyl)-, —($C_1$-$C_{10}$ alkyl)-($C_3$-$C_8$ cycloalkyl)-, —($C_1$-$C_{10}$ alkyl)-aryl-, —($C_2$-$C_{10}$ alkenyl)-($C_3$-$C_8$ cycloalkyl)-, —($C_2$-$C_{10}$ alkenyl)-aryl-, —($C_2$-$C_{10}$ alkynyl)-($C_3$-$C_8$ cycloalkyl)-, —($C_2$-$C_{10}$ alkynyl)-aryl-, —($C_3$-$C_8$ cycloalkyl)-($C_1$-$C_{10}$ alky)-, -aryl-($C_1$-$C_{10}$ alky)-, —($C_3$-$C_8$ cycloalkyl)-($C_2$-$C_{10}$ alkenyl)-, -aryl-($C_2$-$C_{10}$ alkenyl)-, —($C_3$-$C_8$ cycloalkyl)-($C_2$-$C_{10}$ alkynyl)-, -aryl-($C_2$-$C_{10}$ alkynyl)-, -(3- to 8-membered heterocycloalkyl)-, -(5- to 8-membered heteroaryl)-, —($C_1$-$C_{10}$ alkyl)-(3- to 8-membered heterocycloalkyl)-, —($C_1$-$C_{10}$ alkyl)-(5- to 8-membered heteroaryl)-, —($C_2$-$C_{10}$ alkenyl)-(3- to 8-membered heterocycloalkyl)-, —($C_2$-$C_{10}$ alkenyl)-(5- to 8-membered heteroaryl)-, —($C_2$-$C_{10}$ alkynyl)-(3- to 8-membered heterocycloalkyl)-, —($C_2$-$C_{10}$ alkynyl)-(5- to 8-membered heteroaryl)-, -(3- to 8-membered heterocycloalkyl)-($C_1$-$C_{10}$ alkyl)-, -(5- to 8-membered heteroaryl)-($C_1$-$C_{10}$ alkyl)-, -(3- to 8-membered heterocycloalkyl)-($C_2$-$C_{10}$ alkenyl)-, -(5- to 8-membered heteroaryl)-($C_2$-$C_{10}$ alkenyl)-, -(5- to 8-membered heteroaryl)-($C_2$-$C_{10}$ alknyl)-, -(5- to 8-membered heteroaryl)-($C_2$-$C_{10}$ alknyl)-, —O—C(O)—($CH_2CH_2O$)$_r$—($CH_2$)$_2$—, —($CH_2CH_2O$)$_r$—, or —($CH_2CH_2O$)$_r$—($CH_2$)$_2$—, wherein the alkyl, alkenyl, alkynyl, cycloalkyl, aryl, heterocycloalkyl, or heteroaryl is optionally substituted;

$R^8$ is H, hydroxy, or $C_{1-4}$ alkyl;

r is an integer ranging from about 1 to about 12; and

* denotes attachment to PBRM and ** denotes attachment to $L^C$ when $L^C$ is present, or to D when $L^C$ is absent.

In some embodiments, $R^7$ is —O—, —$NR^8$, —($C_1$-$C_{10}$ alkyl)-, —($C_3$-$C_8$ cycloalkyl)-, -aryl-, —O—($C_1$-$C_8$ alkyl)-, —($C_1$-$C_{10}$ alkyl)-aryl-, -aryl-($C_1$-$C_{10}$ alkyl)-, —($C_1$-$C_{10}$ alkyl)-($C_3$-$C_8$ cycloalkyl)-, —($C_3$-$C_8$ cycloalkyl)-($C_1$-$C_{10}$ alkyl)-, -(3- to 8-membered heterocycloalkyl)-, -(5- to 8-membered heteroaryl)-, —($C_1$-$C_{10}$ alkyl)-(3- to 8-membered heterocycloalkyl)-, —($C_1$-$C_{10}$ alkyl)-(5- to 8-membered heteroaryl)-, -(3- to 8-membered heterocycloalkyl)-($C_1$-$C_{10}$ alkyl)-, -(5- to 8-membered heteroaryl)-($C_1$-$C_{10}$ alkyl)-, —O—C(O)—$(CH_2CH_2O)_r$—$(CH_2)_2$—, —$(CH_2CH_2O)_r$—, or —$(CH_2CH_2O)_r$—$(CH_2)_2$—.

In some embodiments, $R^7$ is —($C_1$-$C_{10}$ alkyl)-, —O—($C_1$-$C_8$ alkyl)-, —$(CH_2CH_2O)_r$—, —O—C(O)—$(CH_2CH_2O)_r$—$(CH_2)_2$— or —$(CH_2CH_2O)_r$—$(CH_2)_2$—.

In some embodiments, $R^7$ is —O—, —NH, —$N(CH_3)$, —$CH_2$—, —$(CH_2)_2$—, —$(CH_2)_5$—, —O—C(O)—$(CH_2CH_2O)_6$—$(CH_2)_2$—, —$(CH_2CH_2O)_2$—$(CH_2)_2$—, —$(CH_2CH_2O)_2$—$(CH_2)_2$—, —$(CH_2CH_2O)_4$—$(CH_2)_2$—, or —$(CH_2CH_2O)_6$—$(CH_2)_2$—.

In some embodiments, each $A^1$ independently is:

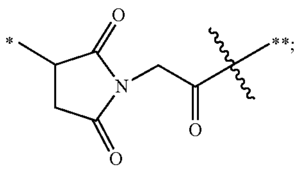

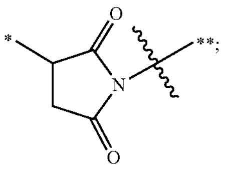

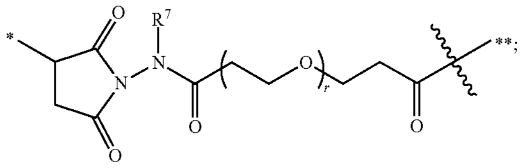

or

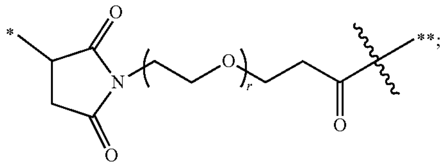

wherein $R^8$ is H, hydroxy, or $C_{1-4}$ alkyl; r is an integer ranging from about 4 to about 6; and * denotes attachment to PBRM and ** denotes attachment to $L^C$ when $L^C$ is present, or to D when $L^C$ is absent.

It is understood that each $A^1$, prior to being connected to PBRM, independently corresponds to a monovalent moiety $A^{1'}$.

In some embodiments, each $A^{1'}$ independently is:

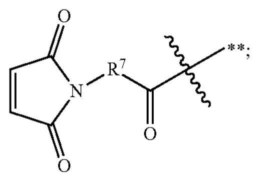

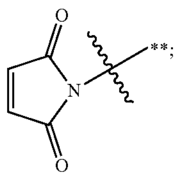

-continued

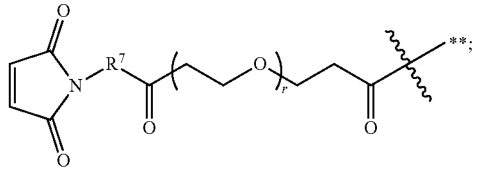

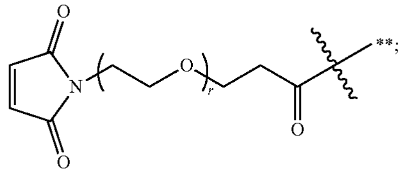

wherein $R^7$, $R^8$, and r are as described herein; and ** denotes attachment to $L^C$ when $L^C$ is present, or to D when $L^C$ is absent.

In some embodiments, each $A^{1'}$ independently is:

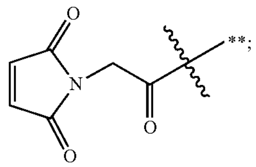

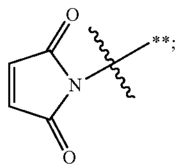

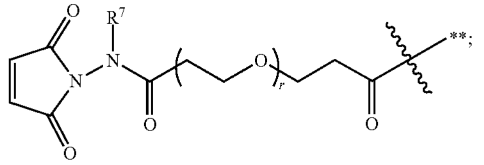

or

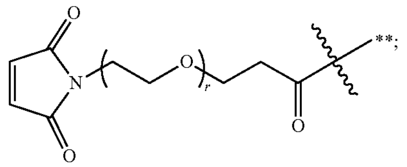

wherein:

r is an integer ranging from about 4 to about 6; and

** denotes attachment to $L^C$ when $L^C$ is present, or to D when $L^C$ is absent.

Variable $L^C$

In some embodiments, each $L^C$, when present, independently is:

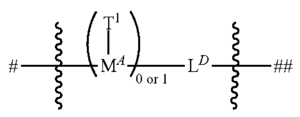

wherein:

# denotes attachment to $A^1$ and ## denotes attachment to D;

$M^A$, when present, is a peptide moiety comprising at least two amino acids;

$T^1$, when present, is a hydrophilic group; and $L^D$ is a divalent linker moiety connecting D to $M^A$ when $M^A$ is present, or to $A^1$ when $M^A$ is absent.

In some embodiments, each $L^D$ comprises at least one cleavable bond such that when the bond is broken, D is released in an active form for its intended therapeutic effect.

In some embodiments, each $L^C$, when present, independently is

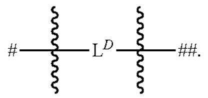

In some embodiments, each $L^C$, when present, independently is

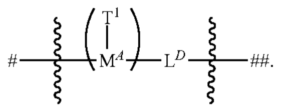

Variable $L^D$

In some embodiments, each $L^D$ independently is a divalent linker moiety connecting D to $M^A$ when $M^A$ is present, or to $A^1$ when $M^A$ is absent.

In some embodiments, each $L^D$ comprises at least one cleavable bond such that when the bond is cleaved, D is released in an active form for its intended therapeutic effect.

In some embodiments, $L^D$ comprises one cleavable bond. In some embodiments, $L^D$ comprises multiple cleavage sites or bonds.

It is understood that each $L^D$, prior to being connected to D, independently corresponds to a monovalent moiety $L^{D'}$.

In some embodiments, $L^{D'}$ comprises a functional group capable of forming the cleavable bond. Functional groups capable of forming the cleavable bond can include, for example, sulfhydryl groups to form disulfide bonds, aldehyde, ketone, or hydrazine groups to form hydrazone bonds, hydroxylamine groups to form oxime bonds, carboxylic or amino groups to form peptide bonds, carboxylic or hydroxy groups to form ester bonds, and sugars to form glycosidic bonds.

In some embodiments, each $L^D$ comprises a disulfide bond that is cleavable through disulfide exchange, an acid-labile bond that is cleavable at acidic pH, and/or bonds that are cleavable by hydrolases. In some embodiments, $L^D$ comprises a carbamate bond (i.e., —O—C(O)—NR—, wherein R is hydrogen or alkyl or the like).

In some embodiments, the structure and sequence of the cleavable bond in $L^D$ can be such that the bond is cleaved by the action of enzymes present at the target site. In some embodiments, the cleavable bond can be cleavable by other mechanisms.

In some embodiments, the structure and sequence of the cleavable bonds in $L^D$ can be such that the bonds are cleaved by the action of enzymes present at the target site. In some embodiments, the cleavable bonds can be cleavable by other mechanisms.

In some embodiments, the cleavable bond(s) can be enzymatically cleaved by one or more enzymes, including a tumor-associated protease, to liberate the Drug unit or D, wherein the conjugate of the present disclosure, or intermediate, or scaffold thereof, is protonated in vivo upon release to provide a Drug unit or D.

In some embodiments, each $L^D$ independent is

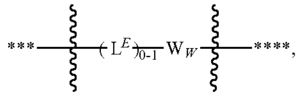

wherein:

$L^E$, when present, is $—NH—[(CH_2CH_2O)_p—(CH_2)_{0-2}]_q—C(O)—$, $—NH—(C_1\text{-}C_6\text{ alkyl})\text{-}O—C(O)—$, or $—NH—[(CH_2CH_2O)_p—(CH_2)_{0-2}]_q—C(O)—NH—(C_1\text{-}C_6\text{ alkyl})\text{-}O—C(O)—$, wherein p is an integer ranging from about 1 to about 20, and q is an integer ranging from about 1 to about 10;

each W independently is a natural or unnatural amino acid unit;

w is an integer ranging from about 0 to about 12;

*** denotes attachment to $M^A$ when $M^A$ is present, or to $A^1$ when $M^A$ is absent; and

**** denotes attachment to D.

In some embodiments, each $L^D$ independent is

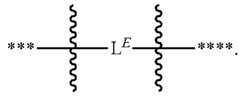

In some embodiments, each $L^D$ independent is

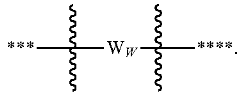

In some embodiments, each $L^D$ independent is

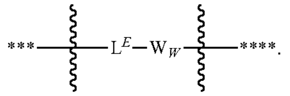

In some embodiments, $L^E$ comprises at least one PEG unit.

In some embodiments, the PEG unit comprises at least 1 subunit, at least 2 subunits, at least 3 subunits, at least 4 subunits, at least 5 subunits, or at least 6 subunits. In some embodiments, the PEG unit comprises at least 4 subunits, at least 3 subunits, at least 2 subunits, or at least 1 subunit. In some embodiments, the PEG unit comprises at least 1 subunit. In some embodiments, the PEG unit comprises at least 2 subunits.

In some embodiments, p is an integer ranging from about 1 to about 15, from about 1 to about 10, from about 1 to about 9, from about 1 to about 8, from about 1 to about 7, from about 1 to about 6, or from about 1 to about 5.

In some embodiments, p is an integer ranging from about 1 to about 6. In some embodiments, p is an integer ranging from about 1 to about 4. In some embodiments, p is an integer ranging from about 1 to about 2.

In some embodiments, p is 2.

In some embodiments, q is an integer ranging from about 1 to about 15, from about 1 to about 10, from about 1 to about 9, from about 1 to about 8, from about 1 to about 7, from about 1 to about 6, or from about 1 to about 5.

In some embodiments, q is 1, 2, 3, 4, or 5. In some embodiments, q is 2.

In some embodiments, $L^E$, when present, is —NH—$(CH_2CH_2O)_{1-4}$—$(CH_2)_2$—C(O)—. In some embodiments, $L^E$, when present, is —NH—$(CH_2CH_2O)_2$—$(CH_2)_2$—C(O)—. In some embodiments, $L^E$, when present, is —NH—$(CH_2CH_2O)_3$—$(CH_2)_{0-2}$—C(O)—. In some embodiments, $L^E$, when present, is —NH—$(CH_2CH_2O)_3$—$(CH_2)_1$—C(O)—. In some embodiments, $L^E$, when present, is —NH—$(CH_2CH_2O)_3$—$(CH_2)_2$—C(O)—. In some embodiments, $L^E$, when present, is —NH—$CH_2CH_2O$—$(CH_2)_{0-2}$—C(O)—. In some embodiments, $L^E$, when present, is —NH—$CH_2CH_2O$—C(O)—. In some embodiments, $L^E$, when present, is —NH—($C_1$-$C_6$ alkyl)-O—C(O)—. In some embodiments, $L^E$, when present, is —NH—$CH_2$—CH($CH_3$)—O—C(O)—. In some embodiments, $L^E$, when present, is —NH—[$(CH_2CH_2O)_{1-4}$—$(CH_2)_2$—C(O)—NH—($C_1$-$C_6$ alkyl)-O—C(O)—. In some embodiments, $L^E$, when present, is —NH—$CH_2CH_2O$—$(CH_2)_2$—C(O)—NH—$(CH_2)_2$—O—C(O)—.

In some embodiments, w is an integer ranging from about 1 to about 12 (e.g., 1 to 6, or 1 to 4, or 1 to 3, or 1, 2, 3, 4, 5, 6, 7, 8, 9, 10, 11, or 12).

In some embodiments, w is 0, 1, 2, 3, 4, or 5. In some embodiments, w is 1, 2, 3, 4, or 5.

In some embodiments, w is 1. In some embodiments, w is 2. In some embodiments, w is 3.

In some embodiments, each W independently is a natural or unnatural amino acid and/or a D or L isomer.

In some embodiments, each W independently is an alpha, beta, or gamma amino acid that is natural or non-natural.

In some embodiments, at least one W is a natural amino acid. In some embodiments, at least one W is a non-natural amino acid.

In some embodiments, $W_w$ does not comprise natural amino acids. In some embodiments, $W_w$ does not comprise non-natural amino acids.

In some embodiments, $W_w$ comprises a natural amino acid linked to a non-natural amino acid. In some embodiments, $W_w$ comprises a natural amino acid linked to a D-isomer of a natural amino acid.

In some embodiments, $W_w$ is a dipeptide, e.g., -Val-Cit-, -Phe-Lys-, -Val-Ala- or Glu-Ala.

In some embodiments, $W_w$ is a monopeptide, a dipeptide, a tripeptide, a tetrapeptide, a pentapeptide, a hexapeptide, a heptapeptide, an octapeptide, a nonapeptide, a decapeptide, an undecapeptide, or a dodecapeptide unit.

In some embodiments, $W_w$ is a peptide (e.g., a peptide of 1 to 12 amino acids), which is conjugated directly to D. In some embodiments, the peptide is a single amino acid. In some embodiments, the peptide is a dipeptide. In some embodiments, the peptide is a tripeptide.

In some embodiments, each amino acid in $W_w$ is independently selected from alanine, 3-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In some embodiments, each amino acid in $W_w$ is independently selected from alanine, 3-alanine, arginine, aspartic acid, asparagine, histidine, glycine, glutamic acid, glutamine, phenylalanine, lysine, leucine, serine, tyrosine, threonine, isoleucine, proline, tryptophan, valine, citrulline, and derivatives thereof.

In some embodiments, each amino acid in $W_w$ is independently selected from the proteinogenic and the non-proteinogenic amino acids.

In some embodiments, each amino acid in $W_w$ is independently selected from L or D isomers of the following amino acids: alanine, β-alanine, arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, valine, citrulline, and derivatives thereof.

In some embodiments, each amino acid in $W_w$ is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, citrulline, or alanine.

In some embodiments, each amino acid in $W_w$ is independently selected from L-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline, and valine.

In some embodiments, each amino acid in $W_w$ is independently selected from D-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline, and valine.

In some embodiments, each amino acid in $W_w$ is alanine, β-alanine, glycine, glutamic acid, isoglutamic acid, isoaspartic acid, valine citrulline, or aspartic acid.

In some embodiments, $W_w$ comprises β-alanine. In some embodiments, W comprises (β-alanine)-(alanine). In some embodiments, $W_w$ comprises (β-alanine) and optionally glutamic acid, isoglutamic acid, aspartic acid, isoaspartic acid, valine, (valine)-(alanine), (alanine)-(alanine), or (valine)-(citruline).

In some embodiments, $W_w$ comprises (glutamic acid)-(alanine).

In some embodiments, $W_w$ comprises glutamic acid and optionally alanine, glycine, isoglutamic acid, aspartic acid, isoaspartic acid, valine, (valine)-(alanine), (alanine)-(alanine), or (valine)-(citruline).

In some embodiments, $W_w$ comprises 2,3-diaminopropanoic acid. In some embodiments, $W_w$ comprises (R)-2,3-diaminopropanoic acid. In some embodiments, $W_w$ comprises glutamic acid. In some embodiments, $W_w$ comprises (glutamic acid)-(alanine). In some embodiments, $W_w$ comprises (glutamic acid)-(glycine)-(alanine).

In some embodiments, $W_w$ comprises L-glutamic acid, D-glutamic acid, (L-glutamic acid)-(L-alanine), (L-glutamic acid)-(D-alanine), (D-glutamic acid)-(L-alanine), (D-glutamic acid)-(D-alanine), (L-glutamic acid)-(glycine)-(L-alanine), D-glutamic acid)-(glycine)-(D-alanine), (L-glutamic acid)-(glycine)-(D-alanine), or (D-glutamic acid)-(glycine)-(L-alanine).

In some embodiments, $W_w$ comprises a carbamate bond in addition to one or more amino acids.

In some embodiments, $L^D$ (e.g., $W_w$) is selective for enzymatic cleavage (e.g., by a particular enzyme). In some embodiments, the particular enzyme is a tumor-associated protease.

In some embodiments, $L^D$ (e.g., $W_w$) comprises a bond whose cleavage is catalyzed by cathepsin B, cathepsin C, cathepsin D, or a plasmin protease.

In some embodiments, $L^D$ comprises a sugar cleavage site.

In some embodiments, $L^D$ comprises a sugar moiety (Su) linked via an oxygen glycosidic bond to a self-immolative group.

In some embodiments, a "self-immolative group" can be a tri-functional chemical moiety that is capable of covalently linking together three spaced chemical moieties (i.e., the sugar moiety (via a glycosidic bond), a drug unit (directly or indirectly), and $M^A$ (directly or indirectly) when $M^A$ is present or $A^1$ when $M^A$ is absent.

In some embodiments, the glycosidic bond can be cleaved at the target site to initiate a self-immolative reaction sequence that leads to a release of the drug.

In some embodiments, each $L^D$, when present, independently is:

(1)

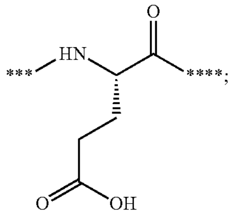

(2)

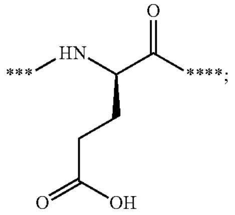

(3)

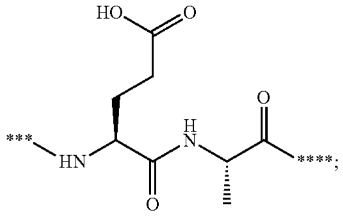

(4)

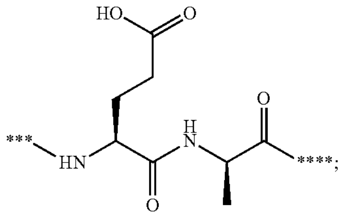

(5)

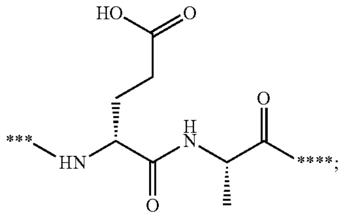

-continued (6)

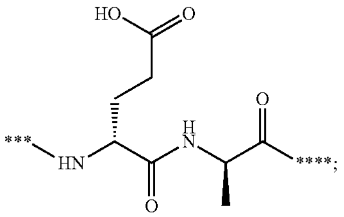

(7)

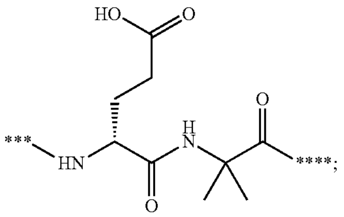

(8)

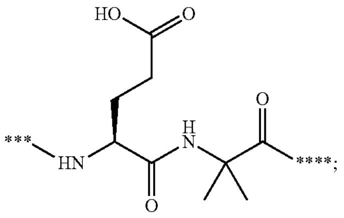

(9)

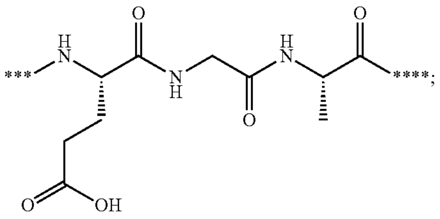

(10)

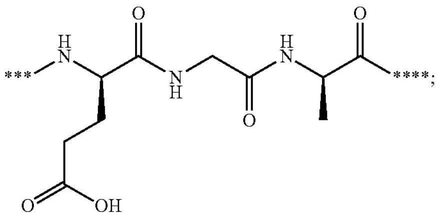

(11)

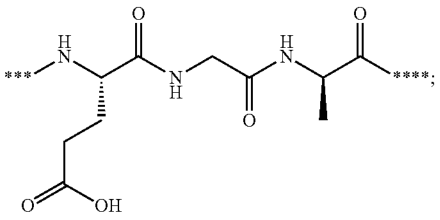

(12)

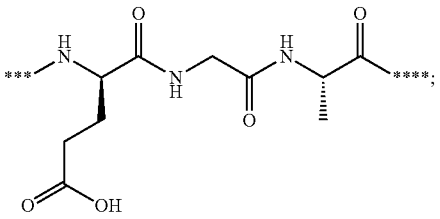

-continued
(13)
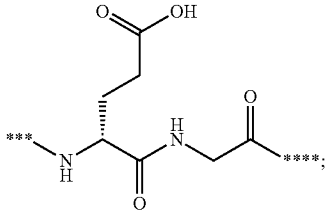
(14)
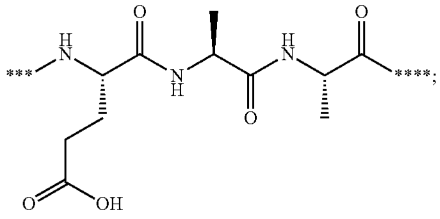
(15)
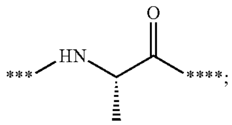
(16)
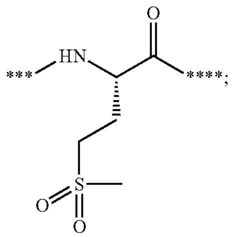
(17)
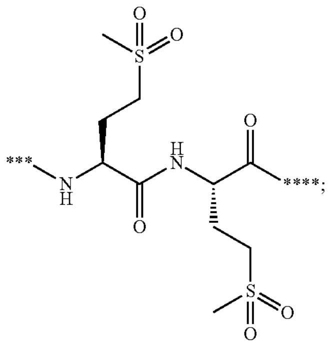
(18)
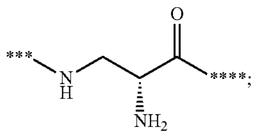
(19)
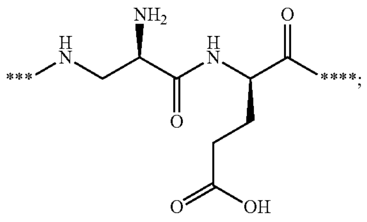
-continued
(20)
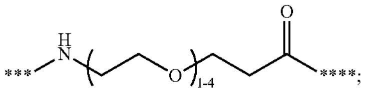
(21)
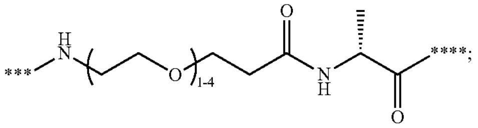
(22)
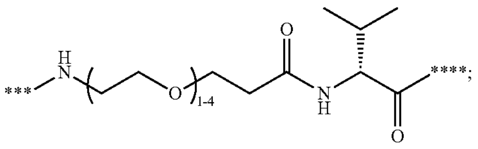
(23)
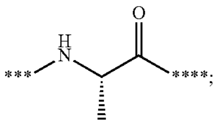
(24)
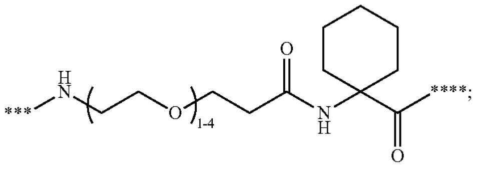
(25)
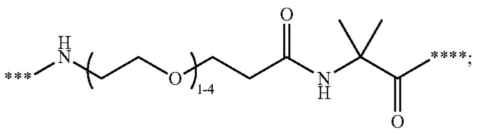
(26)
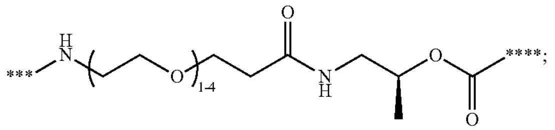
(27)
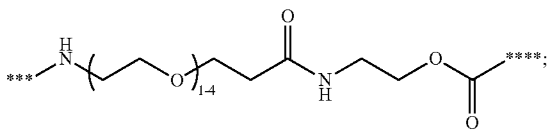
(28)
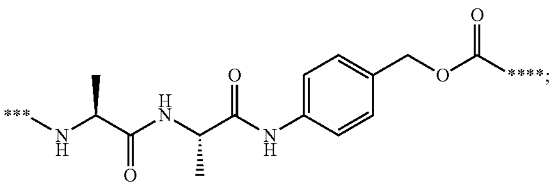
(29)
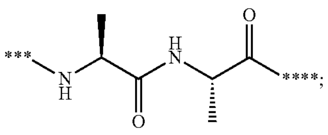

-continued (30)

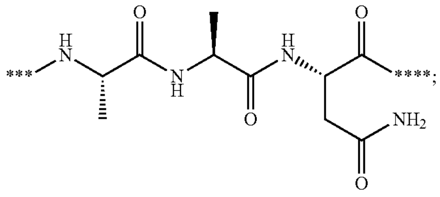

(31)

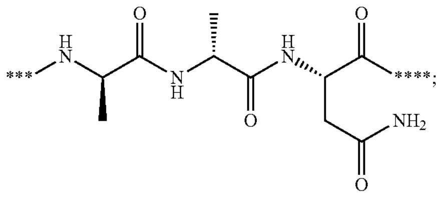

(32)

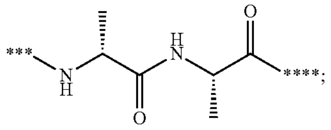

(33)

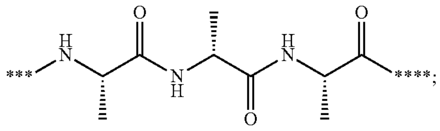

(34)

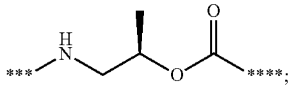

or (35)

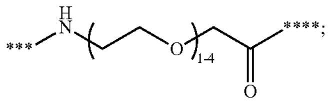

wherein: * denotes attachment to $M^A$, when $M^A$ is present, or to $A^1$ when $M^A$ is absent; and ** denotes attachment to D.

In some embodiments, each $L^D$, when present, independently is:

(1)

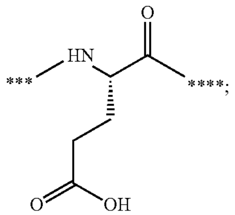

(2)

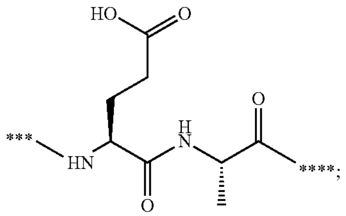

-continued (3)

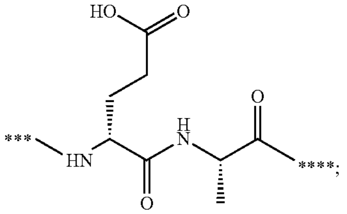

(4)

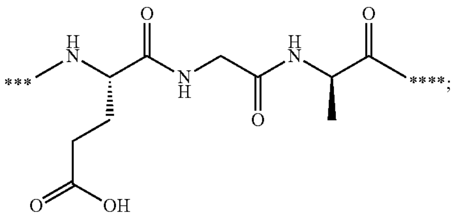

(5)

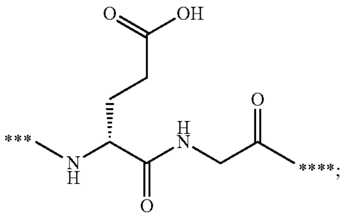

(6)

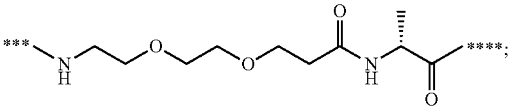

or (7)

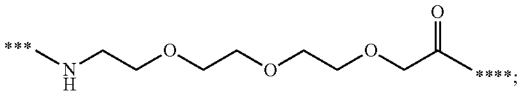

wherein: * denotes attachment to $M^A$ when $M^A$ is present, or to $A^1$ when $M^A$ is absent; and ** denotes attachment to D.

In some embodiments, each $L^D$, when present, independently is:

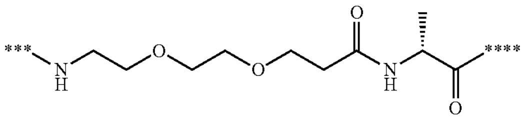

wherein: * denotes attachment to $M^A$ and ** denotes attachment to D.

Variable $M^A$

In some embodiments, $M^A$ comprises a peptide moiety of at least two amino acids.

In some embodiments, amino acid is referred to herein as "AA" and amino acids as "AA's".

In some embodiments, $M^A$ is a moiety that is capable of forming a covalent bond with a -$L^D$-D unit and allows for the attachment of multiple drug.

In some embodiments, $M^A$ comprises a single AA unit or has two or more AA units (e.g., from 2 to 10, from 2 to 6, or 2, 3, 4, 5 or 6) wherein the AA units are each independently a natural or non-natural amino acid, an amino alcohol, an amino aldehyde, a diamine, a polyamine, or combinations thereof.

In some embodiments, in order to have the requisite number of attachments, at least one of the AA units will have a functionalized side chain to provide for attachment of the -$L^D$-D unit. In some embodiments, exemplary functionalized AA units (e.g., amino acids, amino alcohols, or amino aldehydes) include, for example, azido or alkyne functionalized AA units (e.g., amino acid, amino alcohol, or amino aldehyde modified to have an azide group or alkyne group).

In some embodiments, $M^A$ comprises 2 to 12 AA units. In some embodiments, $M^A$ comprises 2 to 10 AA units. In some embodiments, $M^A$ comprises 2 to 6 AA units. In some embodiments, $M^A$ comprises 2, 3, 4, 5 or 6 AA units.

In some embodiments, $M^A$ has 2 AA units. In some embodiments, the peptide moiety has 3 AA units. In some embodiments, the peptide moiety has 4 AA units. In some embodiments, the peptide moiety has 5 AA units. In some embodiments, the peptide moiety has 6 AA units.

In some embodiments, attachment within $M^A$ or with the other components of the conjugate, intermediate thereof, or scaffold, can be, for example, via amino, carboxy, or other functionalities.

In some embodiments, each amino acid in $M^A$ can be independently D or L isomer of a thiol containing amino acid. In some embodiments, each amino acid in $M^A$ can be independently a D isomer of a thiol containing amino acid. In some embodiments, each amino acid in $M^A$ can be independently an L isomer of a thiol containing amino acid. In some embodiments, the thiol containing amino acid can be, for example, cysteine, homocysteine, or penicillamine.

In some embodiments, each amino acid in $M^A$ can be independently the L or D isomer of the following amino acids: alanine (including β-alanine), arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, stereoisomers thereof, or derivatives thereof.

In some embodiments, each amino acid in $M^A$ is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, alanine, or a stereoisomers thereof.

In some embodiments, $M^A$ comprises a monopeptide, a dipeptide, tripeptide, tetrapeptide, or pentapeptide. In some embodiments, $M^A$ comprises a pentapeptide.

In some embodiments, $M^A$ comprises at least about five amino acids (e.g., 5, 6, 7, 8, 9, or 10 amino acids). In some embodiments, $M^A$ comprises at most about ten amino acids.

In some embodiments, each amino acid in $M^A$ independently is glycine, serine, glutamic acid, lysine, aspartic acid, and cysteine.

In some embodiments, $M^A$ comprises at least four glycines and at least one glutamic acid e.g., $(glycine)_4$ and glutamic acid, wherein the glutamic acid is at any position along the peptide chain, such as, for example, (glutamic acid)-$(glycine)_4$; (glycine)-(glutamic acid)-$(glycine)_3$; $(glycine)_2$-(glutamic acid)-$(glycine)_2$; $(glycine)_3$-(glutamic acid)-(glycine); or $(glycine)_4$-(glutamic acid).

In some embodiments, $M^A$ comprises $(glycine)_4$-(glutamic acid). In some embodiments, the peptide moiety comprises (glutamic acid)-$(glycine)_4$.

In some embodiments, $M^A$ comprises at least four glycines and at least one serine, e.g., $(glycine)_4$ and serine wherein the serine is at any position along the peptide chain, such as, for example, (serine)-$(glycine)_4$; (glycine)-(serine)-$(glycine)_3$; $(glycine)_2$-(serine)-$(glycine)_2$; $(glycine)_3$-(serine)-(glycine); or $(glycine)_4$-(serine).

In some embodiments, $M^A$ comprises $(glycine)_4$-(serine). In some embodiments, the peptide moiety comprises (serine)-$(glycine)_4$.

In some embodiments, $M^A$ comprises (β-alanine)-$(glycine)_4$-(serine) wherein the serine is at any position along the peptide chain, such as, for example, (β-alanine)-(serine)-$(glycine)_4$; (β-alanine)-(glycine)-(serine)-$(glycine)_3$; (β-alanine)-$(glycine)_2$-(serine)-$(glycine)_2$; (β-alanine)-$(glycine)_3$-(serine)-(glycine); or (β-alanine)-$(glycine)_4$-(serine).

In some embodiments, $M^A$ comprises $(glycine)_4$-(serine)-(glutamic acid) wherein the serine is at any position along the peptide chain, such as, for example, (serine)-$(glycine)_4$-(glutamic acid); (glycine)-(serine)-$(glycine)_3$-(glutamic acid); $(glycine)_2$-(serine)-$(glycine)_2$-(glutamic acid); $(glycine)_3$-(serine)-(glycine)-(glutamic acid); or $(glycine)_4$-(serine)-(glutamic acid). In some embodiments, the peptide moiety comprises (β-alanine)-$(glycine)_4$-(serine)-(glutamic acid) wherein the serine is at any position along the peptide chain, such as, for example, (β-alanine)-(serine)-$(glycine)_4$-(glutamic acid); (β-alanine)-(glycine)-(serine)-$(glycine)_3$-(glutamic acid); (β-alanine)-$(glycine)_2$-(serine)-$(glycine)_2$-(glutamic acid); (β-alanine)-$(glycine)_3$-(serine)-(glycine)-(glutamic acid); or (β-alanine)-$(glycine)_4$-(serine)-(glutamic acid).

In some embodiments, $M^A$ comprises $(glycine)_4$-(serine). In some embodiments, the peptide moiety comprises (serine)-$(glycine)_4$.

In some embodiments, $M^A$ comprises (β-alanine)-$(glycine)_4$-(serine) wherein the serine is at any position along the peptide chain.

In some embodiments, $M^A$ comprises $(glycine)_4$-(serine)-(glutamic acid) wherein the serine is at any position along the peptide chain.

In some embodiments, $M^A$ comprises (β-alanine)-$(glycine)_4$-(serine)-(glutamic acid) wherein the serine is at any position along the peptide chain.

In some embodiments, $M^A$ comprises (glutamic acid)-$(glycine)_{1-4}$, wherein: the $M^A$ is attached to $A^1$ via one of the glutamic acid; $M^A$ is attached to $T^1$ via the glycine; and $M^A$ is attached to $L^D$ via the glutamic acid.

In some embodiments, $M^A$ comprises

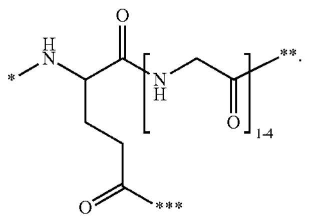

In some embodiments, $M^A$ comprises (glutamic acid)-$(glycine)_4$, wherein: the $M^A$ is attached to $A^1$ via the glutamic acid; $M^A$ is attached to $T^1$ via one of the glycine; and $M^A$ is attached to $L^D$ via the glutamic acid.

In some embodiments, $M^A$ comprises

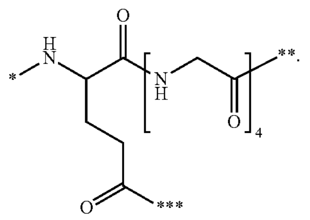

In some embodiments, $M^A$ comprises (glutamic acid)-(glycine), wherein: the $M^A$ is attached to $A^1$ via the glutamic acid; $M^A$ is attached to $T^1$ via the glycine; and $M^A$ is attached to $L^D$ via the glutamic acid.

In some embodiments, the peptide moiety comprises

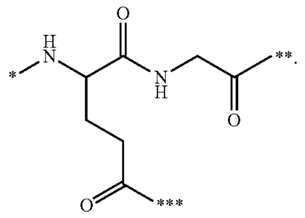

In some embodiments, $M^A$ comprises $(glycine)_{1-4}$-(glutamic acid), wherein $M^A$ is attached to $A^1$ via one of the glycine; $M^A$ is attached to $T^1$ via the glutamic acid; and $M^A$ is attached to $L^D$ via the glutamic acid.

In some embodiments, $M^A$ comprises

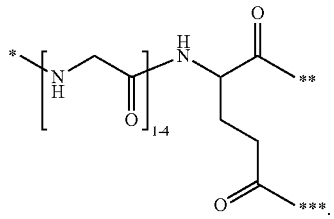

In some embodiments, $M^A$ comprises $(glycine)_4$-(glutamic acid), wherein: $M^A$ is attached to $A^1$ via the glutamic acid; $M^A$ is attached to $T^1$ via the glycine; and $M^A$ is attached to $L^D$ via the glutamic acid.

In some embodiments, $M^A$ comprises

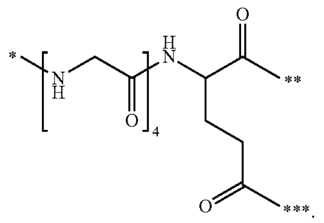

In some embodiments, $M^A$ comprises (glycine)-(glutamic acid), wherein: $M^A$ is attached to $A^1$ via the glycine; $M^A$ is attached to $T^1$ via the glutamic acid; and the $M^A$ is attached to $L^D$ via the glutamic acid.

In some embodiments, $M^A$ comprises

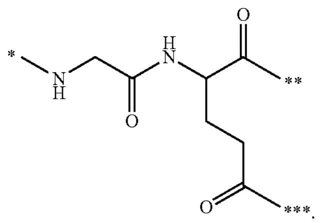

In some embodiments, $M^A$ comprises $(glycine)_{1-4}$-(serine), wherein: $M^A$ is attached to $A^1$ via one of the glycine; $M^A$ is attached to $T^1$ via the serine; and $M^A$ is attached to $L^D$ via the serine.

In some embodiments, $M^A$ comprises

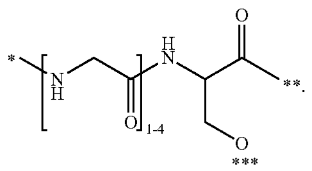

In some embodiments, $M^A$ comprises (glycine)-(serine), wherein: $M^A$ is attached to $A^1$ via the glycine; $M^A$ is attached to $T^1$ via the serine; and $M^A$ is attached to $L^D$ via the serine.

In some embodiments, $M^A$ comprises

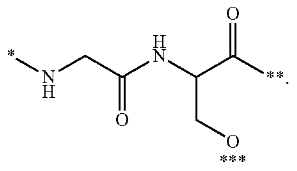

In some embodiments, $M^A$ comprises $(glycine)_4$-(serine), wherein: $M^A$ is attached to $A^1$ via one of the glycine; $M^A$ is attached to $T^1$ via the serine; and $M^A$ is attached to $L^D$ via the serine.

In some embodiments, $M^A$ comprises

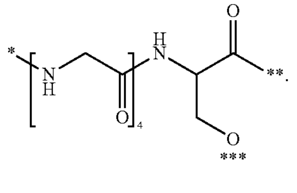

In some embodiments, $M^A$ comprises (serine)-$(glycine)_{1-4}$, wherein: $M^A$ is attached to $A^1$ via the serine; $M^A$ is attached to $T^1$ via one of the glycine; and $M^A$ is attached to $L^D$ via the serine.

In some embodiments, $M^A$ Comprises

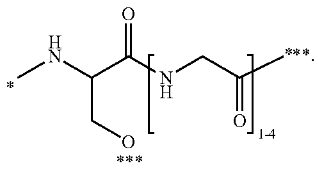

In some embodiments, $M^A$ comprises (serine)-(glycine)$_4$, wherein: $M^A$ is attached to $A^1$ via the serine; $M^A$ is attached to $T^1$ via one of the glycine; and $M^A$ is attached to $L^D$ via the serine.

In some embodiments, $M^A$ comprises

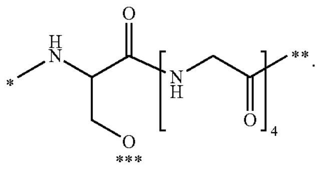

In some embodiments, $M^A$ comprises (serine)-(glycine), wherein: $M^A$ is attached to $A^1$ via the serine; $M^A$ is attached to $T^1$ via one of the glycine; and $M^A$ is attached to $L^D$ via the serine.

In some embodiments, $M^A$ comprises

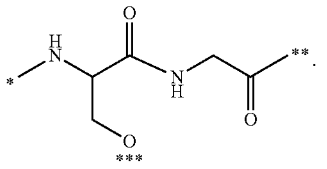

In some embodiments, $M^A$ comprises (β-alanine)-(glycine)$_{1-4}$-(serine), wherein: $M^A$ is attached to $A^1$ via the ρ-alanine; $M^A$ is attached to $T^1$ via the serine; and $M^A$ is attached to $L^D$ via the serine.

In some embodiments, $M^A$ comprises

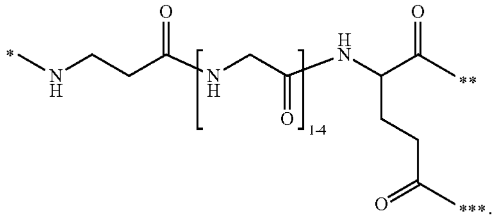

In some embodiments, $M^A$ comprises (β-alanine)-(glycine)$_4$-(serine), wherein: $M^A$ is attached to $A^1$ via the β-alanine; $M^A$ is attached to $T^1$ via the serine; and $M^A$ is attached to $L^D$ via the serine.

In some embodiments, $M^A$ comprises

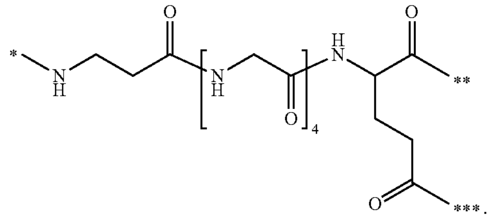

In some embodiments, the peptide moiety comprises (β-alanine)-(glycine)-(glutamic acid), wherein: the peptide moiety is attached to $L^3$ when present, or to $L^M$ when $L^3$ is absent, via the ρ-alanine; the peptide moiety is attached to $T^1$ when present, via the glutamic acid; and the peptide moiety is attached to $L^D$ when present, via the glutamic acid.

In some embodiments, the peptide moiety comprises

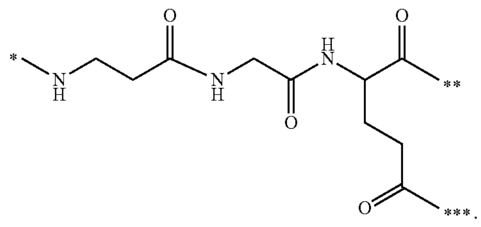 [SMILES: CNCCC(=O)NCC(=O)NC(CCC(C)=O)C(C)=O]

It is understood that for embodiments of $M^A$, * indicates attachment to $A^1$,  indicates attachment to $T^1$, and * indicates attachment to $L^D$.

Hydrophilic Group (Variable $T^1$)

In some embodiments, the hydrophilic group included in the conjugates or scaffolds of the disclosure is a water-soluble and substantially non-antigenic polymer. Examples of the hydrophilic group, include, but are not limited to, polyalcohols, polyethers, polyanions, polycations, polyphosphoric acids, polyamines, polysaccharides, polyhydroxy compounds, polylysines, and derivatives thereof. In some embodiments, one end of the hydrophilic group can be functionalized so that it can be covalently attached to the $M^A$ linker (e.g., to an amino acid in the $M^A$ linker) by means of a non-cleavable linkage or via a cleavable linkage. In some embodiments, functionalization can be, for example, via an amine, thiol, NHS ester, maleimide, alkyne, azide, carbonyl, or other functional group. In some embodiments, the other terminus (or termini) of the hydrophilic group will be free and untethered. In some embodiments, by "untethered", it is meant that the hydrophilic group will not be attached to another moiety, such as D or a Drug Unit, or other components of the conjugates or scaffolds of the disclosure. In some embodiments, the free and untethered end of the hydrophilic group may include a methoxy, carboxylic acid, alcohol or other suitable functional group. In some embodiments, the methoxy, carboxylic acid, alcohol, or other suitable functional group acts as a cap for the terminus or termini of the hydrophilic group.

In some embodiments, a cleavable linkage refers to a linkage that is not substantially sensitive to cleavage while circulating in the plasma but is sensitive to cleavage in an intracellular or intratumoral environment. In some embodiments, a non-cleavable linkage is one that is not substantially sensitive to cleavage in any biological environment. In some embodiments, chemical hydrolysis of a hydrazone, reduction of a disulfide, and enzymatic cleavage of a peptide bond or glycosidic linkage are examples of cleavable linkages. In some embodiments, exemplary attachments of the hydrophilic group are via amide linkages, ether linkages, ester linkages, hydrazone linkages, oxime linkages, disulfide linkages, peptide linkages, or triazole linkages. In some embodiments, the attachment of the hydrophilic group to the $M^A$ linker (e.g., to an amino acid in the $M^A$ linker) is via an amide linkage.

In some embodiments wherein the conjugate or scaffold of the disclosure comprises more than one hydrophilic groups, the multiple hydrophilic groups may be the same or different chemical moieties (e.g., hydrophilic groups of different molecular weight, number of subunits, or chemical structure). In some embodiments, the multiple hydrophilic groups can be attached to the $M^A$ linker at a single attachment site or different sites.

In some embodiments, the addition of the hydrophilic group may have two potential impacts upon the pharmacokinetics of the resulting conjugate. In some embodiments, the desired impact is the decrease in clearance (and consequent in increase in exposure) that arises from the reduction in non-specific interactions induced by the exposed hydrophobic elements of the drug or drug-linker. In some embodiments, the undesired impact is the decrease in volume and rate of distribution that may arise from the increase in the molecular weight of the conjugate. In some embodiments, increasing the molecular weight of the hydrophilic group increases the hydrodynamic radius of a conjugate, resulting in decreased diffusivity that may diminish the ability of the conjugate to penetrate into a tumor. Because of these two competing pharmacokinetic effects, it may be desirable to use a hydrophilic group that is sufficiently large to decrease the conjugate clearance thus increasing plasma exposure, but not so large as to greatly diminish its diffusivity, which may reduce the ability of the conjugate to reach the intended target cell population.

In some embodiments, the hydrophilic group, includes, but is not limited to, a sugar alcohol (also known as polyalcohol, polyhydric alcohol, alditol or glycitol, such as inositol, glycerol, erythritol, threitol, arabitol, xylitol, ribitol, galactitol, mannitol, sorbitol, and the like) or a derivative thereof (e.g., amino polyalcohol), carbohydrate (e.g., a saccharide), a polyvinyl alcohol, a carbohydrate-based polymer (e.g., dextrans), a hydroxypropylmethacrylamide (HPMA), a polyalkylene oxide, and/or a copolymer thereof.

In some embodiments, $T^1$ comprises a plurality of hydroxyl ("—OH") groups, such as moieties that incorporate monosaccharides, oligosaccharides, polysaccharides, and the like.

In some embodiments, $T^1$ comprises a plurality of —$(CR_{58}OH)$— groups, wherein $R^{58}$ is —H or $C_{1-8}$ alkyl.

In some embodiments, $T^1$ is —OH or

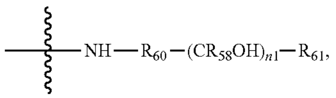

wherein:

$n_1$ is an integer from 0 to about 6;

each $R_{58}$ is independently —H or $C_{1-8}$ alkyl;

$R_{60}$ is a bond, a $C_{1-6}$ alkyl linker, or —$CHR_{59}$— wherein $R_{59}$ is —H, $C_{1-8}$ alkyl, cycloalkyl, or arylalkyl;

$R_{61}$ is $CH_2OR_{62}$, $COOR_{62}$, —$(CH_2)_{n2}COOR_{62}$, or a heterocycloalkyl substituted with one or more hydroxyl;

$R_{62}$ is —H or $C_{1-8}$ alkyl; and $n_2$ is an integer from 1 to about 5.

In some embodiments, $T^1$ is —OH. In some embodiments, $T^1$ is

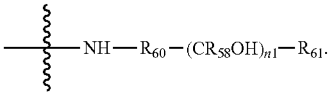

In some embodiments, $R_{58}$ is —H; $R_{60}$ is a bond or a $C_{1-6}$ alkyl linker; $n_1$ is an integer from 1 to about 6; and $R_{61}$ is $CH_2OH$ or COOH.

In some embodiments, $R_{58}$ is —H; $R_{60}$ is —$CHR_{59}$—; $n_1$ is 0; and $R_{61}$ is a heterocycloalkyl substituted with one or more hydroxyl, e.g., a monosaccharide.

In some embodiments, $T^1$ comprises a glucosyl-amine, a di-amine, or a tri-amine.

In some embodiments, $T^1$ comprises one or more of the following fragments or a stereoisomer thereof:

(1)

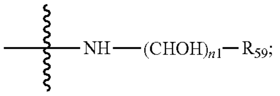

(2)

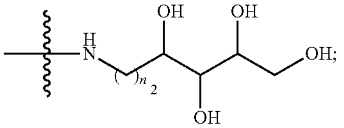

(3)

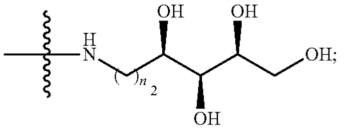

(4)

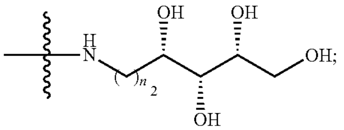

(5)

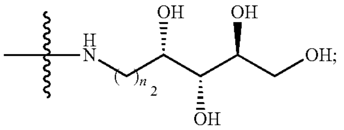

(6)

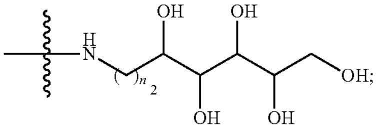

(7)

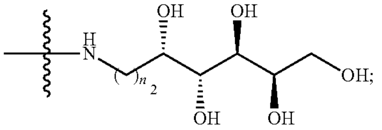

(8)

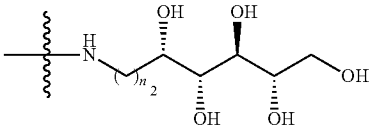

-continued (9)

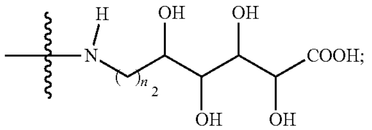

(10)

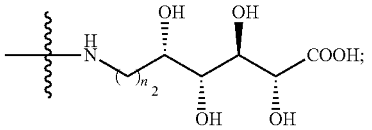

(11)

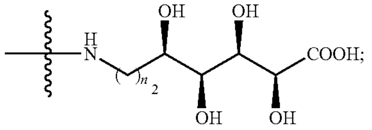

(12)

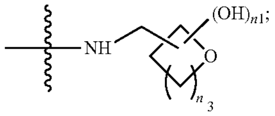

(13)

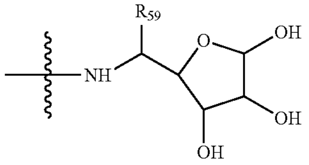

(14)

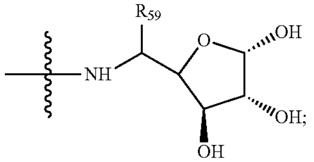

(15)

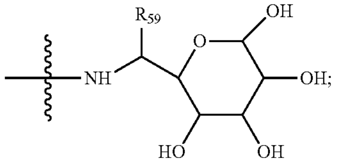

(16)

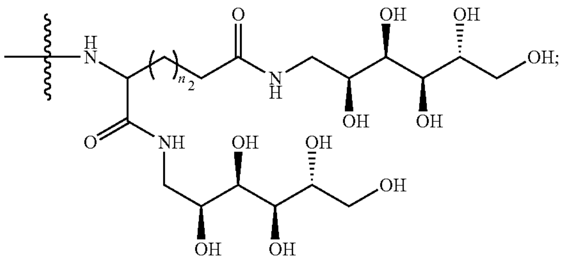

-continued (17)

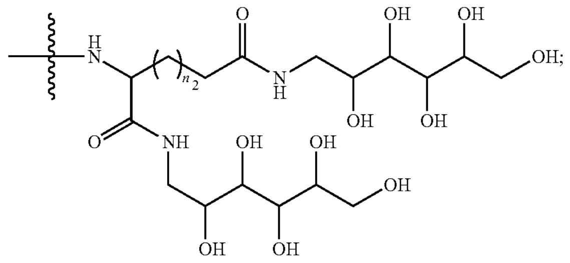

(18)

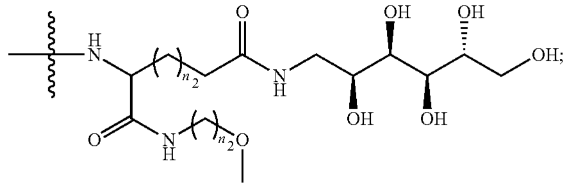

(19)

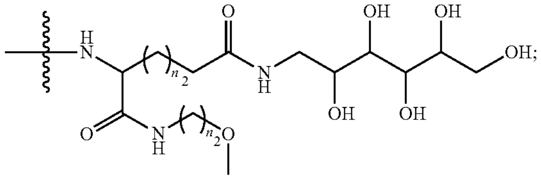

or (20)

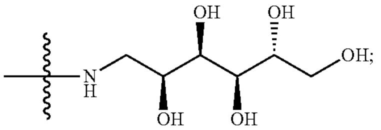

wherein: $R^{59}$ is —H, $C_{1-8}$ alkyl, cycloalkyl, or arylalkyl; $n_1$ is an integer from 1 to about 6; $n_2$ is an integer from 1 to about 5; and $n_3$ is an integer from about 1 to about 3.

It is understood that all stereochemical forms of the hydrophilic groups are contemplated herein. For example, in the above formula, the hydrophilic group may be derived from ribose, xylose, glucose, mannose, galactose, or other sugar and retain the stereochemical arrangements of pendant hydroxyl and alkyl groups present on those molecules.

It is to be understood that in the foregoing formulae, various deoxy compounds are also contemplated. Illustratively, one or more of the following features are contemplated for the hydrophilic groups when applicable.

In some embodiments, $n_3$ is 2 or 3.

In some embodiments, $n_1$ is 1, 2, or 3.

In some embodiments, $n_2$ is 1.

In some embodiments, $R_{59}$ is hydrogen.

In some embodiments, $T^1$ is

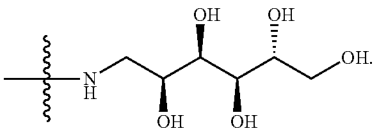 [SMILES: *NC[C@H](O)[C@@H](O)[C@H](O)[C@H](O)CO]

In some embodiments, $T^1$ is
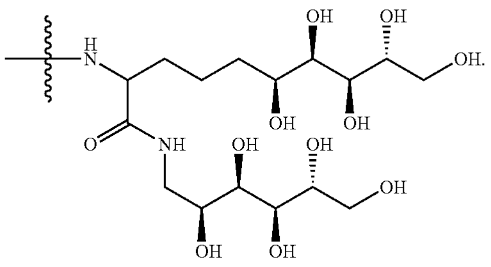 [SMILES: *NC(CCC[C@H](O)[C@@H](O)[C@H](O)[C@H](O)CO)C(=O)NC[C@H](O)[C@@H](O)[C@H](O)[C@H](O)CO]
In some embodiments, $T^1$ is
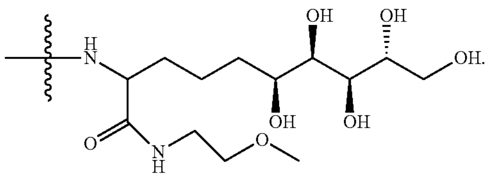 [SMILES: *NC(CCC[C@H](O)[C@@H](O)[C@H](O)[C@H](O)CO)C(=O)NCCOC]
In some embodiments, $T^1$ is
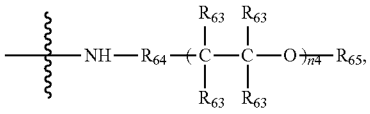
wherein
$n_4$ is an integer from 1 to about 25;
each $R_{63}$ is independently —H or $C_{1-8}$ alkyl;
$R_{64}$ is a bond or a $C_{1-8}$ alkyl linker;
$R_{65}$ is —H, $C_{1-8}$ alkyl, $-(CH_2)_{n2}COOR_{62}$, or $-(CH_2)_{n2}COR_{66}$;
$R_{62}$ is H or $C_{1-8}$ alkyl;
$R_{66}$ is H,
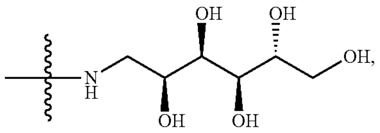
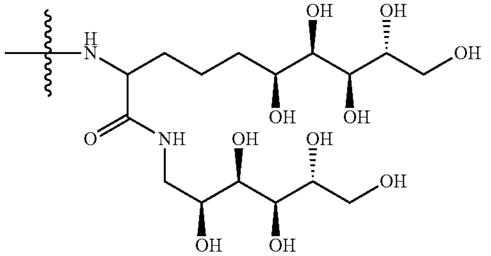
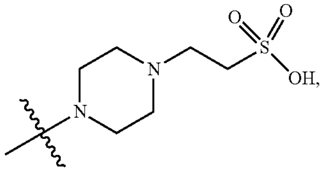
-continued
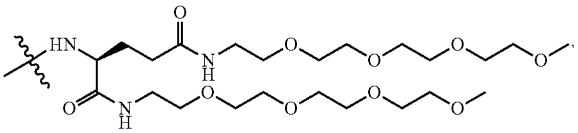
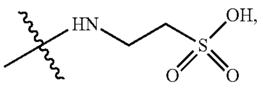
or
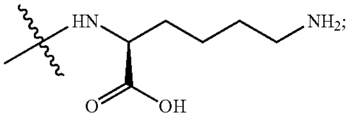
and
$n_2$ is an integer from 1 to about 5.
In some embodiments, $T^1$ is:
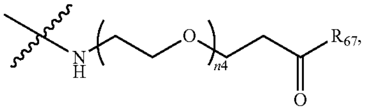
wherein $R_{67}$ is: (1) —OH;
(2)
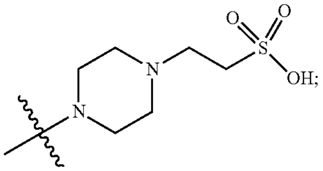
(3)
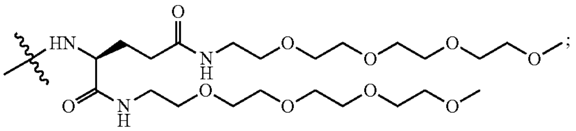
(4)
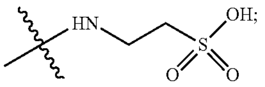
(5)
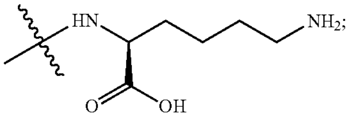
(6)
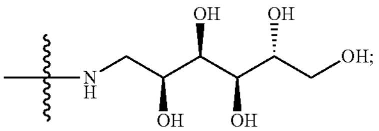
or -continued (7)

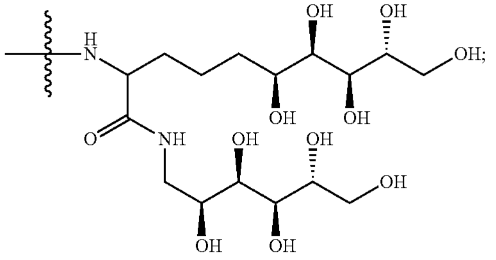

wherein $n_4$ is an integer from about 2 to about 20, from about 4 to about 16, from about 6 to about 12, from about 8 to about 12.

In some embodiments, $T^1$ is

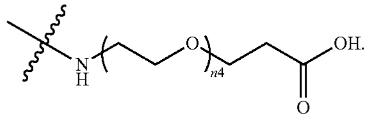

In some embodiments, $n_4$ is an integer from about 2 to about 20, from about 4 to about 16, from about 6 to about 12, from about 8 to about 12.

In some embodiments, $n_4$ is 6, 7, 8, 9, 10, 11, or 12.

In some embodiments, $n_4$ is 8 or 12.

In some embodiments, $T^1$ is

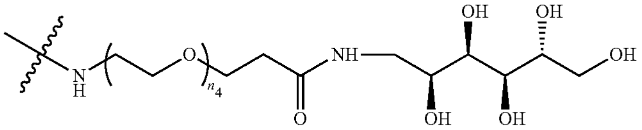

or

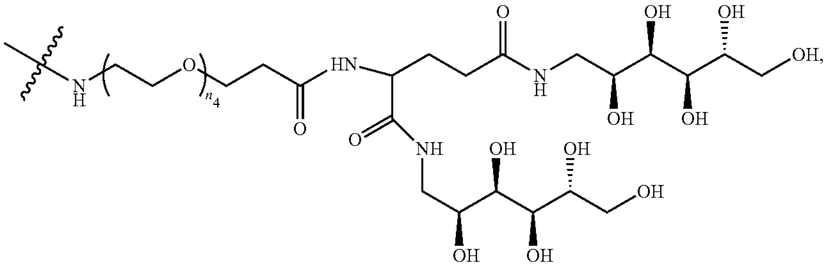

wherein $n_4$ is an integer from about 2 to about 24, from about 4 to about 16, from about 6 to about 12, from about 8 to about 12.

In some embodiments, $n_4$ is 6, 7, 8, 9, 10, 11, or 12.

In some embodiments, $n_4$ is 8 or 12. In some embodiments, $n_4$ is 8.

In some embodiments, $T^1$ is

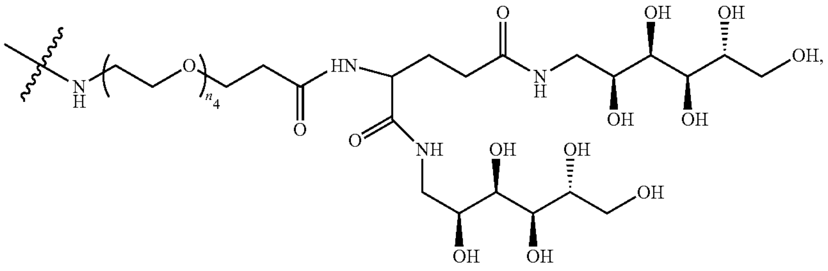

wherein $n_4$ is 8.

In some embodiments, $T^1$ comprises a polyether, e.g., a polyalkylene glycol (PAO). PAO includes but is not limited to, polymers of lower alkylene oxides, in particular polymers of ethylene oxide, such as, for example, propylene oxide, polypropylene glycols, polyethylene glycol (PEG), polyoxyethylenated polyols, copolymers thereof, and block copolymers thereof.

In some embodiments, the polyalkylene glycol is a polyethylene glycol (PEG) including, but not limited to, polydisperse PEG, monodisperse PEG, and discrete PEG. Polydisperse PEGs are a heterogeneous mixture of sizes and molecular weights whereas monodisperse PEGs are typically purified from heterogeneous mixtures and are therefore provide a single chain length and molecular weight. In some embodiments, the PEG units are discrete PEGs provide a single molecule with defined and specified chain length. In some embodiments, the polyethylene glycol is mPEG.

In some embodiments, $T^1$ comprises a PEG unit which comprises one or multiple PEG chains. The PEG chains can be linked together, for example, in a linear, branched or star shaped configuration. The PEG unit, in addition to comprising repeating PEG subunits, may also comprise non-PEG material (e.g., to facilitate coupling of multiple PEG chains to each other or to facilitate coupling to the amino acid). Non-PEG material refers to the atoms in the PEG chain that are not part of the repeating $—CH_2CH_2O—$ subunits. In some embodiments, the PEG chain can comprise two monomeric PEG chains linked to each other via non-PEG elements. In some embodiments, the PEG Unit can comprise two linear PEG chains attached to a central core that is attached to the amino acid (i.e., the PEG unit itself is branched).

The PEG unit may be covalently bound to the $M^A$ linker (e.g., to an amino acid in the $M^A$ linker) via a reactive group. Reactive groups are those to which an activated PEG molecule may be bound (e.g., a free amino or carboxyl group). In some embodiments, N-terminal amino acids and lysines (K) have a free amino group; and C-terminal amino acid residues have a free carboxyl group. Sulfhydryl groups (e.g., as found on cysteine residues) may also be used as a reactive group for attaching PEG.

In some embodiments, the PEG unit may be attached to the $M^A$ linker (e.g., to an amino acid in the $M^A$ linker) by using methoxylated PEG ("mPEG") having different reactive moieties, including, but not limited to, succinimidyl succinate (SS), succinimidyl carbonate (SC), mPEG-imidate, para-nitrophenylcarbonate (NPC), succinimidyl propionate (SPA), and cyanuric chloride. Examples of mPEGs include, but are not limited to, mPEG-succinimidyl succinate (mPEG-SS), $mPEG_2$-succinimidyl succinate ($mPEG_2$-SS), mPEG-succinimidyl carbonate (mPEG-SC), $mPEG_2$-succinimidyl carbonate ($mPEG_2$-SC), mPEG-imidate, mPEG-para-nitrophenylcarbonate (mPEG-NPC), mPEG-imidate, $mPEG_2$-para-nitrophenylcarbonate ($mPEG_2$-NPC), mPEG-succinimidyl propionate (mPEG-SPA), $mPEG_2$-succinimidyl propionate ($mPEG_2$-SPA), mPEG-N-hydroxy-succinimide (mPEG-NHS), $mPEG_2$-N-hydroxy-succinimide ($mPEG_2$-NHS), mPEG-cyanuric chloride, $mPEG_2$-cyanuric chloride, $mPEG_2$-Lysinol-NPC, and $mPEG_2$-Lys-NHS. A wide variety of PEG species can be used, and substantially any suitable reactive PEG reagent can be used. In some embodiments, the reactive PEG reagent will result in formation of a carbamate or amide bond upon attachment to the Multifunctional Linker or $M^A$ linker (e.g., to an amino acid in the $M^A$ linker). The reactive PEG reagents include, but are not limited to, $mPEG_2$-N-hydroxy-succinimide ($mPEG_2$-NHS), bifunctional PEG propionaldehyde ($mPEG_2$-ALD), multi-Arm PEG, maleimide-containing PEG ($mPEG(MAL)_2$, $mPEG_2(MAL)$), $mPEG-NH_2$, mPEG-succinimidyl propionate (mPEG-SPA), succinimide of mPEG butanoate acid (mPEG-SBA), mPEG-thioesters, mPEG-double Esters, mPEG-BTC, mPEG-ButyrALD, mPEG-acetaldehyde diethyl acetal (mPEG-ACET), heterofunctional PEGs (e.g., $NH_2$-PEG-COOH, Boc-PEG-NHS, Fmoc-PEG-NHS, NHS-PEG-vinylsulfone (NHS-PEG-VS), or NHS-PEG-MAL), PEG acrylates (ACRL-PEG-NHS), PEG-phospholipids (e.g., mPEG-DSPE), multi-armed PEGs of the SUNBRITE™ series including the glycerine-based PEGs activated by a chemistry chosen by those skilled in the art, any SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In some such embodiments, the PEG unit comprises no more than about 72 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, or at least 20 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, or at least 18 subunits.

In some embodiments, the PEG unit comprises at least 6 subunits, at least 7 subunits, at least 8 subunits, at least 9 subunits, at least 10 subunits, at least 11 subunits, or at least 12 subunits.

In some embodiments, the PEG unit comprises at least 8 subunits, at least 9 subunits, at least 10 subunits, at least 11 subunits, or at least 12 subunits.

In some embodiments, the PEG unit comprises at least 6 subunits, at least 7 subunits, or at least 8 subunits.

In some embodiments, a linear PEG unit is:

(i)

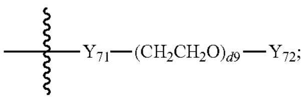

(ii)

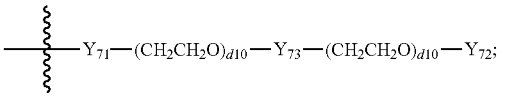

or (iii)

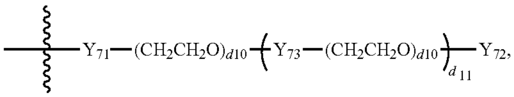

, wherein:

indicates site of attachment to the $M^A$ linker (e.g., to an amino acid in the $M^A$ linker);

$Y_{71}$ is a PEG attachment unit;

$Y_{72}$ is a PEG capping unit;

$Y_{73}$ is an PEG coupling unit (i.e., for coupling multiple PEG subunit chains together);

$d_9$ is an integer from 2 to 72;

each $d_{10}$ is independently an integer from 1 to 72; and $d_{11}$ is an integer from 2 to 5.

In some embodiments, $d_9$ is an integer from 2 to 24. In some embodiments, $d_9$ is an integer from 4 to 24. In some embodiments, $d_9$ is an integer from 6 to 24, from 8 to 24, from 10 to 24, or from 12 to 24.

In some embodiments, there are at least 6 PEG subunits in the PEG unit. In some embodiments, there are at least 8 PEG subunits in the PEG unit. In some embodiments, there are at least 10 PEG subunits in the PEG unit. In some embodiments, there are at least 12 PEG subunits in the PEG unit.

In some embodiments, $d_9$ is 8 or about 8, 12 or about 12, 24 or about 24.

In some embodiments, each $Y_{72}$ is independently —$C_{1-10}$ alkyl, —$C_{2-10}$ alkyl-$CO_2H$, —$C_{2-10}$ alkyl-OH, —$C_{2-10}$ alkyl-$NH_2$, —$C_{2-10}$ alkyl-NH($C_{1-3}$ alkyl), or $C_{2-10}$ alkyl-N($C_{1-3}$ alkyl)$_2$.

In some embodiments, $Y_{72}$ is —$C_{1-10}$ alkyl, —$C_{2-10}$ alkyl-$CO_2H$, —$C_{2-10}$ alkyl-OH, or —$C_{2-10}$ alkyl-$NH_2$.

In some embodiments, the PEG coupling unit is part of the PEG unit and is non-PEG material that acts to connect two or more chains of repeating $CH_2CH_2O$— subunits. In some embodiments, the PEG coupling unit $Y_{73}$ is —$C_{2-10}$ alkyl-C(O)—NH—, —$C_{2-10}$ alkyl-NH—C(O)—, —$C_{2-10}$ alkyl-NH—, —$C_{2-10}$ alkyl-C(O)—, —$C_{2-10}$ alkyl-O—, or —$C_{2-10}$ alkyl-S—.

In some embodiments, each $Y_{73}$ is independently —$C_{1-10}$ alkyl-C(O)—NH—, —$C_{1-10}$ alkyl-NH—C(O)—, —$C_{2-10}$ alkyl-NH—, —$C_{2-10}$ alkyl-O—, —$C_{1-10}$ alkyl-S—, or —$C_{1-10}$ alkyl-NH—.

In some embodiments, the PEG attachment unit is part of the PEG unit and acts to link the PEG unit to the $M^A$ linker (e.g., to an amino acid in the $M^A$ linker). In some embodiments, the amino acid has a functional group that forms a bond with the PEG Unit. In some embodiments, the functional groups for attachment of the PEG unit to the amino acid include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. In some embodiments, the PEG unit can be attached to the amino acid, for example, via a disulfide, thioether, hydrazone, oxime, peptide, ester, sulfonamide, carbamate, or amide bond. In some embodiments, the reaction for attaching the PEG unit can be a cycloaddition, addition, addition/elimination or substitution reaction, or a combination thereof when applicable.

Examples of Linear PEG Units Include:

(i)

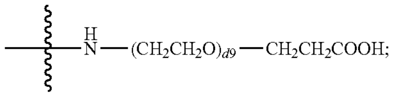

(ii)

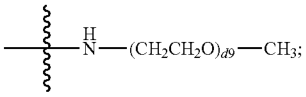

(iii)

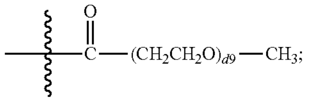

(iv)

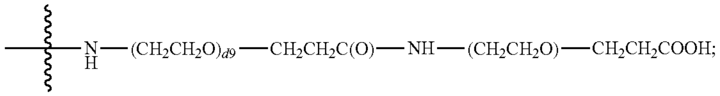

and (v)

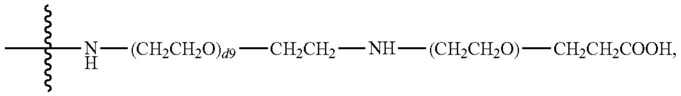

wherein indicates site of attachment to the Multifunctional Linker or $M^A$ linker (e.g., to an amino acid in the $M^A$ linker), and each $d_9$ is independently an integer from 4 to 24, 6 to 24, 8 to 24, 10 to 24, 12 to 24, 14 to 24, or 16 to 24.

In some embodiments, $d_9$ is about 8, about 12, or about 24. In some embodiments, $d_9$ is about 8.

In some embodiments, the PEG unit is from about 300 Da to about 5 kDa; from about 300 Da to about 4 kDa; from about 300 Da to about 3 kDa; from about 300 Da to about 2 kDa; or from about 300 Da to about 1 kDa. In some embodiments, the PEG unit has at least 6 subunits or at least 8, 10 or 12 subunits. In some embodiments, the PEG unit has at least 6 subunits or at least 8, 10 or 12 subunits but no more than 24 subunits.

In some embodiments, suitable polyethylene glycols may have a free hydroxy group at each end of the polymer molecule, or may have one hydroxy group etherified with a lower alkyl, e.g., a methyl group. In some embodiments suitable polyethylene glycols are derivatives of polyethylene glycols having esterifiable carboxy groups. In some embodiments, polyethylene glycols are commercially available under the trade name PEG, usually as mixtures of polymers characterized by an average molecular weight. In some embodiments, polyethylene glycols having an average molecular weight from about 300 to about 5000. In some embodiments, polyethylene glycols having an average molecular weight from about 600 to about 1000.

In some embodiments, examples of hydrophilic groups that are suitable for the conjugates, scaffolds, and methods disclosed herein can be found in e.g., U.S. Pat. No. 8,367,065 column 13; U.S. Pat. No. 8,524,696 column 6; WO2015/057699 and WO 2014/062697, the contents of each of which are hereby incorporated by reference in their entireties.

STING Agonist Drug Moiety (Variable D)

In some embodiments, the STING agonist drug moiety (D) is a compound of Formula (A):

(A)

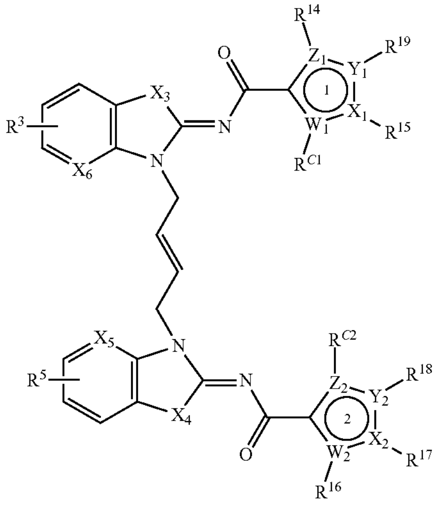

or a prodrug, solvate, pharmaceutically acceptable salt, or tautomer thereof, wherein:

$Y_1$, $Y_2$, $Z_1$ and $Z_2$ are each independently O, S, C or N;

$X_1$, $X_2$, $W_1$ and $W_2$ are each independently C or N;

$X_3$ and $X_4$ are each independently S or $NR^f$;

$X_5$ is N or $CR^{A2}$;

$X_6$ is N or $CR^{A1}$;

$R^3$ and $R^5$ are each independently —$CON(R^d)(R^f)$, —$CH_2N(R^d)(R^f)$, —$N(R^d)(R^f)$, —$N(R^d)CO(R^f)$, —$CH_2N(R^d)CO(R^f)$ or one of $R^3$ and $R^5$ is —$CON(R^d)(R^f)$, —$CH_2N(R^d)(R^f)$, —$N(R^d)(R^f)$, —$N(R^d)CO(R^f)$ or —$CH_2N(R^d)CO(R^f)$, and the other of $R^3$ and $R^5$ is H, —COOH, or —$CO_2(R^C)$;

$R^c$ is $C_{1-4}$ alkyl;

$R^{A2}$ and $R^{A1}$ are each independently H, halogen, hydroxy, amino, amino($C_{1-4}$ alkyl)-, optionally substituted ($C_{1-6}$ alkyl), or optionally substituted ($C_{1-6}$ alkyl)oxy-, wherein $C_{1-6}$ alkyl of said optionally substituted ($C_{1-6}$ alkyl), or optionally substituted ($C_{1-6}$ alkyl)oxy- is optionally substituted with 1-4 substituents each independently selected from the group comprising hydroxyl, $C_{1-4}$ alkoxyl, —$N(R^e)(R^f)$, —$CO_2(R^f)$, —$CON(R^e)(R^f)$, and —COOH;

each $R^d$ is independently H, hydroxy, or $C_{1-4}$ alkyl;

$R^e$ is selected from H, ($C_{1-4}$ alkyl), —CO($C_{1-4}$ alkyl), —OCO($C_{1-4}$ alkyl), and —$CO_2$($C_{1-4}$ alkyl);

each $R^f$ is independently H, hydroxy, or ($C_{1-4}$ alkyl);

$R^{14}$ and $R^{C2}$ are each independently absent or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;

$R^{16}$ and $R^{C1}$ are each independently absent, H or $C_{1-4}$ alkyl; and $R^{15}$, $R^{17}$, $R^{18}$, or $R^{19}$ are each independently absent, H, or $C_{1-4}$ alkyl, wherein $C_{1-4}$ alkyl is optionally substituted by a substituent selected from halogen, —$OR^c$, —$NR^cR^d$, —$CO_2R^c$, —$CONR^cR^d$, —$SO_2NR^cR^d$, and —$OCONR^cR^d$;

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound of Formula (A-a):

(A-a)

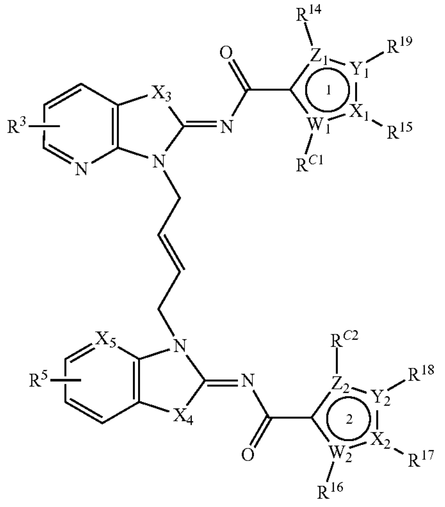

or a prodrug, solvate, pharmaceutically acceptable salt, or tautomer thereof, wherein:

$Y_1$, $Y_2$, $Z_1$, $Z_2$, $X_1$, $X_2$, $W_1$, $W_2$, $X_3$, $X_4$, $R^3$, $R^5$, $R^c$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

$X_5$ is $CR^{A2}$; and $R^{A2}$ is halogen, hydroxyl, optionally substituted ($C_{1-6}$ alkyl), substituted ($C_{1-6}$ alkyl)oxy-, optionally substituted ($C_{1-6}$ alkyl)amino-, or optionally substituted ($C_{1-6}$ alkyl)($C_{1-4}$ alkyl)amino-, wherein $C_{1-6}$ alkyl of said optionally substituted ($C_{1-6}$ alkyl) or substituted ($C_{1-6}$ alkyl)oxy- is optionally substituted with 1-4 substituents each independently selected from the group comprising hydroxyl, $C_{1-4}$ alkoxyl, —$N(R^e)(R^f)$, —$CO_2(R^f)$, —$CON(R^e)(R^f)$, and —COOH;

wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-b):

(A-b)

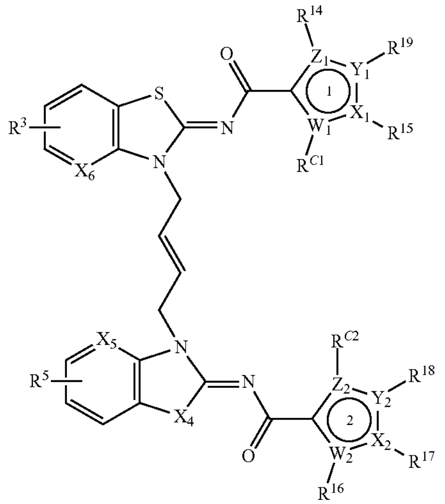

or a prodrug, solvate, pharmaceutically acceptable salt, or tautomer thereof, wherein:

$Y_1$, $Y_2$, $Z_1$, $Z_2$, $X_1$, $X_2$, $W_1$, $W_2$, $X_4$, $X_5$, $X_6$, $R^3$, $R^5$, $R^c$, $R^{A2}$, $R^{A1}$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-c):

(A-c)

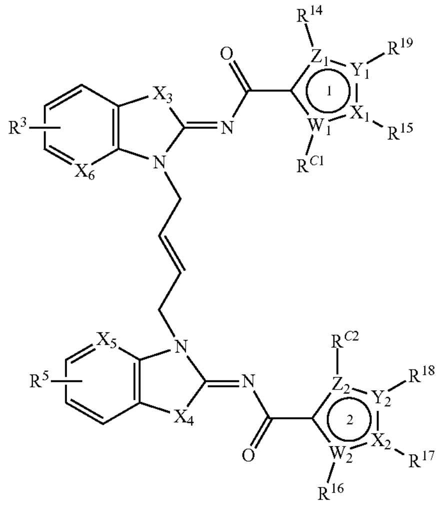

or a prodrug, solvate, pharmaceutically acceptable salt, or tautomer thereof, wherein:

$Y_2$, $Z_2$, $X_2$, $W_2$, $X_3$, $X_4$, $X_5$, $X_6$, $R^3$, $R^5$, $R^c$, $R^{A2}$, $R^{A1}$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

wherein one of $W_1$, $X_1$, $Y_1$, and $Z_1$ is N and the additional $W_1$, $X_1$, $Y_1$, and $Z_1$ are O, S, or C;

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-d):

(A-d)

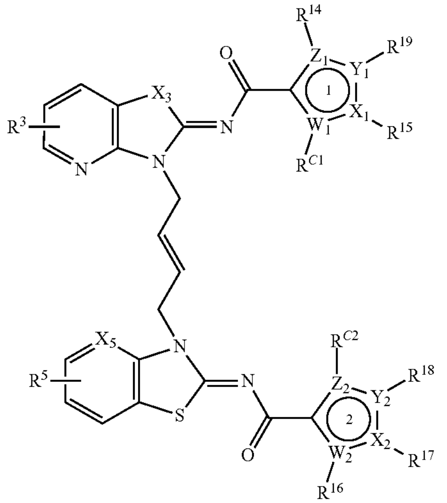

or a prodrug, solvate, pharmaceutically acceptable salt, or tautomer thereof, wherein:

$Y_1$, $Y_2$, $Z_1$, $Z_2$, $X_1$, $X_2$, $W_1$, $W_2$, $X_3$, $R^3$, $R^5$, $R^c$, $R^d$, $R^e$, $R^f$, $R^{14}$, $R^{A2}$, $R^{C2}$, $R^{16}$, $R^{C1}$, $R^{15}$, $R^{17}$, $R^{18}$, and $R^{19}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-e):

(A-e)

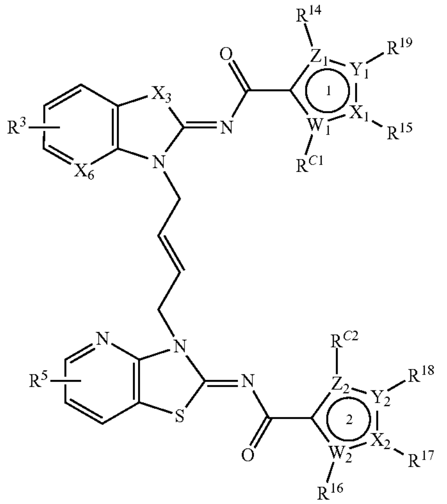

or a prodrug, solvate, pharmaceutically acceptable salt, or tautomer thereof, wherein:

$Y_1$, $Y_2$, $Z_1$, $Z_2$, $X_1$, $X_2$, $X_3$, $W_1$, $W_2$, $R^{A1}$, R3, $R^5$, $R^c$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A);

$X_6$ is $CR^{A1}$; and wherein: (i) $R^{A1}$ is connected to $L^D$ via a functional group of $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f):

(A-f)

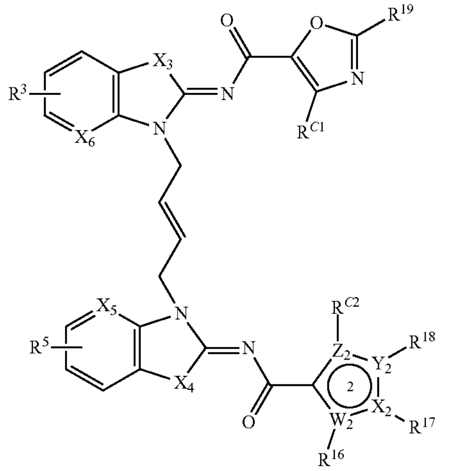

or a prodrug, solvate, pharmaceutically acceptable salt, or tautomer thereof, wherein:

$X_2$, $X_3$, $X_4$, $X_5$, $X_6$, $W_2$, $Y_2$, $Z_2$, $R^3$, $R^5$, $R^c$, $R^{A2}$, $R^{A1}$, $R^d$, $R^e$, $R^f$, $R^{16}$, $R^{17}$, $R^{18}$, $R^{19}$, $R^{C2}$, and $R^{C1}$, are as defined in Formula (A), and wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f1):

(A-f1)

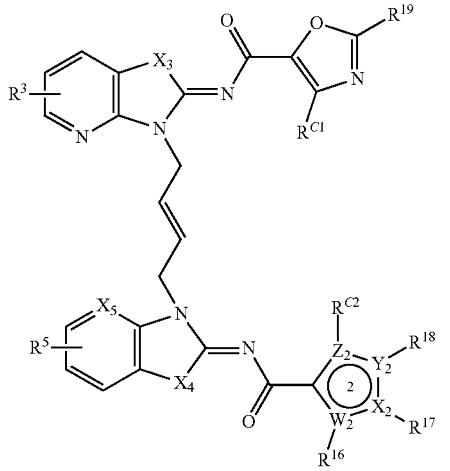

or a prodrug, solvate, pharmaceutically acceptable salt, or tautomer thereof, wherein:

$X_2$, $X_3$, $X_4$, $W_2$, $Y_2$, $Z_2$, $R^3$, $R^5$, $R^c$, $R^d$, $R^e$, $R^f$, $R^{16}$, $R^{A2}$, $R^{17}$, $R^{18}$, $R^{19}$, $R^{C2}$, and $R^{C1}$, are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f2):

(A-f2)

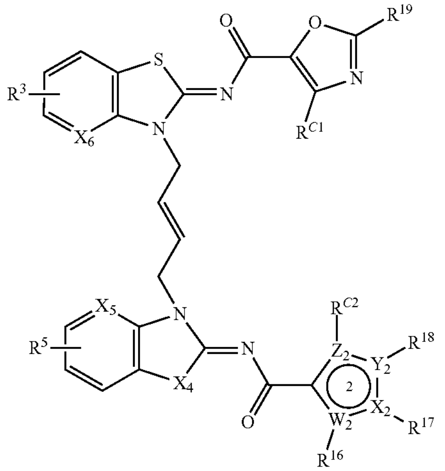

or a prodrug, solvate, pharmaceutically acceptable salt, or tautomer thereof, wherein:

$X_2$, $X_4$, $X_5$, $X_6$, $W_2$, $Y_2$, $Z_2$ $R^3$, $R^5$, $R^c$, $R^{A2}$, $R^{A1}$, $R^d$, $R^e$, $R^{C1}$, $R^{C2}$, $R^{16}$, $R^{17}$, $R^{18}$, $R^{19}$, and $R^f$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f3):

(A-f3)

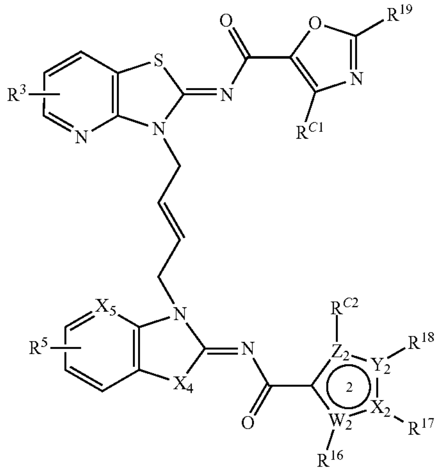

or a prodrug, solvate, pharmaceutically acceptable salt, or tautomer thereof, wherein:

$X_2$, $X_4$, $W_2$, $Y_2$, $Z_2$, $R^3$, $R^5$, $R^c$, $R^d$, $R^e$, $R_f$, $R^{16}$, $R^{A2}$, $R^{C2}$, $R^{16}$, $R^{17}$, $R^{18}$, $R^{19}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f4):

(A-f4)

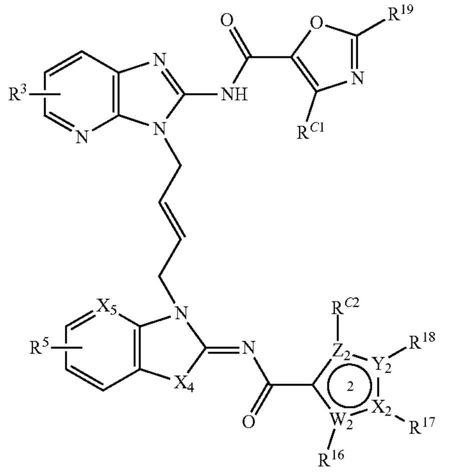

or a prodrug, solvate, pharmaceutically acceptable salt, or tautomer thereof, wherein:

$X_2$, $X_4$, $W_2$, $Y_2$, $Z_2$, $R^3$, $R^5$, $R^c$, $R^d$, $R^e$, $R^f$, $R^{16}$, $R^{A2}$, $R^{C2}$, $R^{16}$, $R^{17}$, $R^{18}$, $R^{19}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-f5):

(A-f5)

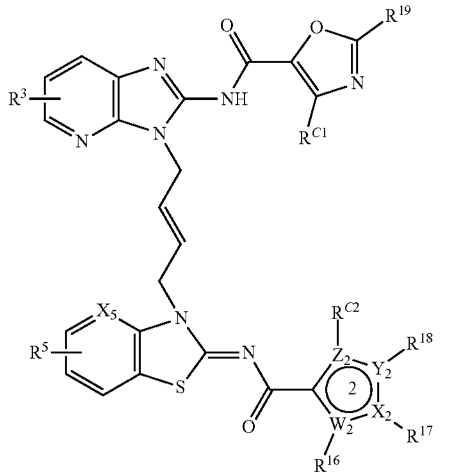

or a prodrug, solvate, pharmaceutically acceptable salt, or tautomer thereof, wherein:

$X_2$, $W_2$, $Y_2$, $Z_2$, $R^3$, $R^5$, $R^c$, $R^d$, $R^e$, $R^f$, $R^{16}$, $R^{A2}$, $R^{C2}$, $R^{16}$, $R^{17}$, $R^{18}$, $R^{19}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g):

(A-g)

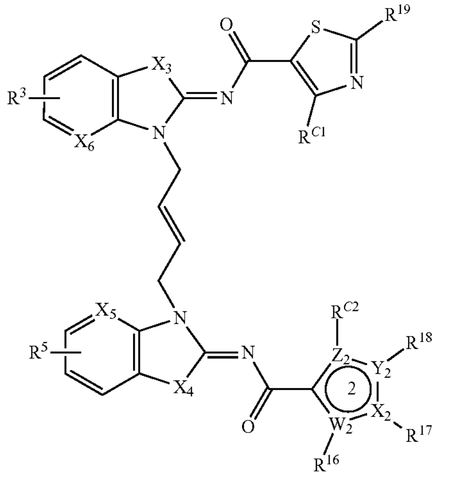

or a prodrug, solvate, pharmaceutically acceptable salt, or tautomer thereof, wherein:

$X_3$, $X_4$, $X_5$, $X_6$, $R^3$, $R^5$, $R^c$, $R^{A2}$, $R^{A1}$, $R^{C2}$, $R^{17}$, $R^{18}$, $R^{19}$, $R^d$, $R^e$, $R^f$, $R^{16}$, and $R^{C1}$ are as defined in Formula (A);

$Y_2$ and $Z_2$ are each independently O, S, C or N;

$X_2$ and $W_2$ are each independently C or N;

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g1):

(A-g1)

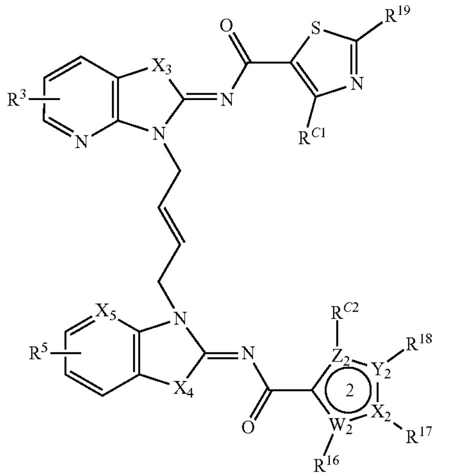

or a prodrug, solvate, pharmaceutically acceptable salt, or tautomer thereof, wherein:

$X_2$, $W_2$, $Y_2$, $Z_2$, $X_3$, $X_4$, $X_5$, $R^3$, $R^5$, $R^c$, $R^d$, $R^e$, $R^f$, $R^{A2}$, $R^{C2}$, $R^{17}$, $R^{18}$, $R^{19}$, $R^{16}$ and $R^{C1}$ are as defined in Formula (A); wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g2):

(A-g2)

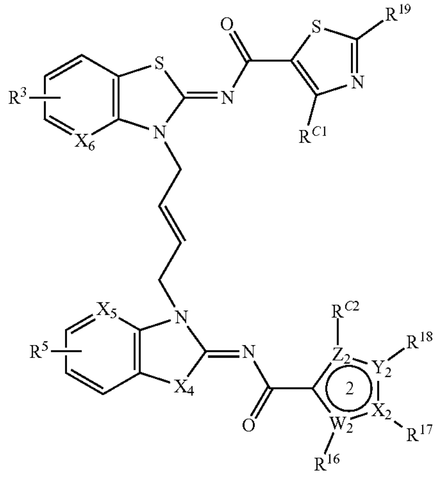

or a prodrug, solvate, pharmaceutically acceptable salt, or tautomer thereof, wherein:

$X_2$, $X_4$, $X_5$, $X_6$, $W_2$, $Y_2$, $Z_2$, $R^3$, $R^5$, $R^c$, $R^{A2}$, $R^{A1}$, $R^{C2}$, $R^{17}$, $R^{18}$, $R^{19}$, $R^d$, $R^e$, $R^f$, $R^{16}$, and $R^{C1}$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g3):

(A-g3)

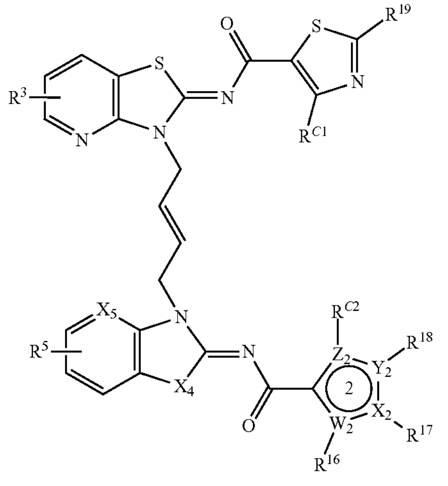

or a prodrug, solvate, pharmaceutically acceptable salt, or tautomer thereof, wherein:

$X_2$, $X_4$, $W_2$, $Y_2$, $Z_2$, $R^3$, $R^5$, $R^c$, $R^{A2}$, $R^{C2}$, $R^{17}$, $R^{18}$, $R^{19}$, $R^{16}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$; and optionally, wherein $R^{A2}$ is connected to $L^D$ via a functional group of RA.

In some embodiments, the STING agonist drug moiety is a compound is of Formula (A-g4):

(A-g4)

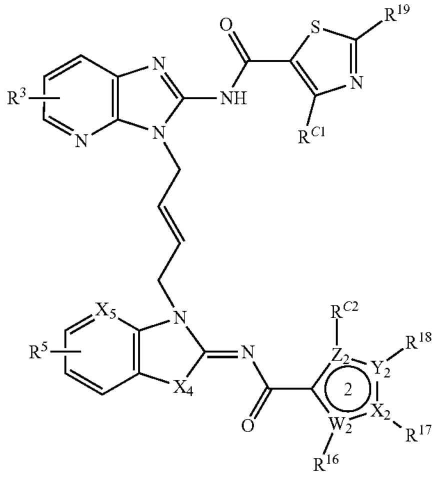

or a prodrug, solvate, pharmaceutically acceptable salt, or tautomer thereof, wherein:

$X_2$, $X_4$, $W_2$, $Y_2$, $Z_2$ $R^3$, $R^5$, $R_c$, $R^d$, $R^e$, $R^f$, $R^{A2}$, $R^{C2}$, $R^{17}$, $R^{18}$, $R^{19}$, $R^{16}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-g5):

(A-g5)

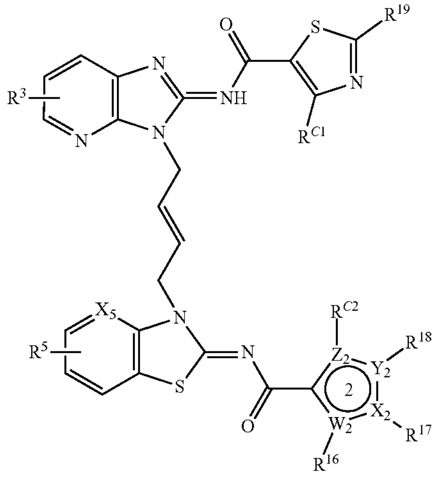

or a prodrug, solvate, pharmaceutically acceptable salt, or tautomer thereof, wherein:

$X_2$, $W_2$, $Y_2$, $Z_2$, $R^3$, $R^5$, $R^c$, $R^d$, $R^e$, $R^f$, $R^{A2}$, $R^{C2}$, $R^{17}$, $R^{18}$, $R^{19}$, $R^{16}$, and $R^{C1}$ are as defined in Formula (A);

$X_5$ is $CR^{A2}$; and wherein: (i) $R^{A2}$ is connected to $L^D$ via a functional group of $R^{A2}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-h):

(A-h)

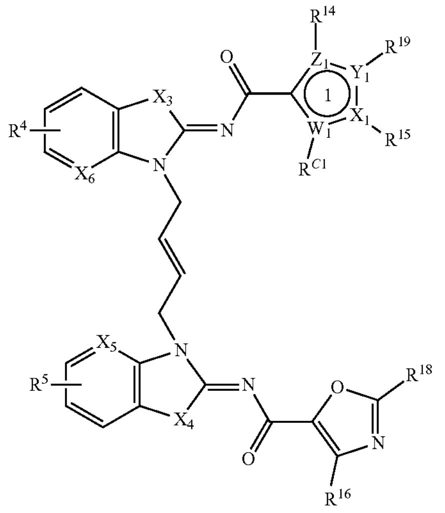

or a prodrug, solvate, pharmaceutically acceptable salt, or tautomer thereof, wherein:

$X_1$, $W_1$, $Y_1$, $Z_1$, $X_3$, $X_4$, $X_5$, $X_6$, $R^3$, $R^5$, $R^c$, $R^{A2}$, $R^{A1}$, $R^d$, $R^e$, $R^f$, $R^{14}$, $R^{15}$, $R^{18}$, $R^{19}$, $R^{16}$, and $R^{C1}$ are as defined in Formula (A); wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-h1):

(A-h1)

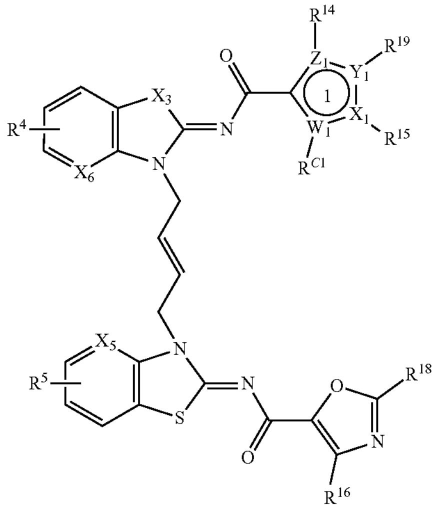

or a prodrug, solvate, pharmaceutically acceptable salt, or tautomer thereof, wherein:

$X_1$, $X_3$, $W_1$, $Y_1$, $Z_1$, $X_5$, $X_6$, $R^3$, $R^5$, $R_c$, $R^{A2}$, $R^{A1}$, $R^d$, $R^e$, $R_f$, $R^{14}$, $R^{15}$, $R^{18}$, $R^{19}$, $R^{16}$, and $R^{C1}$ are as defined in Formula (A);

wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety is a compound is of Formula (A-h2):

(A-h2)

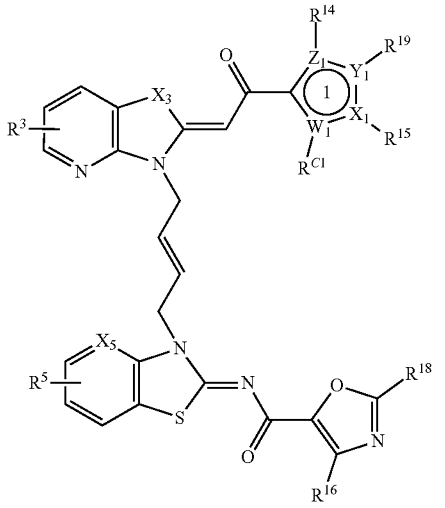

or a prodrug, solvate, pharmaceutically acceptable salt, or tautomer thereof, wherein:

$X_1$, $X_3$, $W_1$, $Y_1$, $Z_1$, $R^3$, $R^5$, $R^c$, $R^d$, $R^e$, $R^f$, $R^{A2}$, $R^{14}$, $R^{15}$, $R^{18}$, $R^{19}$, $R^{16}$, and $R^{C1}$ are as defined in Formula (A);

$X_5$ is $CR^{A2}$; and wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$;

or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, the STING agonist drug moiety (D) is a compound of Formula (A), wherein the compound is of Formula (A-i):

(A-i)

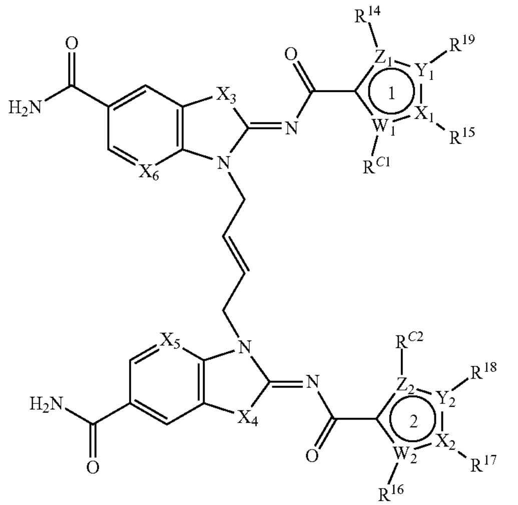

or a prodrug, solvate, pharmaceutically acceptable salt, or tautomer thereof, wherein:

$Y_1$, $Y_2$, $Z_1$, $Z_2$, $X_1$, $X_2$, $X_3$, $X_6$, $W_1$, $W_2$, $R^{A1}$, $R^{A2}$, $R^c$, $R^d$, $R^e$, $R^f$, $R^{14}$, $R^{C2}$, $R^{16}$, $R^{C1}$, $R^{15}$, $R^{17}$, $R^{18}$, and $R^{19}$ are as defined in Formula (A); and wherein: (i) at least one of $R^{A2}$ and $R^{A1}$ is present, and wherein at least one of $R^{A2}$ and $R^{A1}$ is connected to $L^D$ via at least one functional group of the $R^{A2}$ and/or $R^{A1}$; or (ii) at least one of $R^{C2}$ and $R^{C1}$ is present, and wherein at least one of $R^{C2}$ and $R^{C1}$ is connected to $L^D$ via at least one functional group of the $R^{C2}$ and/or $R^{C1}$.

In some embodiments, each STING agonist drug moiety (D) independently is:

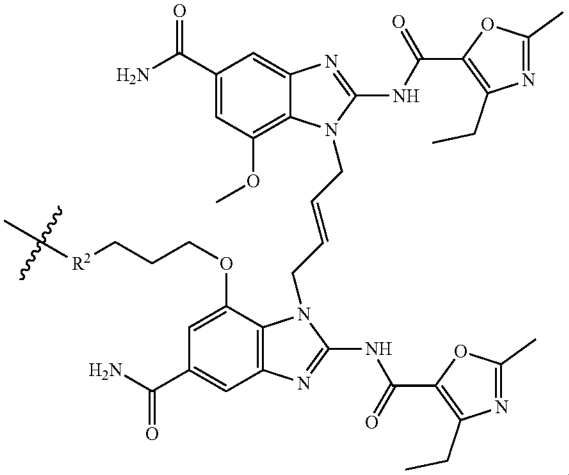

;

-continued

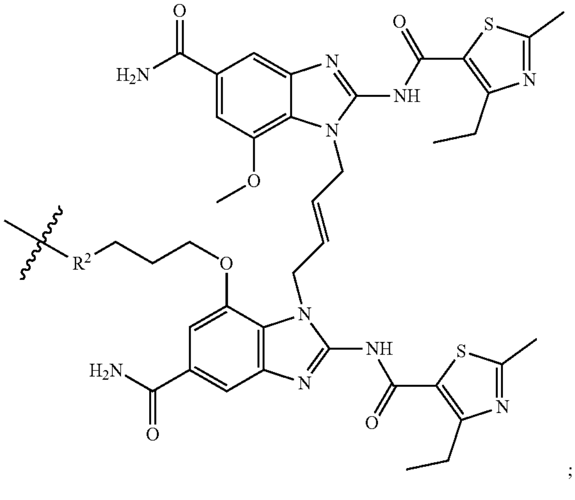

;

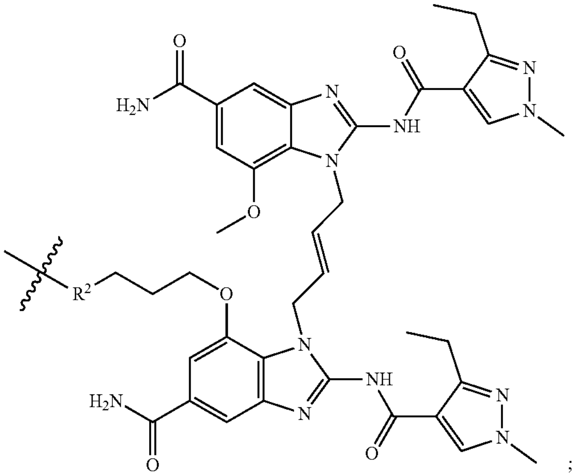

;

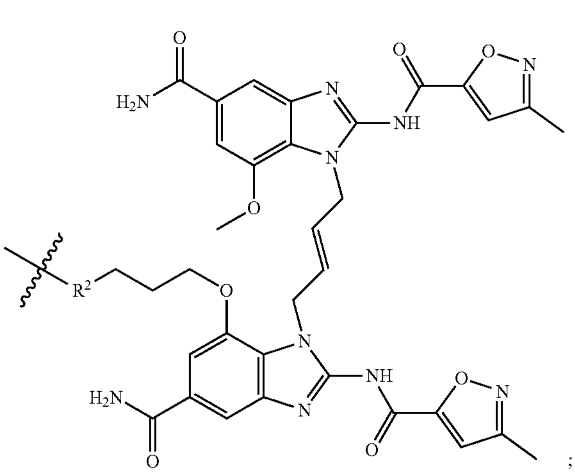

;

-continued
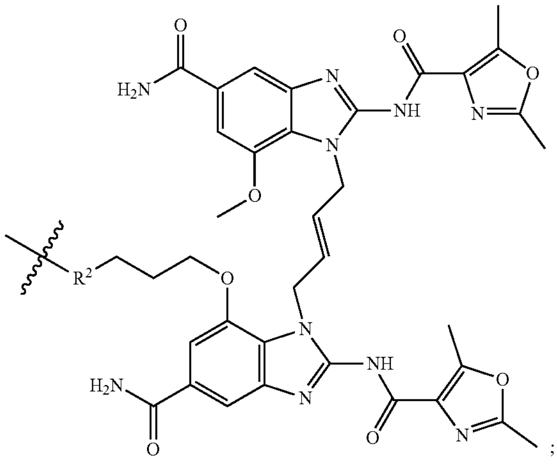
;
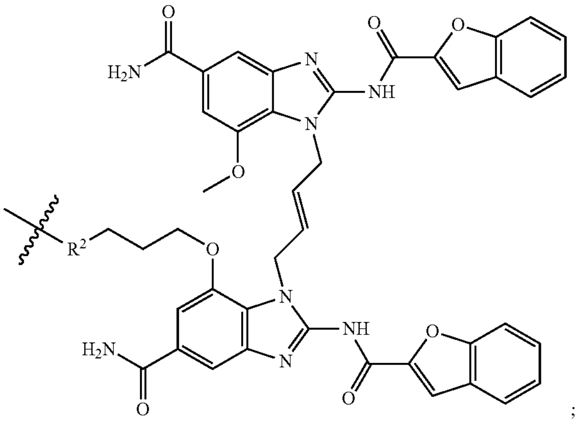
;
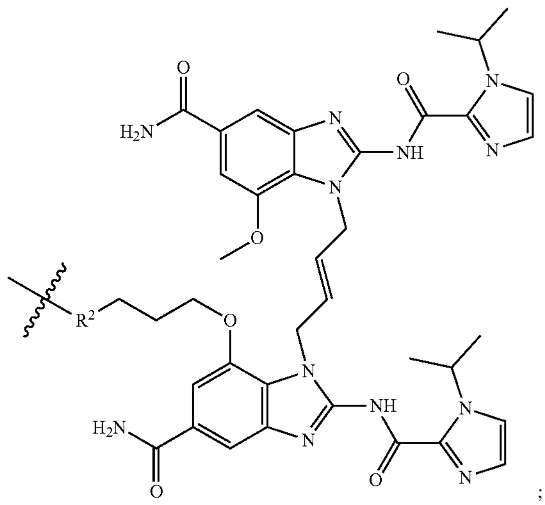
;
-continued
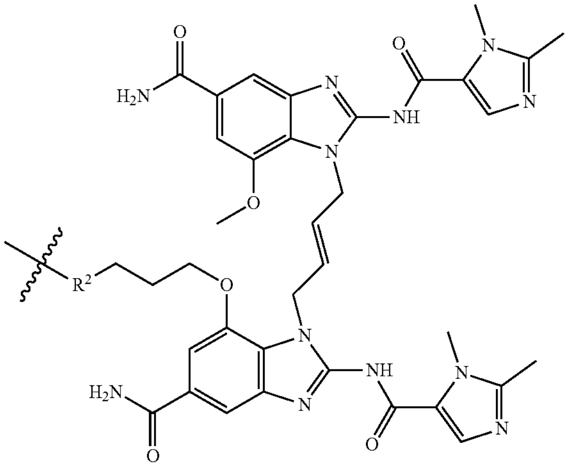
;
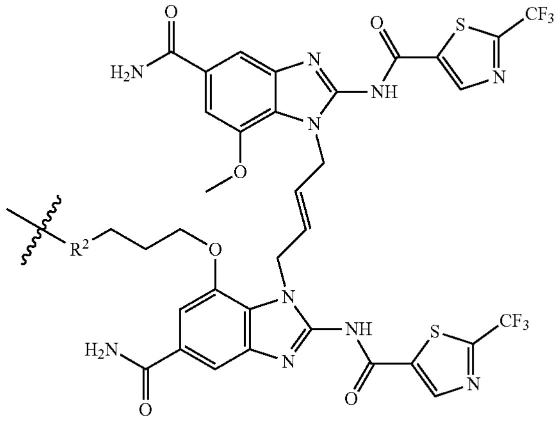
;
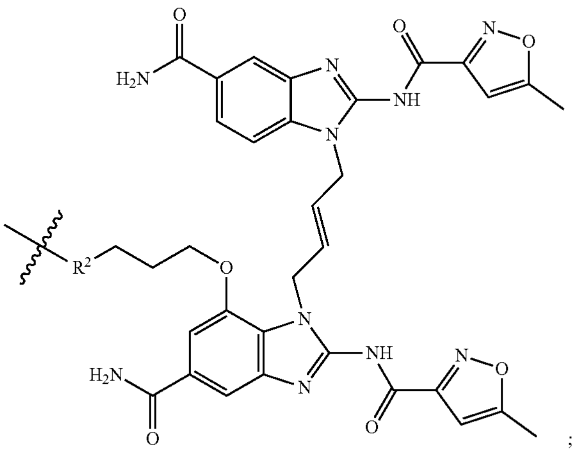
;

-continued
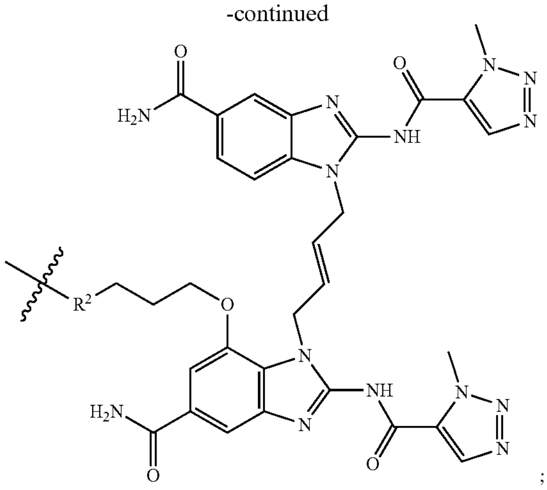
;
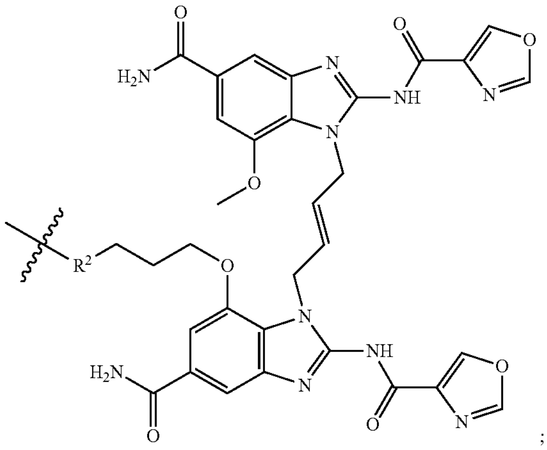
;
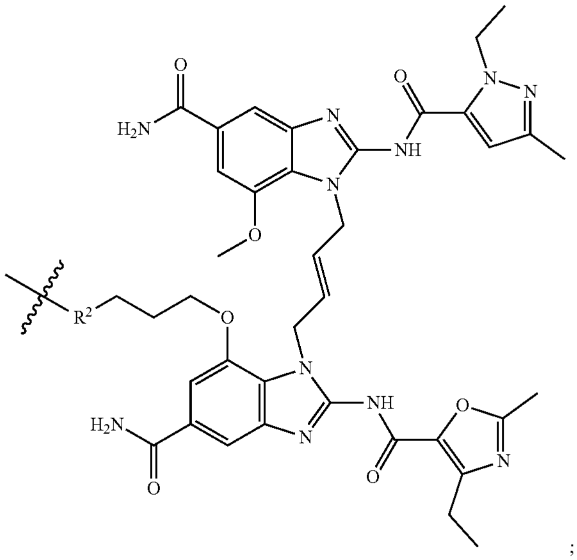
;
-continued
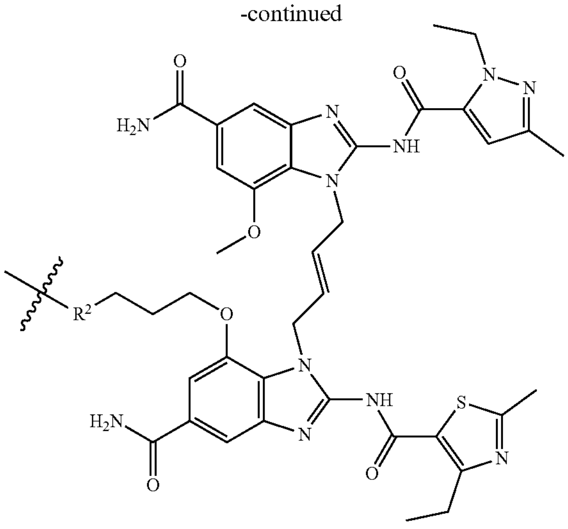
;
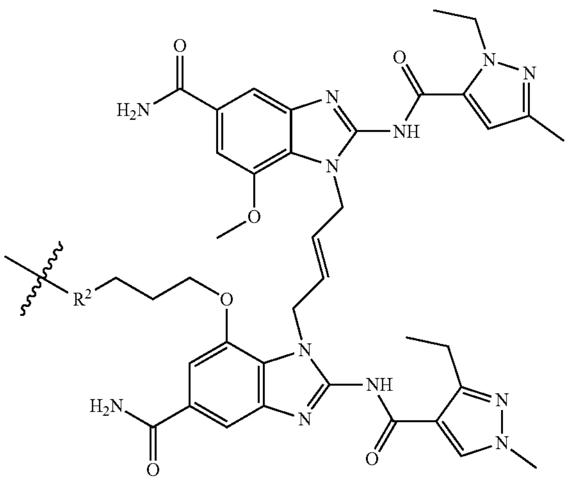
;
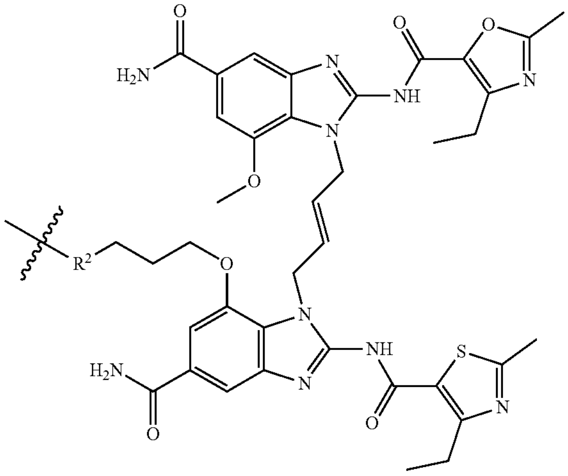
;

-continued
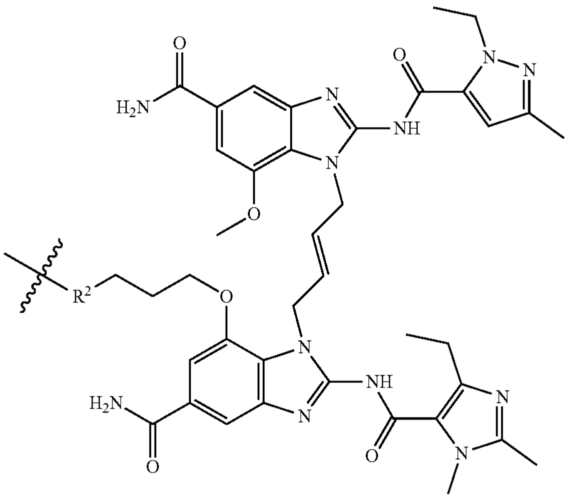
;
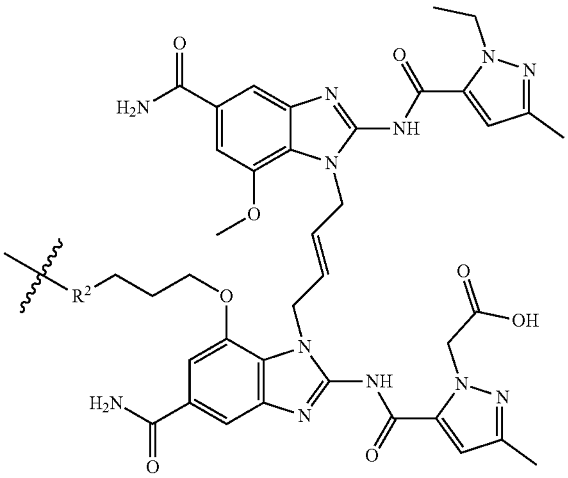
;
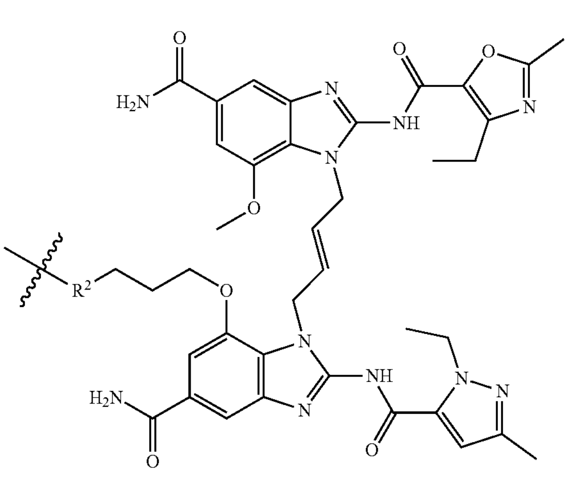
;
-continued
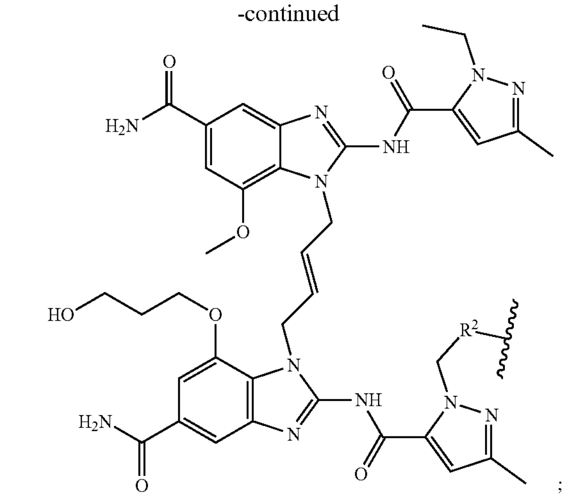
;
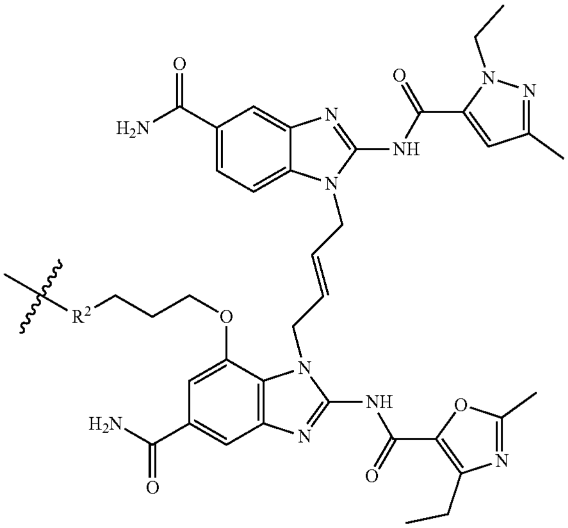
;
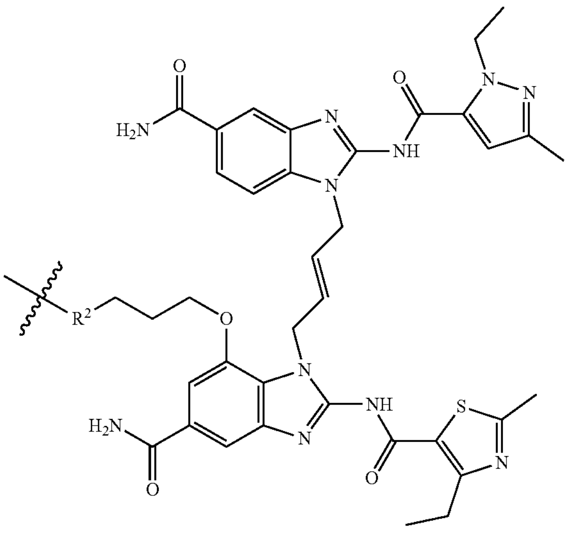
;

-continued
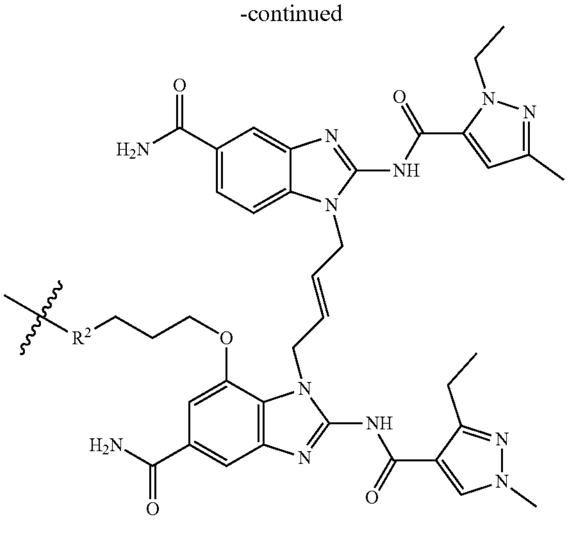
;
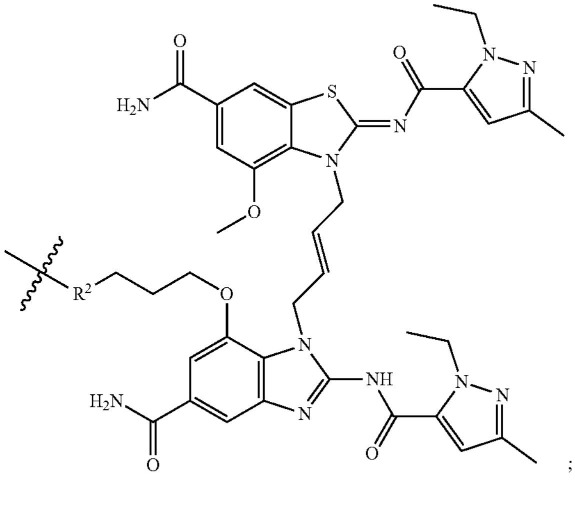
;
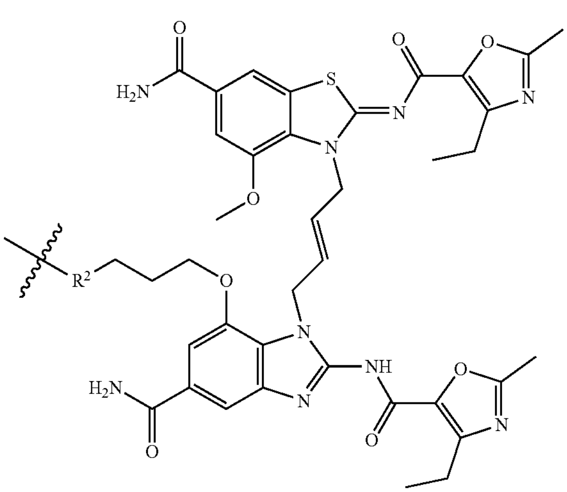
;
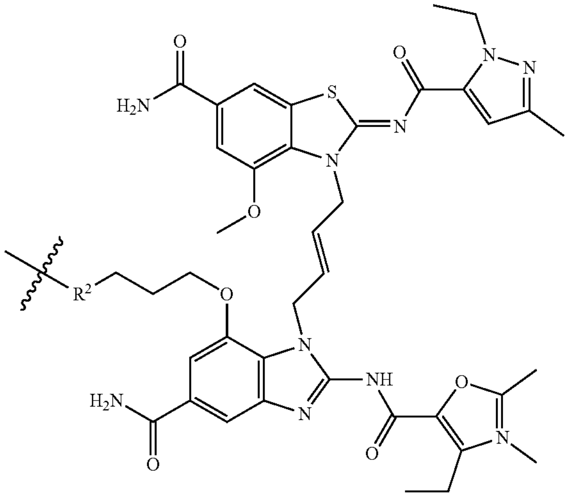
;
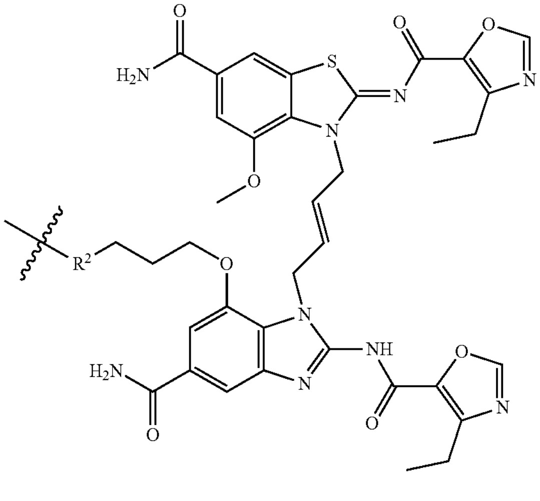
;
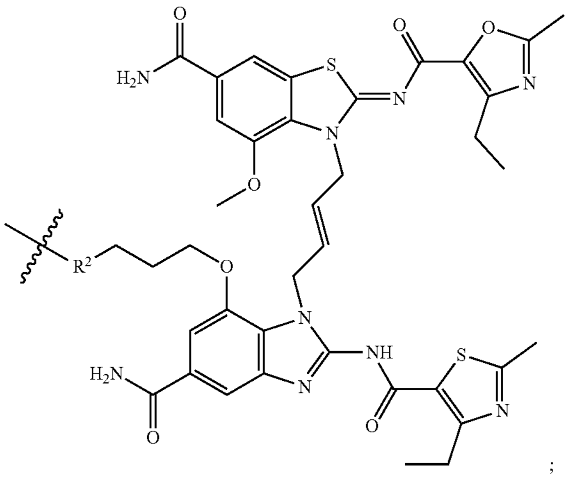
;

-continued
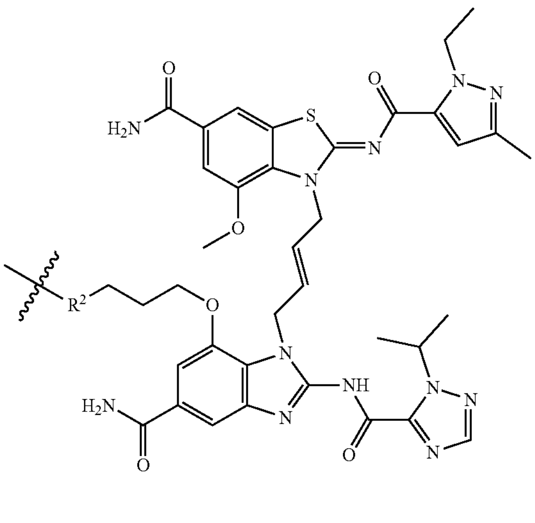
;
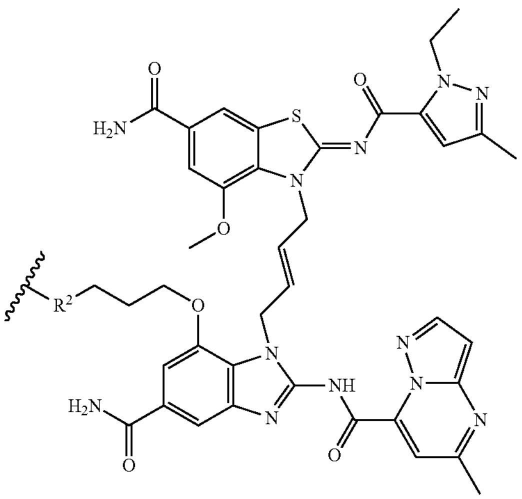
;
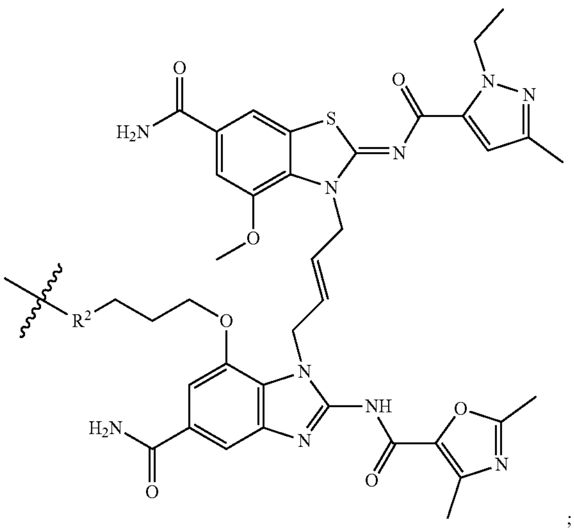
;
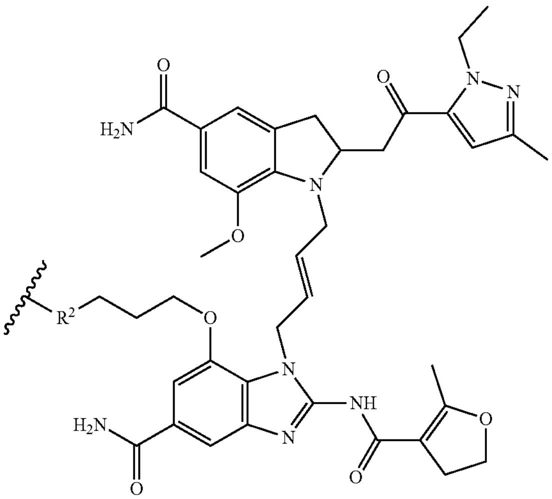
;
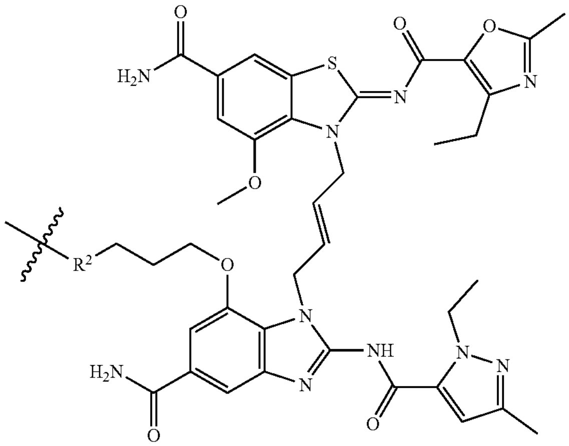
;
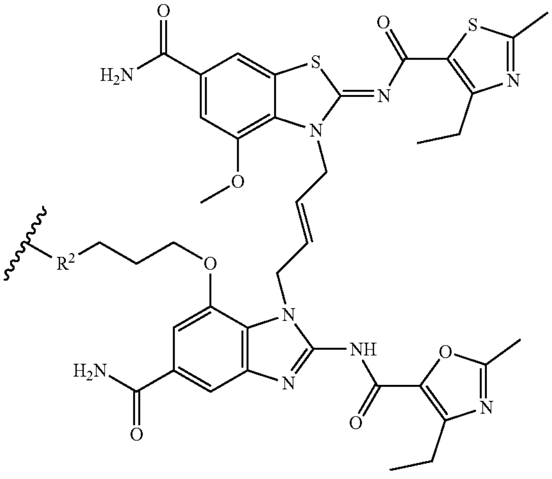
;

-continued
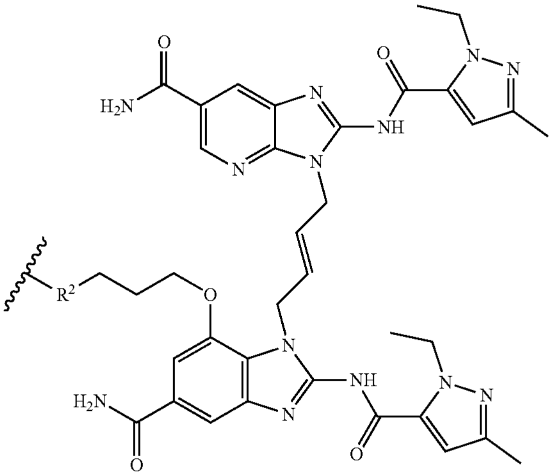
;
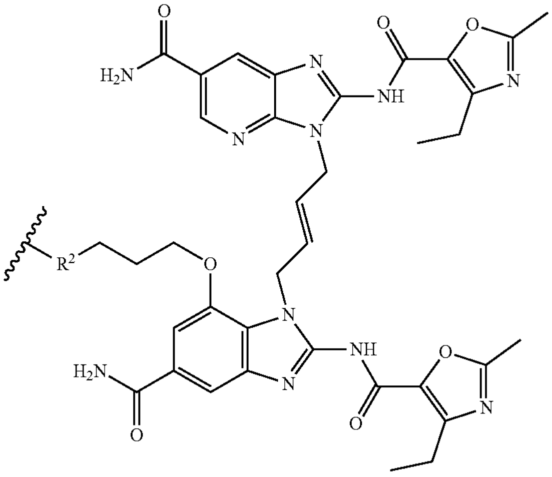
;
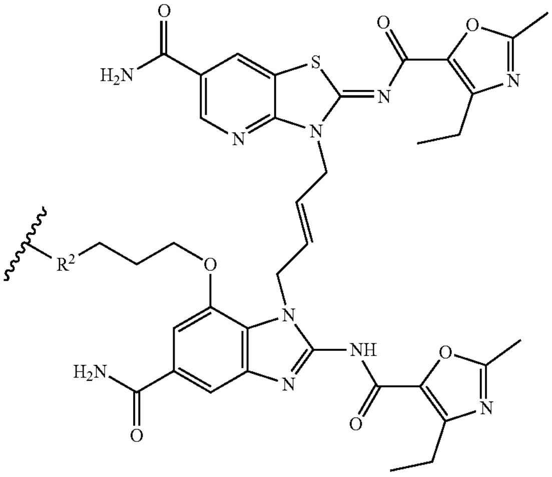
;
-continued
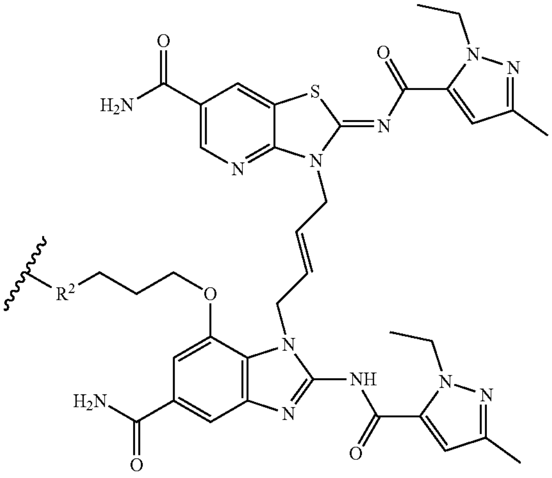
;
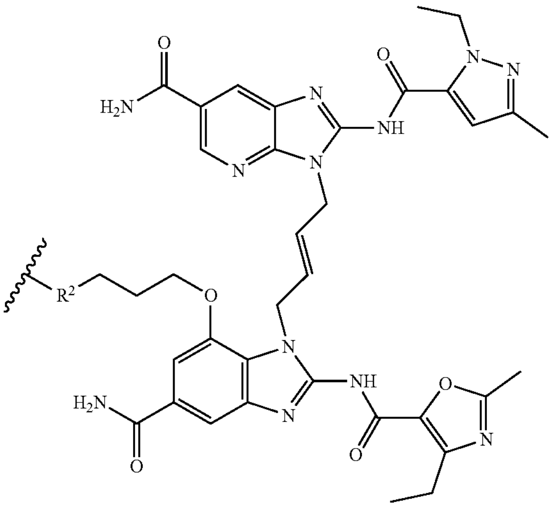
;
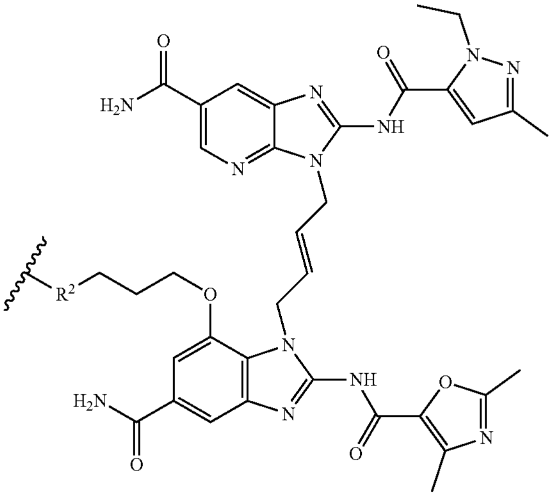
;

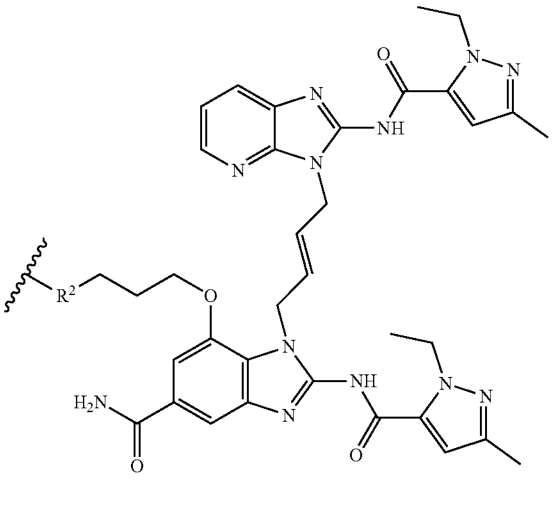
;
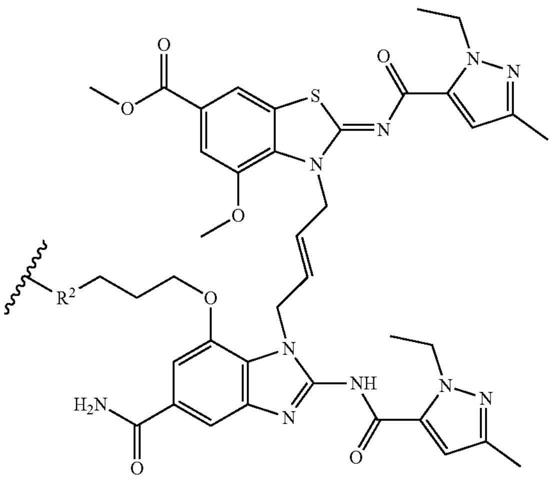
;
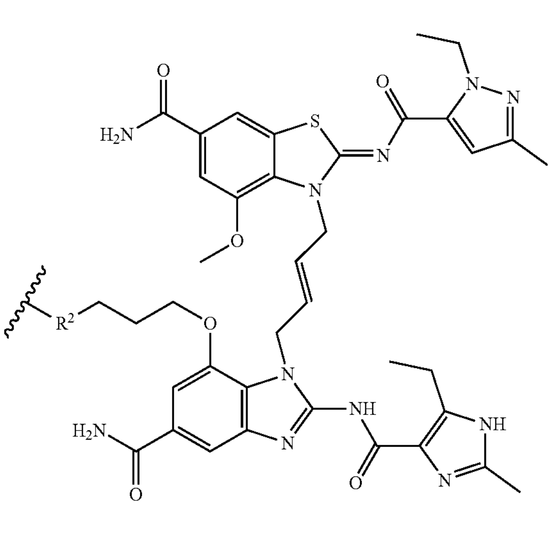
;
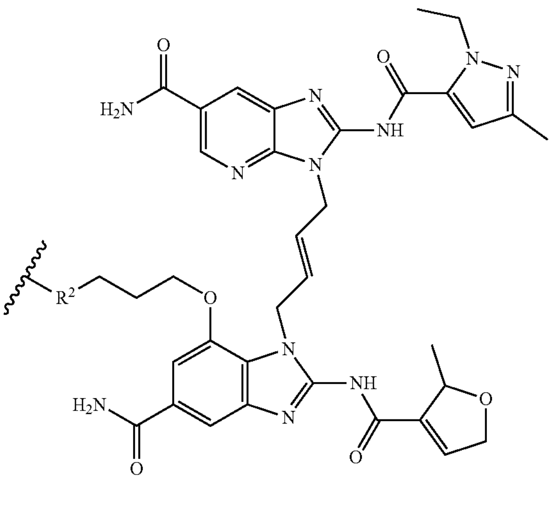
;
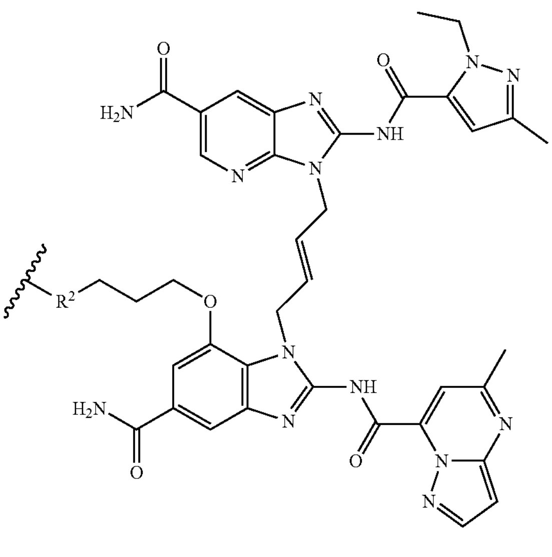
;
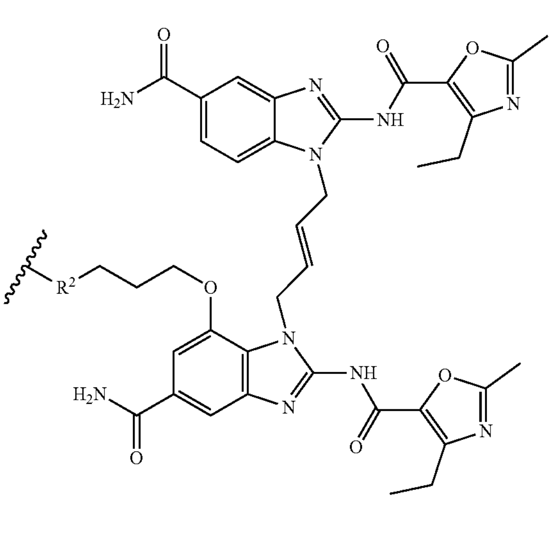
;

-continued
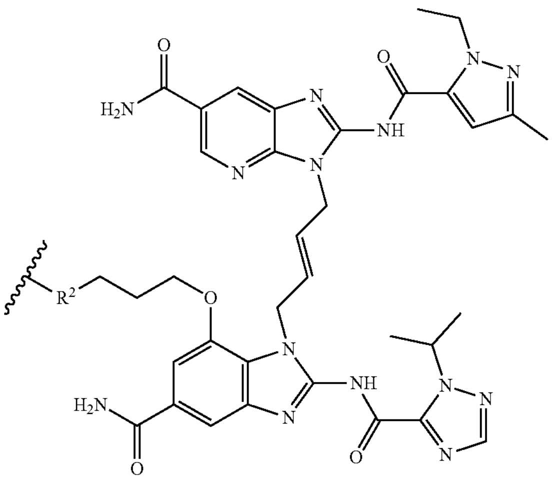
;
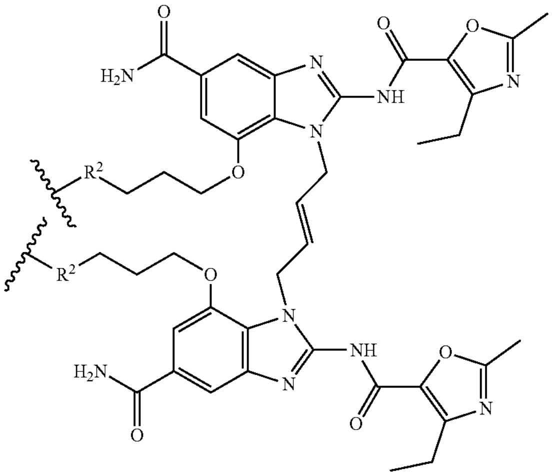
;
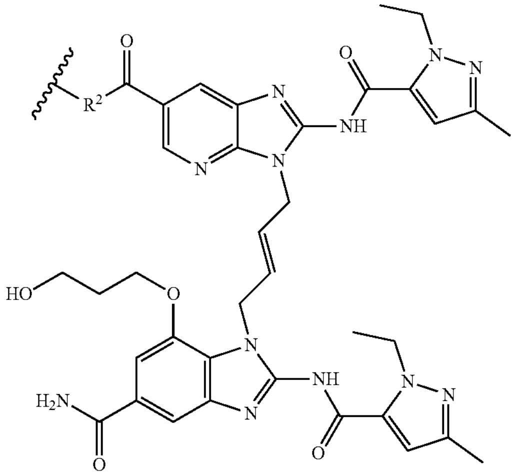
;
-continued
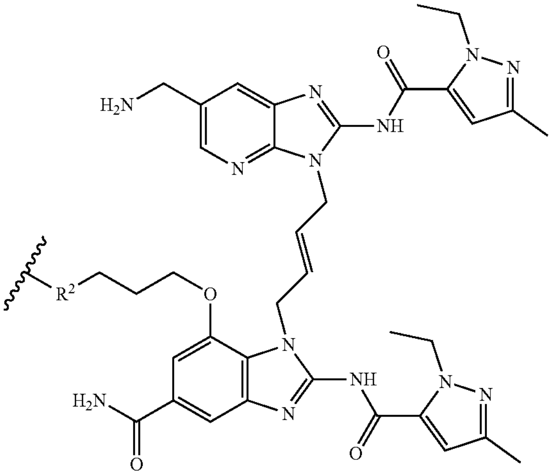
;
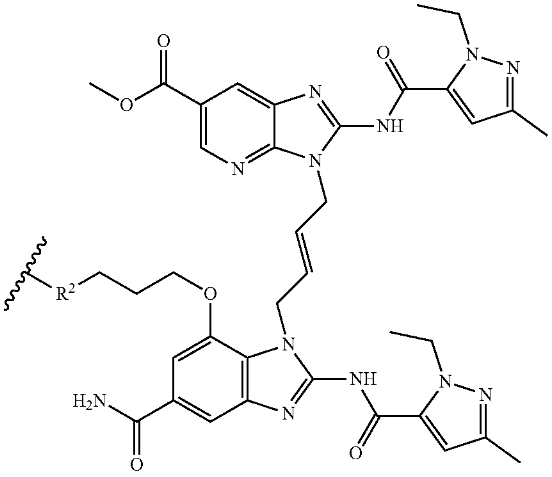
;
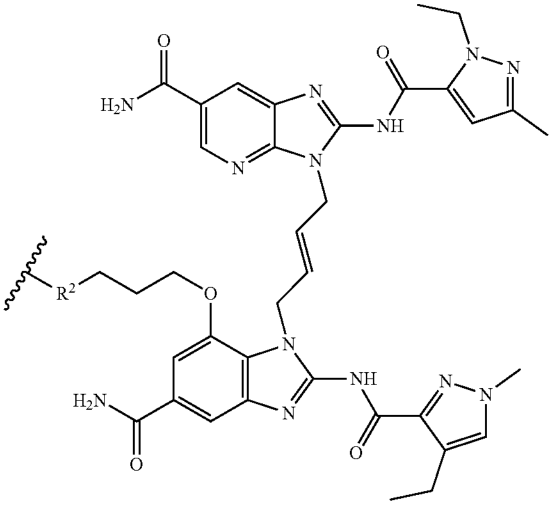
;

-continued
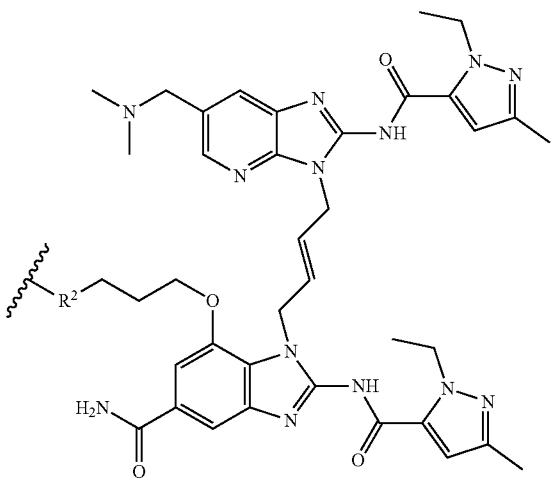
;
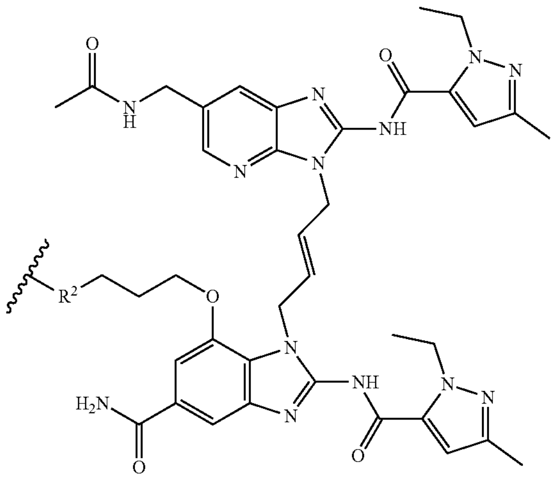
;
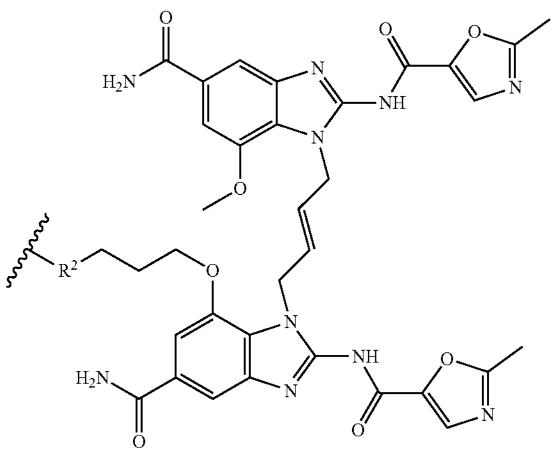
;
-continued
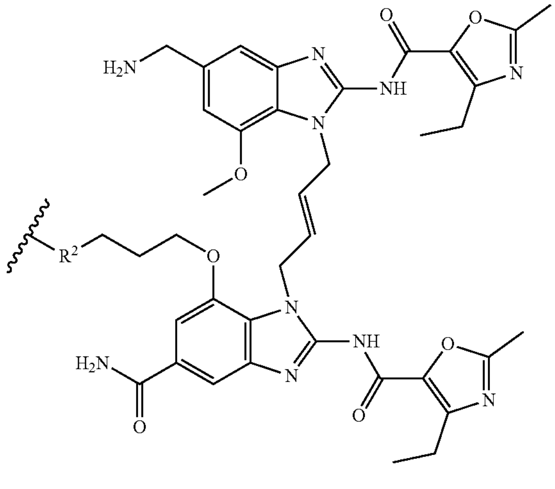
;
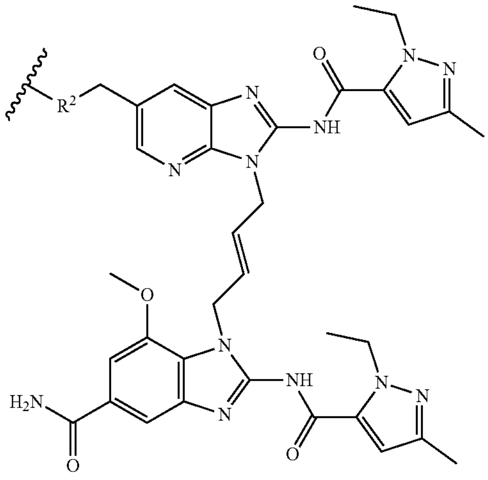
;
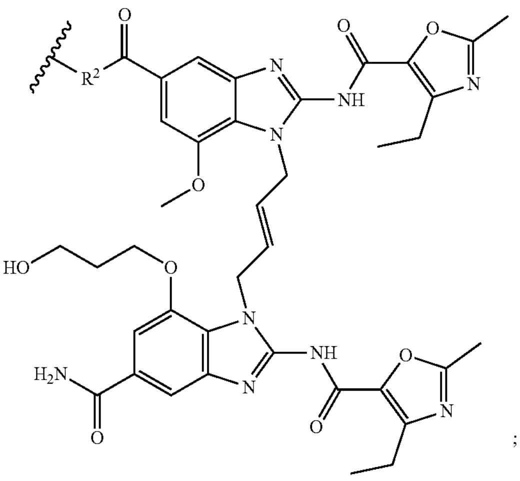
;

-continued
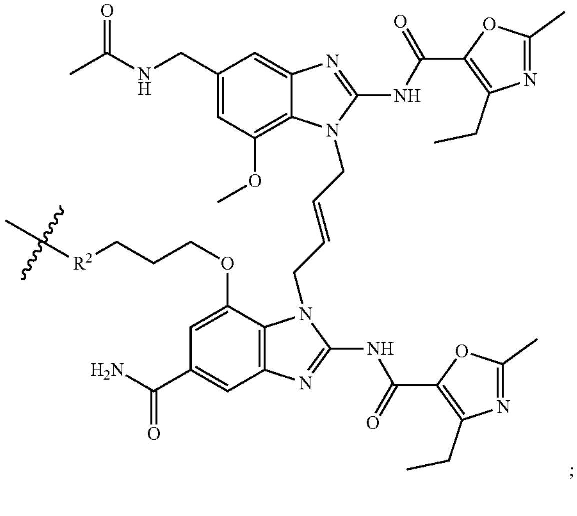
;
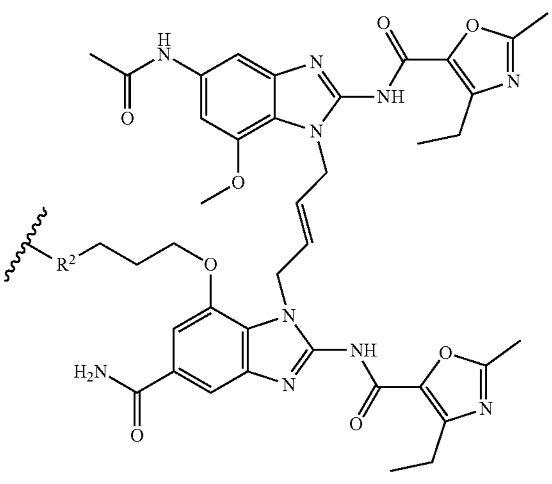
;
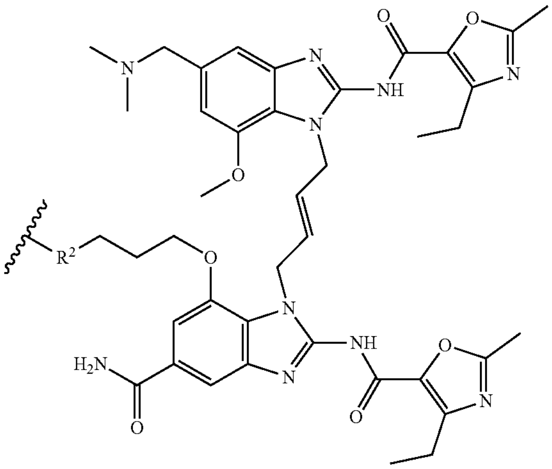
;
-continued
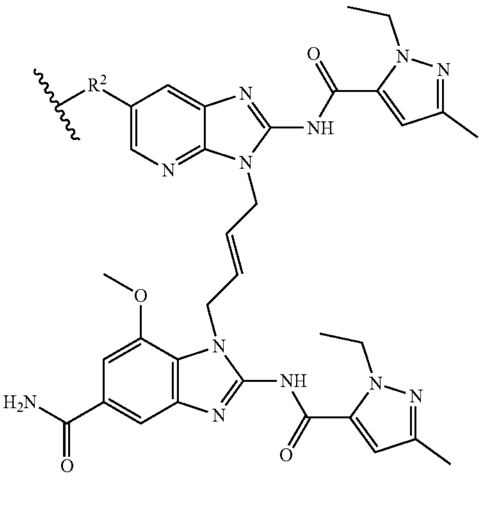
;
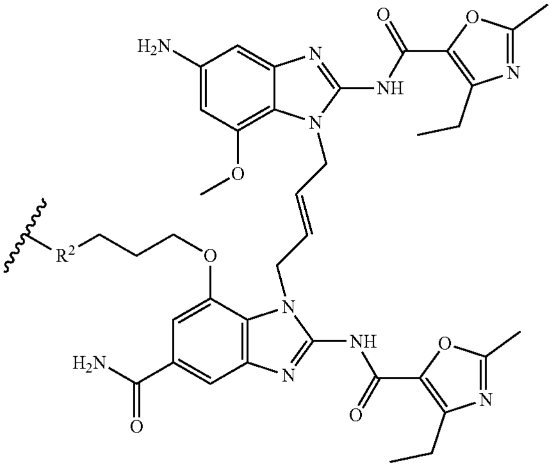
;
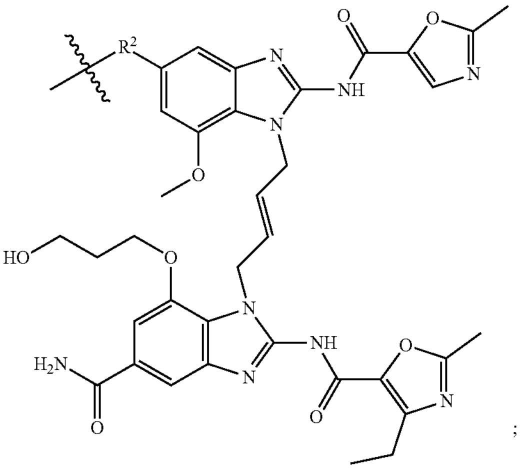
;

-continued
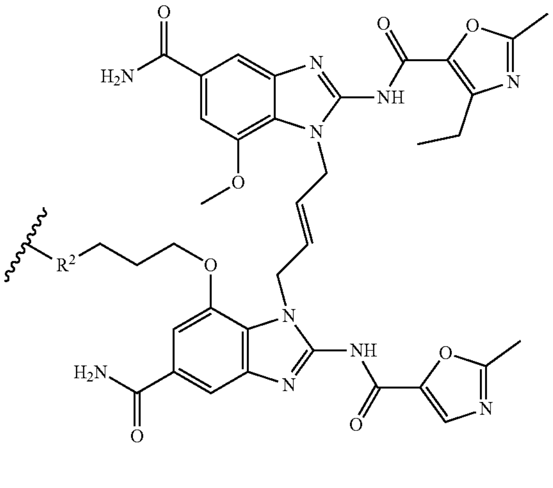
;
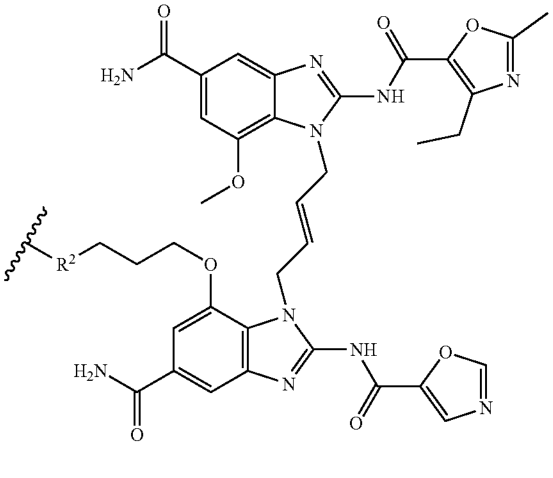
;
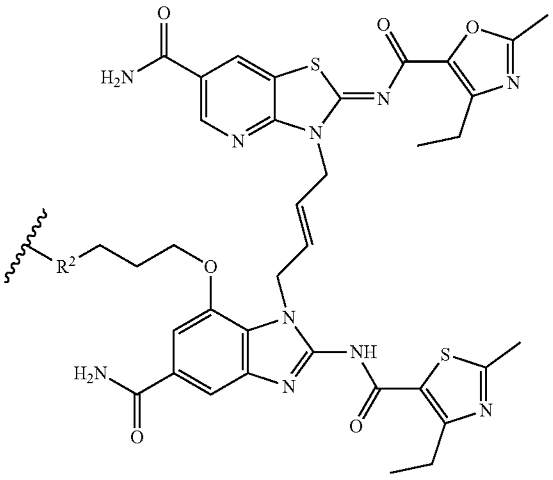
;
-continued
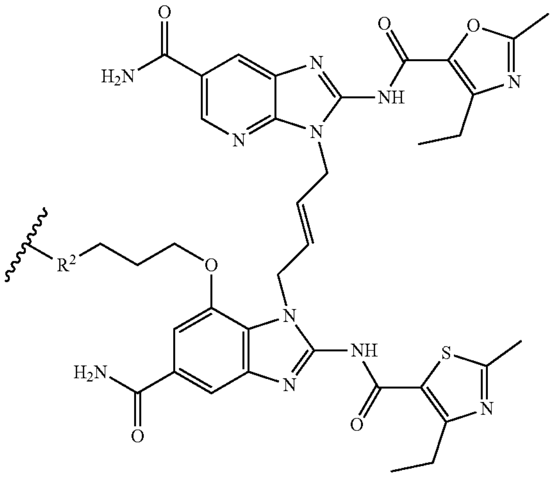
;
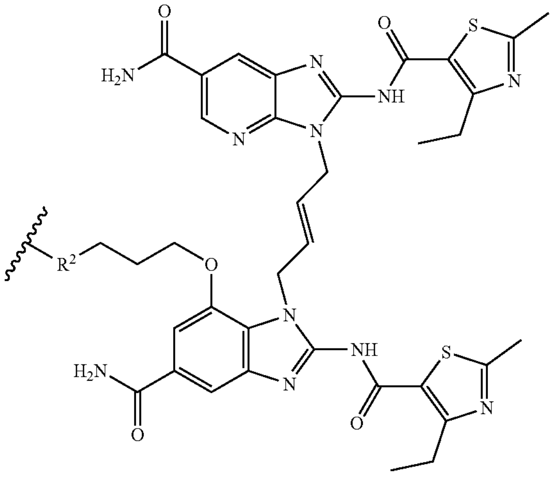
;
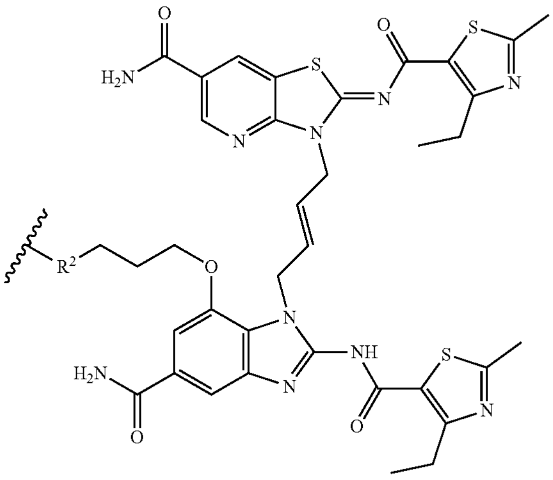
;

-continued
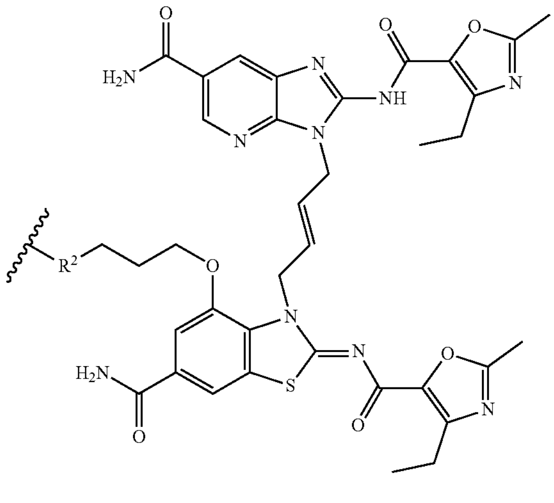
;
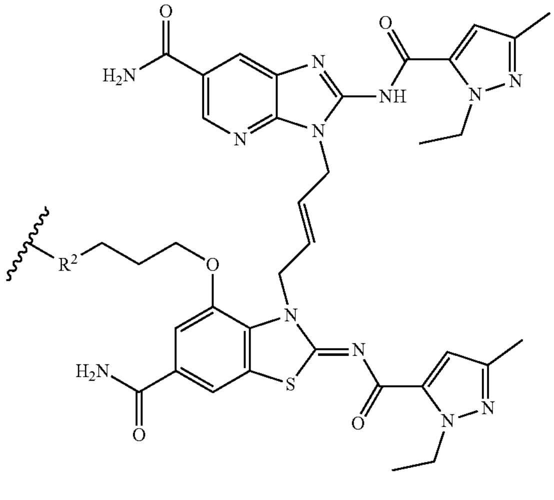
;
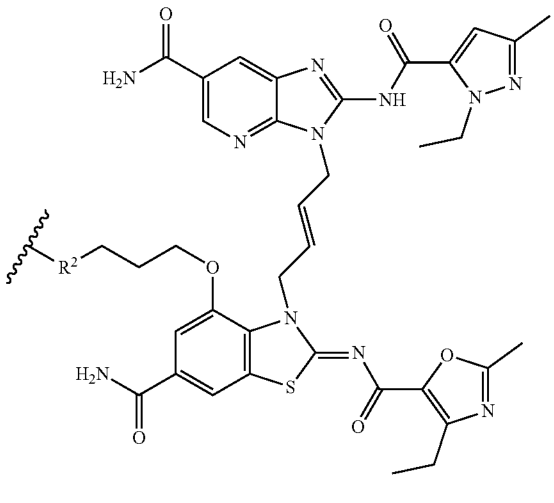
;
-continued
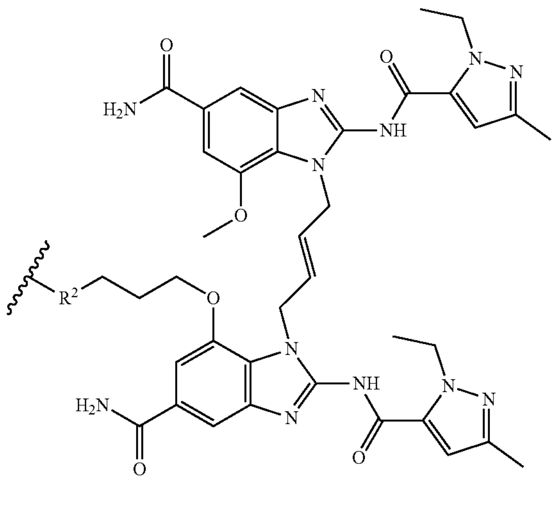
;
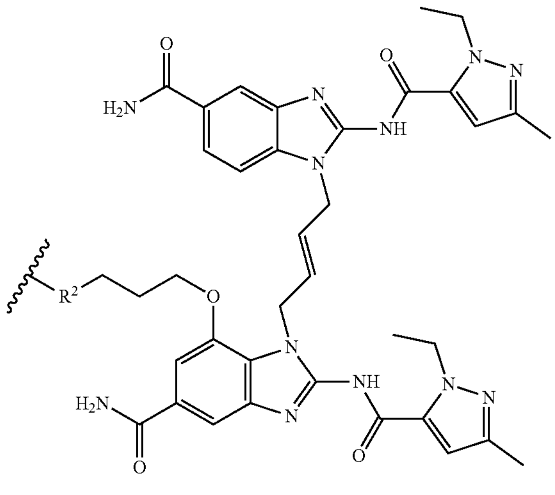
;
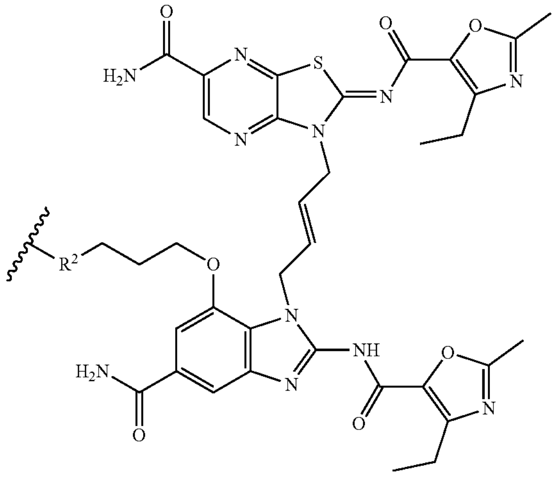
;

-continued
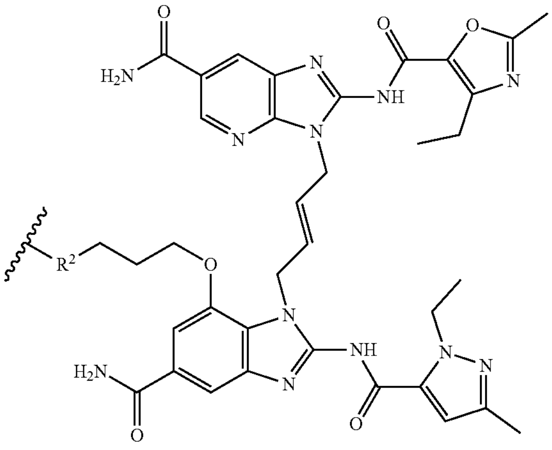
;
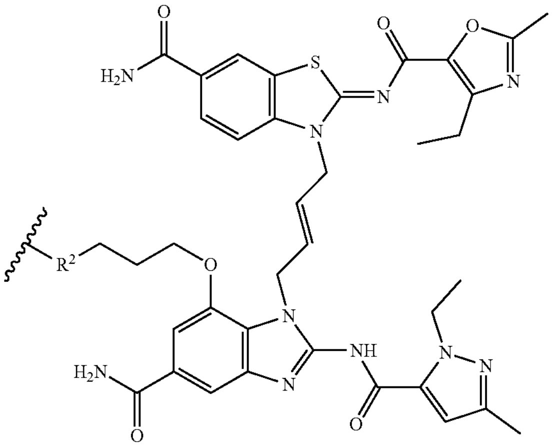
;
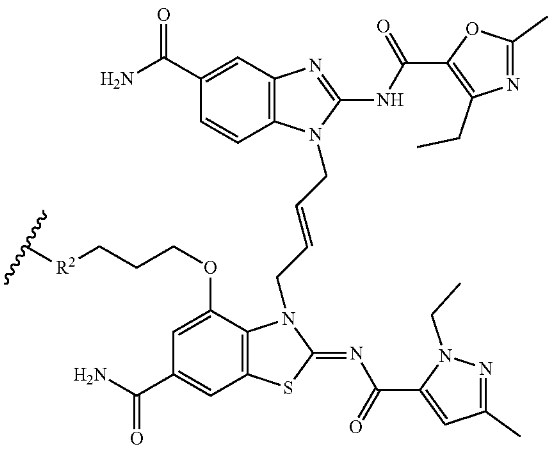
;
-continued
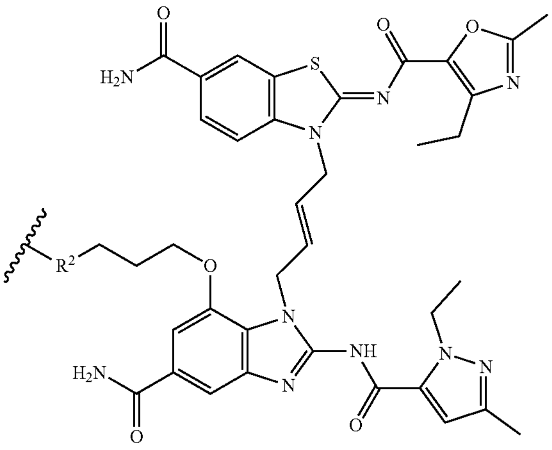
;
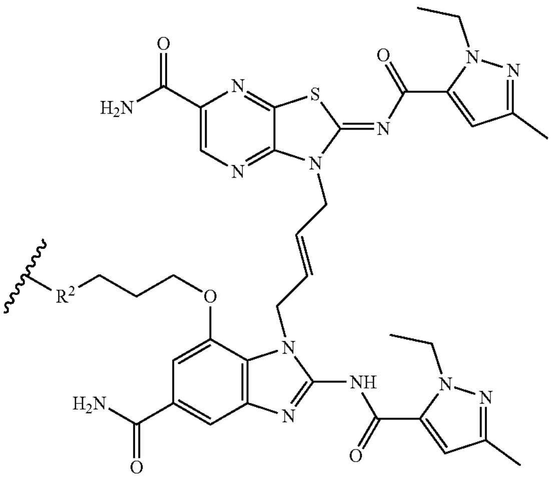
;
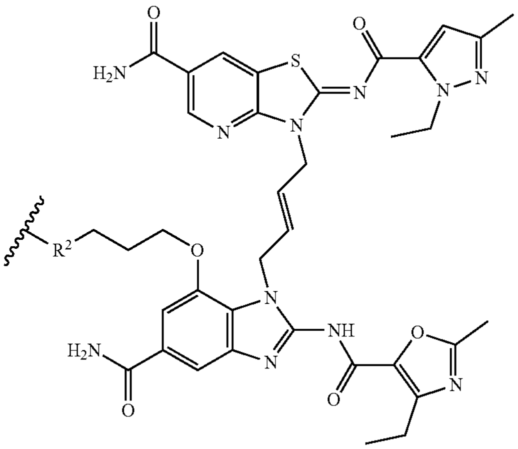
; or -continued
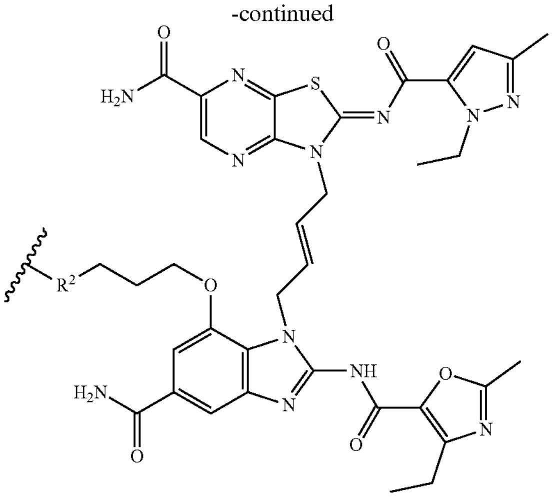
;
wherein:
$R^2$ is absent, —O— or —$NR^4$—; $R_4$ is H or $C_{1-3}$ alkyl; and
denotes attachment to $L^D$.
In some embodiments, each STING agonist drug moiety (D) independently is:
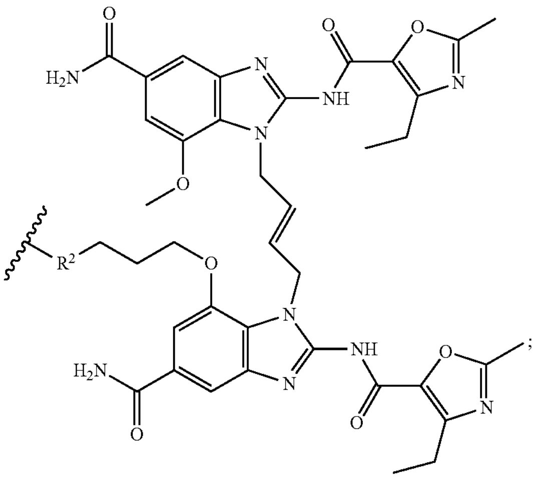
;
-continued
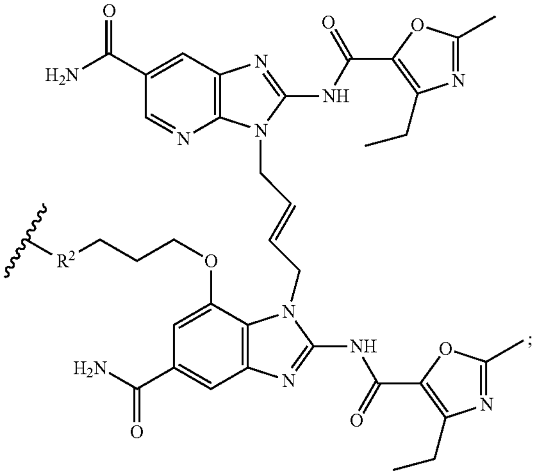
;
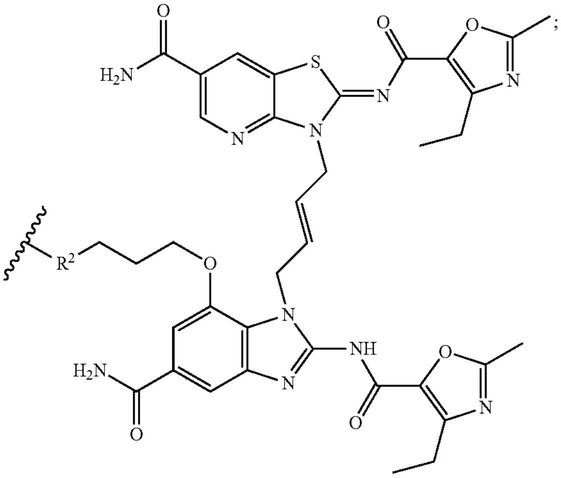
;
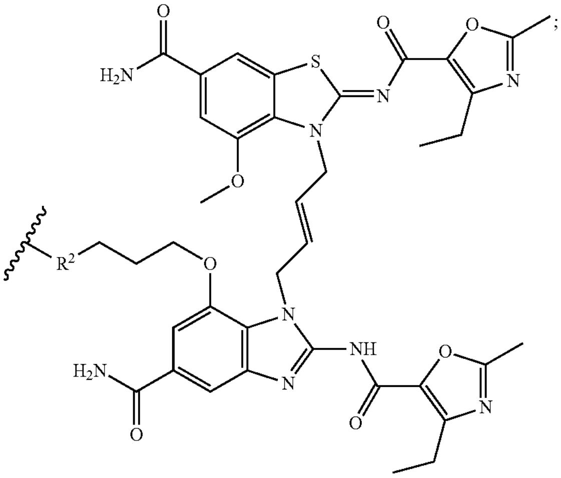
;

-continued
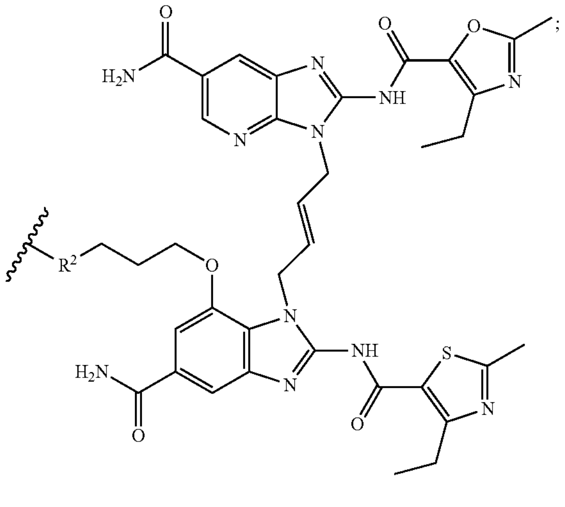
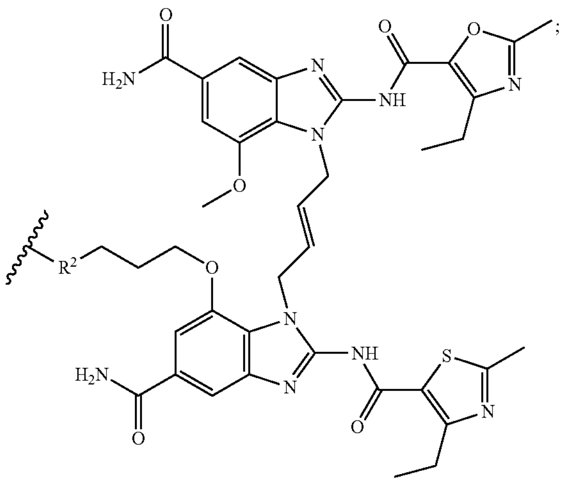
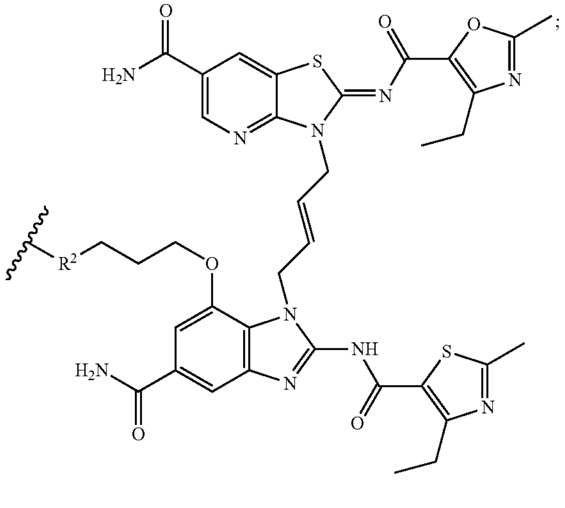
-continued
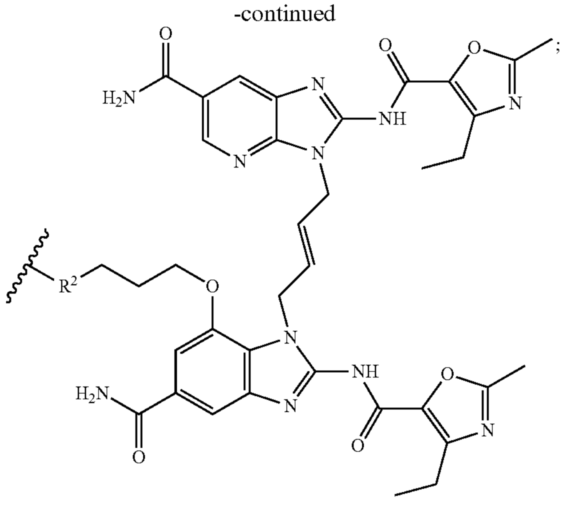
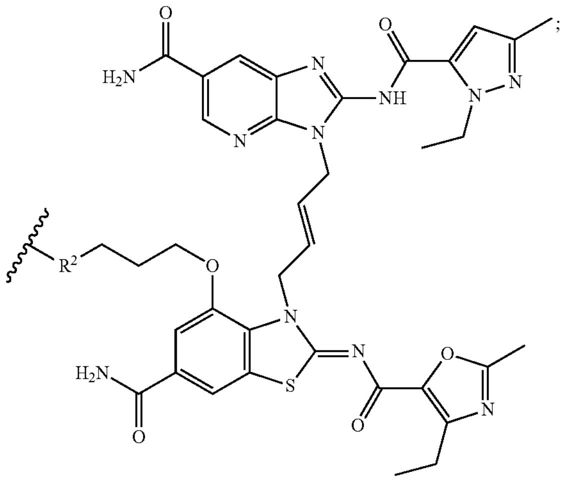
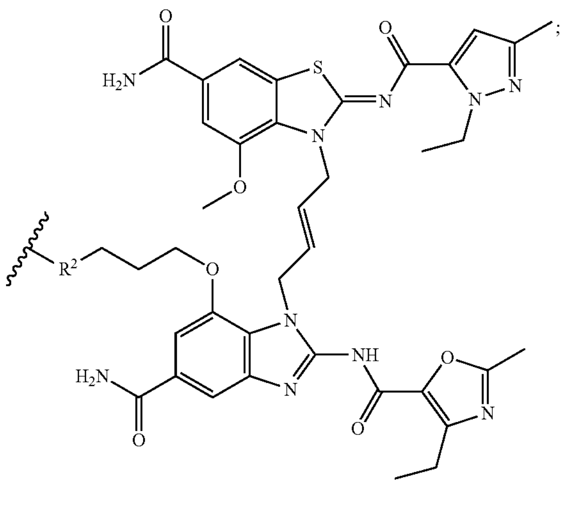

-continued
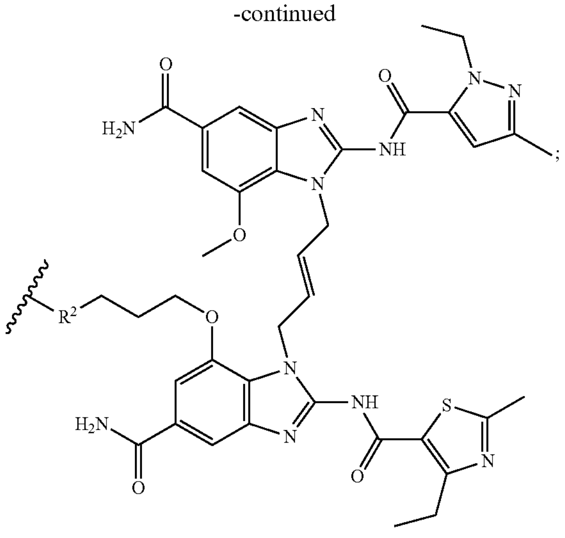
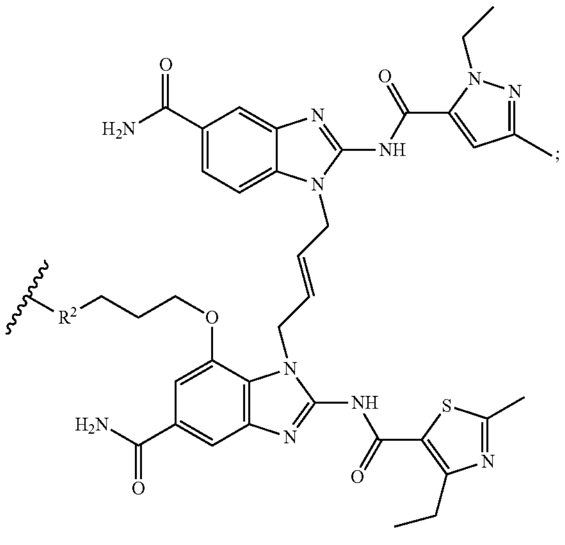
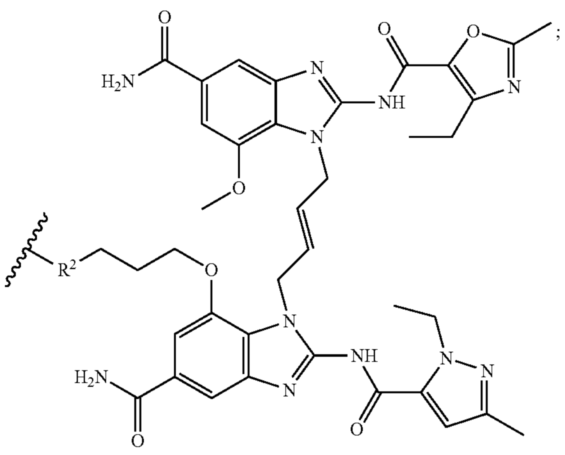
-continued
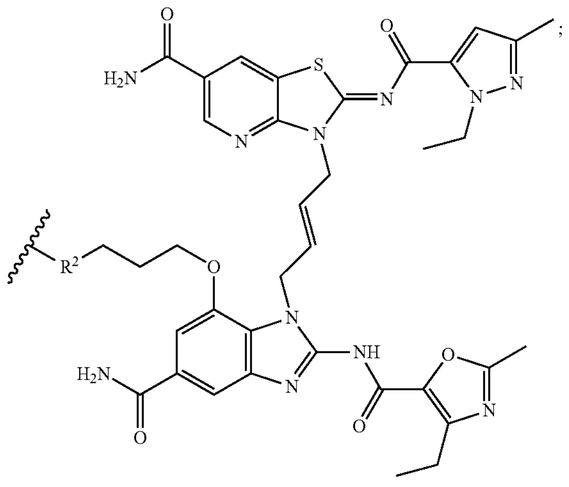
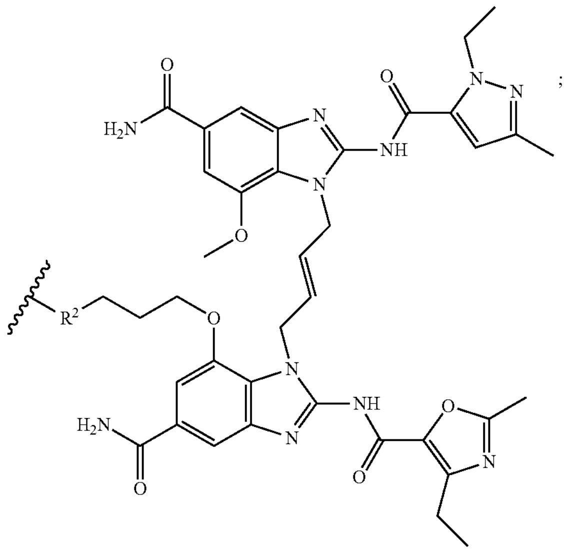
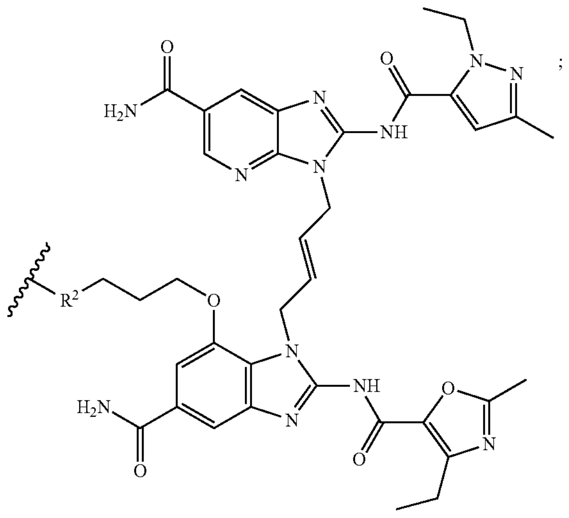

-continued
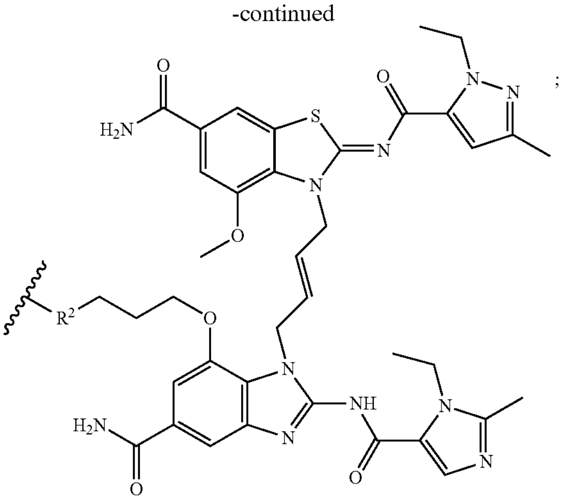
;
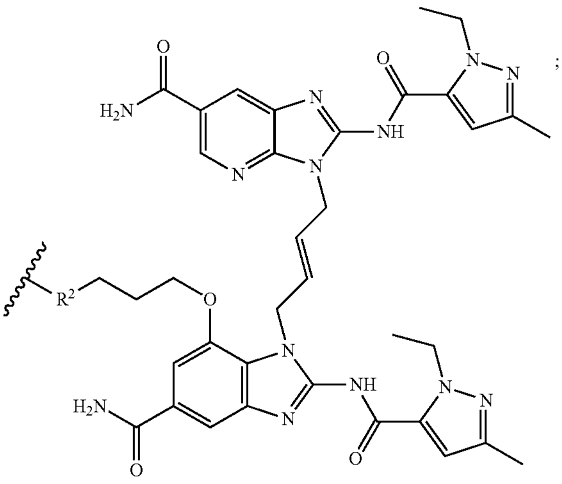
;
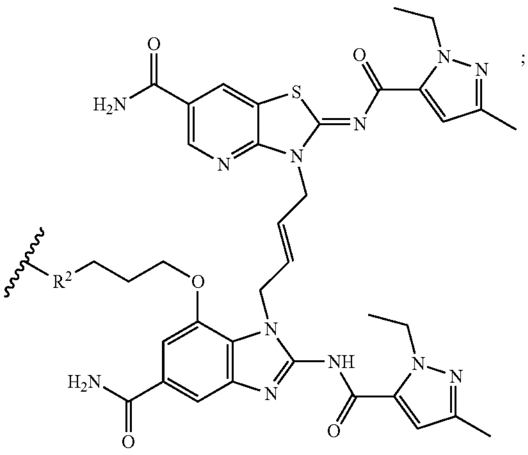
; or
-continued
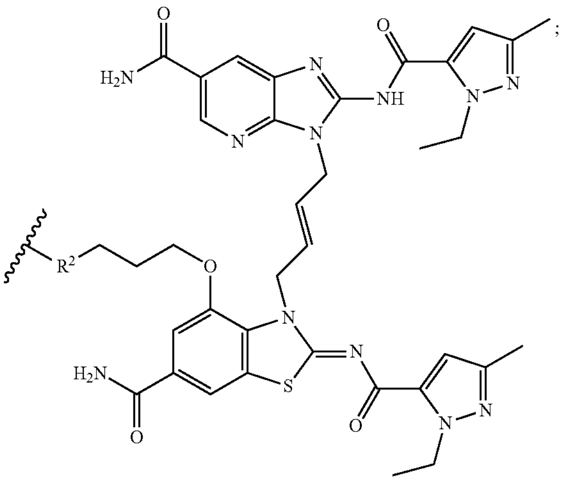
;
wherein:
$R^2$ is absent, —O— or —$NR^4$—; $R^4$ is H or $C_{1-3}$ alkyl; and
denotes attachment to $L^D$.
In some embodiments, each STING agonist drug moiety (D) independently is:
wherein:
$R^2$ is absent, —O— or —$NR^4$—; $R_4$ is H or $C_{1-3}$ alkyl; and
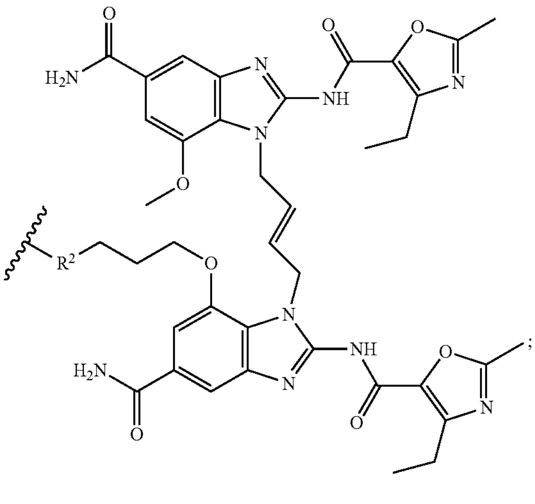
;

-continued
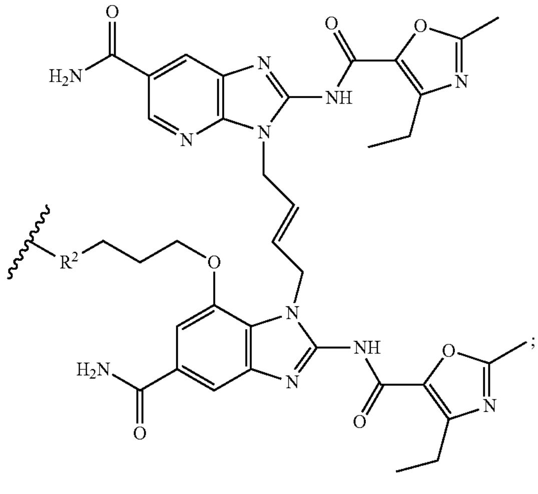
;
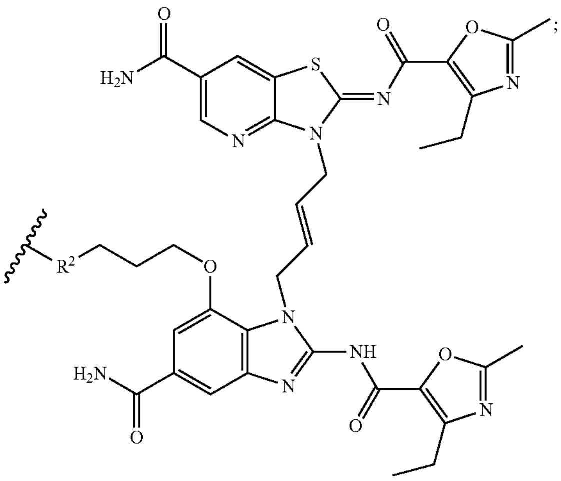
;
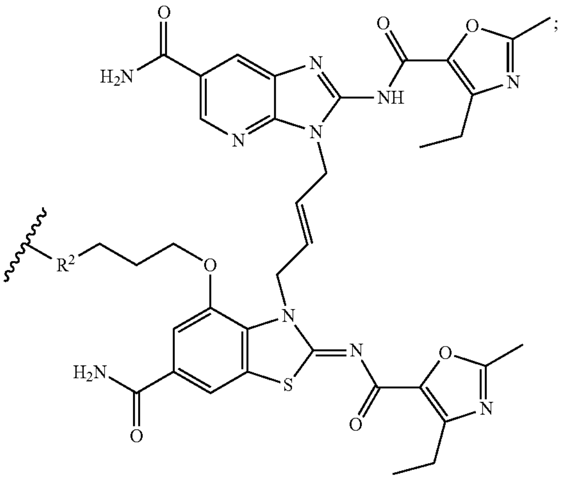
;
-continued
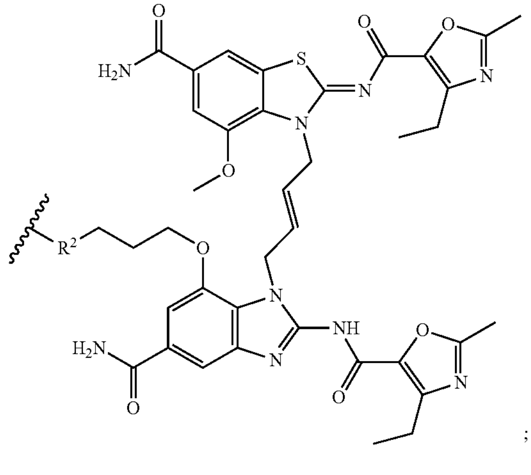
; or
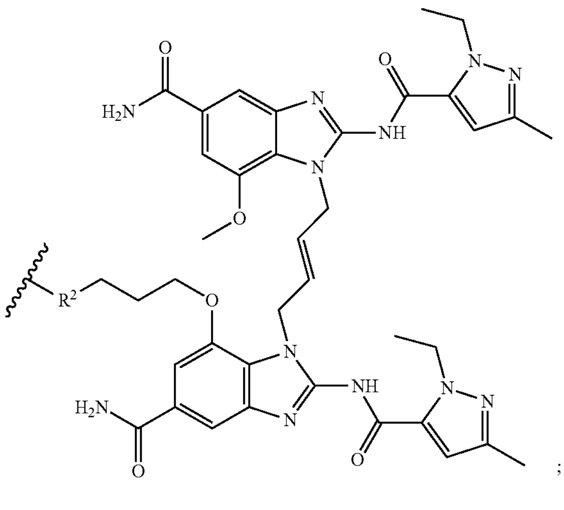
;
denotes attachment to $L^D$.
In some embodiments, each STING agonist drug moiety (D) independently is:
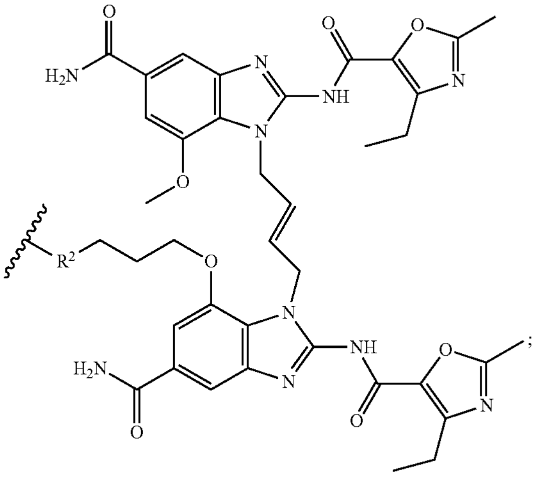
;

-continued
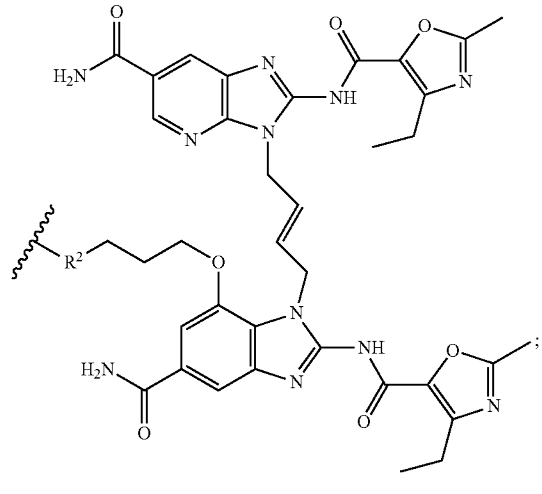
;
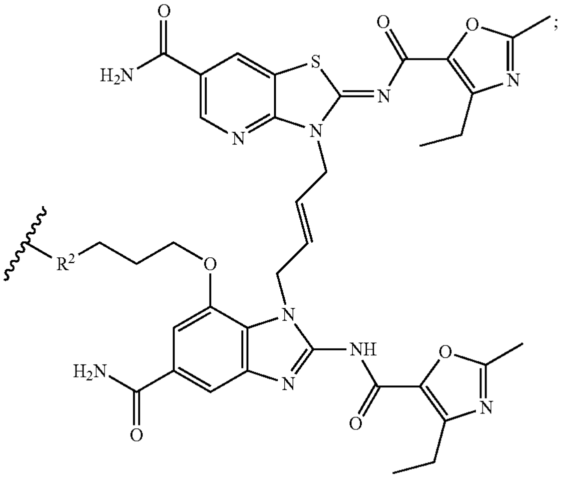
;
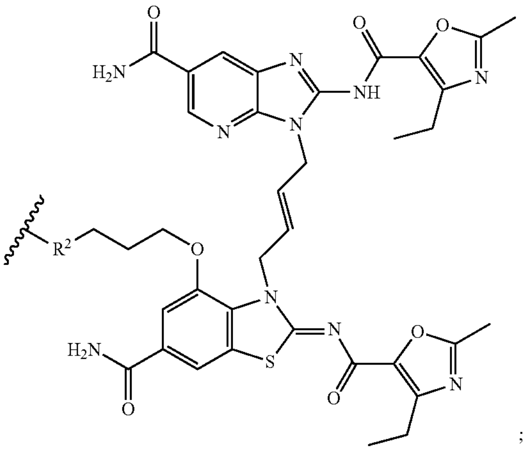
; or
-continued
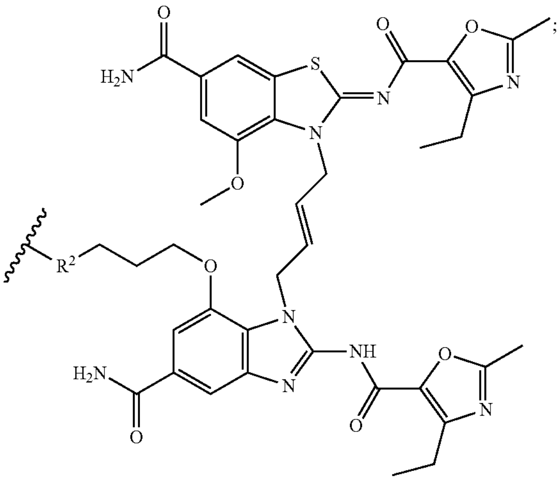
;
wherein:
$R^2$ is absent, —O— or —$NR^4$—; $R^4$ is H or $C_{1-3}$ alkyl; and
denotes attachment to $L^D$.
In some embodiments, each STING agonist drug moiety (D) independently is:
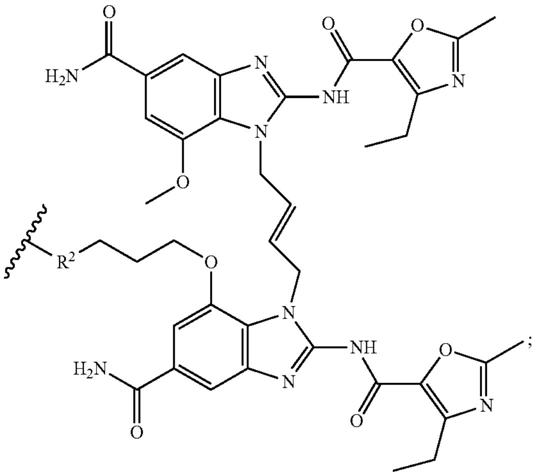
;

-continued

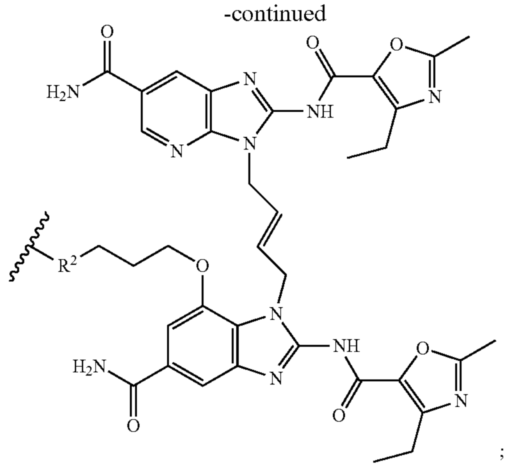

; or

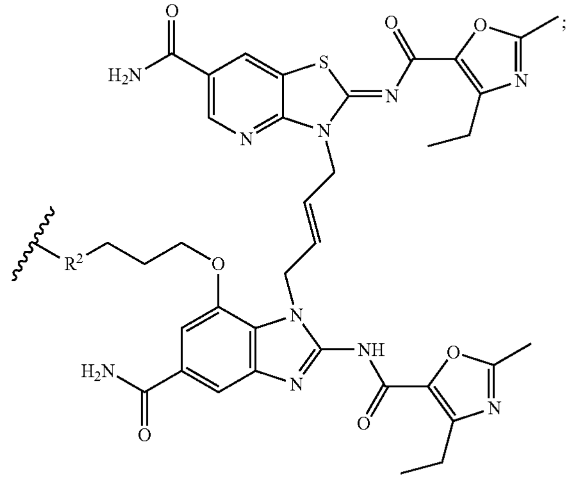

;

wherein:

$R^2$ is absent, —O— or —$NR^4$—; $R^4$ is H or $C_{1-3}$ alkyl; and denotes attachment to $L^D$.

Protein-Based Recognition-Molecule (PBRM)

In some embodiments, protein-based recognition molecule directs the conjugates to specific tissues, cells, or locations in a cell. In some embodiments, the protein-based recognition molecule can direct the conjugate in culture or in a whole organism, or both. In each case, the protein-based recognition molecule may have a ligand that is present on the cell surface of the targeted cell(s) to which it binds with an effective specificity, affinity, and avidity. In some embodiments, the protein-based recognition molecule targets the conjugate to tissues other than the liver. In some embodiments the protein-based recognition molecule targets the conjugate to a specific tissue such as the liver, kidney, lung, or pancreas. The protein-based recognition molecule can target the conjugate to a target cell such as a cancer cell, such as a receptor expressed on a cell such as a cancer cell, a matrix tissue, or a protein associated with cancer such as tumor antigen. Alternatively, cells comprising the tumor vasculature may be targeted. The protein-based recognition molecules can direct the conjugate to specific types of cells such as specific targeting to hepatocytes in the liver as opposed to Kupffer cells. In some embodiments, protein-based recognition molecules can direct the conjugate to cells of the reticular endothelial or lymphatic system, or to professional phagocytic cells such as macrophages or eosinophils. In some embodiments, the conjugate itself may also be an effective delivery system, without the need for specific targeting.

In some embodiments, the protein-based recognition molecule can target the conjugate to a location within the cell, such as the nucleus, the cytoplasm, or the endosome, for example. In some embodiments, the protein-based recognition molecule can enhance cellular binding to receptors, or cytoplasmic transport to the nucleus and nuclear entry or release from endosomes or other intracellular vesicles.

In some embodiments, the protein-based recognition molecule is an antibody, an antibody fragment, a protein, a peptide, or a peptide mimic.

In some embodiments, the protein-based recognition molecule is an antibody. In some embodiments, the protein-based recognition molecule is an antibody fragment. In some embodiments, the protein-based recognition molecule is a protein. In some embodiments, the protein-based recognition molecule is a peptide. In some embodiments, the protein-based recognition molecule is a peptide mimic.

In some embodiments, the antibody or antibody fragment is an antibody or antibody fragment wherein one or more amino acids of the corresponding parent antibody or antibody fragment (e.g., the corresponding wild type antibody or antibody fragment) are substituted with cysteines (e.g., engineered cysteine). In some embodiments, the parent antibody or antibody fragment may be wild type or mutated.

In some embodiments, the antibody or antibody fragment may be a mutated antibody or antibody fragment. In some embodiments, a monoclonal antibody known in the art is engineered to form the antibody. In some embodiments, an antibody fragment (e.g., a Fab antibody fragment) known in the art is engineered to form the antibody fragment (e.g., a cysteine engineered Fab antibody fragment). In some embodiments, a single site mutation of a Fab gives a single residue in a Fab whereas a single site mutation in an antibody yields two amino acids in the resulting antibody due to the dimeric nature of the IgG antibody.

In some embodiments, the antibody or antibody fragment retains the antigen binding capability of its corresponding wild type antibody or antibody fragment. In some embodiments, the antibody or antibody fragment is capable of binding to the one or more antigens for its corresponding wild type antibody or antibody fragment.

In some embodiments, exemplary antibodies or antibodies derived from Fab, Fab2, scFv or camel antibody heavy-chain fragments specific to the cell surface markers, include, but are not limited to, 5T4, AOC3, ALK, AXL, B7-H4, C242, C4.4a, CA-125, CCL11, CCR 5, CD2, CD3, CD4, CD5, CD15, CA15-3, CD18, CD19, CA19-9, CDH6, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD103, CD138, CD141, CD147, CD152, CD 154, CD326, CEA, CEACAM-5, clumping factor, Clec9A, CSFR1, CTLA-4, CXCR2, DEC205, EGFR (HER1), ErbB1, ErbB2, ErbB3, EpCAM, EPHA2, EPHB2, EPHB4, FAP, FGFR (i.e. FGFR1, FGFR2, FGFR3, FGFR4), FLT3, fibronectin-EDB, folate receptor, GD2, GD3, GPNMB, GCC (GUCY2C), HGF, HER2, HER3, HMI.24, ICAM, ICOS-L, IGF-1 receptor, VEGFR1, EphA2, TRPV1, CFTR, gpNMB, CA9, Cripto, c-KIT, c-MET, ACE, APP, adrenergic receptor-beta2, Claudine 3, LIV1, LY6E, Mesothelin, MUC1, MUC13, NaPi2b, NOTCH1, NOTCH2, NOTCH3, NOTCH4, RON, ROR1, PD-L1, PD-L2, PTK7, B7-H3, B7-B4, IL-2 receptor, IL-4 receptor, IL-13 receptor, TROP-2, frizzled-7, integrins (including $\alpha_4$, $\alpha_v\beta_3$, $\alpha_v\beta_5$, $\alpha_v\beta_6$, $\alpha_1\beta_4$, $\alpha_4\beta_1$, $\alpha_4\beta_7$, $\alpha_5\beta_1$, $\alpha_6\beta_4$, $\alpha_{IIb}\beta_3$ integrins), IFN-$\alpha$, IFN-$\gamma$, IgE, IgE, IGF-1 receptor, IL-1, IL-12, IL-23, IL-13, IL-22, IL-4, IL-5, IL-6, interferon receptor, ITGB2

(CD18), LFA-1 (CD11a), CD11b, L-selectin (CD62L), mucin, myostatin, NCA-90, NGF, PDGFRα, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-β2, TGF-β, TNF-α, TRAIL-R1, TRAIL-R2, tumor antigen CTAA16.88, VEGF-A, VEGFR2, vimentin, and the like.

In some embodiments the antibodies or antibody derived from Fab, Fab2, scFv or camel antibody heavy-chain fragments specific to the cell surface markers include CA-125, C242, CD3, CD11b, CD19, CD22, CD25, CD30, CD31, CD33, CD37, CD40, CD44, CD51, CD54, CD56, CD62E, CD62P, CD62L, CD70, CD103, CD138, CD141, CD326, CEA, Clec9A, CSFR1, CTLA-4, DEC205, EGFR (HER1), ErbB2, ErbB3, FAP, fibronectin-EDB, folate receptor, IGF-1 receptor, GD3, GPNMB, HGF, HER2, VEGF-A, VEGFR2, VEGFR1, EphA2, EpCAM, 5T4, PTK7, TAG-72, tenascin C, TRPV1, CFTR, gpNMB, CA9, Cripto, ACE, APP, PDGFR α, phosphatidylserine, prostatic carcinoma cells, adrenergic receptor-beta2, Claudine 3, mucin, MUC1, NaPi2b, B7H3, B7H4, C4.4a, CEACAM-5, MUC13, TROP-2, frizzled-7, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ intergins), tenascin C, TRAIL-$R^2$, and vimentin.

In some embodiments, the antibodies are directed to cell surface markers for 5T4, CA-125, CEA, CDH6, CD3, CD11b, CD19, CD20, CD22, CD30, CD33, CD40, CD44, CD51, CD-103, CTLA-4, CEACAM5, Clec9A, CSFR1, DEC205, EpCAM, HER2, EGFR (HER1), FAP, fibronectin-EDB, folate receptor, GCC (GUCY2C), HGF, integrin $\alpha_v\beta_3$, integrin $\alpha_5\beta_1$, IGF-1 receptor, GD3, GPNMB, mucin, LIV1, LY6E, mesothelin, MUC1, MUC13, NaPi2b, PTK7, phosphatidylserine, prostatic carcinoma cells, PDGFR α, TAG-72, tenascin C, TRAIL-$R^2$, VEGF-A and VEGFR2. In this embodiment the antibodies, include but are not limited to, abagovomab, adecatumumab, alacizumab, altumomab, anatumomab, arcitumomab, bavituximab, bevacizumab (AVASTIN®), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN©), rilotumumab, robatumumab, satumomab, sibrotuzumab, taplitumomab, tenatumomab, tenatumomab, ticilimumab (tremelimumab), tigatuzumab, trastuzumab (HERCEPTIN©), tositumomab, tremelimumab, tucotuzumab celmoleukin, volociximab, and zalutumumab.

In some embodiments the antibodies directed to cell surface markers for HER2 are pertuzumab or trastuzumab and for EGFR (HER1) the antibody is cetuximab or panitumumab; and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In some embodiments, the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments, the protein-drug conjugates comprise broad spectrum cytotoxins in combination with cell surface markers for HER2, such as, for example, pertuzumab or trastuzumab; for EGFR such as cetuximab and panitumumab; for CEA such as labetuzumab; for CD20 such as rituximab; for VEGF-A such as bevacizumab; or for CD-22 such as epratuzumab or veltuzumab.

In some embodiments, the protein-drug conjugates or protein conjugates used in the disclosure comprise combinations of two or more protein-based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3-CD19 plus CD28-CD22 bispecific antibodies.

In some embodiments, the protein-drug conjugates or protein conjugates used in the disclosure comprise protein-based recognition molecules are antibodies against antigens, such as, for example, Trastuzumab, Cetuximab, Rituximab, Bevacizumab, Epratuzumab, Veltuzumab, Labetuzumab, B7-H4, B7-H3, CD11b, CD103, CA125, CDH6, CD33, CXCR2, CEACAM5, Clec9A, CSFR1, DEC205, EGFR, FAP, fibronectin-EDB, FGFR1, FGFR2, FGFR3, FGFR4, GCC (GUCY2C), HER2, LIV1, LY6E, NaPi2b, c-Met, mesothelin, NOTCH1, NOTCH2, NOTCH3, NOTCH4, PD-L1, PTK7, c-Kit, MUC1, MUC13. and 5T4.

In some embodiments, the protein-drug conjugates or protein conjugates of the disclosure comprise protein-based recognition molecules which are CSRF1, CD11b, DEC205, clec9A, CD103, B7H4, mesothelin, PTK7, Ly6E, FAP, fibronectin-EDB, Her-2 or NaPi2b antibodies.

NaPi2b Antibodies

In some embodiments, the NaPi2b antibodies suitable for conjugation bind to the extracellular region of SLC34A2. In some embodiments, the present disclosure provides NaPi2b-targeted monoclonal antibodies that specifically recognizes NaPi2b, also known as sodium-dependent phosphate transport protein 2B. In some embodiments, the NaPi2b antibodies used in the conjugates disclosed herein are capable of and useful in modulating, e.g., blocking, inhibiting, reducing, antagonizing, neutralizing or otherwise interfering with at least one biological activity of NaPi2b. In some embodiments, antibodies disclosed herein also include antibodies that bind soluble NaPi2b. In some embodiments, the NaPi2b antibodies specifically bind to an epitope on an extracellular domain (ECD) of the human NaPi2b. These antibodies are collectively referred to herein as "NaPi2b" antibodies.

In some embodiments, the NaPi2b antibody-drug conjugates provided herein include antibodies that bind to a NaPi2b epitope with an equilibrium dissociation constant ($K_d$ or $K_D$) of ≤1 μM (e.g., ≤100 nM; ≤10 nM; and ≤1 nM). In some embodiments, the NaPi2b antibodies used in the antibody-drug conjugates disclosed herein exhibit a $K_d$ in the range approximately between ≤1 nM to about 1 pM.

In some embodiments, the NaPi2b antibody-drug conjugates provided herein can include antibodies that serve to modulate, block, inhibit, reduce, antagonize, neutralize, or otherwise interfere with the functional activity of NaPi2b. In some embodiments, functional activities of NaPi2b include for example, participating in the transcellular inorganic phosphate (Pi) absorption, thereby contributing to the maintenance of phosphate homeostasis in the body. In some embodiments, the NaPi2b antibodies completely or partially inhibit NaPi2b functional activity by partially or completely modulating, blocking, inhibiting, reducing antagonizing, neutralizing, or otherwise interfering with transcellular inorganic phosphate absorption.

In some embodiments, the NaPi2b antibodies are considered to completely modulate, block, inhibit, reduce, antagonize, neutralize, or otherwise interfere with NaPi2b functional activity when the level of NaPi2b functional activity in the presence of the NaPi2b antibody is decreased by at least 95%, e.g., by 96%, 97%, 98%, 99%, or 100% as compared to the level of NaPi2b functional activity in the absence of binding with a NaPi2b antibody described herein. In some embodiments, the NaPi2b antibodies are considered to partially modulate, block, inhibit, reduce, antagonize, neutralize or otherwise interfere with NaPi2b functional activity when the level of NaPi2b activity in the presence of the NaPi2b antibody is decreased by less than 95%, e.g., 10%, 20%, 25%, 30%, 40%, 50%, 60%, 75%, 80%, 85% or 90% as compared to the level of NaPi2b activity in the absence of binding with a NaPi2b antibody described herein.

In some embodiments, exemplary antibodies disclosed herein include, the XMT-1535 antibody. These antibodies show specificity for human NaPi2b and they have been shown to inhibit NaPi2b activity.

NaPi2b human or humanized monoclonal antibody, XMT-1535, includes a heavy chain (HC), heavy chain variable region (VH), light chain (LC), and a light chain variable region (VL), as shown in the amino acid and corresponding nucleic acid sequences presented in Table I below. The variable heavy chain region and variable light chain region for each antibody are shaded in the amino acid sequences below. The complementarity determining regions (CDRs) of the heavy chain and the light chain are underlined in the amino acid sequences presented below. The amino acids encompassing the complementarity determining regions (CDRs) for the XMT-1535 antibody are disclosed in U.S. Pat. No. 8,603,474.

TABLE I

NaPi2b human or humanized monoclonal antibody XMT-1535 sequences

| SEQ ID NO: | Sequence Description |
|---|---|
| 1 | XMT-1535 Heavy Chain Amino Acid Sequence |
| 2 | XMT-1535 Light Chain Amino Acid Sequence |
| 3 | XMT-1535 Heavy chain variable region |
| 4 | XMT-1535 Light chain variable region |
| 5 | XMT-1535 CDRH1 |
| 6 | XMT-1535 CDRH2 |
| 7 | XMT-1535 CDRH3 |
| 8 | XMT-1535 CDRL1 |
| 9 | XMT-1535 CDRL2 |
| 10 | XMT-1535 CDRL3 |
| 11 | XMT-1535 IgG1 Heavy chain constant region |
| 12 | XMT-1535 Light chain constant region |
| 13 | XMT-1535 Heavy chain variable region nucleic acid sequence |

TABLE I-continued

NaPi2b human or humanized monoclonal antibody XMT-1535 sequences

| SEQ ID NO: | Sequence Description |
|---|---|
| 14 | XMT-1535 Light chain variable region nucleic acid sequence |
| 15 | Full-length human NaPi2b sequence |

Antibodies disclosed herein specifically bind to an epitope on an extracellular domain (ECD) of the human NaPi2b.

In some embodiments, those skilled in the art will recognize that it is possible to determine, without undue experimentation, if a monoclonal antibody has the same specificity as a monoclonal antibody disclosed herein (e.g., XMT-1535, 10H1.11.4B) by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

An alternative method for determining whether a monoclonal antibody has the specificity of monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. If the monoclonal antibody being tested is inhibited then, in all likelihood, it has the same, or functionally equivalent, epitopic specificity as the monoclonal antibody disclosed herein.

Screening of monoclonal antibodies disclosed herein, can also be carried out, e.g., by measuring NaPi2b-mediated activity, and determining whether the test monoclonal antibody is able to modulate, block, inhibit, reduce, antagonize, neutralize or otherwise interfere with NaPi2b activity.

In some embodiments, the antibodies disclosed herein comprise a heavy chain variable region having an amino acid sequence at least 85%, 86%, 87% 88%, 89%, 90%, 91%, 92%, 93%, 94%, 95%, 96%, 97% 98%, 99% or more identical to a sequence selected from SEQ ID NOs: 3 and a light chain variable region having an amino acid sequence at least 85%, 86%, 87% 88%, 89%, 90%, 91%, 92%, 93%, 94%, 95%, 96%, 97% 98%, 99% or more identical to a sequence selected from SEQ ID NOs: 4.

In some embodiments, the antibodies disclosed herein comprise a heavy chain amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 1 and a light chain amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 2.

In some embodiments, the antibodies disclosed herein comprise the heavy chain variable region amino acid sequence of SEQ ID NO: 3 and the light chain variable region amino acid sequence of SEQ ID NO: 4.

In some embodiments, the antibodies disclosed herein comprise the heavy chain amino acid sequence of SEQ ID NO: 1 and the light chain amino acid sequence of SEQ ID NO: 2.

In some embodiments, the antibodies disclosed herein comprise the CDRH1 amino acid sequence of SEQ ID NO:

5, the CDRH2 amino acid sequence of SEQ ID NO: 6, the CDRH3 amino acid sequence of SEQ ID NO: 7, the CDRL1 amino acid sequence of SEQ ID NO: 8, the CDRL2 amino acid sequence of SEQ ID NO: 9, and the CDRL3 amino acid sequence of SEQ ID NO: 10.

In some embodiments, the antibodies disclosed herein that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 5; a CDRH2 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 6; a CDRH3 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 7; a CDRL1 that comprises the amino acid sequence at 85%, 86%, 87% 88%, 89%, 90%, 91%, 92%, 93%, 94%, 95%, 96%, 97% 98%, 99% or more identical to the amino acid sequence of SEQ ID NO: 8; a CDRL2 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 9; and a CDRL3 that comprises the amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 10.

In some embodiments, the antibodies disclosed herein include one or more conservative amino acid substitutions in a variable domain sequence such as 1, 2, 3, 4, 5, 6, 7, 8, 9, 10, 11, 12, 13, 14, 15, or more conservative substitutions in a variable domain sequence. In some embodiments, these conservative amino acid substitutions are in a CDR region, e.g., 1, 2, 3, 4, 5, 6, 7, 8, 9, 10, 11, 12, 13, 14, 15, or more conservative substitutions are made cumulatively across all CDRs and in some particular embodiments, up to 1, 2, 3, or 4 conservative amino acid substitutions may be present in each CDR sequence, e.g., SEQ ID NOs: 5-10.

In some embodiments, those skilled in the art will recognize that it is possible to determine, without undue experimentation, if a monoclonal antibody has the same specificity as a monoclonal antibody XMT-1535, by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

In some embodiments, an alternative method for determining whether a monoclonal antibody has the specificity of a monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. In some embodiments, if the monoclonal antibody being tested is inhibited then it has the same, or functionally equivalent, epitopic specificity as the monoclonal antibody disclosed herein.

Screening of monoclonal antibodies disclosed herein, can be also carried out, e.g., by measuring NaPi2b-mediated activity, and determining whether the test monoclonal antibody is able to modulate, block, inhibit, reduce, antagonize, neutralize or otherwise interfere with NaPi2b activity.

In some embodiments, the NaPi2b antibodies suitable for conjugation can be generated and purified by well-known techniques e.g., WO 2009/097128, WO 2017/160754, and U.S. Ser. No. 16/136,706, each of which is incorporated herein in its entirety by reference.

HER2 Antibodies

In some embodiments, the HER2 antibodies suitable conjugation bind the human HER2 in soluble form, or membrane bound (i.e., when expressed on a cell surface). In some embodiments, the present disclosure provides monoclonal antibodies that bind HER2 and are humanized or fully human. In some embodiments, the present disclosure provides monoclonal antibodies that bind HER2 specifically. These antibodies are collectively referred to herein as "HER2" antibodies.

In some embodiments, the HER2 antibodies suitable for conjugation bind to a HER2 epitope with an equilibrium dissociation constant ($K_d$ or $K_D$) of ≤1 μM (e.g., ≤100 nM; ≤10 nM; ≤1 nM). In some embodiments, the present disclosure provides monoclonal antibodies that bind HER2 and are humanized or fully human. for example, the HER2 antibodies provided herein exhibit a $K_d$ in the range approximately between ≤1 nM to about 1 pM.

In some embodiments, the HER2 antibodies disclosed herein serve to modulate, block, inhibit, reduce, antagonize, neutralize, or otherwise interfere with the functional activity of HER2. HER2. In some embodiments, functional activities of HER2 include for example, modulation of PI3K-Akt pathway activity. In some embodiments, the HER2 antibodies completely or partially inhibit HER2 functional activity by partially or completely modulating, blocking, inhibiting, reducing antagonizing, neutralizing, or otherwise interfering with PI3K-Akt pathway activity. PI3K-Akt pathway activity is assessed using any art-recognized method for detecting PI3K-Akt pathway activity, including, but not limited to detecting levels of phosphorylated Akt in the presence and absence of an antibody or antigen binding fragment disclosed herein.

In some embodiments, the HER2 antibodies are considered to completely modulate, block, inhibit, reduce, antagonize, neutralize, or otherwise interfere with HER2 functional activity when the level of HER2 functional activity in the presence of the HER2 antibody is decreased by at least 80%, e.g., by 81%, 82%, 83%, 84%, 85%, 86%, 87%, 88%, 89%, 90%, 91%, 92%, 93%, 94%, 95%, 96%, 97%, 98%, 99%, or 100% as compared to the level of HER2 functional activity in the absence of binding with a HER2 antibody described herein. In some embodiments, the HER2 antibodies are considered to partially modulate, block, inhibit, reduce, antagonize, neutralize, or otherwise interfere with HER2 functional activity when the level of HER2 activity in the presence of the HER2 antibody is decreased by less than 95%, e.g., 10%, 20%, 25%, 30%, 40%, 50%, 60%, 75%, 80%, 85%, or 90% as compared to the level of HER2 activity in the absence of binding with a HER2 antibody described herein.

In some embodiments, exemplary antibodies disclosed herein include, the XMT-1519 antibody. This antibody show specificity for human HER2 and they have been shown to inhibit the functional activity of HER2 in vitro.

HER-2 monoclonal antibody XMT-1519 includes a heavy chain (HC), heavy chain variable region (VH), light chain (LC), and a light chain variable region (VL), as shown in the amino acid and corresponding nucleic acid sequences presented in Table II below. The variable heavy chain region and variable light chain region for each antibody are shaded in the amino acid sequences below. The complementarity determining regions (CDRs) of the heavy chain and the light chain are underlined in the amino acid sequences presented below.

TABLE II

| HER2 human or humanized monoclonal antibody XMT-1519 sequences | |
|---|---|
| SEQ ID NO: | Sequence Description |
| 16 | Full-length human HER2 receptor |
| 17 | XMT-1519 Heavy chain variable region |
| 18 | XMT-1519 IgG1 Heavy chain constant region |
| 19 | XMT-1519 Heavy Chain Amino Acid Sequence |
| 20 | XMT-1519 CDRH1 |
| 21 | XMT-1519 CDRH2 |
| 22 | XMT-1519 CDRH3 |
| 23 | XMT-1519 Heavy Chain variable region nucleic acid sequence |
| 24 | XMT-1519 Light chain variable region |
| 25 | XMT-1519 Light chain constant region |
| 26 | XMT-1519 Light Chain Amino Acid Sequence |
| 27 | XMT-1519 CDRL1 |
| 28 | XMT-1519 CDRL2 |
| 29 | XMT-1519 CDRL3 |
| 30 | XMT-1519 Light Chain variable region nucleic acid sequence |
| 31 | Extracellular domain (ECD) of the human HER2 receptor |

Antibodies and antigen binding fragments thereof disclosed herein specifically bind to an epitope on the full-length human HER2 receptor comprising the amino acid sequence of SEQ ID NO: 16.

Antibodies and antigen binding fragments thereof disclosed herein specifically bind to an epitope on the extracellular domain (ECD) of the human HER2 receptor comprising the amino acid sequence of SEQ ID NO: 31.

In some embodiments, the antibodies of the present disclosure exhibit HER2 binding characteristics that differ from antibodies described in the art. In some embodiments, the antibodies disclosed herein bind to a different epitope of HER2, in that they cross-block each other but not trastuzumab, pertuzumab, Fab37, or chA21 from binding to HER2. Further, as opposed to the known antibodies, the antibodies disclosed herein can internalize efficiently into HER2-expressing cells without promoting cell proliferation.

In some embodiments, the antibodies disclosed herein are fully human monoclonal antibodies that bind to novel epitopes and/or have other favorable properties for therapeutic use. In some embodiments, exemplary properties include, but are not limited to, favorable binding characteristics to cancer cells expressing human HER2 at high or low levels, specific binding to recombinant human and cynomolgus monkey HER2, efficient internalization upon binding to HER2, high capacity for killing cancer cells expressing high or low levels of HER2 when administered as an antibody drug conjugate (ADC), no substantial agonistic effect on the proliferation of HER2-expressing cancer cells, and/or provide for effective antibody-dependent cellular cytotoxicity (ADCC)-mediated killing of HER2-expressing cells, as well as any combination of the foregoing properties.

In some embodiments, the antibodies disclosed herein also include an antibody or antigen binding fragment thereof that specifically binds to an epitope of the human HER2 receptor that includes residues 452 to 531 of the extracellular domain of the human HER2 receptor, residues 474 to 553 of SEQ ID NO: 16 or residues 452 to 531 of SEQ ID NO: 31.

In some embodiments, the antibodies disclosed herein include an antibody or an antigen binding fragment thereof that binds at least a portion of the N-terminus of domain IV of human HER2 receptor but does not cross-compete with an antibody that binds to epitope 4D5 of the human HER2 receptor. In some embodiments, the antibodies or antigen binding fragments thereof described herein do not cross-compete with trastuzumab for binding to the human HER2 receptor, as trastuzumab is known to bind epitope 4D5 of the human HER2 receptor. As used herein, the term epitope 4D5 of the human HER2 receptor refers to amino acid residues 529 to 627 of the extracellular domain of the human HER2 receptor, residues 551 to 649 of SEQ ID NO: 16 or residues 529 to 627 of SEQ ID NO: 31. In some embodiments, the antibody or antigen binding fragment thereof also binds at least one epitope on cynomolgus monkey HER2 receptor.

In some embodiments, the antibodies disclosed herein also include an antibody or antigen binding fragment thereof that specifically binds to an epitope of the human HER2 receptor that includes residues 452 to 500 of the extracellular domain of the human HER2 receptor, residues 474 to 522 of SEQ ID NO: 16 or residues 452 to 500 of SEQ ID NO: 31.

In some embodiments, the antibodies disclosed herein also include an antibody or antigen binding fragment thereof that specifically binds to an epitope of the human HER2 receptor that includes at least one of amino acid residue selected from amino acid residues E521, L525 and R530 of the extracellular domain of the human HER2 receptor, e.g., residues 543, 547, and 552 of SEQ ID NO: 16, and residues 521, 525, and 530 of SEQ ID NO: 31. In some embodiments, the antibodies disclosed herein include an antibody or antigen binding fragment thereof that specifically binds to an epitope of the extracellular domain of the human HER2 receptor that includes at least two amino acid residues selected from amino acid residues E521, L525 and R530 of the extracellular domain of the human HER2 receptor. In some embodiments, the antibodies disclosed herein also include an antibody or antigen binding fragment thereof that specifically binds to an epitope of the human HER2 receptor that includes at least amino acid residues E521, L525 and R530 of the extracellular domain of the human HER2 receptor. In some embodiments, any or all of these antibodies or antigen binding fragments thereof also bind at least one epitope on cynomolgus monkey HER2 receptor.

In some embodiments, antibodies disclosed herein also include an antibody or an antigen binding fragment thereof that binds to at least a portion of domain III and at least a portion of the N-terminus of domain IV of human HER2 receptor but does not cross-compete with Fab37 monoclonal antibody or an antibody that binds to epitope 4D5 of the human HER2 receptor. In some embodiments, the antibodies or antigen binding fragments thereof described herein do not cross-compete with the Fab37 monoclonal antibody and/or trastuzumab for binding to the human HER2 receptor. In some embodiments, the antibody or antigen binding fragment thereof also binds at least one epitope on cynomolgus monkey HER2 receptor.

In some embodiments, the antibodies disclosed herein also include an antibody or antigen binding fragment thereof that specifically binds to an epitope of the human HER2 receptor that includes residues 520 to 531 of the extracellular domain of the human HER2 receptor, residues 542 to 553 of SEQ ID NO: 16 or residues 520 to 531 of SEQ ID NO: 31.

In some embodiments, the antibodies disclosed herein also include an antibody or antigen binding fragment thereof that specifically binds to an epitope of the human HER2 receptor that includes at least one amino acid residue selected from residues C453, H456, H473, N476, R495, G496, H497, and W499 of the extracellular domain of the human HER2 receptor, e.g., residues 475, 478, 495, 498, 517, 518, 519, and 521 of SEQ ID NO: 16 or residues 453, 456, 473, 476, 495, 496, 497 and 499 of SEQ ID NO: 31. In some embodiments, the antibodies disclosed herein include an antibody or antigen binding fragment thereof that specifically binds to an epitope of the extracellular domain of the human HER2 receptor that includes at least two amino acid residues, at least three amino acid residues, at least four amino acid residues, at least five amino acid residues, or at least six amino acid residues selected from amino acid residues C453, H456, H473, N476, R495, G496, H497, and W499 of the extracellular domain of the human HER2 receptor. In some embodiments, the antibodies disclosed herein include an antibody or antigen binding fragment thereof that specifically binds to an epitope of the extracellular domain of the human HER2 receptor that includes at least amino acid residues C453, H456, H473, N476, R495, G496, H497, and W499 of the extracellular domain of the human HER2 receptor. In some embodiments, any or all of these antibodies or antigen binding fragments thereof also bind at least one epitope on cynomolgus monkey HER2 receptor.

In some embodiments, the antibodies disclosed herein also include an antibody or antigen binding fragment thereof that specifically binds to an epitope of the human HER2 receptor that includes at least one amino acid residue selected from residues C453, H473, N476, R495, H497, and W499 of the extracellular domain of the human HER2 receptor, e.g., residues 475, 495, 498, 517, 519, and 521 of SEQ ID NO: 16 or residues 453, 473, 476, 495, 497 and 499 of SEQ ID NO: 31. In some embodiments, the antibodies disclosed herein include an antibody or antigen binding fragment thereof that specifically binds to an epitope of the extracellular domain of the human HER2 receptor that includes at least two amino acid residues, at least three amino acid residues, at least four amino acid residues, at least five amino acid residues, or at least six amino acid residues selected from amino acid residues C453, H473, N476, R495, H497, and W499 of the extracellular domain of the human HER2 receptor. In some embodiments, the antibodies disclosed herein include an antibody or antigen binding fragment thereof that specifically binds to an epitope of the extracellular domain of the human HER2 receptor that includes at least amino acid residues C453, H473, N476, R495, H497, and W499 of the extracellular domain of the human HER2 receptor. In some embodiments, any or all of these antibodies or antigen binding fragments thereof also bind at least one epitope on cynomolgus monkey HER2 receptor.

In some embodiments, these antibodies show specificity for human HER2, and they have been shown to modulate, e.g., block, inhibit, reduce, antagonize, neutralize, or otherwise interfere with the PI3K-Akt pathway which promotes cell survival by reducing levels of phosphorylated AKT. In some embodiments, these antibodies internalize from the cell surface of HER2-expressing cells at a rate that is the same or substantially similar to the rate at which trastuzumab or a biosimilar thereof internalizes. In some embodiments, these antibodies and antigen binding fragments have a rate of internalization that is about 50% of the total surface bound at time 0 being internalized by 4 hours.

In some embodiments the antibodies disclosed herein comprise a heavy chain variable region having an amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to a sequence selected from SEQ ID NOs: 17 and a light chain variable region having an amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to a sequence selected from SEQ ID NOs: 24.

In some embodiments, the antibodies disclosed herein comprise a heavy chain amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to the amino acid sequence of SEQ ID NO: 19 and a light chain amino acid sequence at least 80%, 81%, 82%, 83%, 84%, 85%, 86%, 87% 88%, 89%, 90%, 91%, 92%, 93%, 94%, 95%, 96%, 97% 98%, 99% or more identical to the amino acid sequence of SEQ ID NO: 26.

In some embodiments, the antibodies disclosed herein comprise the heavy chain variable region amino acid sequence of SEQ ID NO: 17 and the light chain variable region amino acid sequence of SEQ ID NO: 24.

In some embodiments, the antibodies disclosed herein comprise the heavy chain amino acid sequence of SEQ ID NO: 19 and the light chain amino acid sequence of SEQ ID NO: 26.

In some embodiments, the antibodies disclosed herein comprise the CDRH1 amino acid sequence of SEQ ID NO: 20, the CDRH2 amino acid sequence of SEQ ID NO: 21, the CDRH3 amino acid sequence of SEQ ID NO: 22, the CDRL1 amino acid sequence of SEQ ID NO: 27, the CDRL2 amino acid sequence of SEQ ID NO: 28, and the CDRL3 amino acid sequence of SEQ ID NO: 29.

In some embodiments, the antibodies disclosed herein include one or more conservative amino acid substitutions in a variable domain sequence such as 1, 2, 3, 4, 5, 6, 7, 8, 9, 10, 11, 12, 13, 14, 15, or more conservative substitutions in a variable domain sequence. In some embodiments, these conservative amino acid substitutions are in a CDR region, e.g., 1, 2, 3, 4, 5, 6, 7, 8, 9, 10, 11, 12, 13, 14, 15, or more conservative substitutions are made cumulatively across all CDRs. In some embodiments, up to 1, 2, 3, or 4 conservative amino acid substitutions may be present in each CDR sequence, e.g., SEQ ID NOs: 20-22 and 27-29.

Those skilled in the art will recognize that it is possible to determine, without undue experimentation, if a monoclonal antibody has the same specificity as a monoclonal antibody XMT-1519, by ascertaining whether the former prevents the latter from binding to a natural binding partner or other molecule known to be associated with HER2. In some embodiments, if the monoclonal antibody being tested competes with the monoclonal antibody disclosed herein, as shown by a decrease in binding by the monoclonal antibody disclosed herein, then the two monoclonal antibodies bind to the same, or a closely related, epitope.

In some embodiments, an alternative method for determining whether a monoclonal antibody has the specificity of monoclonal antibody disclosed herein is to pre-incubate the monoclonal antibody disclosed herein with soluble HER2 (with which it is normally reactive), and then add the monoclonal antibody being tested to determine if the monoclonal antibody being tested is inhibited in its ability to bind HER2. If the monoclonal antibody being tested is inhibited then, in all likelihood, it has the same, or functionally equivalent, epitopic specificity as the monoclonal antibody disclosed herein.

In some embodiments, screening of monoclonal antibodies disclosed herein, can be also carried out, e.g., by measuring HER2-mediated PI3K-Akt pathway activity, and determining whether the test monoclonal antibody is able to modulate, block, inhibit, reduce, antagonize, neutralize or otherwise interfere with PI3K-Akt pathway activity. In some embodiments, the HER2 antibodies suitable for conjugation can be generated and purified by well-known techniques e.g., WO 2015/195917 and PCT/US2018/019873, each of which is incorporated herein in its entirety by reference.

Conjugates

In some embodiments, conjugates of the disclosure comprise one or more occurrences of D, wherein D is a STING agonist, wherein the one or more occurrences of D may be the same or different.

In some embodiments, one or more occurrences of PBRM is attached to the Linker-Drug moiety, wherein the one or more occurrences of PBRM may be the same or different. In some embodiments, one or more Linker-Drug moieties that comprises one or more occurrences of D are connected to one PBRM (e.g., a antibody).

In some embodiments, the conjugate of the disclosure comprise a PBRM that has a molecular weight of about 40 kDa or greater (e.g., about 60 kDa or greater; about 80 kDa or greater; about 100 kDa or greater; about 120 kDa or greater; about 140 kDa or greater; about 160 kDa or greater; about 180 kDa or greater; or about 200 kDa or greater, or about 40-200 kDa, about 40-180 kDa, about 40-140 kDa, about 60-200 kDa, about 60-180 kDa, about 60-140 kDa, about 80-200 kDa, about 80-180 kDa, about 80-140 kDa, about 100-200 kDa, about 100-180 kDa, or about 100-140 kDa) and has a sulfhydryl (i.e., —SH or thiol) group.

In some embodiments, the total number of sulfide bonds formed between the Linker-drug moieties and the PBRM (or total number of attachment points) is 10 or less (e.g., 8, 6, 4, or 2).

In some embodiments, for conjugation with one or more Linker-Drug moieties, the PBRM has a molecular weight of about 40 kDa or greater (e.g., about 60 kDa or greater, about 80 kDa or greater, about 100 kDa or greater, about 120 kDa or greater, about 140 kDa or greater, about 160 kDa or greater, or about 180 kDa or greater; or about 40-200 kDa, about 40-180 kDa, about 40-140 kDa, about 60-200 kDa, about 60-180 kDa, about 60-140 kDa, about 80-200 kDa, about 80-180 kDa, about 80-140 kDa, about 100-200 kDa, about 100-180 kDa, or about 100-140 kDa).

In some embodiments, for conjugation with one or more Linker-Drug moieties, the PBRM has a molecular weight of about 40 kDa to about 200 kDa. In some embodiments, for conjugation with one or more Linker-Drug moieties, the PBRM has a molecular weight of about 40 kDa to about 80 kDa.

In some embodiments, for conjugation with one or more Linker-Drug moieties, the PBRM has a molecular weight of 40 kDa to 200 kDa. In some embodiments, for conjugation with one or more Linker-Drug moieties, the PBRM has a molecular weight of 40 kDa to 80 kDa.

In some embodiments, PBRMs in this molecular weight range include, but are not limited to, for example, antibody fragments, such as, for example, Fabs.

In some embodiments, for conjugation with one or more Linker-Drug moieties, the PBRM has a molecular weight of about 60 kDa to about 120 kDa.

In some embodiments, for conjugation with one or more Linker-Drug moieties, the PBRM has a molecular weight of 60 kDa to 120 kDa.

In some embodiments, PBRMs in this molecular weight range include, but are not limited to, for example, camelids, Fab2, scFvFc, and the like.

In some embodiments, for conjugation with one or more Linker-Drug moieties, the PBRM has a molecular weight of about 140 kDa to about 180 kDa.

In some embodiments, for conjugation with one or more Linker-Drug moieties, the PBRM has a molecular weight of 140 kDa to 180 kDa.

In some embodiments, PBRMs in this molecular weight range include, but are not limited to, for example, full length antibodies, such as, IgG, IgM.

In some embodiments, the targeting ligands, the linkers and the drug or prodrug fragments described herein can be assembled into the conjugate or scaffold of the disclosure, for example according to the disclosed techniques and methods. Therapeutic and targeting conjugates of the disclosure, and methods for producing them, are described below by way of non-limiting example.

In some embodiments, the total number of sulfide bonds formed between the Linker-Drug moiety and the PBRM (or total number of attachment points) is 8 or less.

In some embodiments, the total number of sulfide bonds formed between the Linker-Drug moiety and the PBRM (or total number of attachment points) is 8. In some embodiments, the total number of sulfide bonds formed between the Linker-Drug moiety and the PBRM (or total number of attachment points) is 6. In some embodiments, the total number of sulfide bonds formed between the Linker-Drug moiety and the PBRM (or total number of attachment points) is 5. In some embodiments, the total number of sulfide bonds formed between the Linker-Drug moiety and the PBRM (or total number of attachment points) is 4. In some embodiments, the total number of sulfide bonds formed between the Linker-Drug moiety and the PBRM (or total number of attachment points) is 3. In some embodiments, the total number of sulfide bonds formed between the Linker-Drug moiety and the PBRM (or total number of attachment points) is 2.

In some embodiments, the ratio between Linker-Drug moiety and the PBRM is between about 1:1 and about 8:1. In some embodiments, the ratio between Linker-Drug moiety and the PBRM is between about 1:1 and about 6:1. In some embodiments, the ratio between Linker-Drug moiety and the PBRM is between about 1:1 and about 4:1. In some embodiments, the ratio between Linker-Drug moiety and the PBRM is between about 2:1 and about 2:1.

In some embodiments, the ratio between Linker-Drug moiety and the PBRM is between about 6:1 and about 8:1.

In some embodiments, the ratio between Linker-Drug moiety and the PBRM is about 8:1.

In some embodiments, the ratio between Linker-Drug moiety and the PBRM is about 6:1.

In some embodiments, the disclosure also relates to a Linker-Drug moiety comprising at least two moieties, wherein each moiety is capable of conjugation to a thiol group in a PBRM so as to form a protein-Linker-Drug conjugate.

In some embodiments, one or more thiol groups of a PBRM are produced by reducing a protein. The one or more thiol groups of the PBRM may then react with one or more Linker-Drug moieties that are capable of conjugation to a thiol group from the PBRM with the Linker-Drug moiety. In some embodiments, the at least two moieties connected to the PBRM are maleimide groups.

In some embodiments, the antibodies may be activated for conjugation with Linker-Drug moiety by treatment with a reducing agent such as DTT (Cleland's reagent, dithiothreitol) or TCEP (tris(2-carboxyethyl)phosphine hydrochloride). In some embodiments, full length, monoclonal antibodies can be reduced with an excess of TCEP to reduce disulfide bonds (e.g., between the cysteine present in the corresponding parent antibodies) to yield a reduced form of the antibody. The newly introduced and unpaired cysteine may remain available for reaction with Linker-Drug moiety to form the antibody conjugates of the present disclosure. In some embodiments, an excess of Linker-drug moiety is added to effect conjugation and form the antibody-drug conjugate, and the conjugation mixture is purified to remove excess Linker-drug intermediate and other impurities.

In some embodiments, for conjugating of the Linker-Drug moiety, a PBRM has a molecular weight of 40 kDa or greater (e.g., 60 kDa or greater; 80 kDa or greater; or 100 kDa or greater; 120 kDa or greater; 140 kDa or greater; 160 kDa or greater or 180 kDa or greater). In some embodiments, the ratio of PBRM per Linker-Drug moiety is between about 1:1 and about 1:8; about 1:1 and about 1:6; between about 1:1 and about 1:5; between about 1:1 and about 1:4; between about 1:1 and about 1:3; or between about 1:1 and about 1:2.

PBRMs in this molecular weight range include, but are not limited to, for example, full length antibodies, such as, IgG, IgM.

In some embodiments, for conjugation with one or more Linker-Drug moieties a PBRM has a molecular weight of 60 kDa to 120 kDa. In some embodiments, the ratio of PBRM per Linker-Drug moiety is about 1:1 and about 1:8; between about 1:1 and about 1:6; between about 1:1 and about 1:5; between about 1:1 and about 1:4; between about 1:1 and about 1:3; or between about 1:1 and about 1:2.

PBRMs in this molecular weight range include, but are not limited to, for example, antibody fragments such as, for example Fab2, scFcFv and camelids.

In some embodiments, for conjugation with one or more Linker-Drug moieties a PBRM has a molecular weight of 40 kDa to 80 kDa. In some embodiments, the ratio of PBRM per Linker-Drug moiety is about 1:1 and about 1:8; between about 1:1 and about 1:6; between about 1:1 and about 1:5; between 1:1 and about 1:4; between about 1:1 and about 1:3, or between about 1:1 and about 1:2.

In some embodiments, PBRMs in this molecular weight range include, but are not limited to, for example, antibody fragments, such as, Fabs.

In some embodiments, the disclosure features a scaffold useful to conjugate with either or both of a protein-based recognition-molecule (PBRM) and a STING agonist moiety (D).

In some embodiments, the drug-carrying scaffolds (i.e., without linking to a PBRM), described herein each typically have a polydispersity index (PDI) of 1.

Conjugates and scaffolds disclosed herein can be purified (i.e., removal of any starting materials) by extensive diafiltration. If necessary, additional purification by size exclusion chromatography can be conducted to remove any aggregated conjugates. In general, the conjugates as purified typically contain less than 5% (e.g., <2% w/w) aggregated conjugates as determined by SEC; less than 0.5% (e.g., <0.1% w/w) free (unconjugated) drug as determined by RP-HPLC; less than 1% drug carrying-peptide-containing scaffolds as determined by SEC and less than 2% (e.g., <1% w/w) unconjugated PBRM as determined by HIC-HPLC.

In some embodiments, the scaffold is selected from the scaffolds described in Table A1.

In some embodiments, the scaffold is selected from the scaffolds described in Table A2.

In some embodiments, the conjugate is selected from the conjugates described in Table B1.

In some embodiments, the conjugate is selected from the conjugates described in Table B2.

TABLE A1

| Structure |
|---|
| 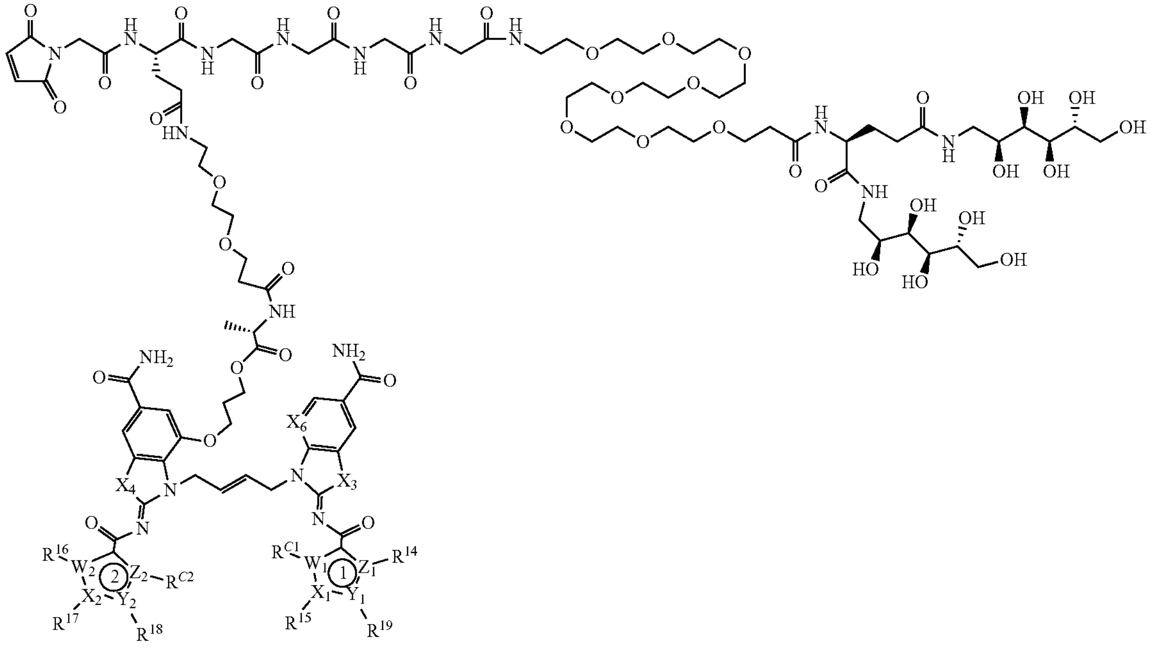 |

TABLE A1-continued
| Structure |
|---|
| 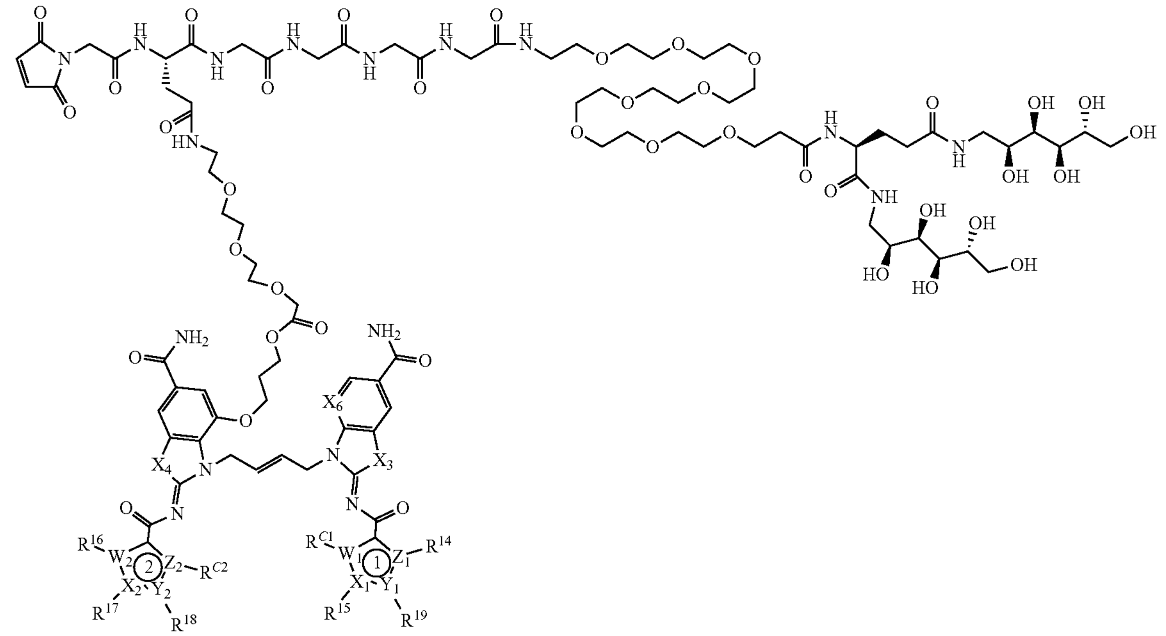 |
| 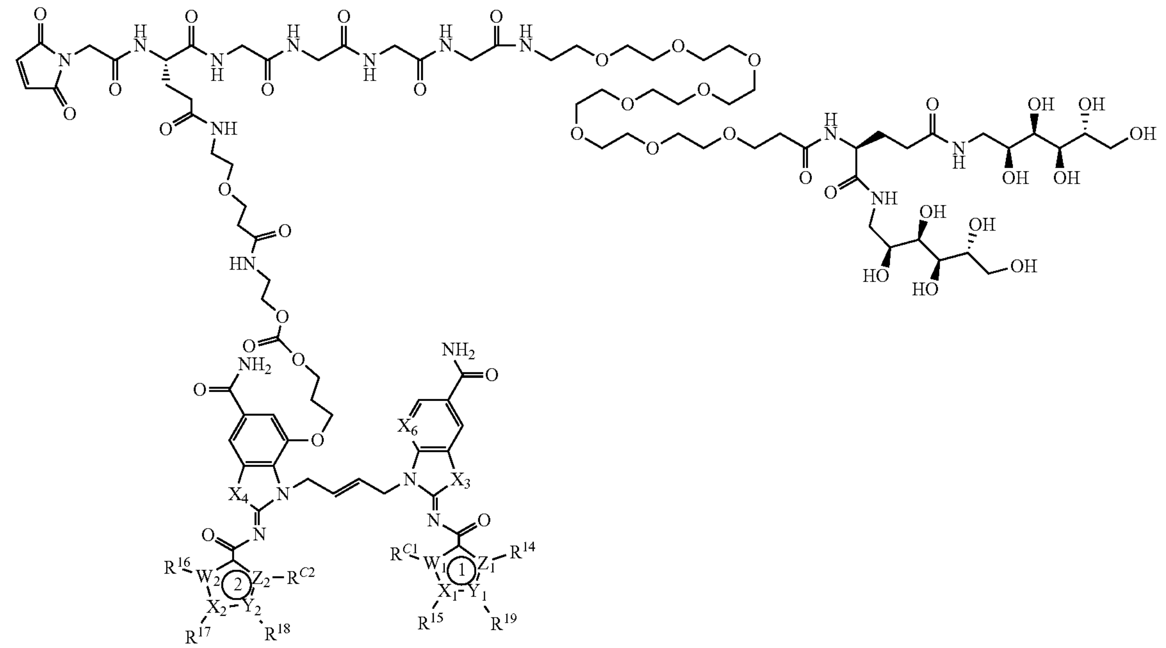 |

TABLE A1-continued
| Structure |
| --- |
| 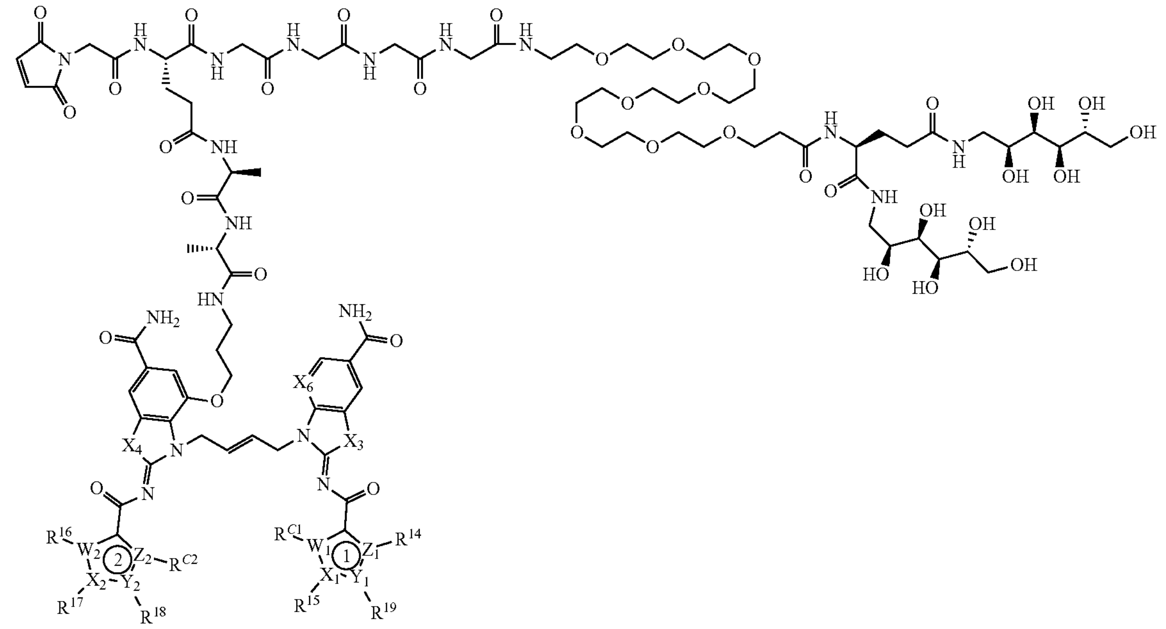 |
| 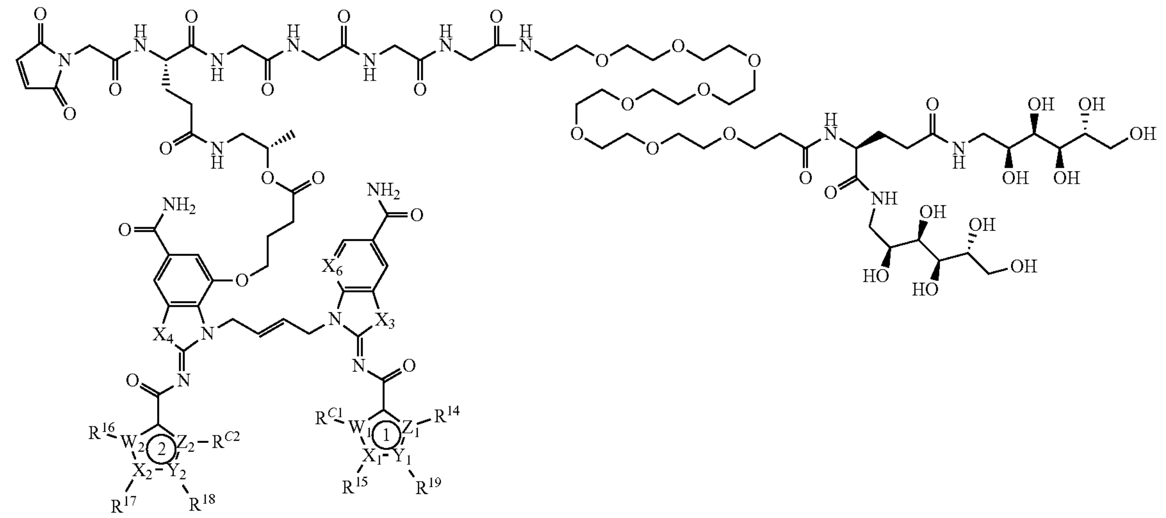 |
| 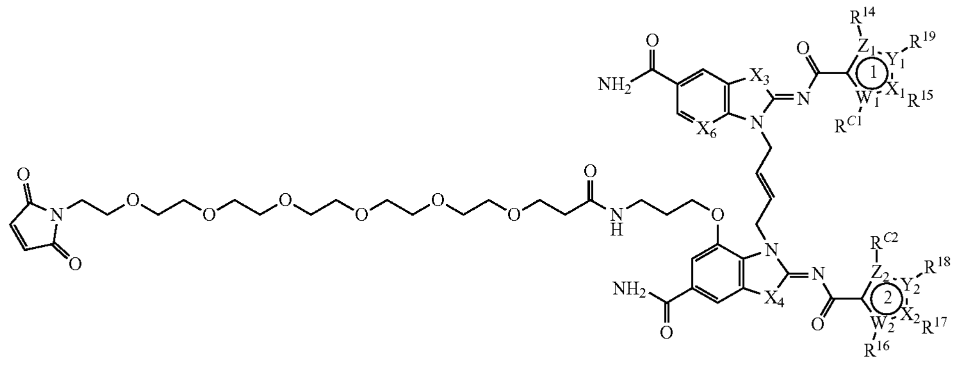 |

TABLE A1-continued
| Structure |
| --- |
| 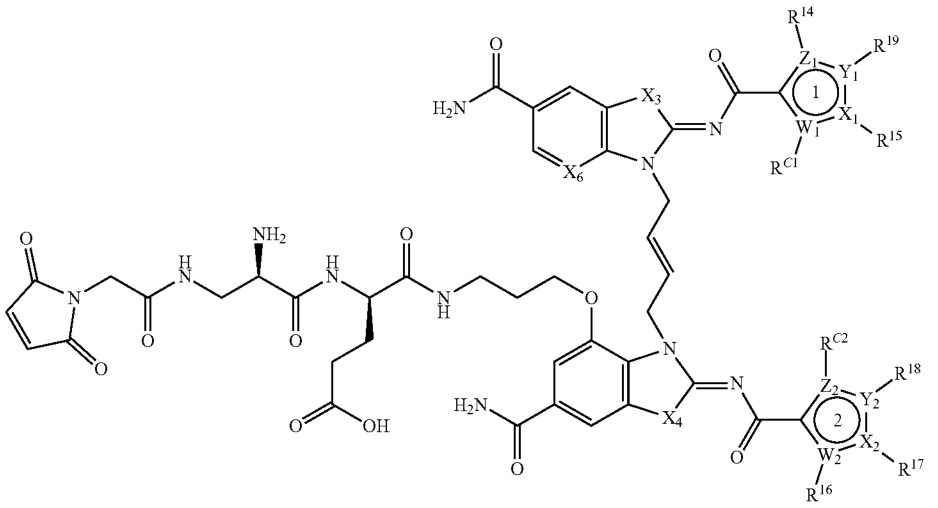 |
| 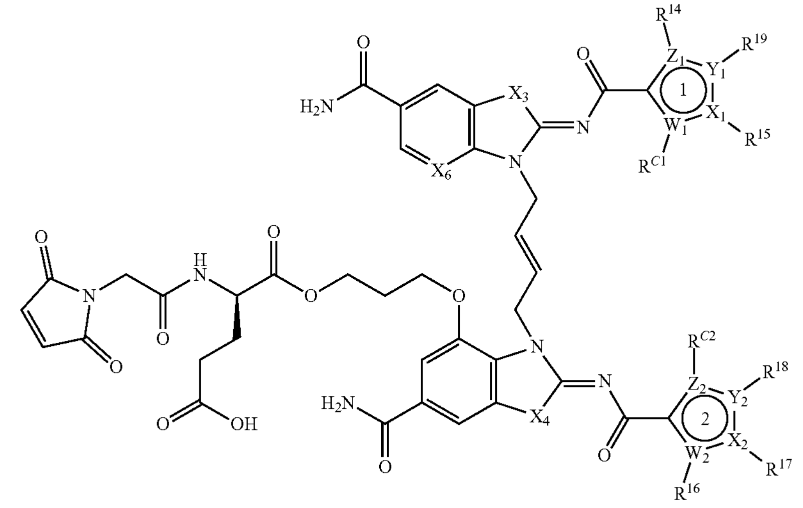 |
| 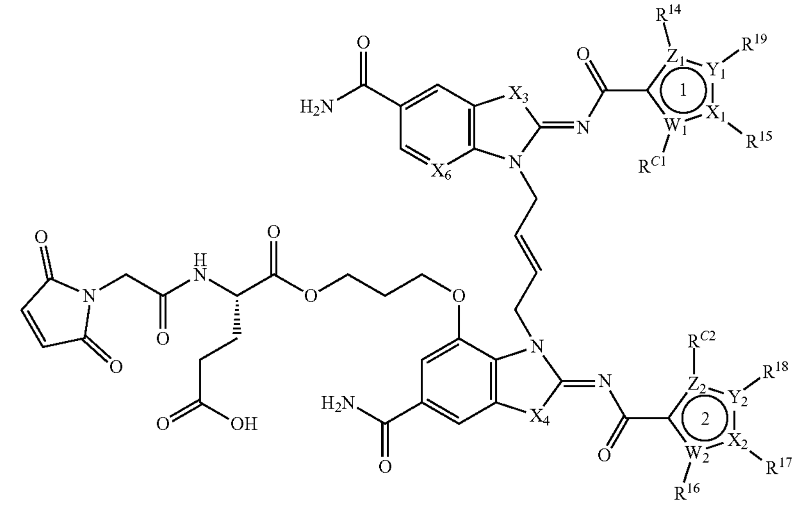 |

TABLE A1-continued
| Structure |
|---|
| 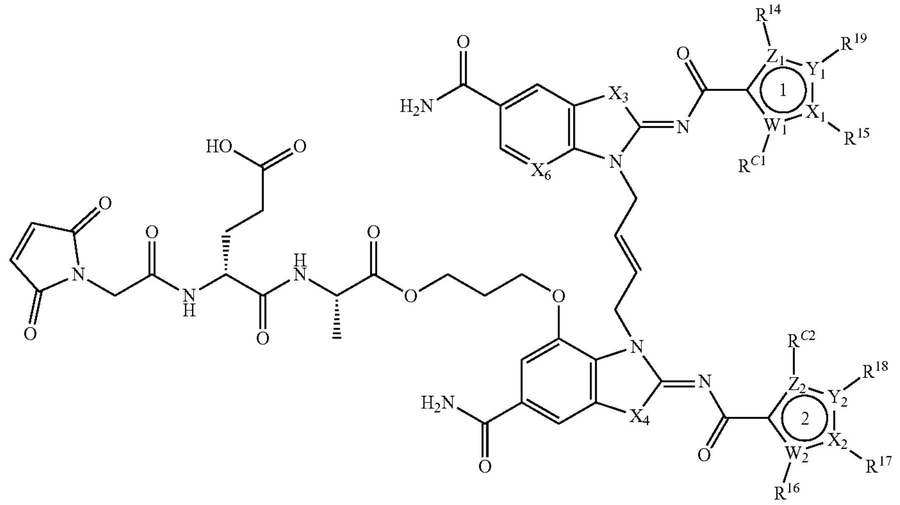 |
| 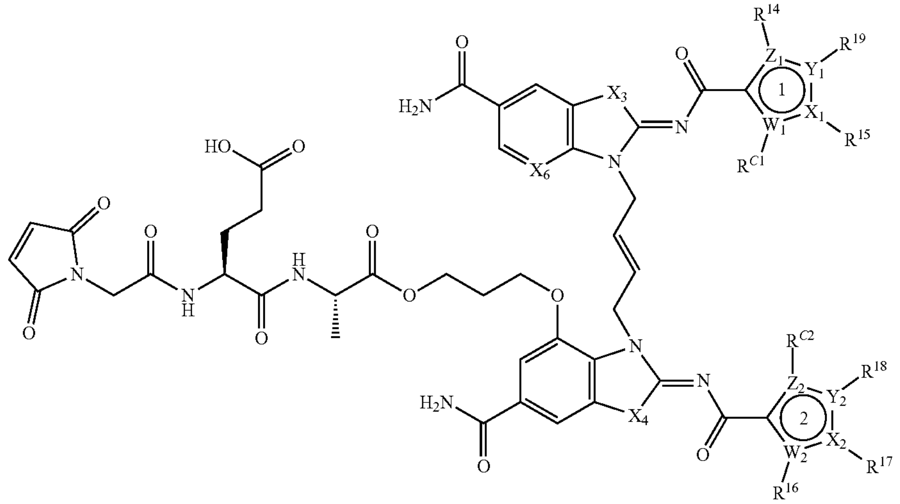 |
| 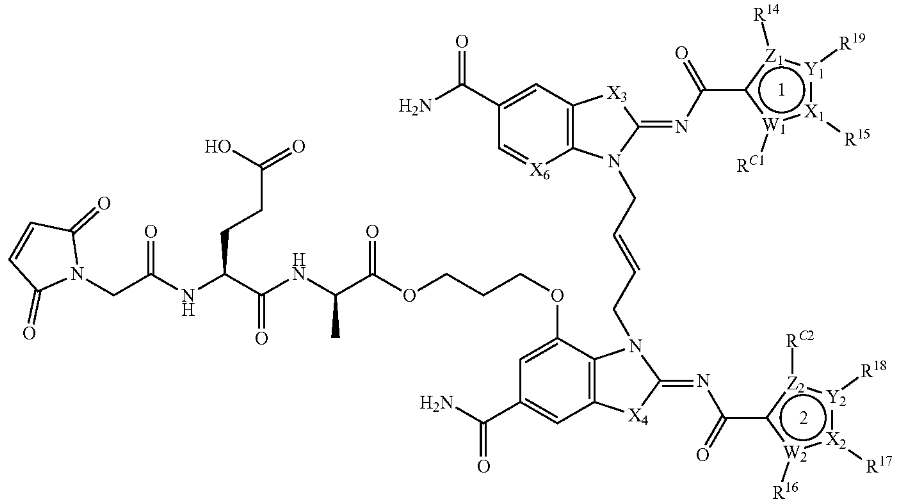 |

TABLE A1-continued
| Structure |
|---|
| 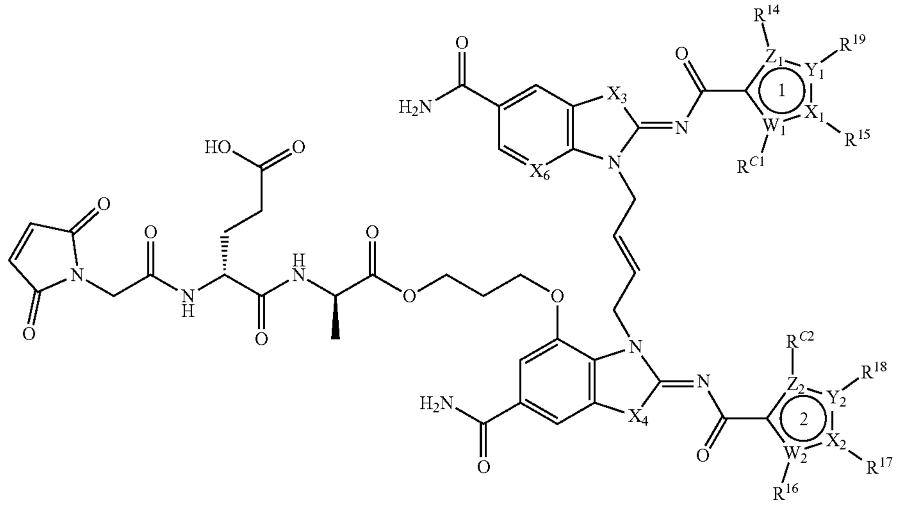 |
| 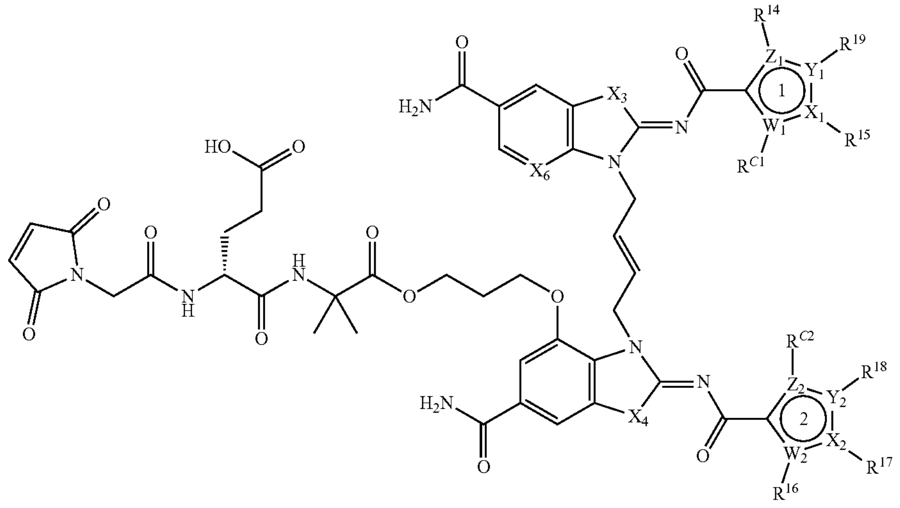 |
| 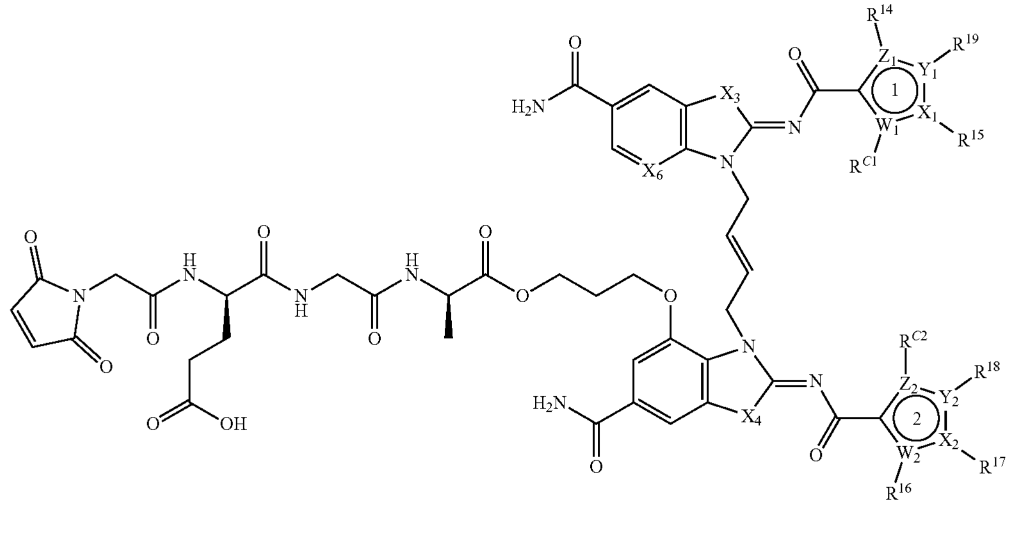 |

TABLE A1-continued
| Structure |
|---|
| 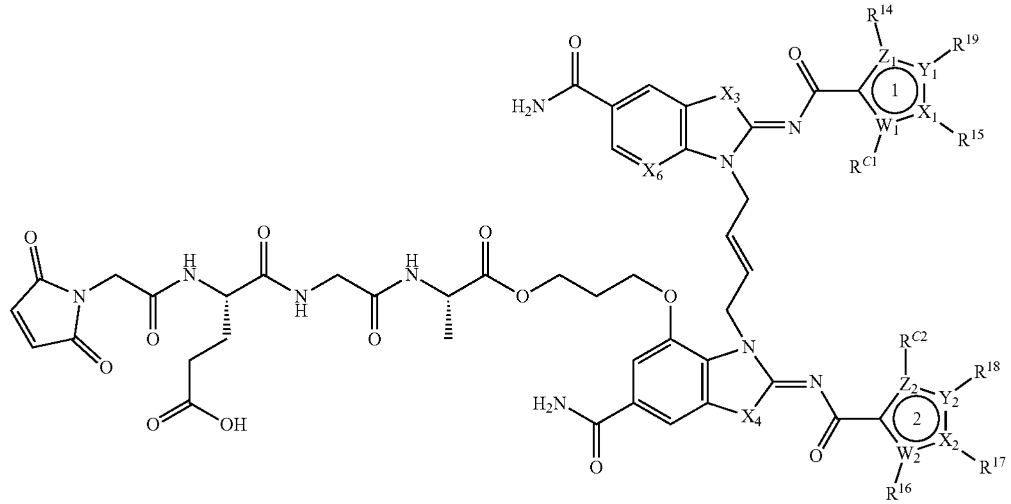 |
| 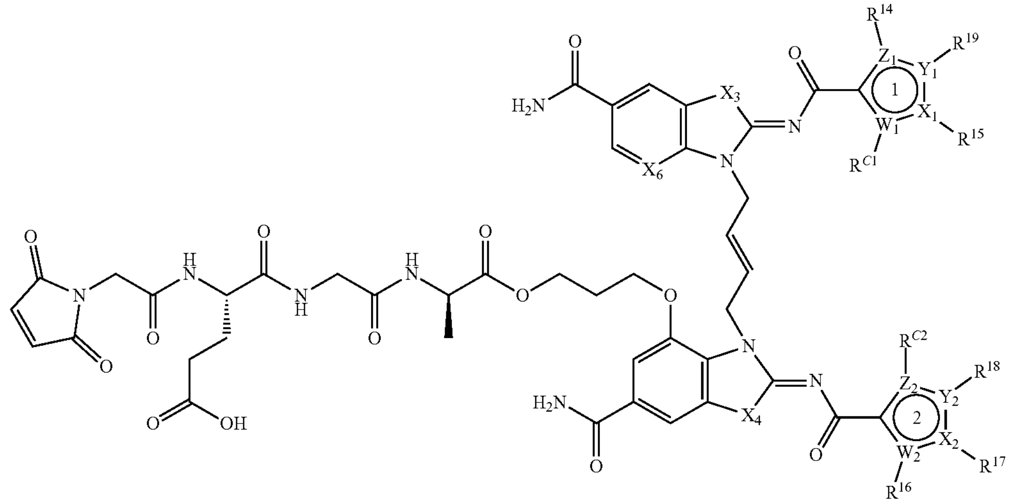 |
| 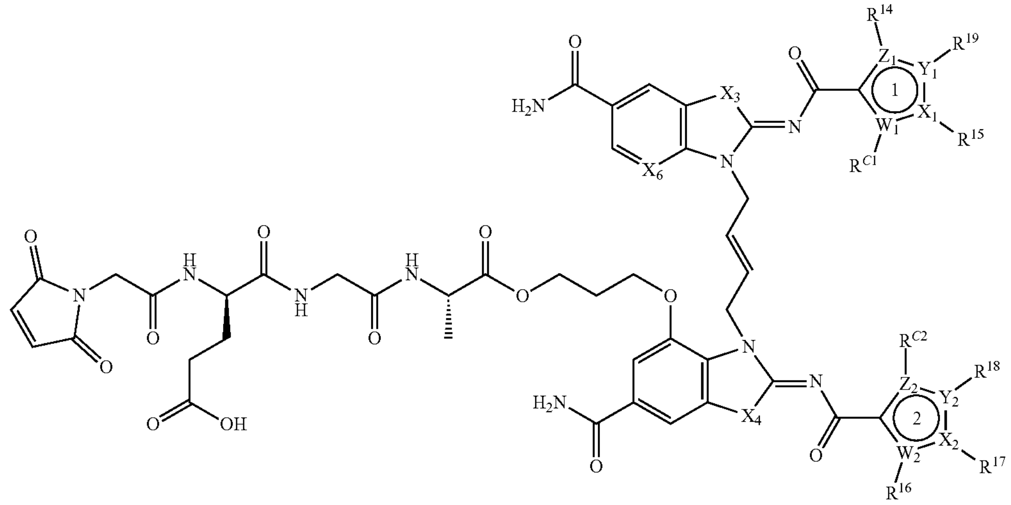 |

TABLE A1-continued
| Structure |
| --- |
| 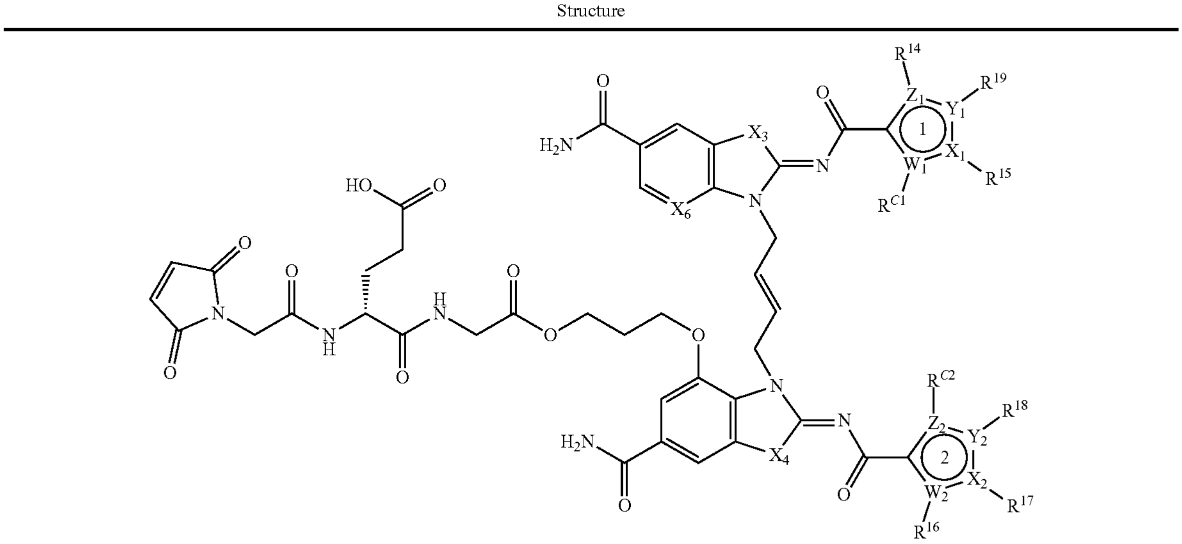 |
wherein $R^{14}$, $R^{15}$, $R^{16}$, $R^{17}$, $R^{18}$, $R^{19}$, $R^{C1}$, $R^{C2}$, $X_3$, $X_4$, $X_6$, $X_1$, $W_1$, $Y_1$, $Z_1$, $X_2$, $W_2$, $Y_2$, $Z_2$, are as defined herein.

TABLE A2
| Ex No. | Cmpd No. | Structure | LCMS |
|---|---|---|---|
| | | 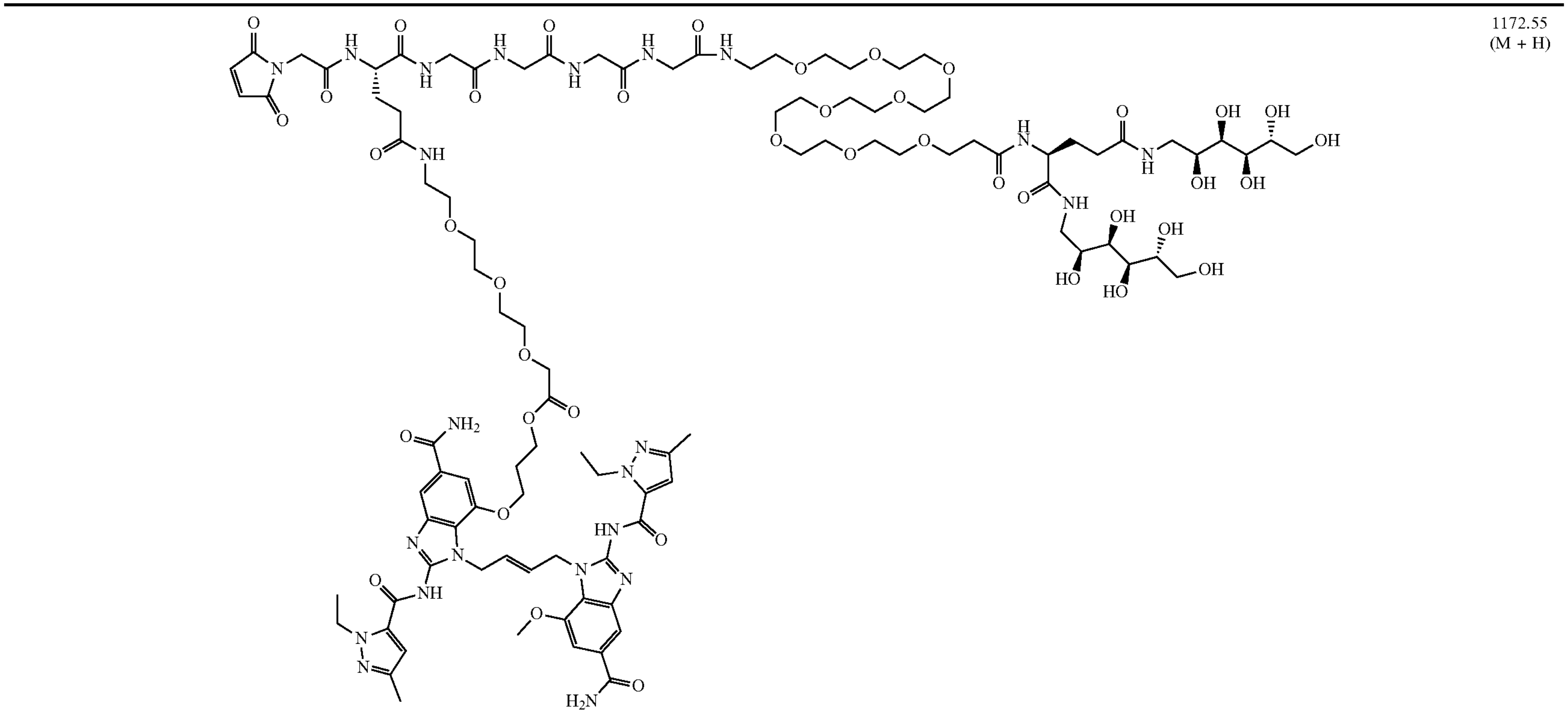 | 1172.55 (M + H) |

TABLE A2-continued
| Ex No. | Cmpd No. | Structure | LCMS |
|---|---|---|---|
| 1 | 7 | 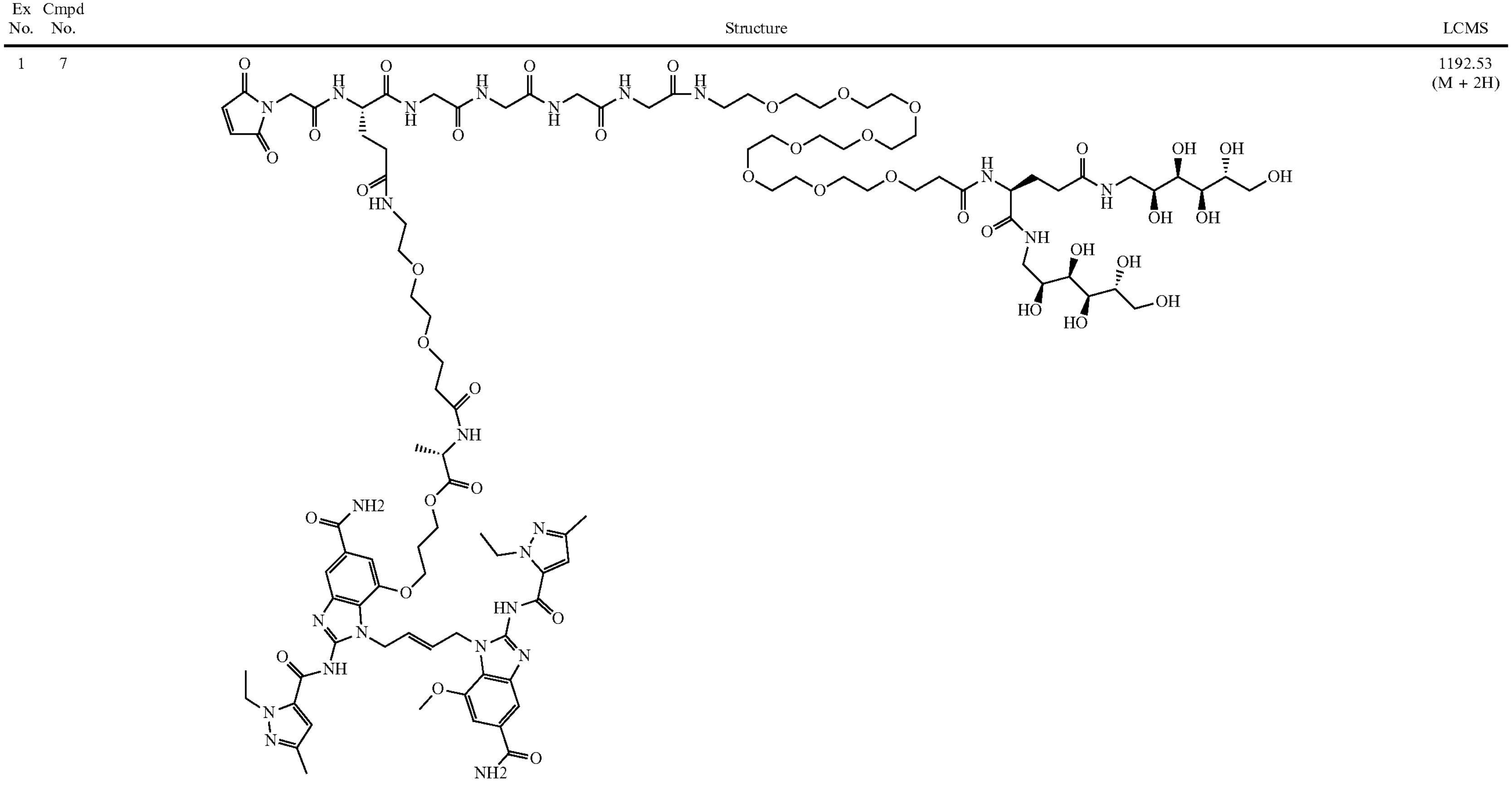 | 1192.53 (M + 2H) |

TABLE A2-continued
| Ex No. | Cmpd No. | Structure | LCMS |
| --- | --- | --- | --- |
| | | 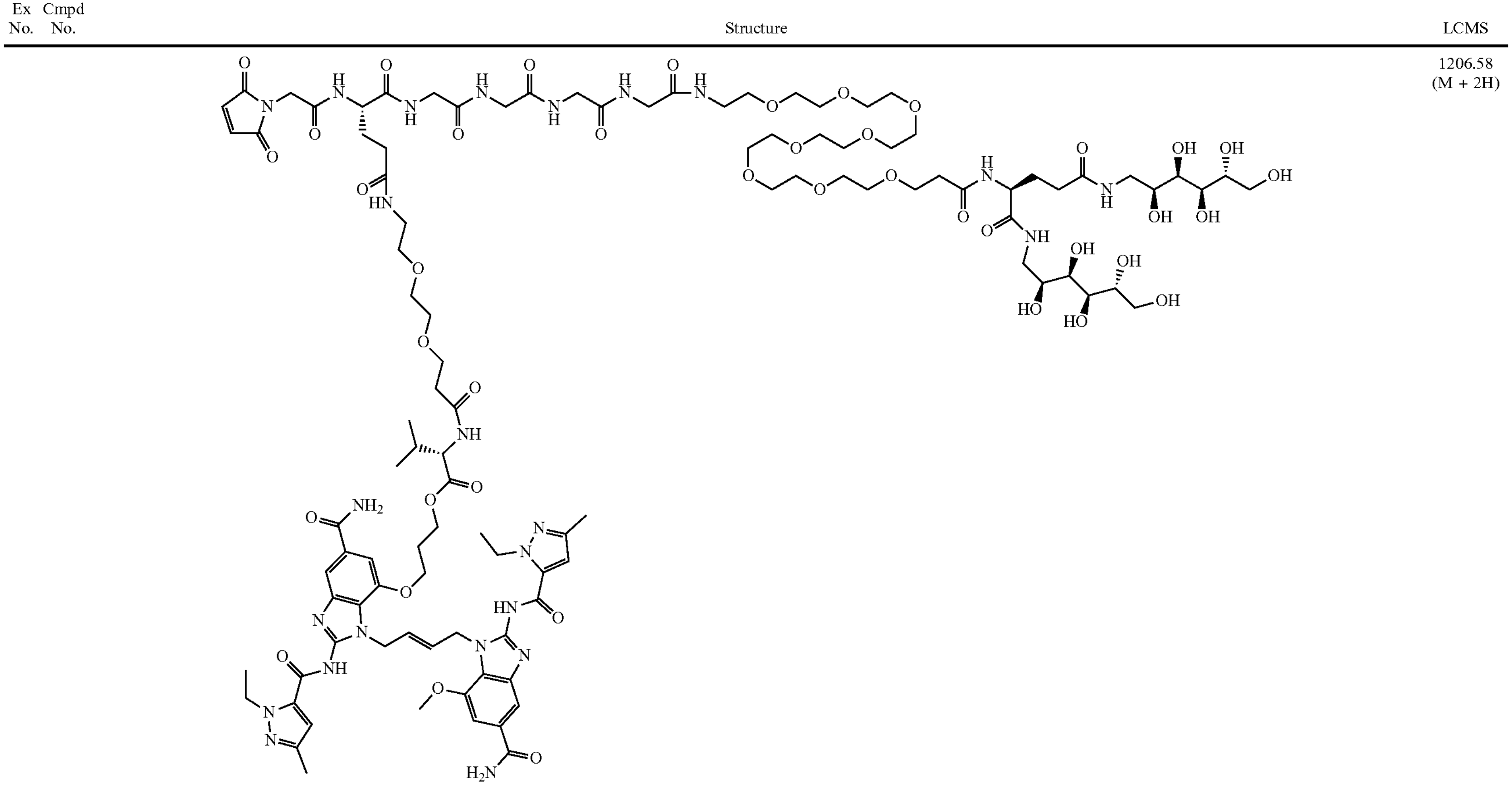 | 1206.58 (M + 2H) |

TABLE A2-continued
| Ex No. | Cmpd No. | Structure | LCMS |
| --- | --- | --- | --- |
| | | 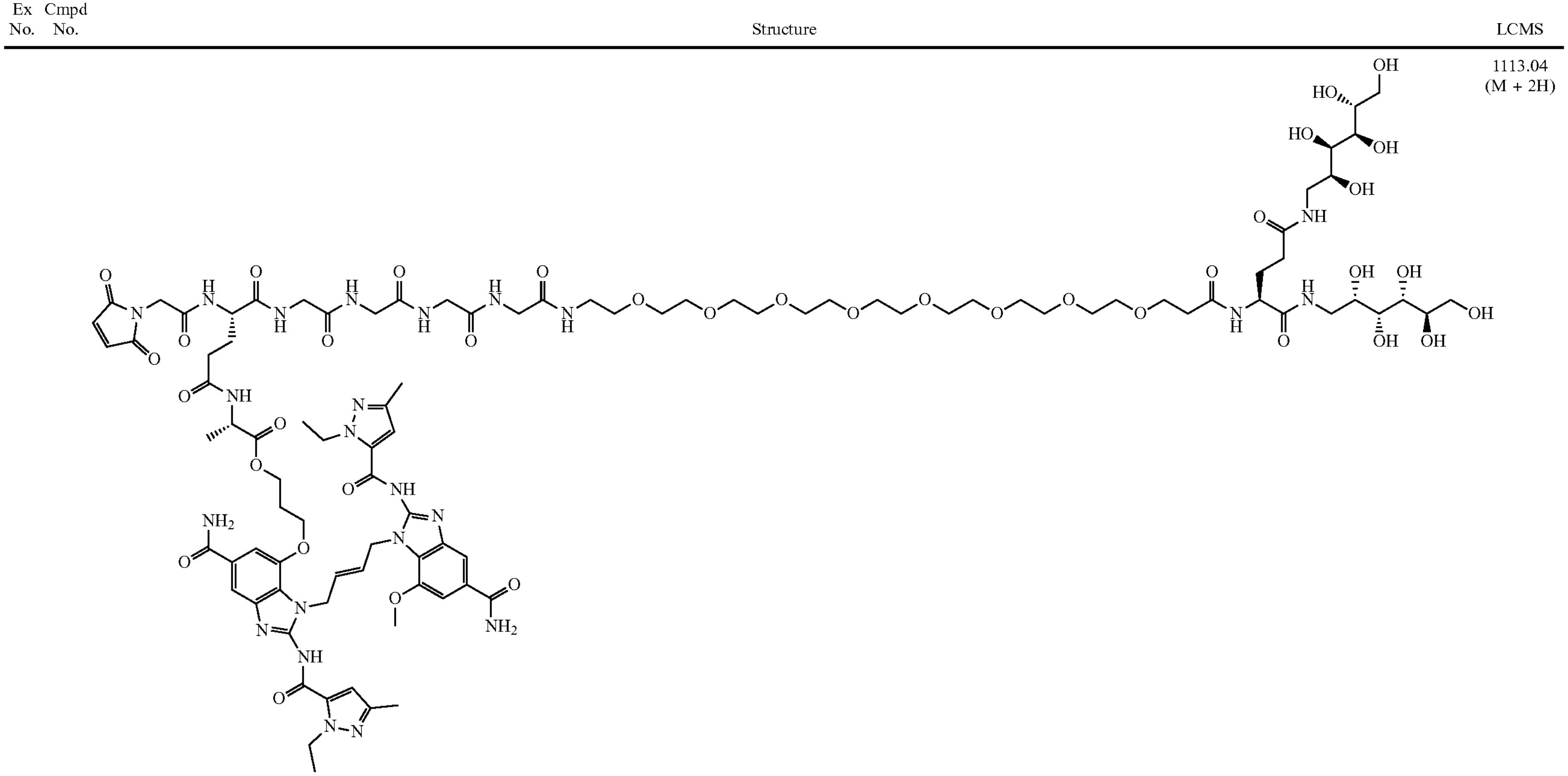 | 1113.04 (M + 2H) |

TABLE A2-continued
| Ex No. | Cmpd No. | Structure | LCMS |
|---|---|---|---|
| | | 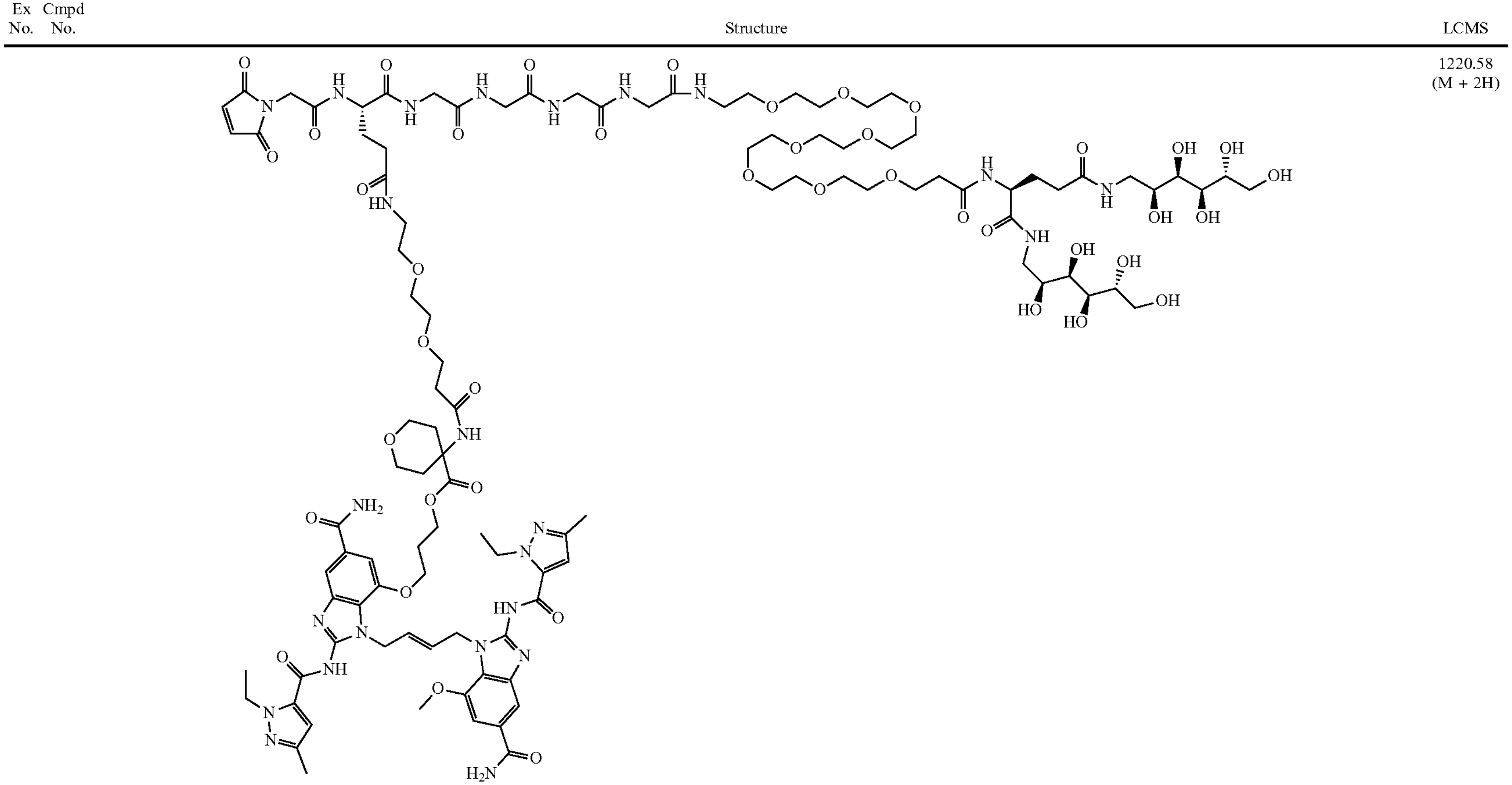 | 1220.58 (M + 2H) |

TABLE A2-continued
| Ex No. | Cmpd No. | Structure | LCMS |
|---|---|---|---|
| | | 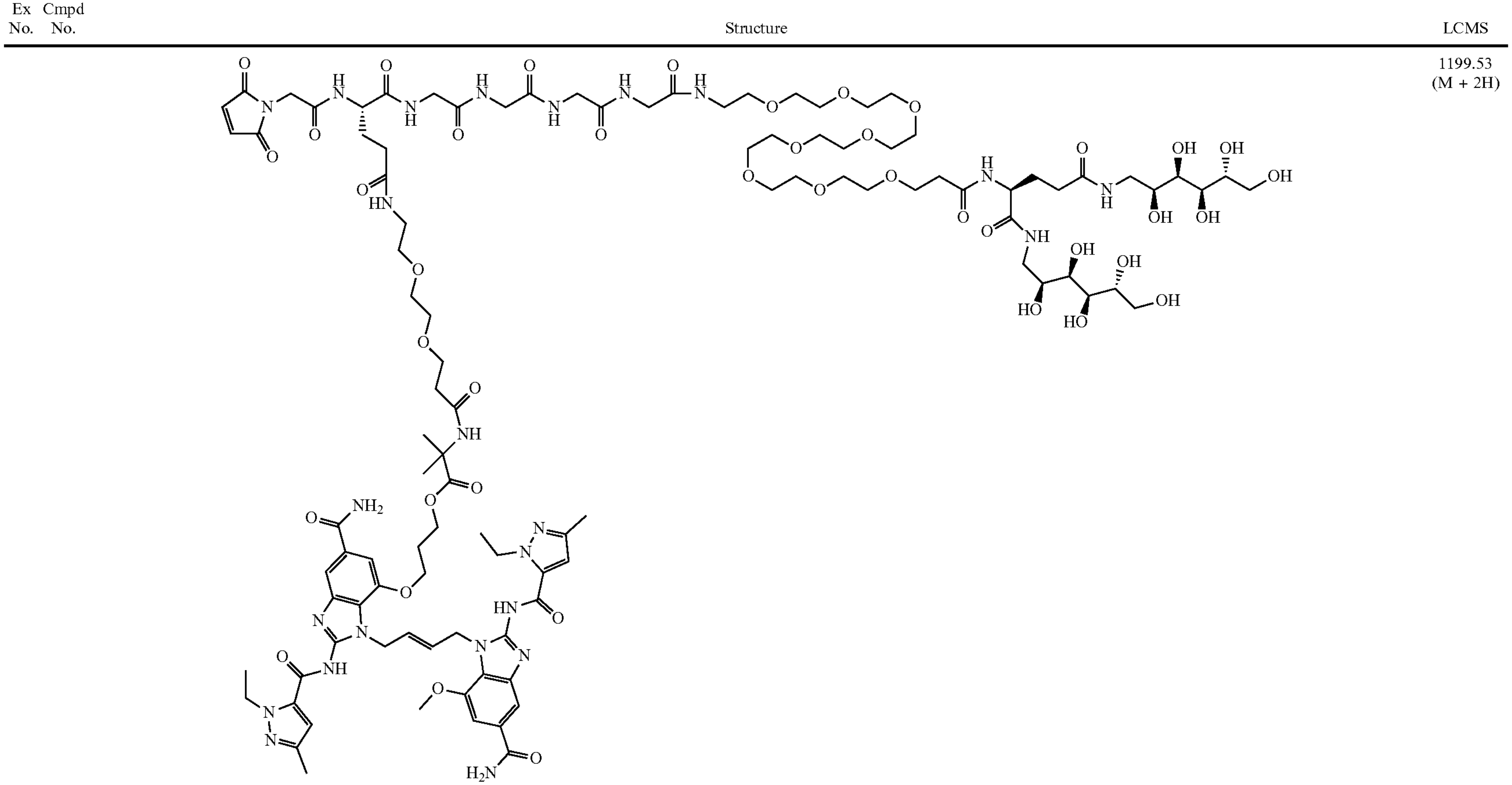 | 1199.53 (M + 2H) |

TABLE A2-continued
| Ex No. | Cmpd No. | Structure | LCMS |
|---|---|---|---|
| | | 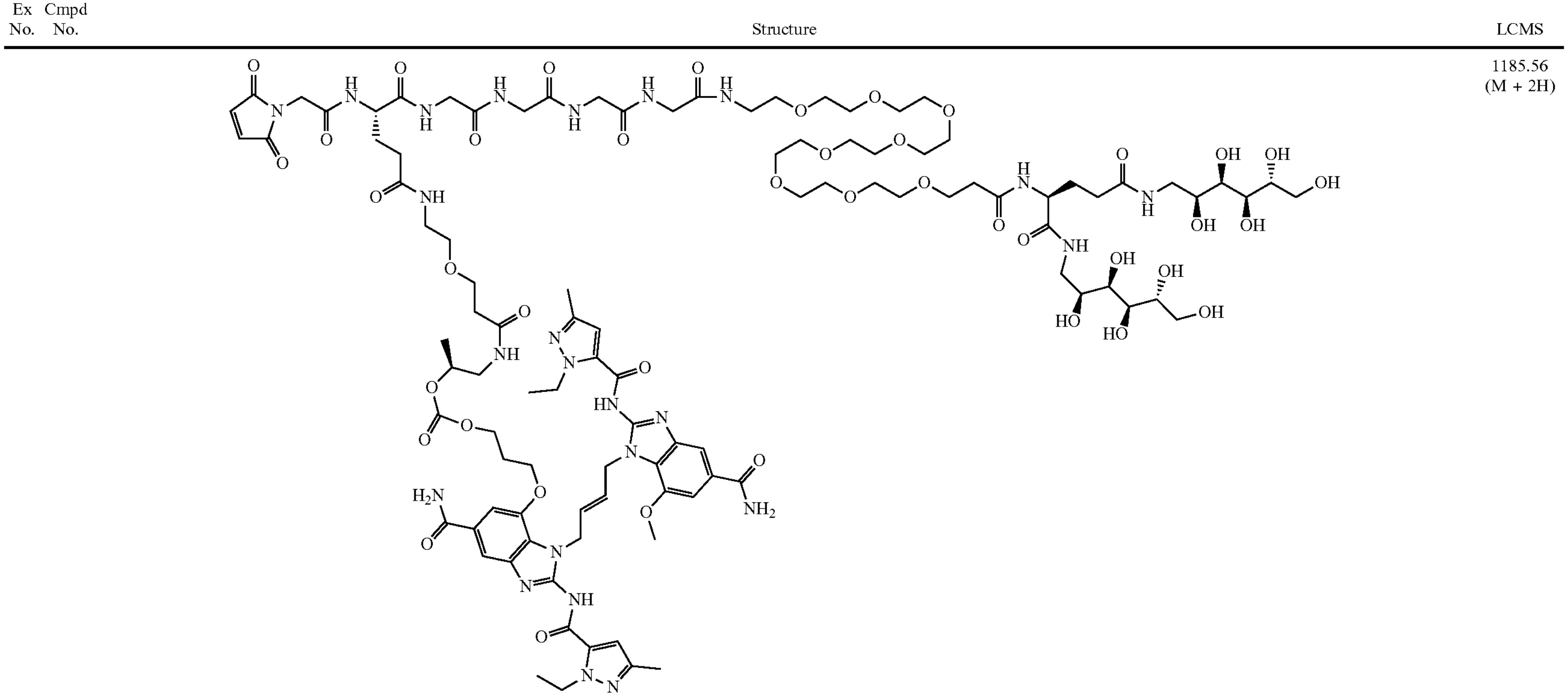 | 1185.56 (M + 2H) |

TABLE A2-continued
| Ex No. | Cmpd No. | Structure | LCMS |
|---|---|---|---|
| 2 | 14 | 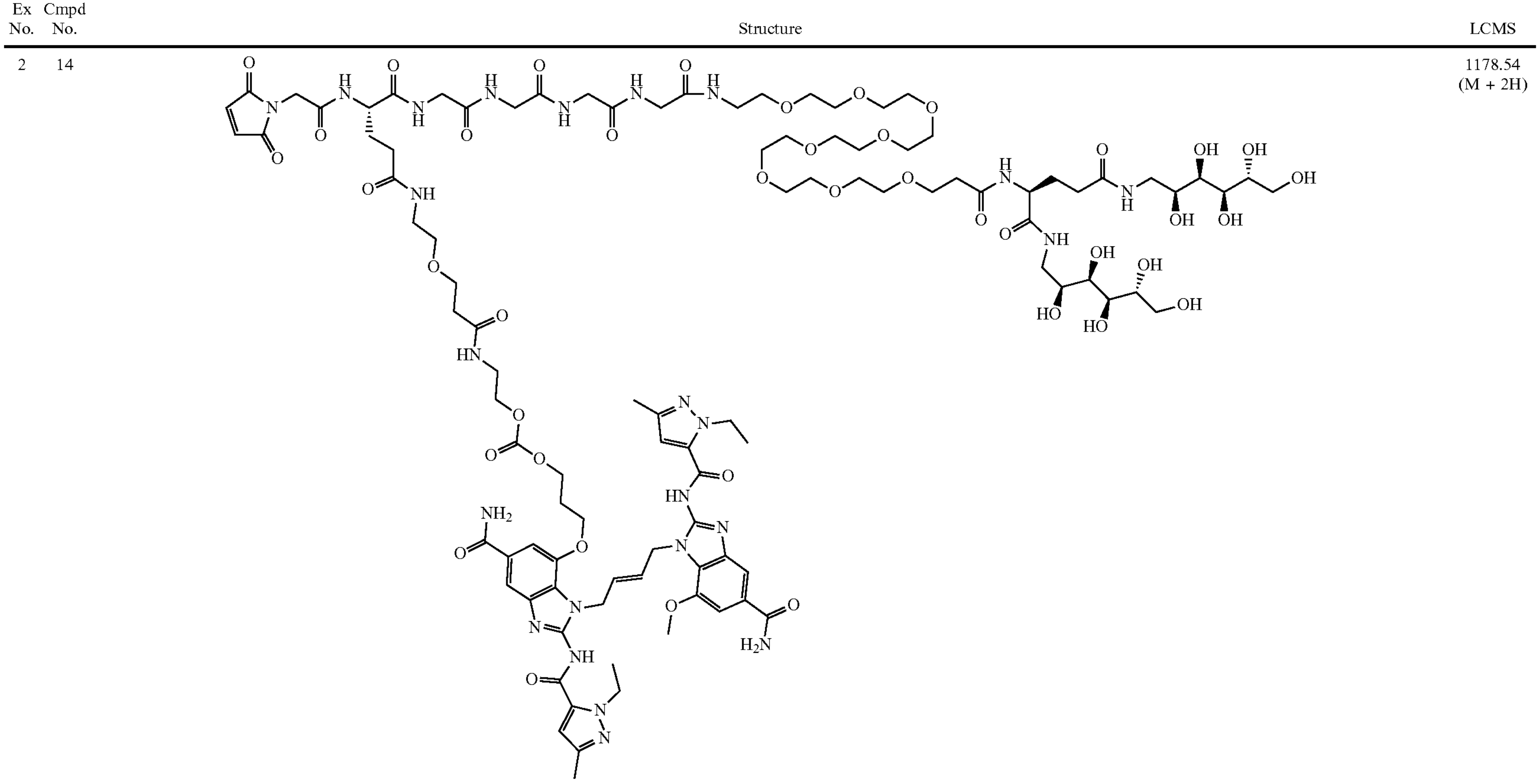 | 1178.54 (M + 2H) |

TABLE A2-continued
| Ex No. | Cmpd No. | Structure | LCMS |
|---|---|---|---|
| | | 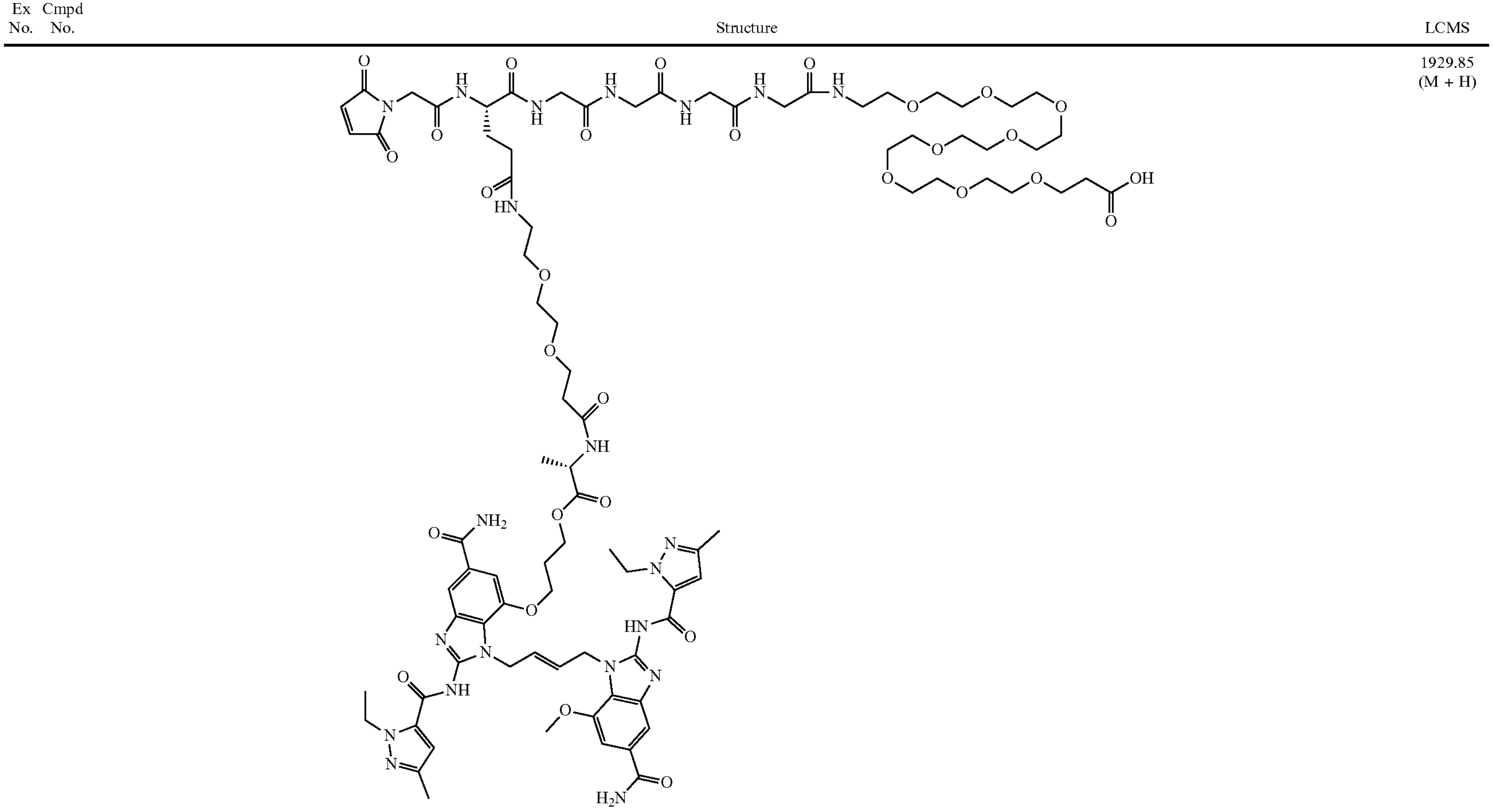 | 1929.85 (M + H) |

TABLE A2-continued
| Ex No. | Cmpd No. | Structure | LCMS |
| --- | --- | --- | --- |
| | | 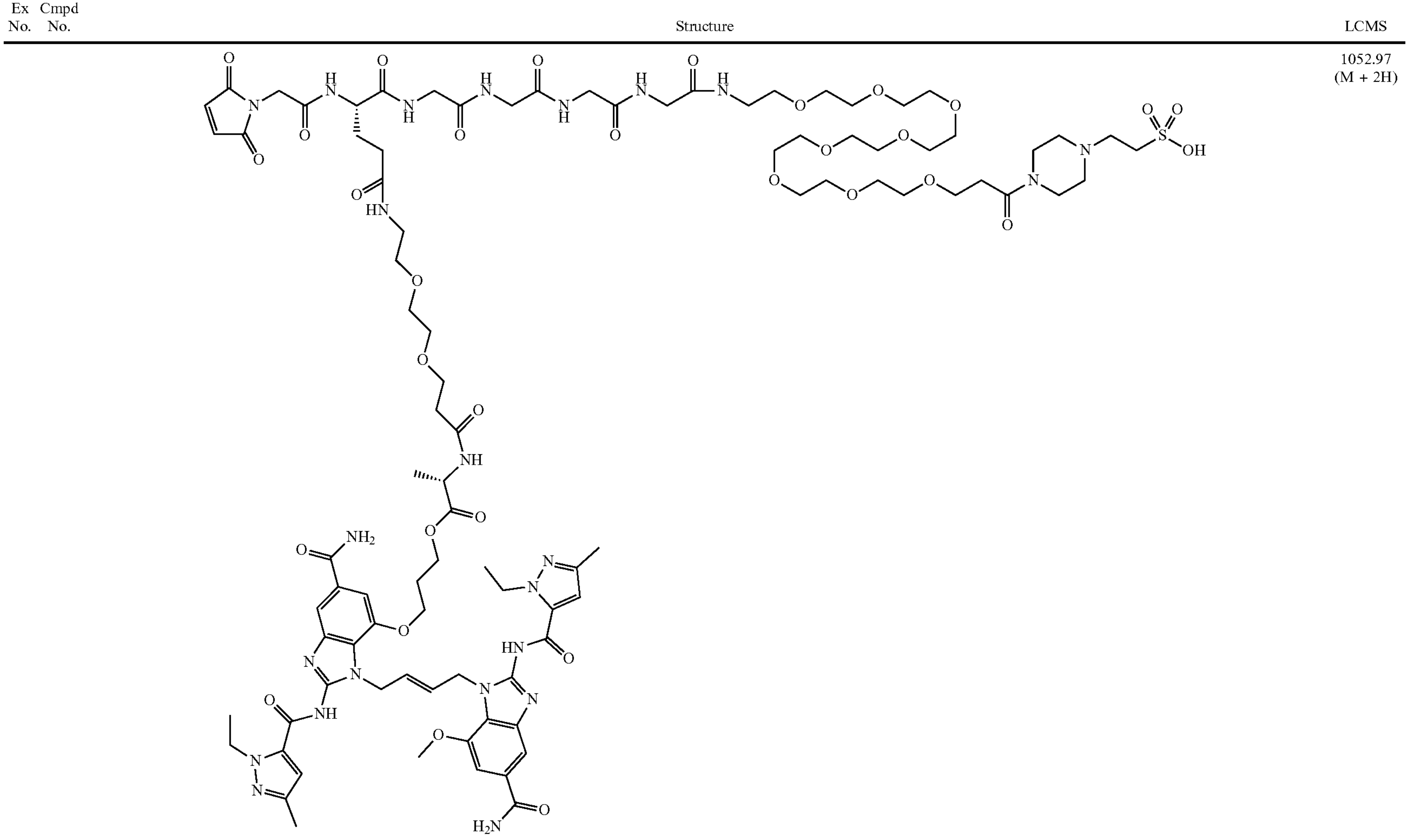 | 1052.97 (M + 2H) |

TABLE A2-continued
| Ex No. | Cmpd No. | Structure | LCMS |
|---|---|---|---|
| | | 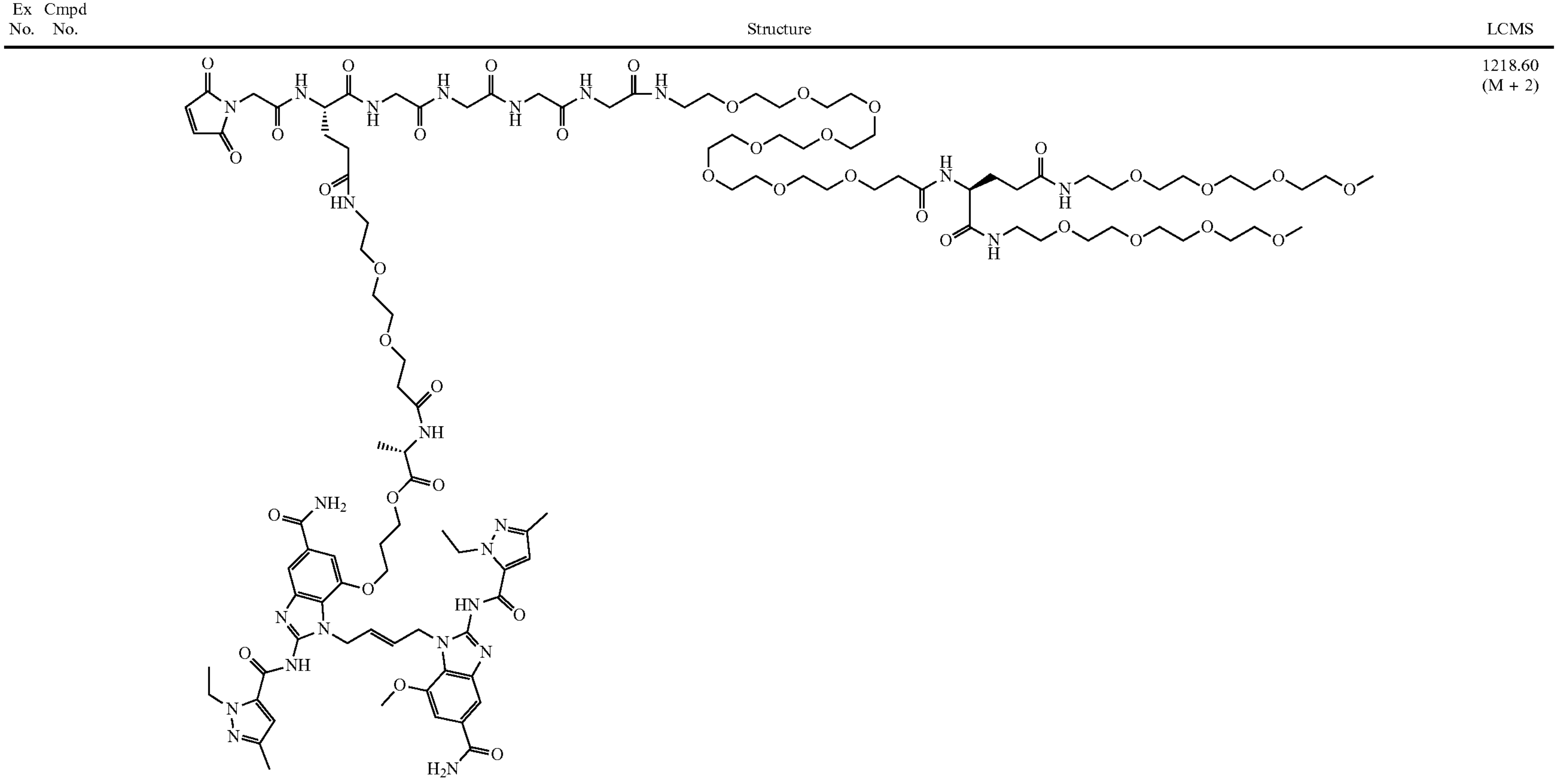 | 1218.60 (M + 2) |

TABLE A2-continued
| Ex No. | Cmpd No. | Structure | LCMS |
|---|---|---|---|
| | | 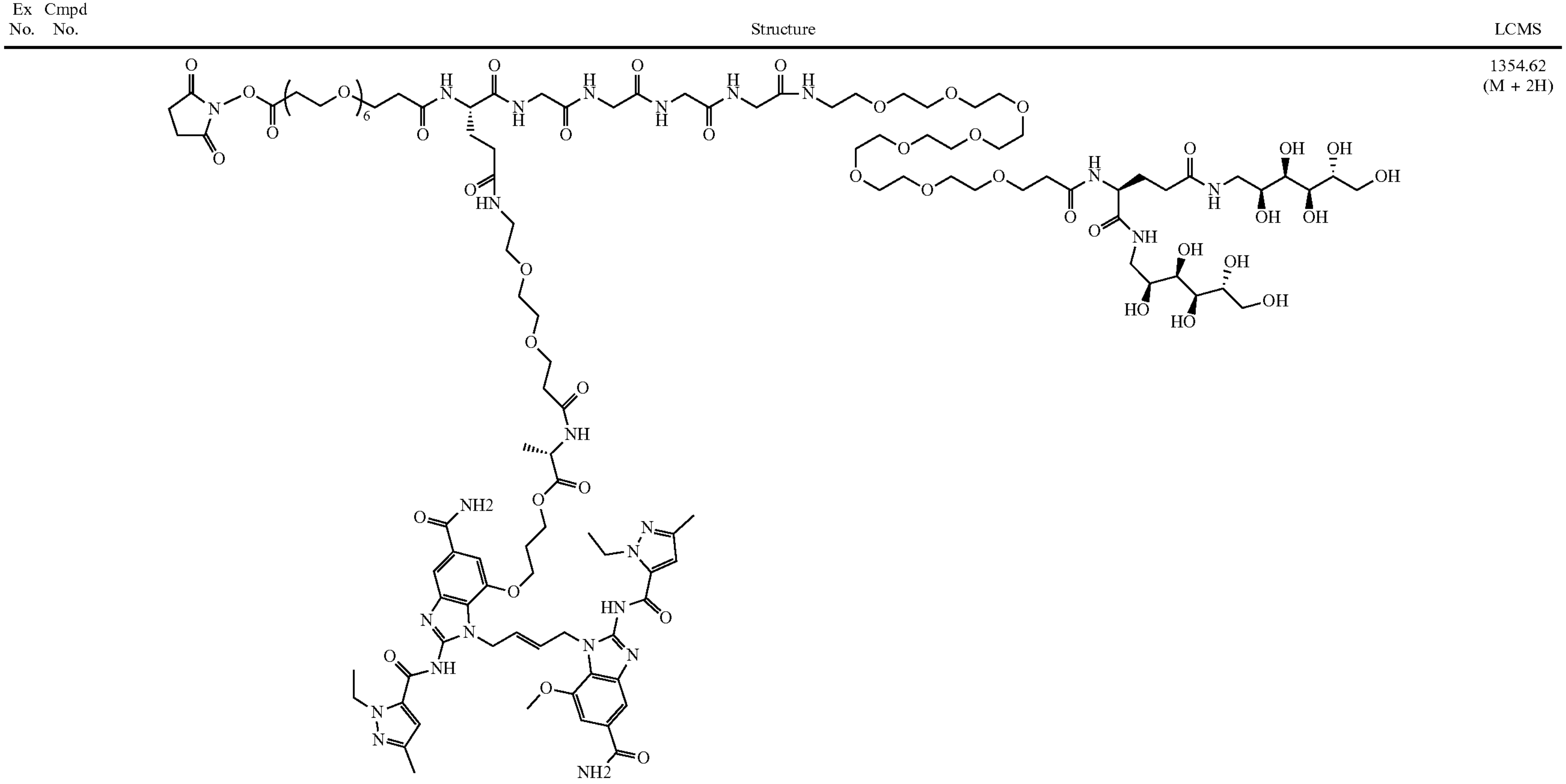 | 1354.62 (M + 2H) |

TABLE A2-continued
| Ex No. | Cmpd No. | Structure | LCMS |
|---|---|---|---|
| | | 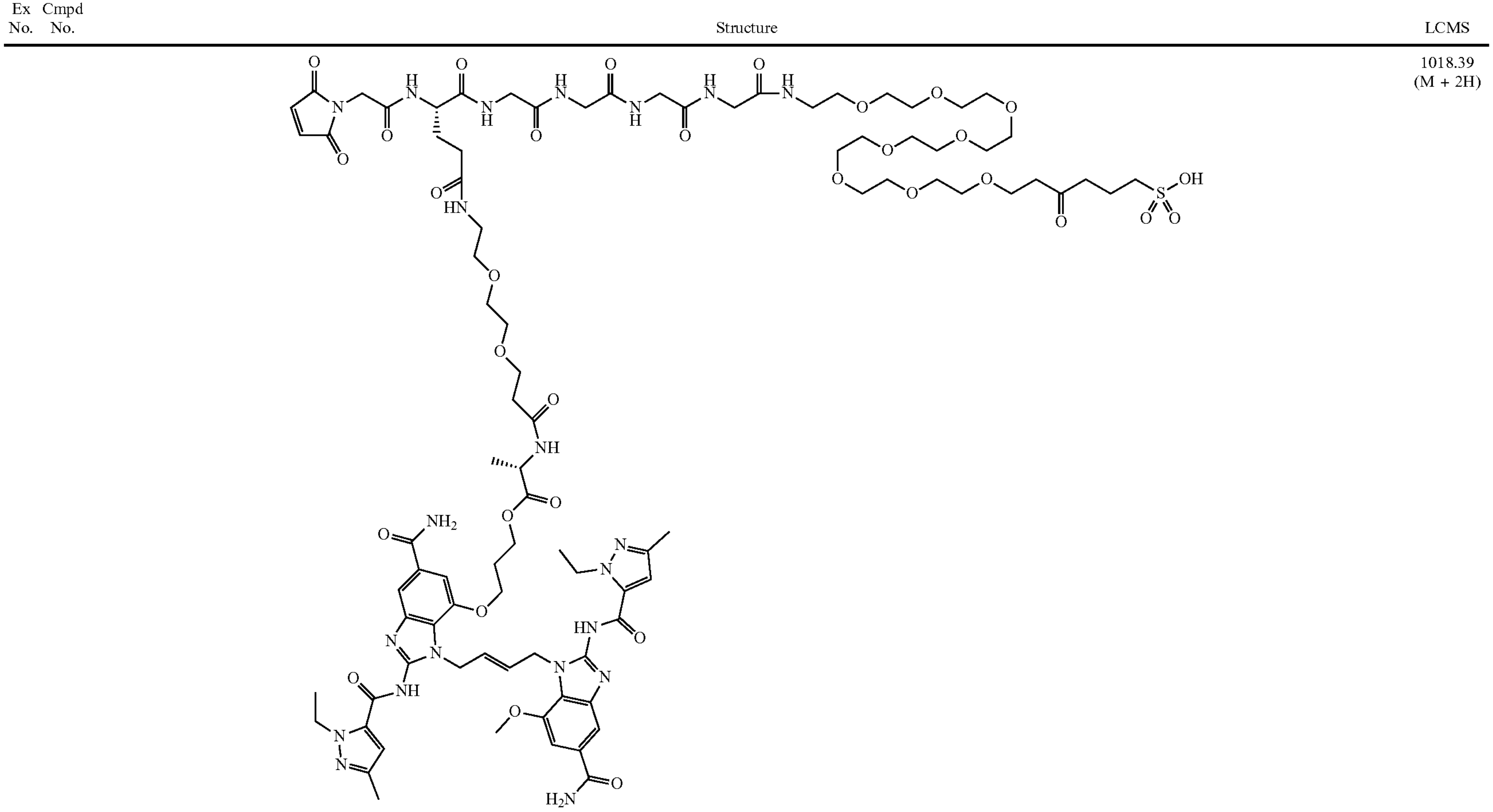 | 1018.39 (M + 2H) |

TABLE A2-continued
| Ex No. | Cmpd No. | Structure | LCMS |
| --- | --- | --- | --- |
| | | 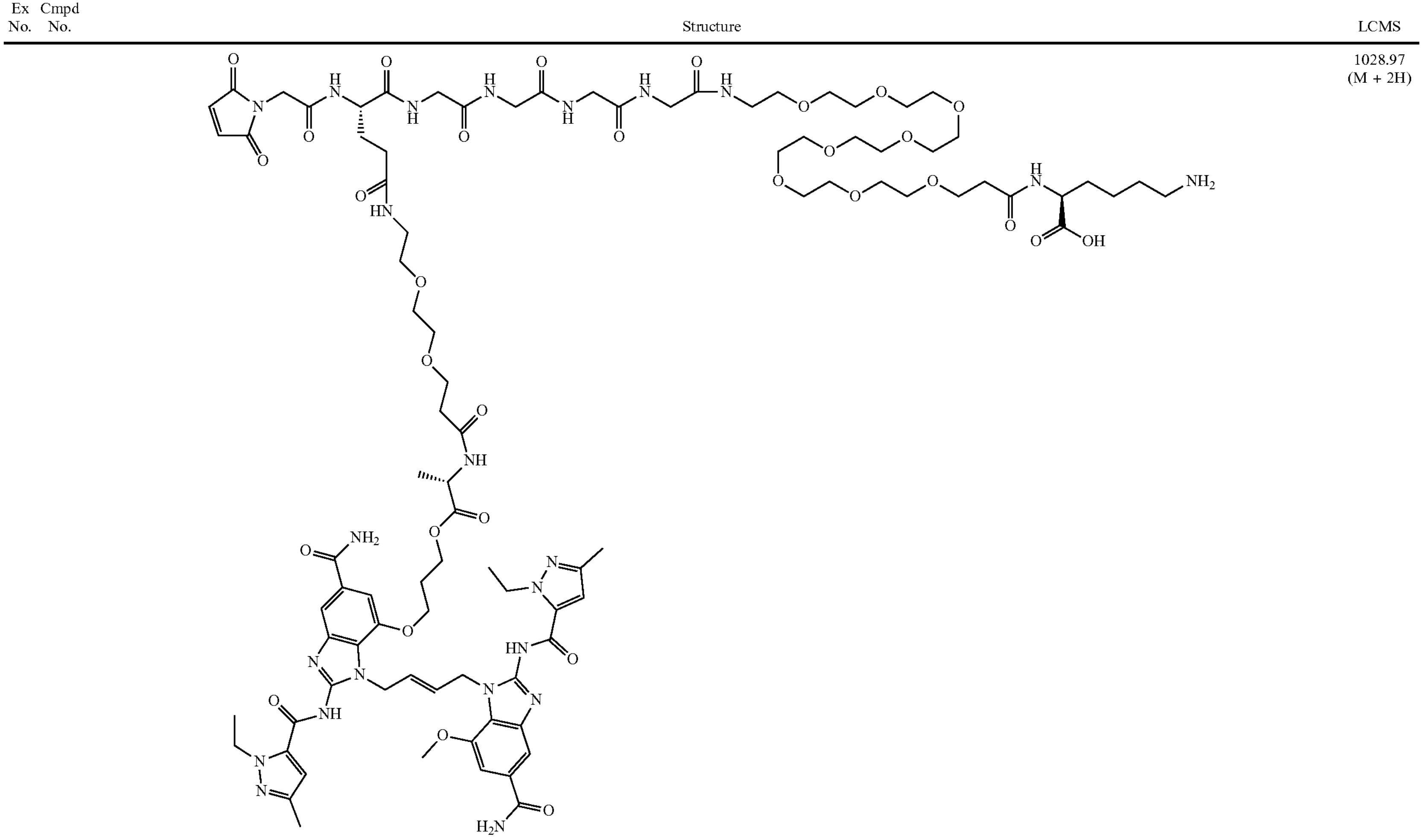 | 1028.97 (M + 2H) |

TABLE A2-continued
| Ex No. | Cmpd No. | Structure | LCMS |
|---|---|---|---|
| | | 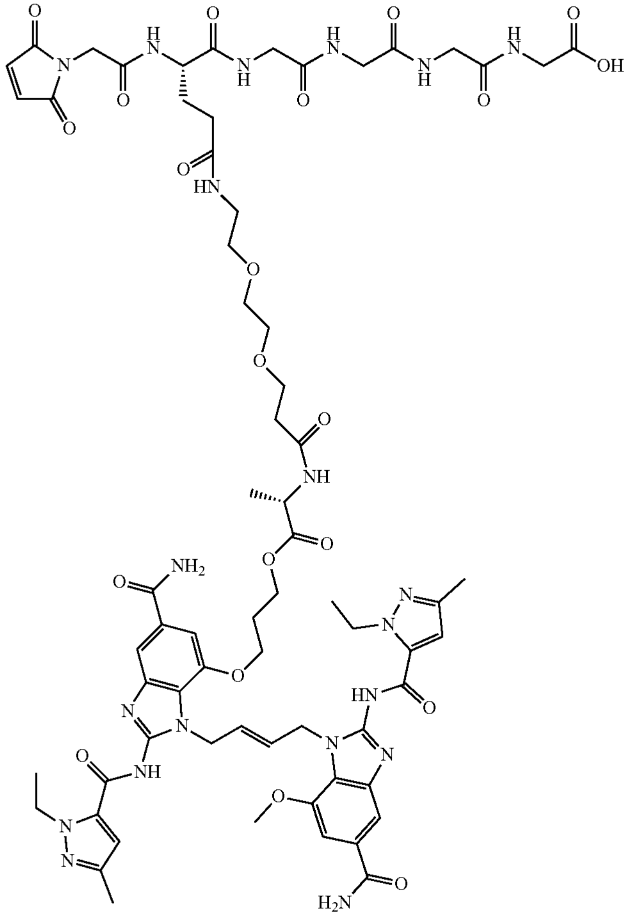 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCOC(=O)[C@H](C)NC(=O)CCOCCOCCNC(=O)CC[C@H](NC(=O)CN3C(=O)C=CC3=O)C(=O)NCC(=O)NCC(=O)NCC(=O)NCC(=O)O)c21] | 1505.56 (M + H) |

TABLE A2-continued
| Ex No. | Cmpd No. | Structure | LCMS |
| --- | --- | --- | --- |
| | | 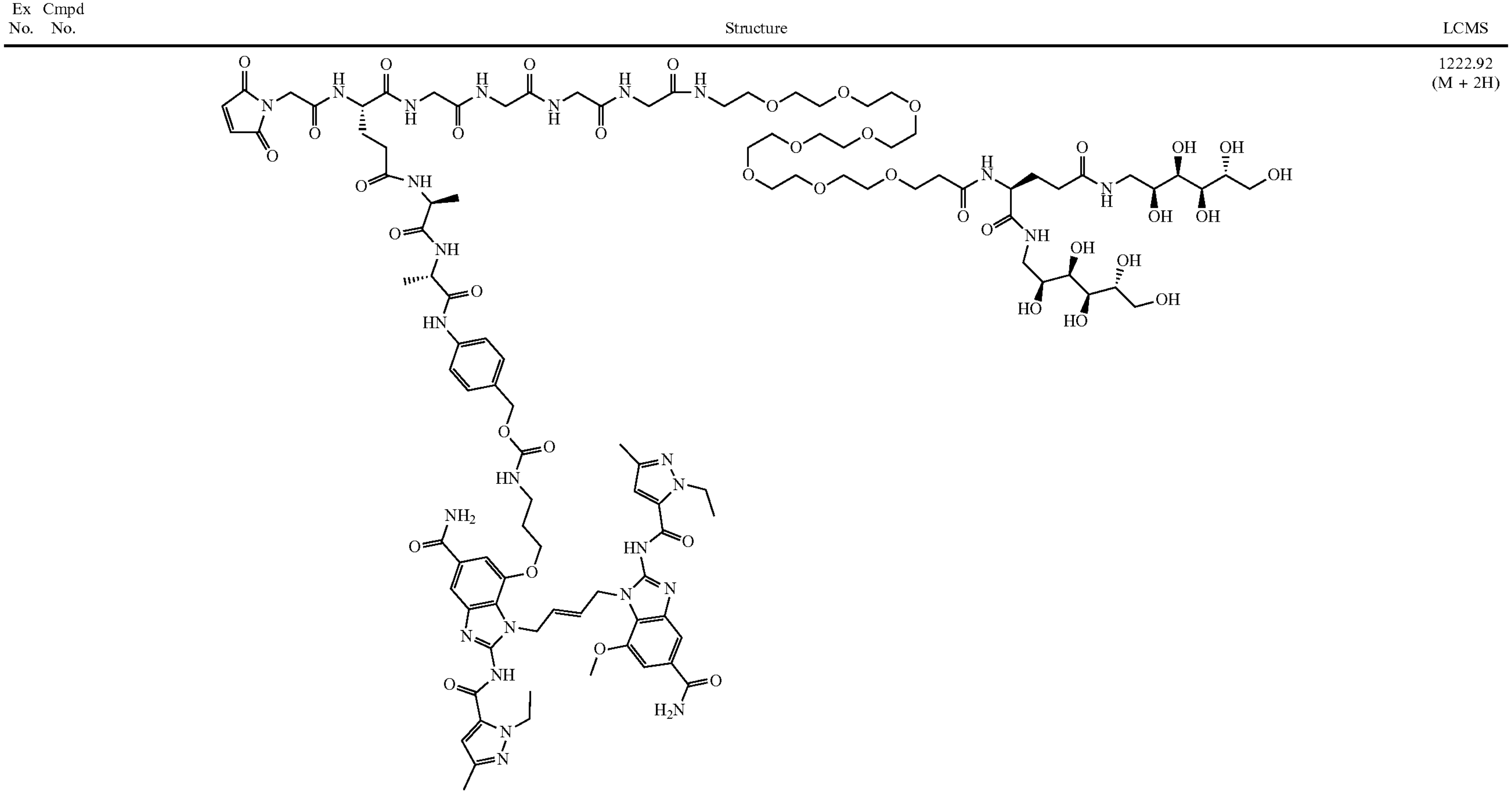 | 1222.92 (M + 2H) |

TABLE A2-continued
| Ex No. | Cmpd No. | Structure | LCMS |
|---|---|---|---|
| 3 | 18 | 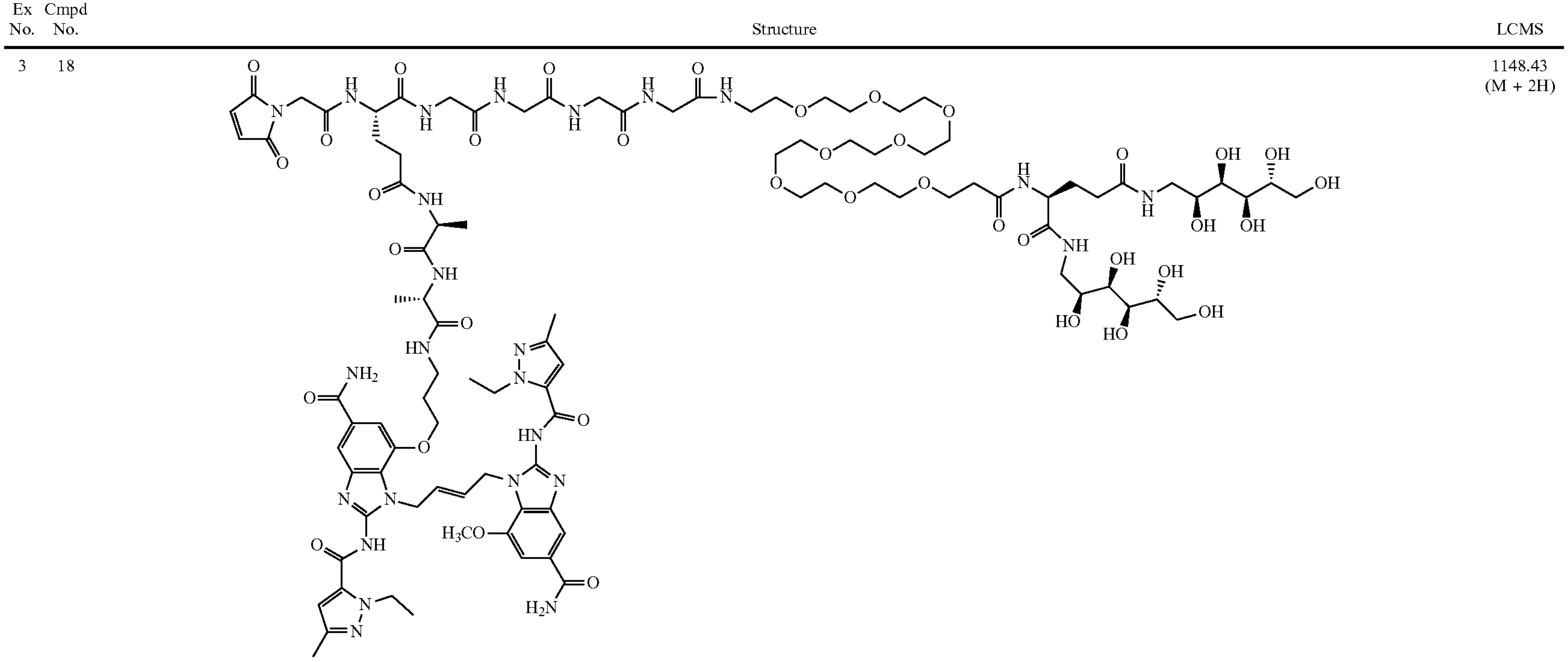 | 1148.43 (M + 2H) |

TABLE A2-continued
| Ex No. | Cmpd No. | Structure | LCMS |
|---|---|---|---|
| | | 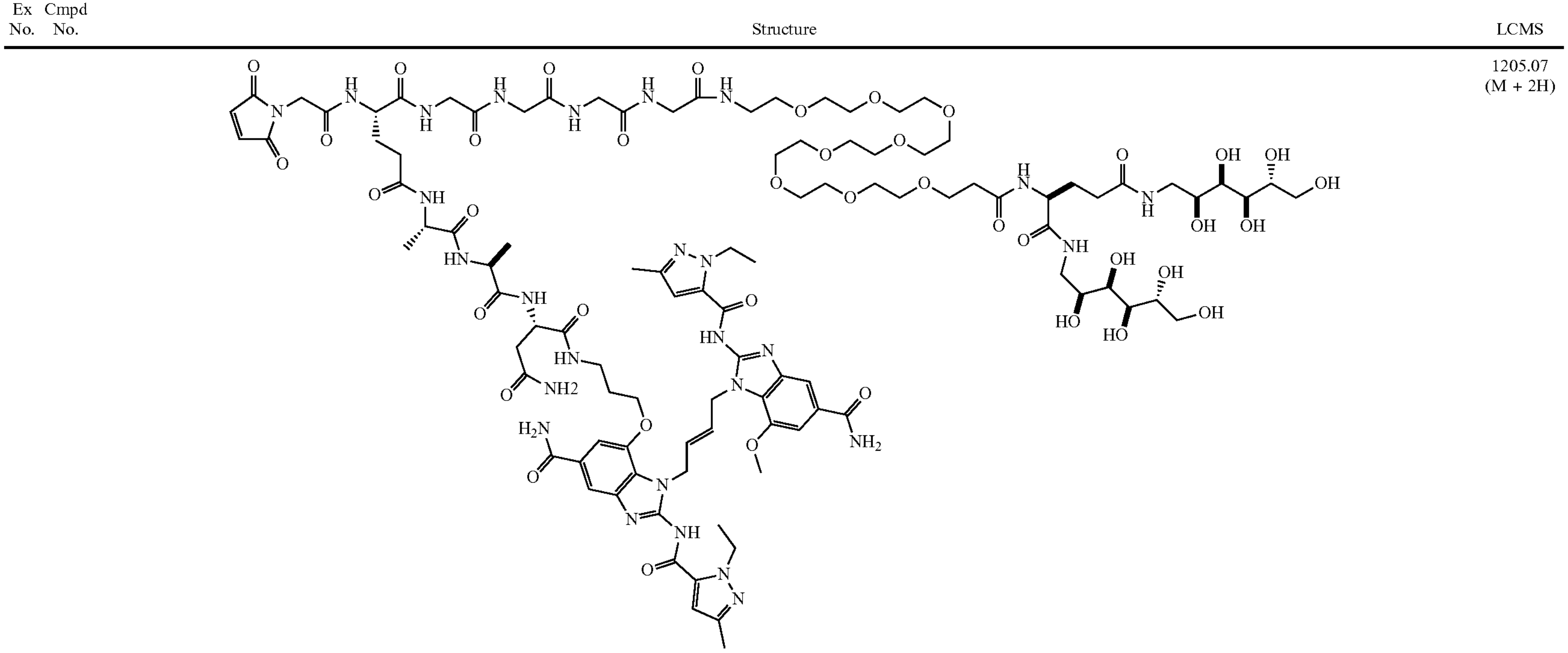 | 1205.07 (M + 2H) |

TABLE A2-continued
| Ex No. | Cmpd No. | Structure | LCMS |
|---|---|---|---|
| | | 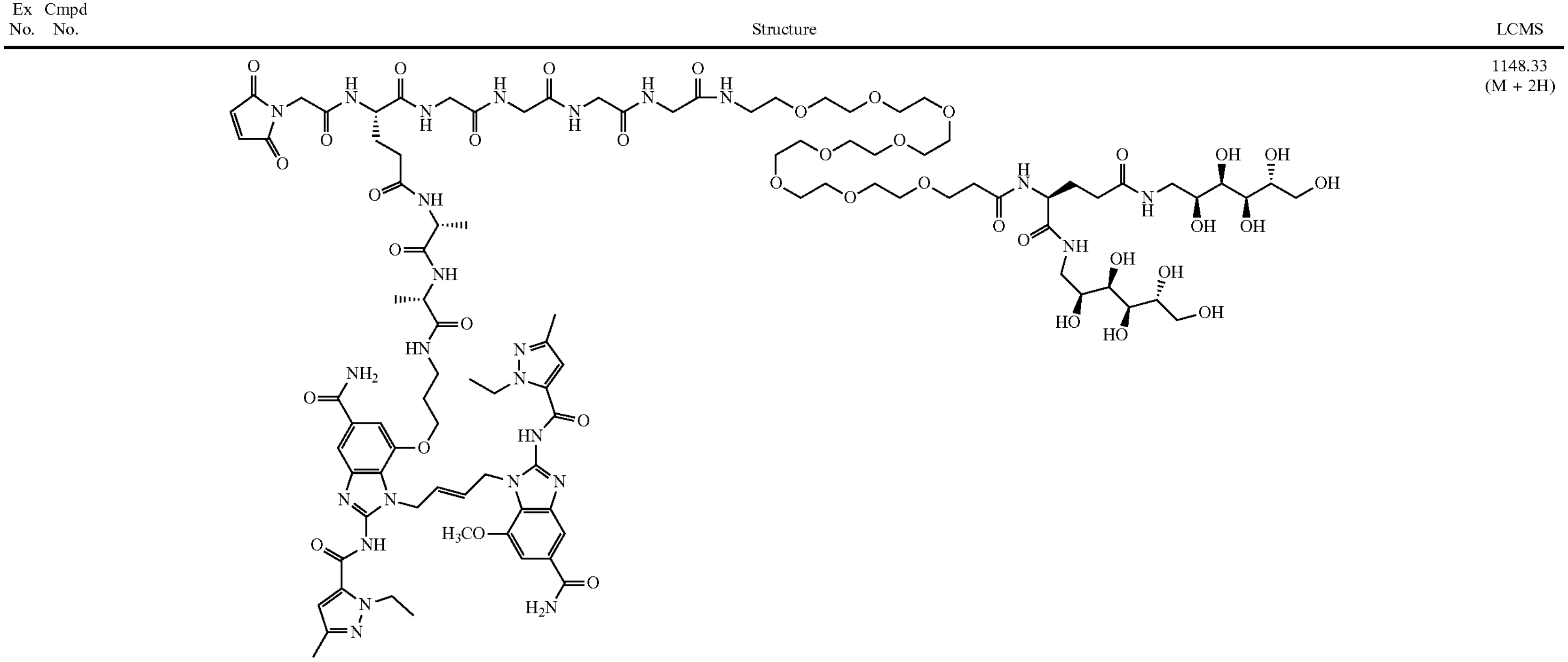 | 1148.33 (M + 2H) |

TABLE A2-continued
| Ex No. | Cmpd No. | Structure | LCMS |
|---|---|---|---|
| | | 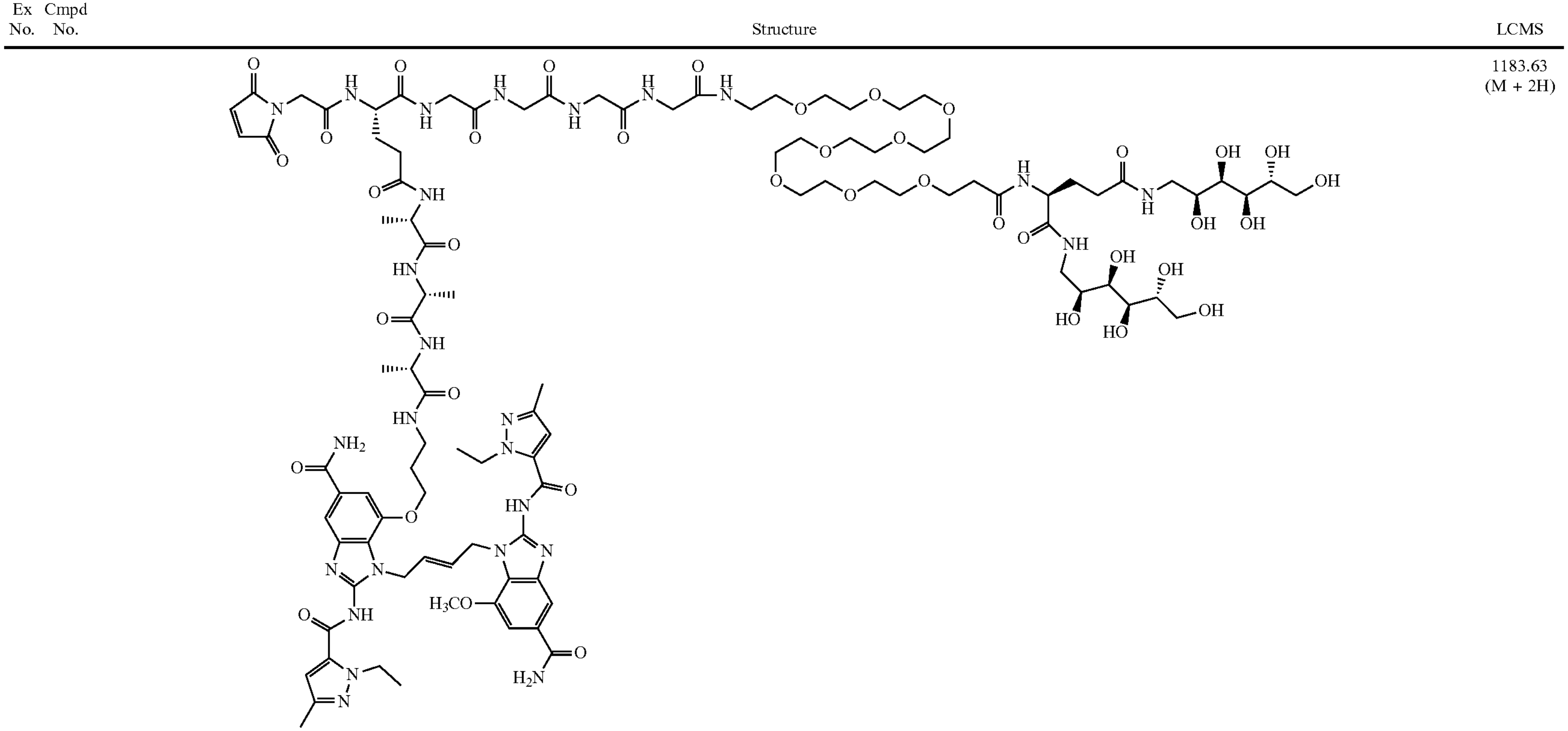 | 1183.63 (M + 2H) |

TABLE A2-continued
| Ex No. | Cmpd No. | Structure | LCMS |
|---|---|---|---|
| 4 | 23 | 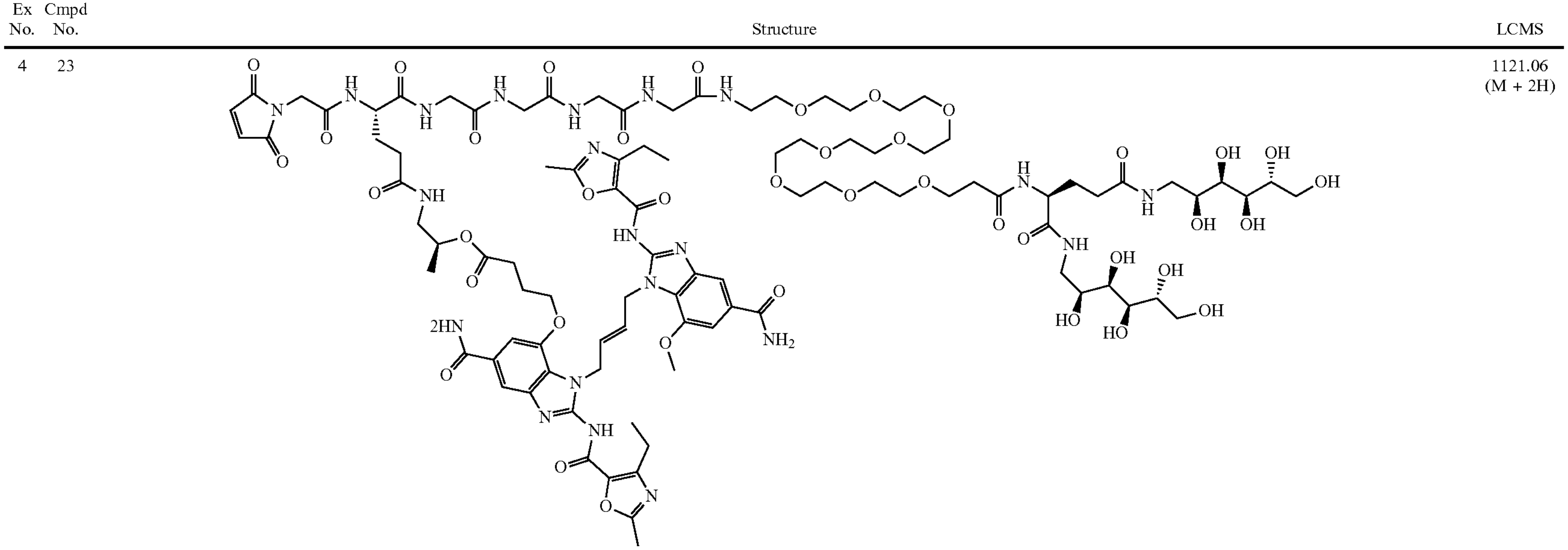 | 1121.06 (M + 2H) |

TABLE A2-continued
| Ex No. | Cmpd No. | Structure | LCMS |
| --- | --- | --- | --- |
| 5 | 37 | 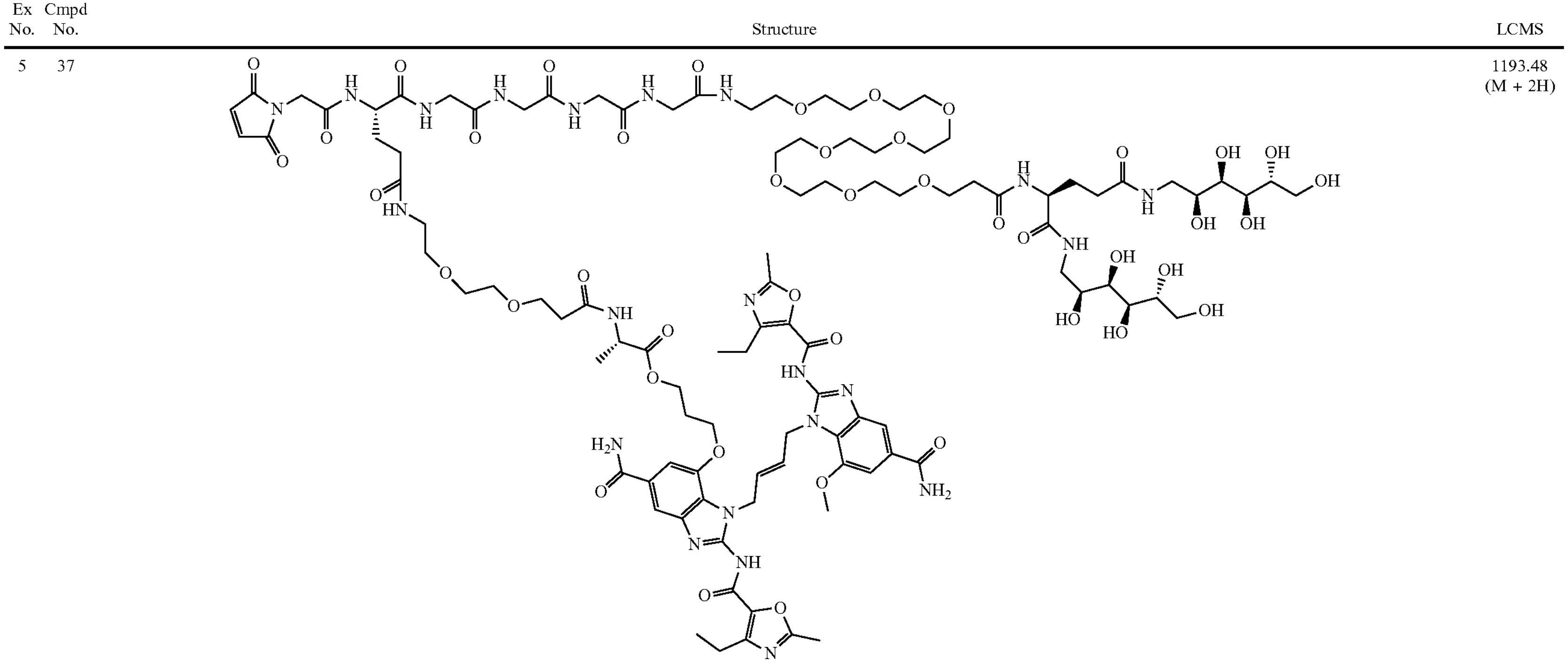 | 1193.48 (M + 2H) |

TABLE A2-continued
| Ex No. | Cmpd No. | Structure | LCMS |
|---|---|---|---|
| 7 | 31 | 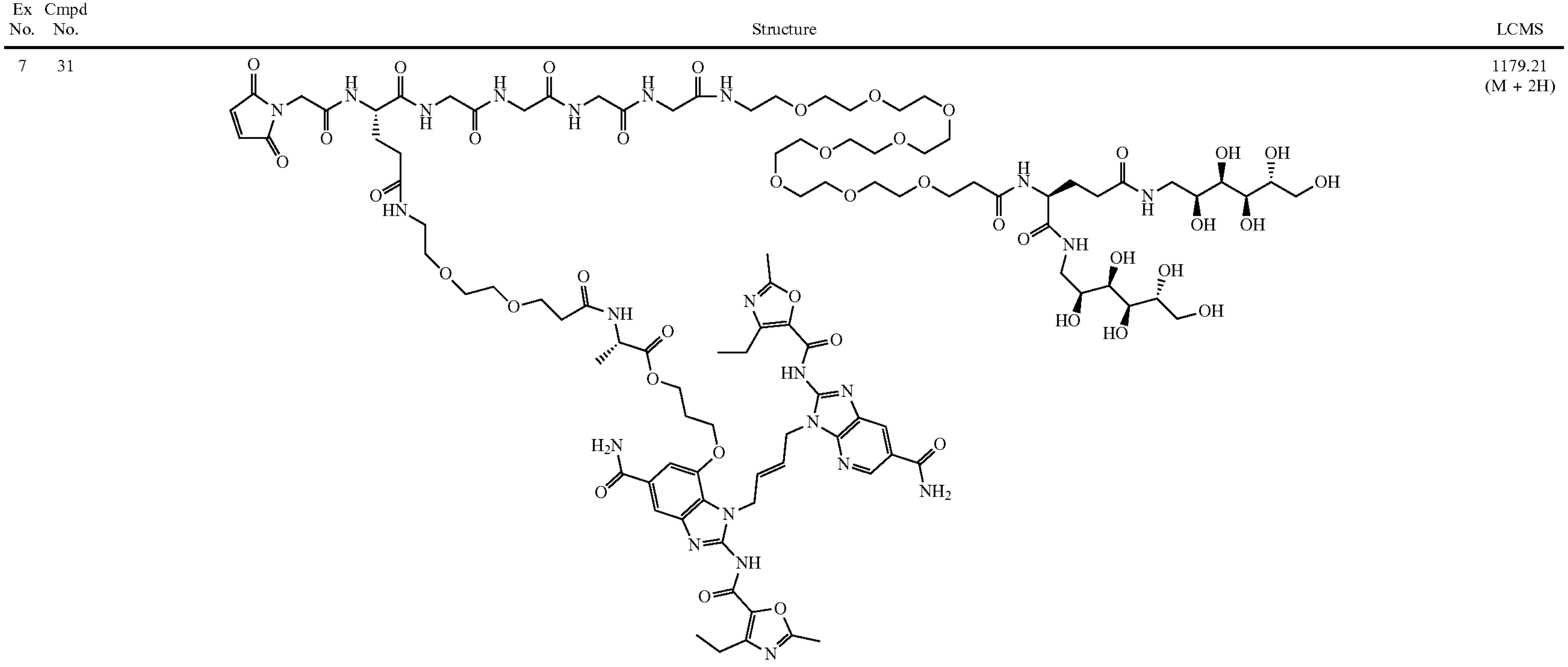 | 1179.21 (M + 2H) |

TABLE A2-continued
| Ex No. | Cmpd No. | Structure | LCMS |
|---|---|---|---|
| | | 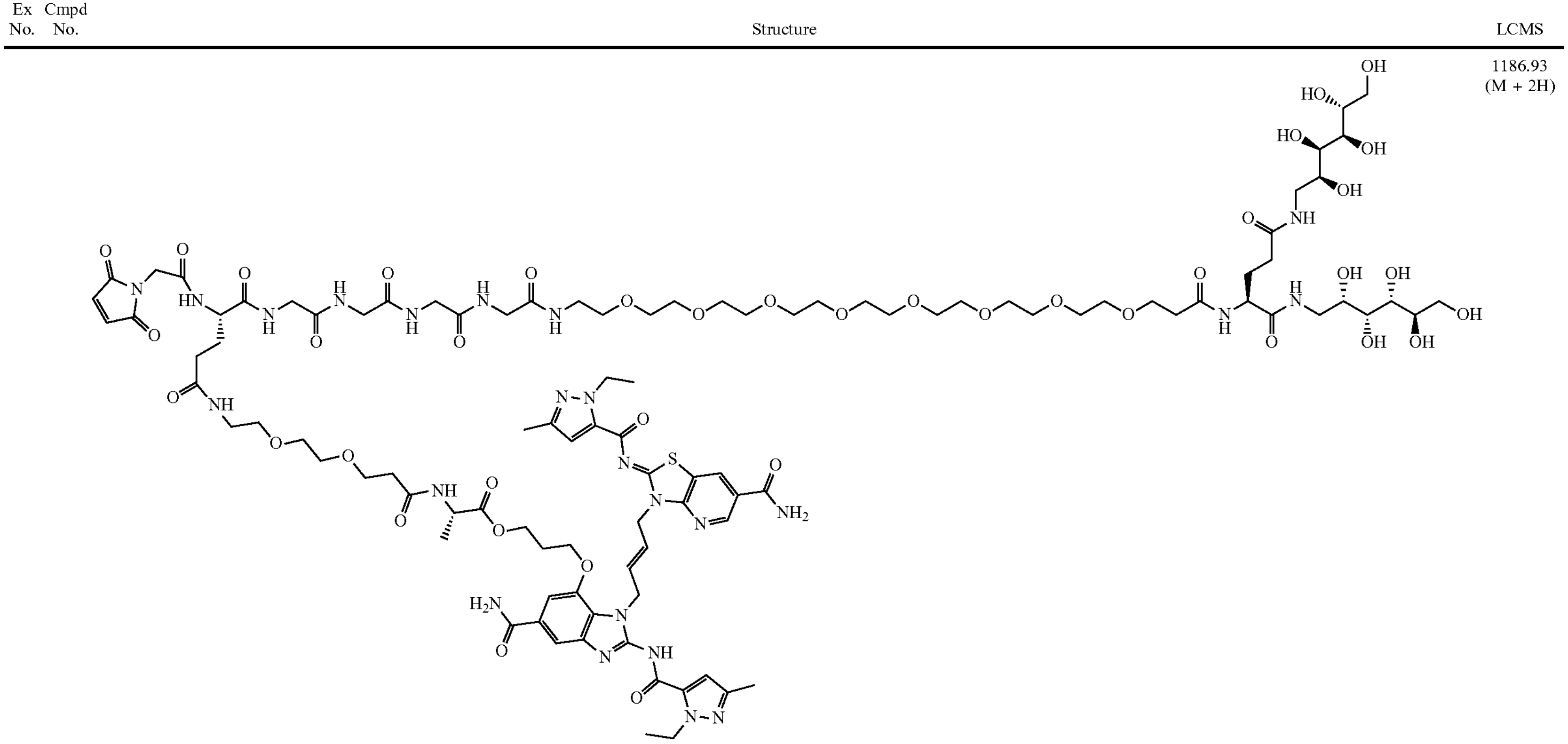 | 1186.93 (M + 2H) |

TABLE A2-continued
| Ex No. | Cmpd No. | Structure | LCMS |
|---|---|---|---|
| | | 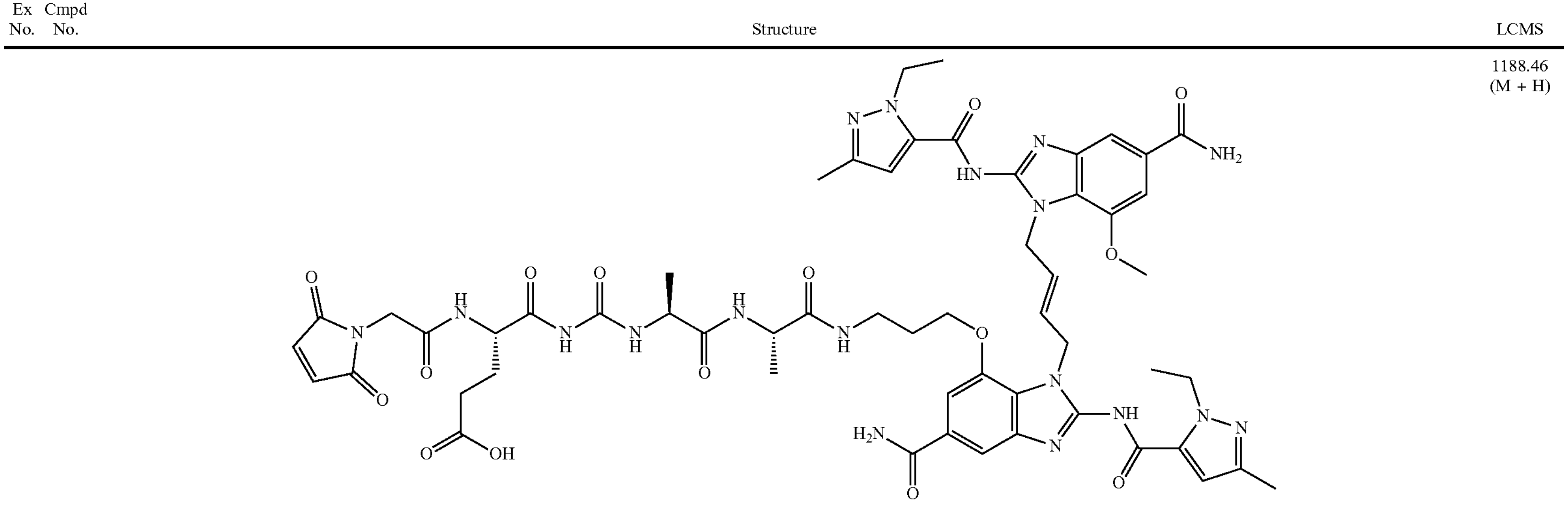 | 1188.46 (M + H) |
| | | 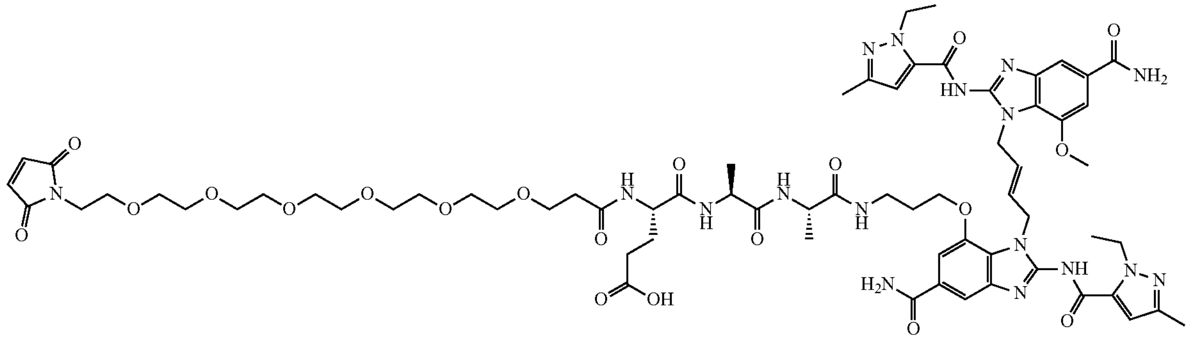 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)[C@H](C)NC(=O)[C@H](C)NC(=O)[C@H](CCC(=O)O)NC(=O)CCOCCOCCOCCOCCOCCOCCN3C(=O)C=CC3=O)c21] | 1466.64 (M + H) |

TABLE A2-continued
| Ex No. | Cmpd No. | Structure | LCMS |
|---|---|---|---|
| | | 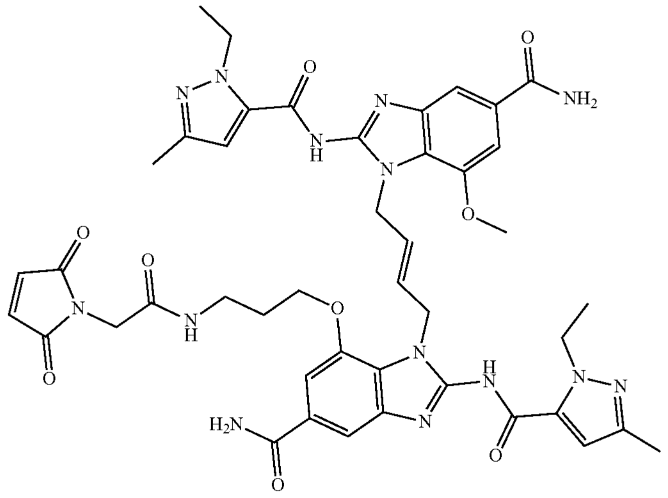 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)CN3C(=O)C=CC3=O)c21] | 917.41 (M + H) |
| 8 | 33 | 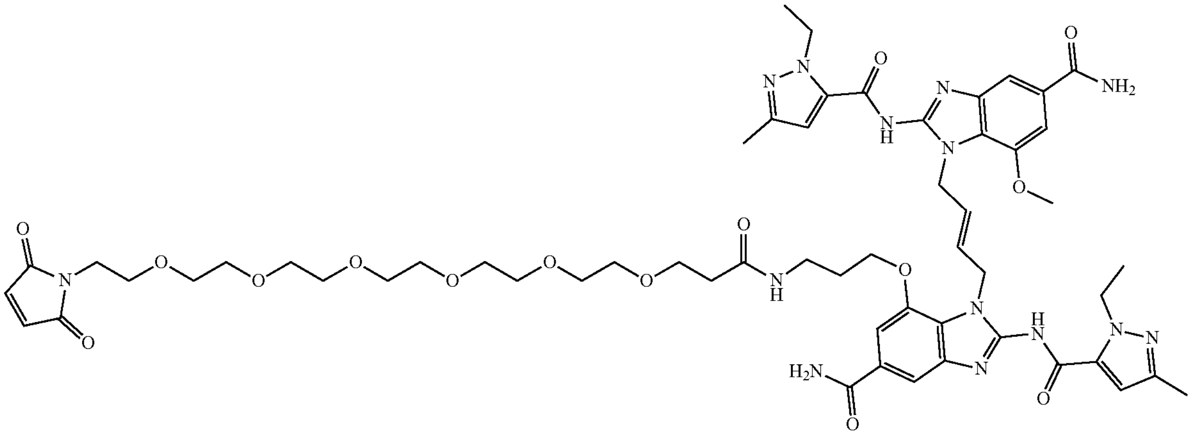 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)CCOCCOCCOCCOCCOCCOCCN3C(=O)C=CC3=O)c21] | 1195.47 (M + H) |

TABLE A2-continued
| Ex No. | Cmpd No. | Structure | LCMS |
|---|---|---|---|
| | | 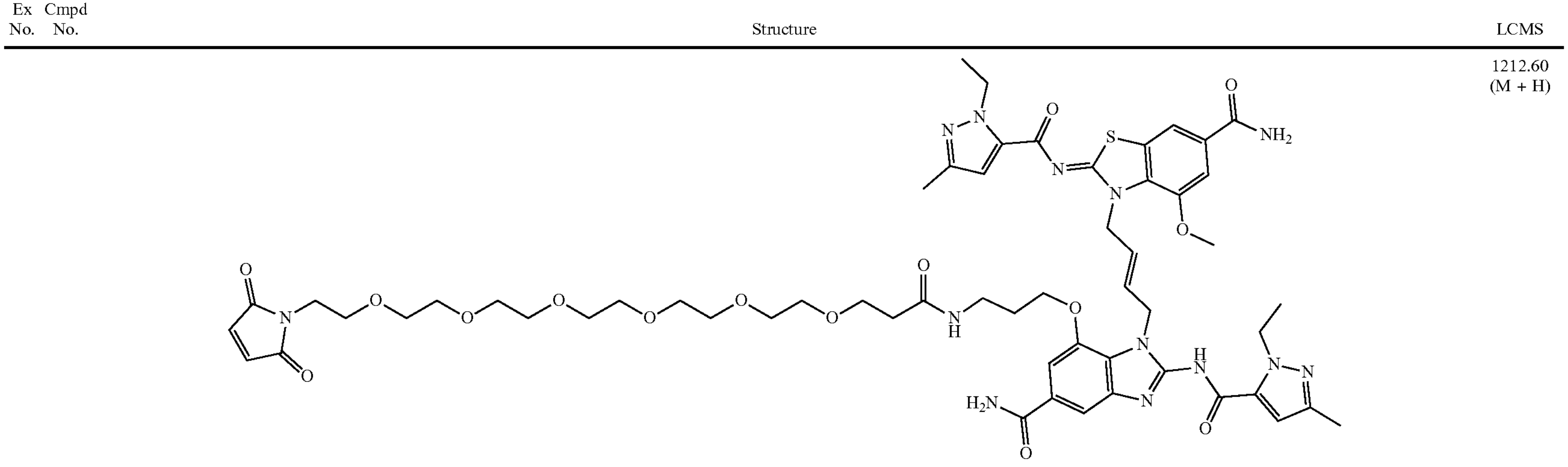 | 1212.60 (M + H) |
| | | 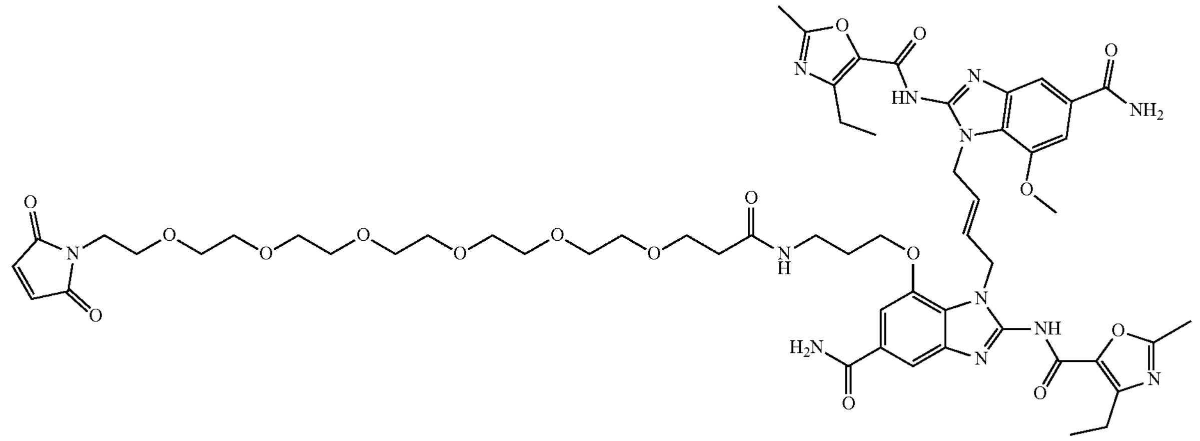 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCNC(=O)CCOCCOCCOCCOCCOCCOCCN3C(=O)C=CC3=O)c21] | 1197.50 (M + H) |

TABLE A2-continued
| Ex No. | Cmpd No. | Structure | LCMS |
|---|---|---|---|
| | | 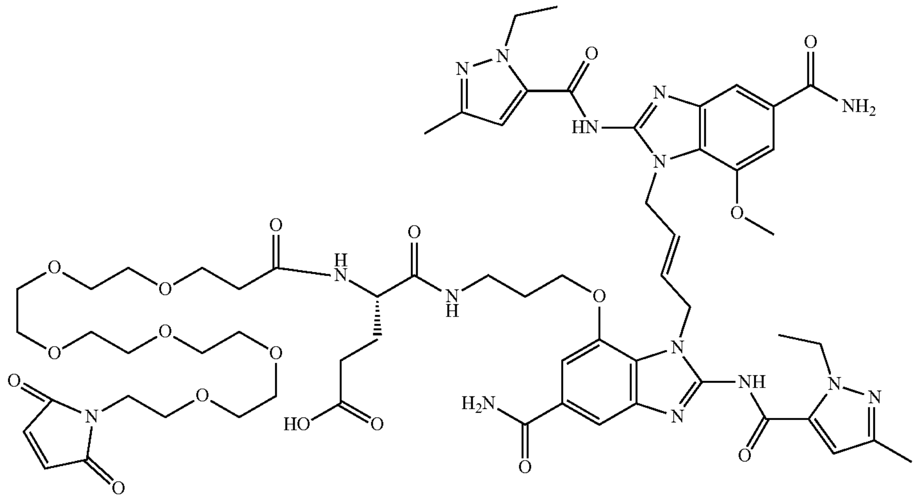 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)[C@H](CCC(=O)O)NC(=O)CCOCCOCCOCCOCCOCCOCCN3C(=O)C=CC3=O)c21] | 1324.40 (M + H) |
| | | 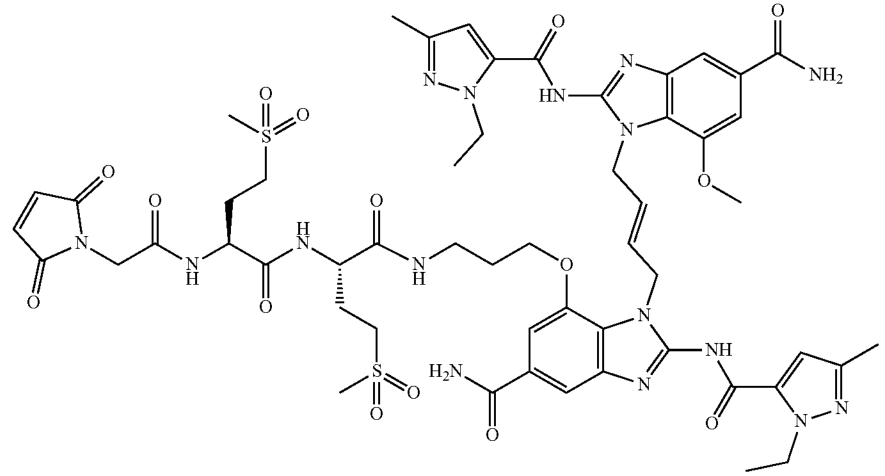 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCNC(=O)[C@H](CCS(C)(=O)=O)NC(=O)[C@H](CCS(C)(=O)=O)NC(=O)CN3C(=O)C=CC3=O)c21] | 1243.24 (M + H) |

TABLE A2-continued
| Ex No. | Cmpd No. | Structure | LCMS |
|---|---|---|---|
| | | 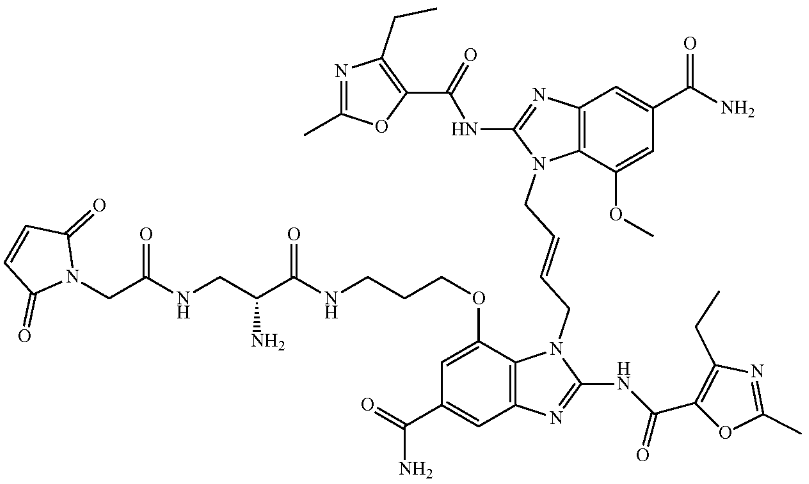 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCNC(=O)[C@H](N)CNC(=O)CN3C(=O)C=CC3=O)c21] | 1005.22 (M + H) |
| 9 | 44 | 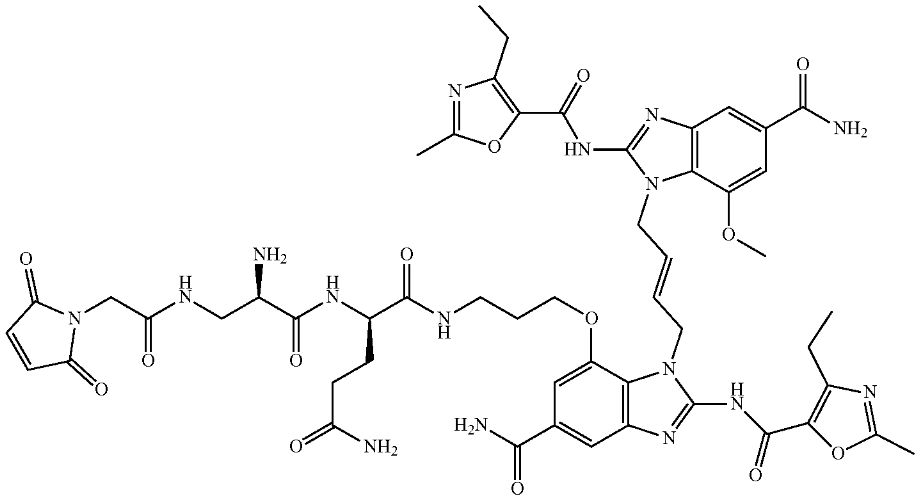 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCNC(=O)[C@@H](CCC(N)=O)NC(=O)[C@H](N)CNC(=O)CN3C(=O)C=CC3=O)c21] | 1134.24 (M + H) |

TABLE A2-continued
| Ex No. | Cmpd No. | Structure | LCMS |
|---|---|---|---|
| | | 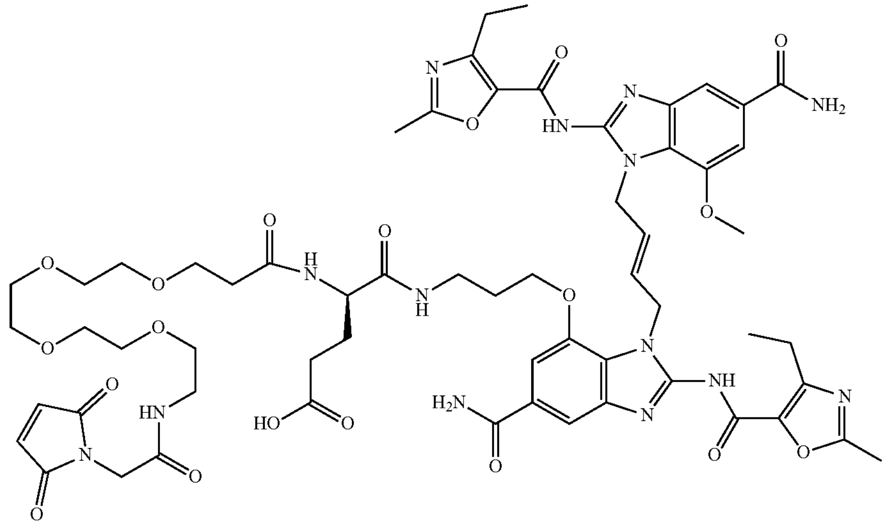 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCNC(=O)[C@@H](CCC(=O)O)NC(=O)CCOCCOCCOCCOCCNC(=O)CN3C(=O)C=CC3=O)c21] | 1295.26 (M + H) |
| 10 | 49 | 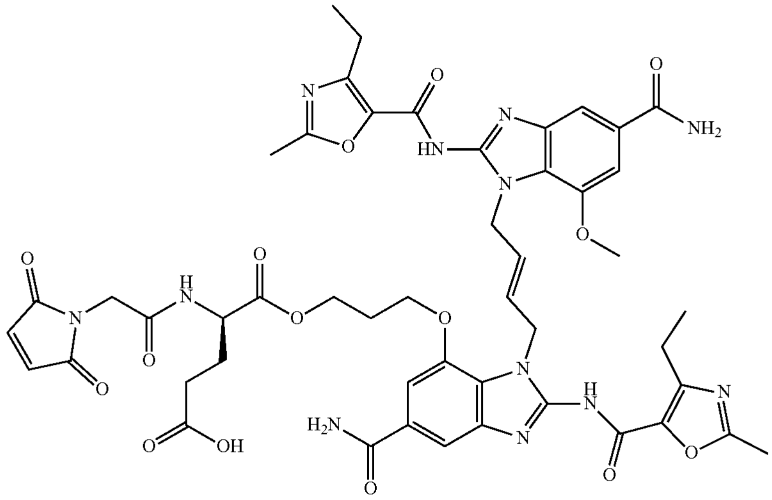 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@@H](CCC(=O)O)NC(=O)CN3C(=O)C=CC3=O)c21] | 1049.15 (M + H) |

TABLE A2-continued
| Ex No. | Cmpd No. | Structure | LCMS |
|---|---|---|---|
| 11 | 51 | 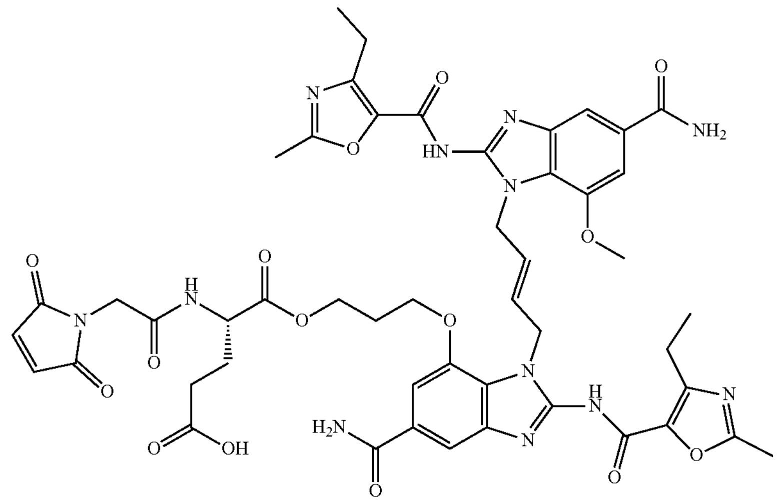 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@H](CCC(=O)O)NC(=O)CN3C(=O)C=CC3=O)c21] | 1049.38 (M + H) |
| 12 | 57 | 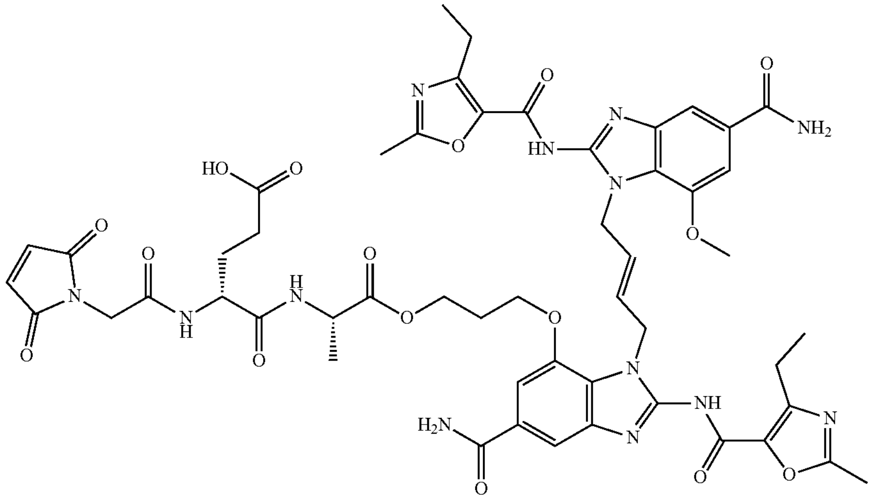 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@H](C)NC(=O)[C@@H](CCC(=O)O)NC(=O)CN3C(=O)C=CC3=O)c21] | 1120.41 (M + H) |

TABLE A2-continued
| Ex No. | Cmpd No. | Structure | LCMS |
| --- | --- | --- | --- |
| 13 | 59 | 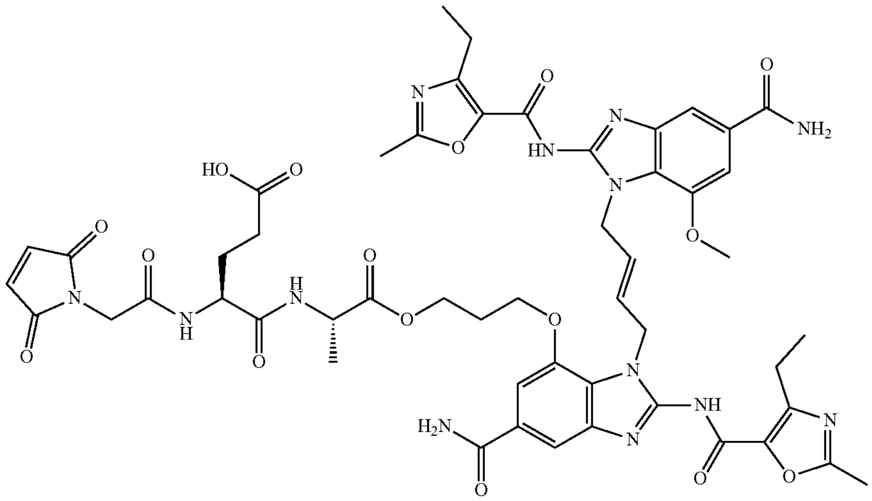 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@H](C)NC(=O)[C@H](CCC(=O)O)NC(=O)CN3C(=O)C=CC3=O)c21] | 1120.38 (M + H) |
| 14 | 61 | 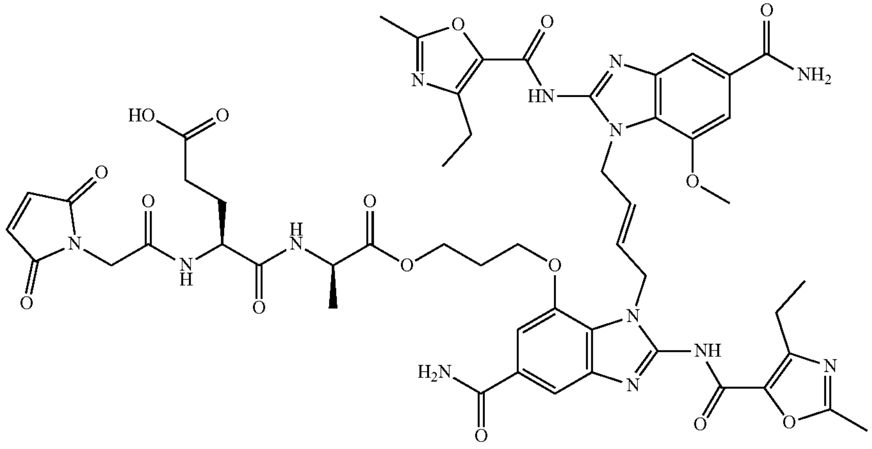 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@@H](C)NC(=O)[C@H](CCC(=O)O)NC(=O)CN3C(=O)C=CC3=O)c21] | 1120.37 (M + H) |

TABLE A2-continued
| Ex No. | Cmpd No. | Structure | LCMS |
| --- | --- | --- | --- |
| 15 | 63 | 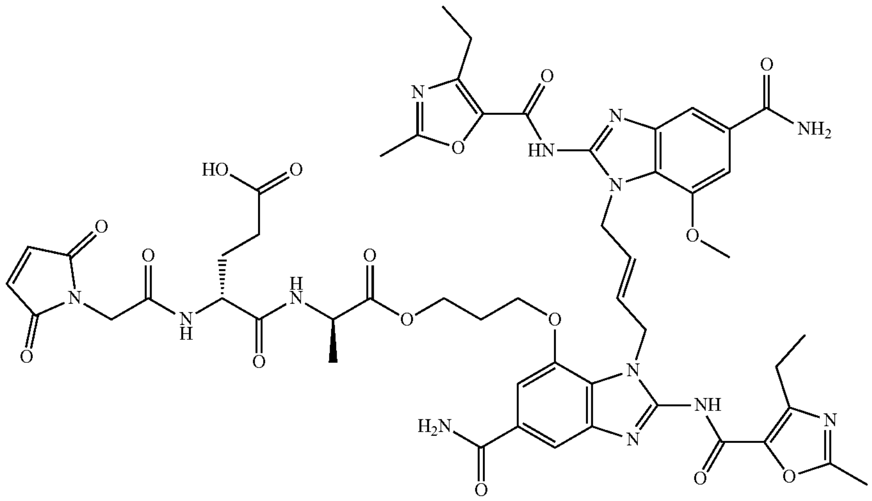 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@@H](C)NC(=O)[C@@H](CCC(=O)O)NC(=O)CN3C(=O)C=CC3=O)c21] | 1120.11 (M + H) |
| 16 | 65 | 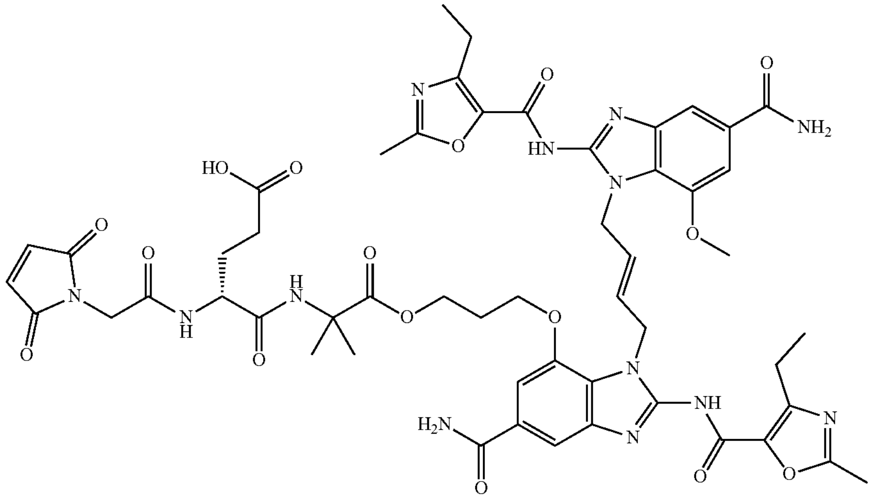 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)C(C)(C)NC(=O)[C@@H](CCC(=O)O)NC(=O)CN3C(=O)C=CC3=O)c21] | 1134.19 (M + H) |

TABLE A2-continued
| Ex No. | Cmpd No. | Structure | LCMS |
|---|---|---|---|
| 17 | 73 | 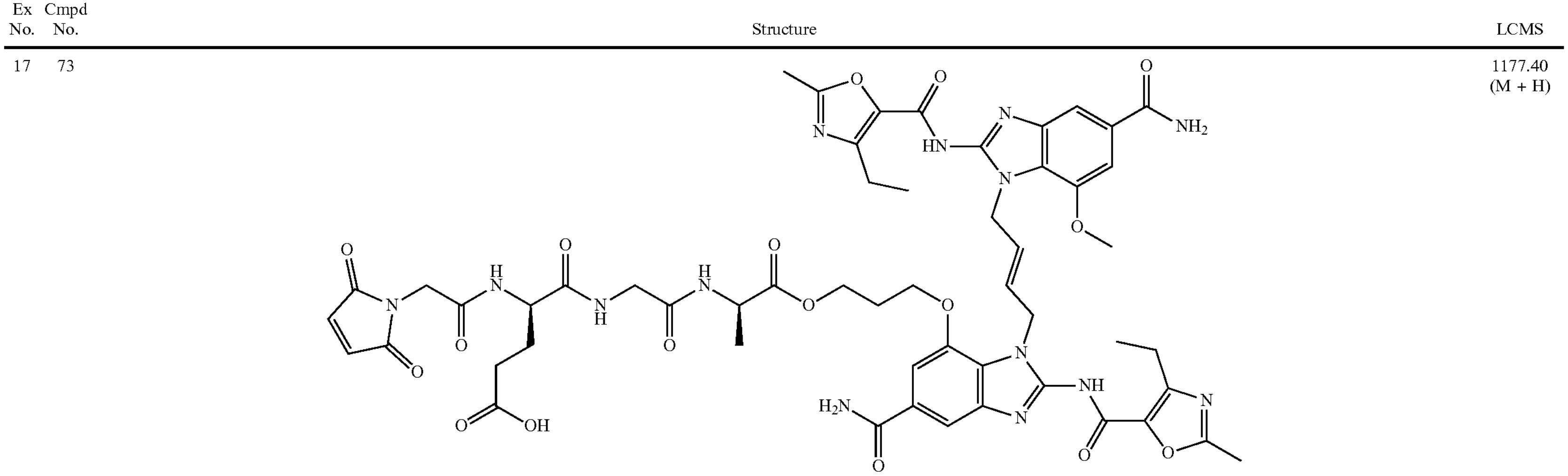 | 1177.40 (M + H) |
| 18 | 75 | 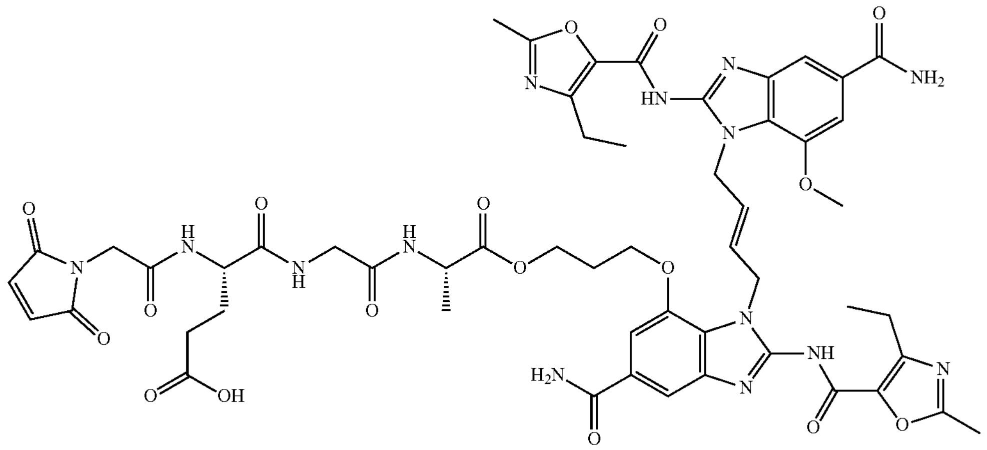 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@H](C)NC(=O)CNC(=O)[C@H](CCC(=O)O)NC(=O)CN3C(=O)C=CC3=O)c21] | 1177.41 (M + H) |

TABLE A2-continued
| Ex No. | Cmpd No. | Structure | LCMS |
|---|---|---|---|
| 19 | 77 | 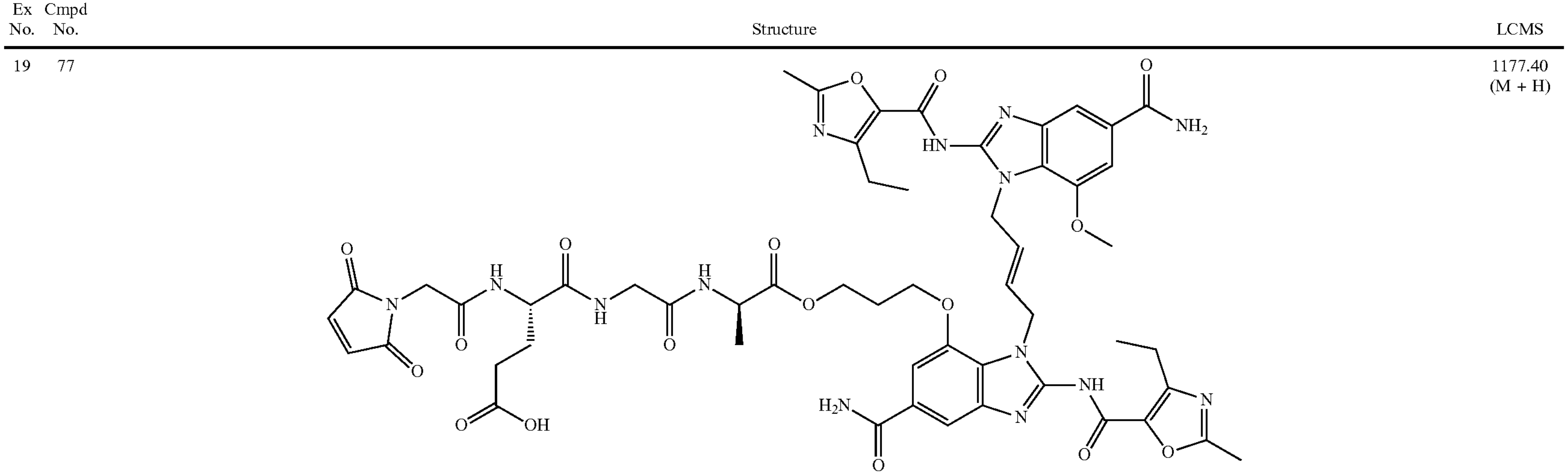 | 1177.40 (M + H) |
| 20 | 79 | 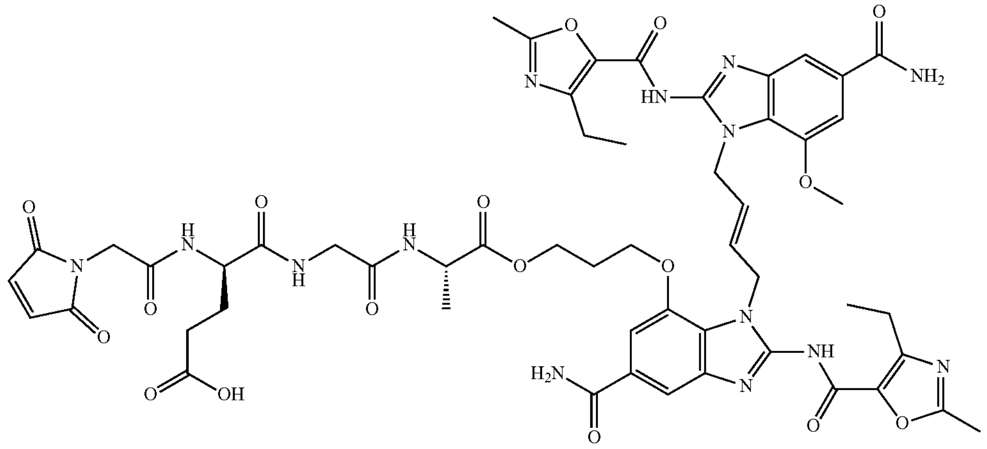 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)[C@H](C)NC(=O)CNC(=O)[C@@H](CCC(=O)O)NC(=O)CN3C(=O)C=CC3=O)c21] | 1177.44 (M + H) |

TABLE A2-continued
| Ex No. | Cmpd No. | Structure | LCMS |
|---|---|---|---|
| 21 | 81 | 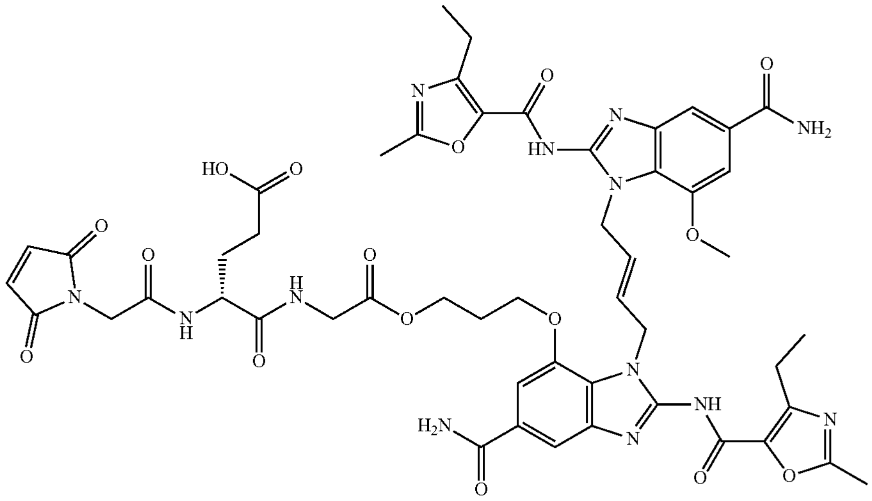 [SMILES: CCc1nc(C)oc1C(=O)Nc1nc2cc(C(N)=O)cc(OC)c2n1C/C=C/Cn1c(NC(=O)c2oc(C)nc2CC)nc2cc(C(N)=O)cc(OCCCOC(=O)CNC(=O)[C@@H](CCC(=O)O)NC(=O)CN3C(=O)C=CC3=O)c21] | 1106.17 (M + H) |
| | | 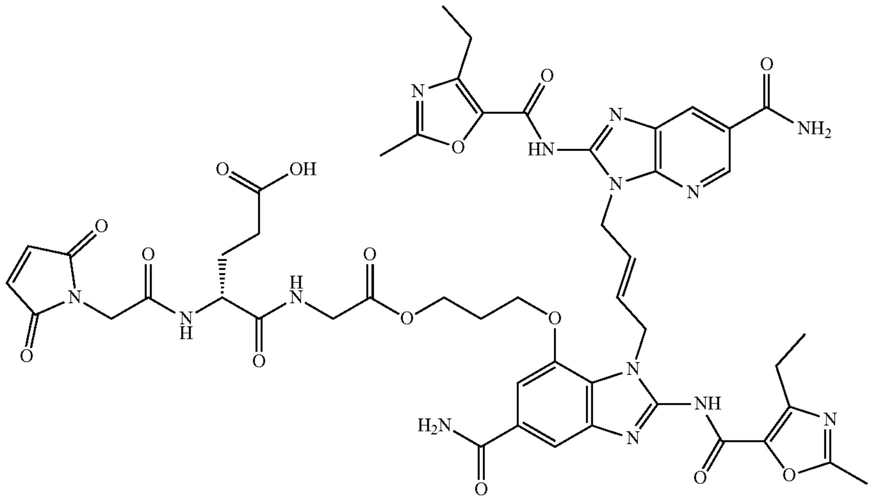 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cc(OCCCOC(=O)CNC(=O)[C@@H](CCC(=O)O)NC(=O)CN3C(=O)C=CC3=O)c21] | 1077.15 (M + H) |

TABLE A2-continued
| Ex No. | Cmpd No. | Structure | LCMS |
| --- | --- | --- | --- |
| | | 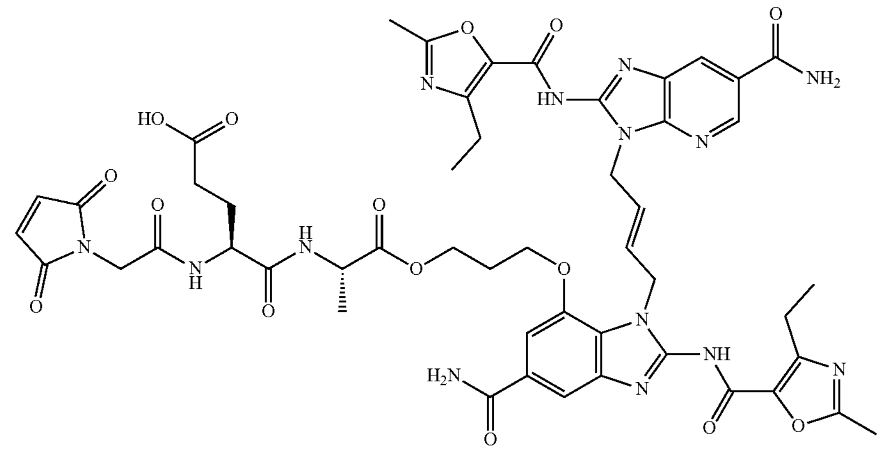 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cc(OCCCOC(=O)[C@H](C)NC(=O)[C@H](CCC(=O)O)NC(=O)CN3C(=O)C=CC3=O)c21] | 1091.18 (M + H) |
| | | 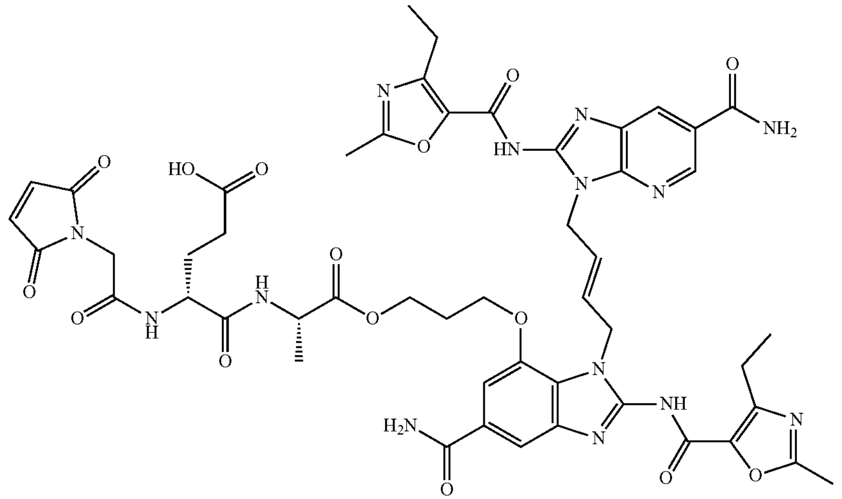 [SMILES: CCc1nc(C)oc1C(=O)Nc1nc2cc(C(N)=O)cnc2n1C/C=C/Cn1c(NC(=O)c2oc(C)nc2CC)nc2cc(C(N)=O)cc(OCCCOC(=O)[C@H](C)NC(=O)[C@@H](CCC(=O)O)NC(=O)CN3C(=O)C=CC3=O)c21] | 1091.17 (M + H) |

TABLE A2-continued
| Ex No. | Cmpd No. | Structure | LCMS |
|---|---|---|---|
| | | 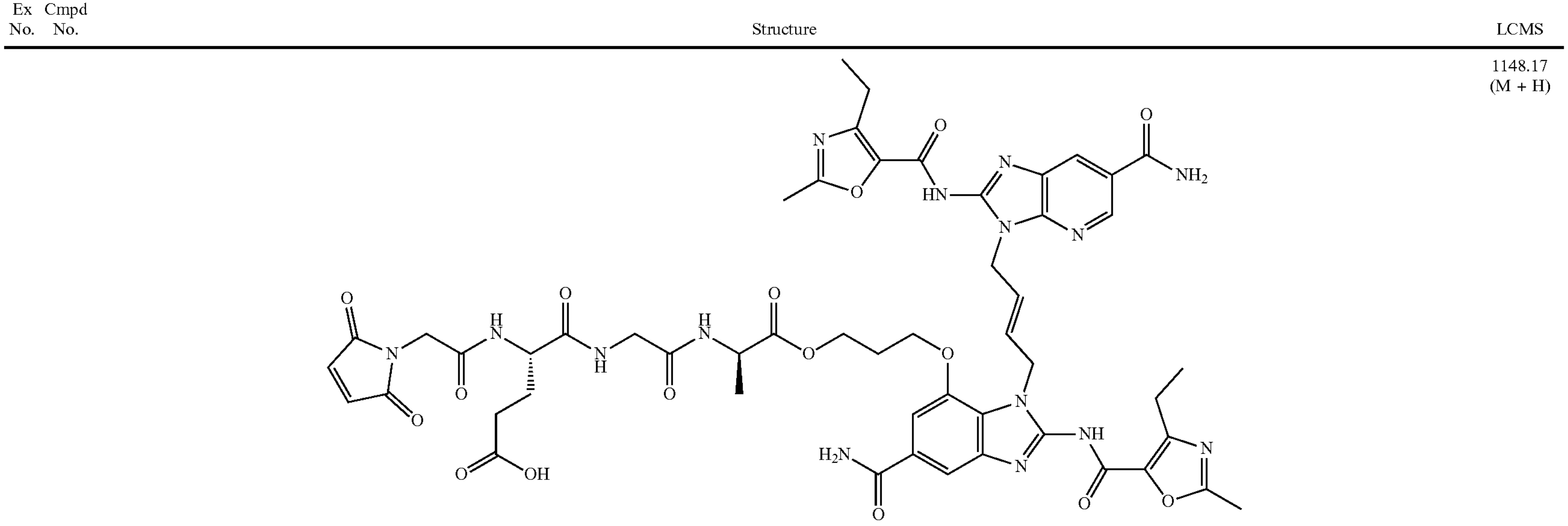 | 1148.17 (M + H) |
| | | 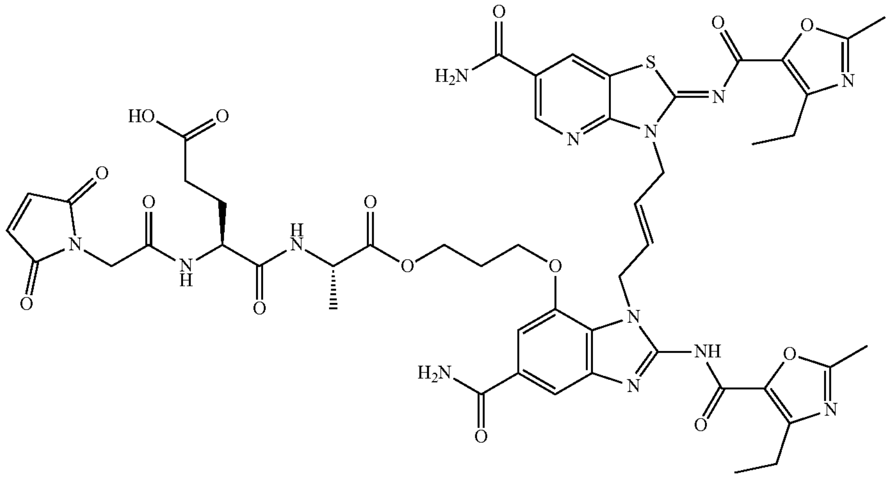 [SMILES: CCc1nc(C)oc1C(=O)/N=c1\sc2cc(C(N)=O)cnc2n1C/C=C/Cn1c(NC(=O)c2oc(C)nc2CC)nc2cc(C(N)=O)cc(OCCCOC(=O)[C@H](C)NC(=O)[C@H](CCC(=O)O)NC(=O)CN3C(=O)C=CC3=O)c21] | 1108.12 (M + H) |

TABLE A2-continued
| Ex No. | Cmpd No. | Structure | LCMS |
| --- | --- | --- | --- |
| | | 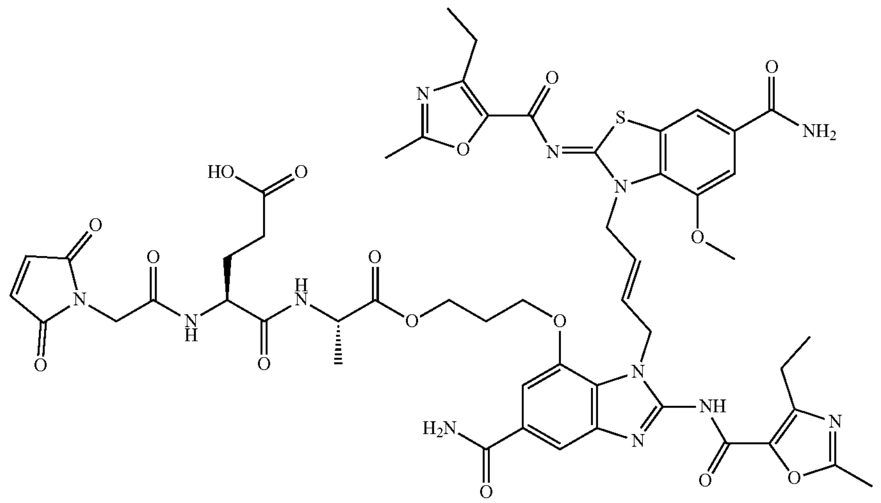 [SMILES: CCc1nc(C)oc1C(=O)/N=c1\sc2cc(C(N)=O)cc(OC)c2n1C/C=C/Cn1c(NC(=O)c2oc(C)nc2CC)nc2cc(C(N)=O)cc(OCCCOC(=O)[C@H](C)NC(=O)[C@H](CCC(=O)O)NC(=O)CN3C(=O)C=CC3=O)c21] | 1137.15 (M + H) |
| | | 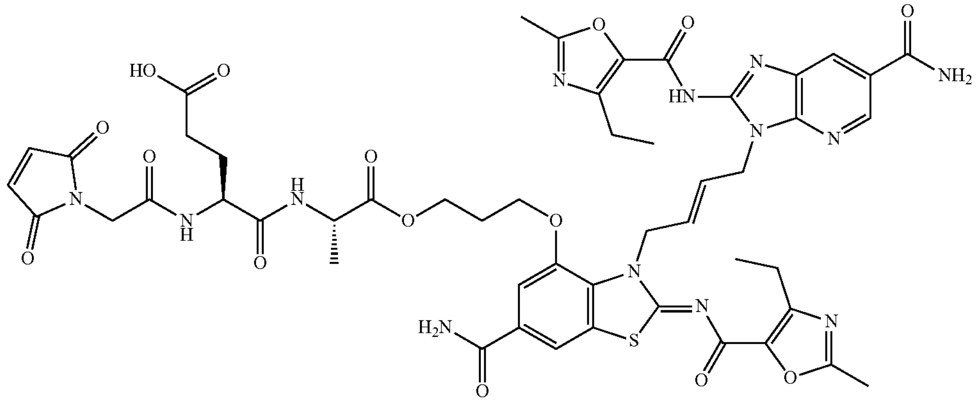 [SMILES: CCc1nc(C)oc1C(=O)/N=c1\sc2cc(C(N)=O)cc(OCCCOC(=O)[C@H](C)NC(=O)[C@H](CCC(=O)O)NC(=O)CN3C(=O)C=CC3=O)c2n1C/C=C/Cn1c(NC(=O)c2oc(C)nc2CC)nc2cc(C(N)=O)cnc21] | 1108.14 (M + H) |

TABLE A2-continued
| Ex No. | Cmpd No. | Structure | LCMS |
|---|---|---|---|
| | | 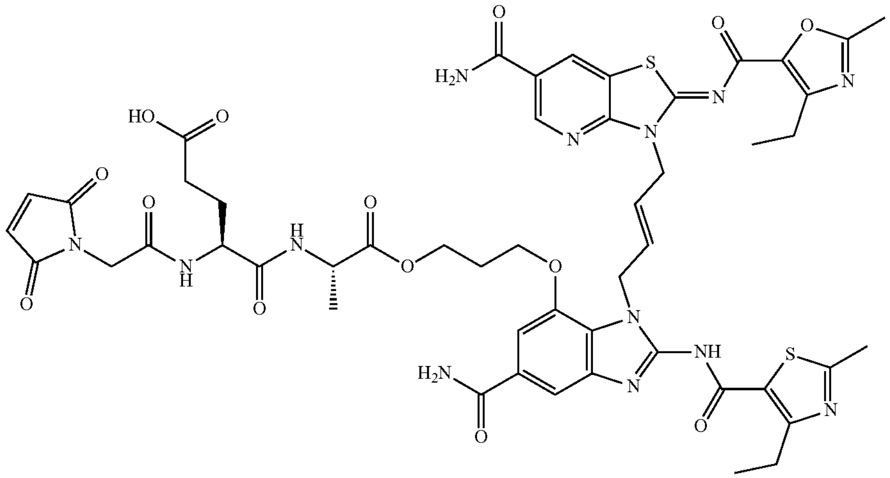 | |
| | | 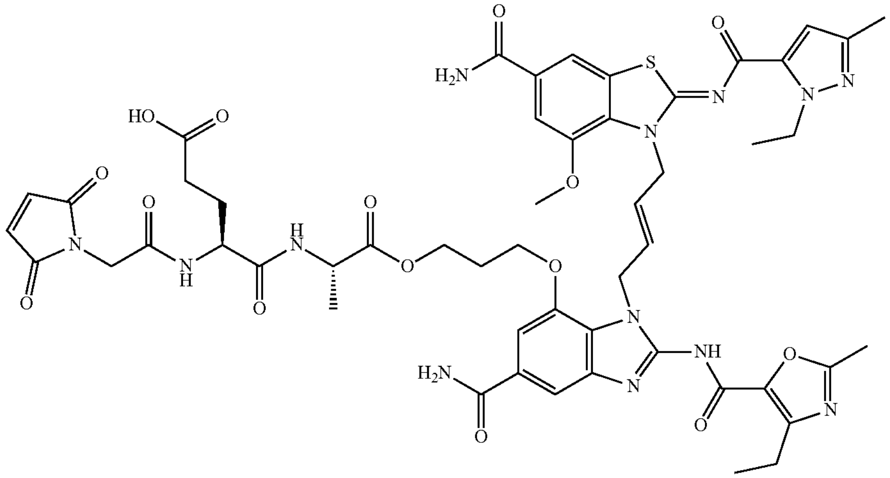 [SMILES: CCc1nc(C)oc1C(=O)Nc1nc2cc(C(N)=O)cc(OCCCOC(=O)[C@H](C)NC(=O)[C@H](CCC(=O)O)NC(=O)CN3C(=O)C=CC3=O)c2n1C/C=C/Cn1/c(=N/C(=O)c2cc(C)nn2CC)sc2cc(C(N)=O)cc(OC)c21] | |

TABLE A2-continued
| Ex No. | Cmpd No. | Structure | LCMS |
| --- | --- | --- | --- |
| | | 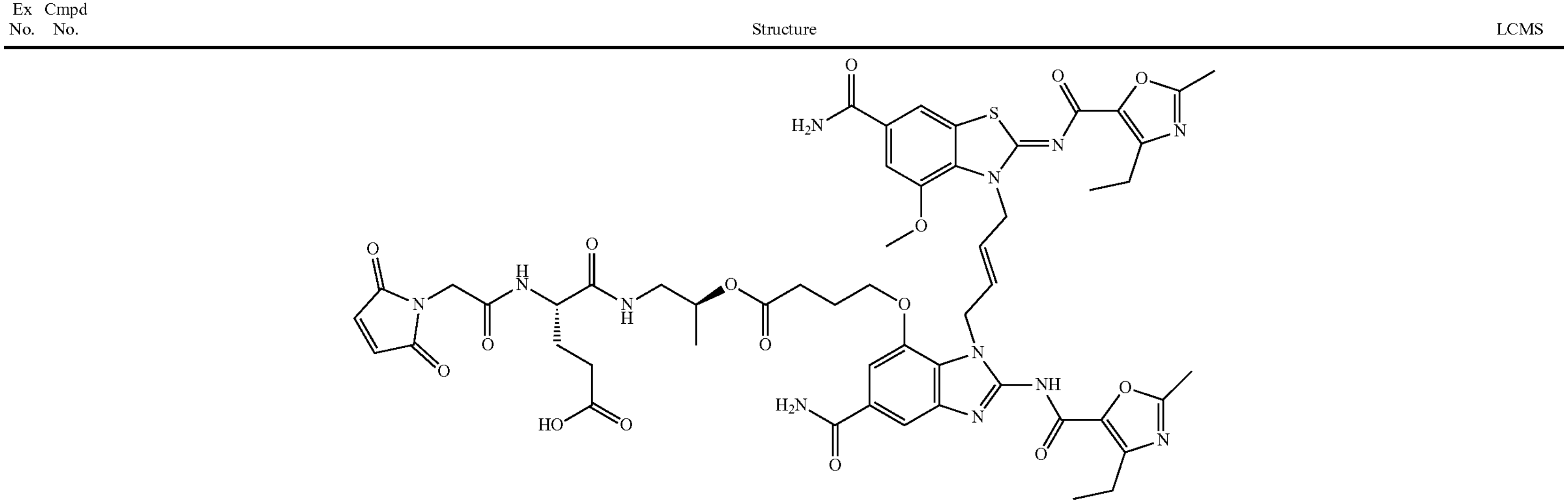 | |
| | | 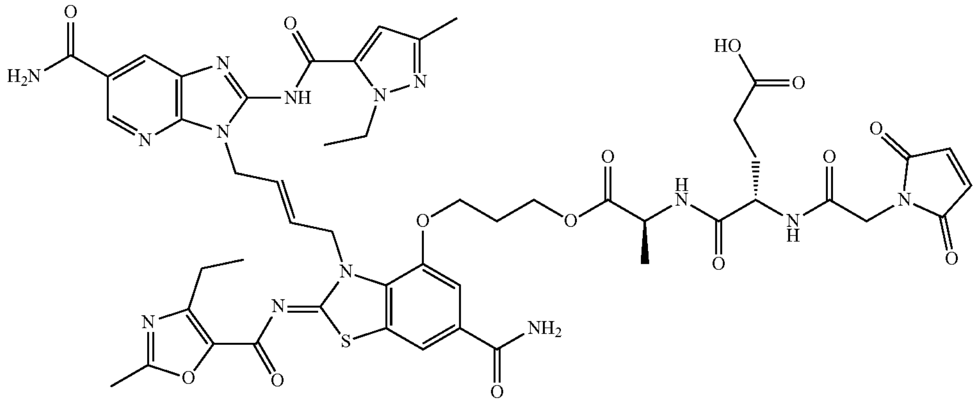 [SMILES: CCc1nc(C)oc1C(=O)/N=c1\sc2cc(C(N)=O)cc(OCCCOC(=O)[C@H](C)NC(=O)[C@H](CCC(=O)O)NC(=O)CN3C(=O)C=CC3=O)c2n1C/C=C/Cn1c(NC(=O)c2cc(C)nn2CC)nc2cc(C(N)=O)cnc21] | |

TABLE A2-continued
| Ex No. | Cmpd No. | Structure | LCMS |
|---|---|---|---|
| | | 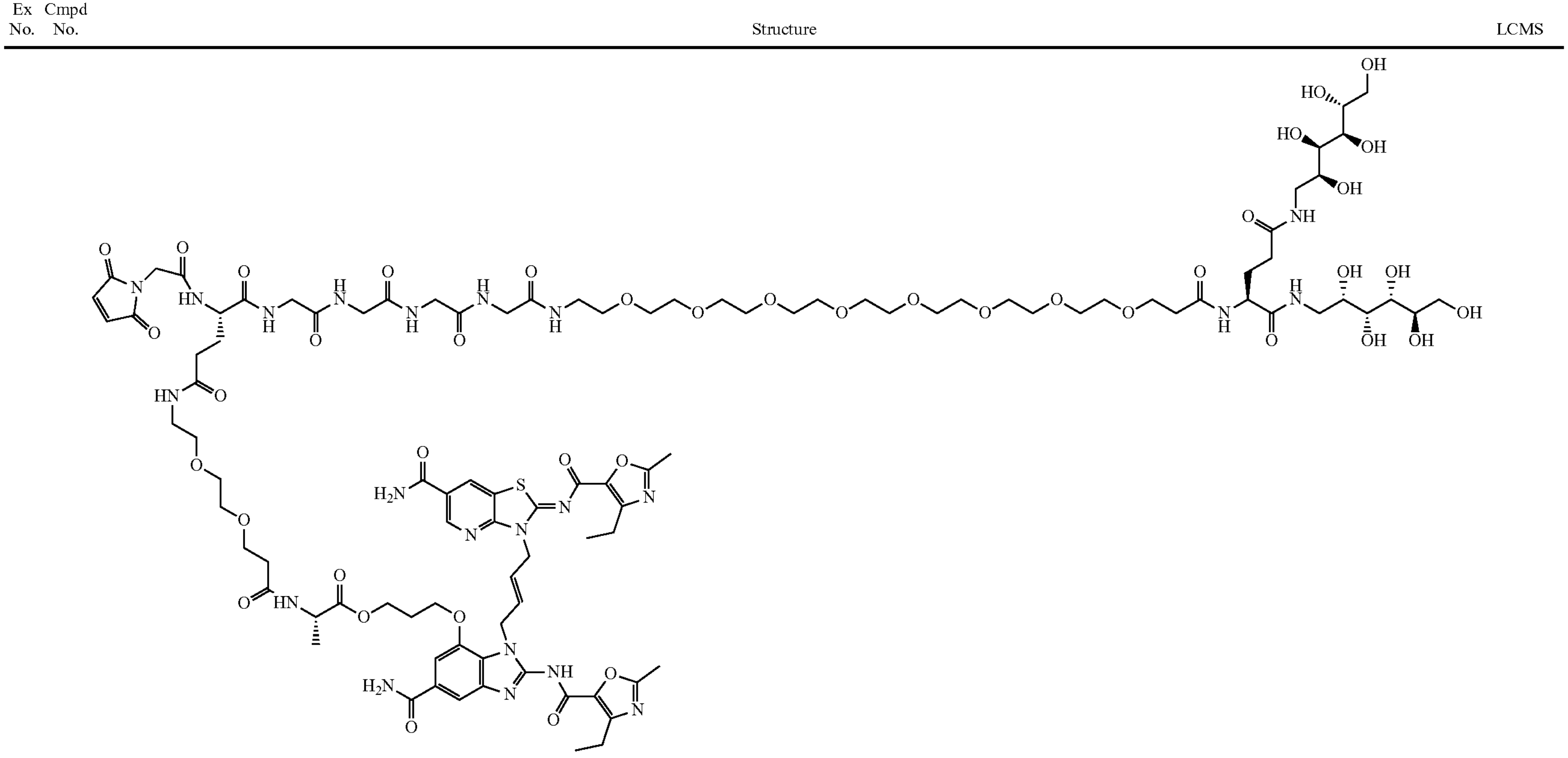 | |

TABLE A2-continued
| Ex No. | Cmpd No. | Structure | LCMS |
|---|---|---|---|
| | | 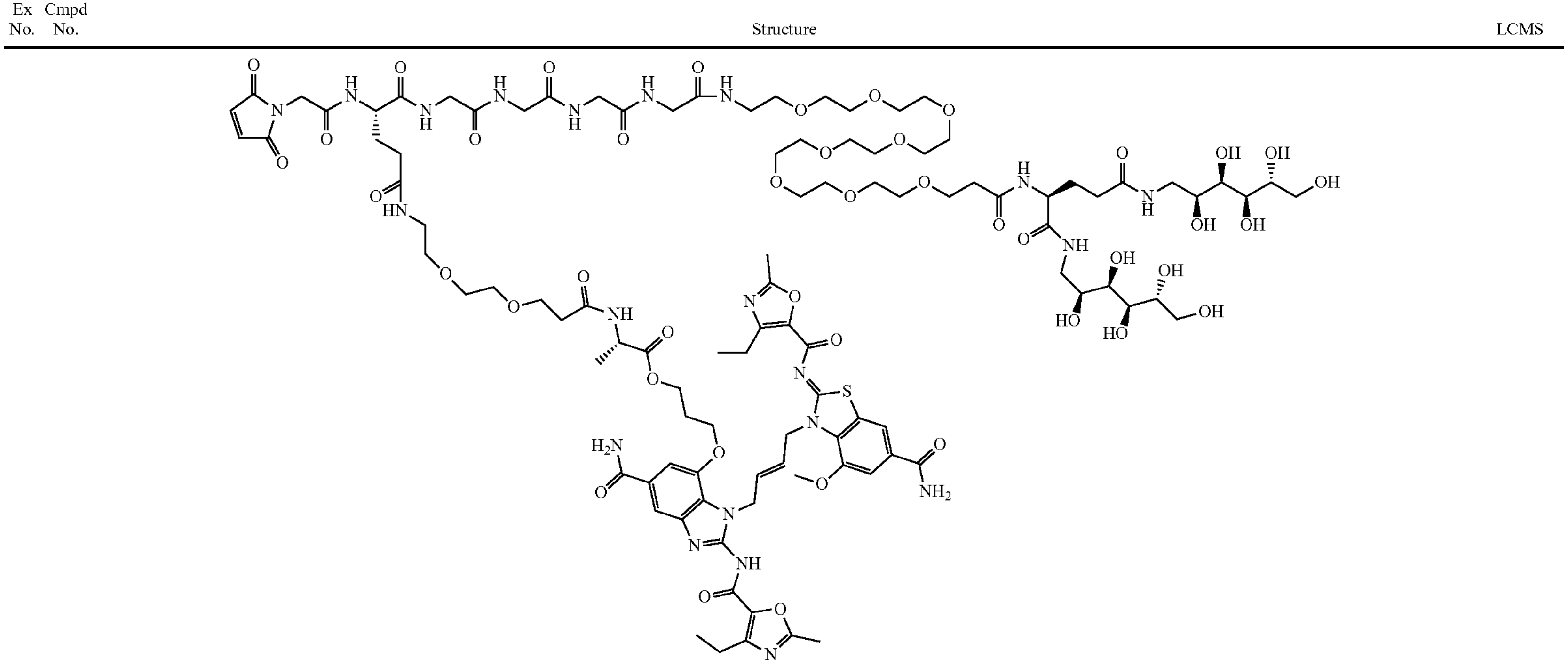 | |

TABLE A2-continued
| Ex No. | Cmpd No. | Structure | LCMS |
|---|---|---|---|
| | | 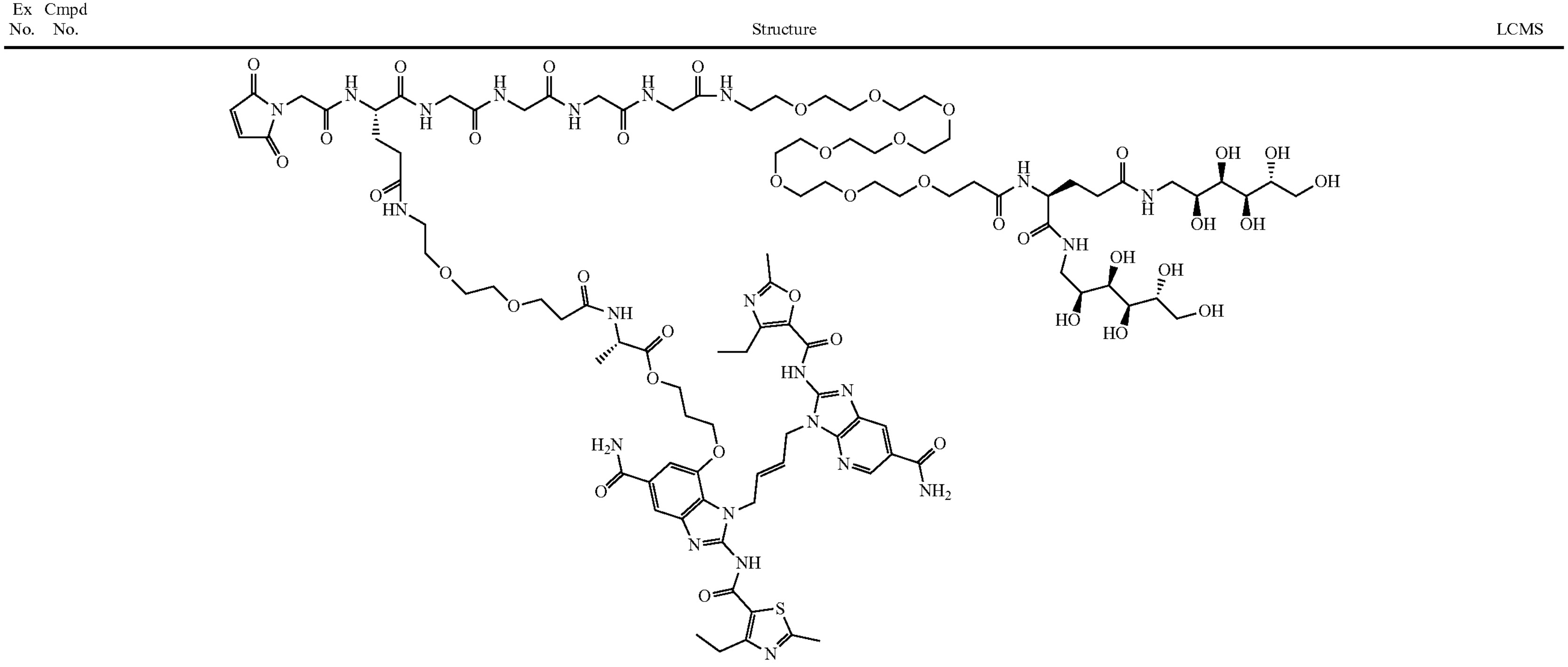 | |

TABLE A2-continued
| Ex No. | Cmpd No. | Structure | LCMS |
|---|---|---|---|
| | | 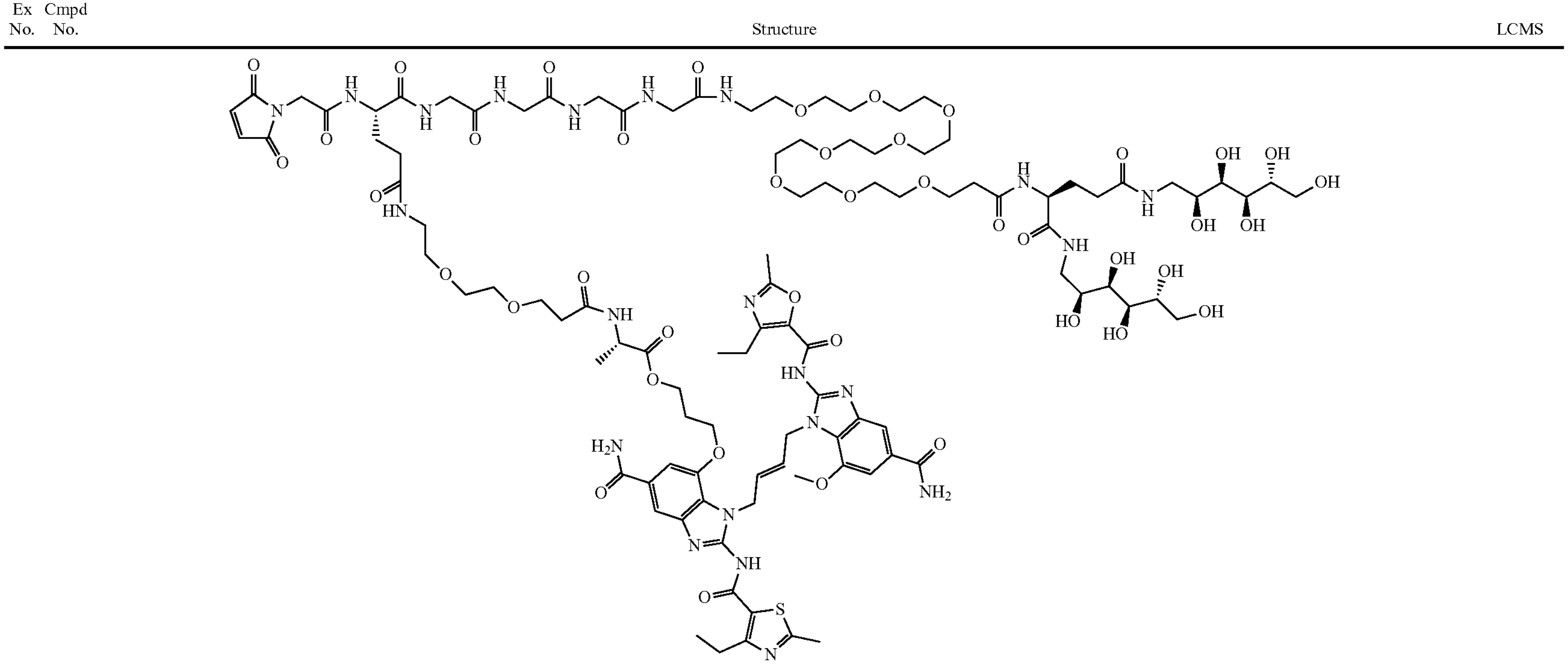 | |

TABLE A2-continued
| Ex No. | Cmpd No. | Structure | LCMS |
|---|---|---|---|
| | | 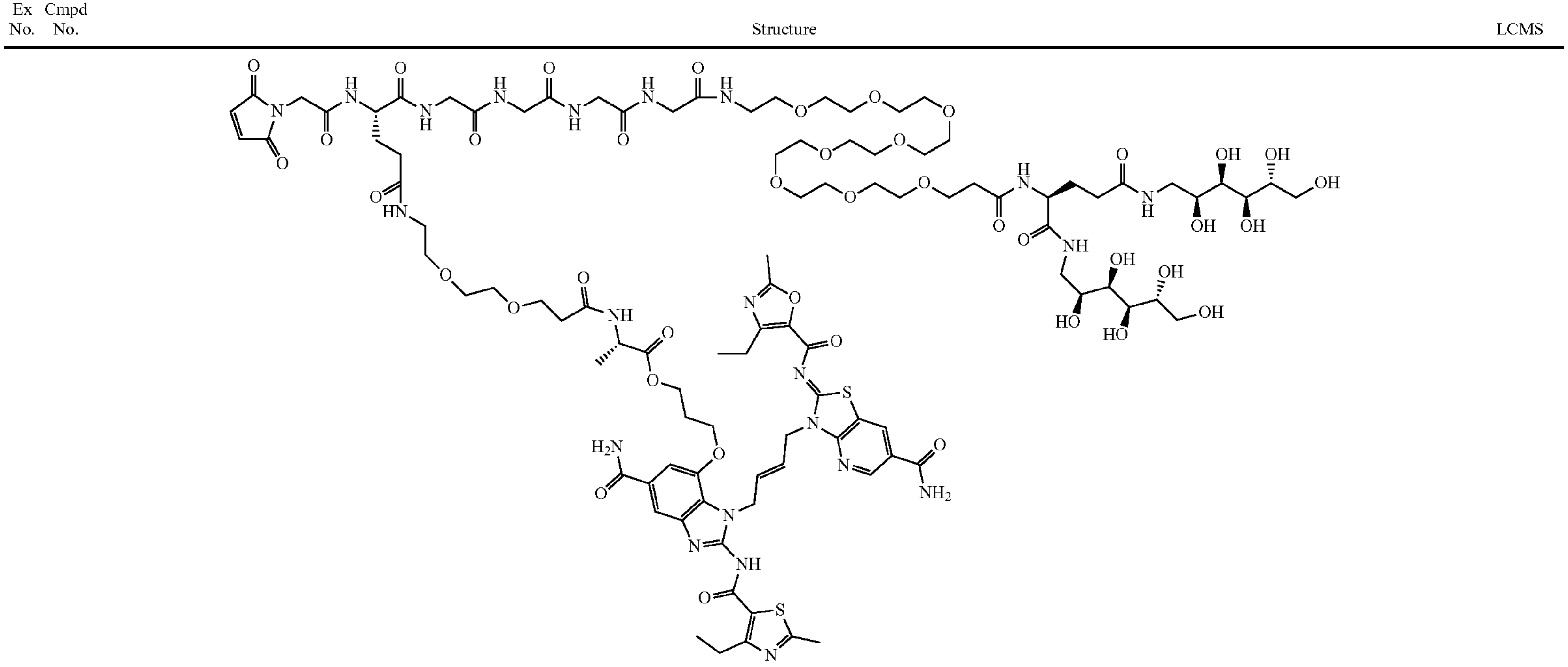 | |

TABLE A2-continued
| Ex No. | Cmpd No. | Structure | LCMS |
|---|---|---|---|
| | | 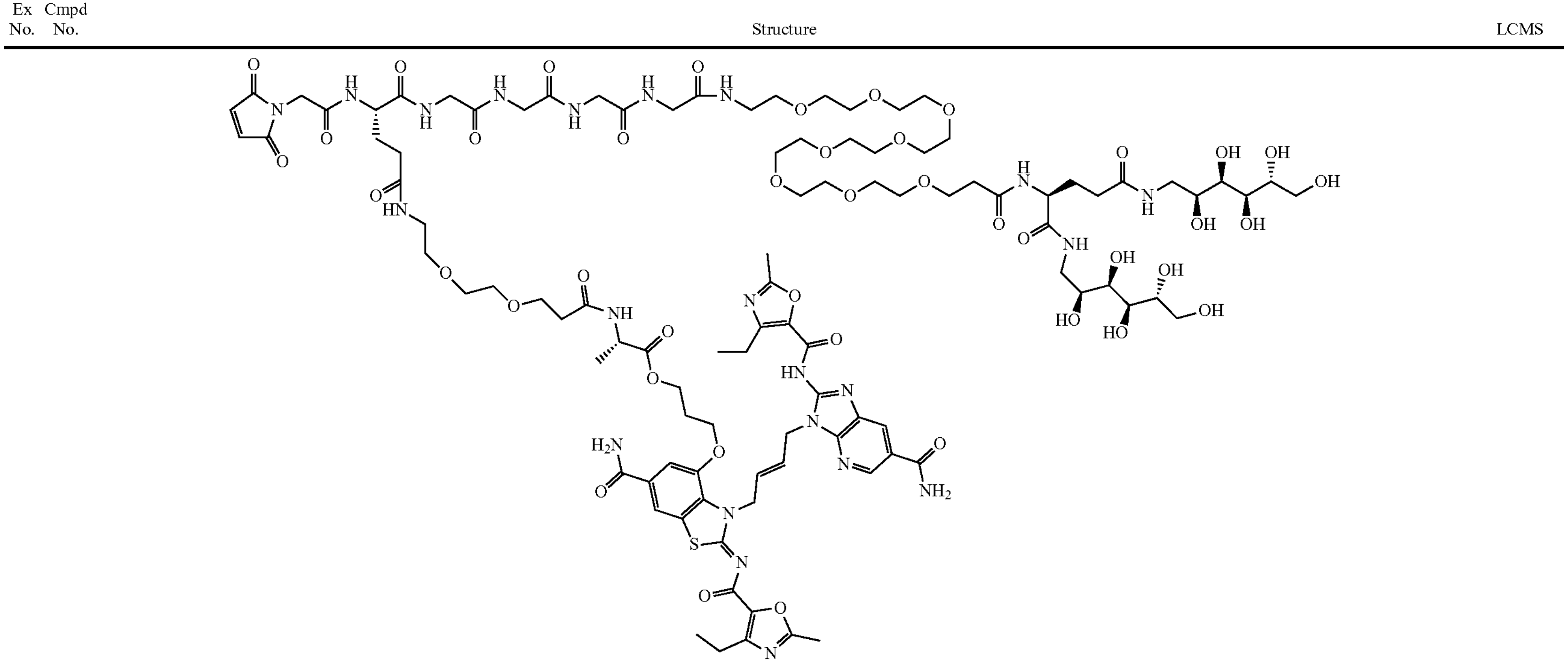 | |

TABLE A2-continued
| Ex No. | Cmpd No. | Structure | LCMS |
|---|---|---|---|
| | | 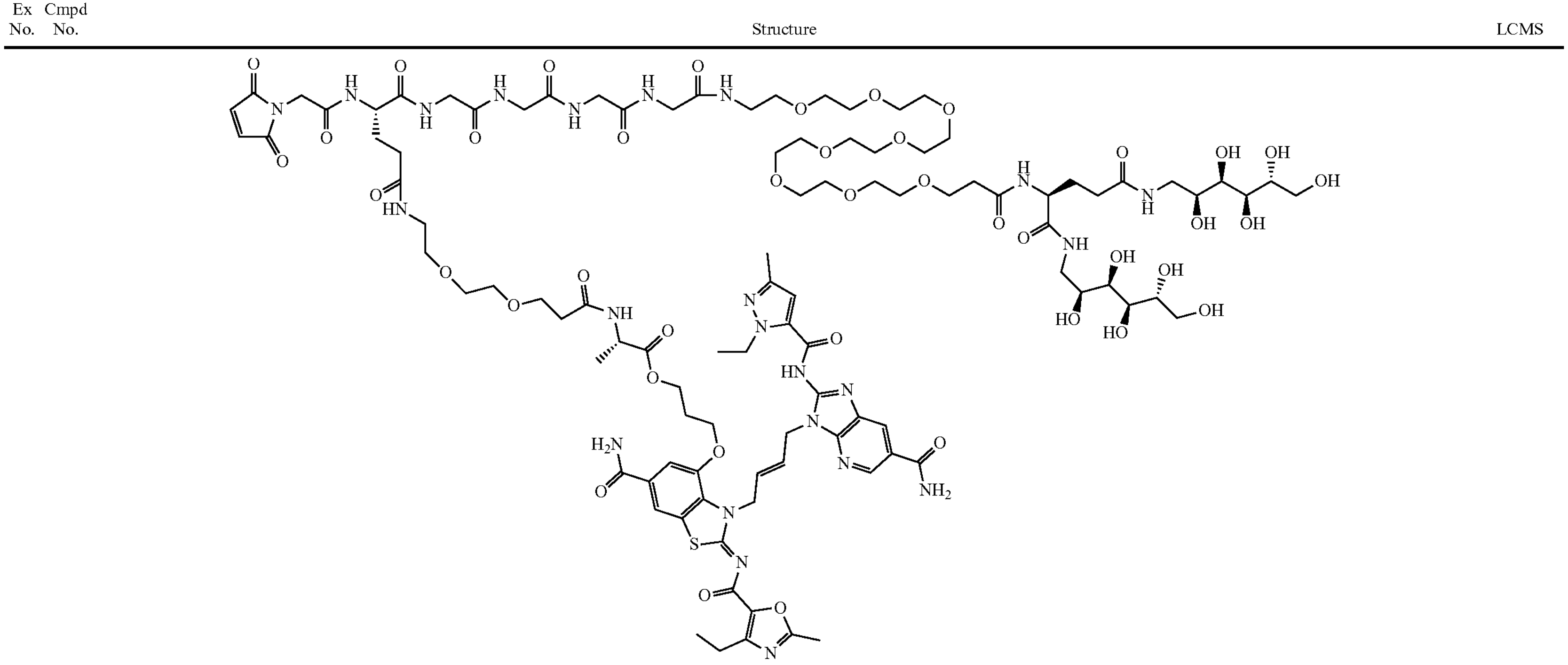 | |

TABLE A2-continued
| Ex No. | Cmpd No. | Structure | LCMS |
|---|---|---|---|
| | | 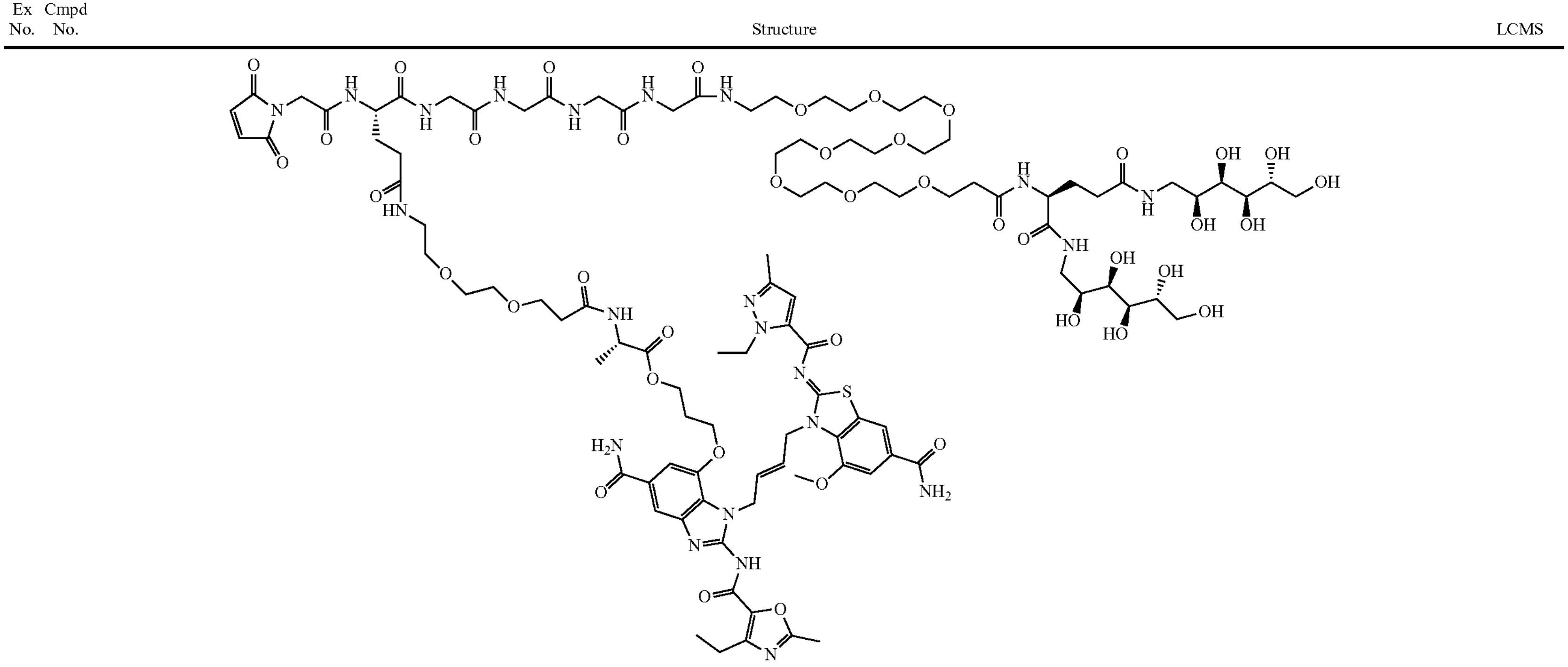 | |

TABLE A2-continued
| Ex No. | Cmpd No. | Structure | LCMS |
|---|---|---|---|
| | | 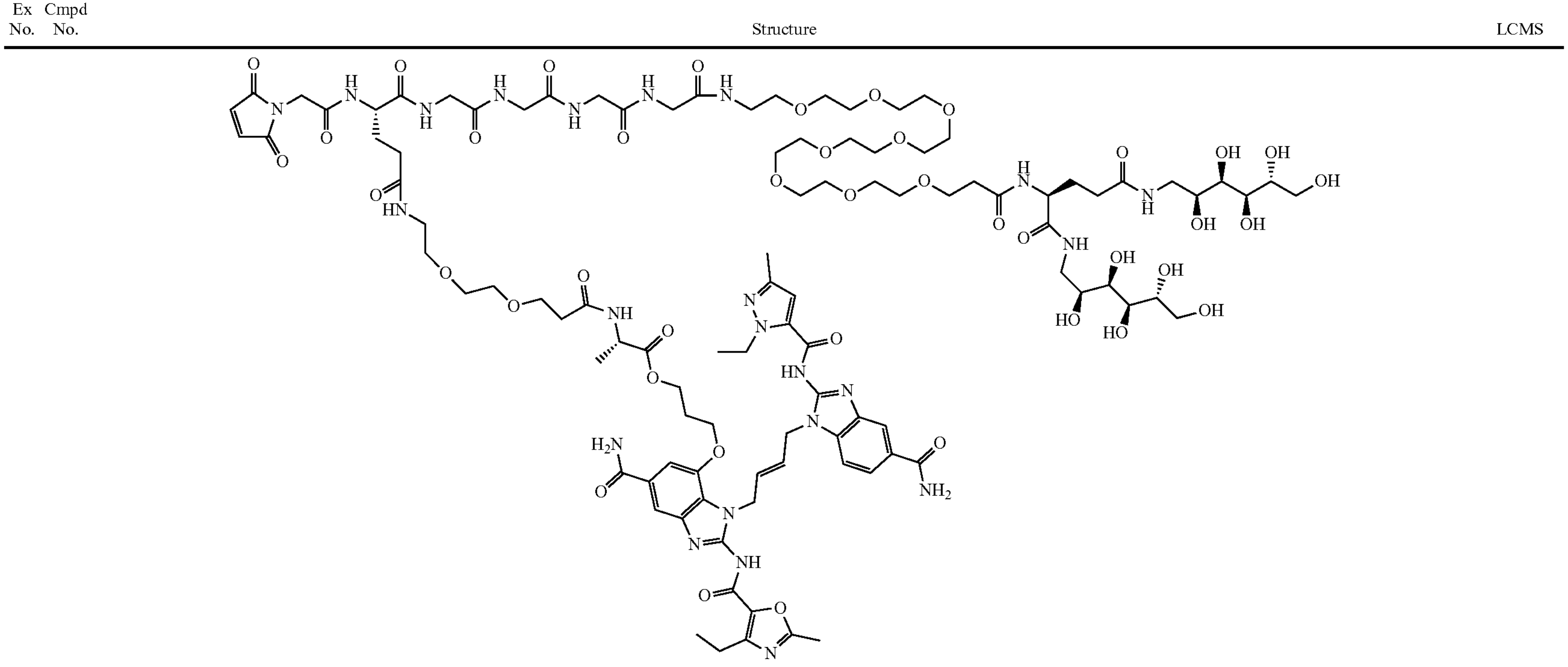 | |

TABLE A2-continued
| Ex No. | Cmpd No. | Structure | LCMS |
| --- | --- | --- | --- |
| | | 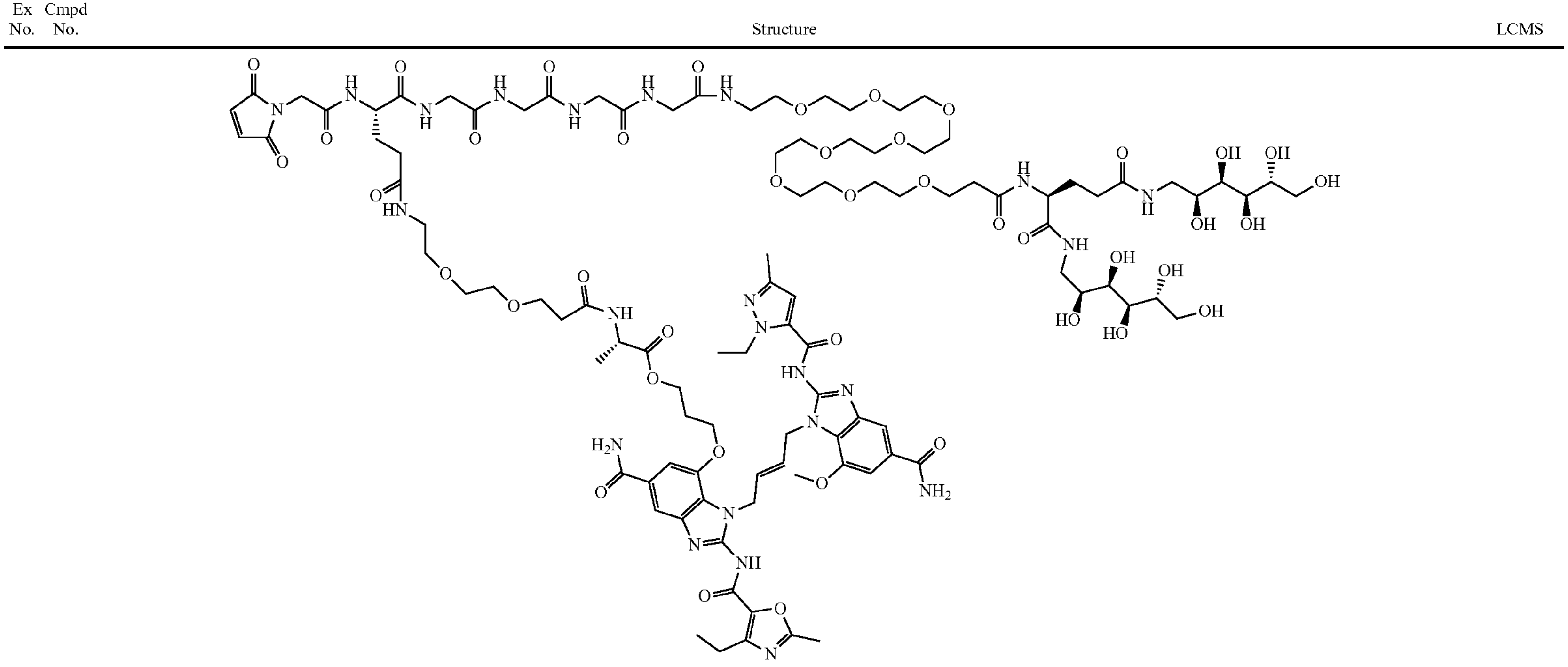 | |

TABLE A2-continued
| Ex No. | Cmpd No. | Structure | LCMS |
| --- | --- | --- | --- |
| | | 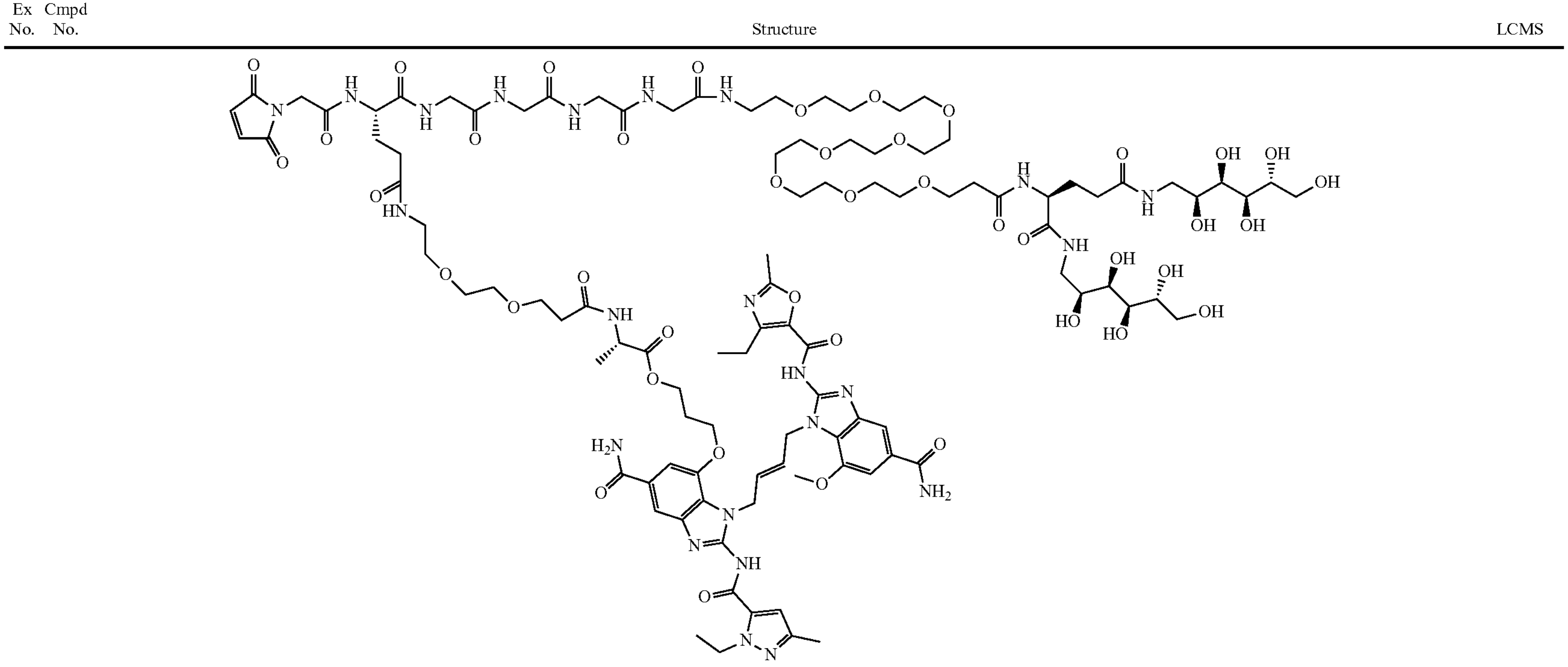 | |

TABLE A2-continued
| Ex No. | Cmpd No. | Structure | LCMS |
|---|---|---|---|
| | | 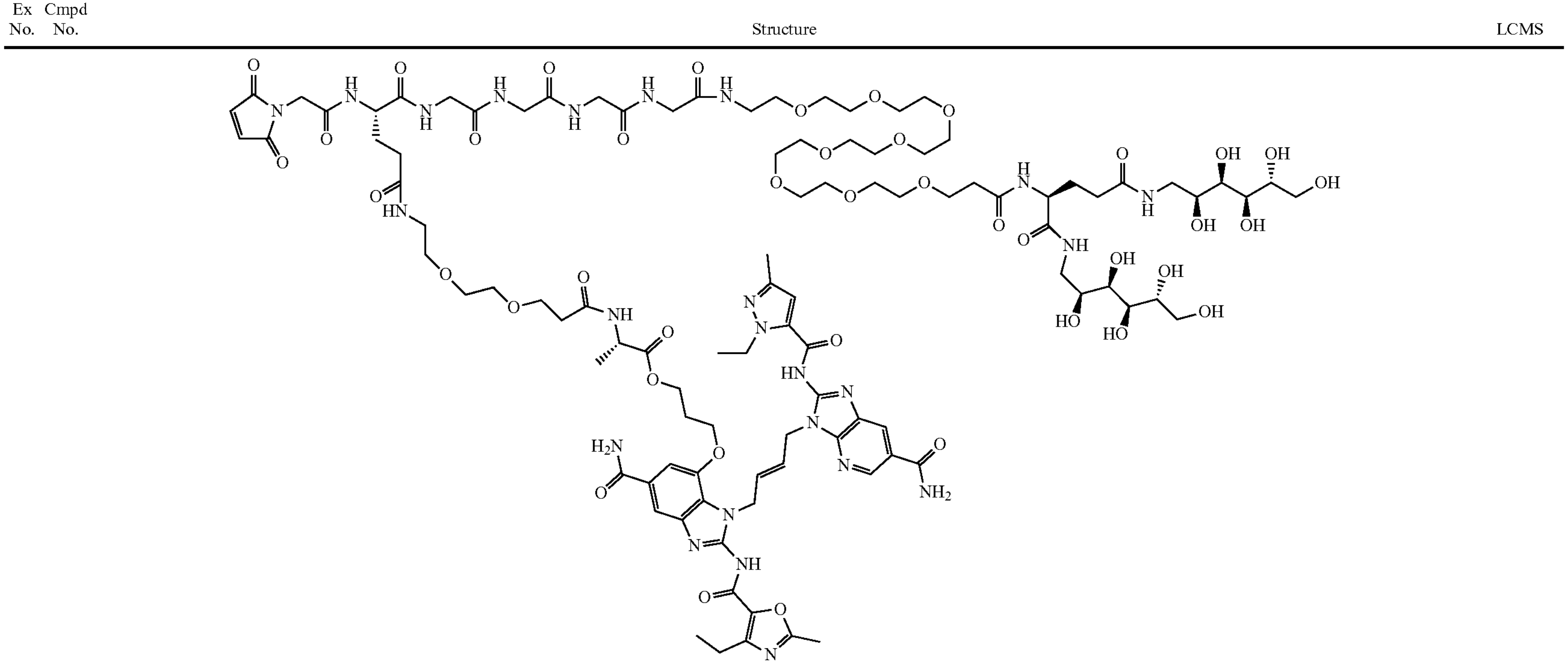 | |

TABLE A2-continued
| Ex No. | Cmpd No. | Structure | LCMS |
|---|---|---|---|
| | | 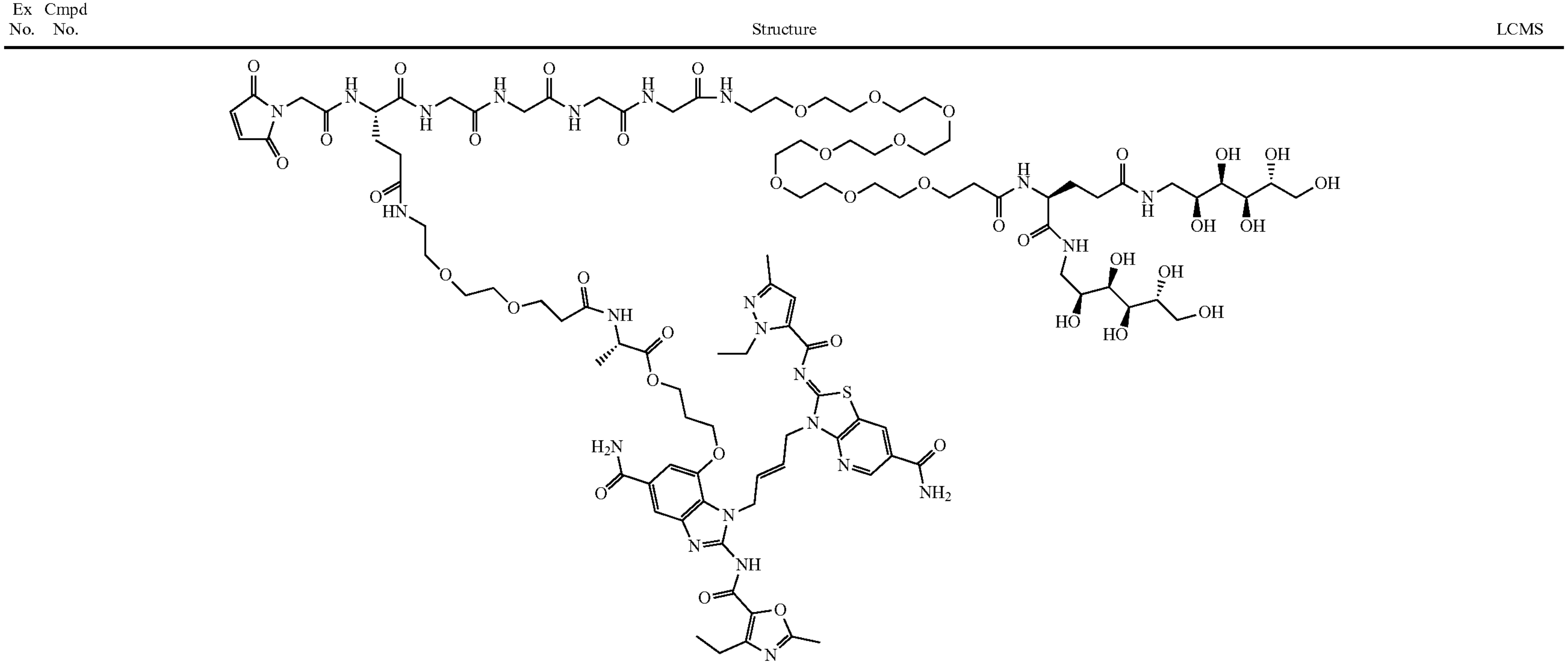 | |

TABLE A2-continued
| Ex No. | Cmpd No. | Structure | LCMS |
| --- | --- | --- | --- |
| | | 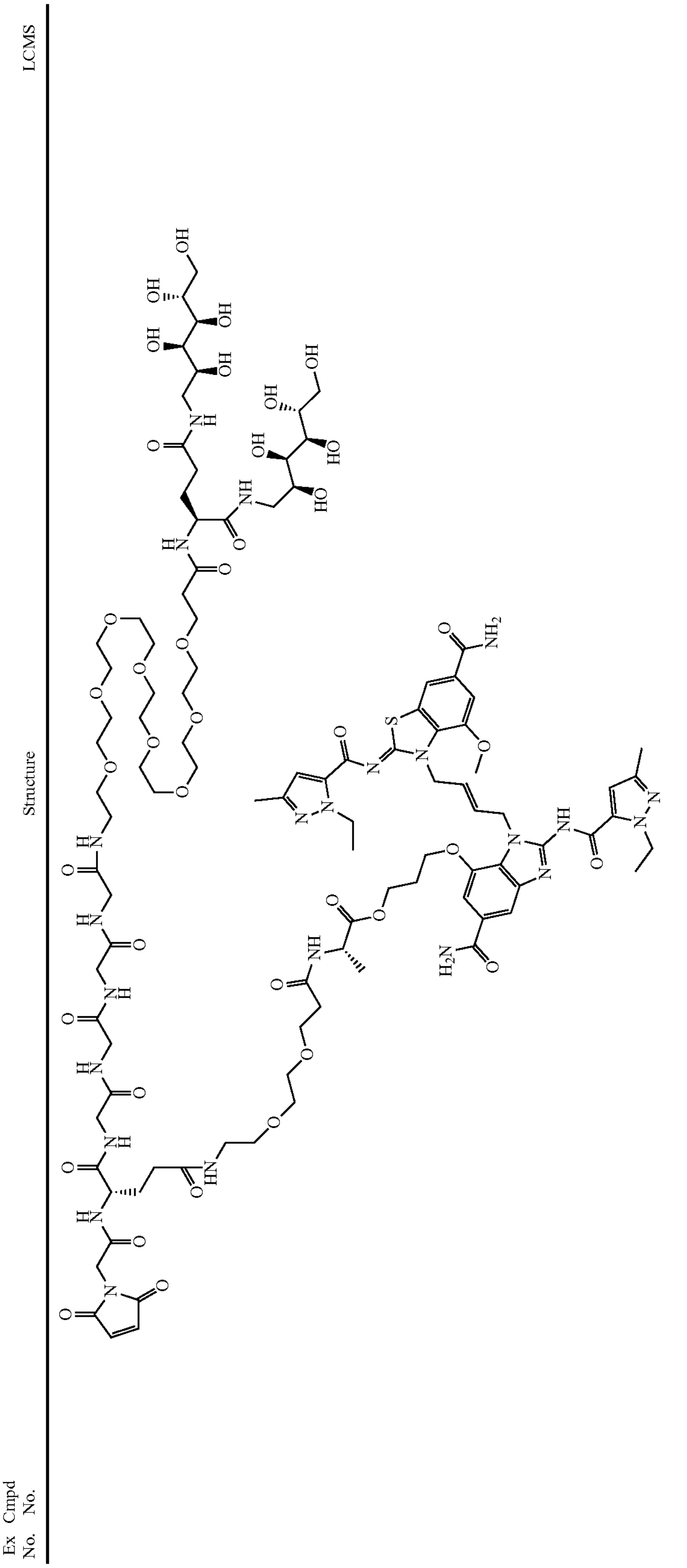 | |

TABLE A2-continued
| Ex No. | Cmpd No. | Structure | LCMS |
|---|---|---|---|
| | | 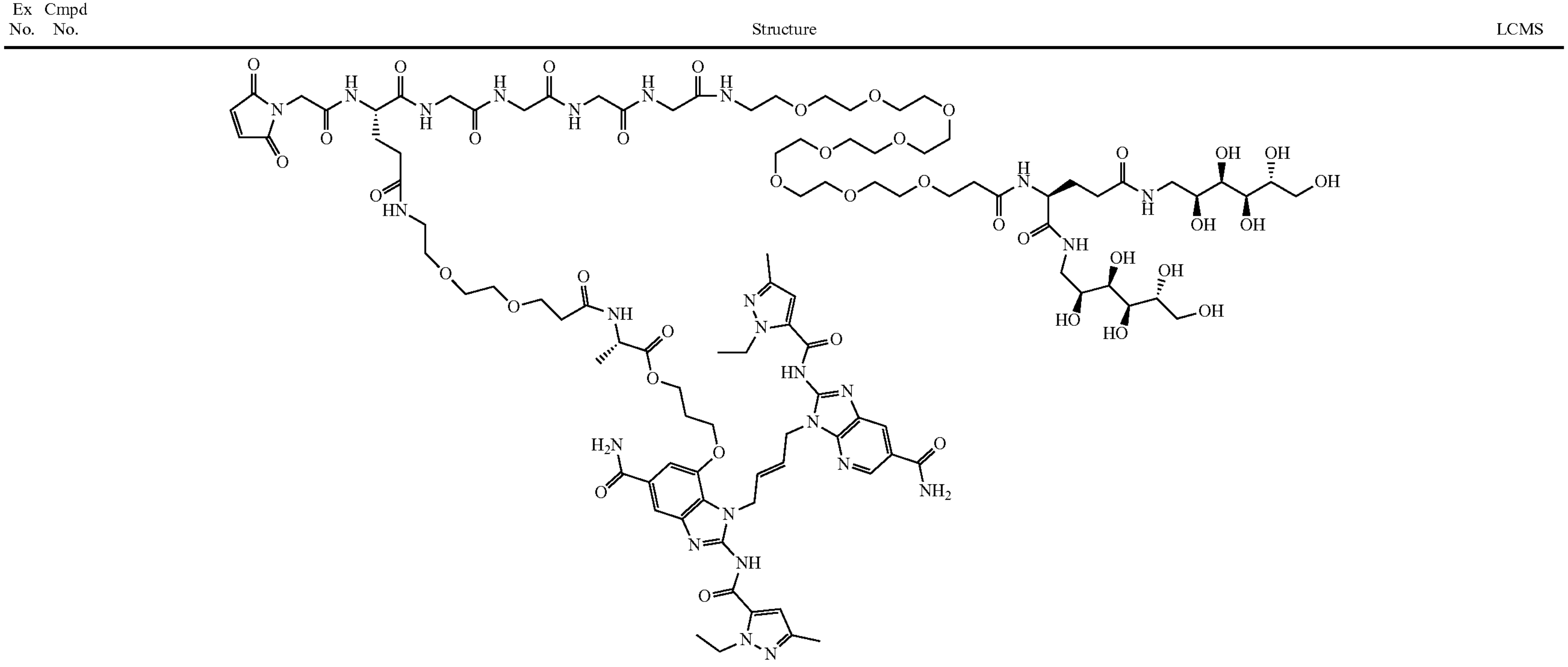 | |

TABLE A2-continued
| Ex No. | Cmpd No. | Structure | LCMS |
|---|---|---|---|
| | | 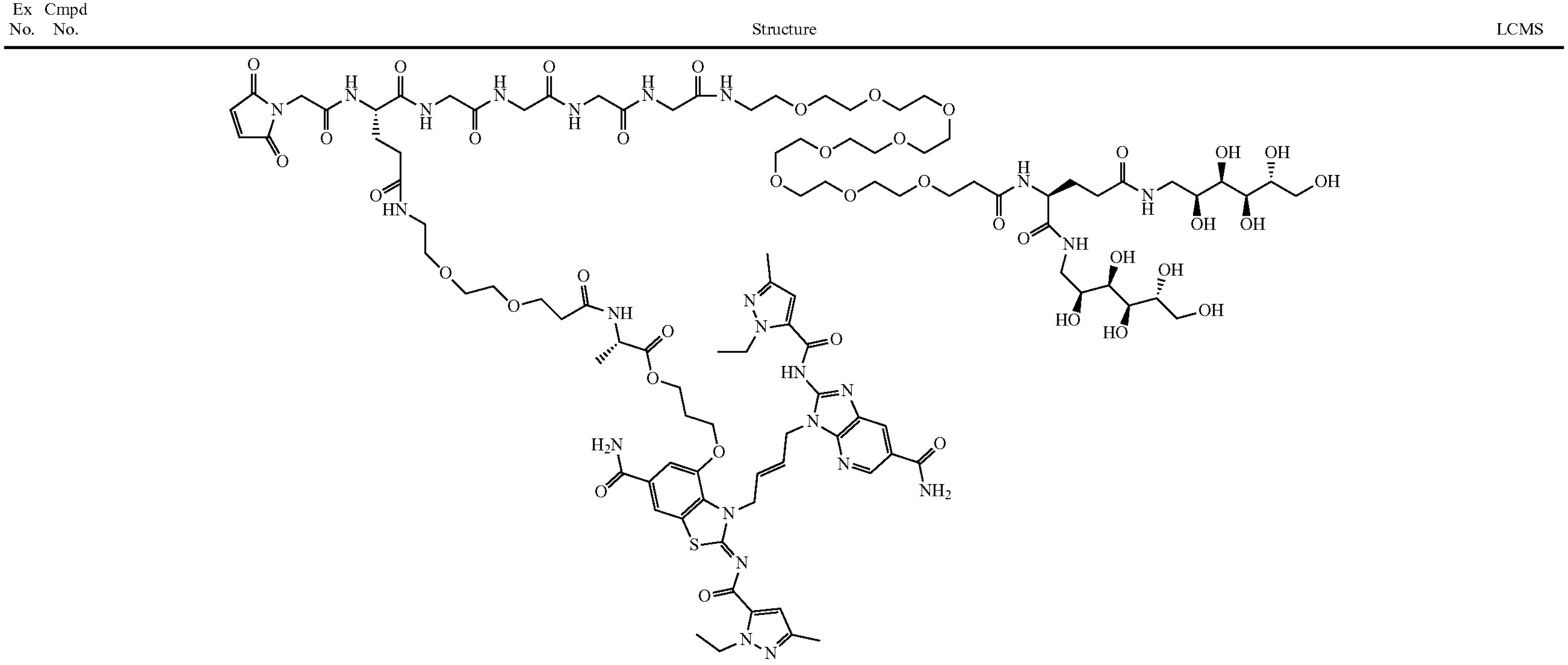 | |

TABLE B1
| Structure |
| --- |
| 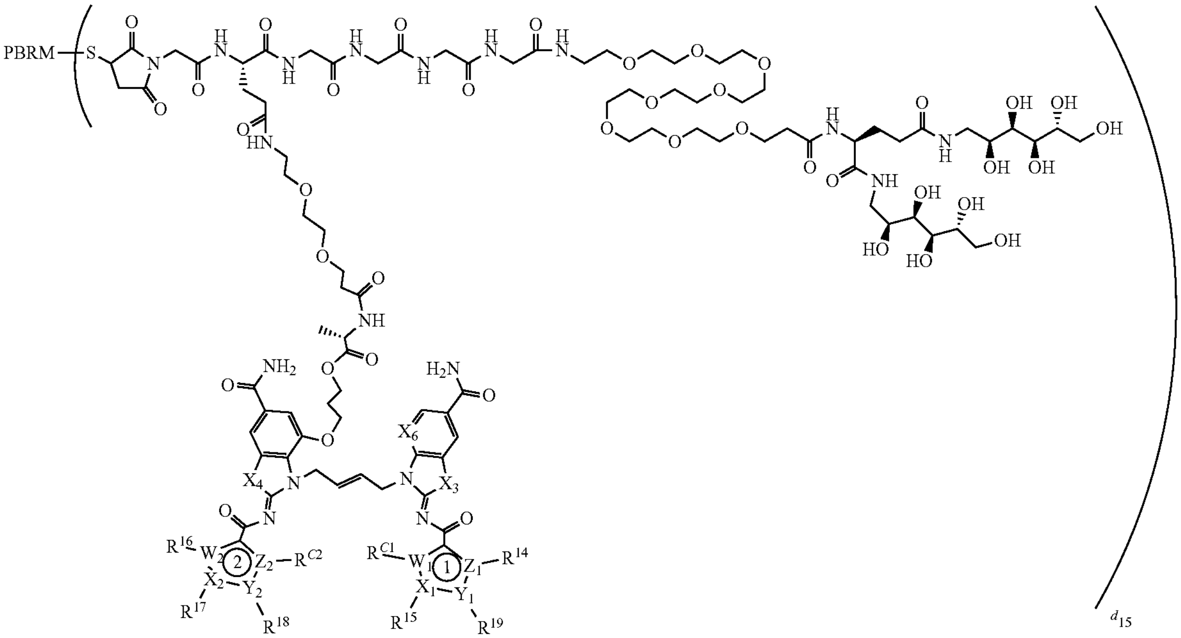 |
| 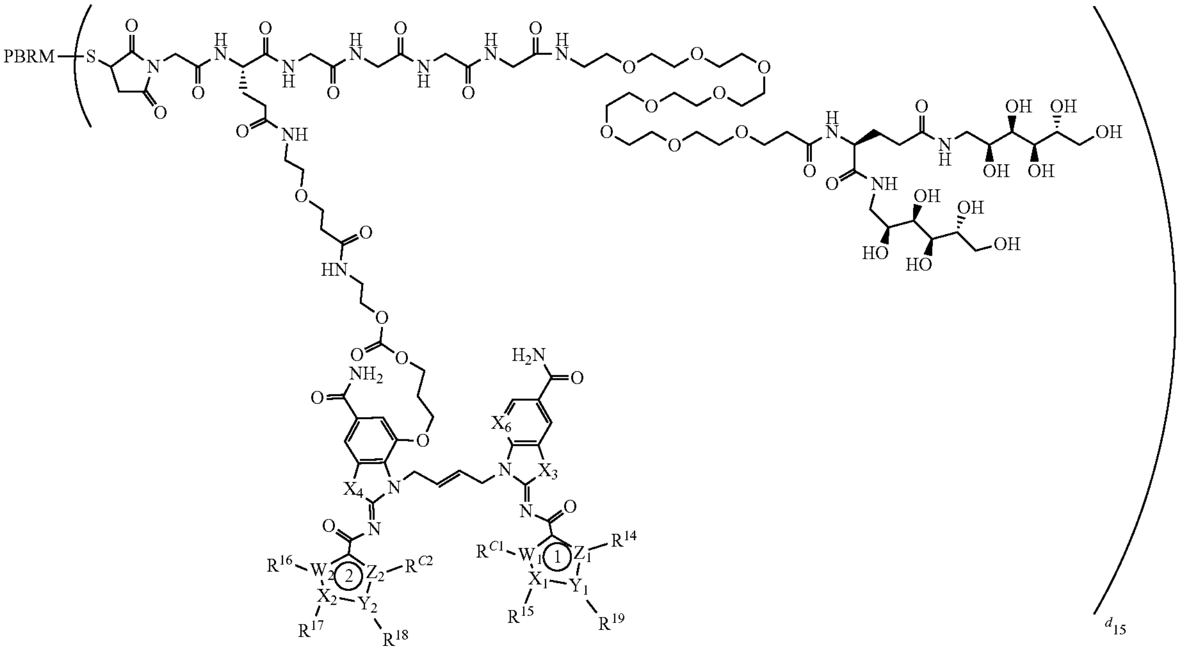 |

TABLE B1-continued
| Structure |
|---|
| 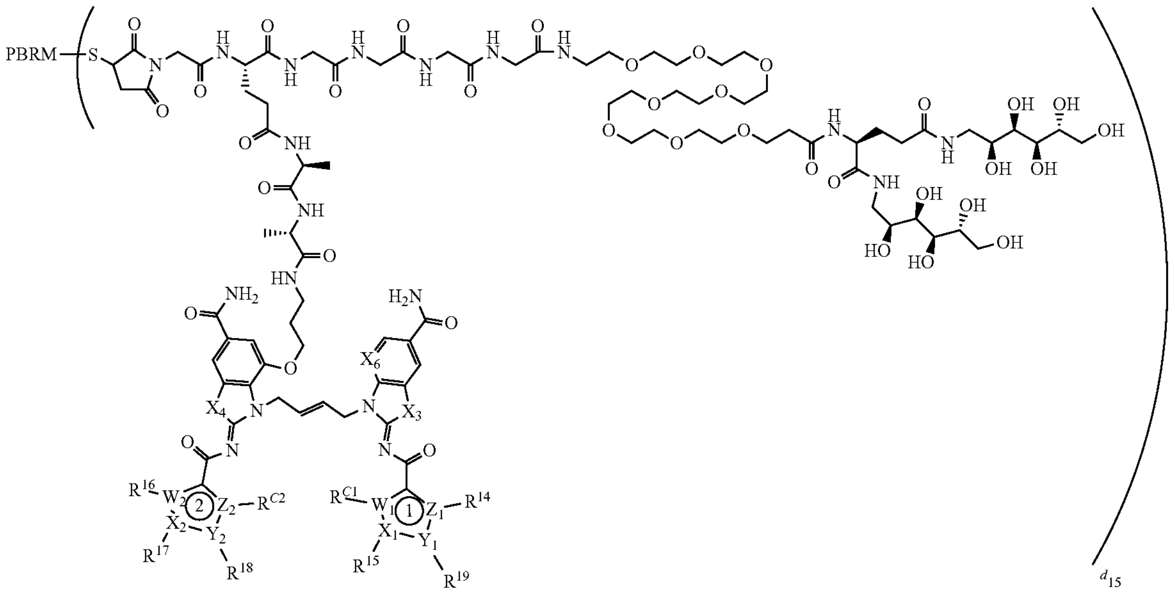 |
| 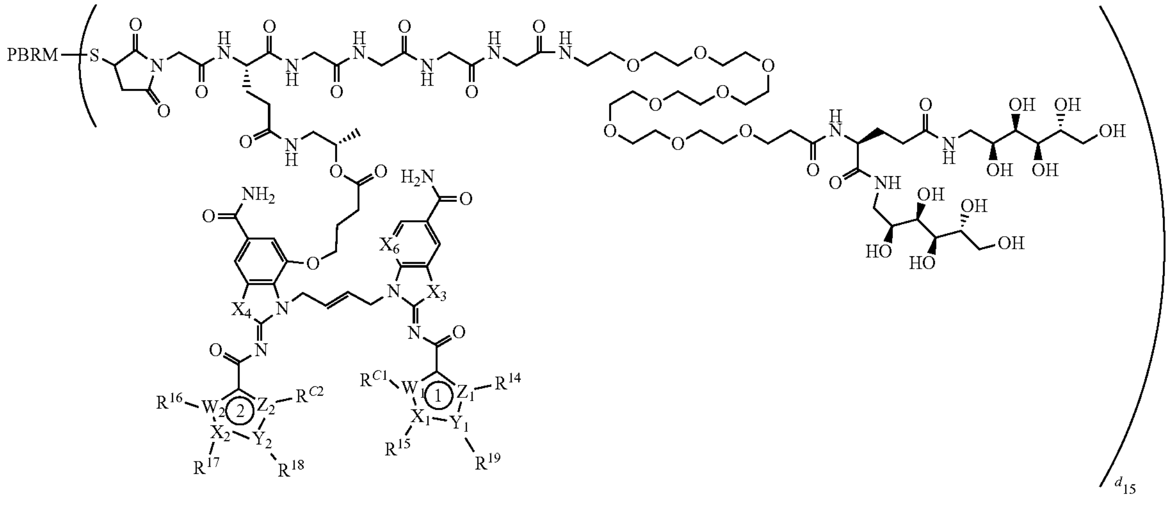 |

TABLE B1-continued
| Structure |
| --- |
| 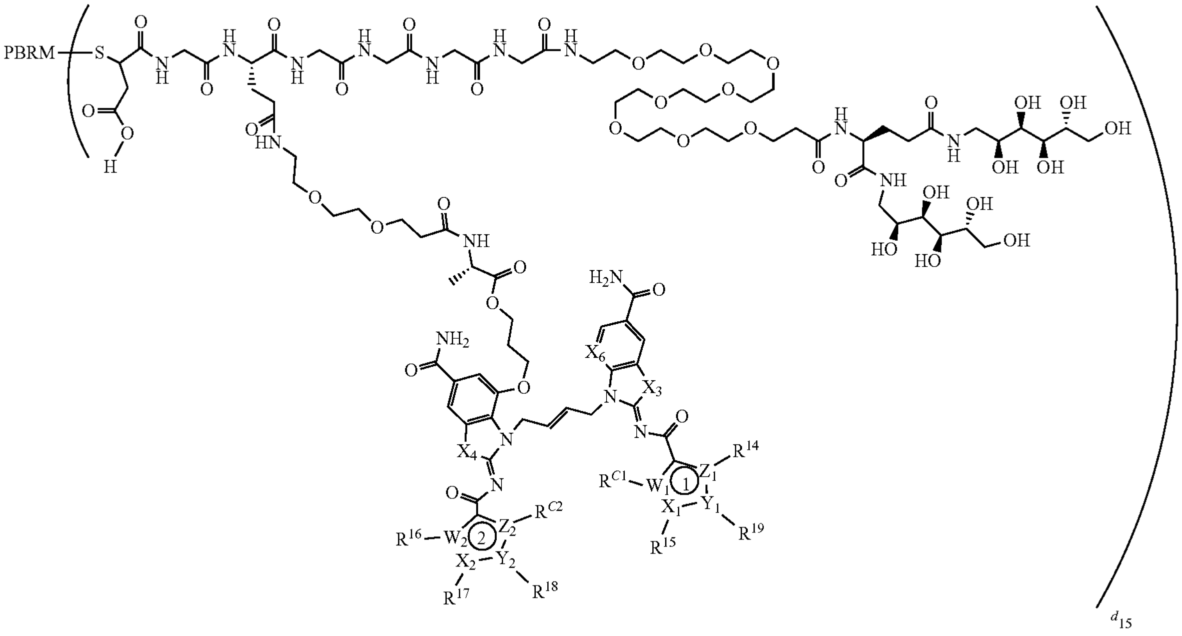 |
| 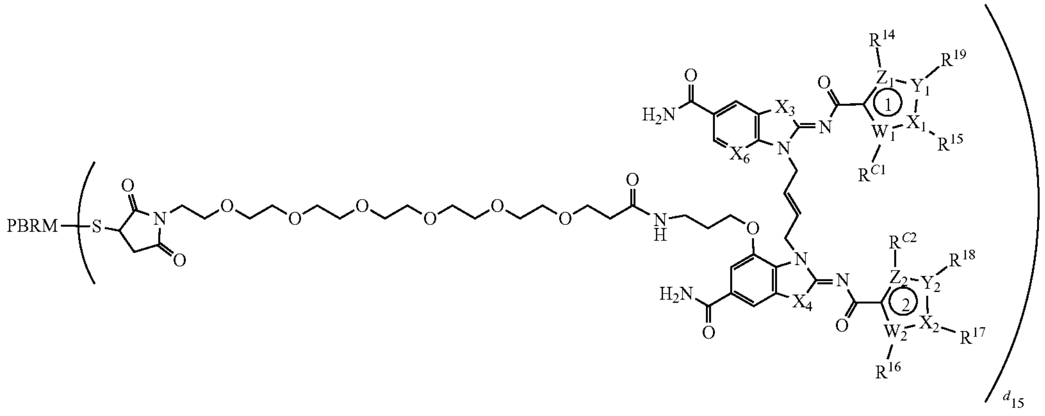 |
| 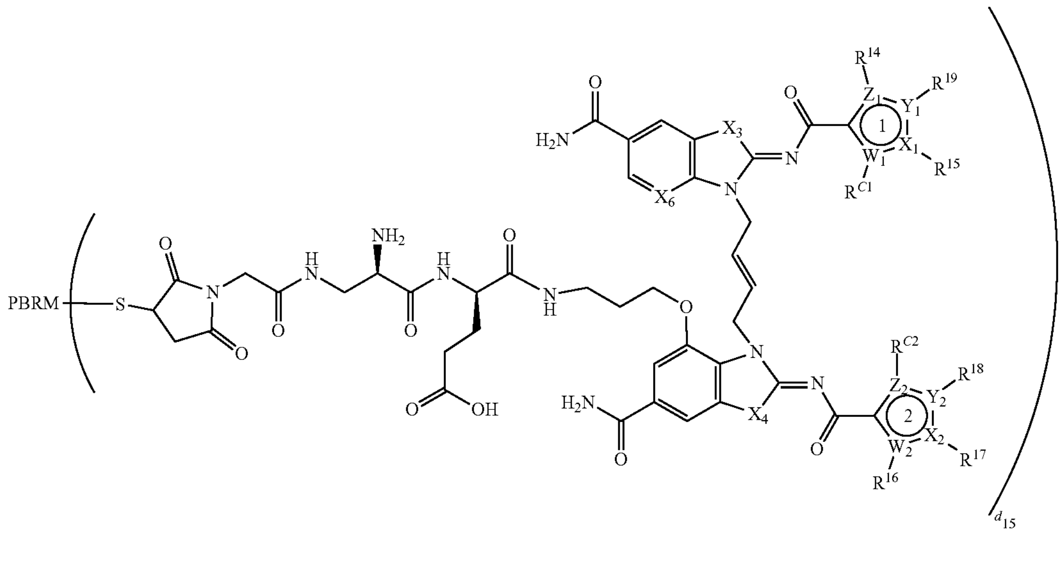 |

TABLE B1-continued
| Structure |
| --- |
| 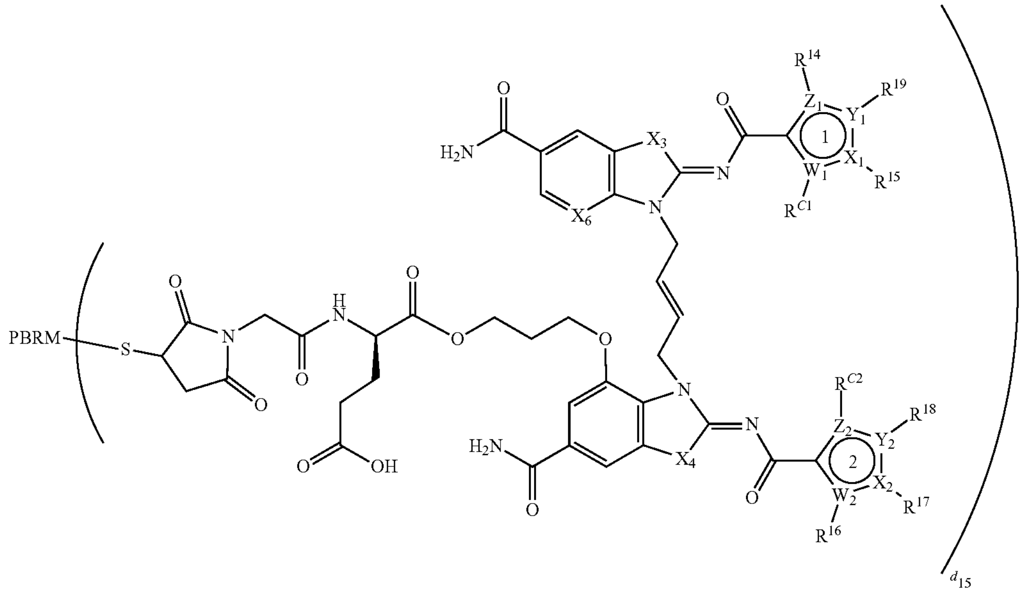 |
| 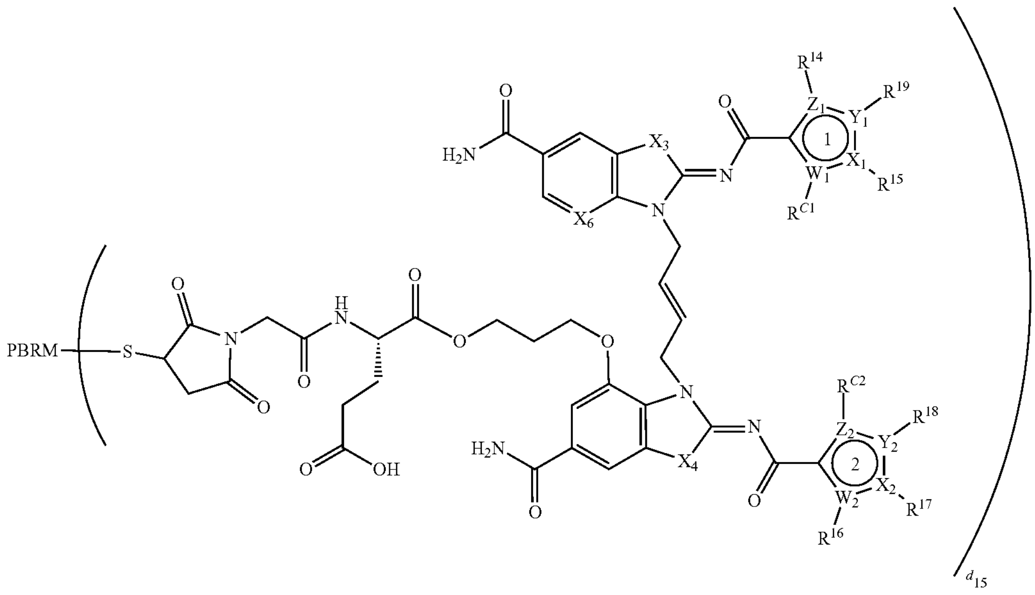 |

TABLE B1-continued
| Structure |
|---|
| 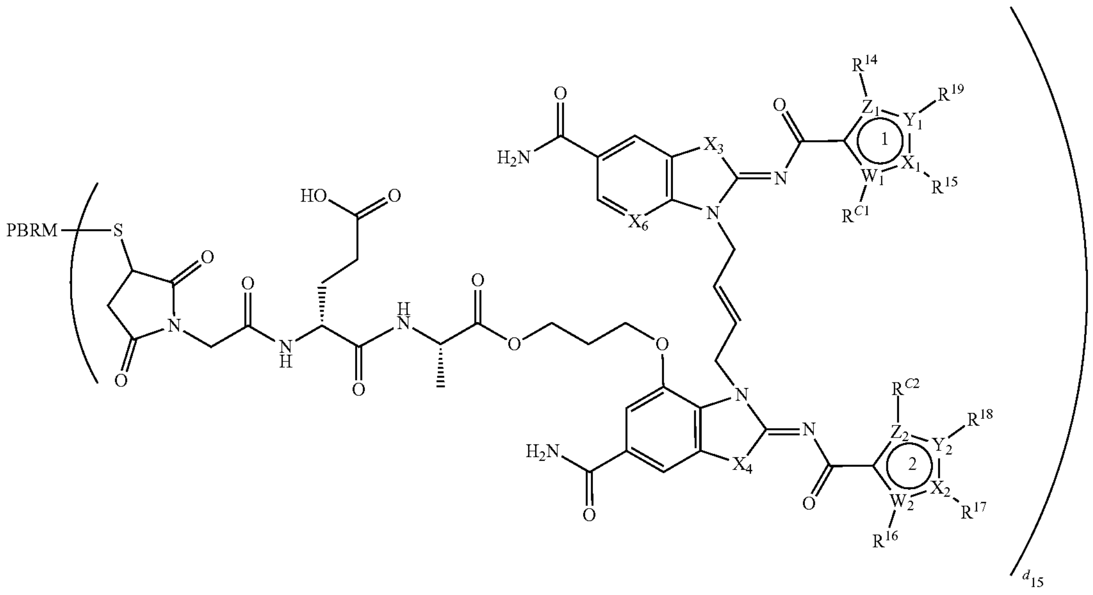 |
| 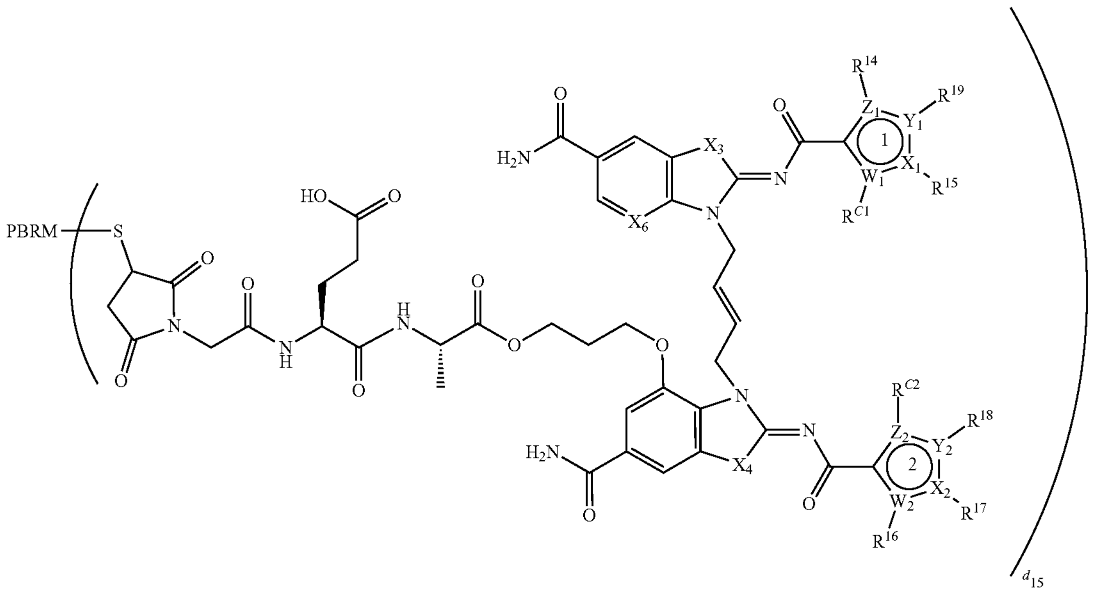 |

TABLE B1-continued
| Structure |
| --- |
| 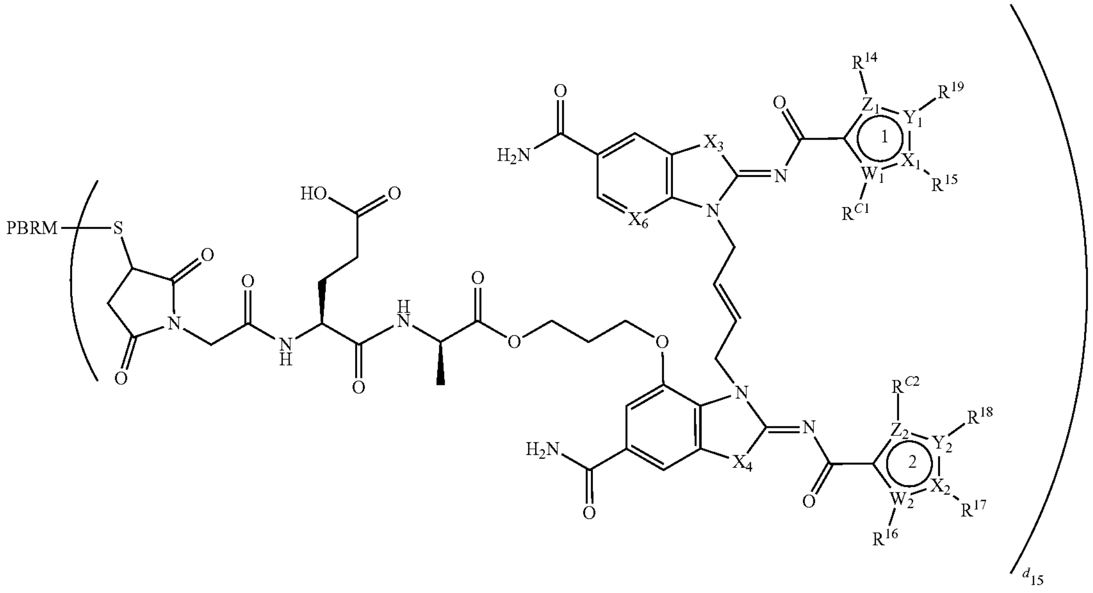 |
| 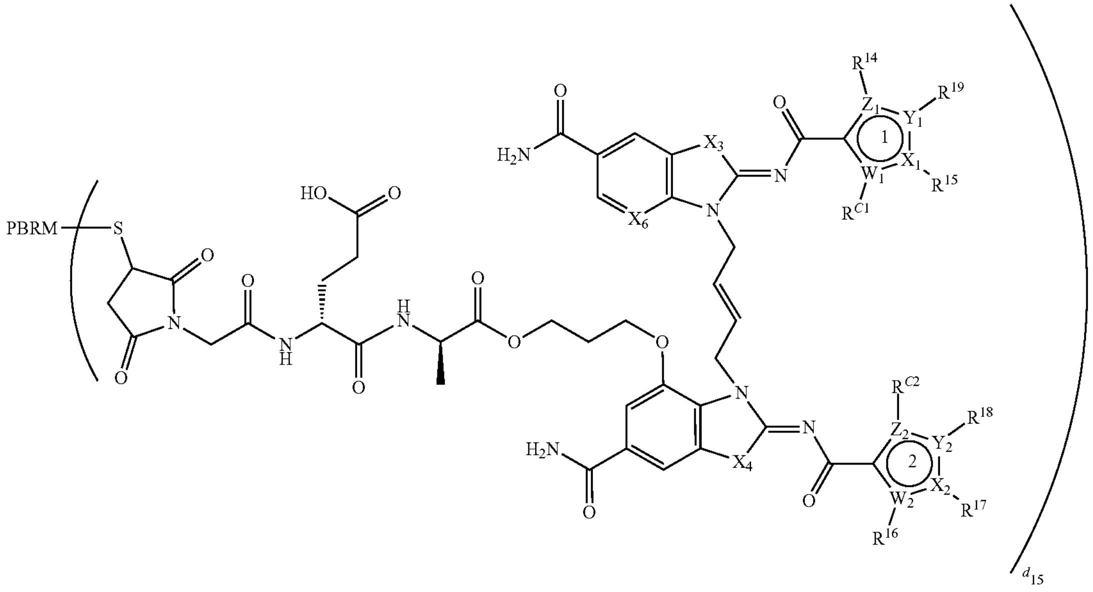 |

TABLE B1-continued
| Structure |
| --- |
| 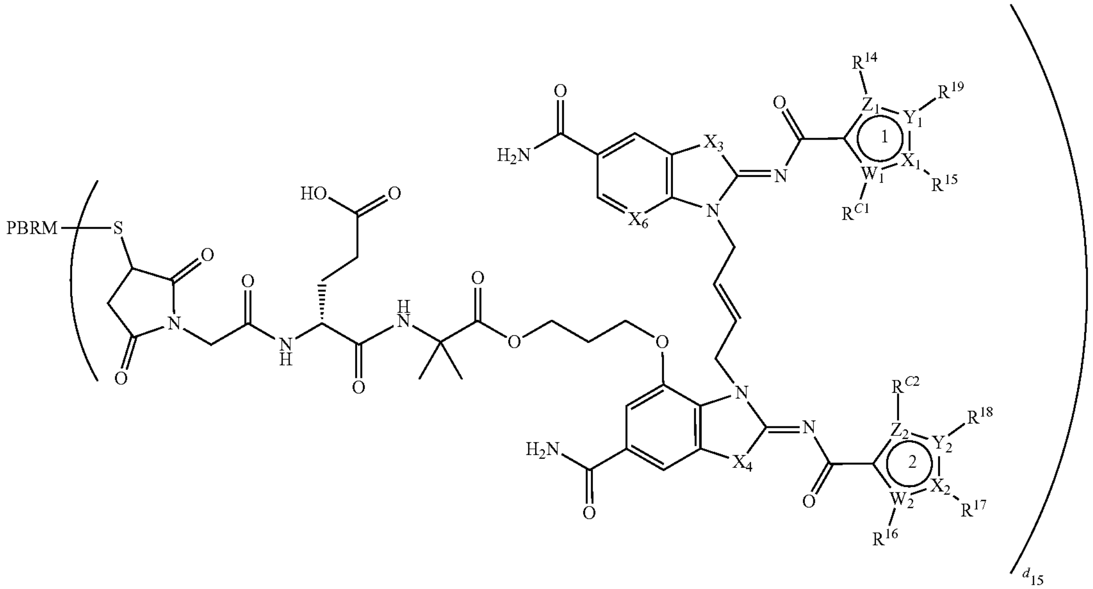 |
| 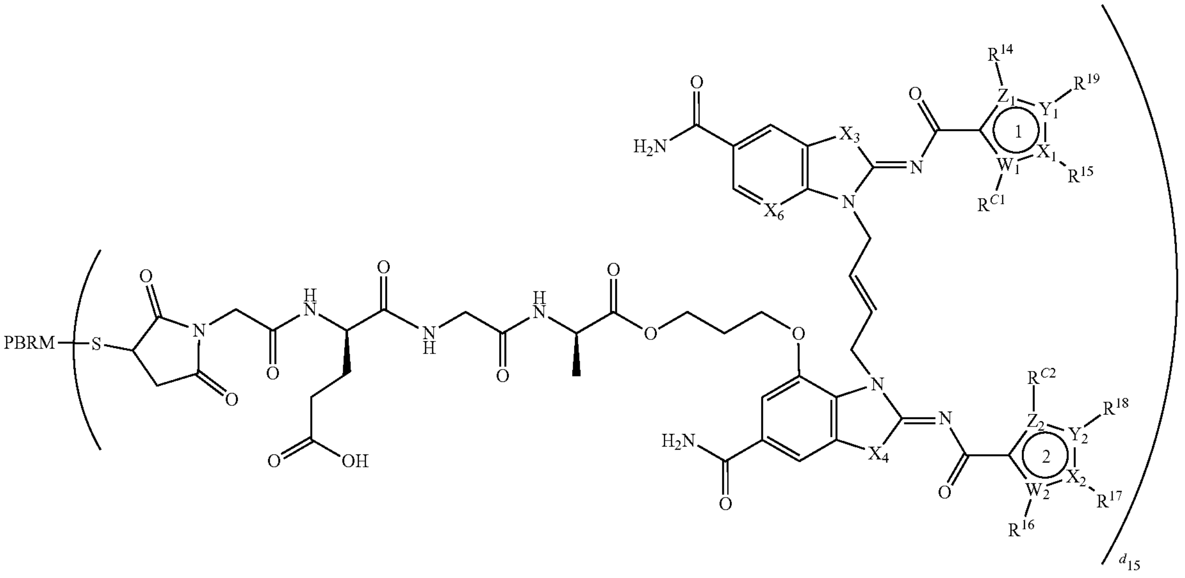 |

TABLE B1-continued
| Structure |
|---|
| 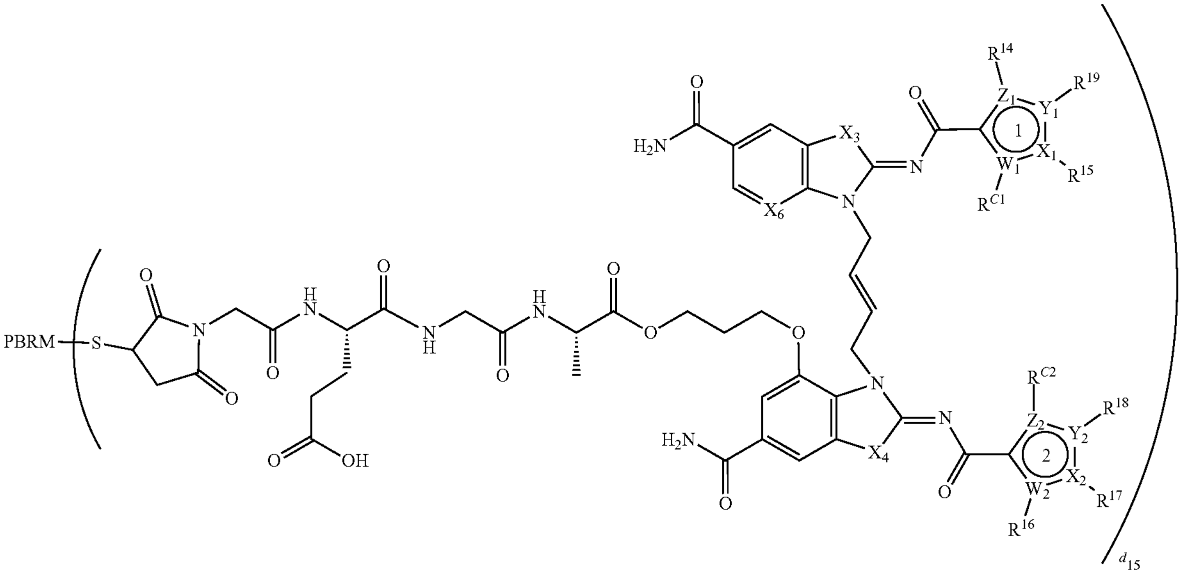 |
| 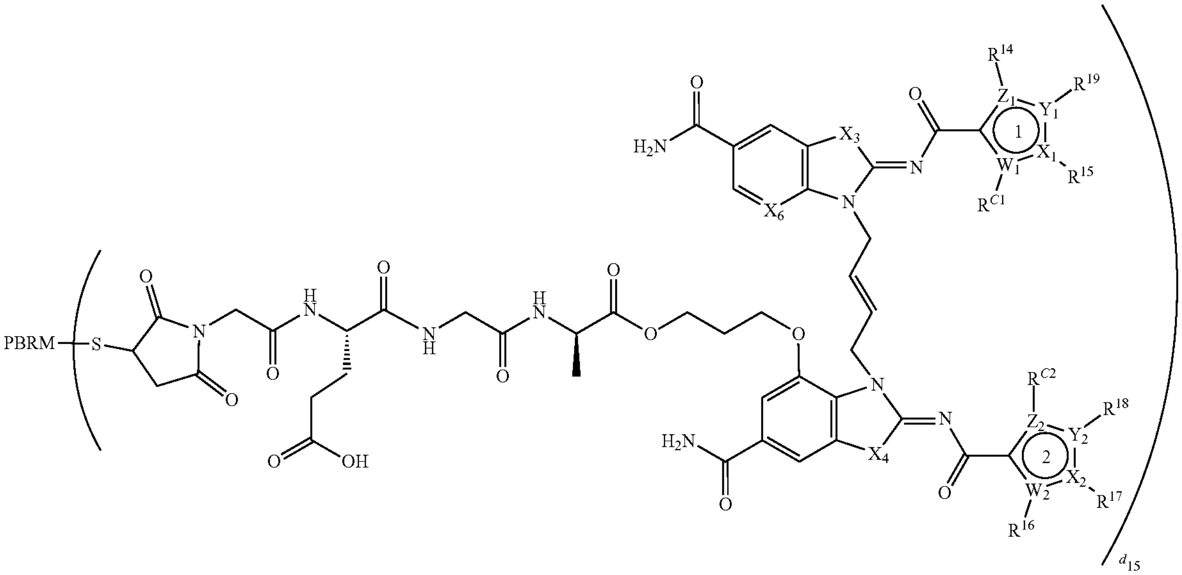 |

TABLE B1-continued
| Structure |
| --- |
| 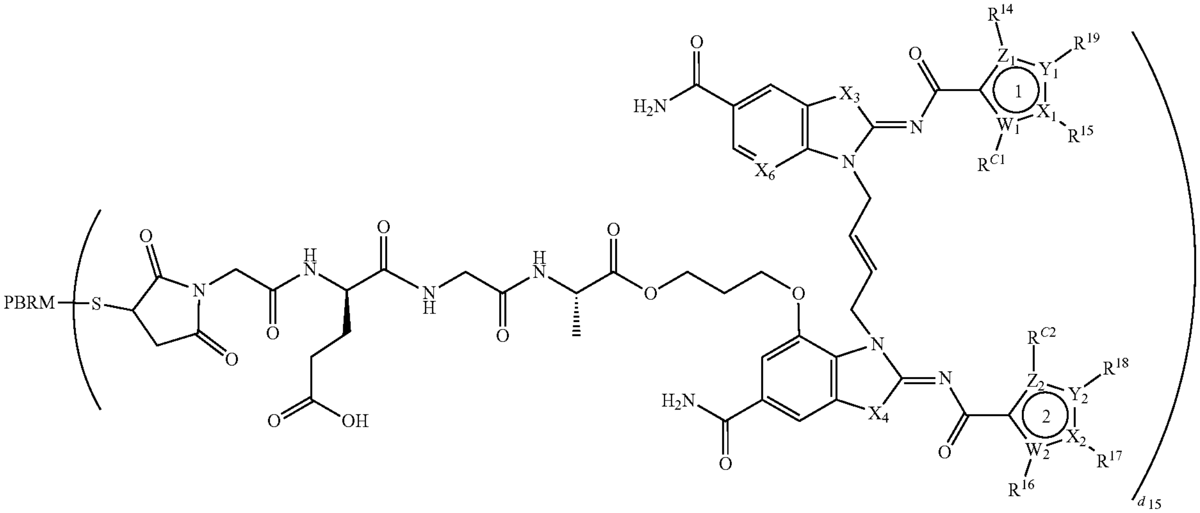 |
| 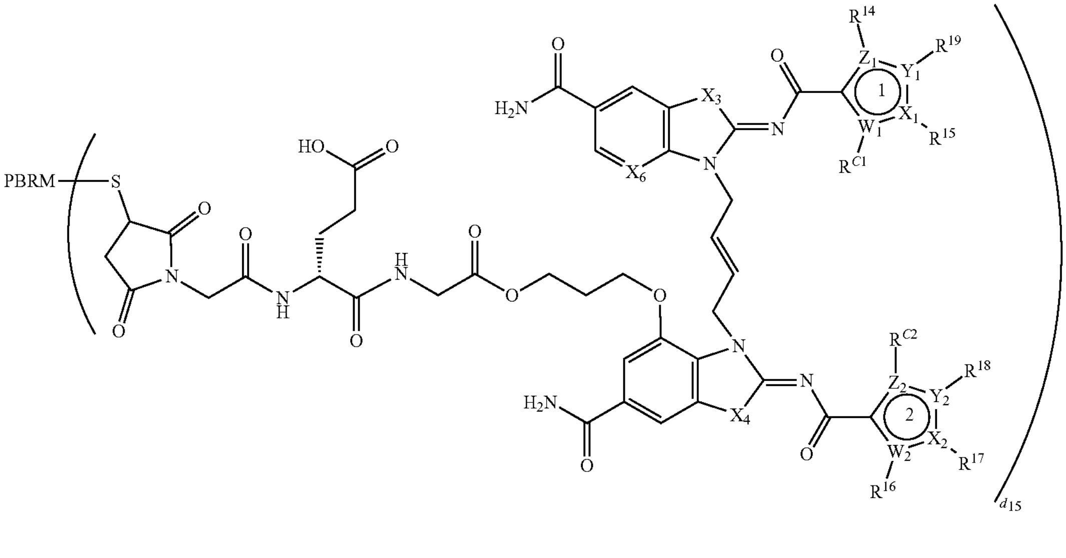 |

TABLE B1-continued
| Structure |
|---|
| 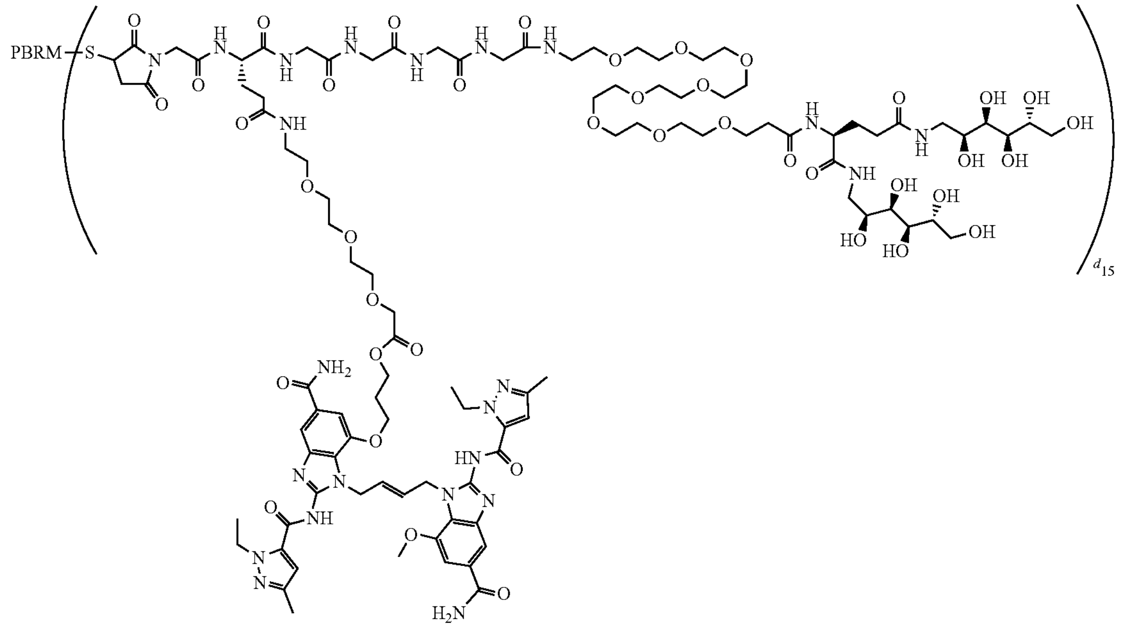 |
| 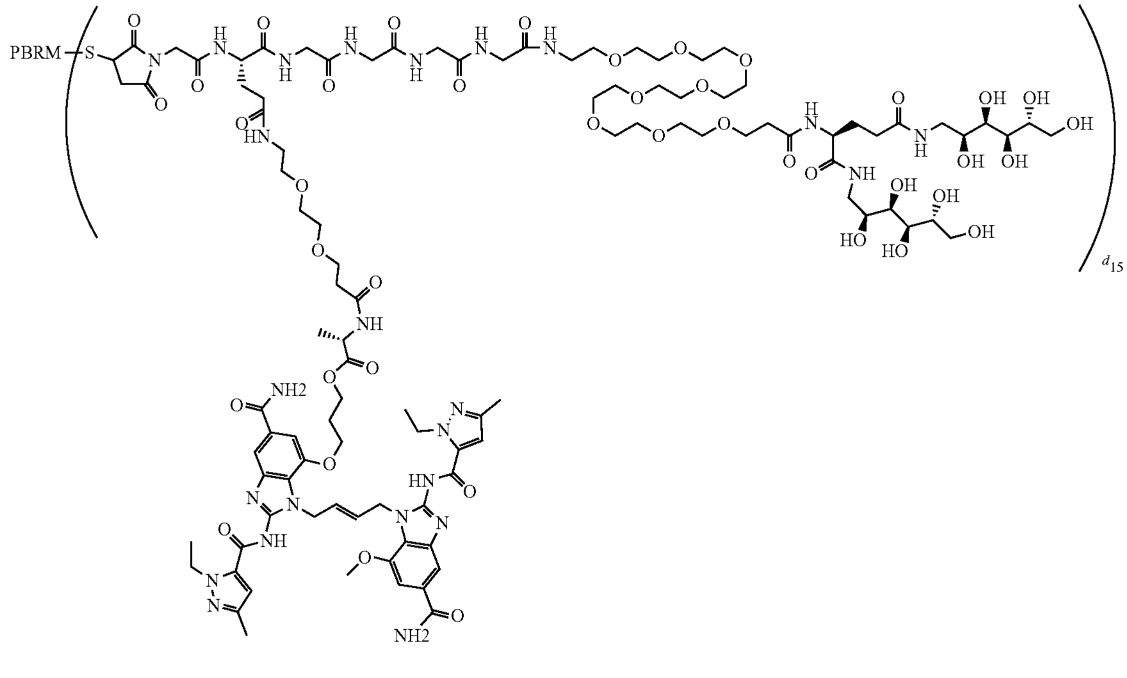 |

TABLE B1-continued
| Structure |
|---|
| 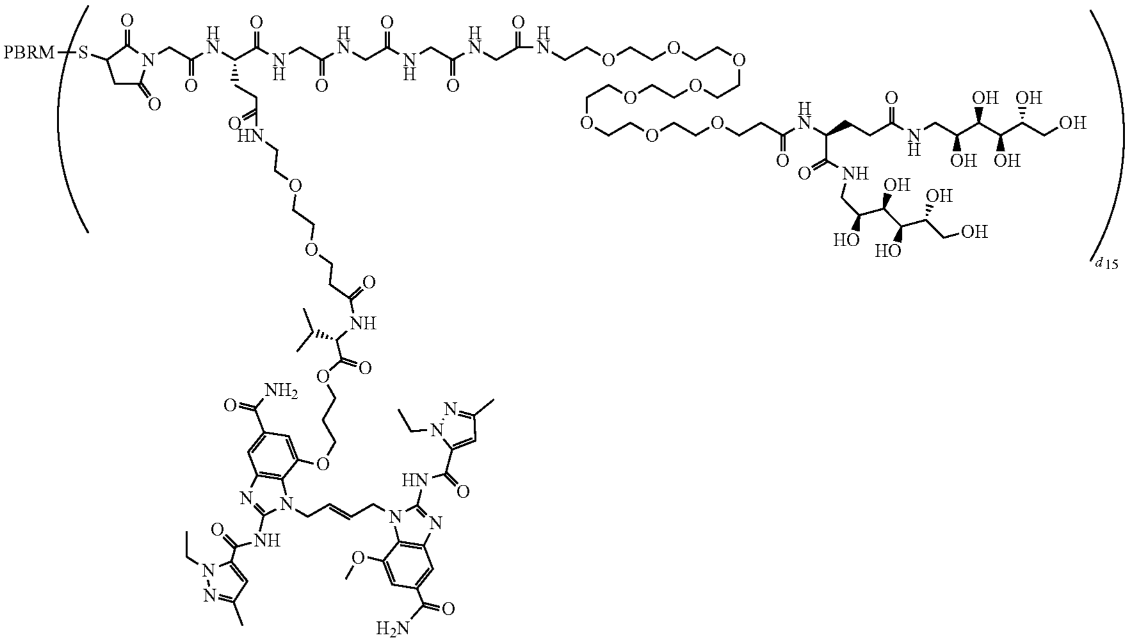 |
| 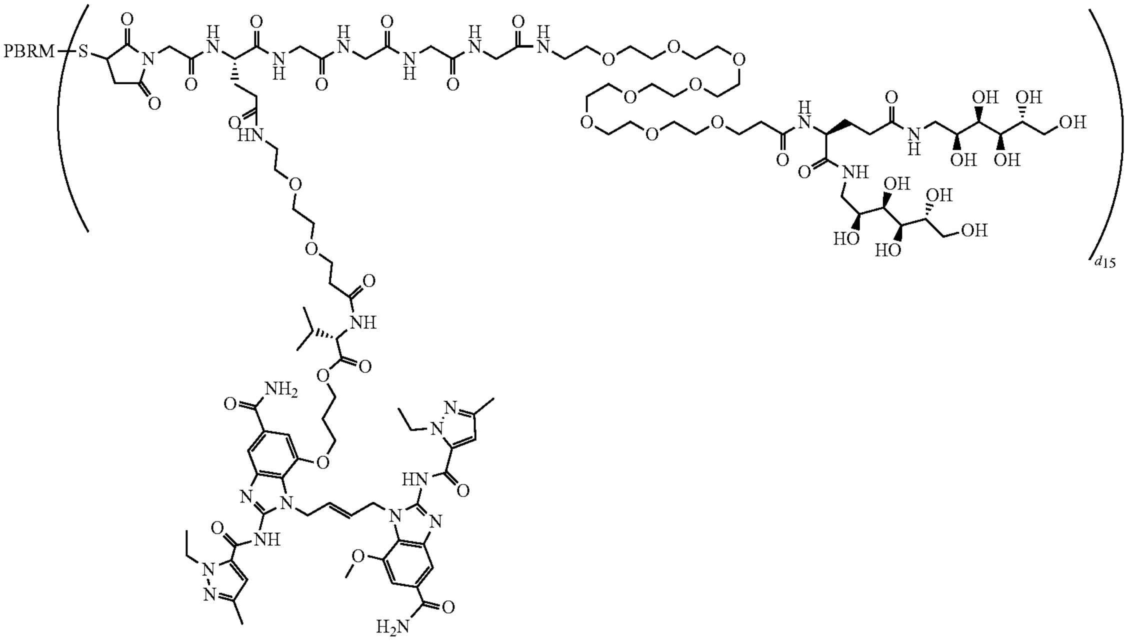 |

TABLE B1-continued
| Structure |
|---|
| 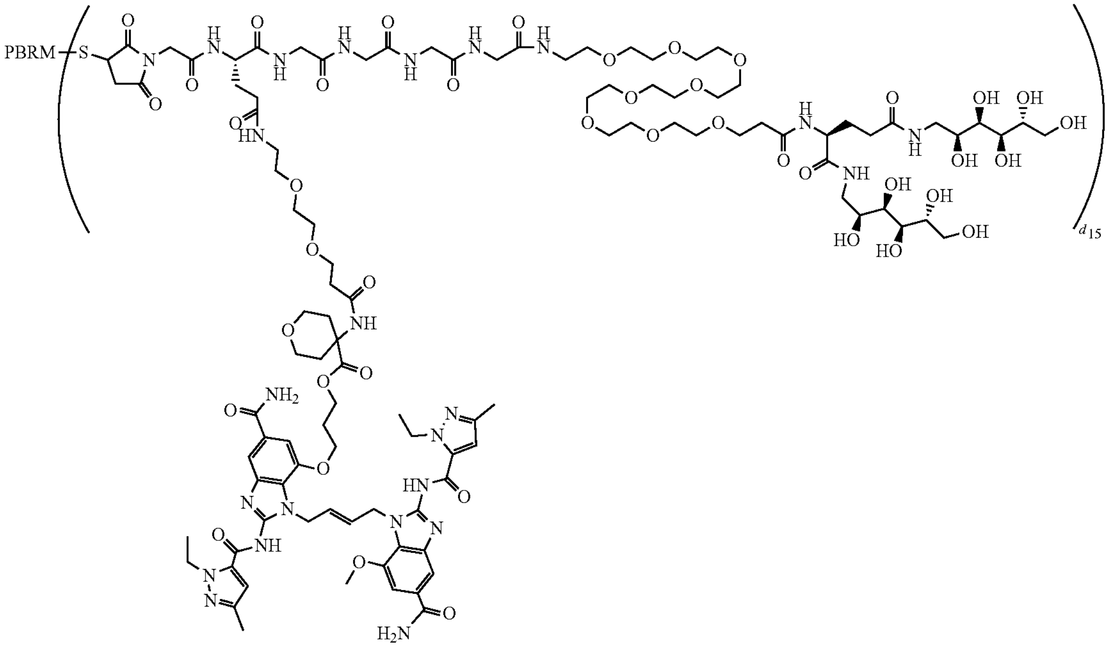 |
| 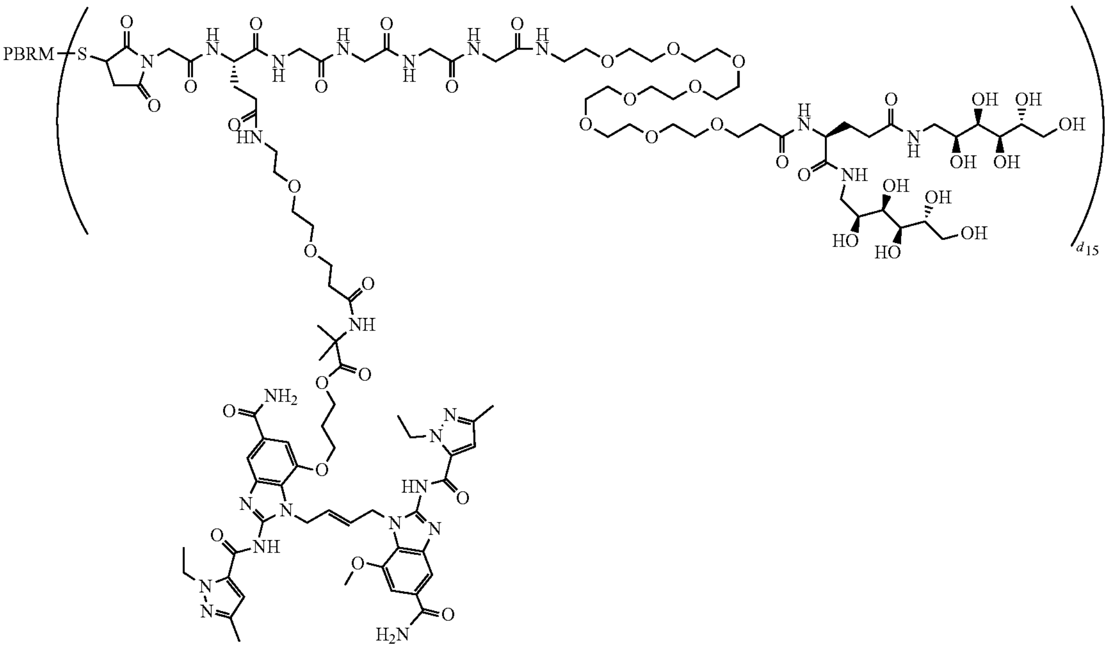 |

TABLE B1-continued
| Structure |
| --- |
| 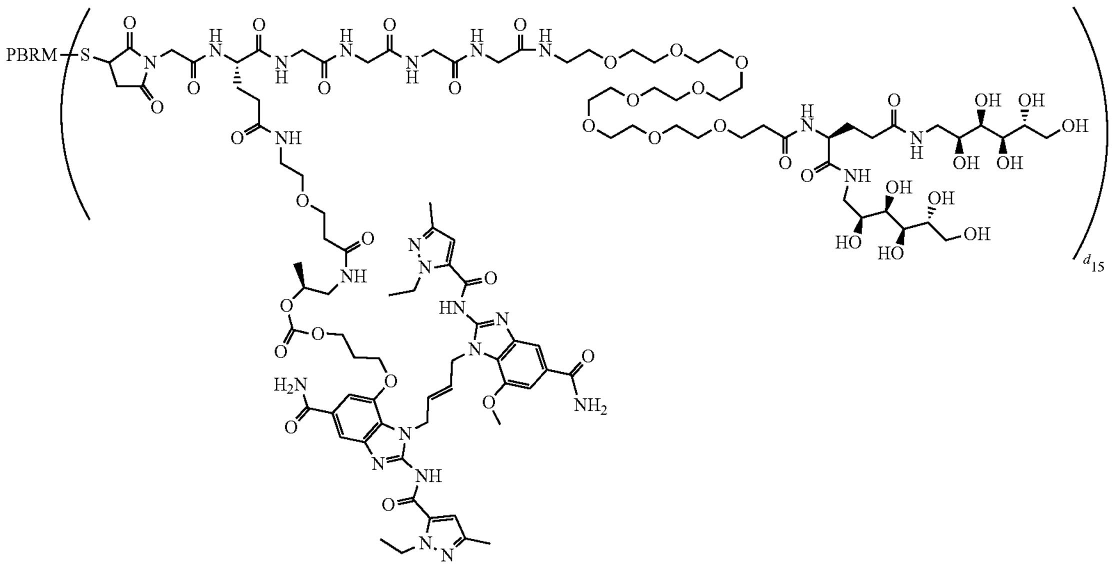 |
| 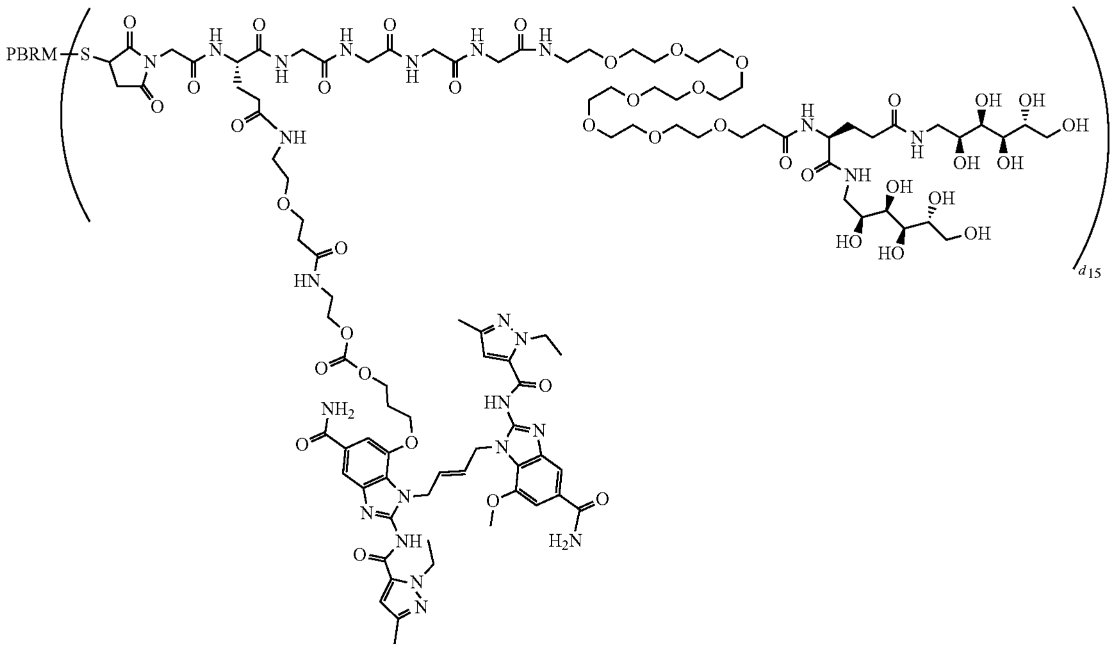 |

TABLE B1-continued
| Structure |
| --- |
| 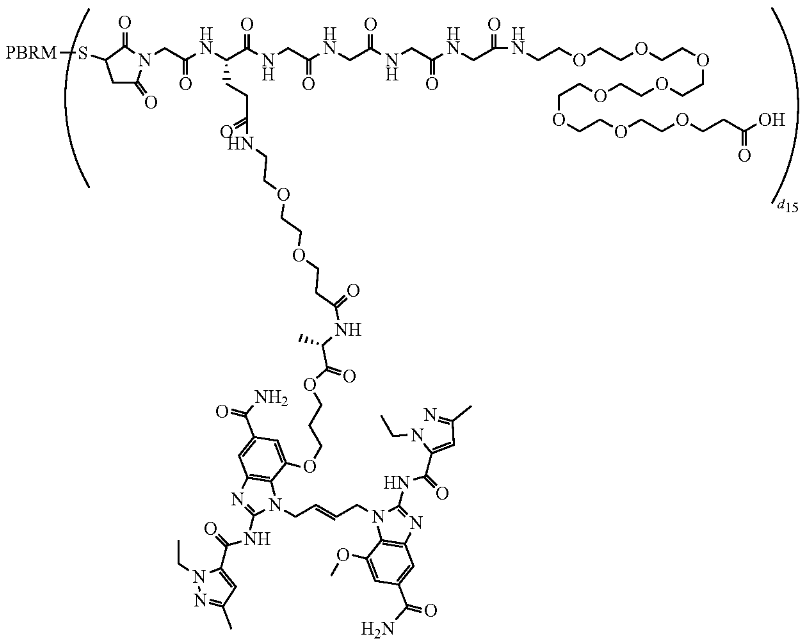 |
| 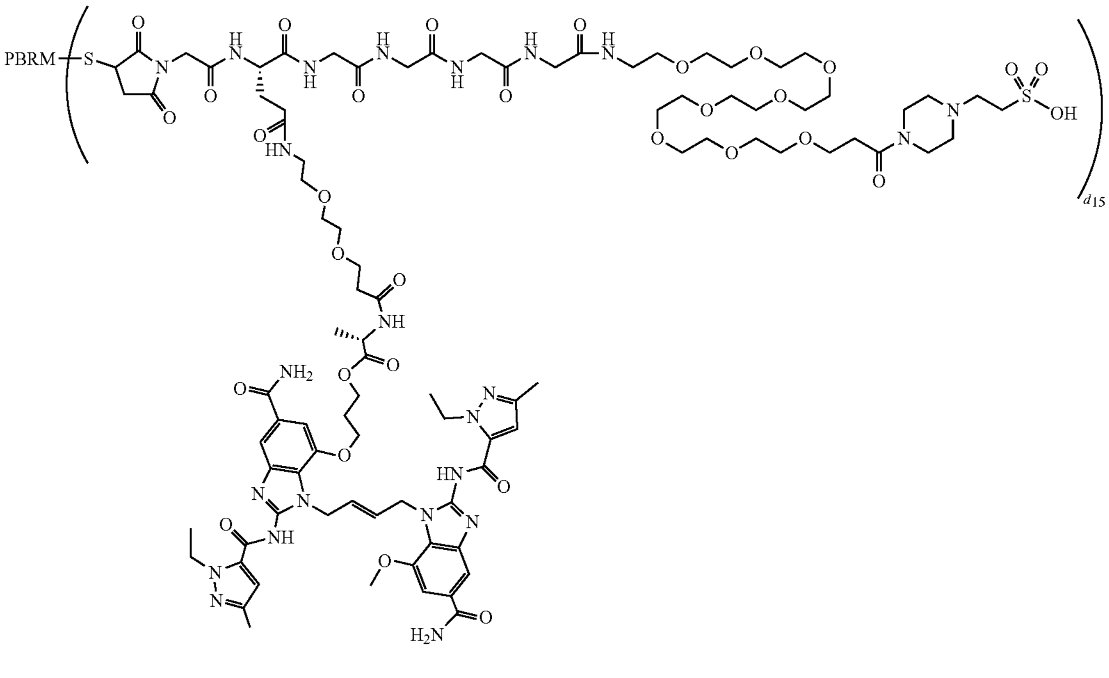 |

TABLE B1-continued
| Structure |
| --- |
| 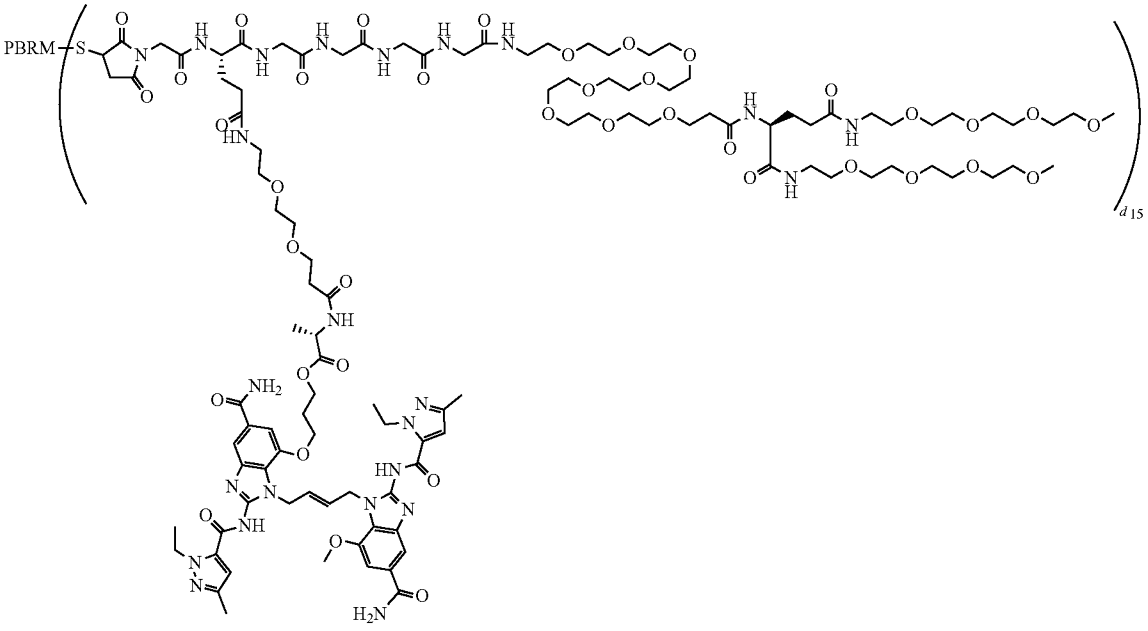 |
| 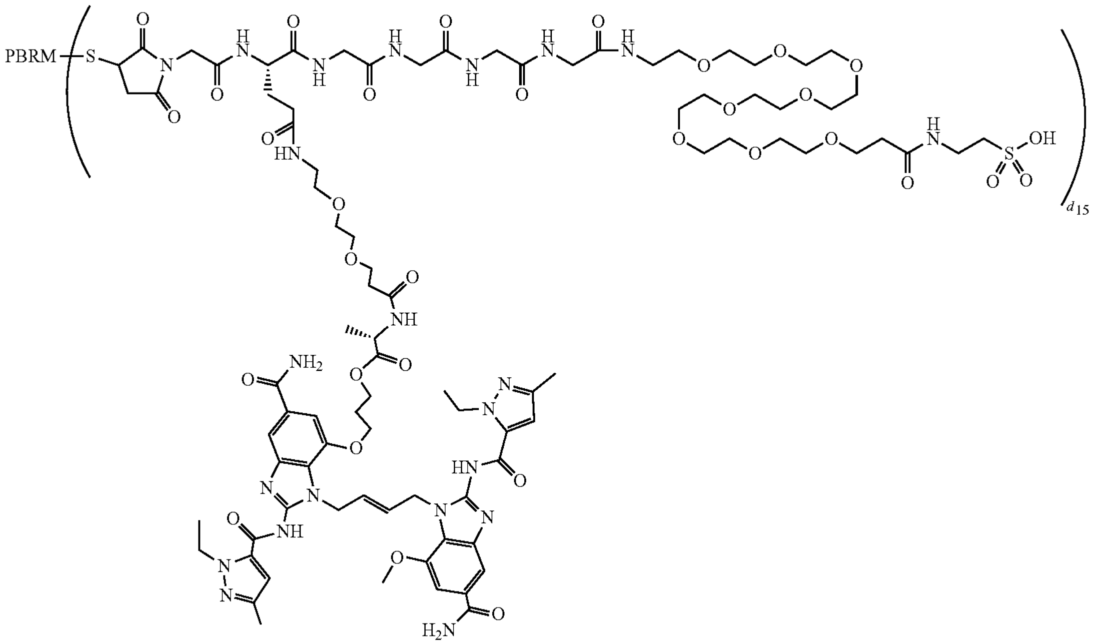 |

TABLE B1-continued
| Structure |
| --- |
| 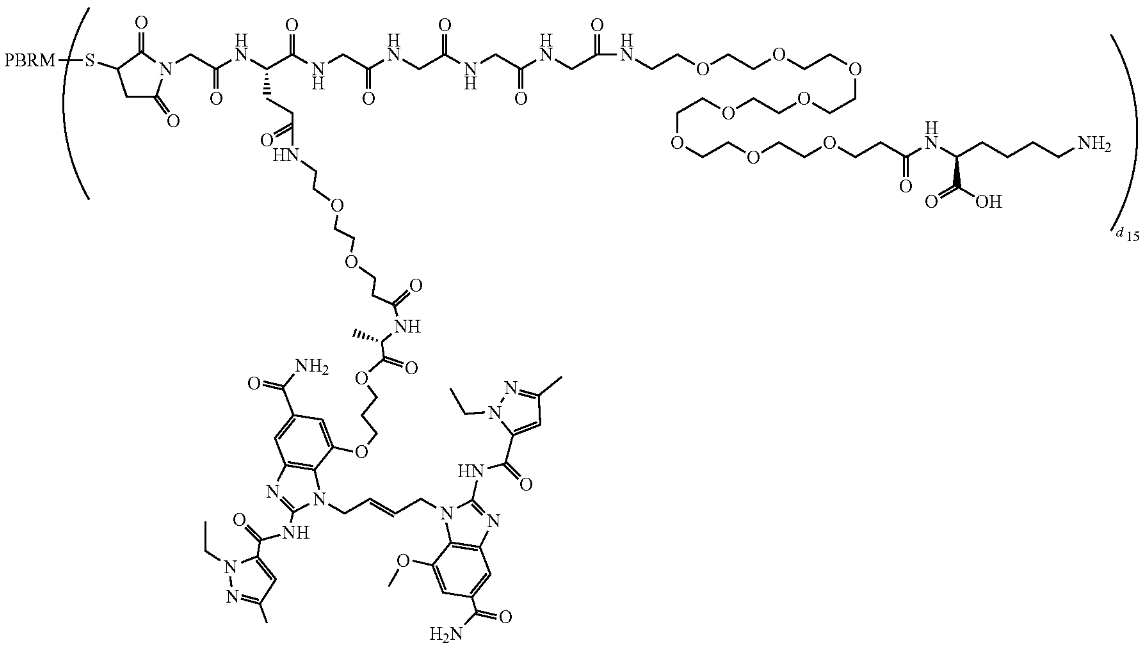 |
| 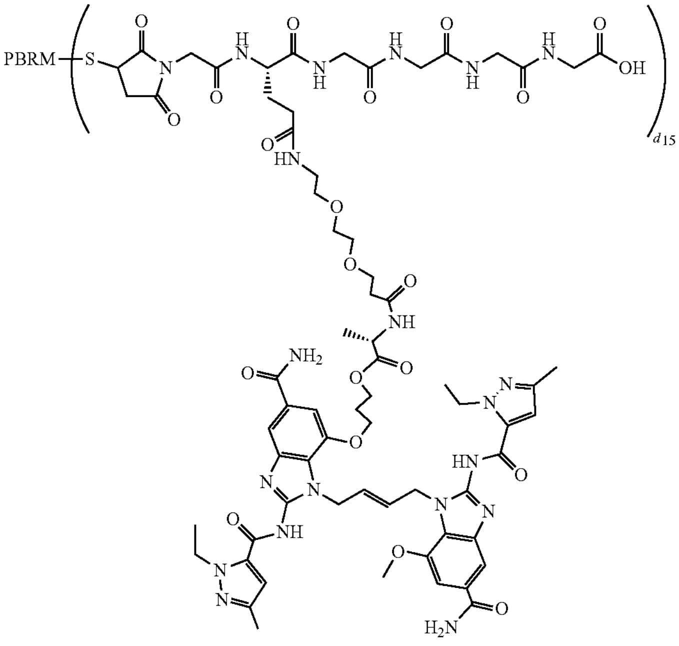 |

TABLE B1-continued
| Structure |
|---|
| 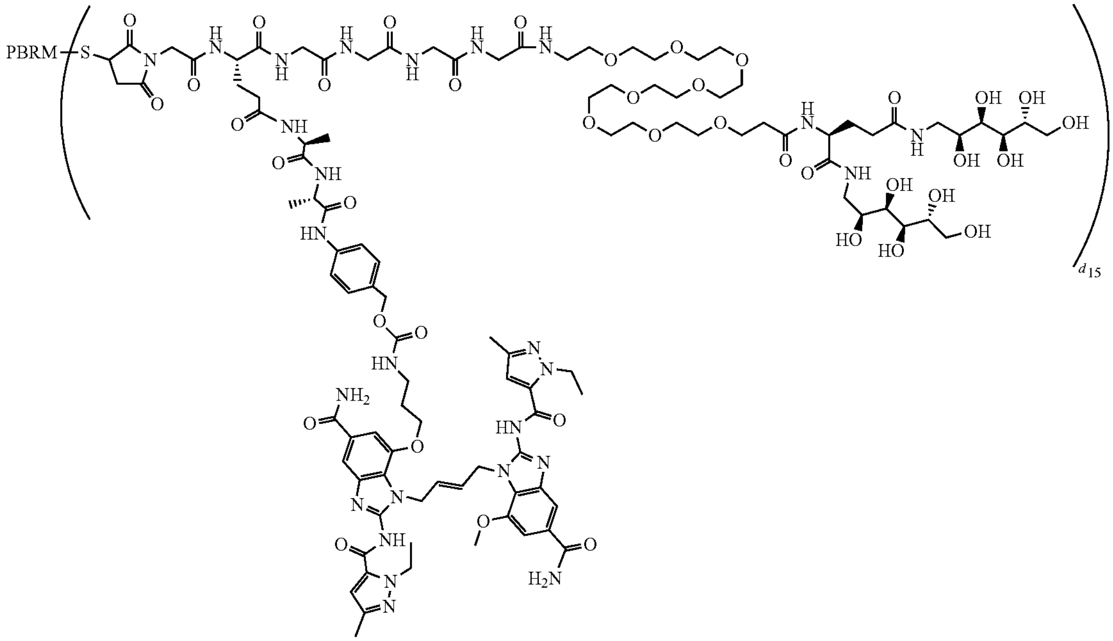 |
| 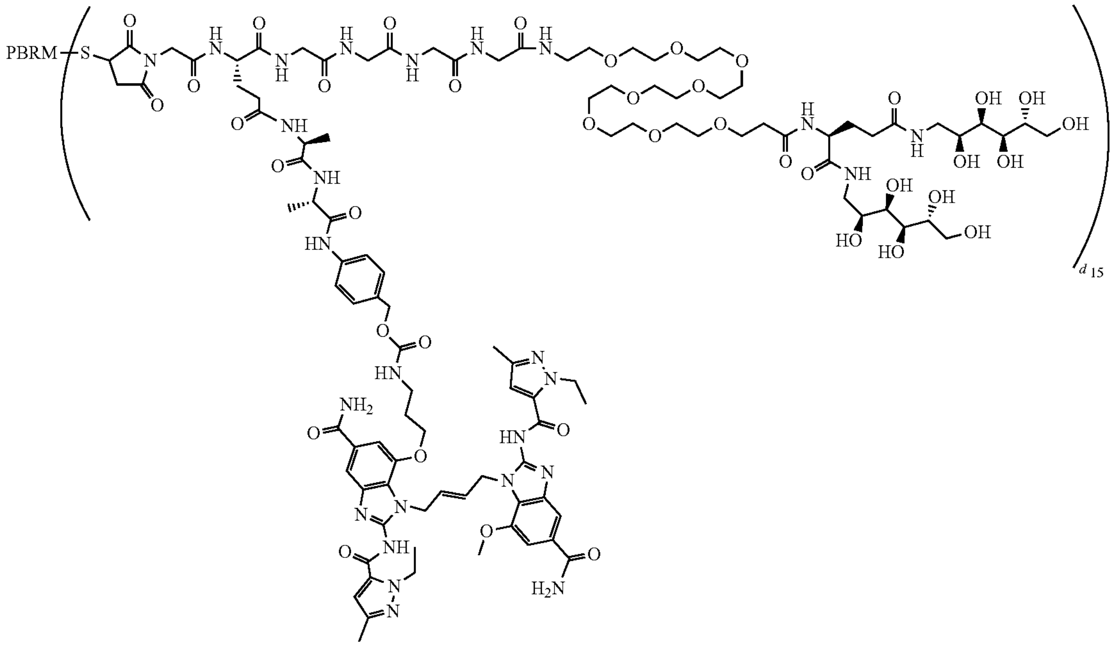 |

TABLE B1-continued
| Structure |
| --- |
| 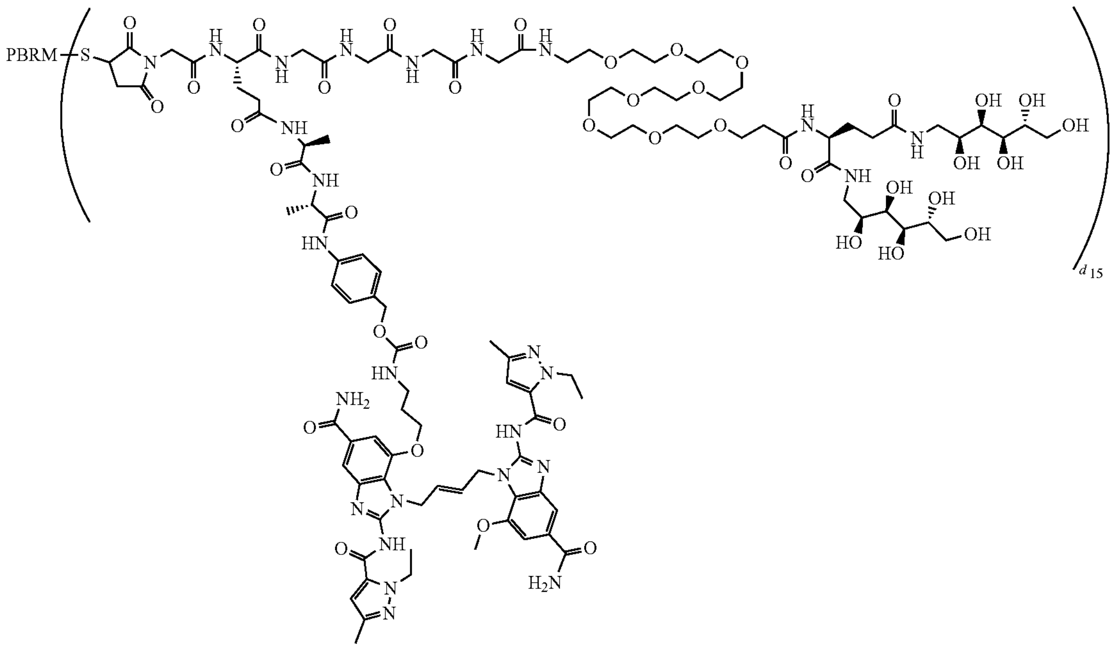 |
| 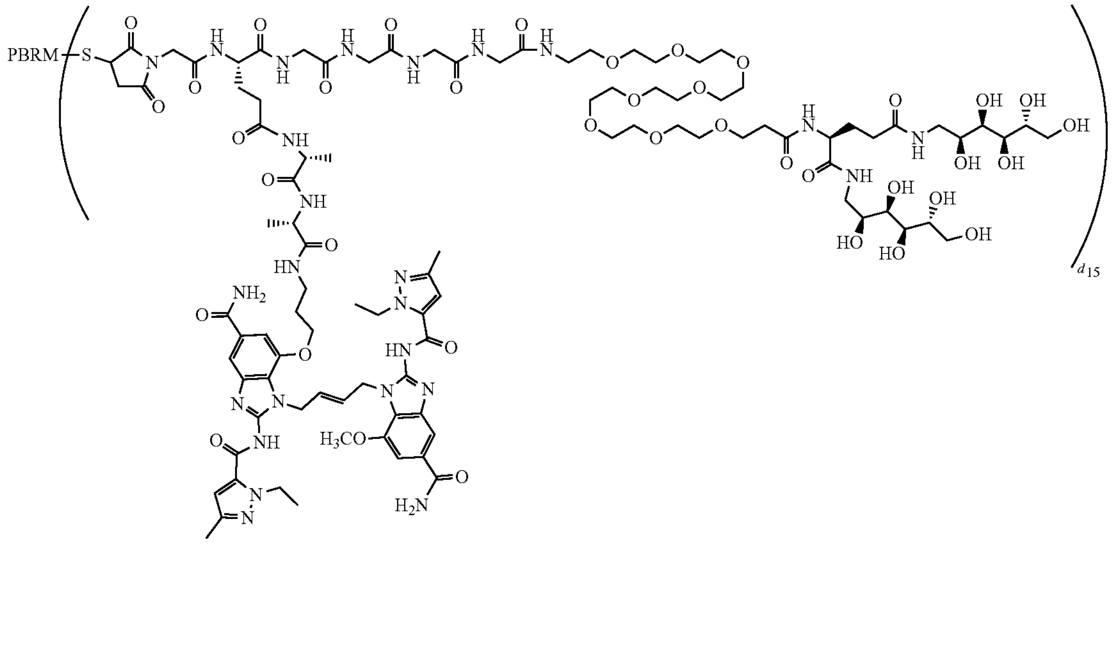 |

TABLE B1-continued
| Structure |
|---|
| 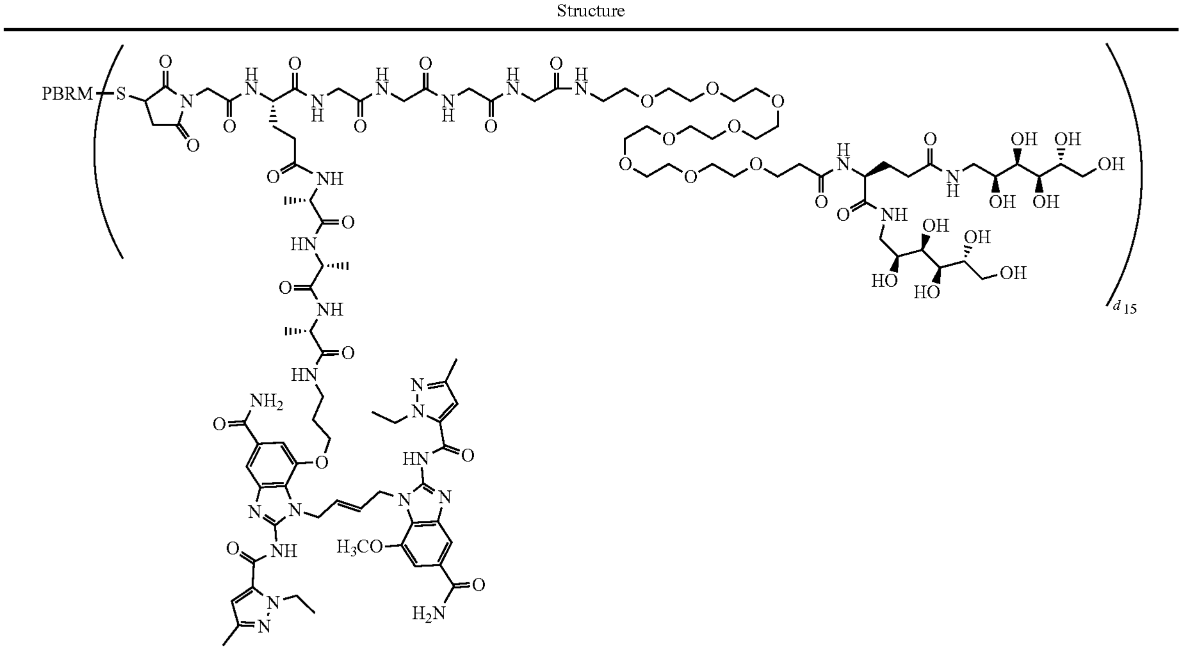 |
| 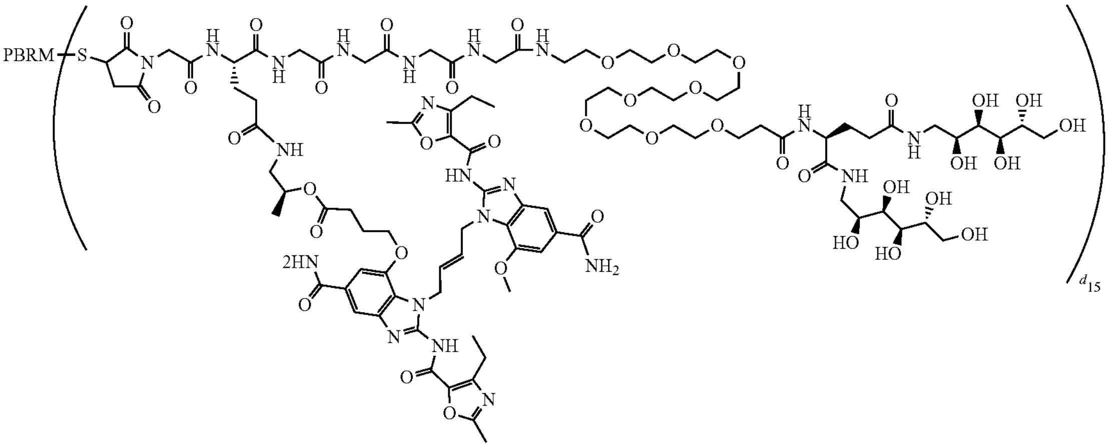 |
| 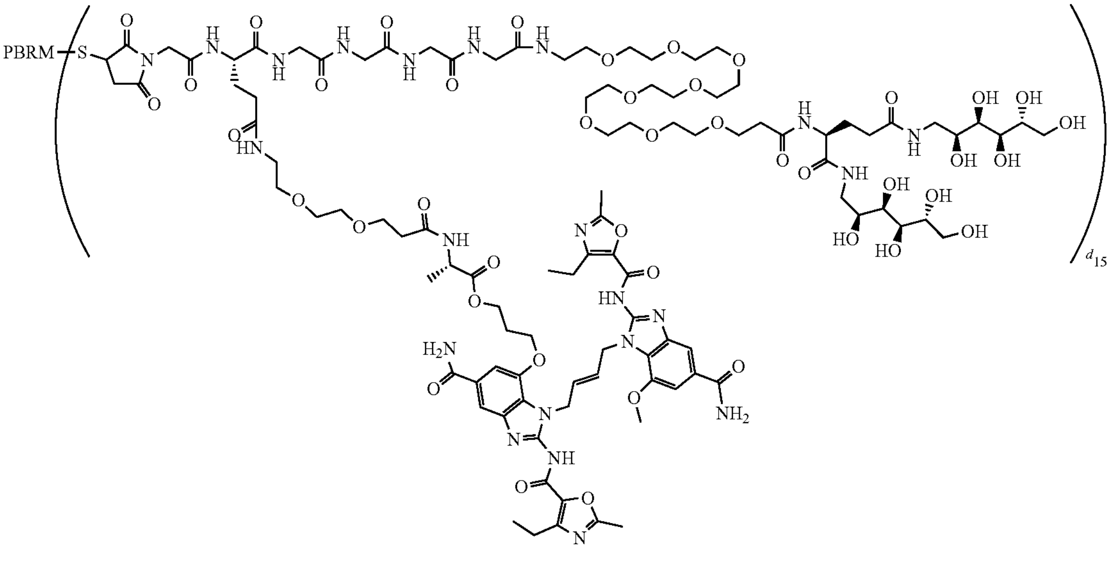 |

TABLE B1-continued
| Structure |
|---|
| 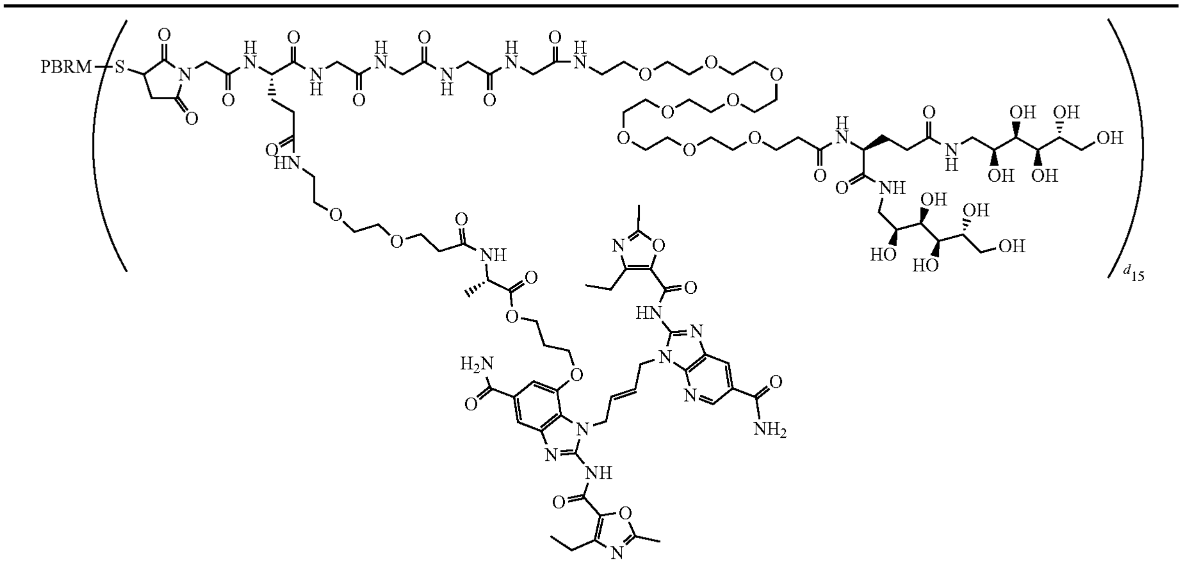 |
| 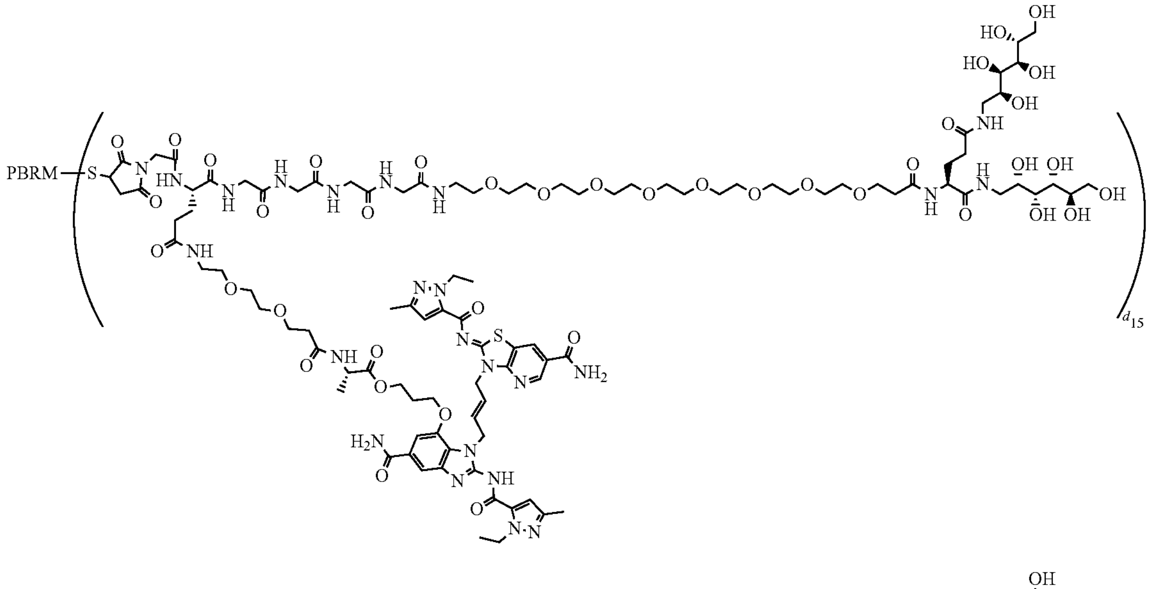 |
| 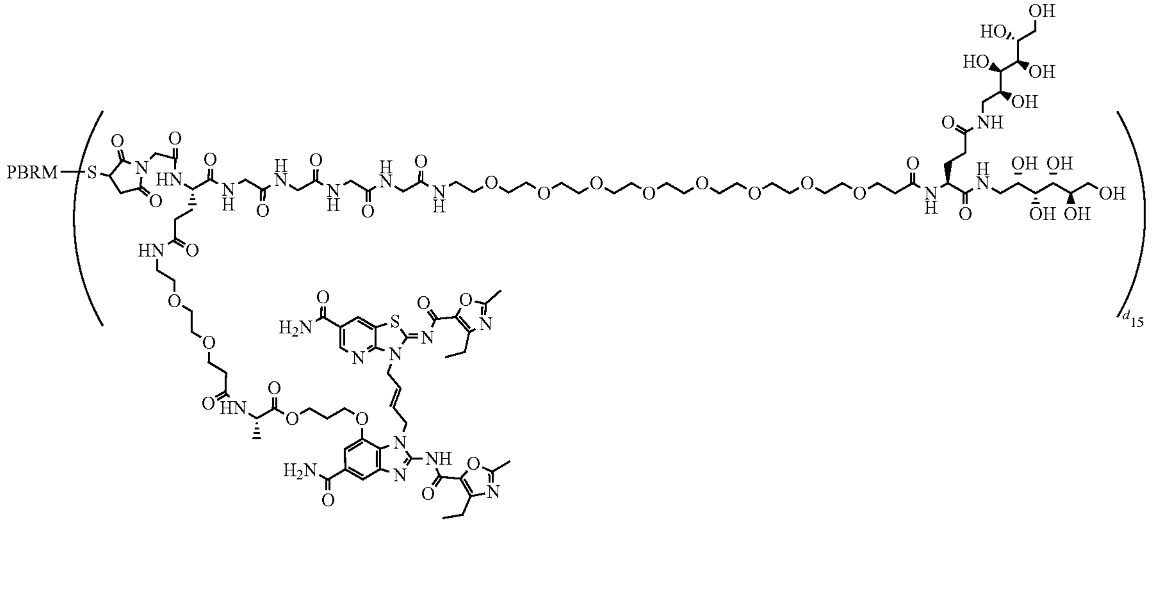 |

TABLE B1-continued
| Structure |
| --- |
| 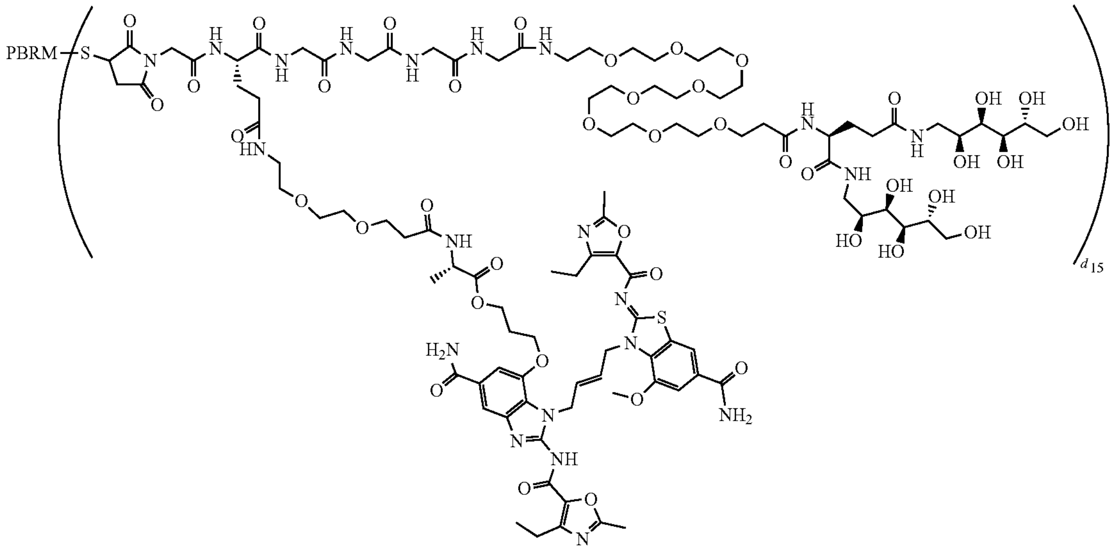 |
| 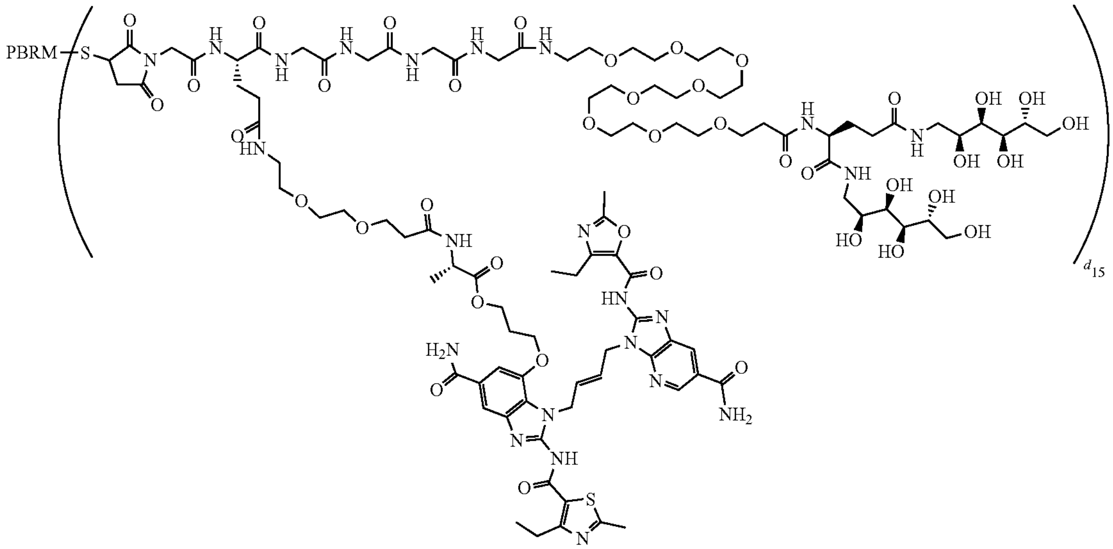 |

TABLE B1-continued
| Structure |
| --- |
| 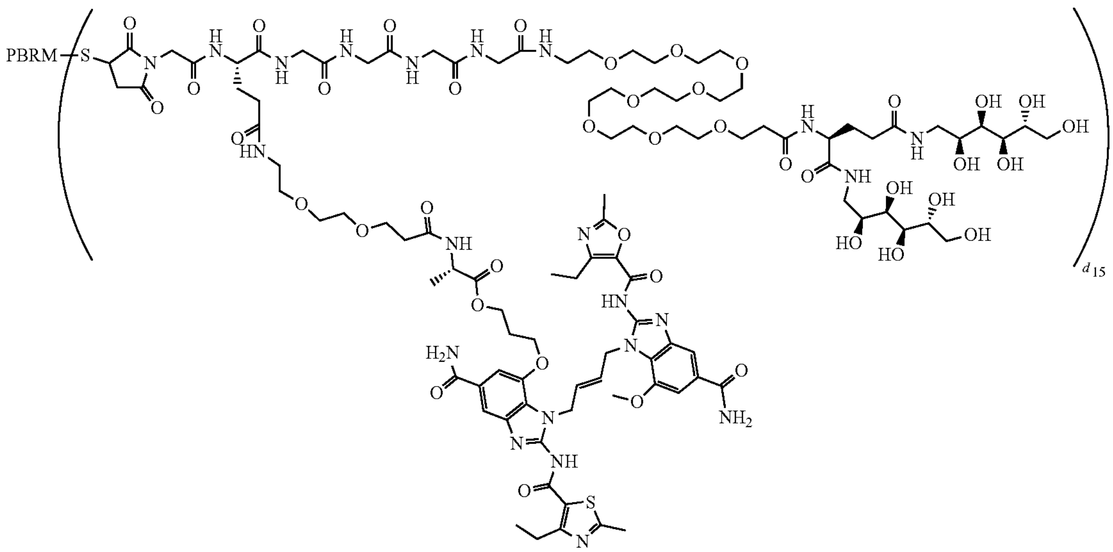 |
| 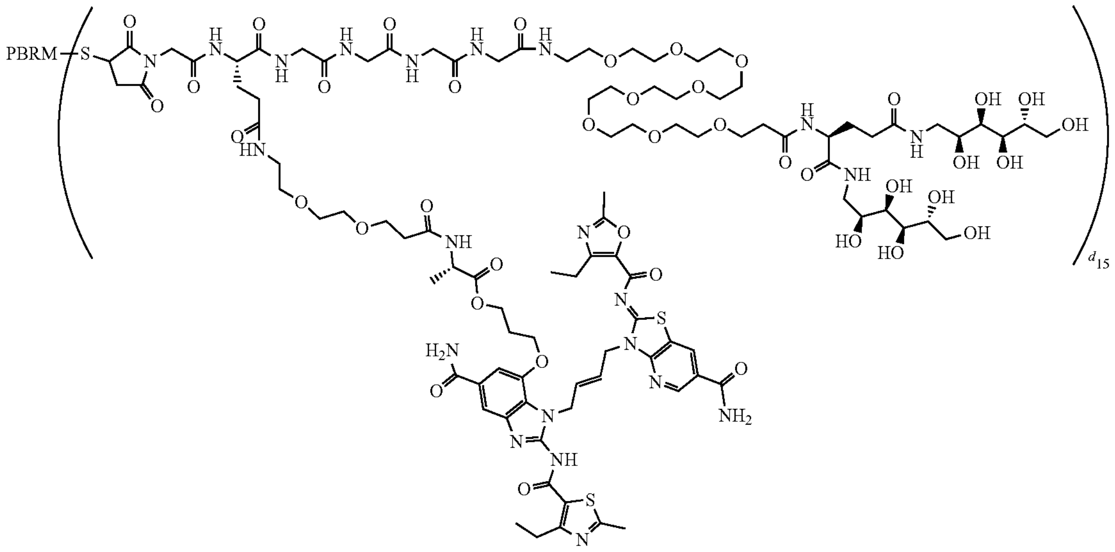 |

TABLE B1-continued
| Structure |
| --- |
| 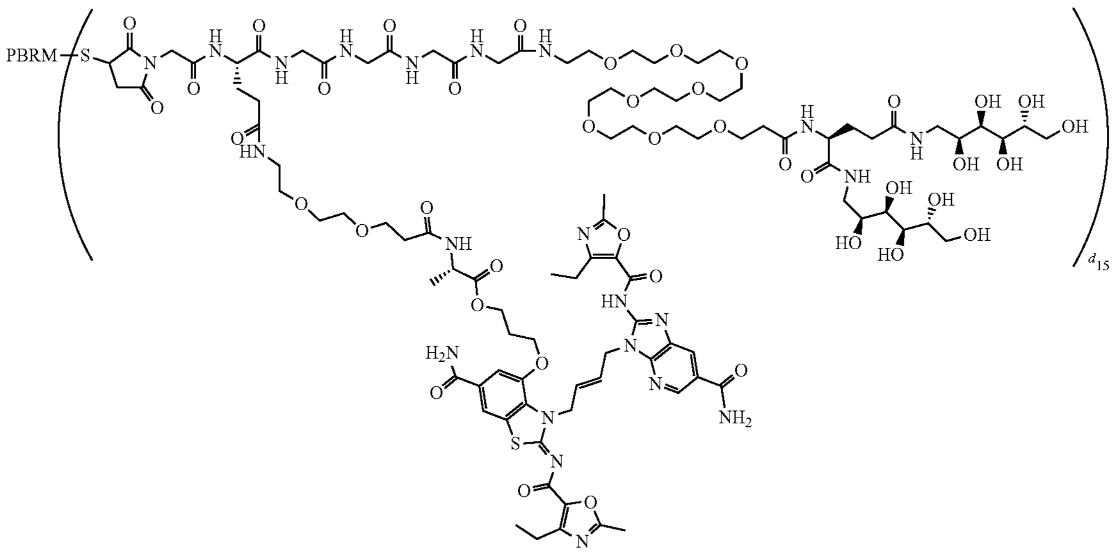 |
| 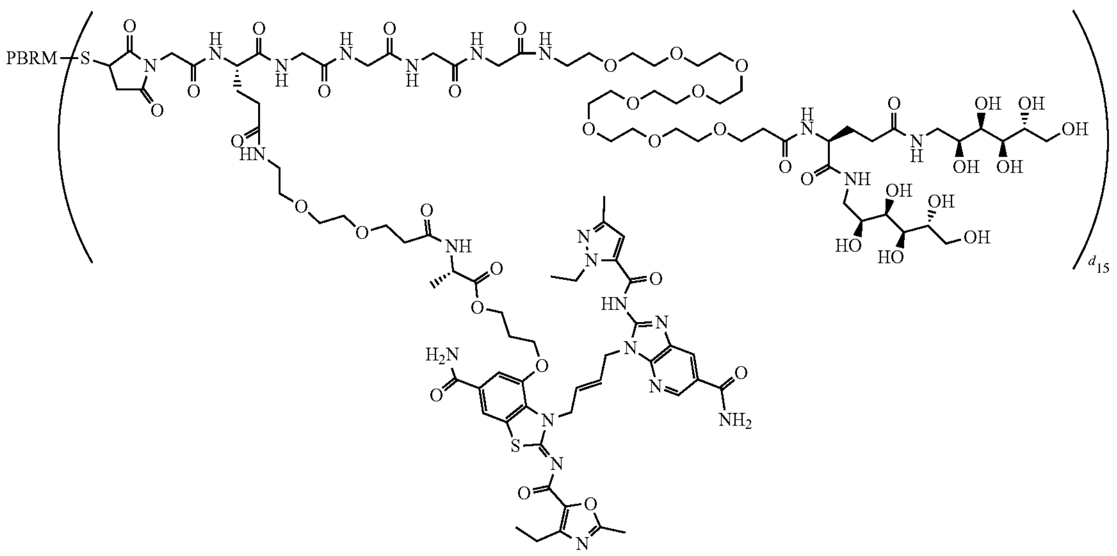 |

TABLE B1-continued
| Structure |
| --- |
| 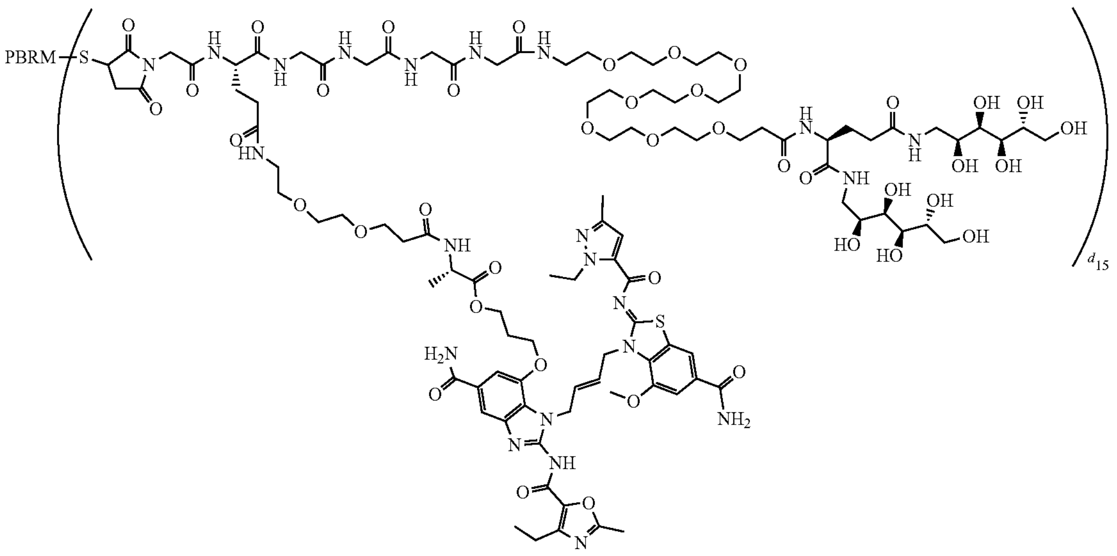 |
| 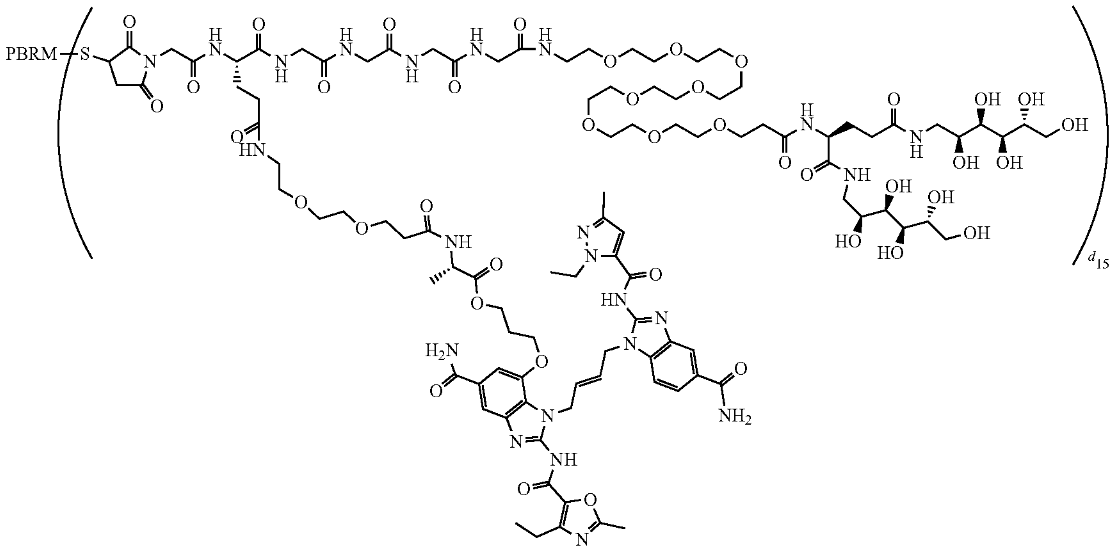 |

TABLE B1-continued
| Structure |
| --- |
| 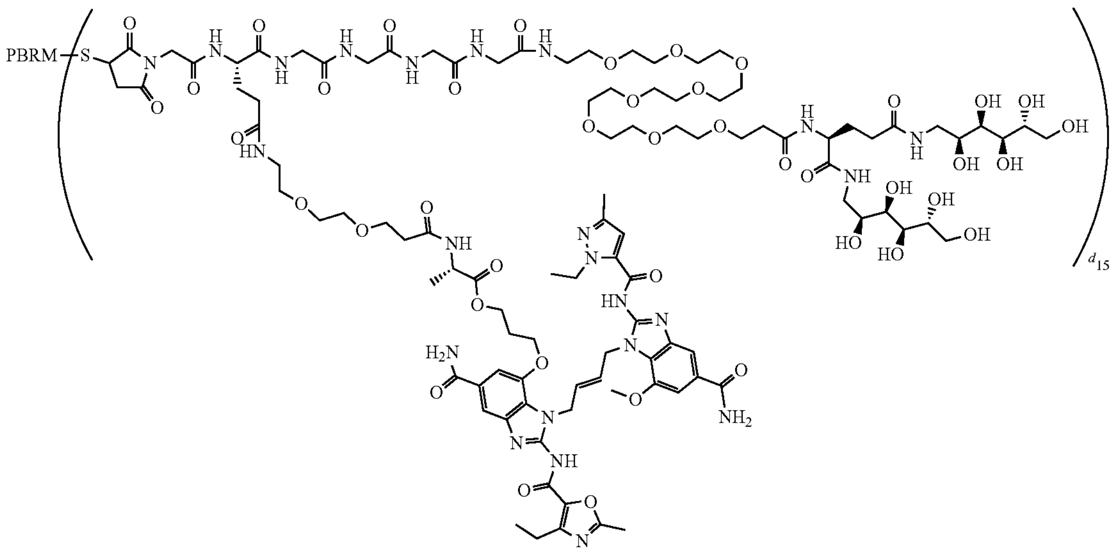 |
| 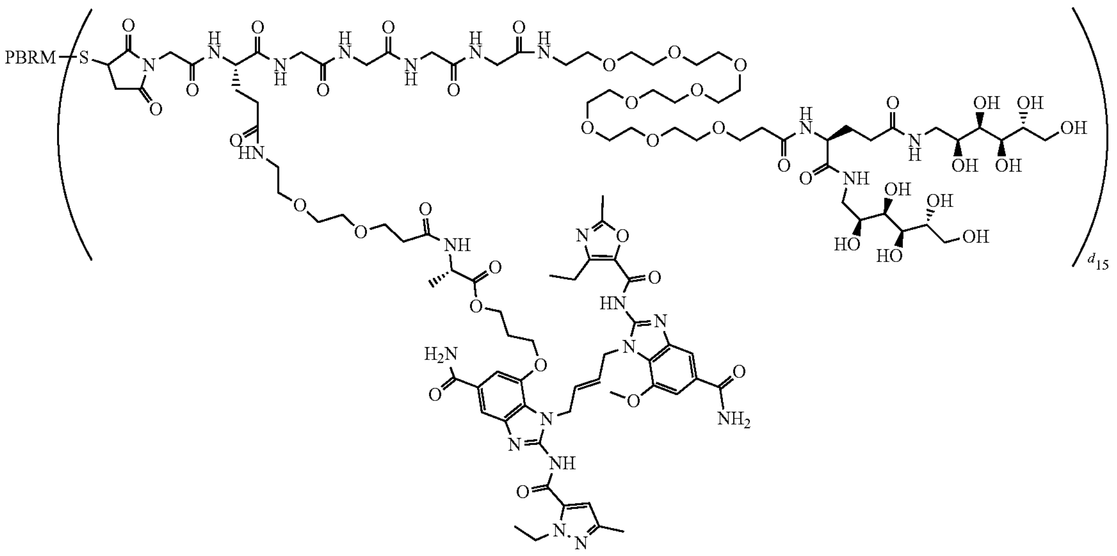 |

TABLE B1-continued
| Structure |
| --- |
| 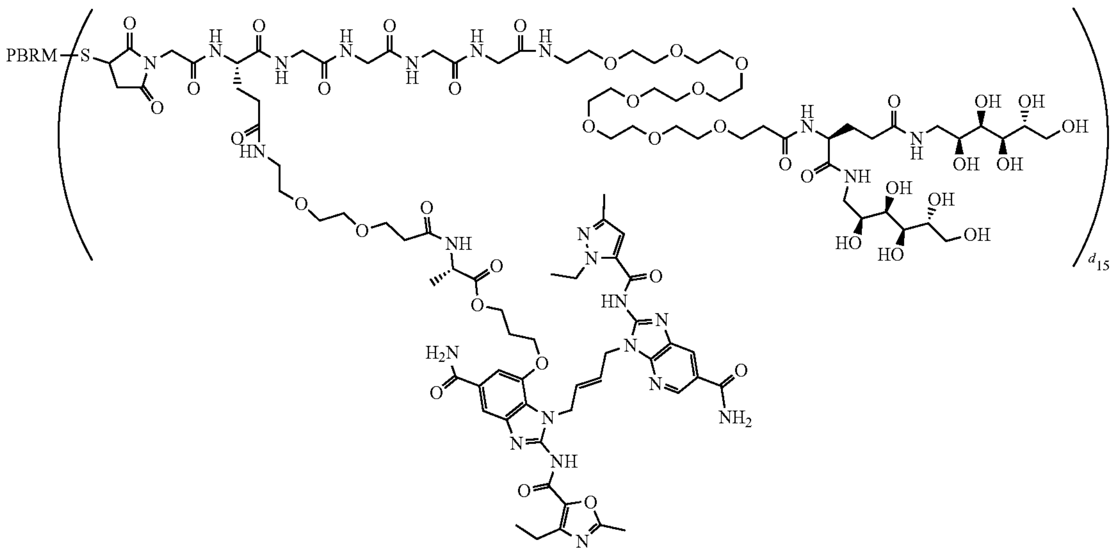 |
| 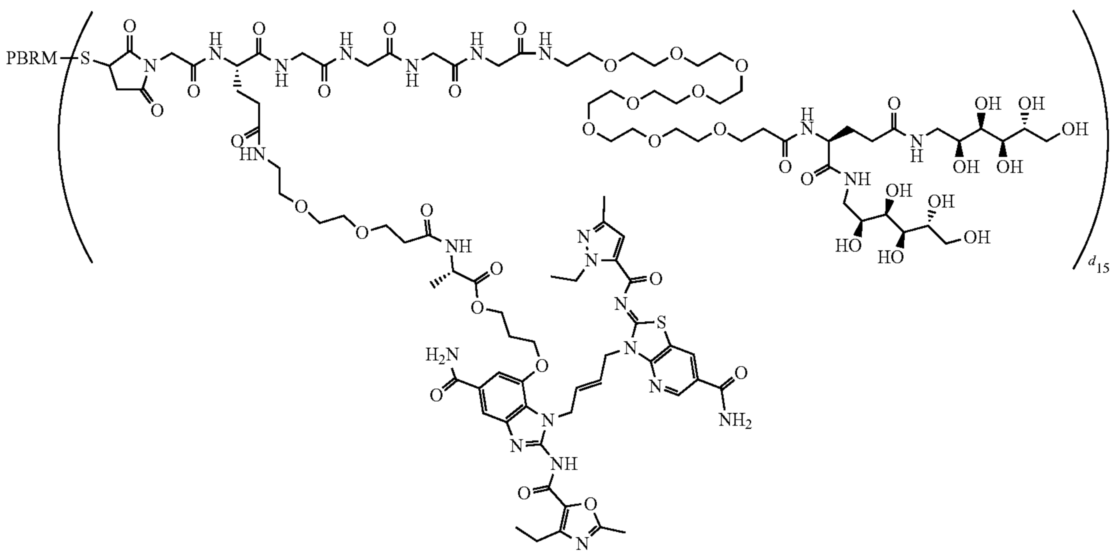 |

TABLE B1-continued
| Structure |
| --- |
| 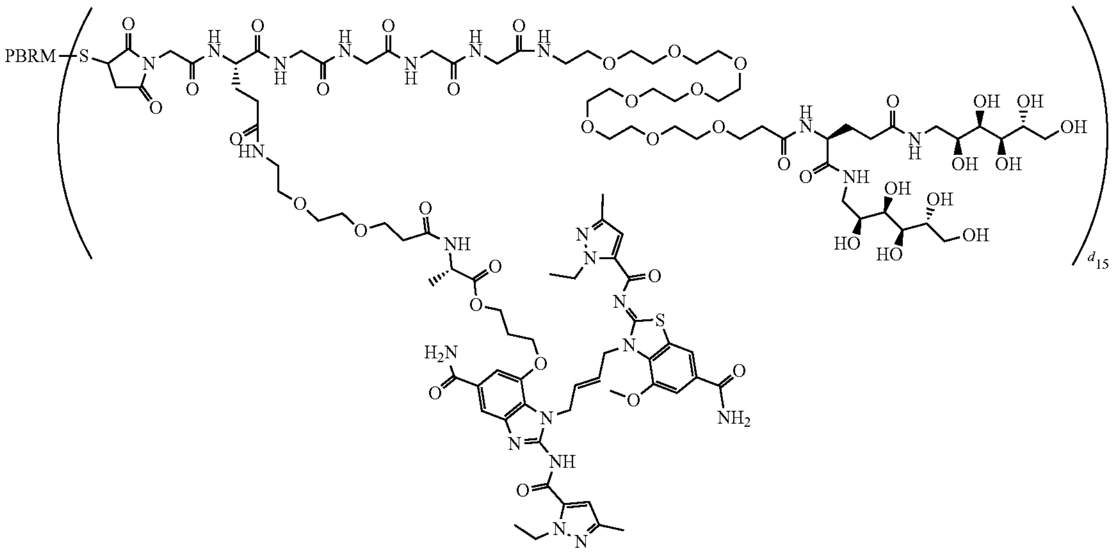 |
| 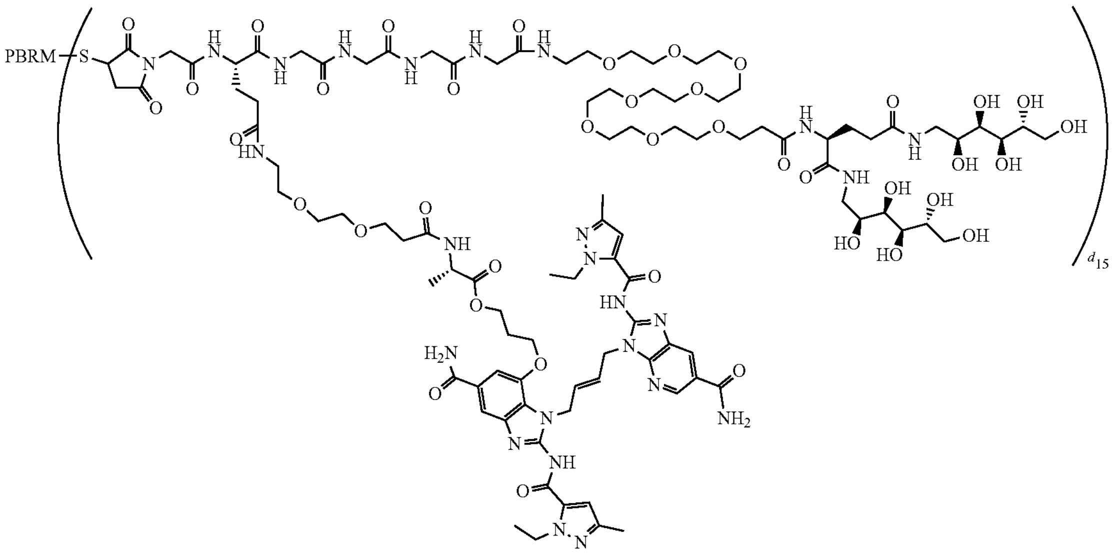 |

TABLE B1-continued
| Structure |
| --- |
| 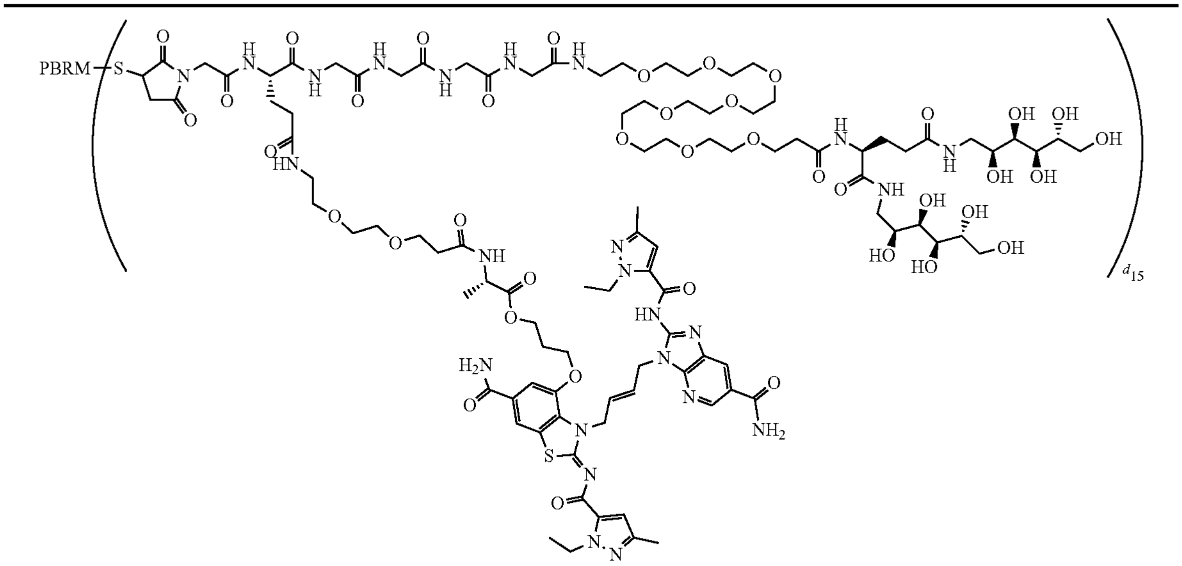 |
| 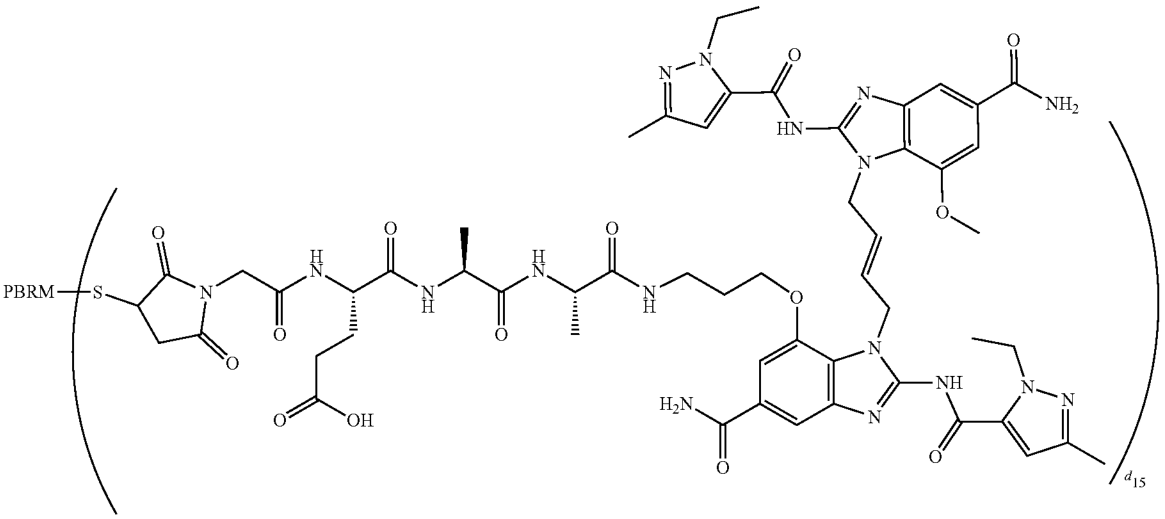 |
| 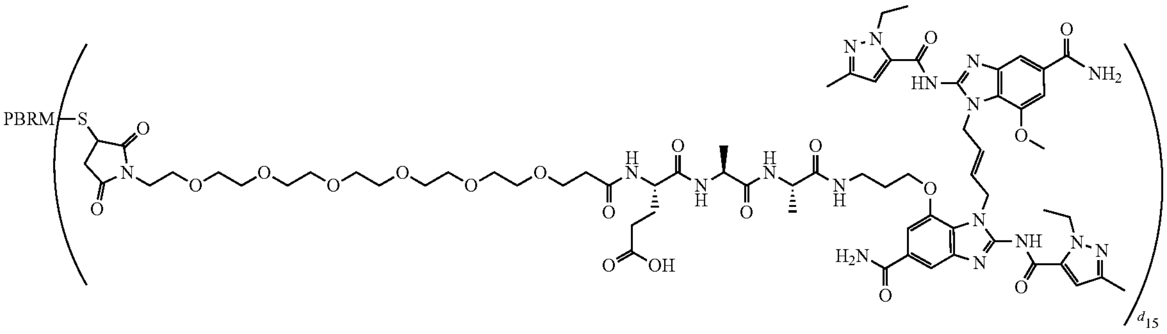 |

TABLE B1-continued
| Structure |
| --- |
| 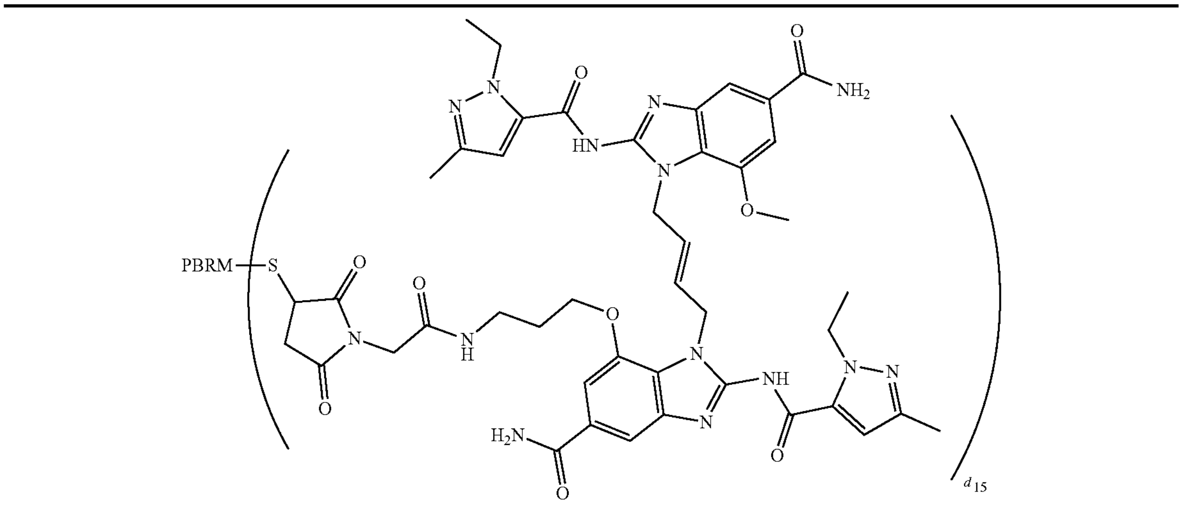 |
| 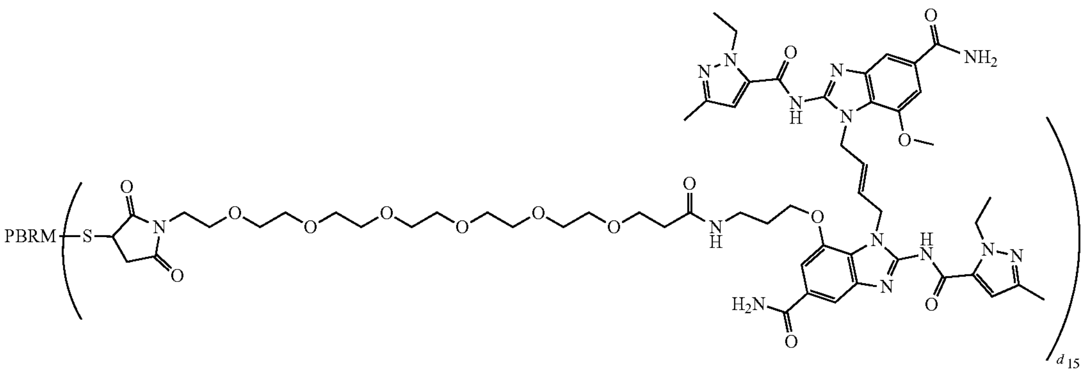 |
| 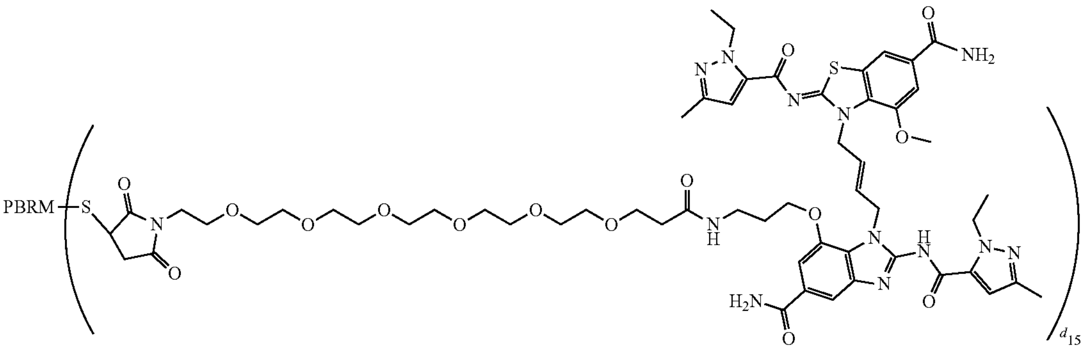 |
| 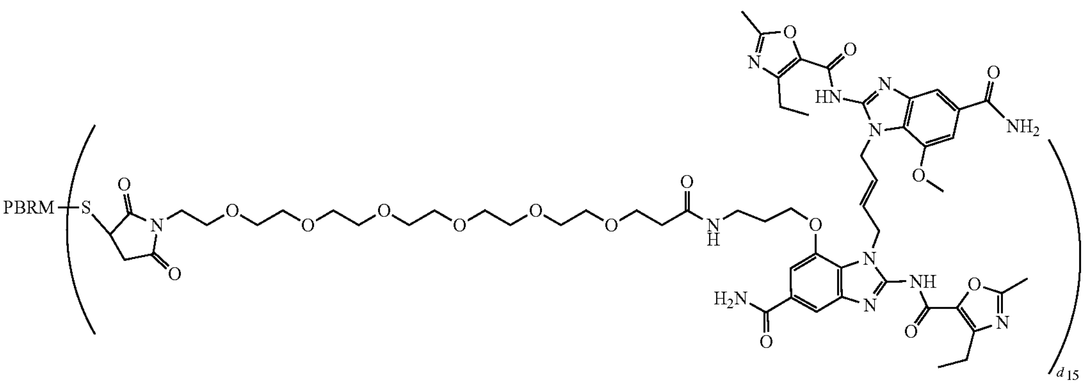 |

TABLE B1-continued
| Structure |
| --- |
| 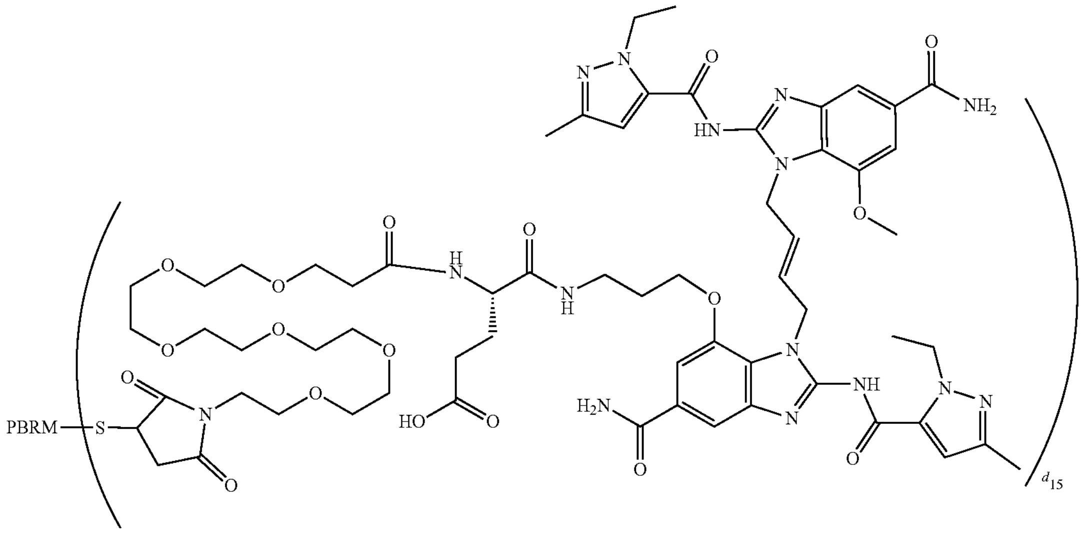 |
| 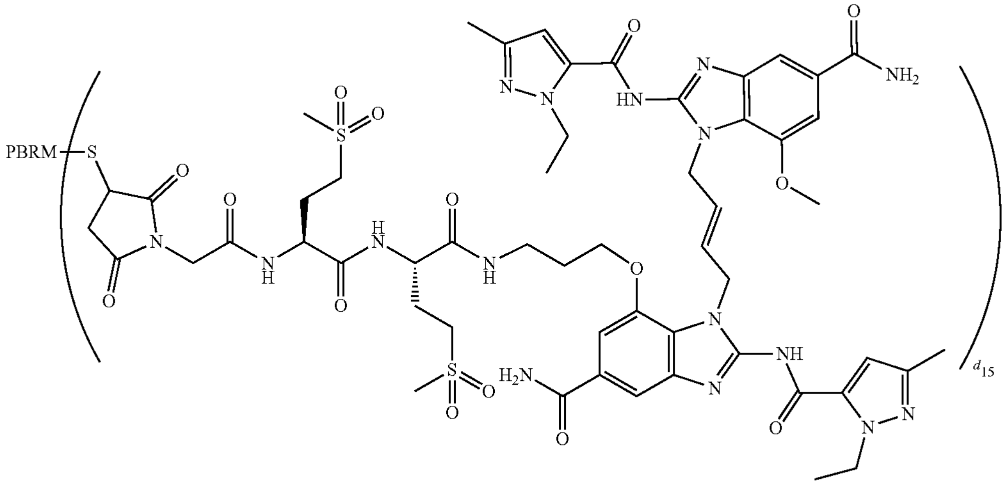 |
| 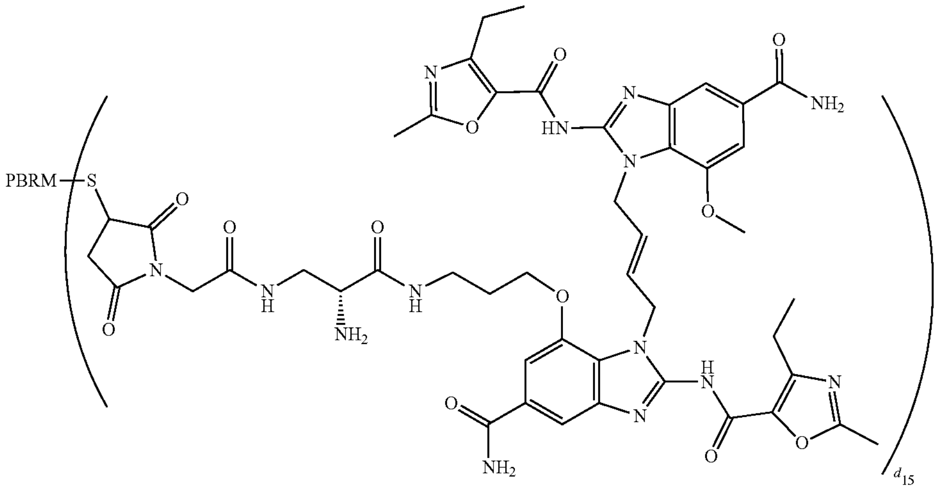 |

TABLE B1-continued
Structure
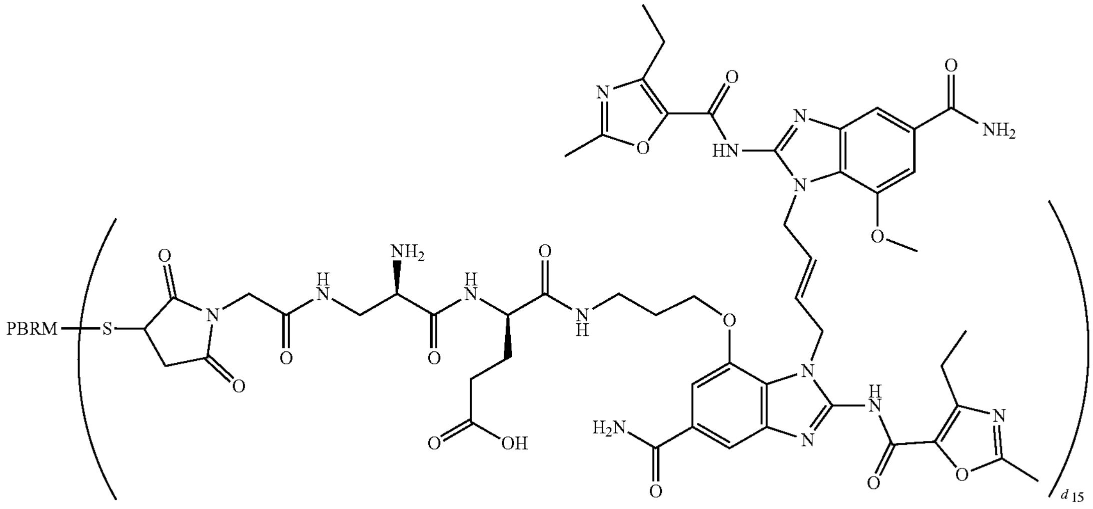
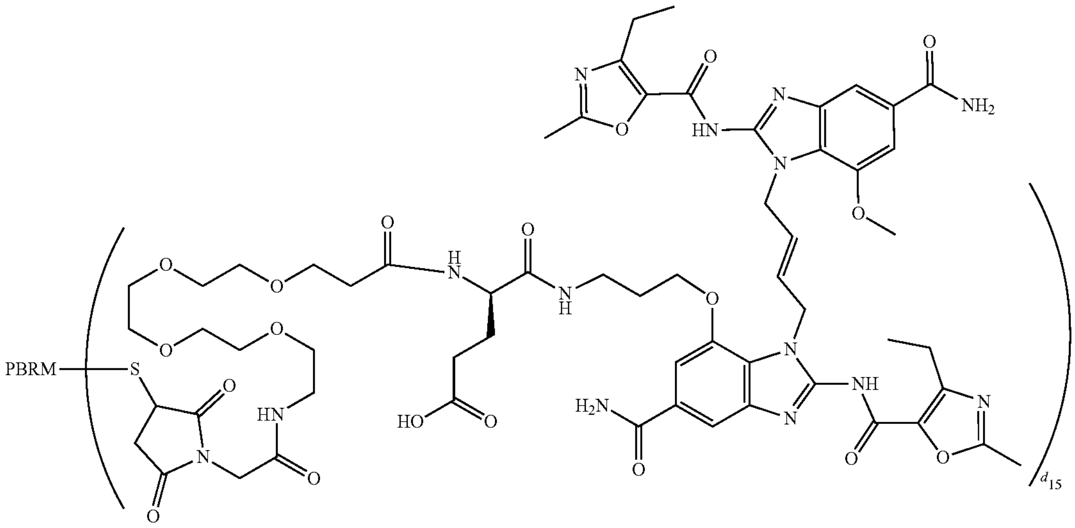
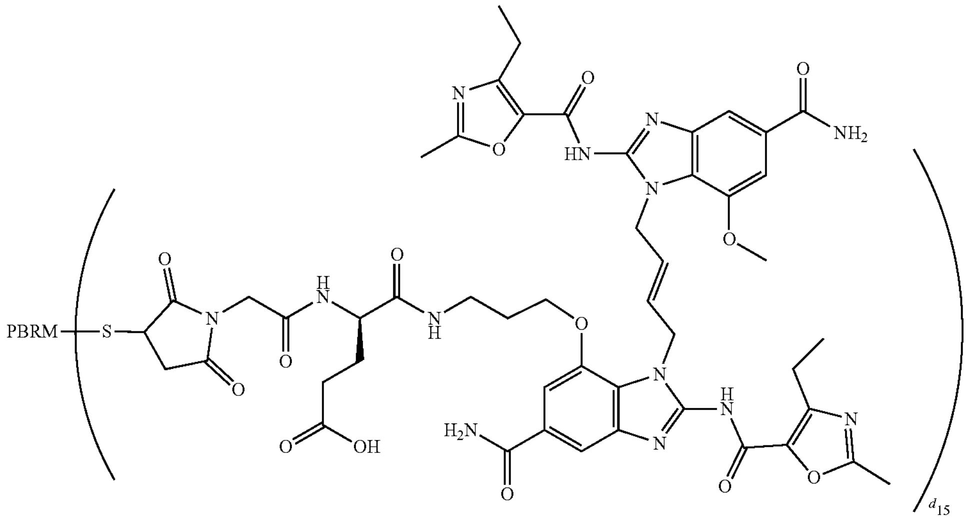

TABLE B1-continued
| Structure |
| --- |
| 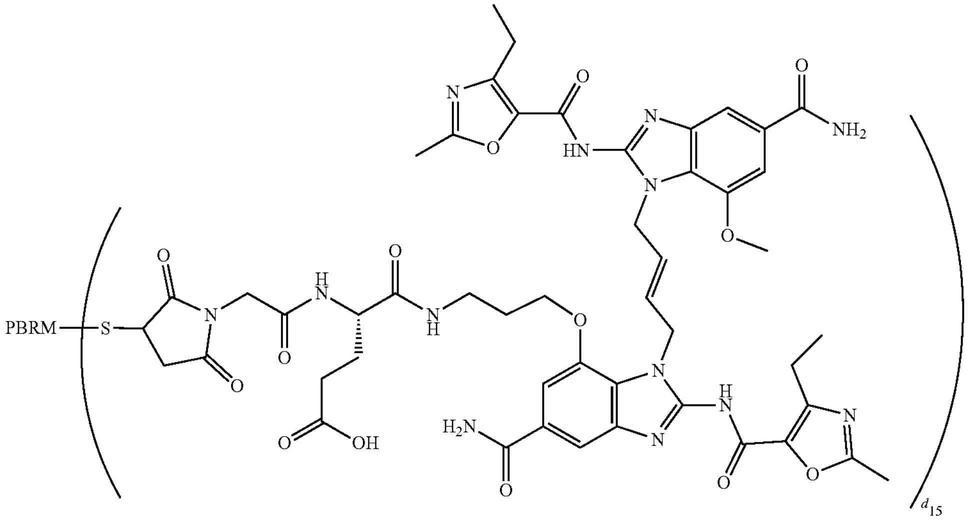 |
| 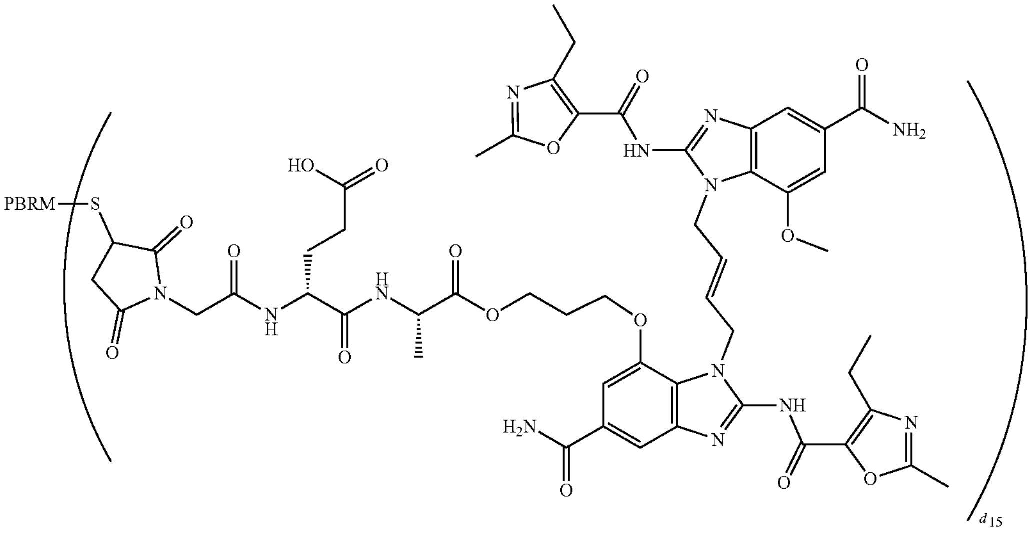 |
| 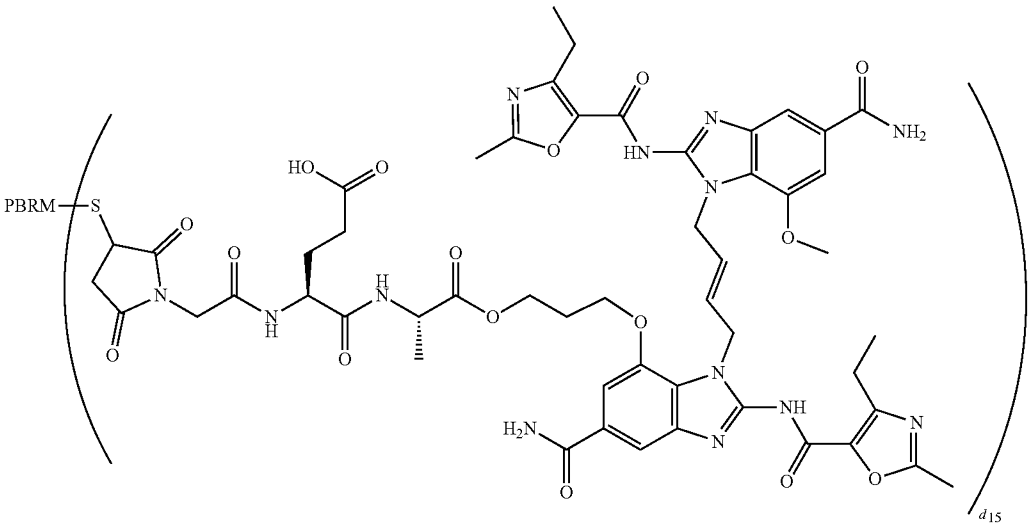 |

TABLE B1-continued
| Structure |
| --- |
| 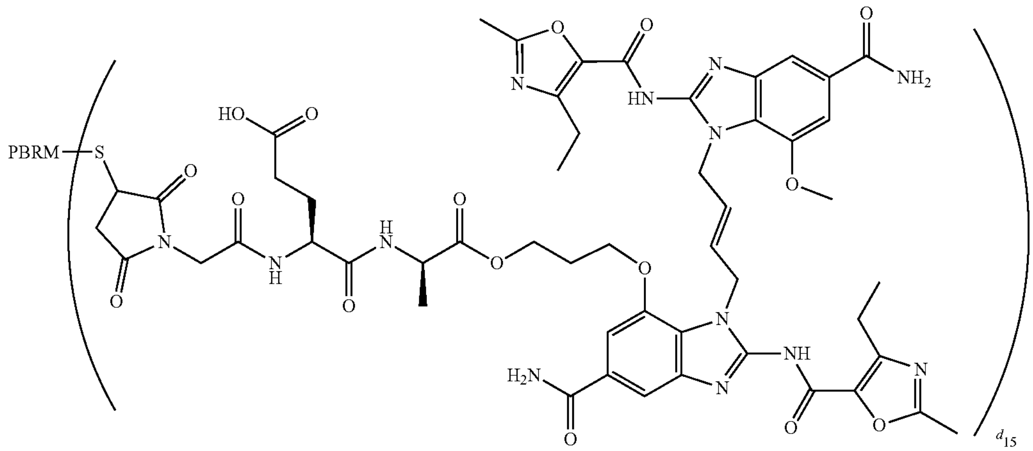 |
| 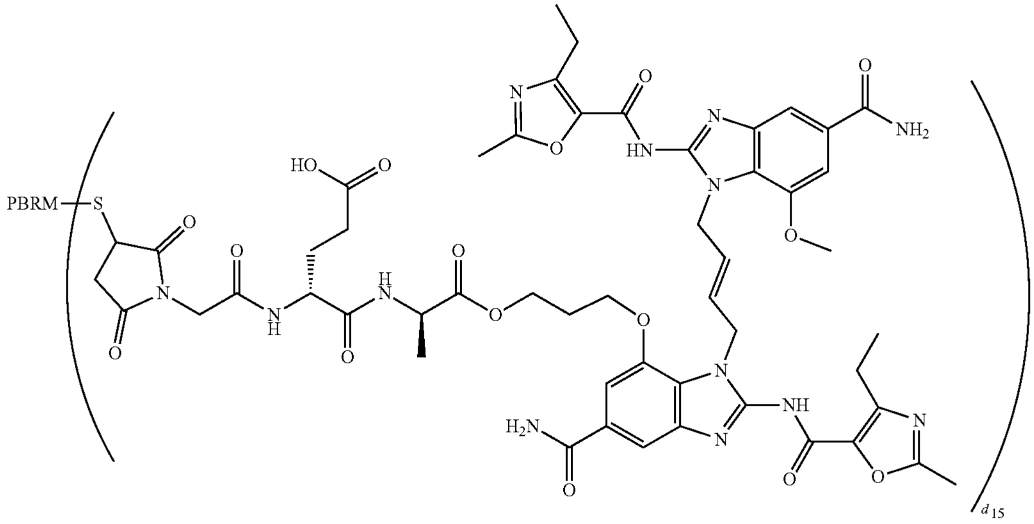 |
| 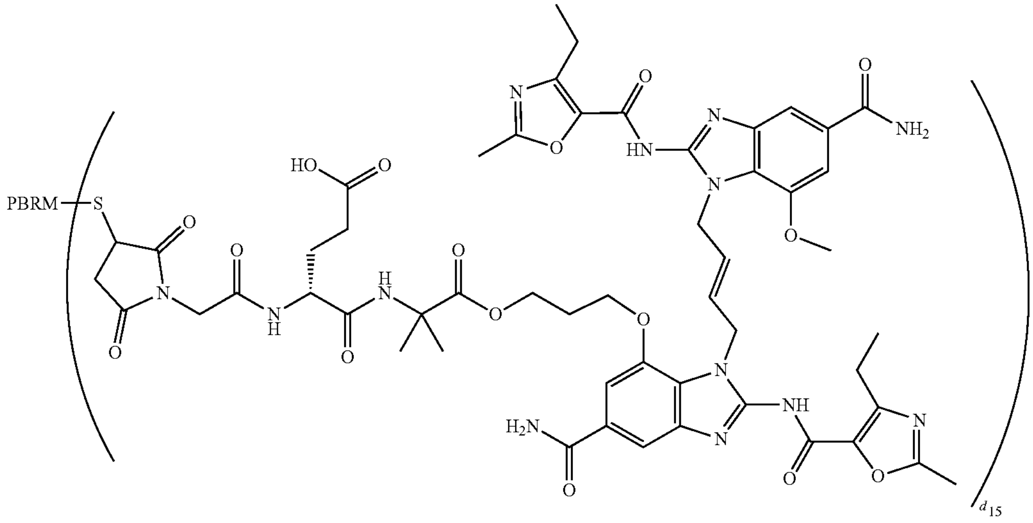 |

TABLE B1-continued
| Structure |
|---|
| 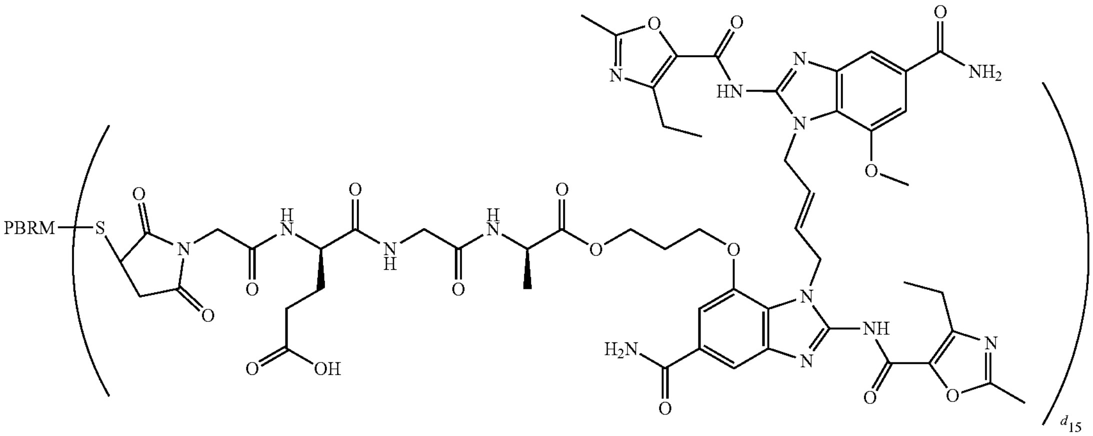 |
| 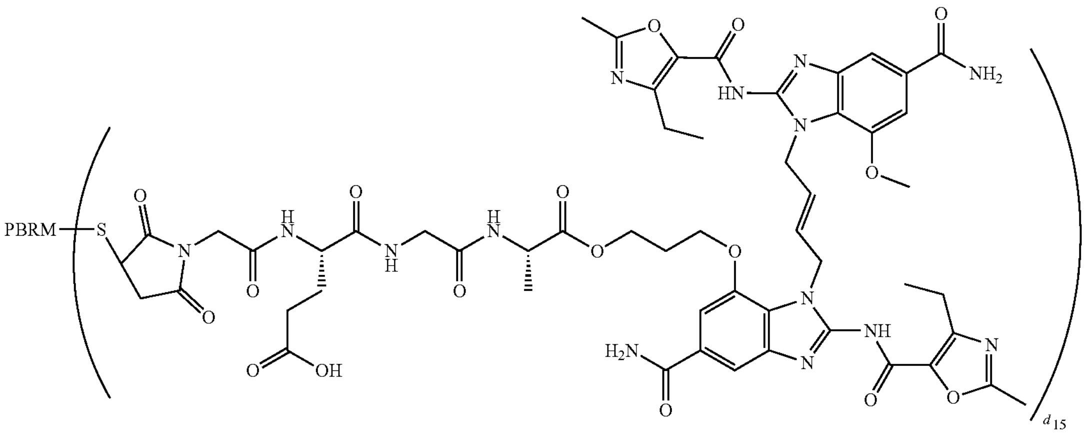 |
| 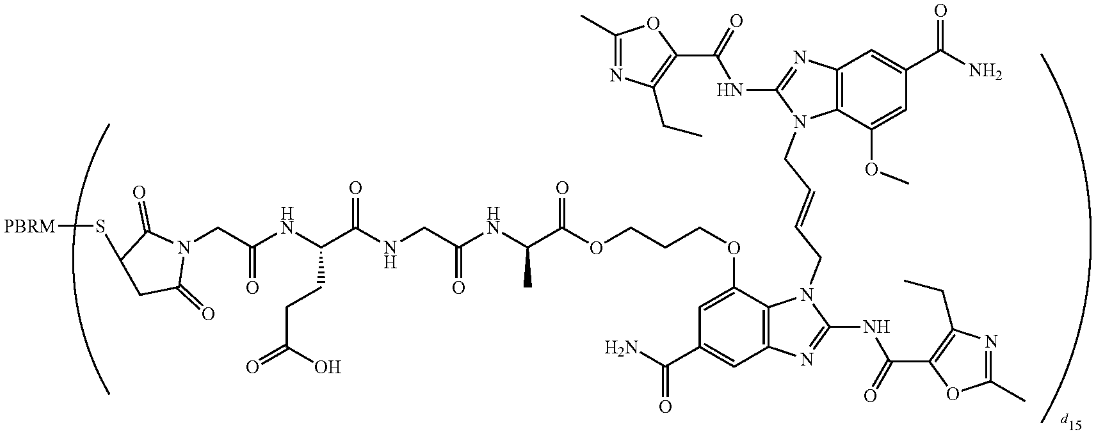 |

TABLE B1-continued
| Structure |
| --- |
| 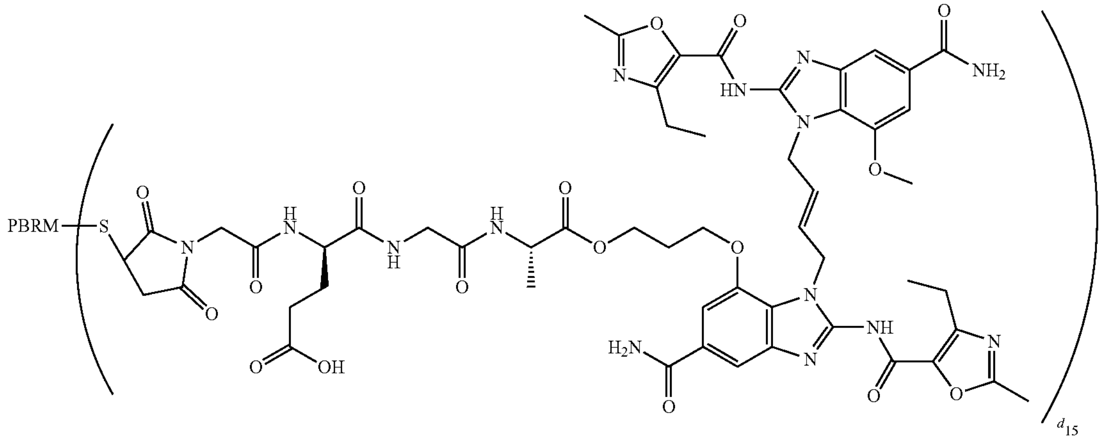 |
| 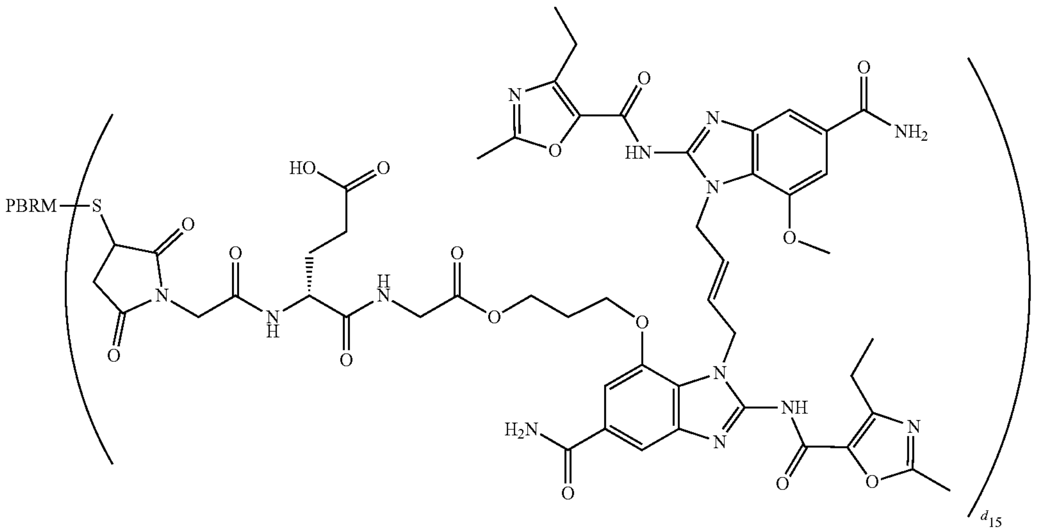 |
| 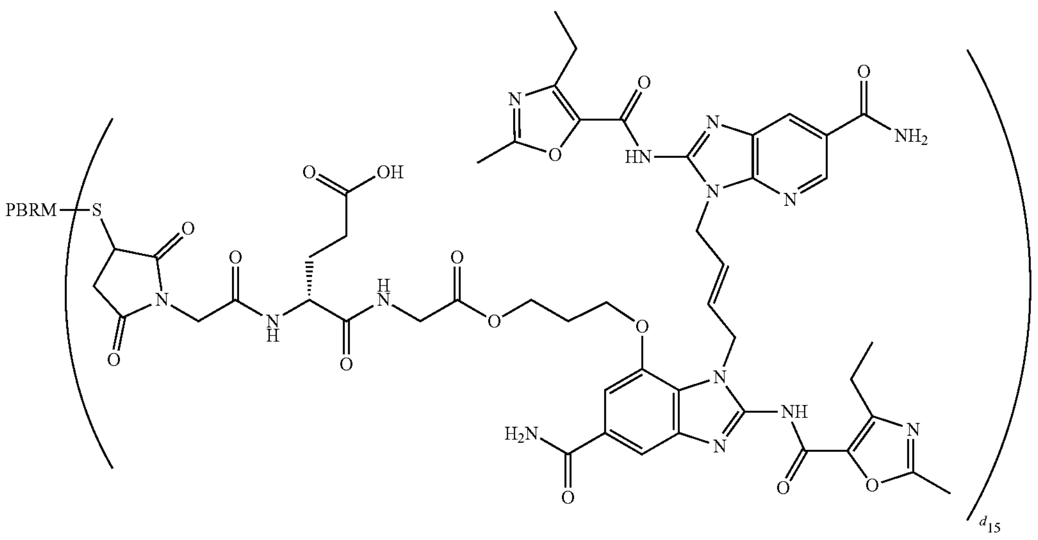 |

TABLE B1-continued
| Structure |
| --- |
| 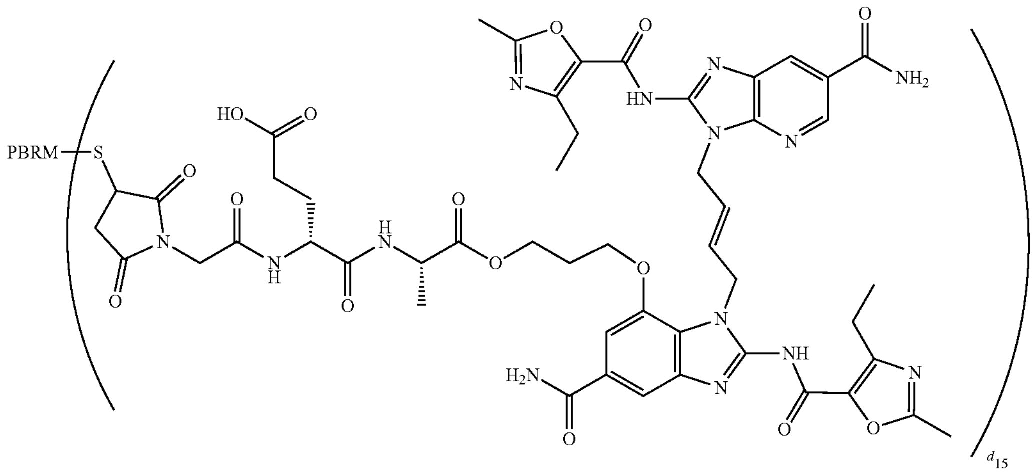 |
| 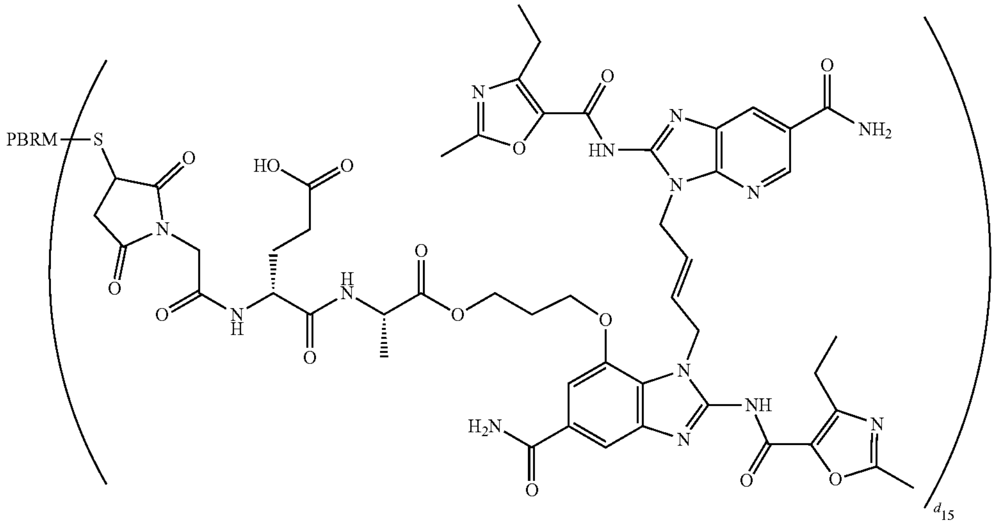 |
| 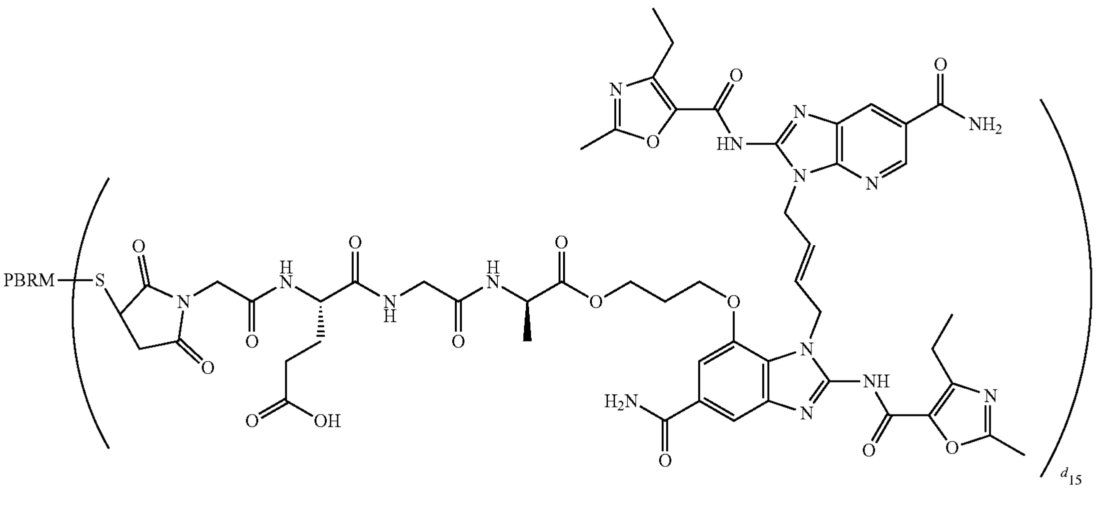 |

TABLE B1-continued
| Structure |
| --- |
| 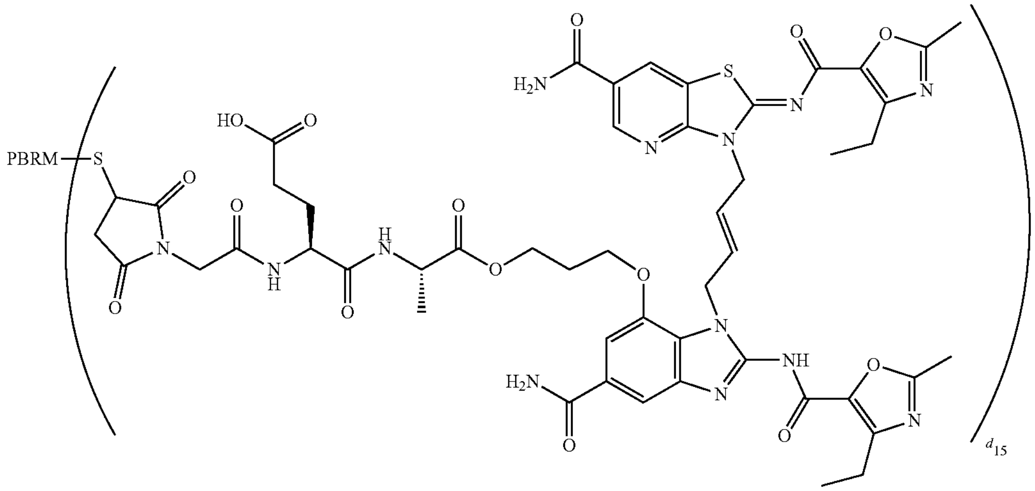 |
| 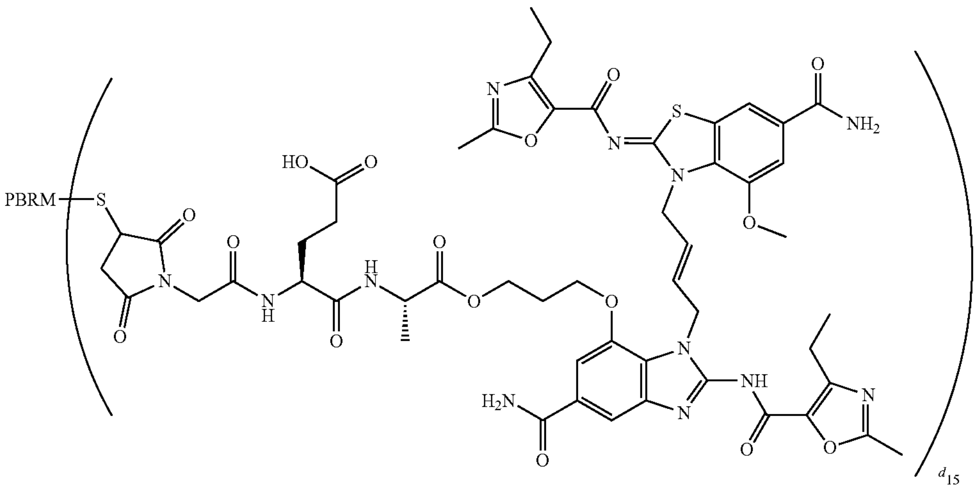 |
| 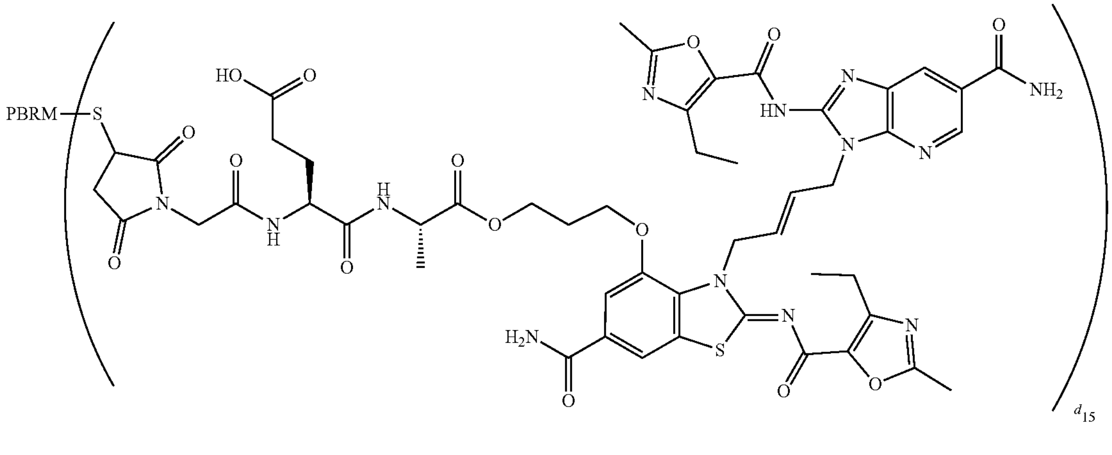 |

TABLE B1-continued
| Structure |
| --- |
| 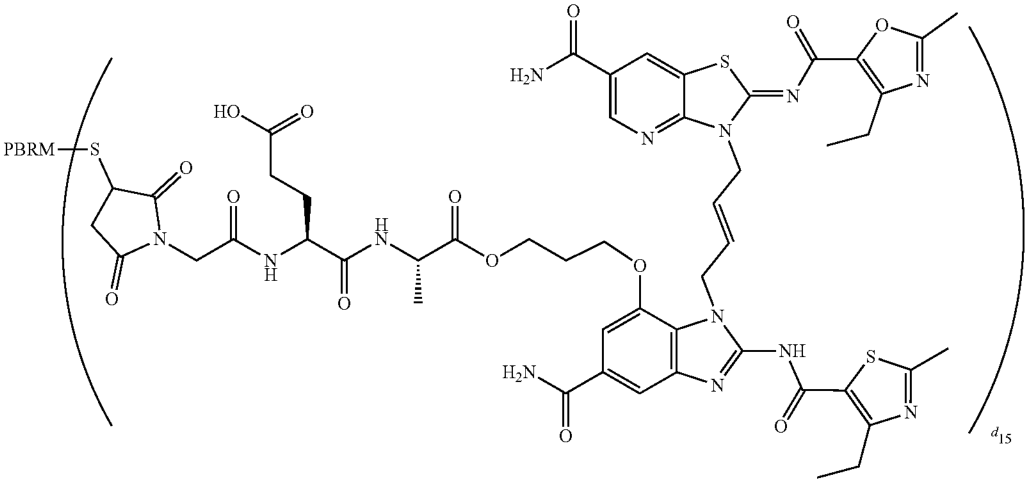 |
| 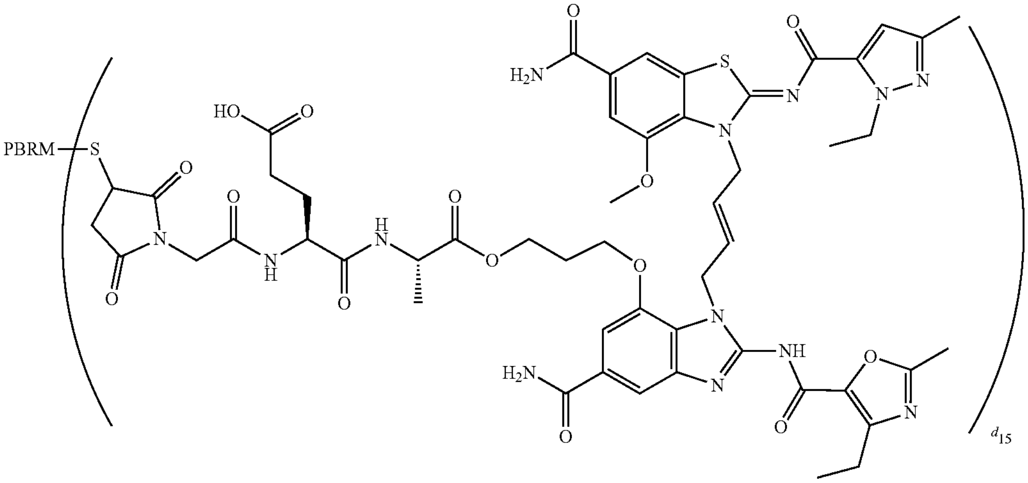 |
| 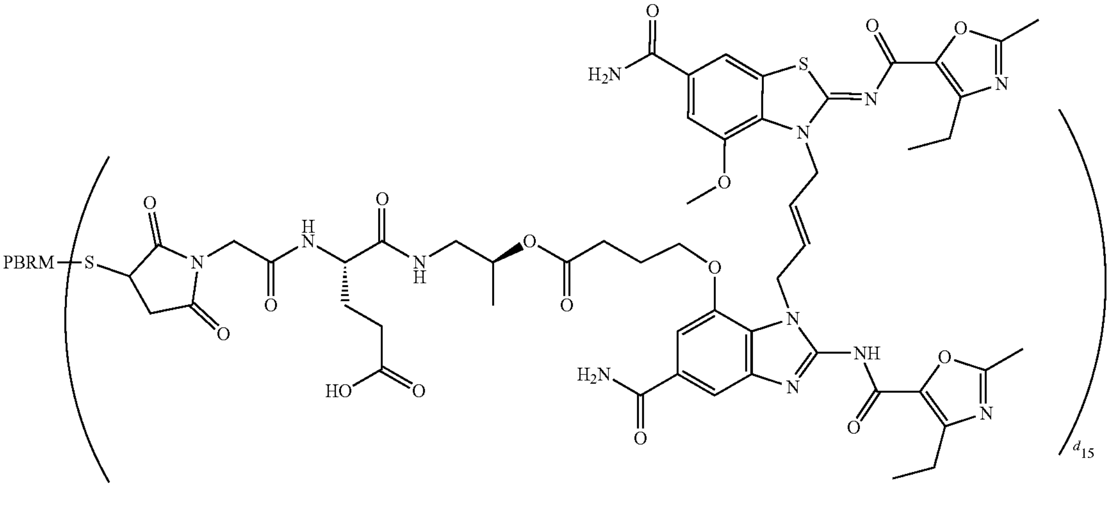 |

TABLE B1-continued
| Structure |
| --- |
| 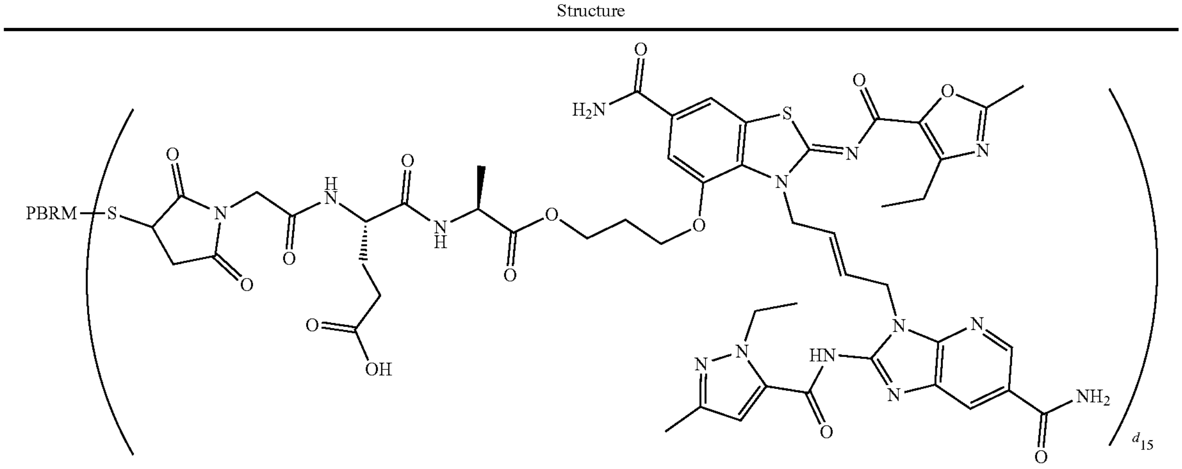 |
wherein $d_{15}$, $R^{14}$, $R^{15}$, $R^{16}$, $R^{17}$, $R^{18}$, $R^{19}$, $R^{C1}$, $R^{C2}$, $X_3$, $X_4$, $X_6$, $X_1$, $W_1$, $Y_1$, $Z_1$, $X_2$, $W_2$, $Y_2$, $Z_2$, are as defined herein.

TABLE B2
| Ex No. | Cmpd No. | Structure |
|---|---|---|
| 1 | 8-1 DAR 6.1 8-2 DAR 6.8 | 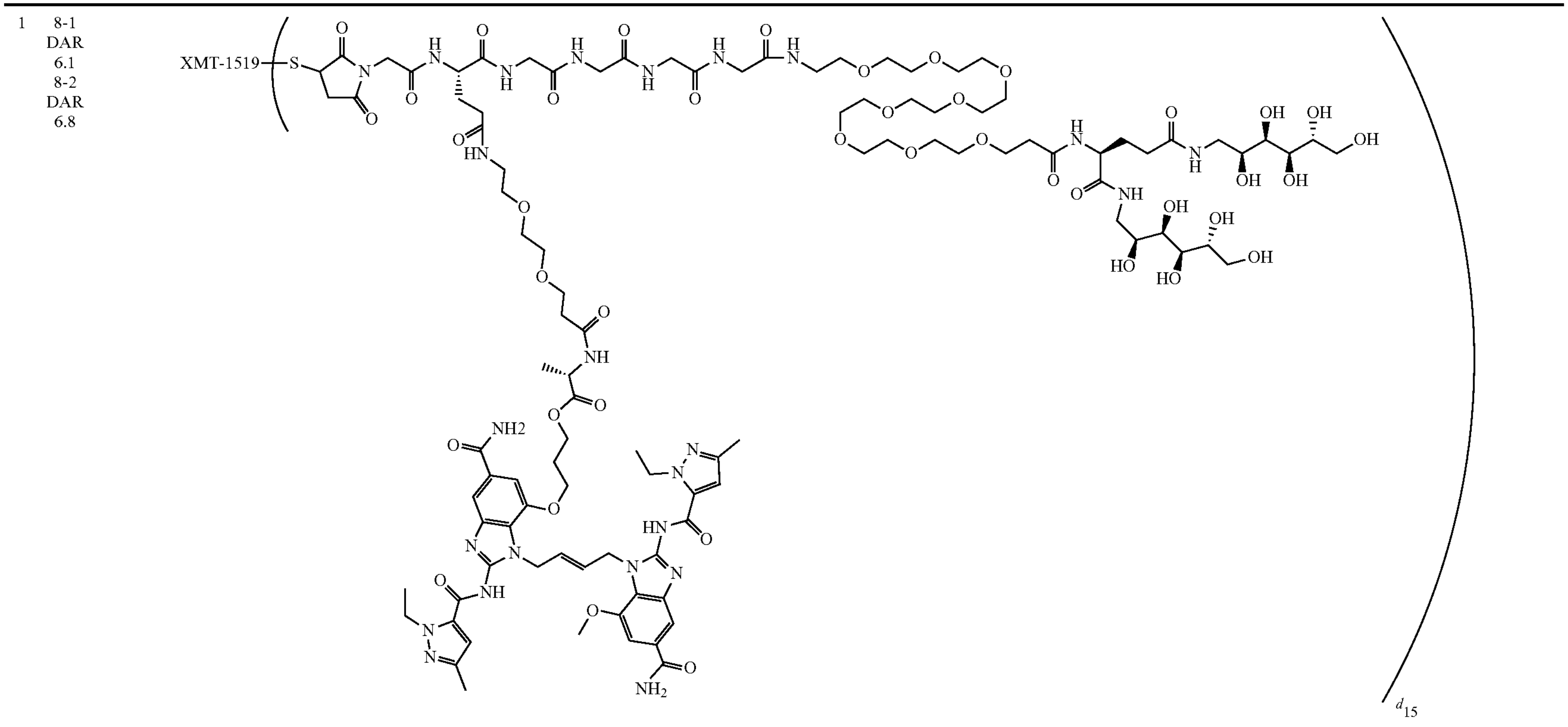 |

TABLE B2-continued
| Ex No. | Cmpd No. | Structure |
| --- | --- | --- |
| 1a | 8a-1 DAR 6.0 8a-2 DAR 7.0 8a-3 DAR 8.4 | 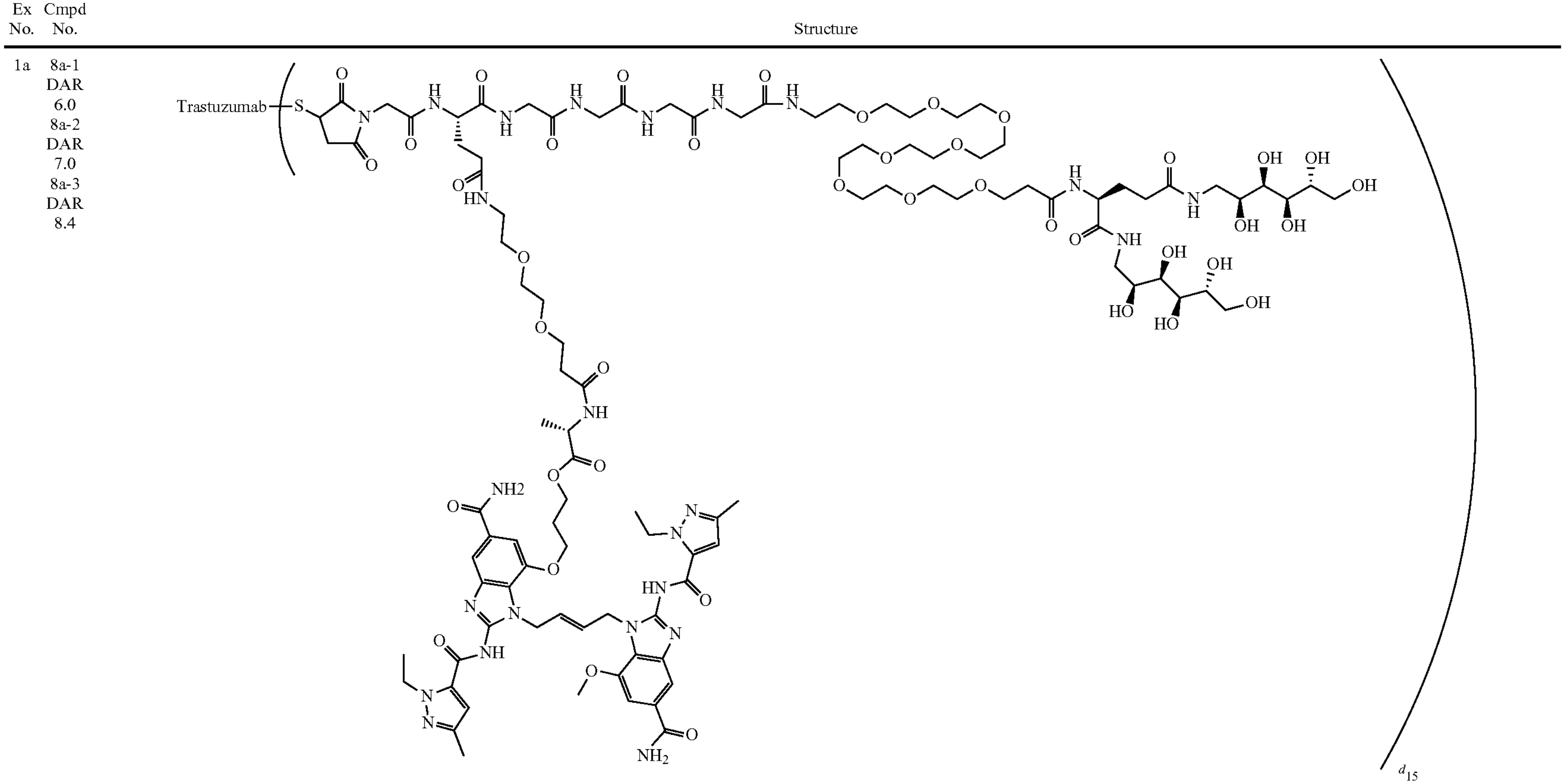 |

TABLE B2-continued
| Ex No. | Cmpd No. | Structure |
|---|---|---|
| 1b | 8b-1 DAR 5.7 8b-2 DAR 6.6 8b-3 DAR 6.4 | 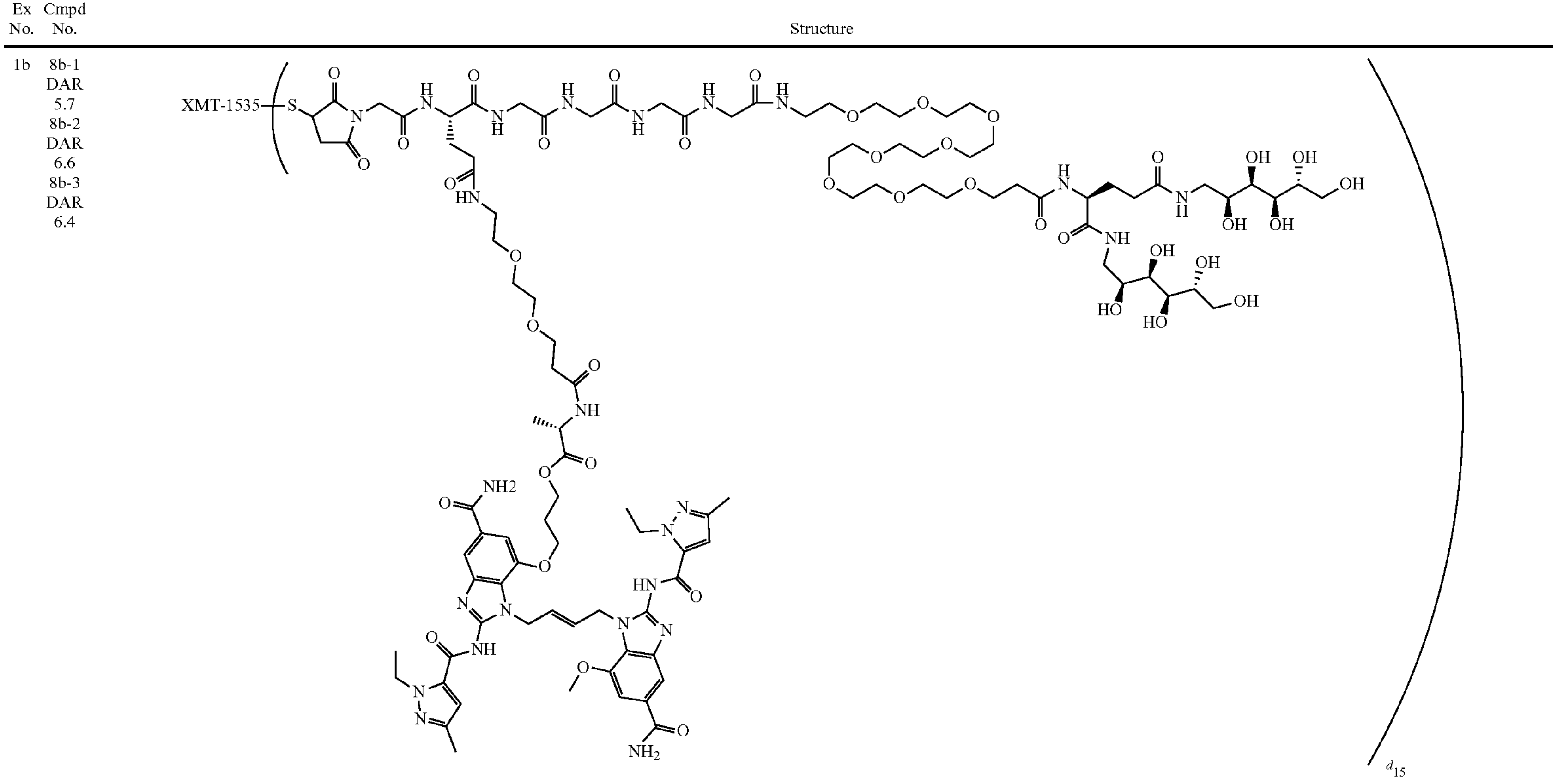 |

TABLE B2-continued
| Ex No. | Cmpd No. | Structure |
|---|---|---|
| 1c | 8c-1 DAR 7.5 8c-2 DAR 5.8 | 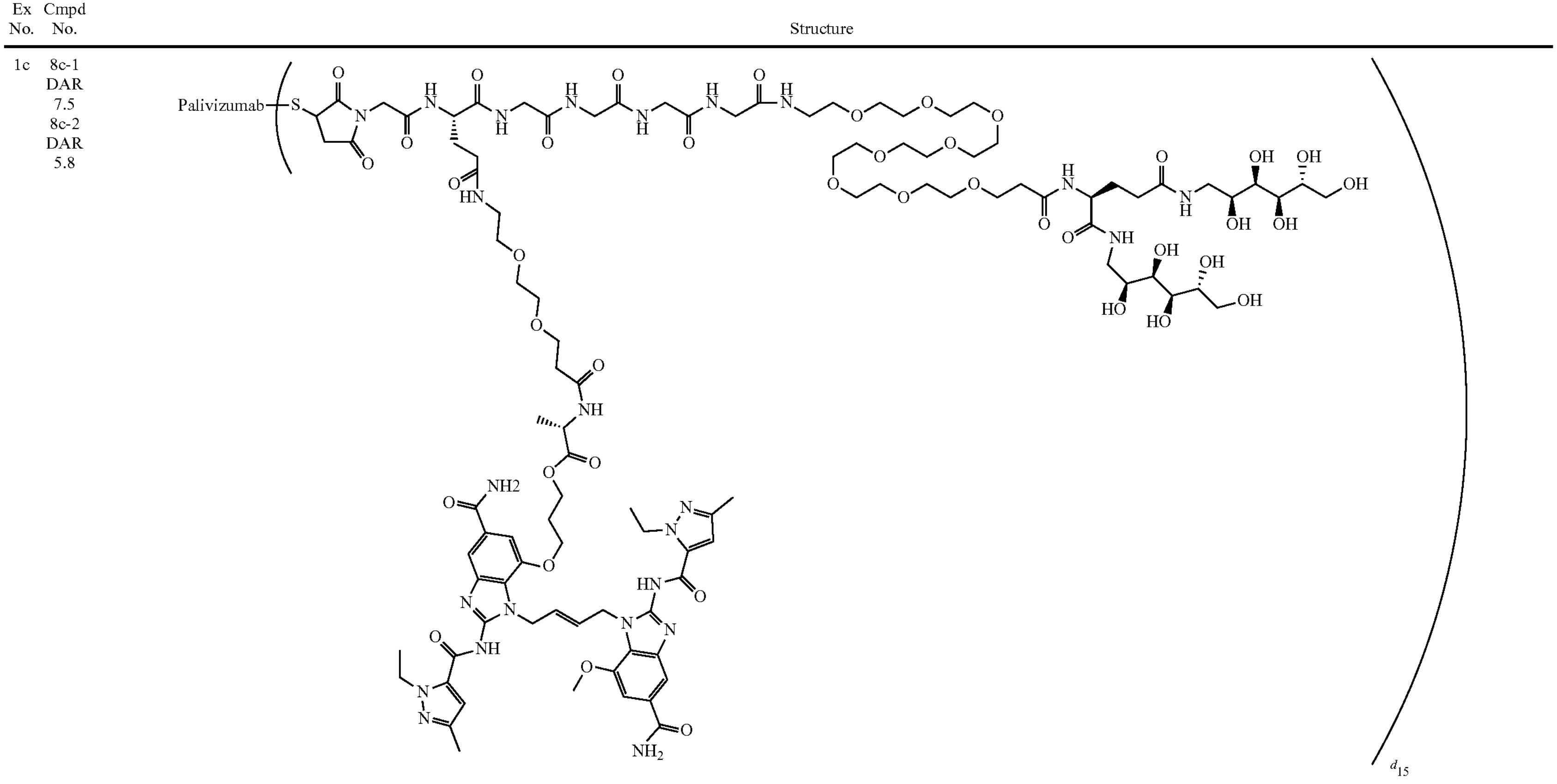 |

TABLE B2-continued
| Ex No. | Cmpd No. | Structure |
|---|---|---|
| 1d | 8d-1 DAR 6.8 8d-2 DAR 6.5 8d-3 DAR 6.0 | Palivizumab mIgG2a 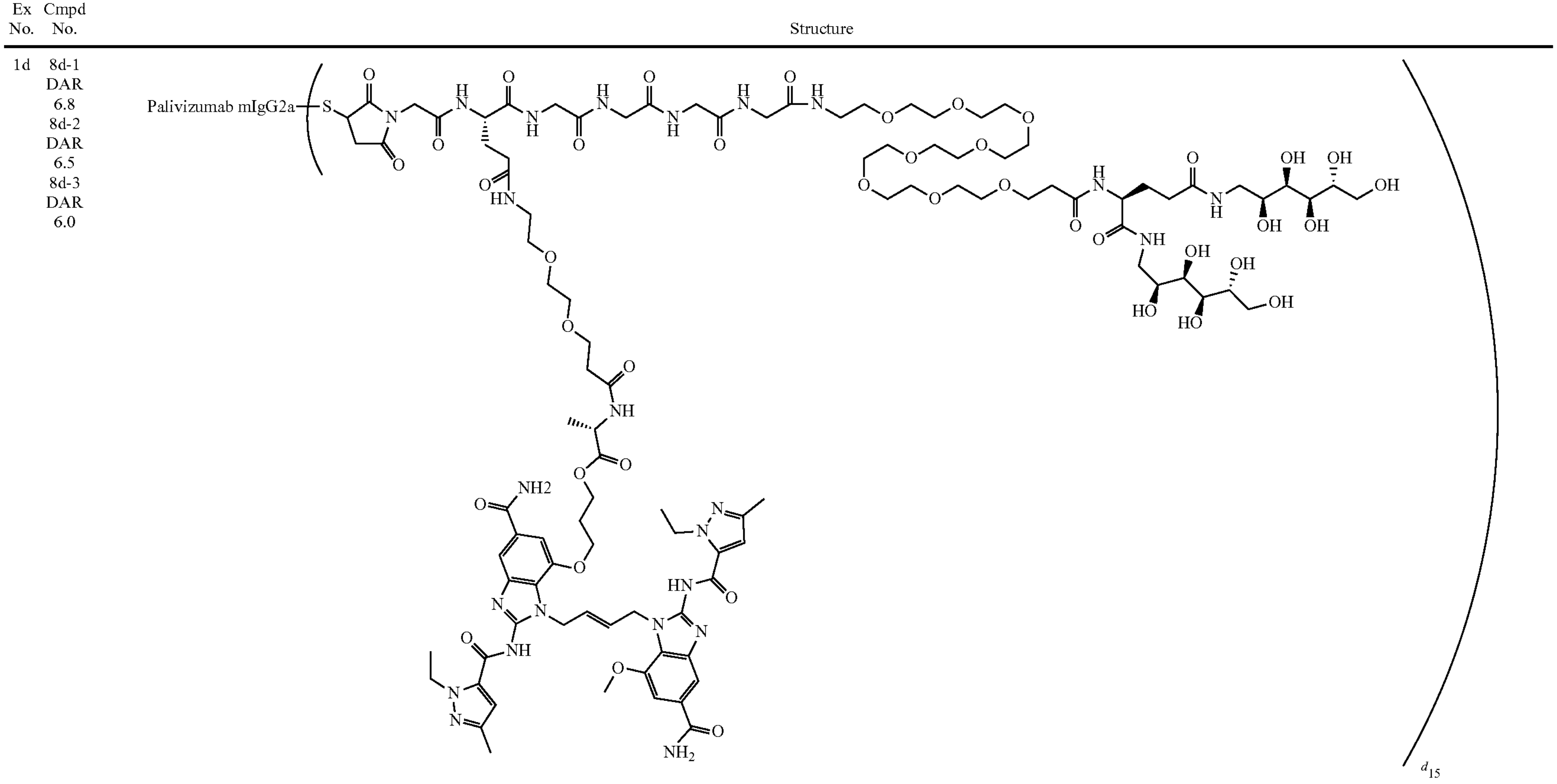 |

TABLE B2-continued
| Ex No. | Cmpd No. | Structure |
|---|---|---|
| 1e | 8e DAR 7.0 | 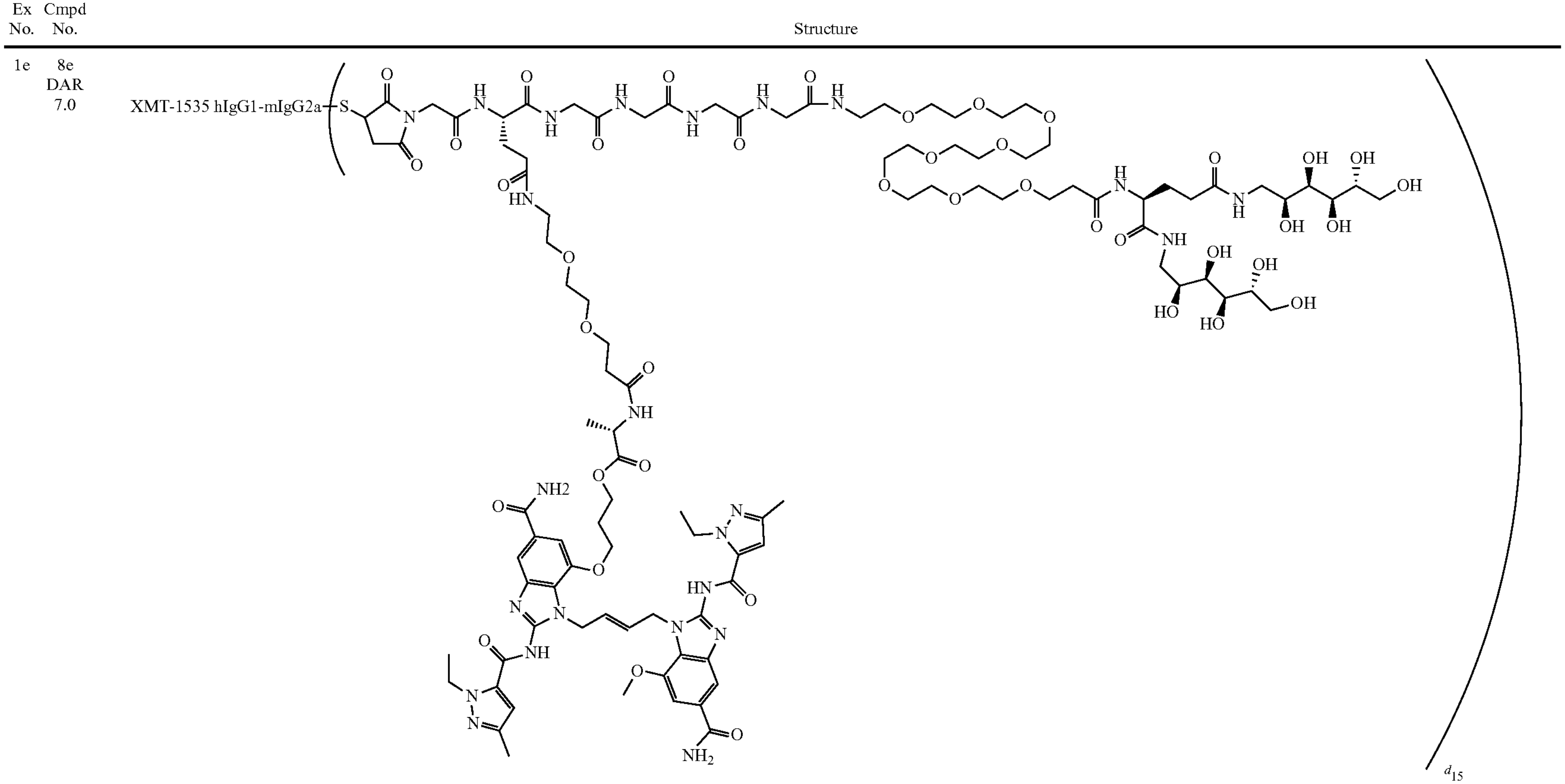 |

TABLE B2-continued
| Ex No. | Cmpd No. | Structure |
|---|---|---|
| 1f | 8f DAR 7.4 | 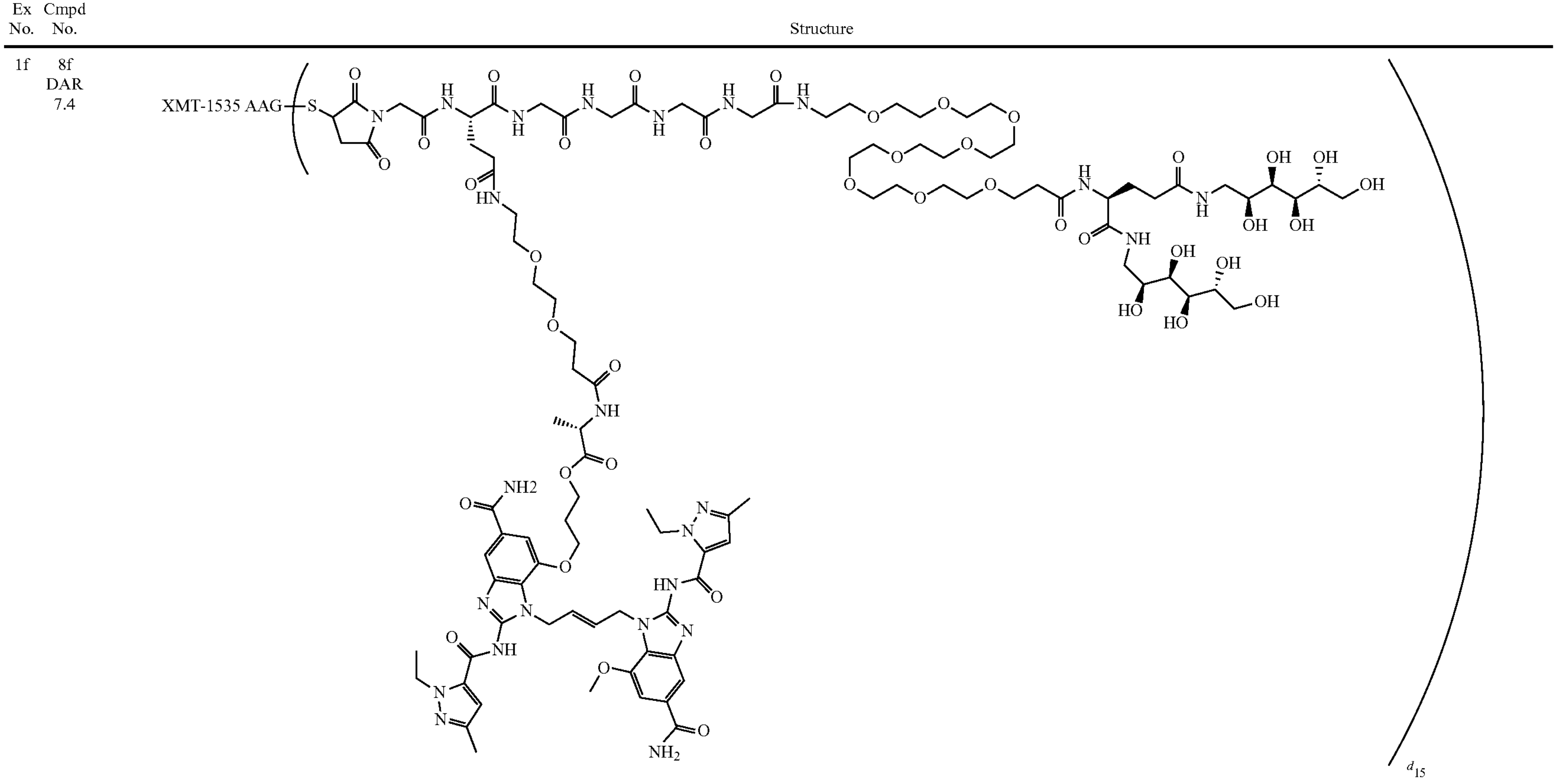 |

TABLE B2-continued
| Ex No. | Cmpd No. | Structure |
|---|---|---|
| 1g | 8g DAR 7.4 | 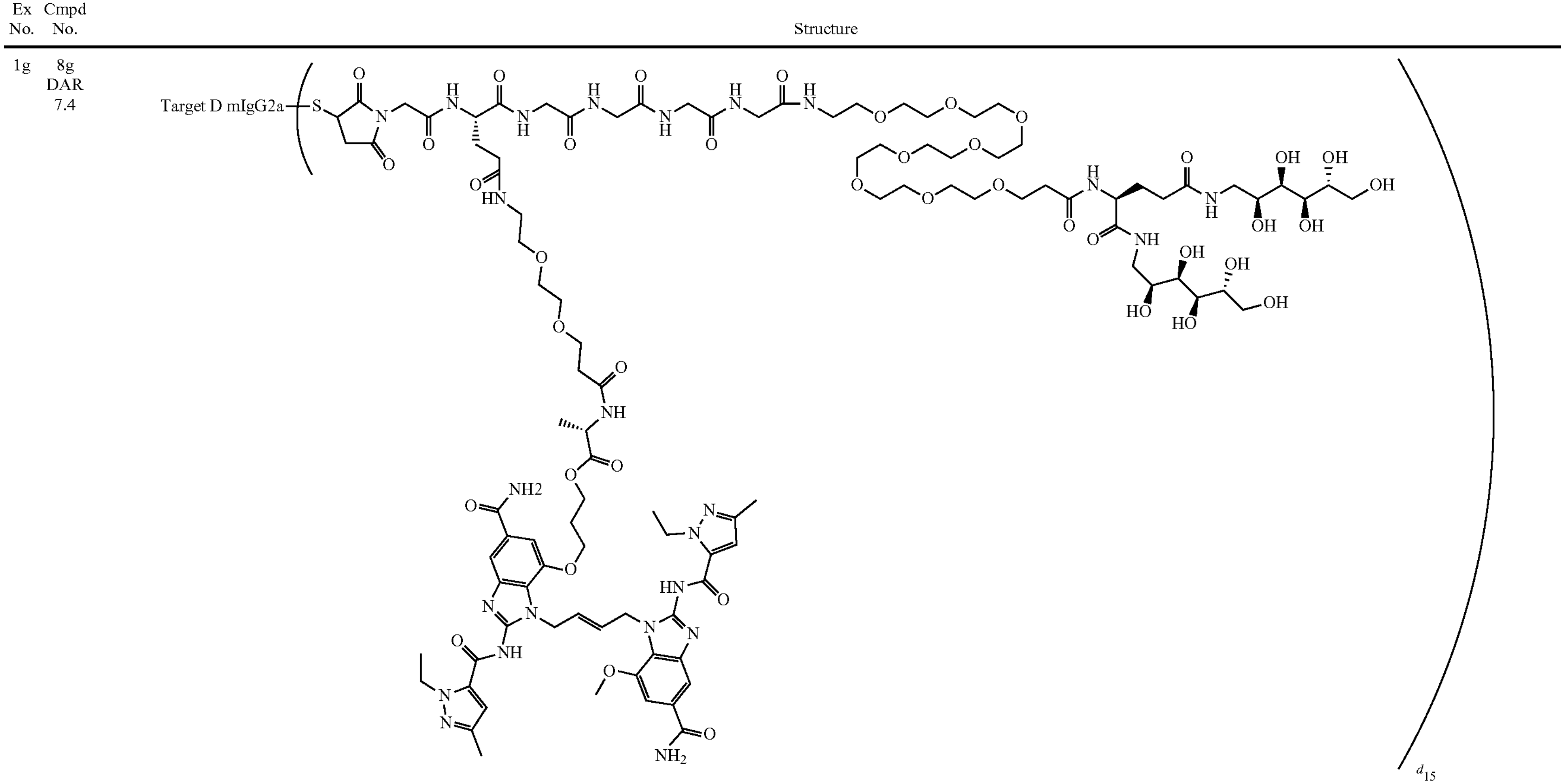 |

TABLE B2-continued
| Ex No. | Cmpd No. | Structure |
|---|---|---|
| 1h | 8h DAR 6.9 | 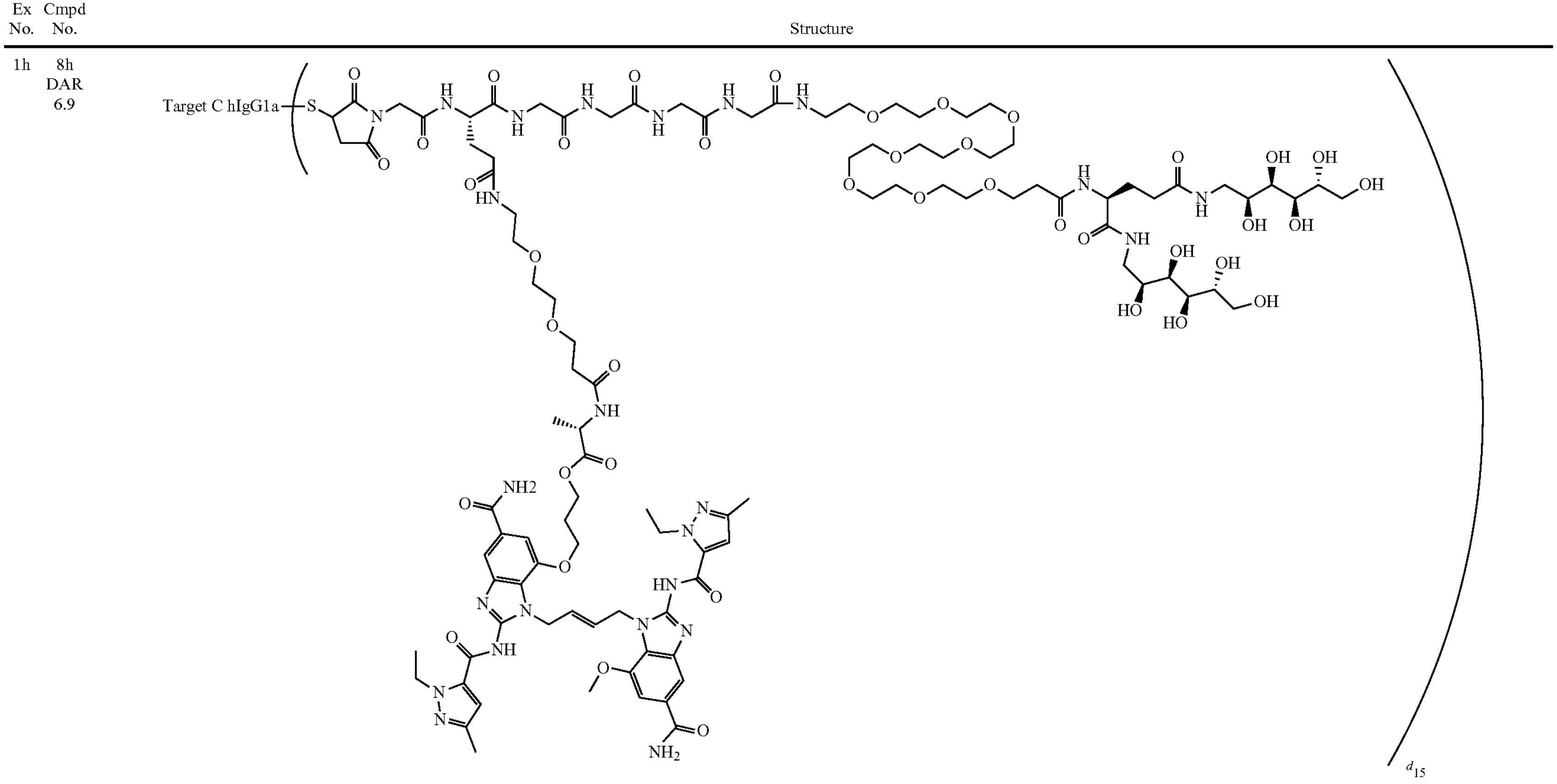 |

TABLE B2-continued
| Ex No. | Cmpd No. | Structure |
|---|---|---|
| 1i | 8i DAR 10.0 | 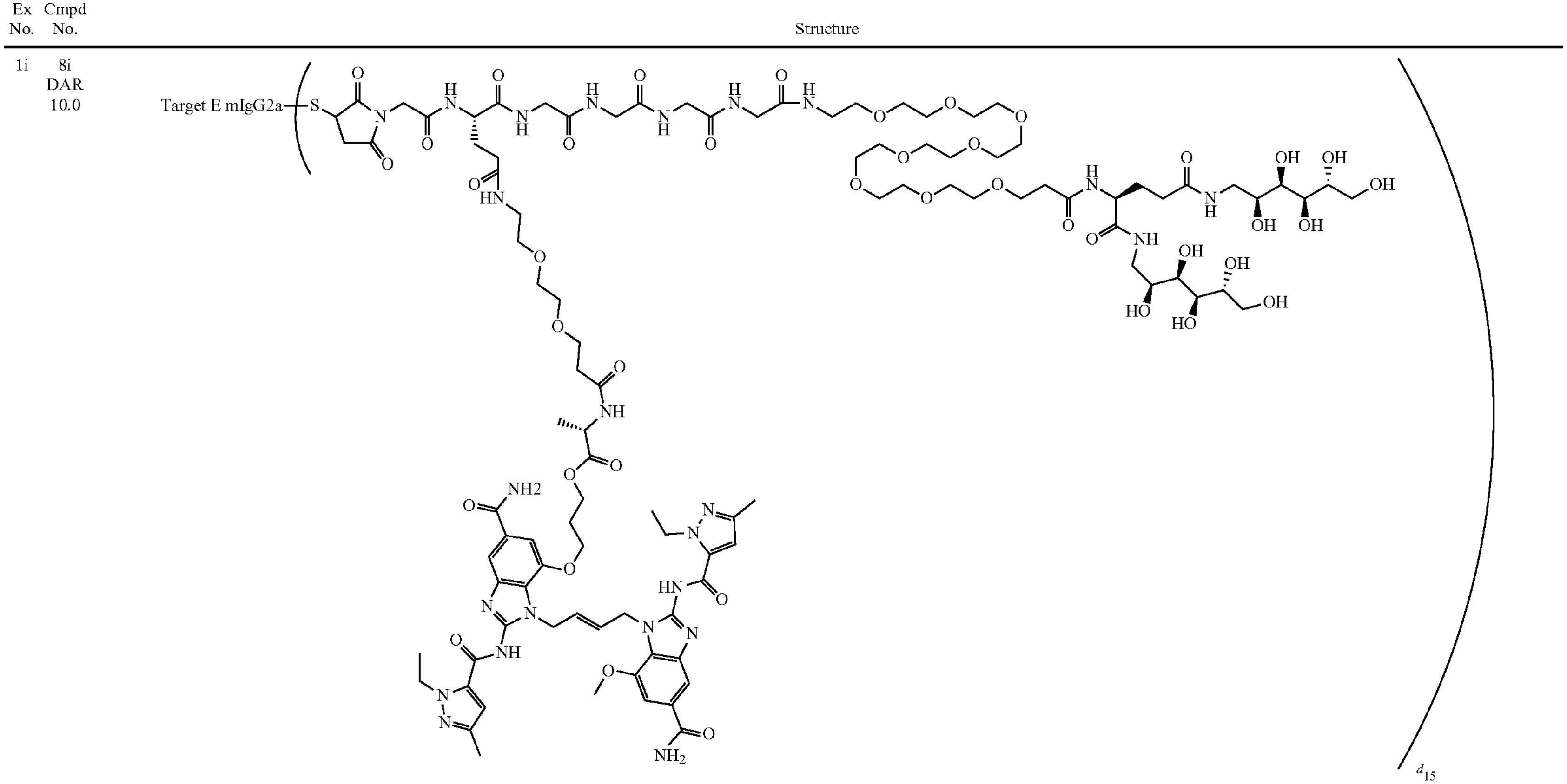 |

TABLE B2-continued
| Ex No. | Cmpd No. | Structure |
|---|---|---|
| 1j | 8j DAR 7.0 8j-1 DAR 4.2 | 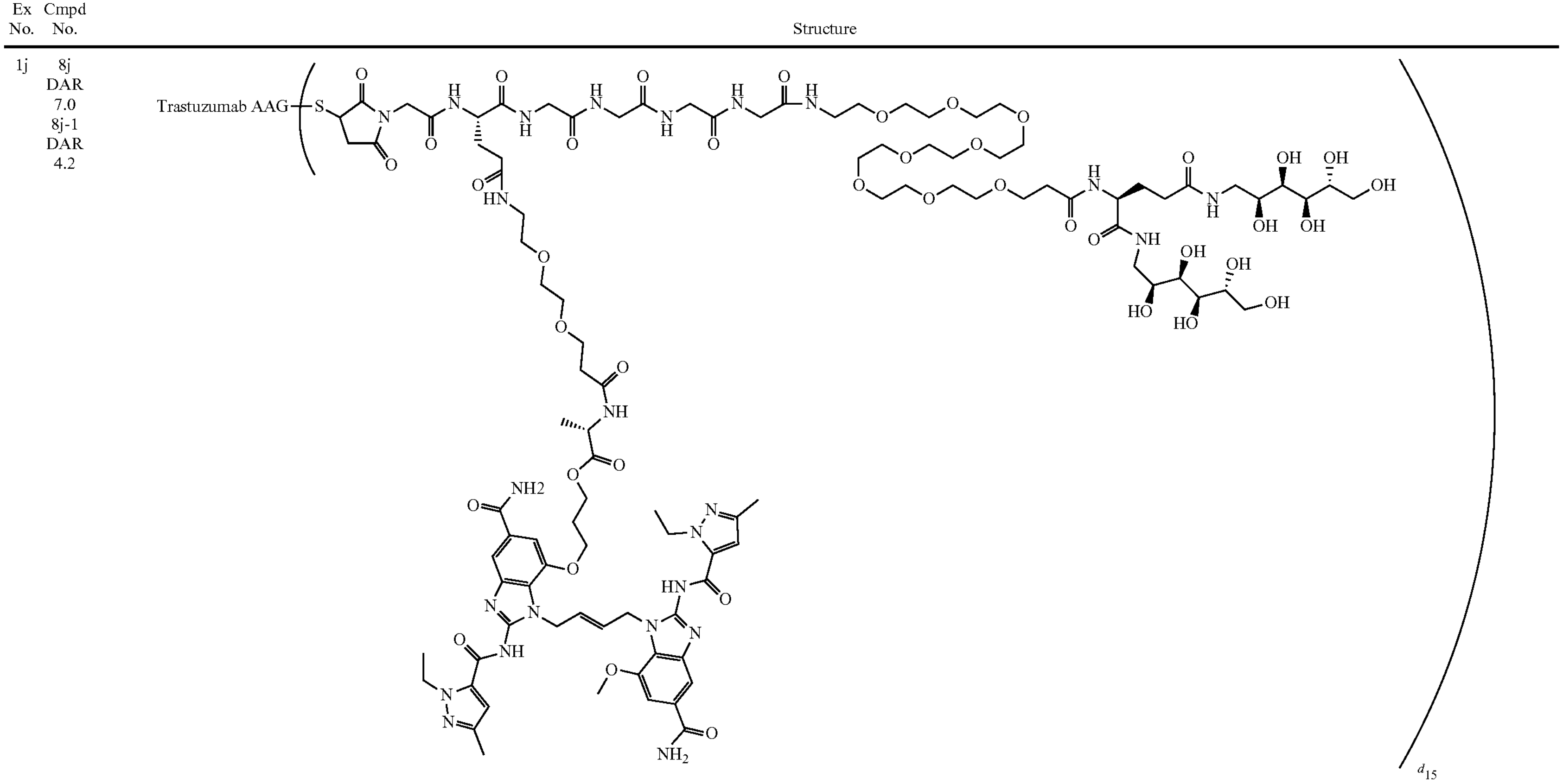 |

TABLE B2-continued
| Ex No. | Cmpd No. | Structure |
|---|---|---|
| 1k | 8k DAR 8.1 | 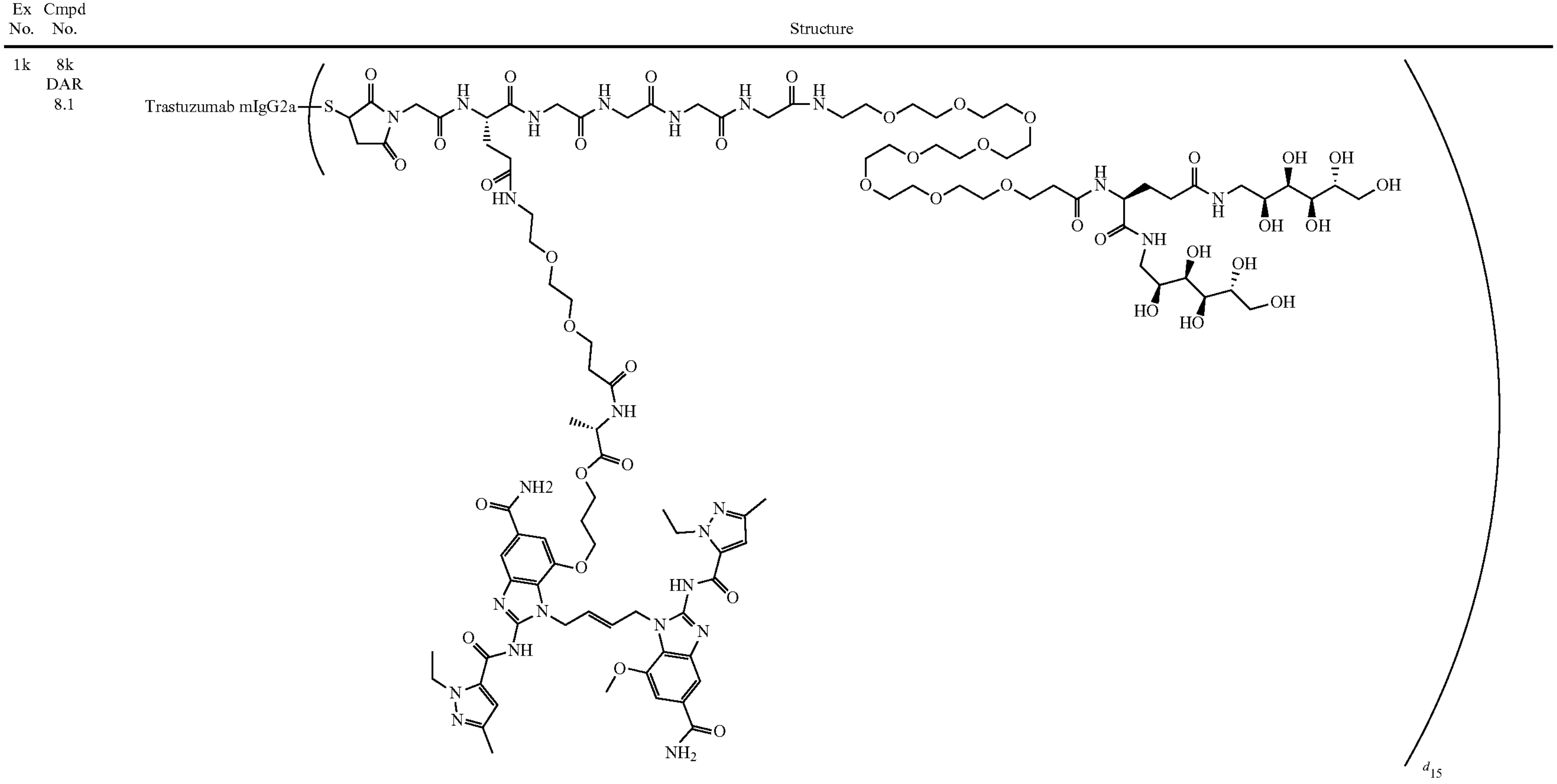 |

TABLE B2-continued
| Ex No. | Cmpd No. | Structure |
|---|---|---|
| 11 | 81<br>DAR<br>4.7 | 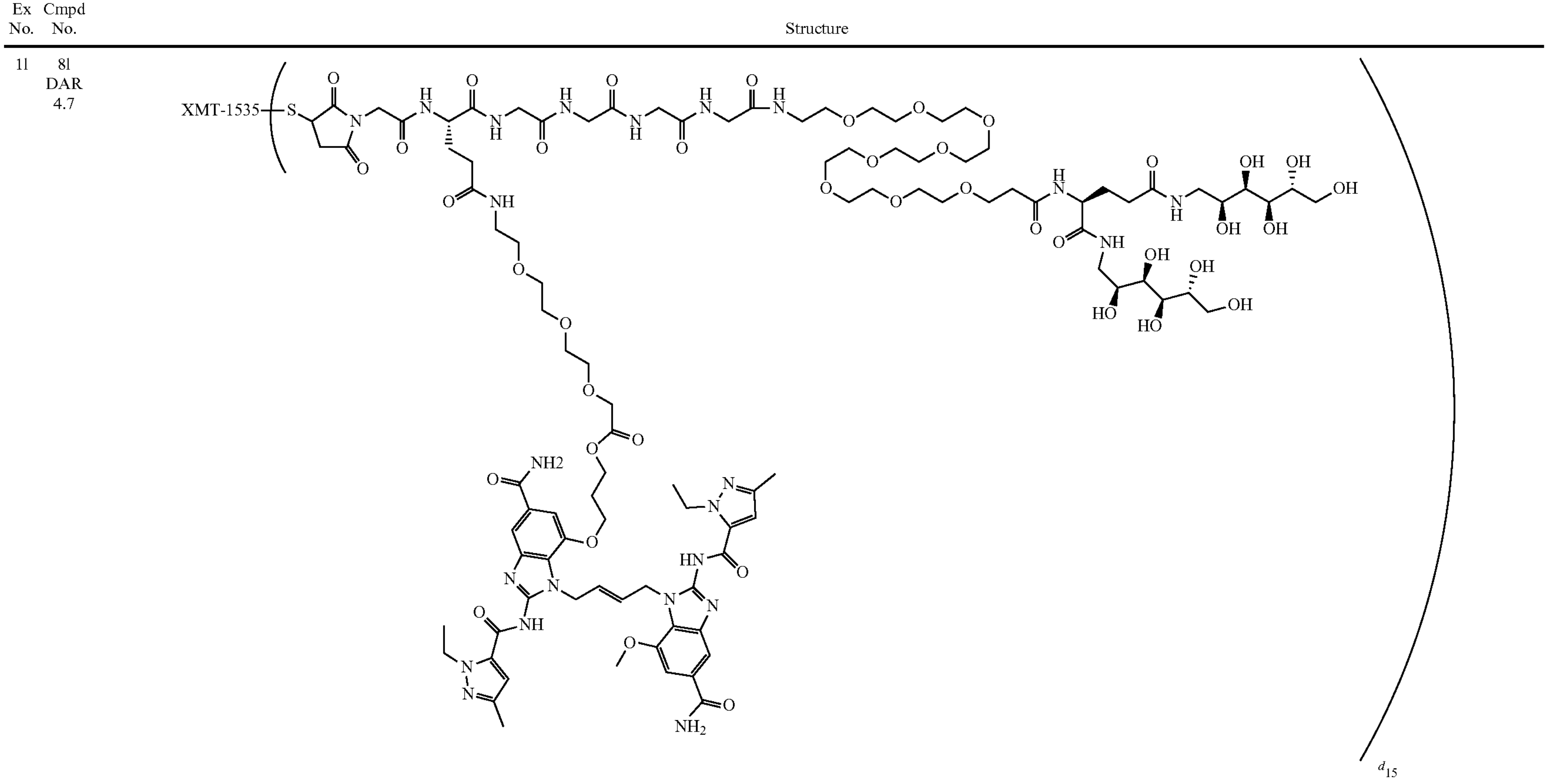 |

TABLE B2-continued
| Ex No. | Cmpd No. | Structure |
|---|---|---|
| 1m | 8m DAR 4.5 | 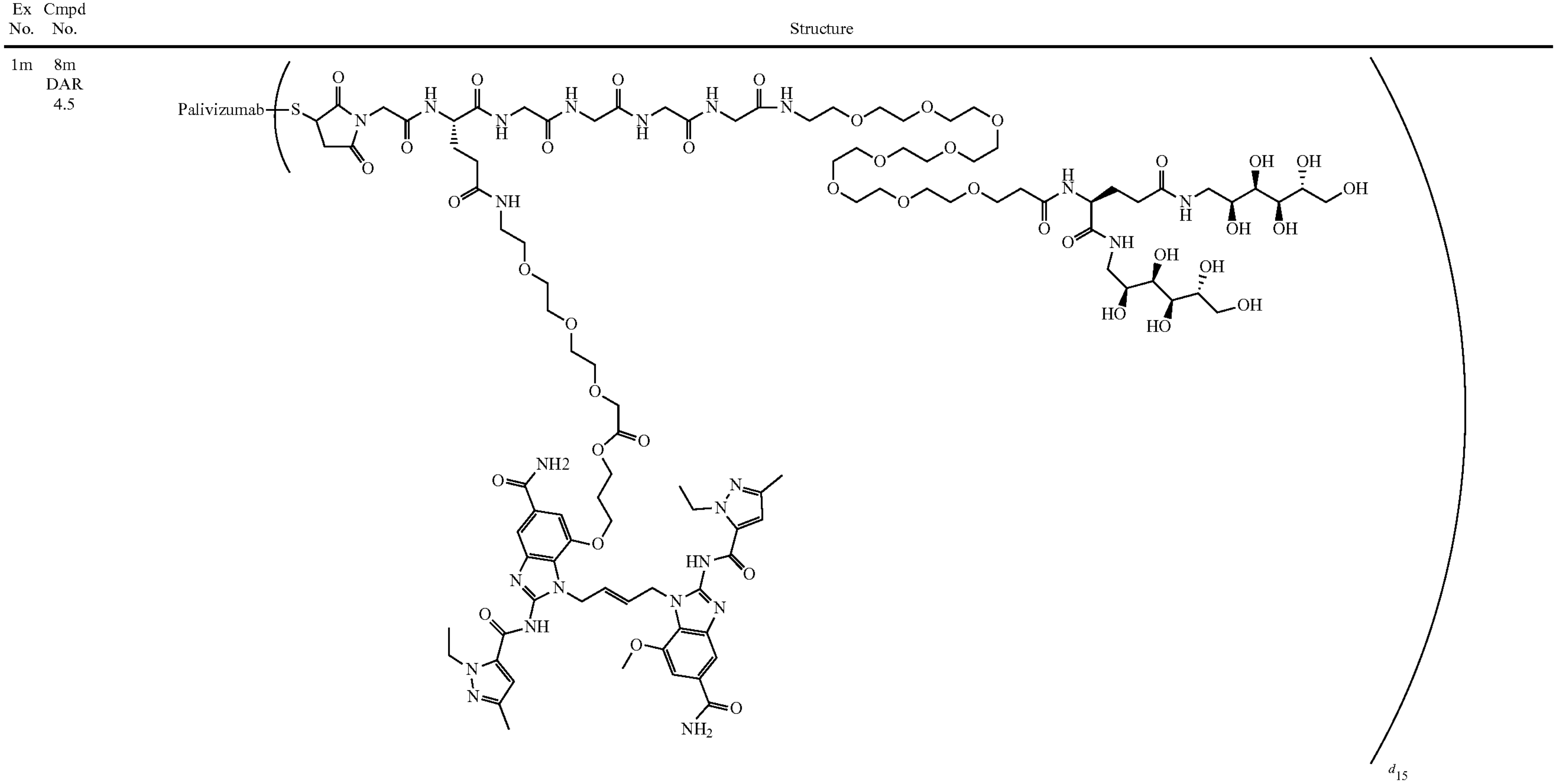 |

TABLE B2-continued
| Ex No. | Cmpd No. | Structure |
| --- | --- | --- |
| 2 | 16 DAR 5.3 | 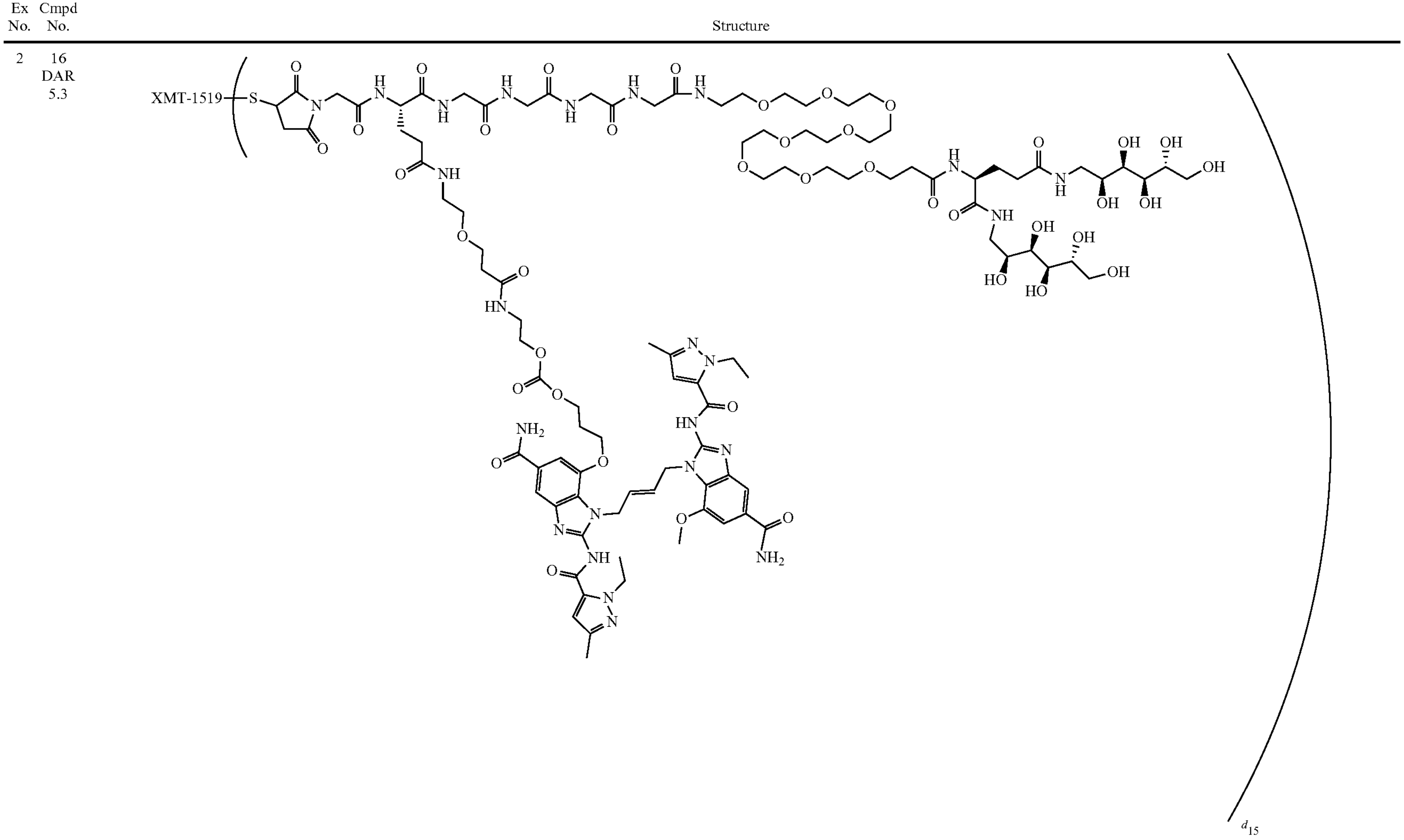 |

TABLE B2-continued
| Ex No. | Cmpd No. | Structure |
|---|---|---|
| 3 | 20-1 DAR 6.0 20-2 DAR 6.1 | 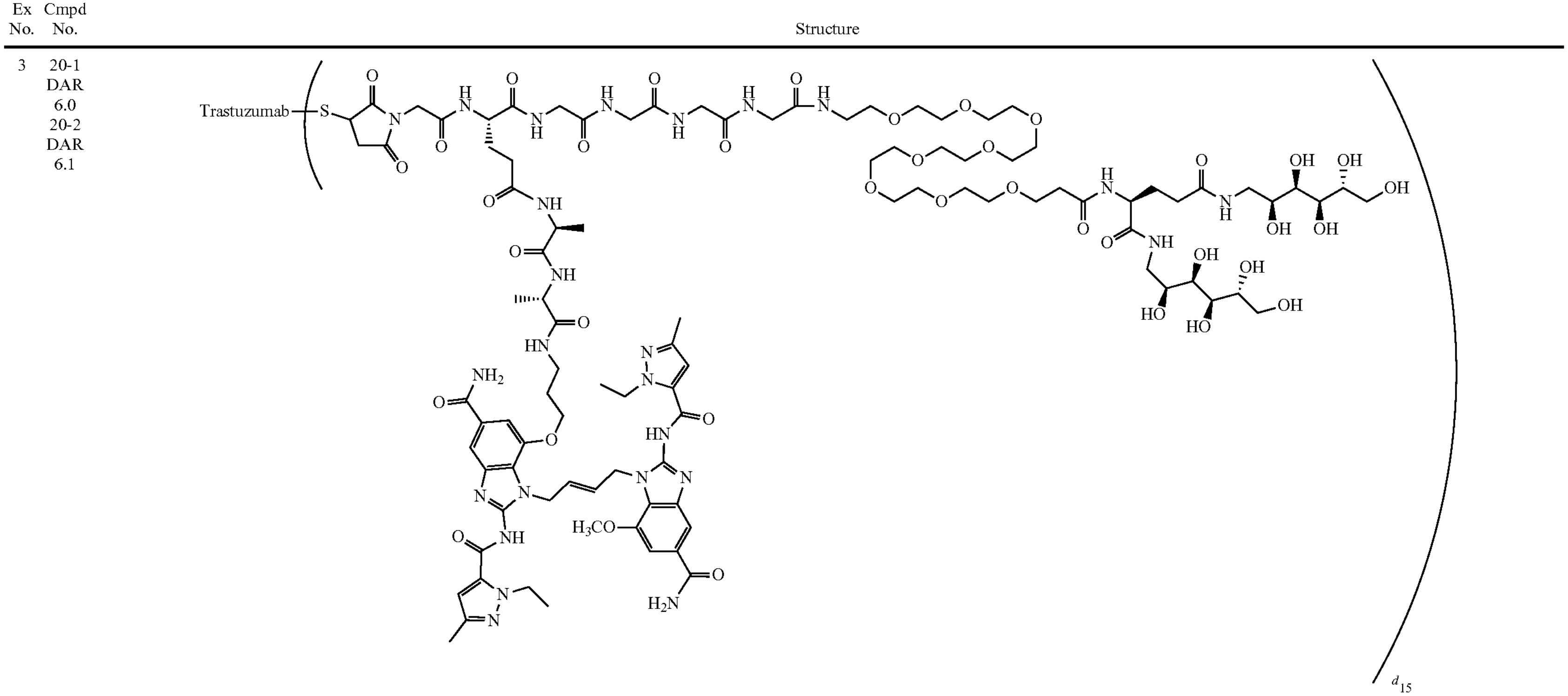 |

TABLE B2-continued
| Ex No. | Cmpd No. | Structure |
|---|---|---|
| 3a | 20a DAR 5.5 | 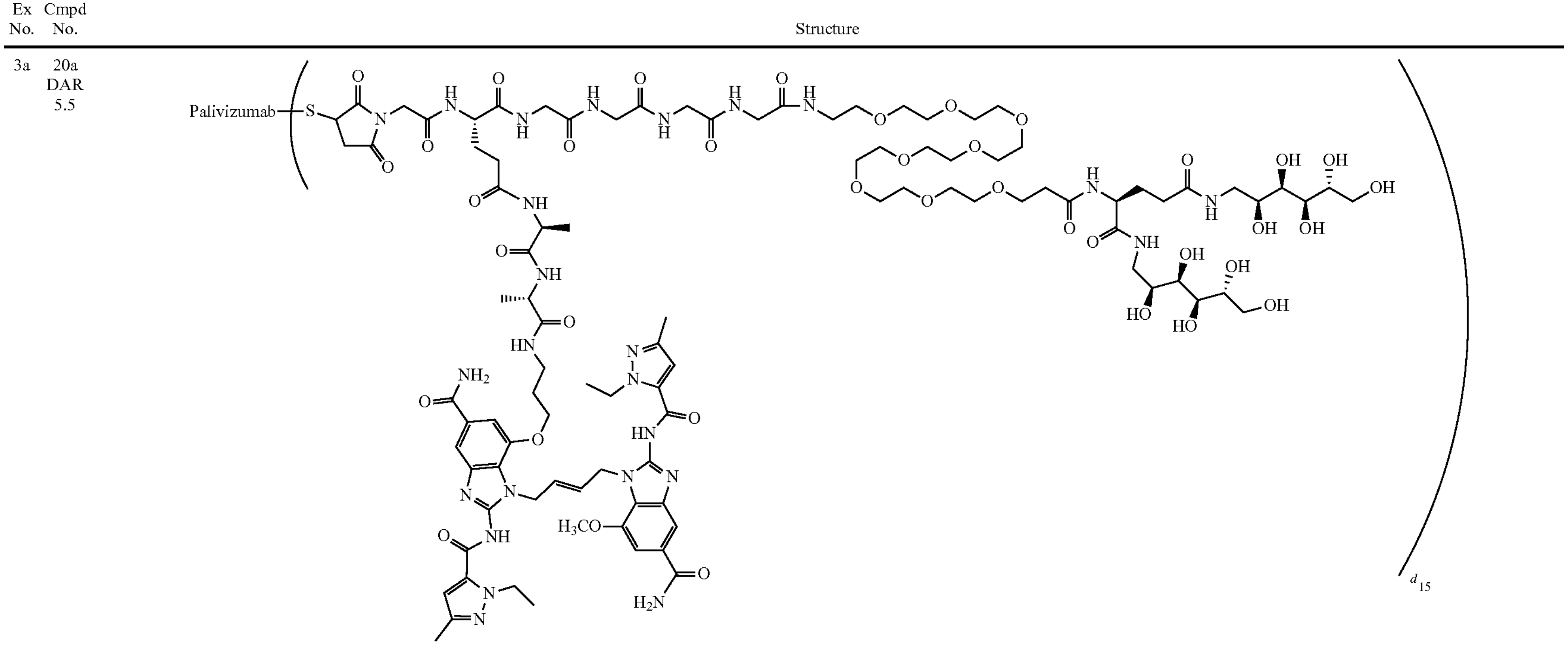 |

TABLE B2-continued
| Ex No. | Cmpd No. | Structure |
|---|---|---|
| 4 | 25 DAR 6.6 | 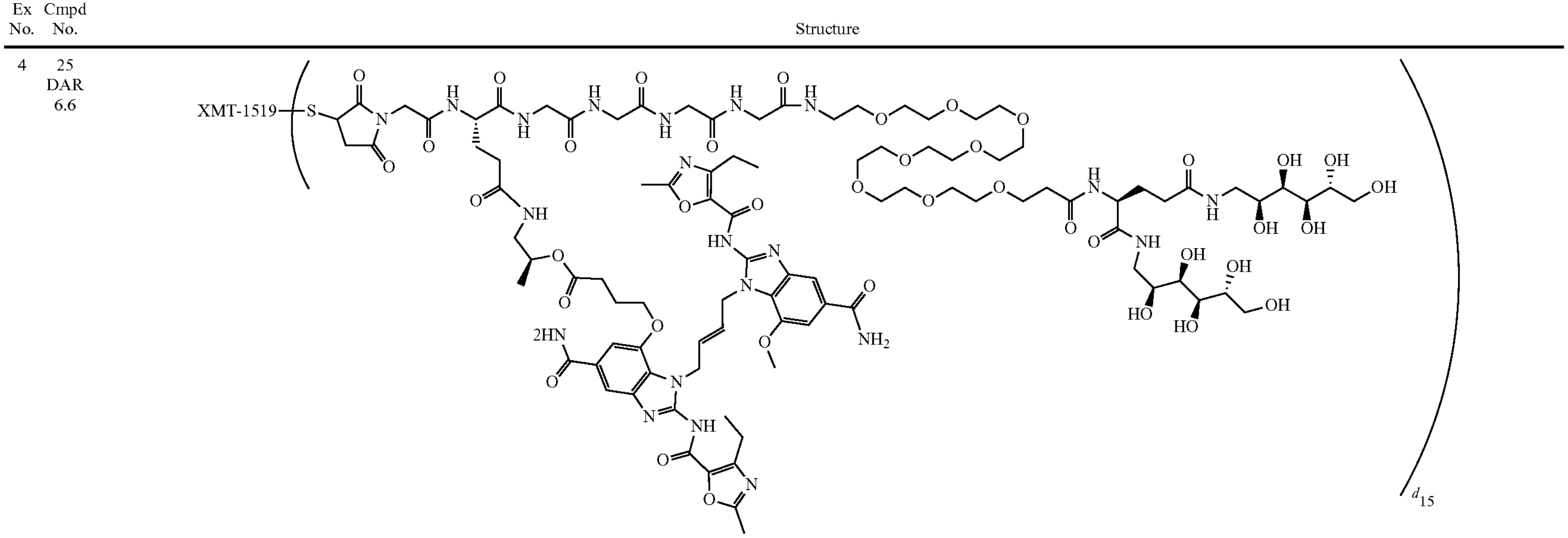 |

TABLE B2-continued
| Ex No. | Cmpd No. | Structure |
|---|---|---|
| 5 | 28<br>DAR<br>6.0 | 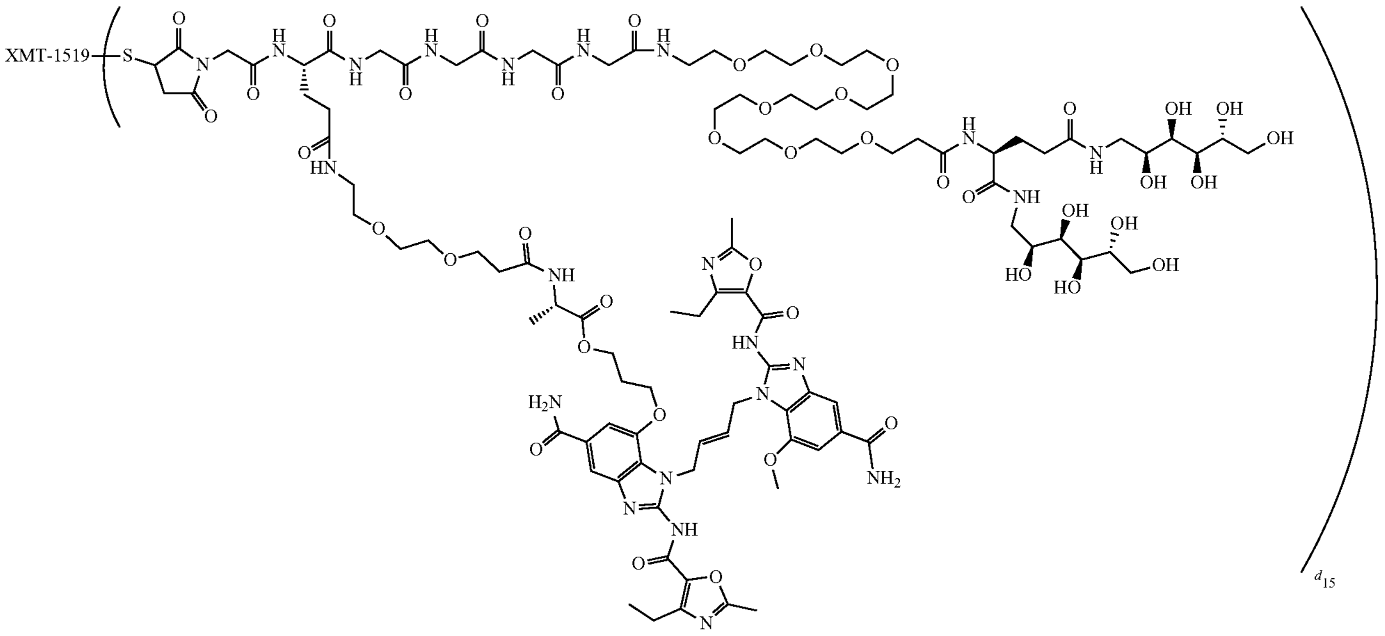 |

TABLE B2-continued
| Ex No. | Cmpd No. | Structure |
|---|---|---|
| 6 | 29 DAR 5.5 | 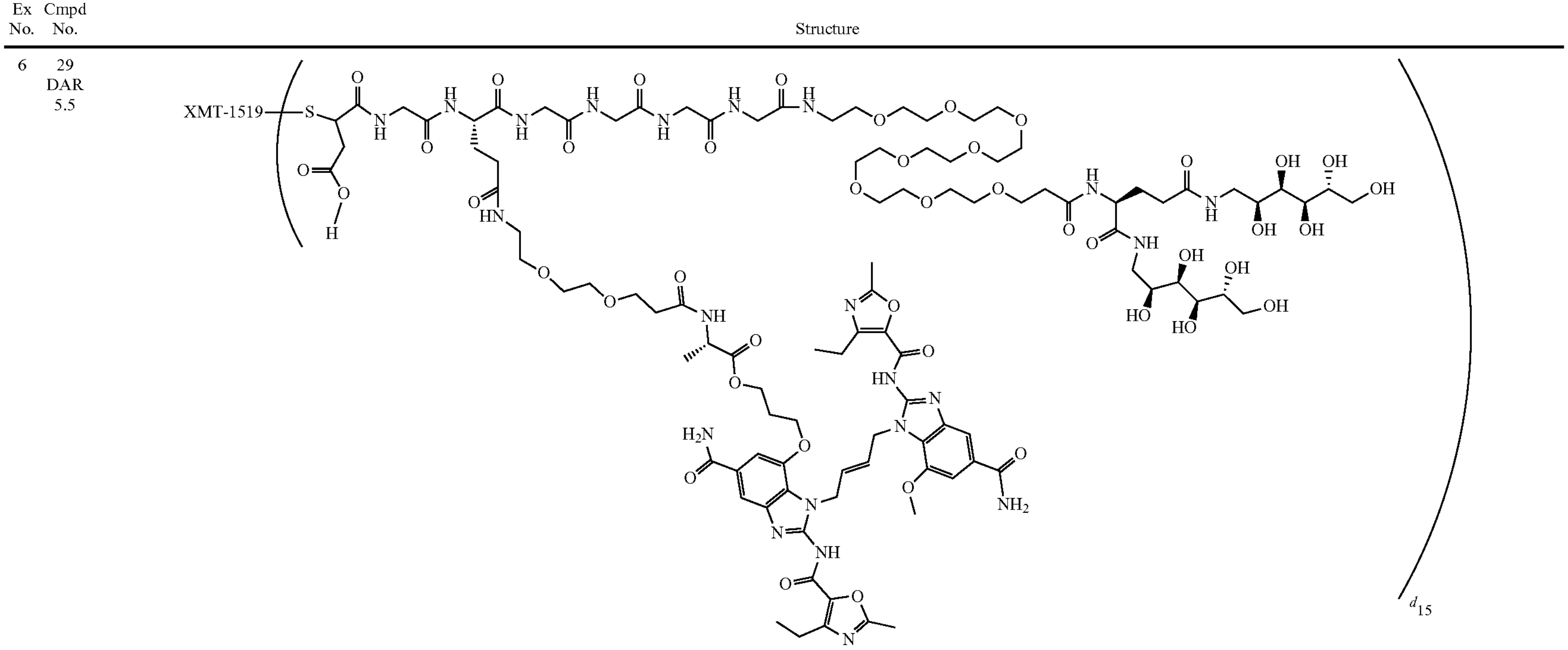 |

TABLE B2-continued
| Ex No. | Cmpd No. | Structure |
| --- | --- | --- |
| 7 | 32-1 DAR 6.5 32-2 DAR 6.4 32-3 DAR 6.7 32-4 DAR 8.6 | 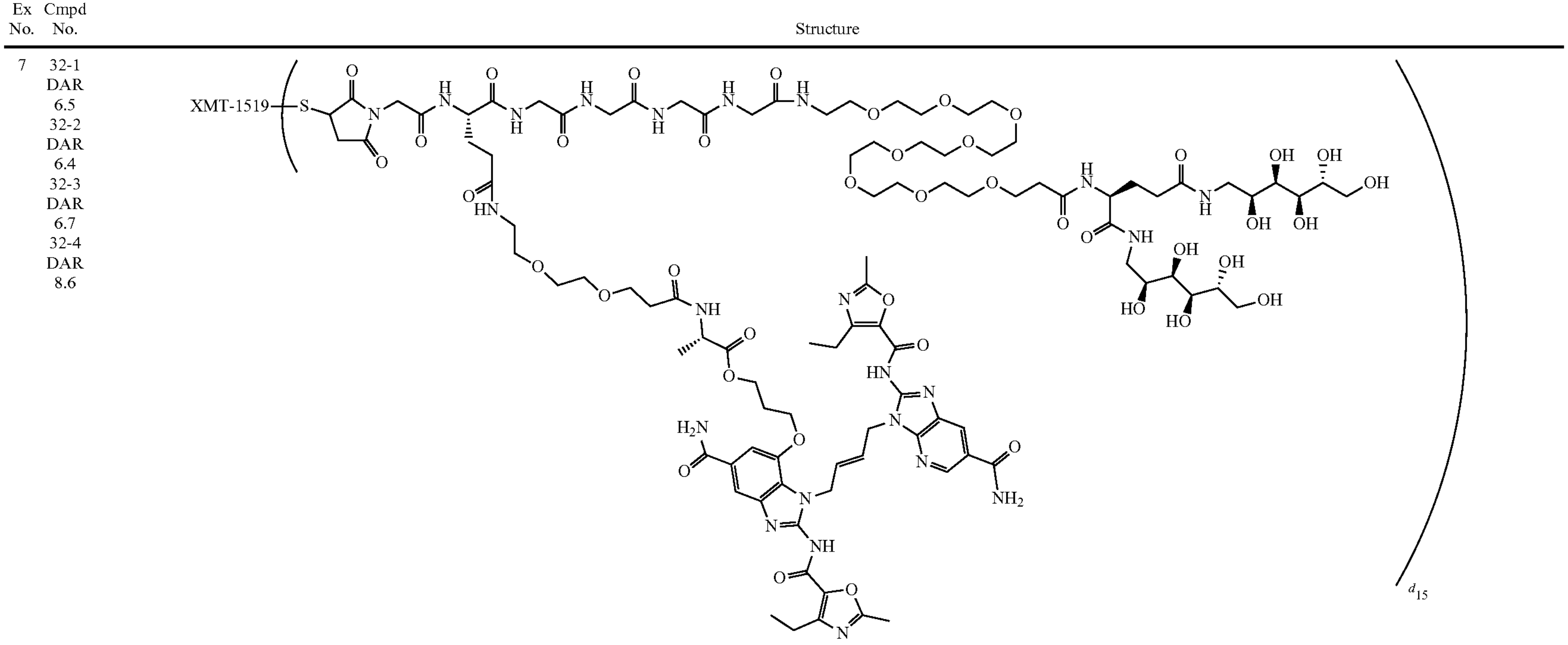 |

TABLE B2-continued
| Ex No. | Cmpd No. | Structure |
| --- | --- | --- |
| 7a | 32a DAR 6.2 32a-1 DAR 7.4 32a-2 DAR 8.0 32a-3 DAR 7.5 32a-4 DAR 8.0 | 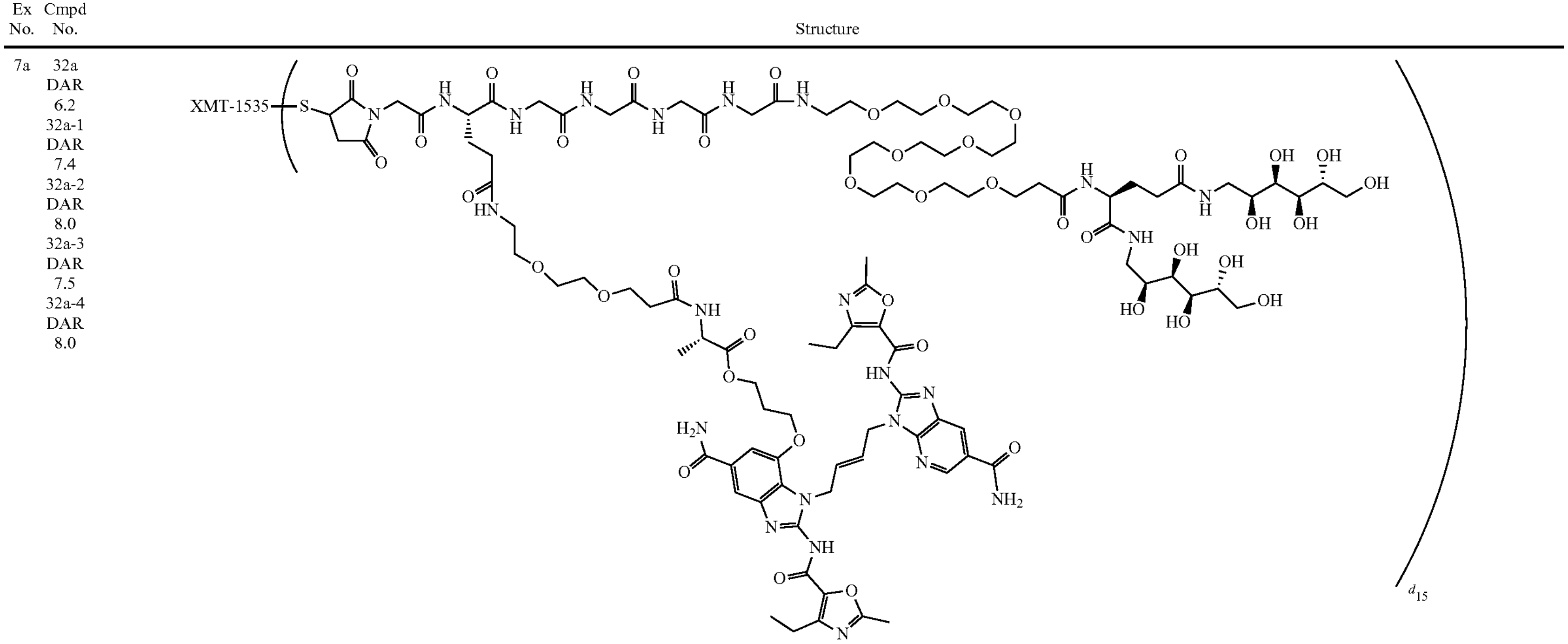 |

TABLE B2-continued
| Ex No. | Cmpd No. | Structure |
|---|---|---|
| 7b | 32b DAR 6.8 32b-1 DAR 5.7 32b-2 DAR 7.2 | 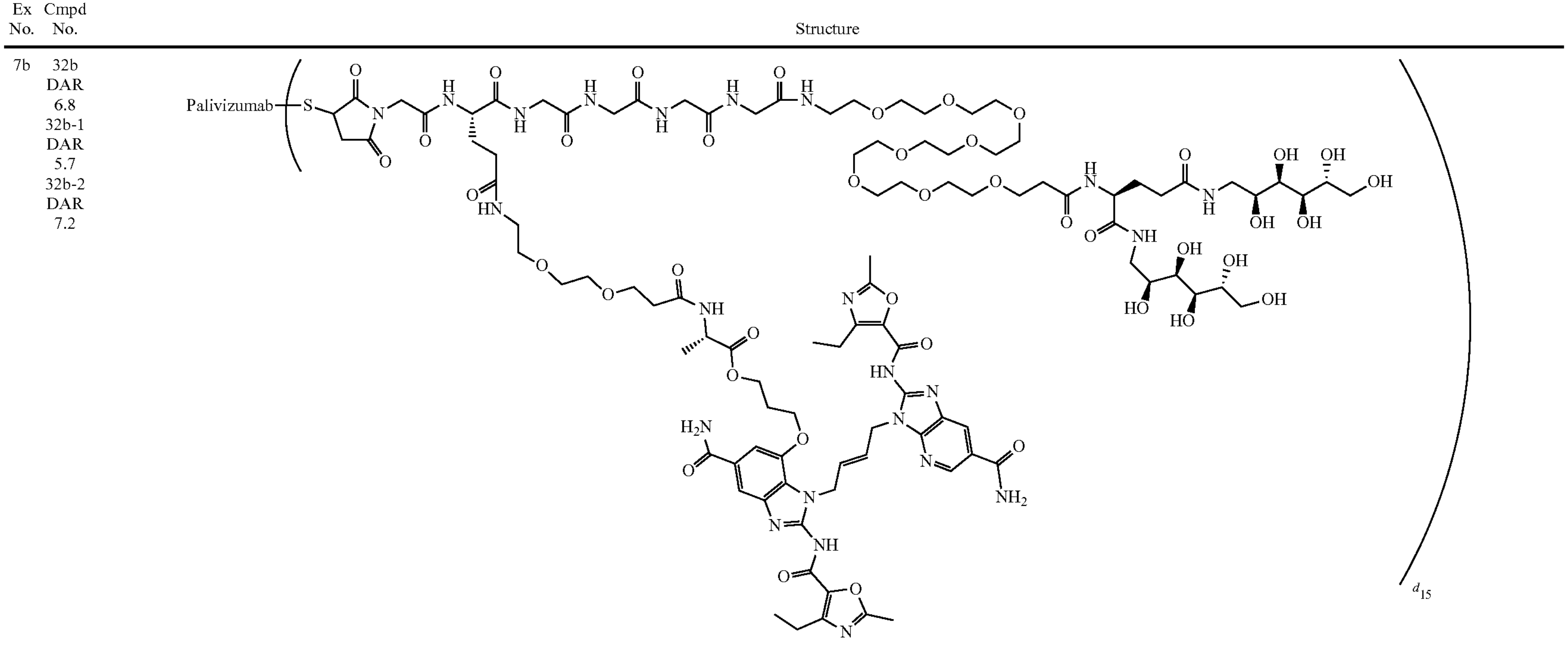 |

TABLE B2-continued
| Ex No. | Cmpd No. | Structure |
|---|---|---|
| 7c | 32c DAR 9.1 | Palivizumab mIgG2a 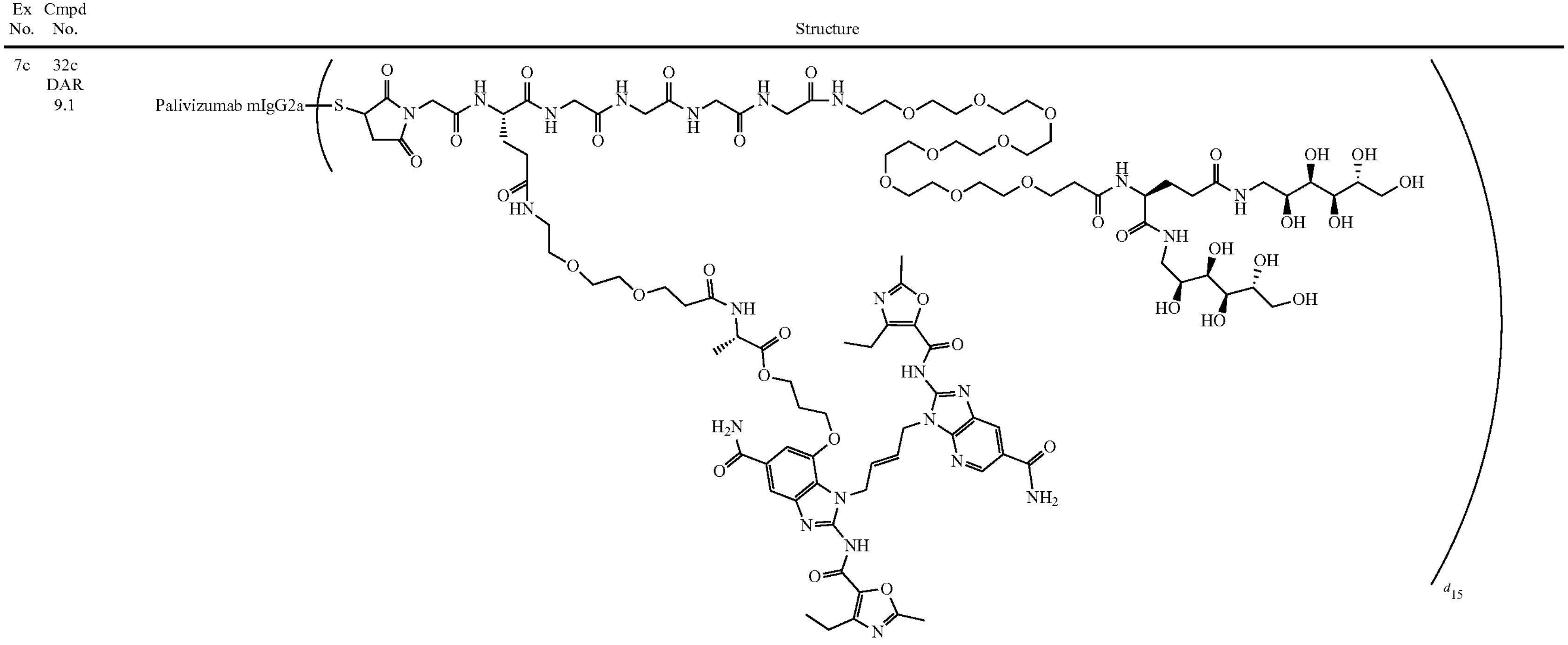 |

TABLE B2-continued
| Ex No. | Cmpd No. | Structure |
|---|---|---|
| 7d | 32d DAR 8.8 | XMT-1535 mIgG2a 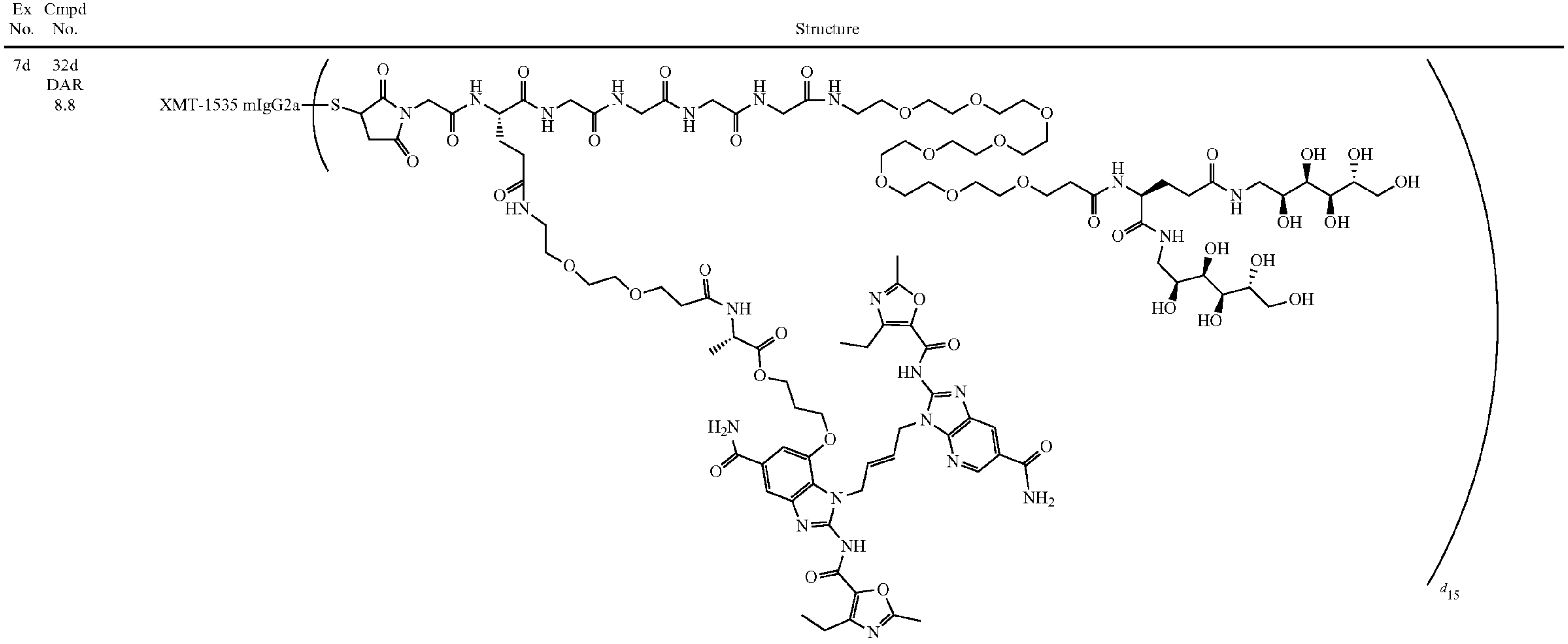 |

TABLE B2-continued
| Ex No. | Cmpd No. | Structure |
|---|---|---|
| 7e | 32e DAR 8.8 | 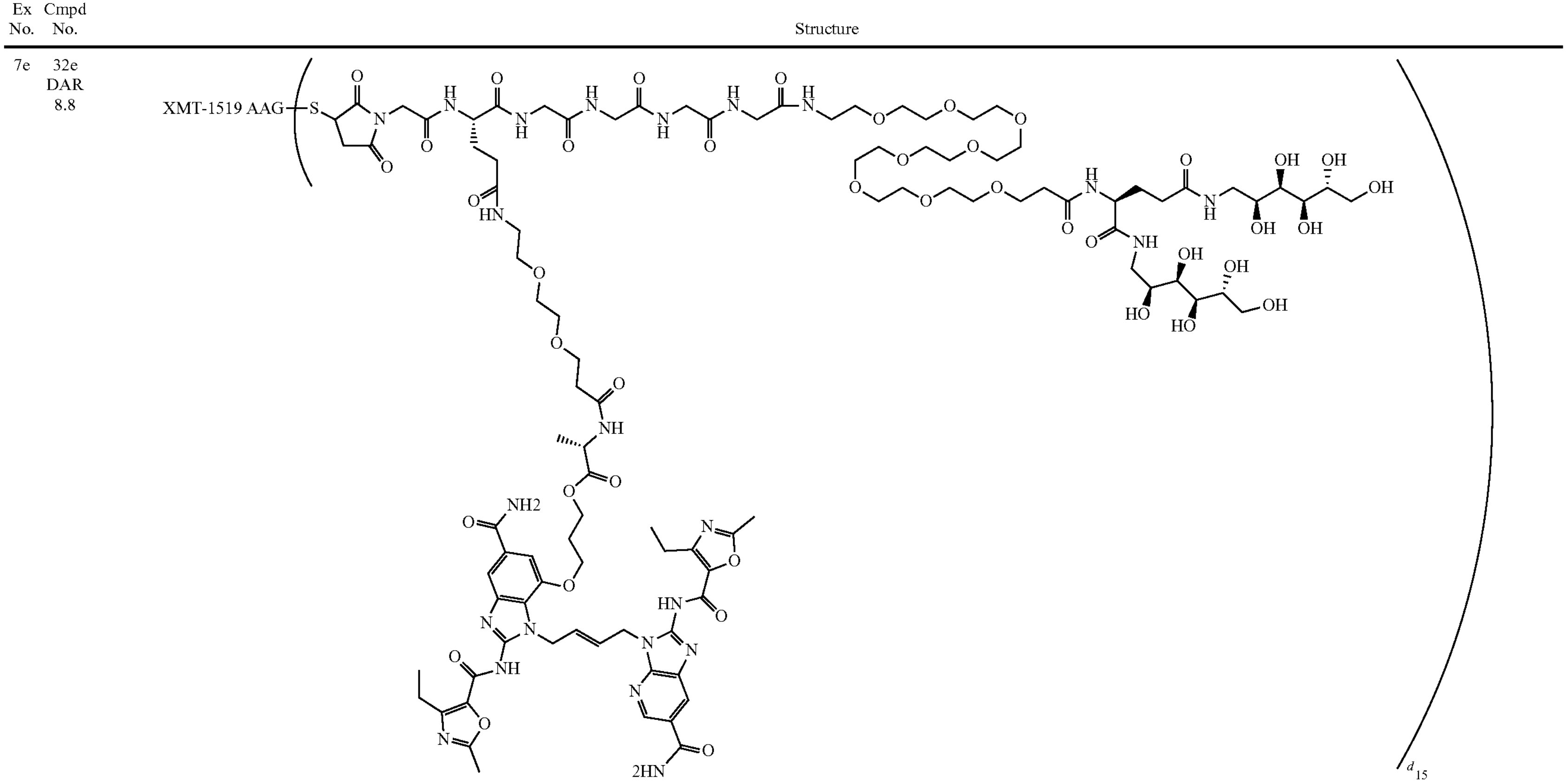 |

TABLE B2-continued
| Ex No. | Cmpd No. | Structure |
|---|---|---|
| 8 | 34 DAR 6.9 | 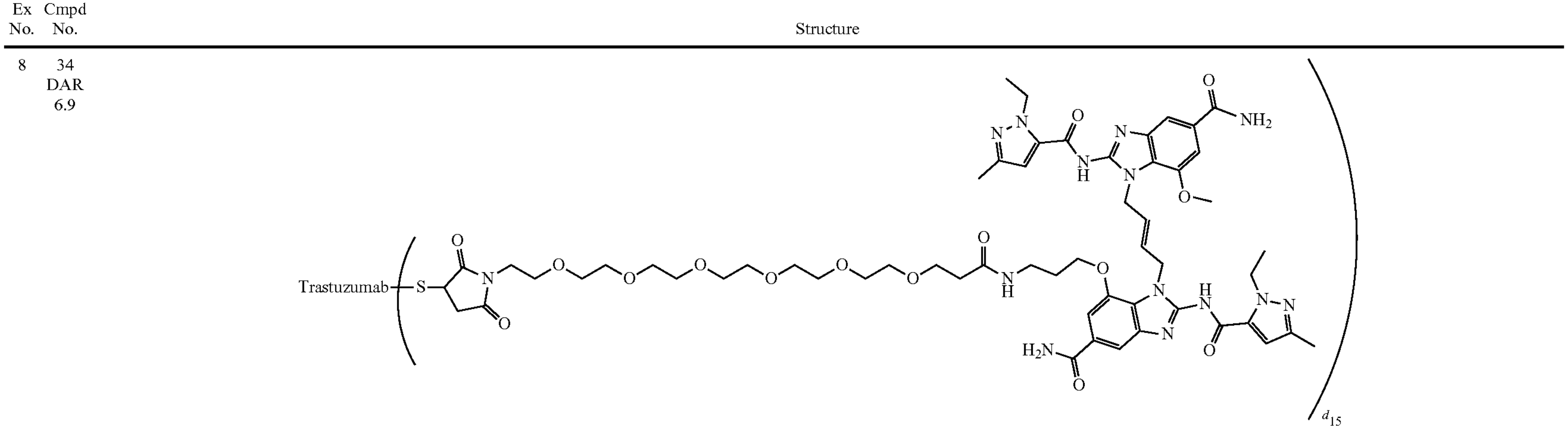 |
| 8a | 34a DAR 7.0 | 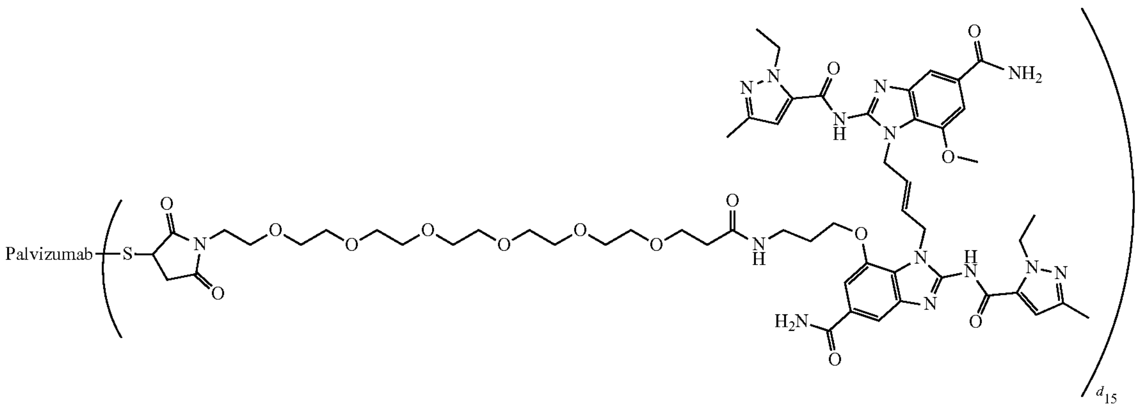 |

TABLE B2-continued
| Ex No. | Cmpd No. | Structure |
|---|---|---|
| 9 | 45 DAR 6.5 | 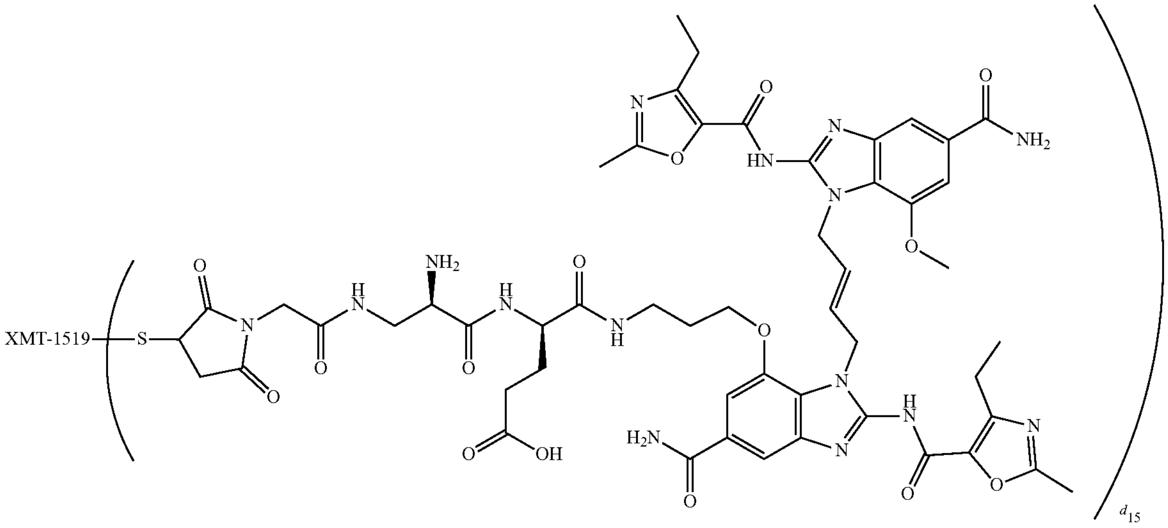 |

TABLE B2-continued
| Ex No. | Cmpd No. | Structure |
|---|---|---|
| 10 | 50 DAR 8.2 | 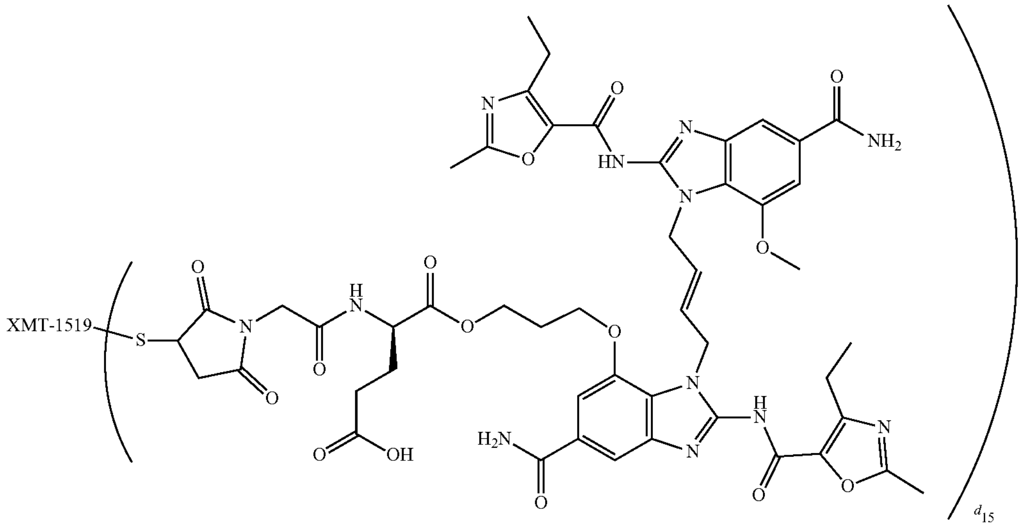 |

TABLE B2-continued
| Ex No. | Cmpd No. | Structure |
|---|---|---|
| 11 | 52 DAR 7.7 | 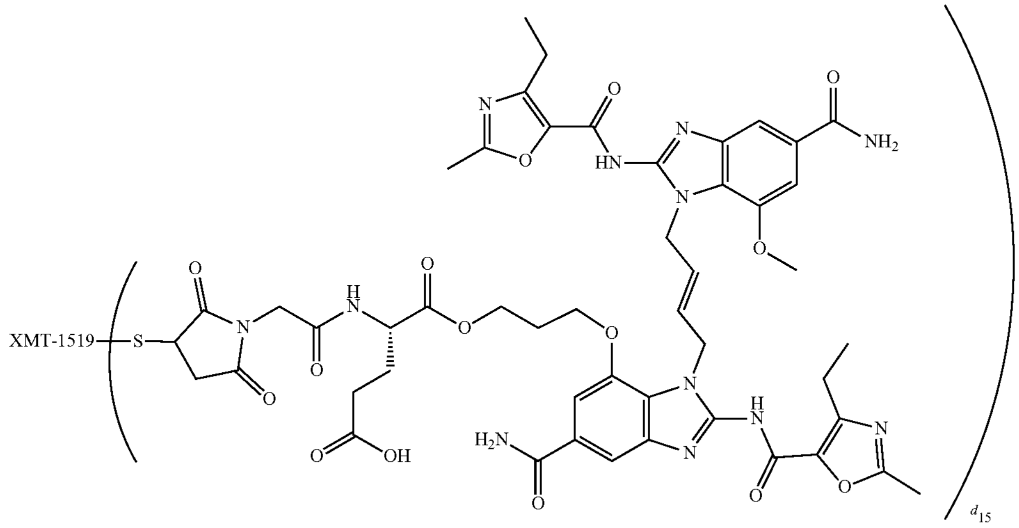 |

TABLE B2-continued
| Ex No. | Cmpd No. | Structure |
|---|---|---|
| 12 | 58 DAR 6.5 | 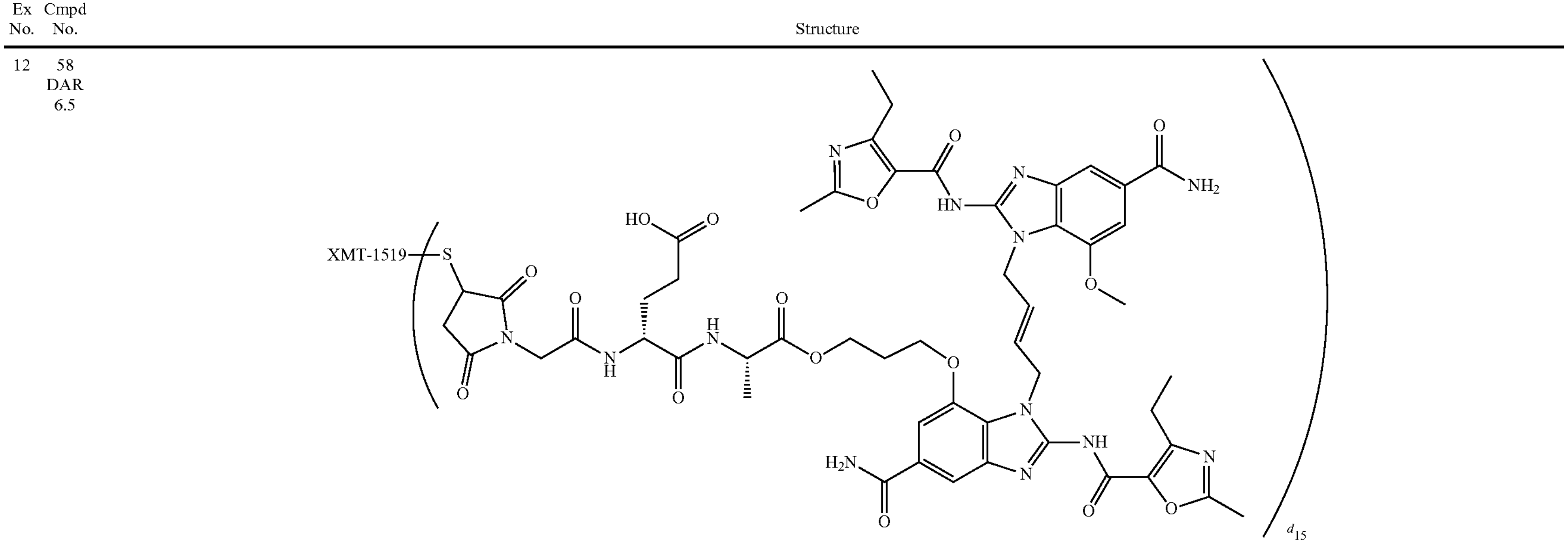 |

TABLE B2-continued
| Ex No. | Cmpd No. | Structure |
|---|---|---|
| 13 | 60-1 (DAR 7.7 60-2 DAR 5.5 | 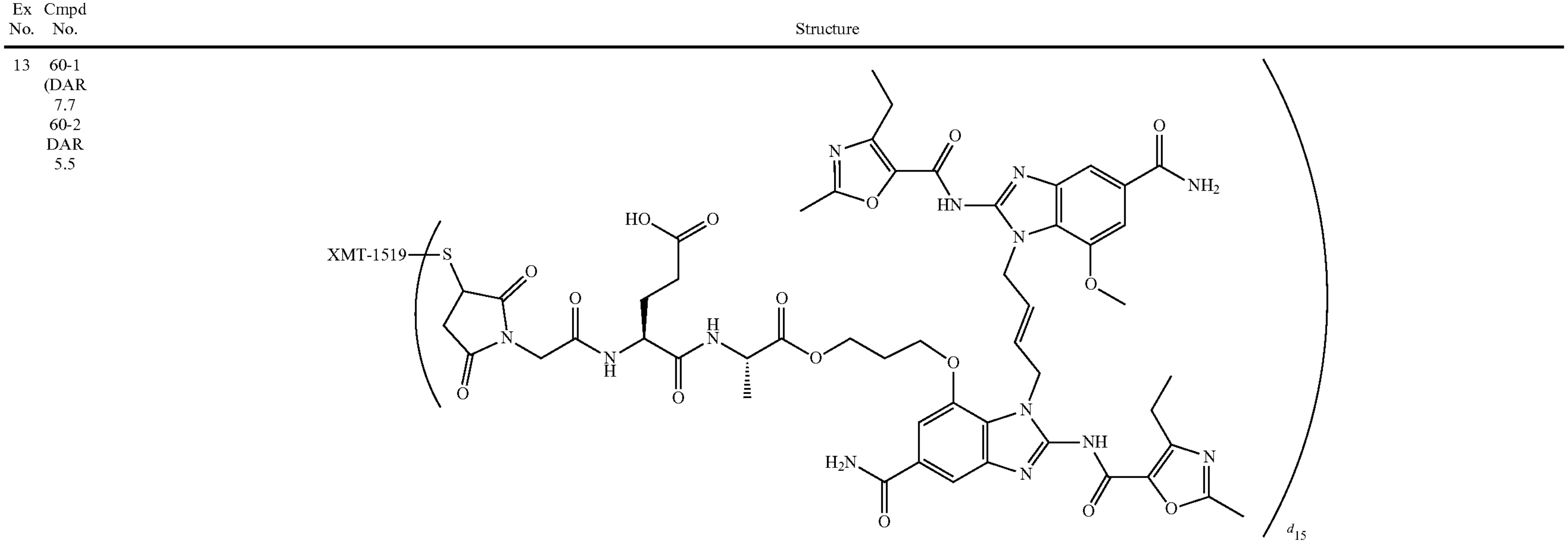 |

TABLE B2-continued
| Ex No. | Cmpd No. | Structure |
|---|---|---|
| 14 | 62 DAR 6.5 | 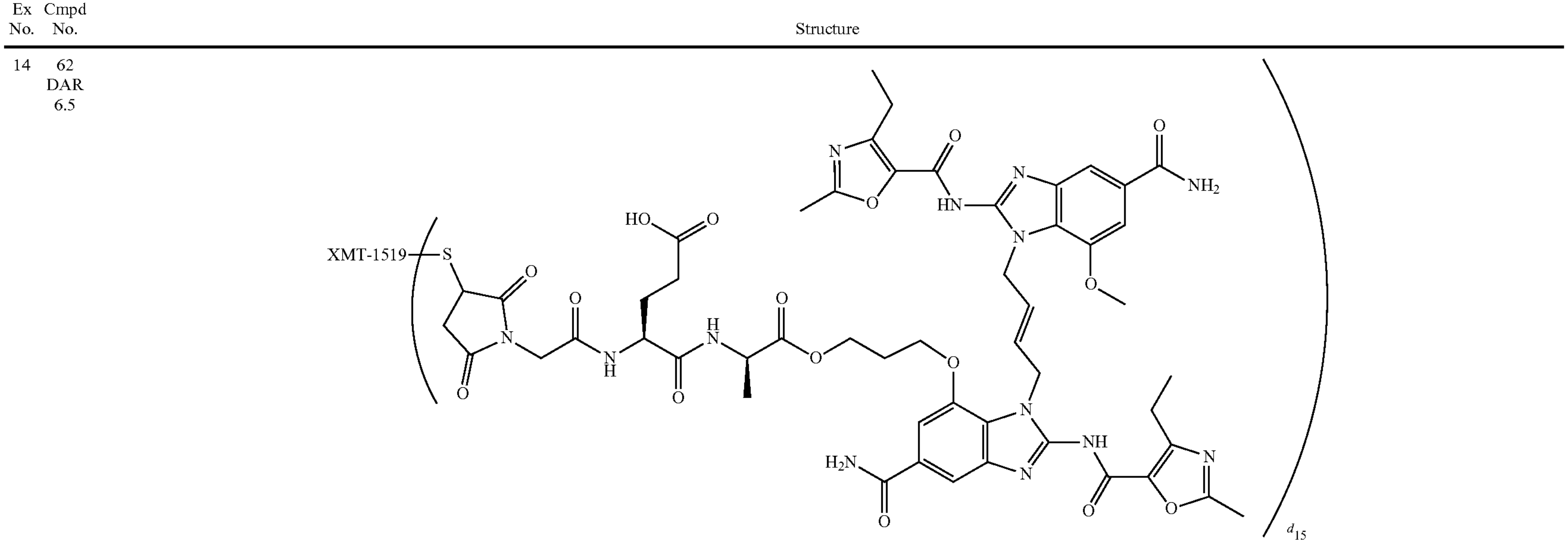 |

TABLE B2-continued
| Ex No. | Cmpd No. | Structure |
|---|---|---|
| 15 | 64 DAR 6.4 | 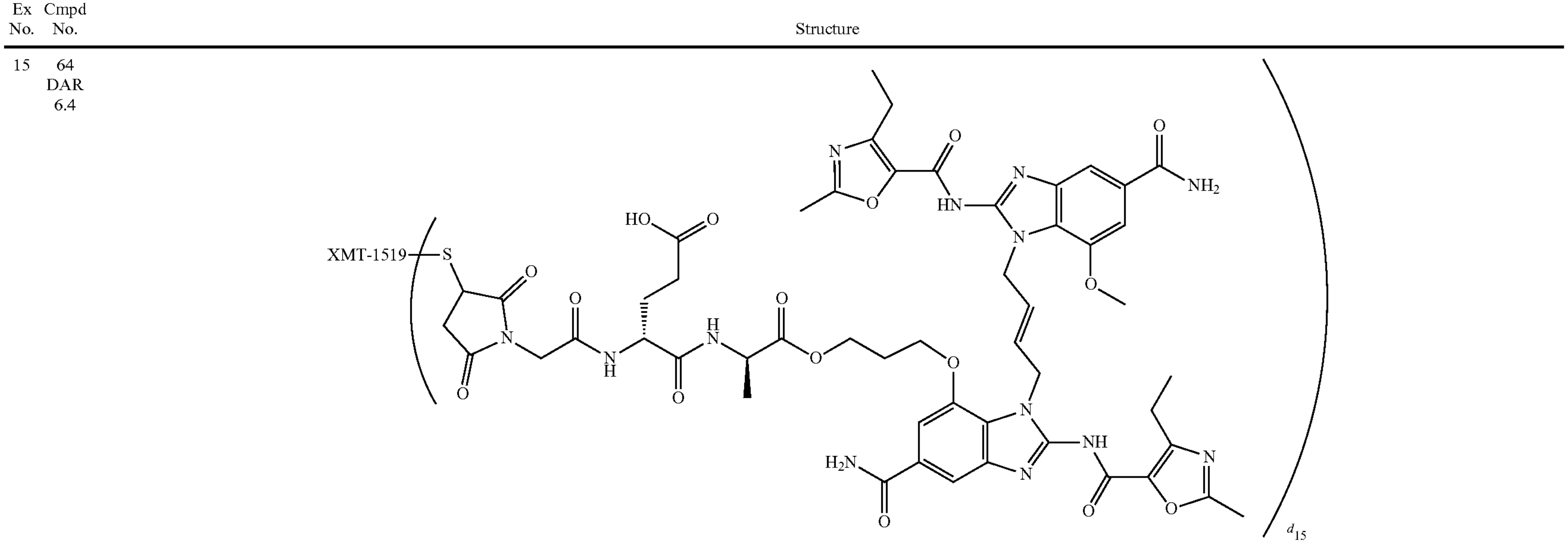 |

TABLE B2-continued
| Ex No. | Cmpd No. | Structure |
|---|---|---|
| 16 | 66-1 DAR 7.5 66-2 DAR 5.3 | 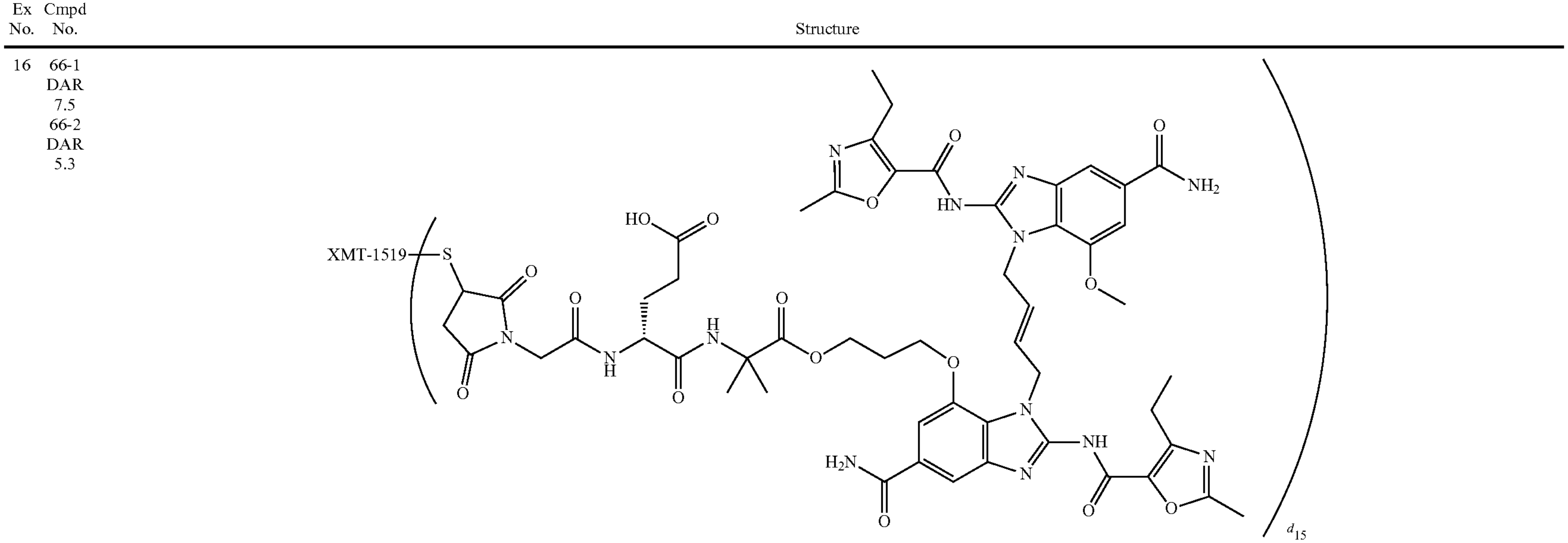 |

TABLE B2-continued
| Ex No. | Cmpd No. | Structure |
|---|---|---|
| 17 | 74 DAR 6.9 | 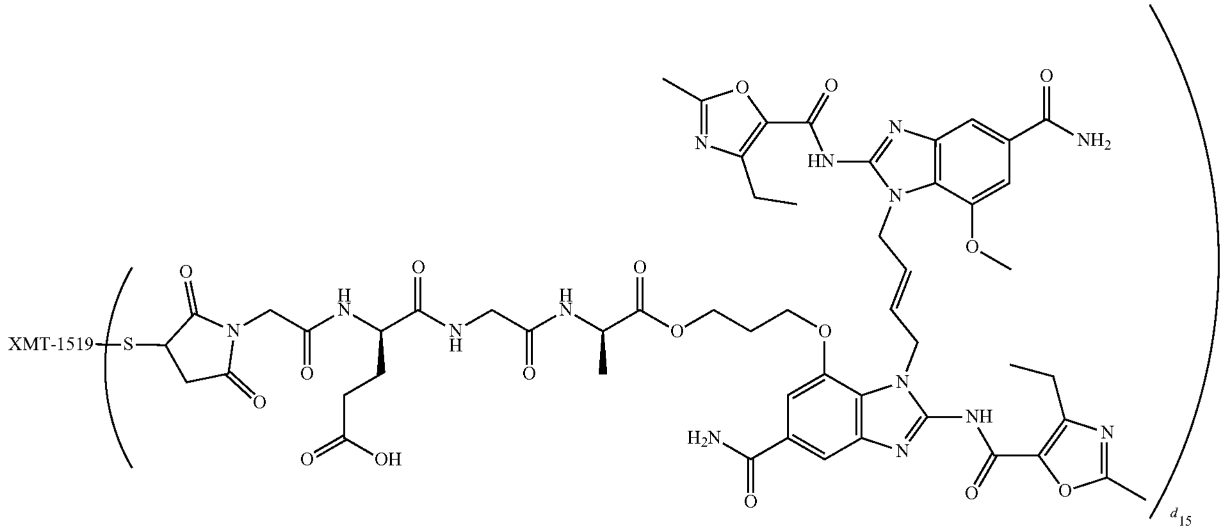 |

TABLE B2-continued
| Ex No. | Cmpd No. | Structure |
|---|---|---|
| 18 | 76 DAR 7.5 | 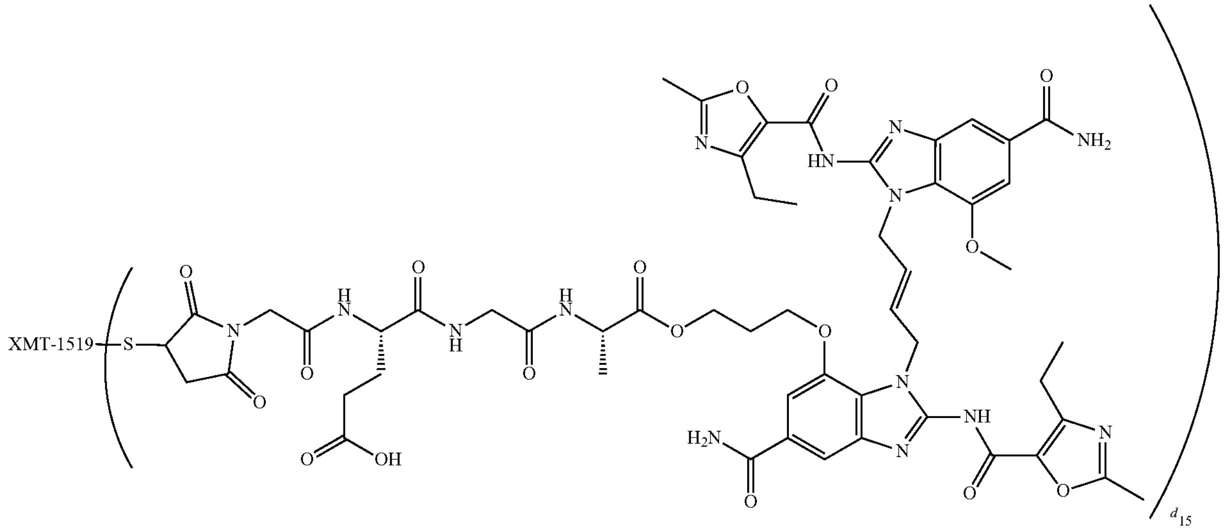 |

TABLE B2-continued
| Ex No. | Cmpd No. | Structure |
|---|---|---|
| 19 | 78 DAR 7.4 | 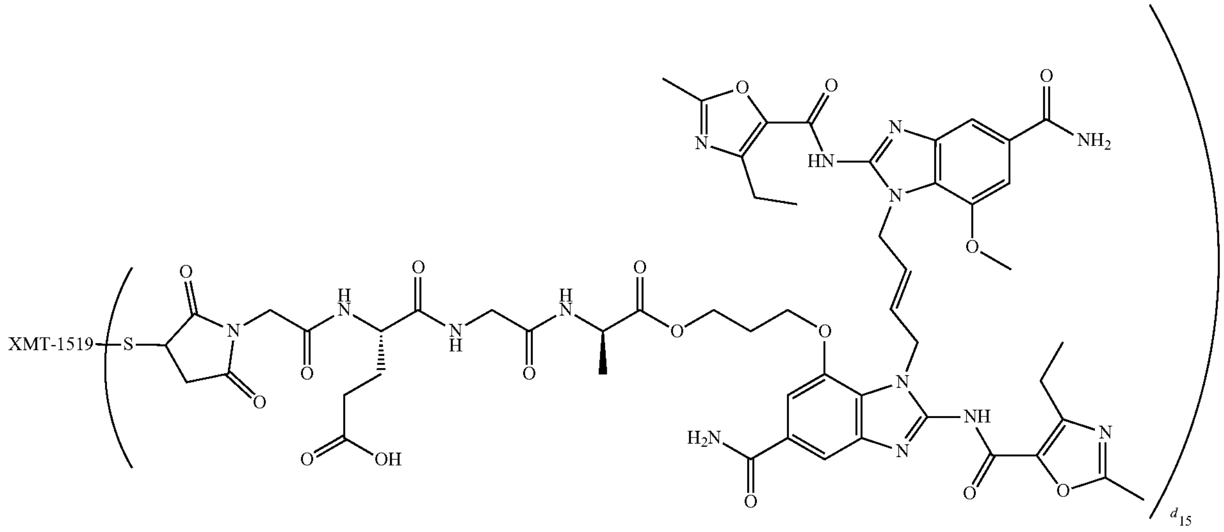 |

TABLE B2-continued
| Ex No. | Cmpd No. | Structure |
|---|---|---|
| 20 | 80 DAR 7.5 | 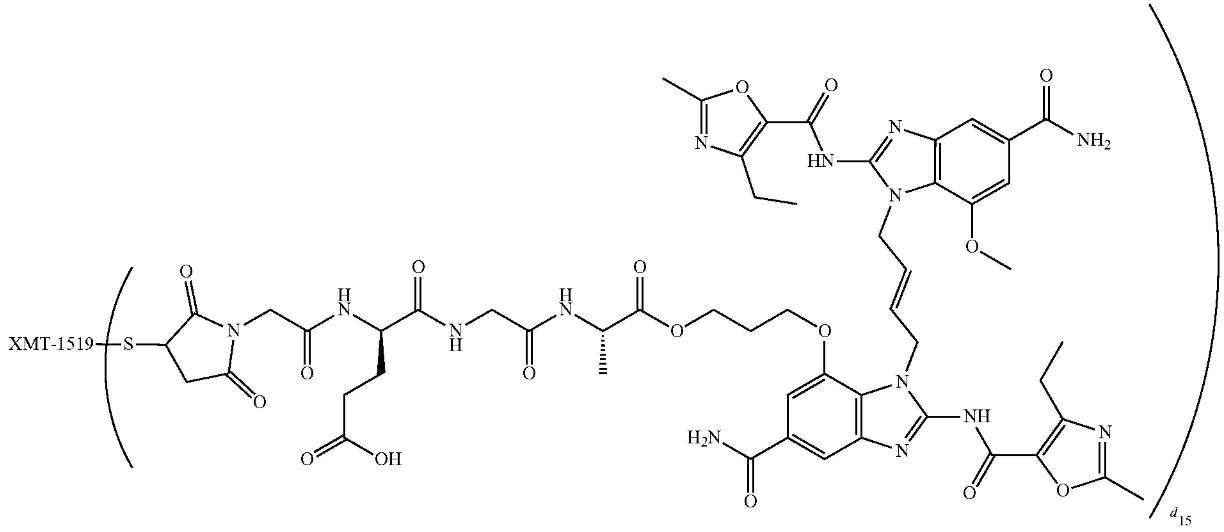 |

TABLE B2-continued
| Ex No. | Cmpd No. | Structure |
|---|---|---|
| 21 | 82 DAR 5.7 | 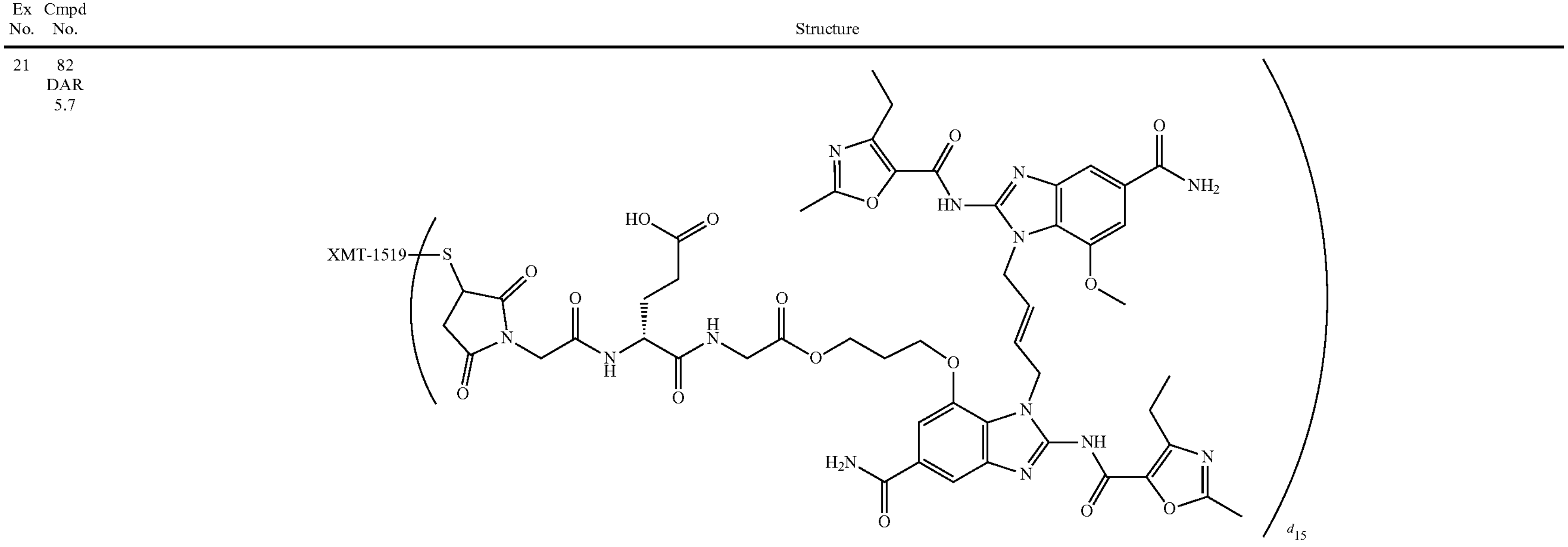 |

TABLE B2-continued
| Ex No. | Cmpd No. | Structure |
| --- | --- | --- |
| | | 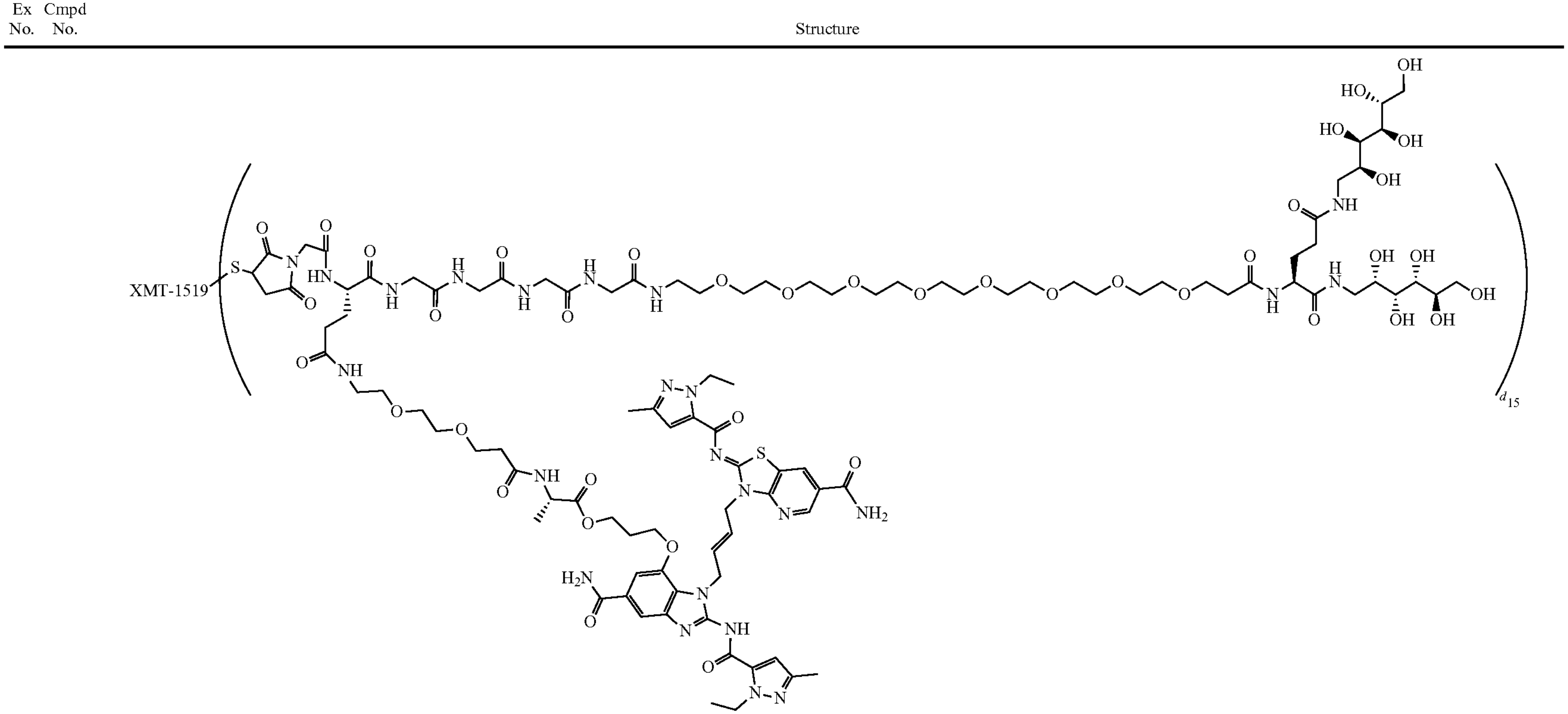 |

TABLE B2-continued
| Ex No. | Cmpd No. | Structure |
|---|---|---|
| 22 | 85 DAR 6.5 | 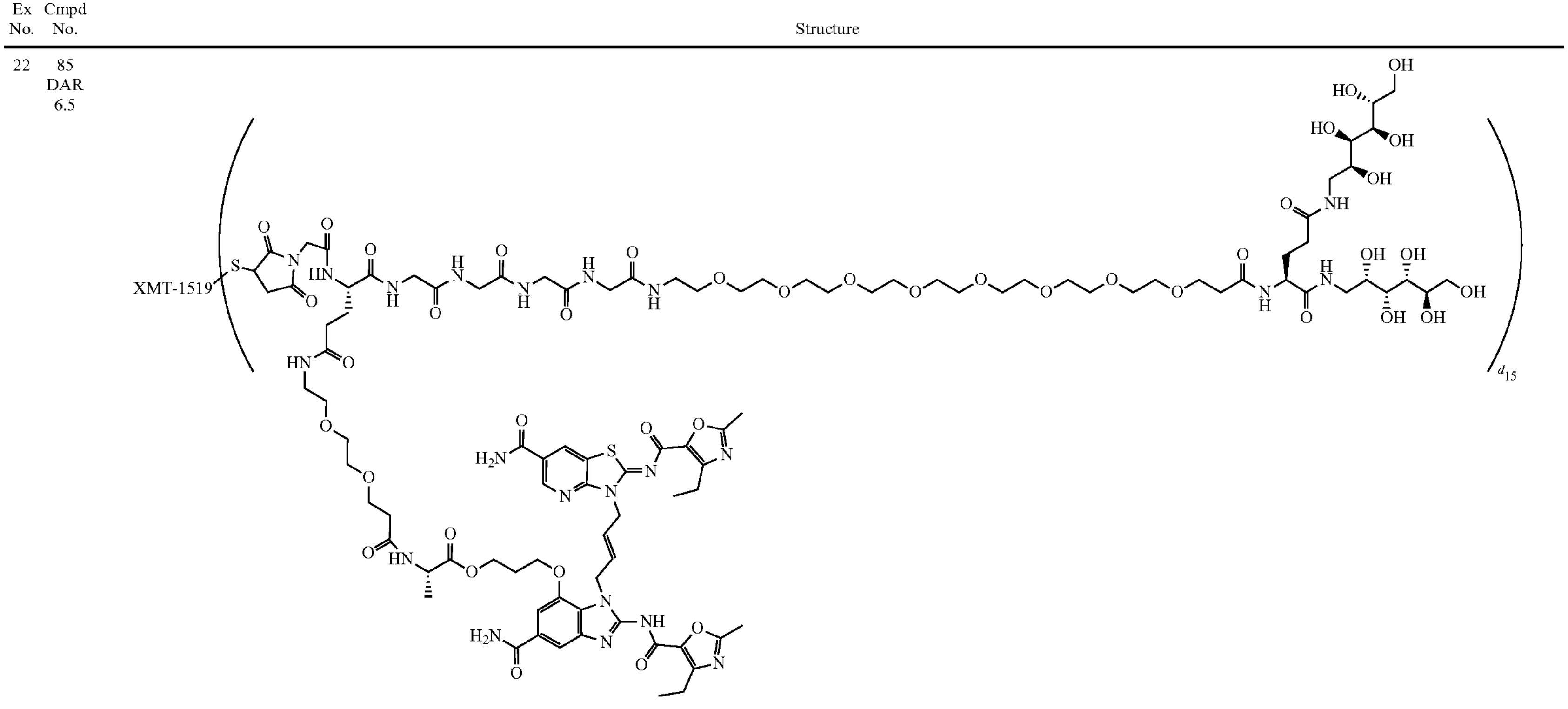 |

TABLE B2-continued
| Ex No. | Cmpd No. | Structure |
|---|---|---|
| 22a | 85a DAR 7.4 | 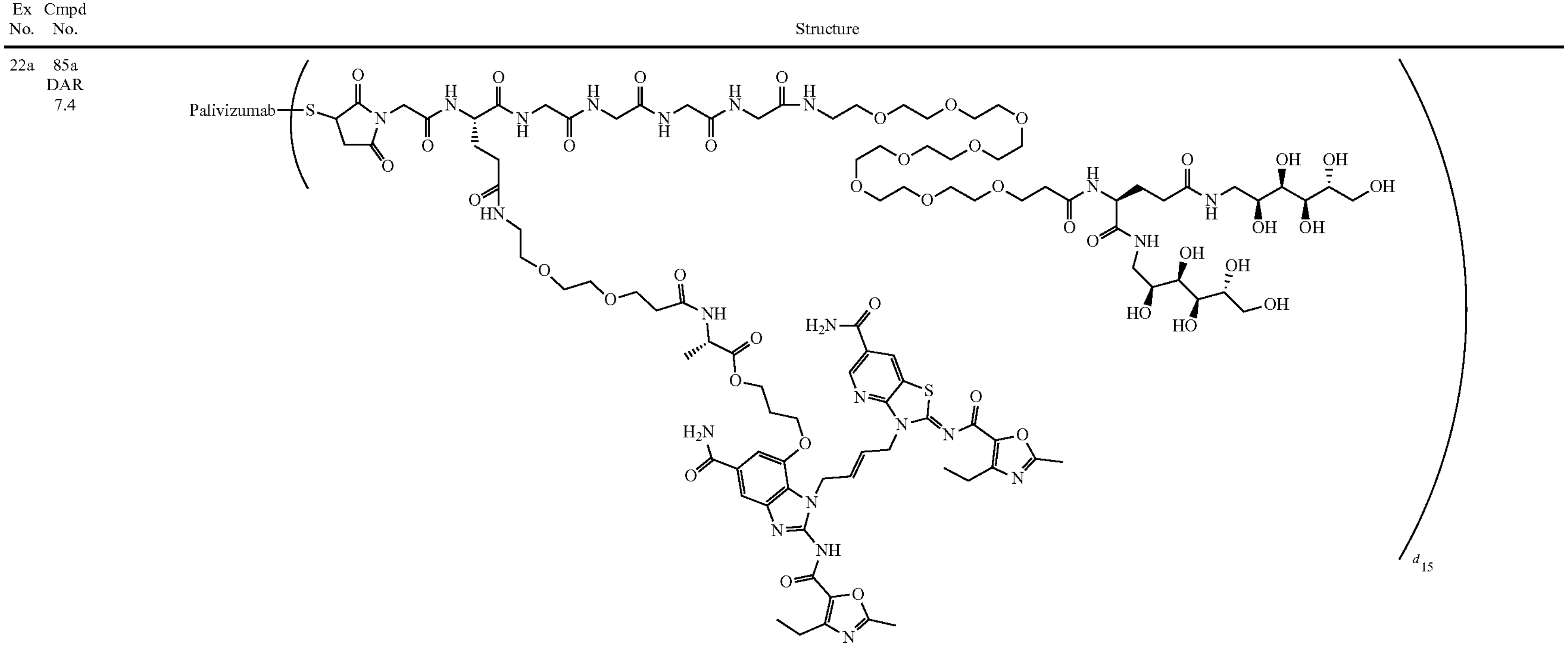 |

TABLE B2-continued
| Ex No. | Cmpd No. | Structure |
|---|---|---|
| 23 | 88 DAR 6.6 | 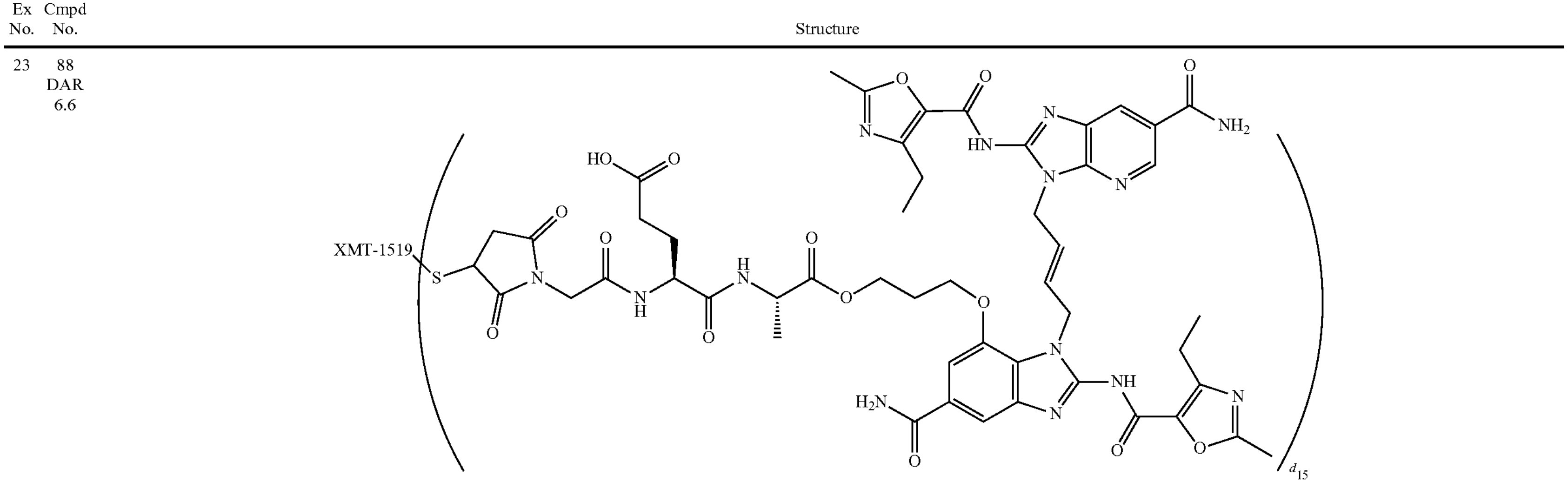 |
| 23a | 89 DAR 5.9 | 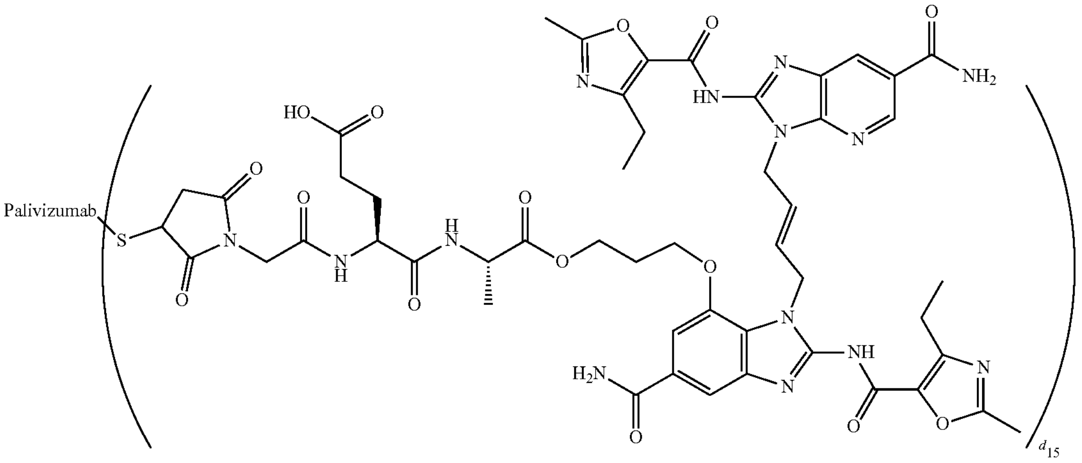 |

TABLE B2-continued
| Ex No. | Cmpd No. | Structure |
|---|---|---|
| 23b | 89a DAR 8.8 | 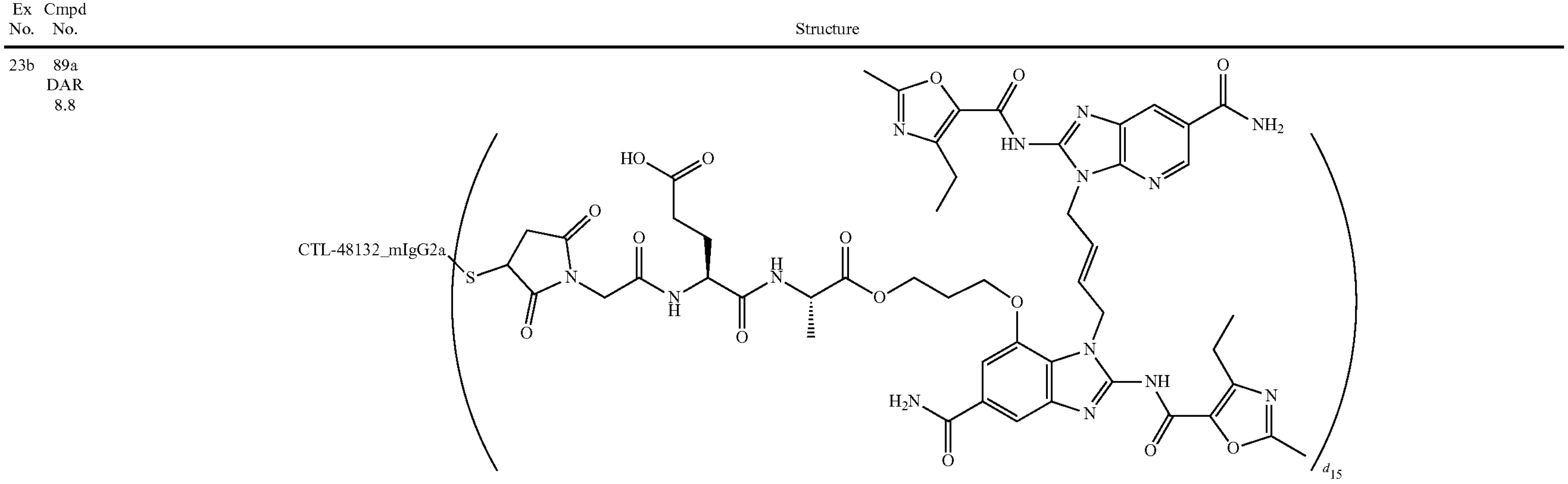 |
| 23c | 89b DAR 9.0 | 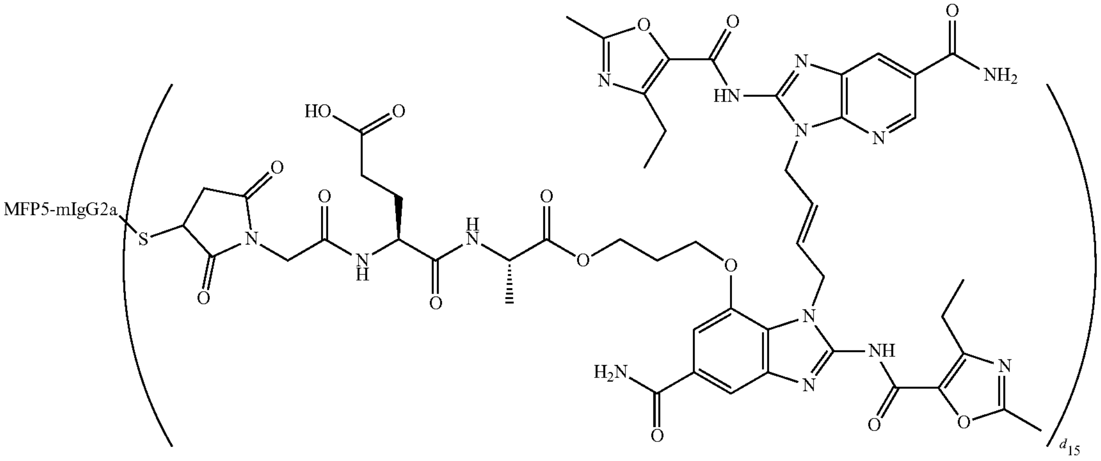 |

TABLE B2-continued
| Ex No. | Cmpd No. | Structure |
|---|---|---|
| 24 | 92 DAR 7.6 | 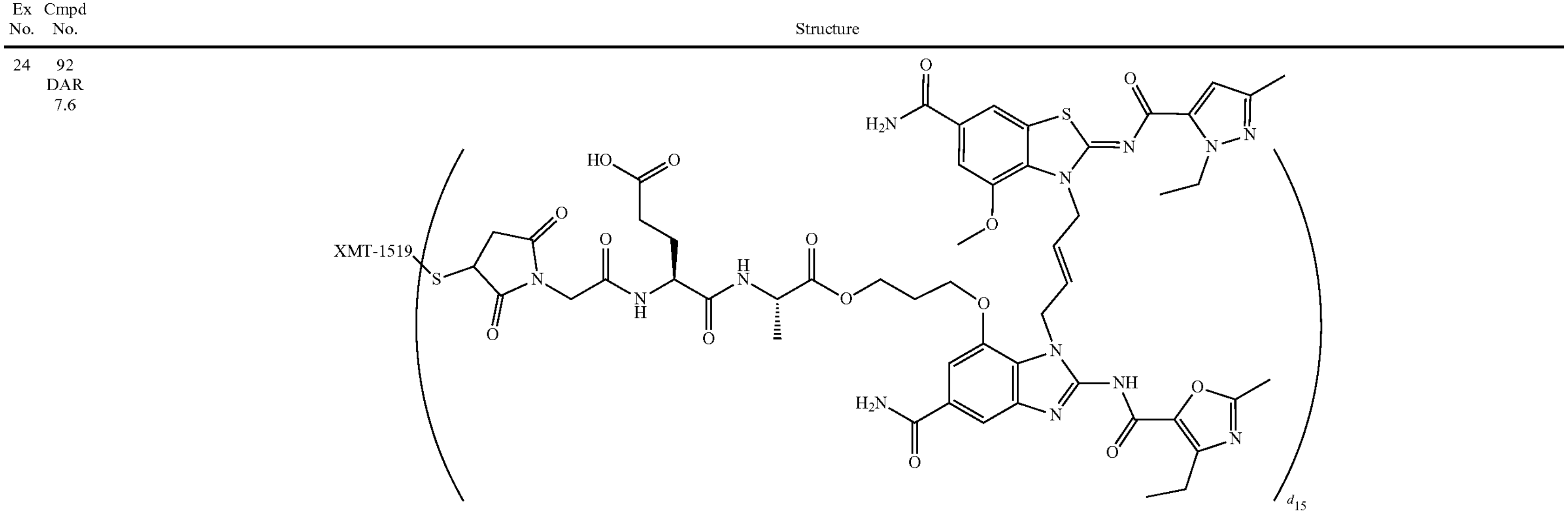 |
| 24a | 93 DAR 6.7 | 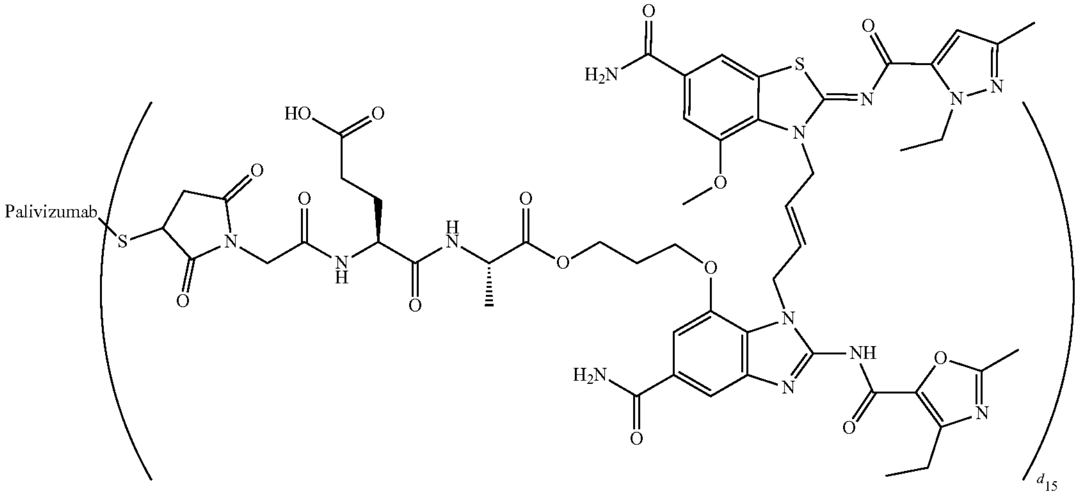 |

TABLE B2-continued
| Ex No. | Cmpd No. | Structure |
|---|---|---|
| 25 | 100 DAR 7.8 | 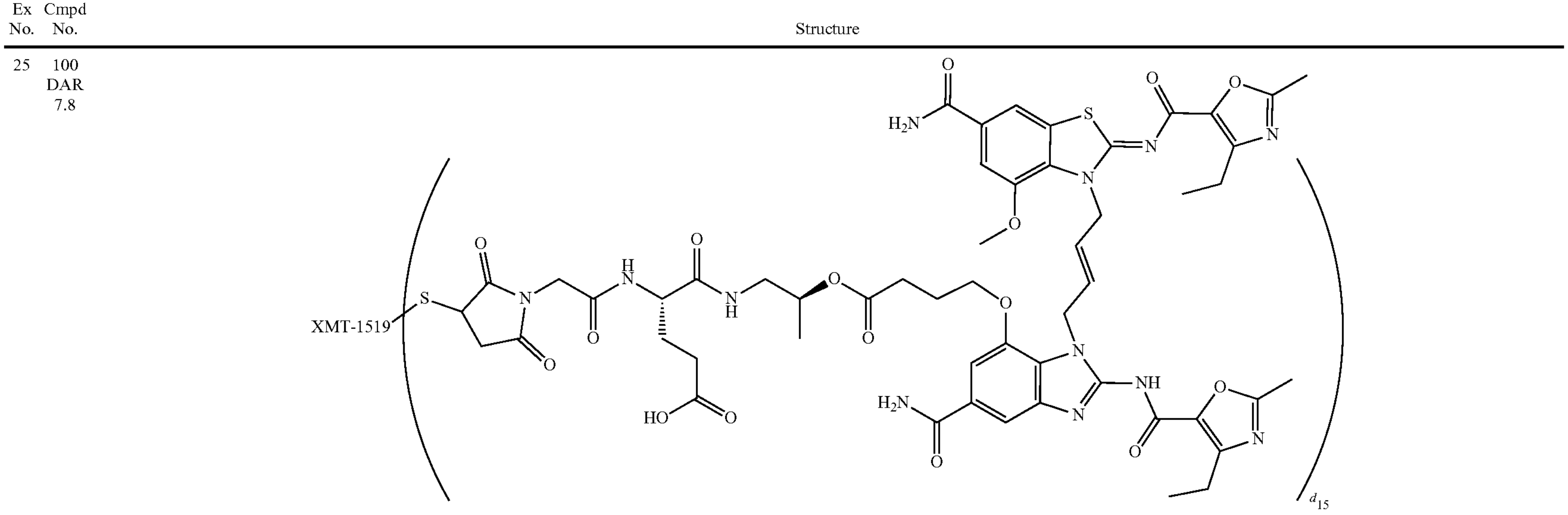 |
| 25a | 101 DAR 6.5 | 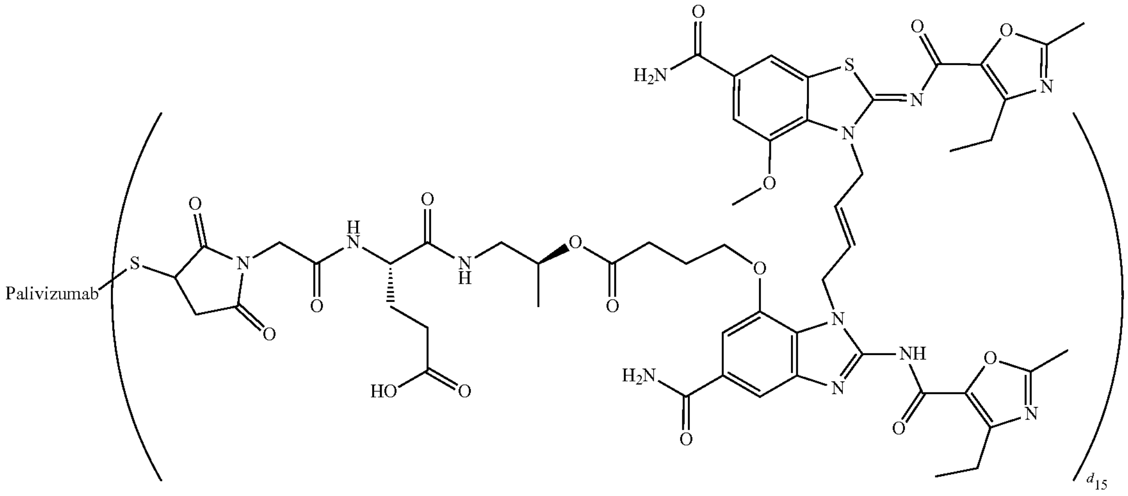 |

TABLE B2-continued
| Ex No. | Cmpd No. | Structure |
|---|---|---|
| | | 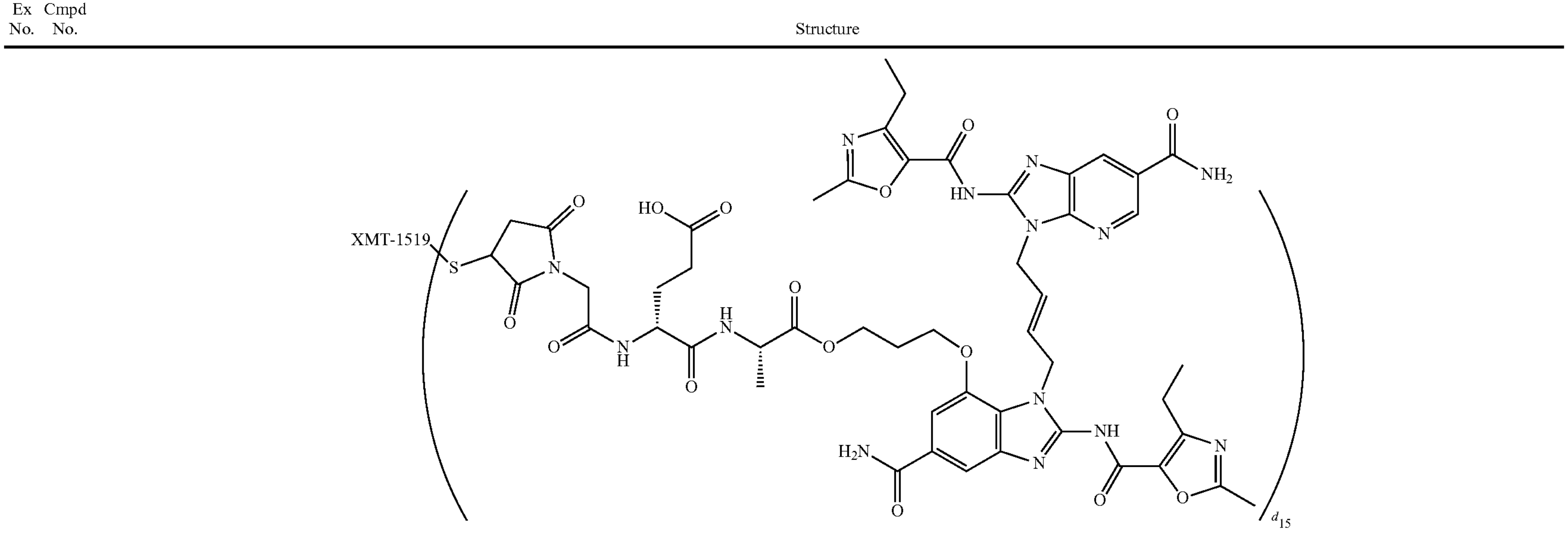 |
| | | 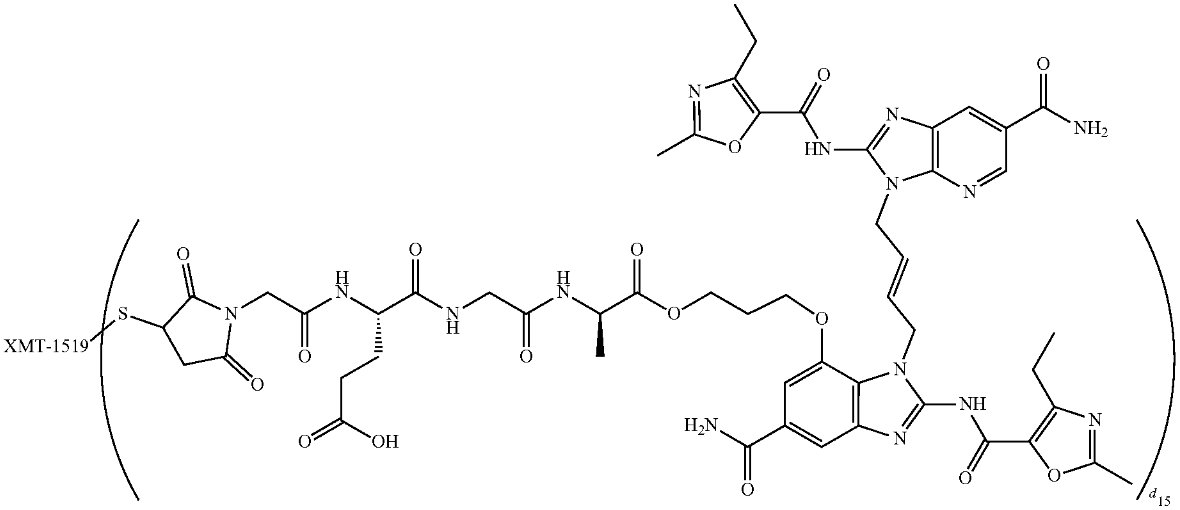 |

TABLE B2-continued
| Ex No. | Cmpd No. | Structure |
|---|---|---|
| | | 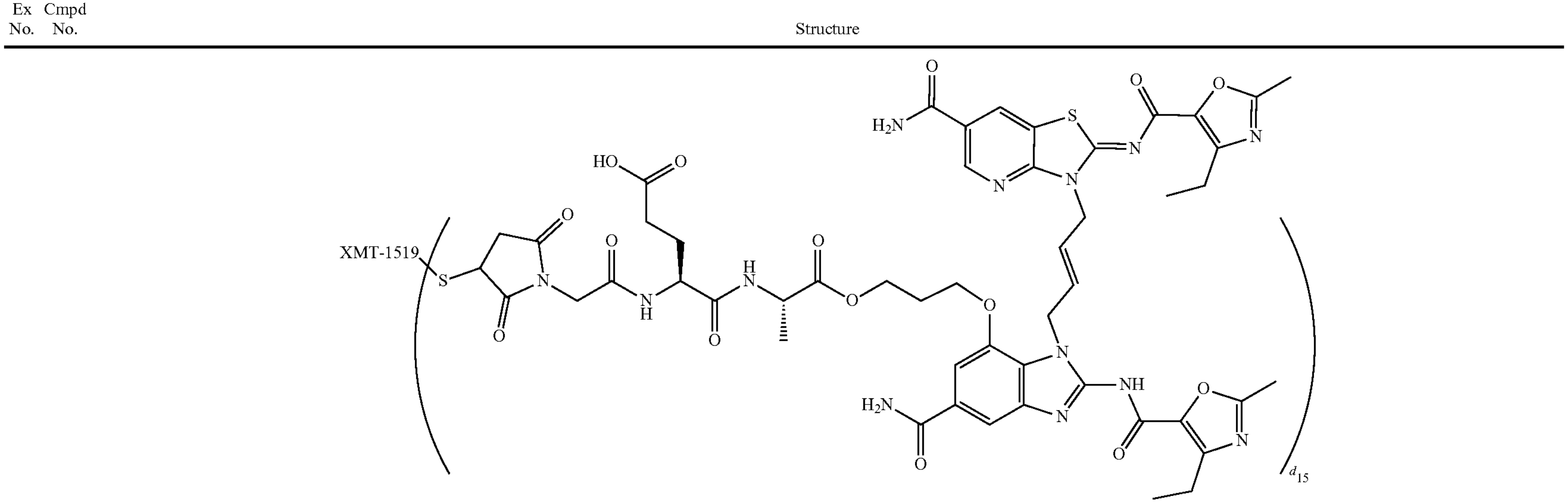 |
| | | 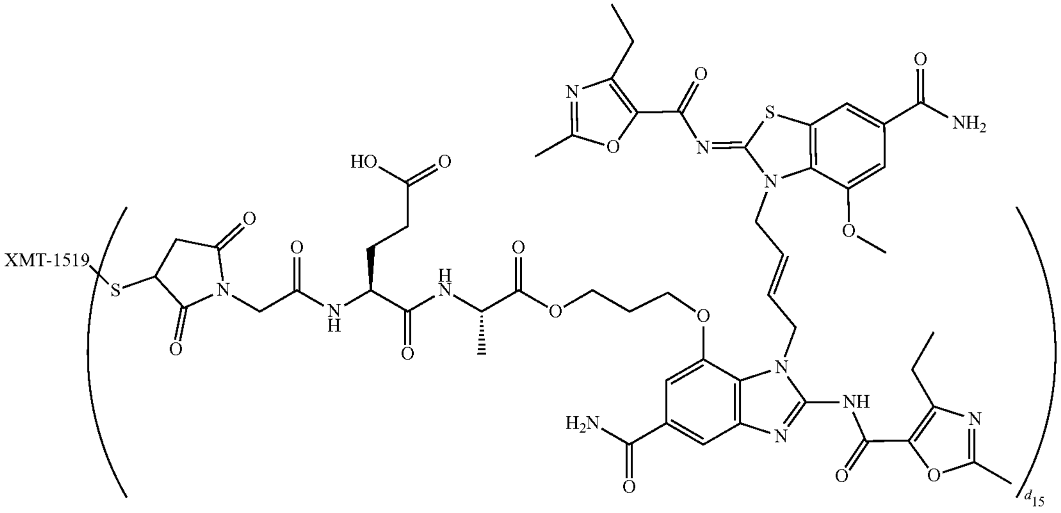 |

TABLE B2-continued
| Ex No. | Cmpd No. | Structure |
| --- | --- | --- |
| | | 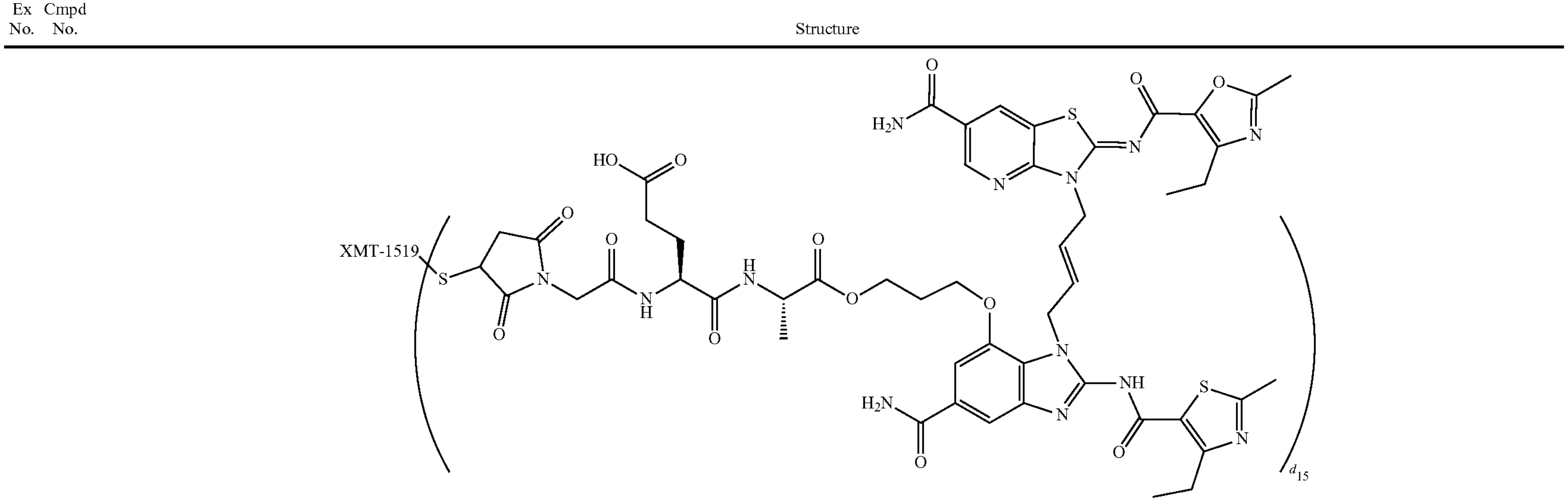 |

In some embodiments, the conjugate is:

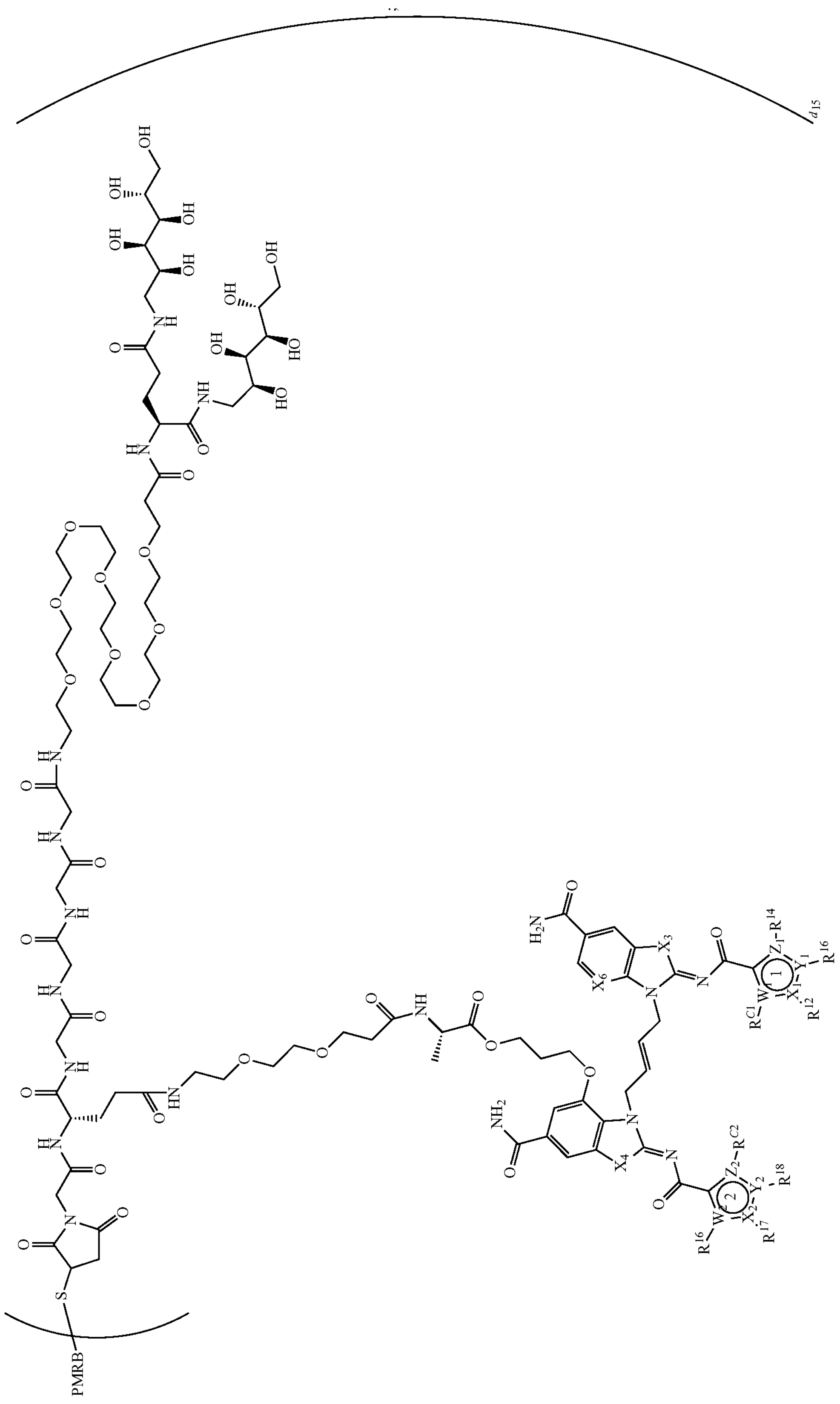

-continued
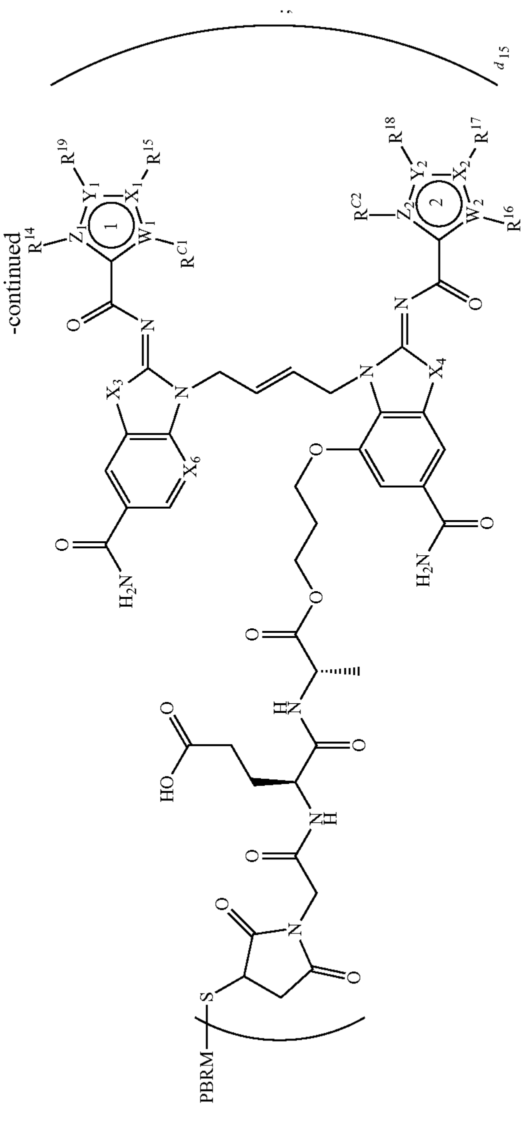
;
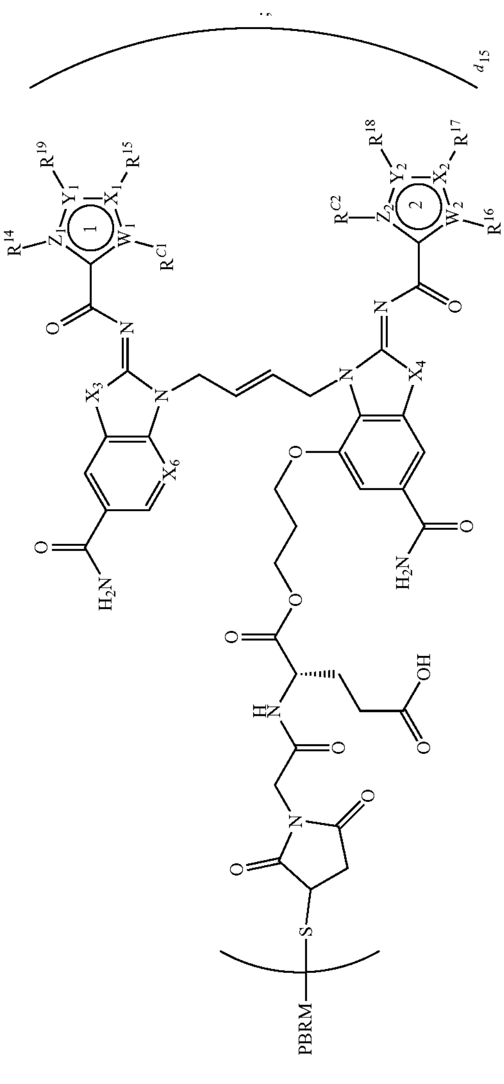
;

-continued
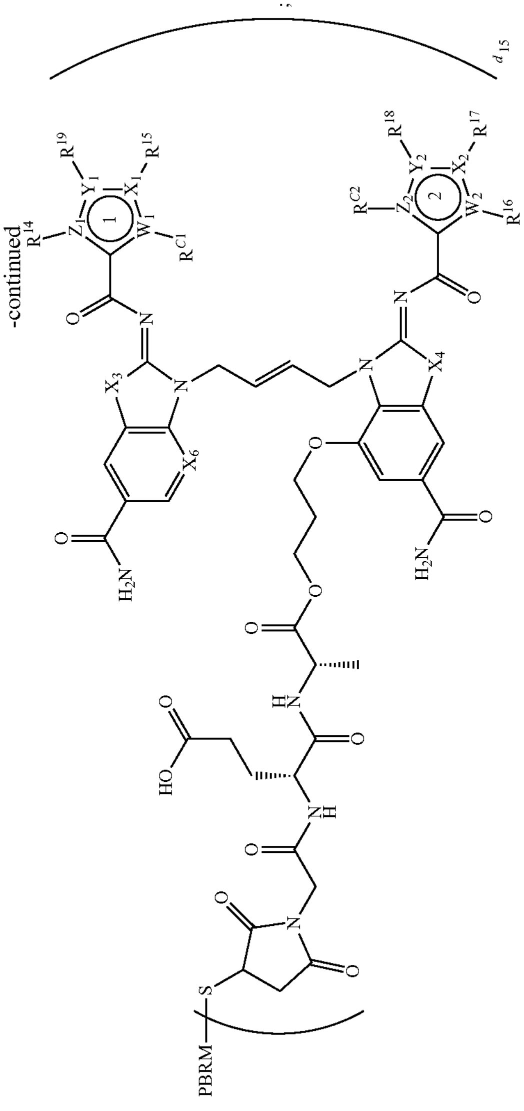
;
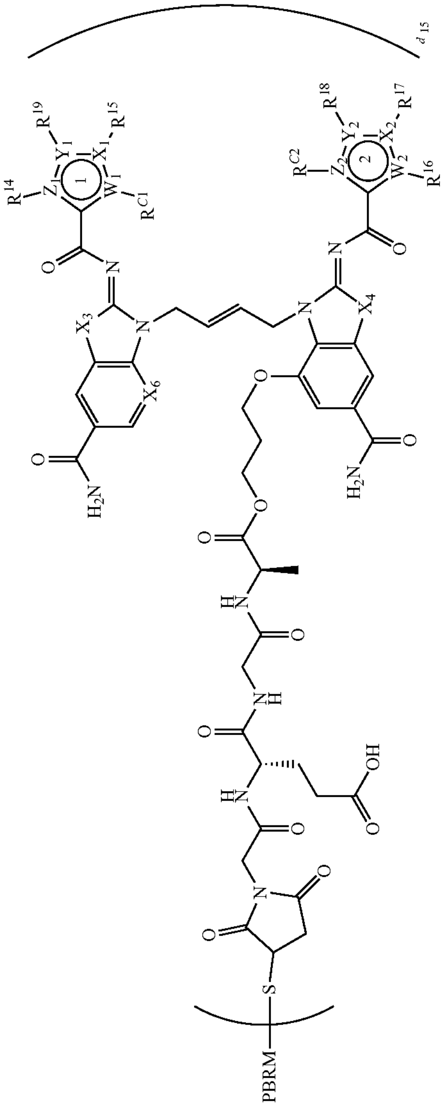
; or

-continued
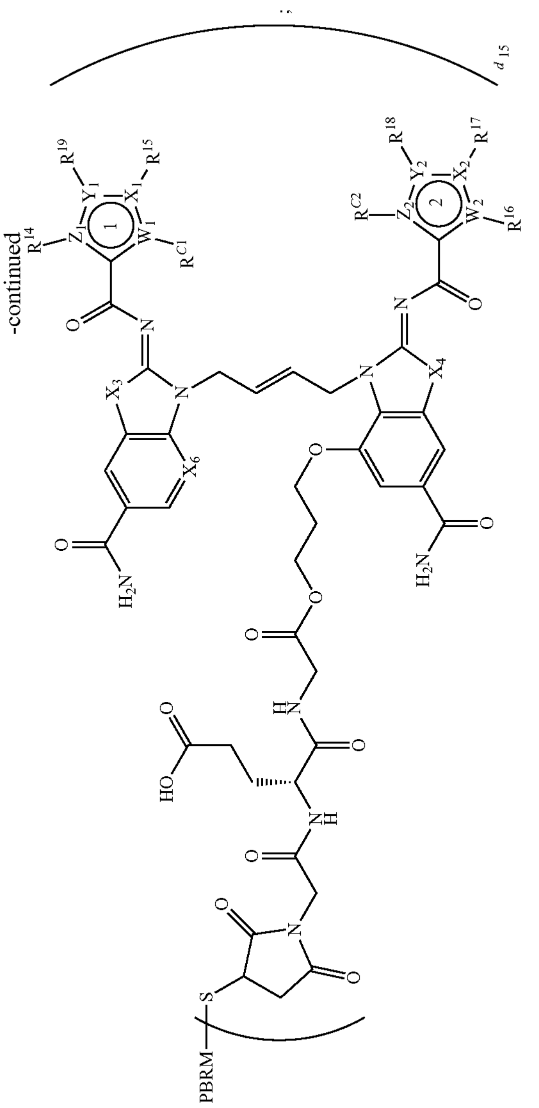

wherein $R^{14}$, $R^{15}$, $R^{16}$, $R^{17}$, $R^{18}$, $R^{19}$, $R^{C1}$, $R^{C2}$, $X_3$, $X_4$, $X_6$, $X_1$, $W_1$, $Y_1$, $Z_1$, $X_2$, $W_2$, $Y_2$, $Z_2$, are as defined herein.
In some embodiments, the conjugate is:
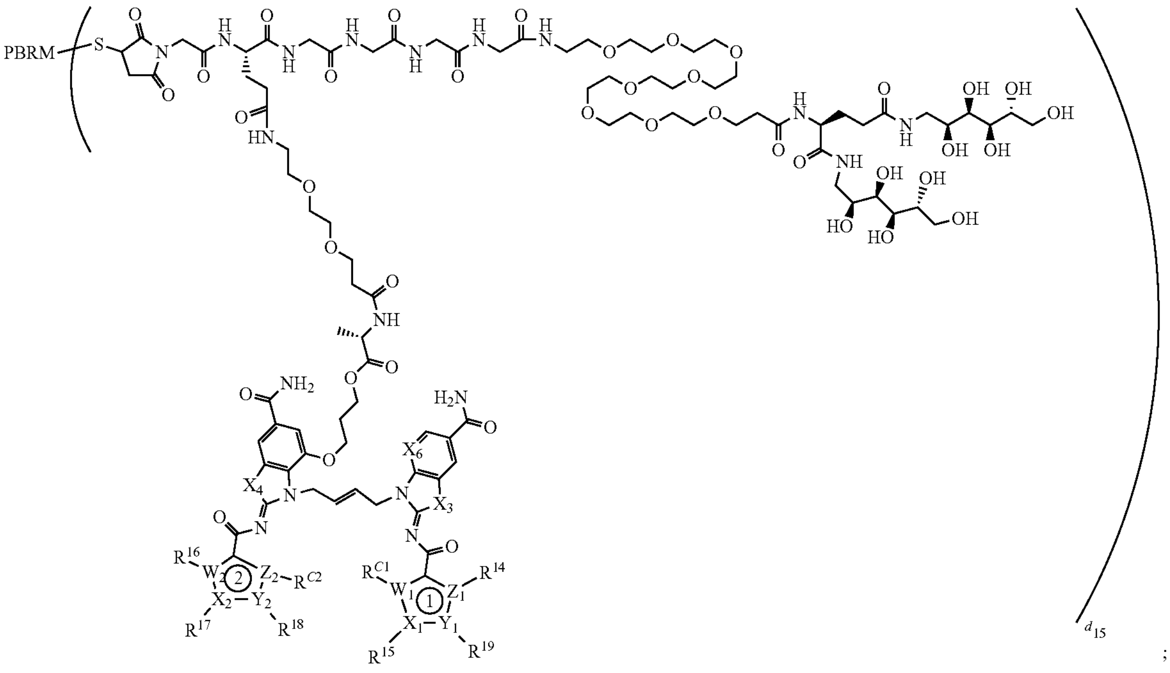
; or
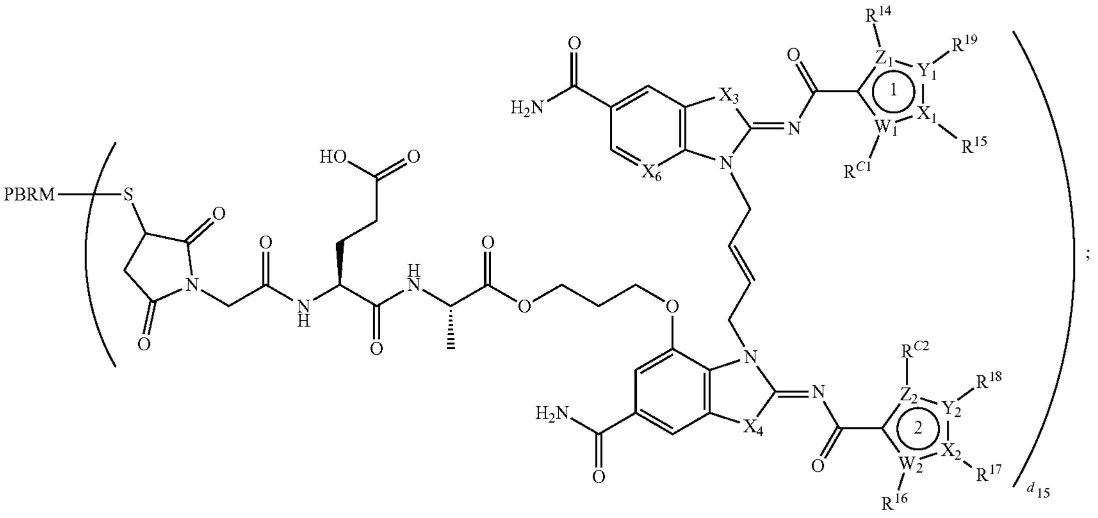
;
wherein $d_{15}$, $R^{14}$, $R^{15}$, $R^{16}$, $R^{17}$, $R^{18}$, $R^{19}$, $R^{C1}$, $R^{C2}$, $X_3$, $X_4$, $X_6$, $X_1$, $W_1$, $Y_1$, $Z_1$, $X_2$, $W_2$, $Y_2$, $Z_2$, are as defined herein.
In some embodiments, the conjugate is:

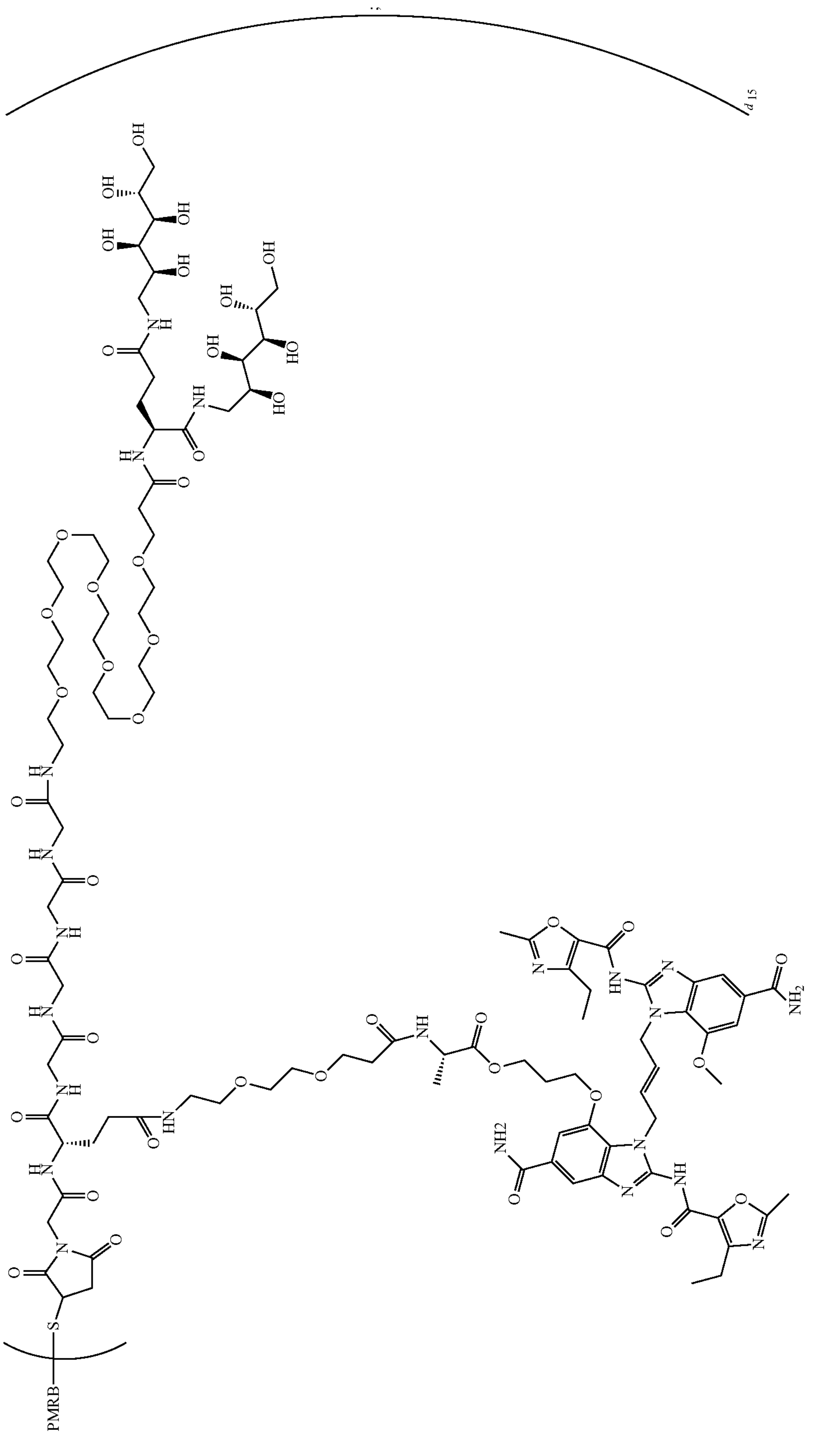

-continued
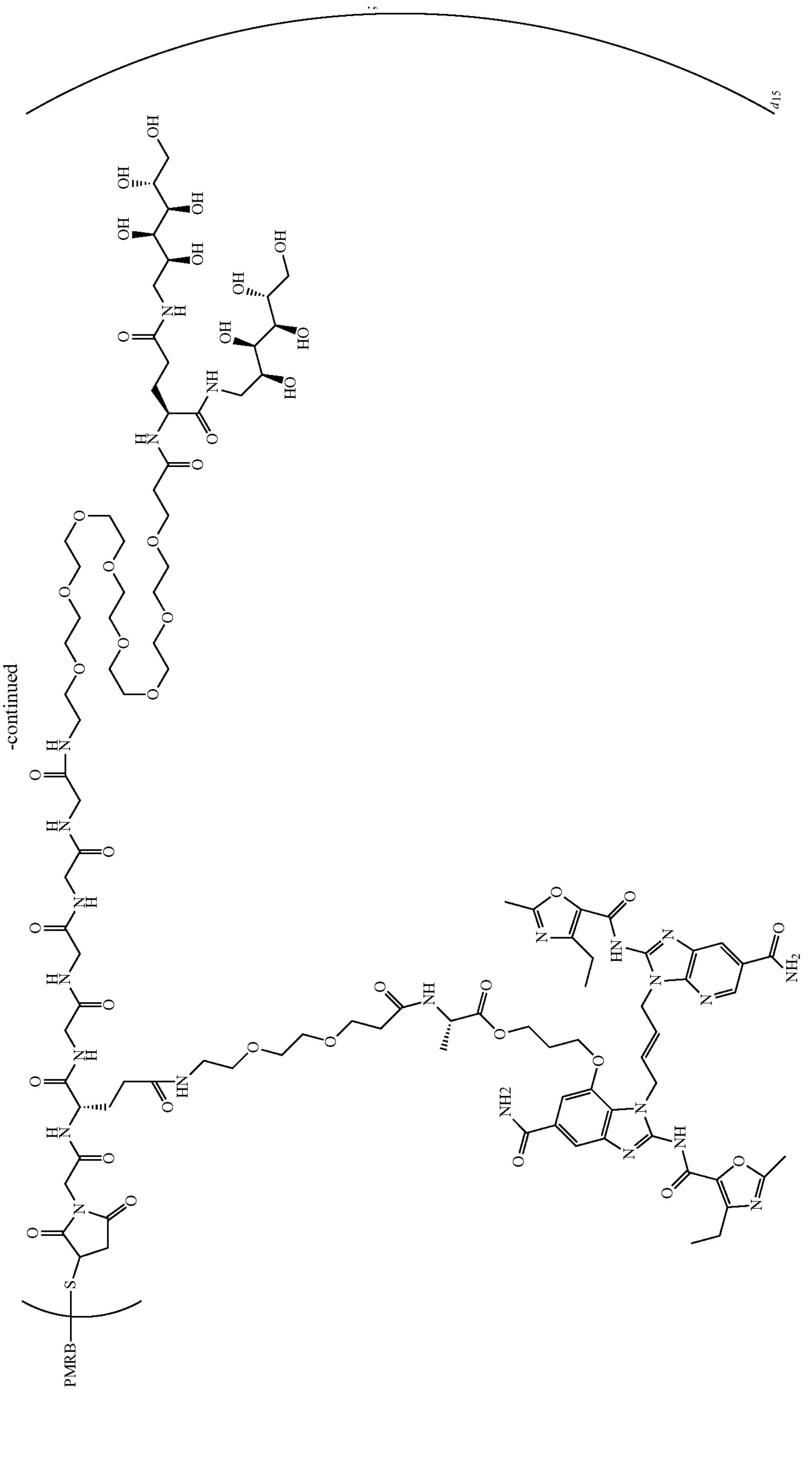

-continued
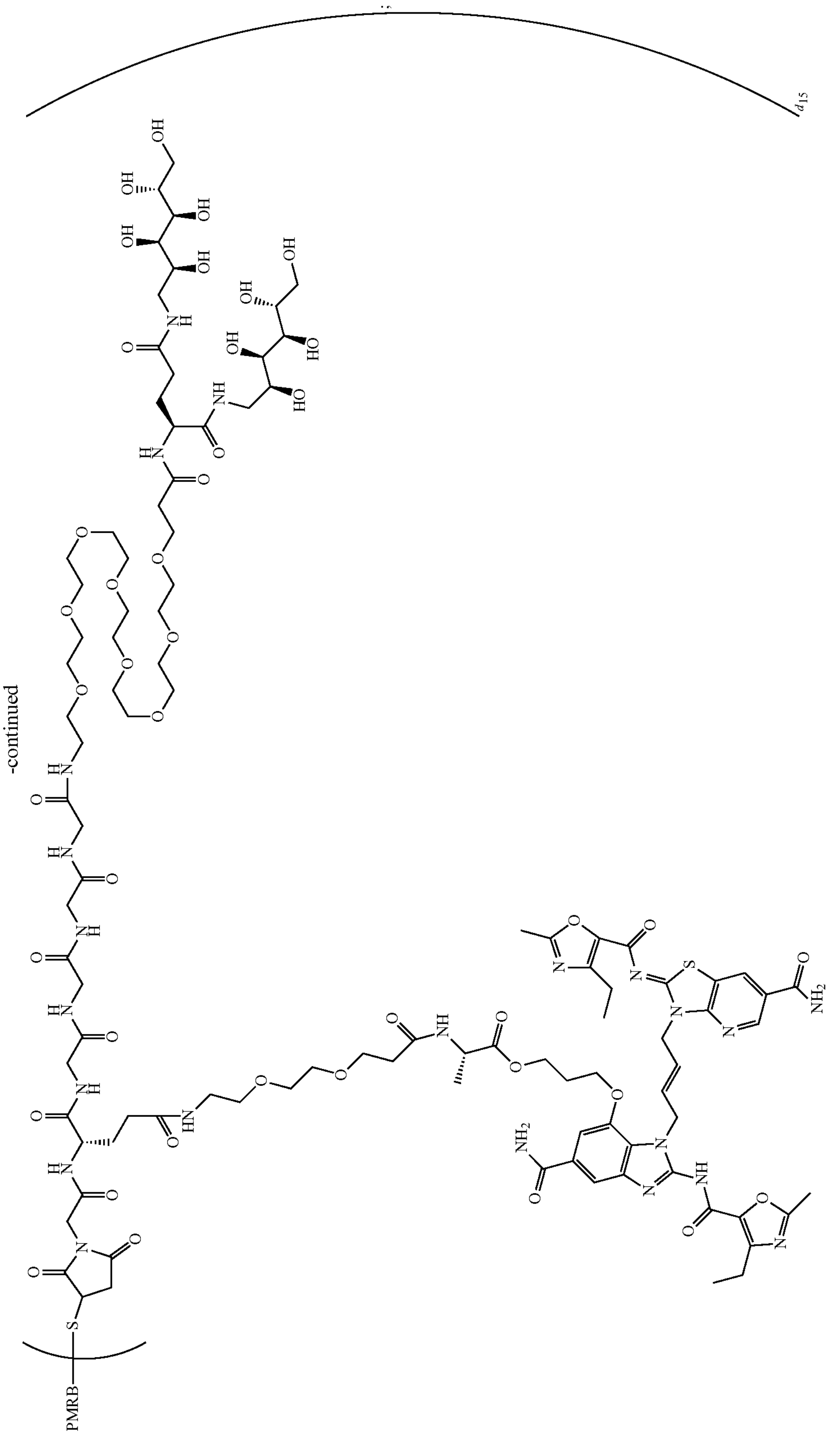

-continued
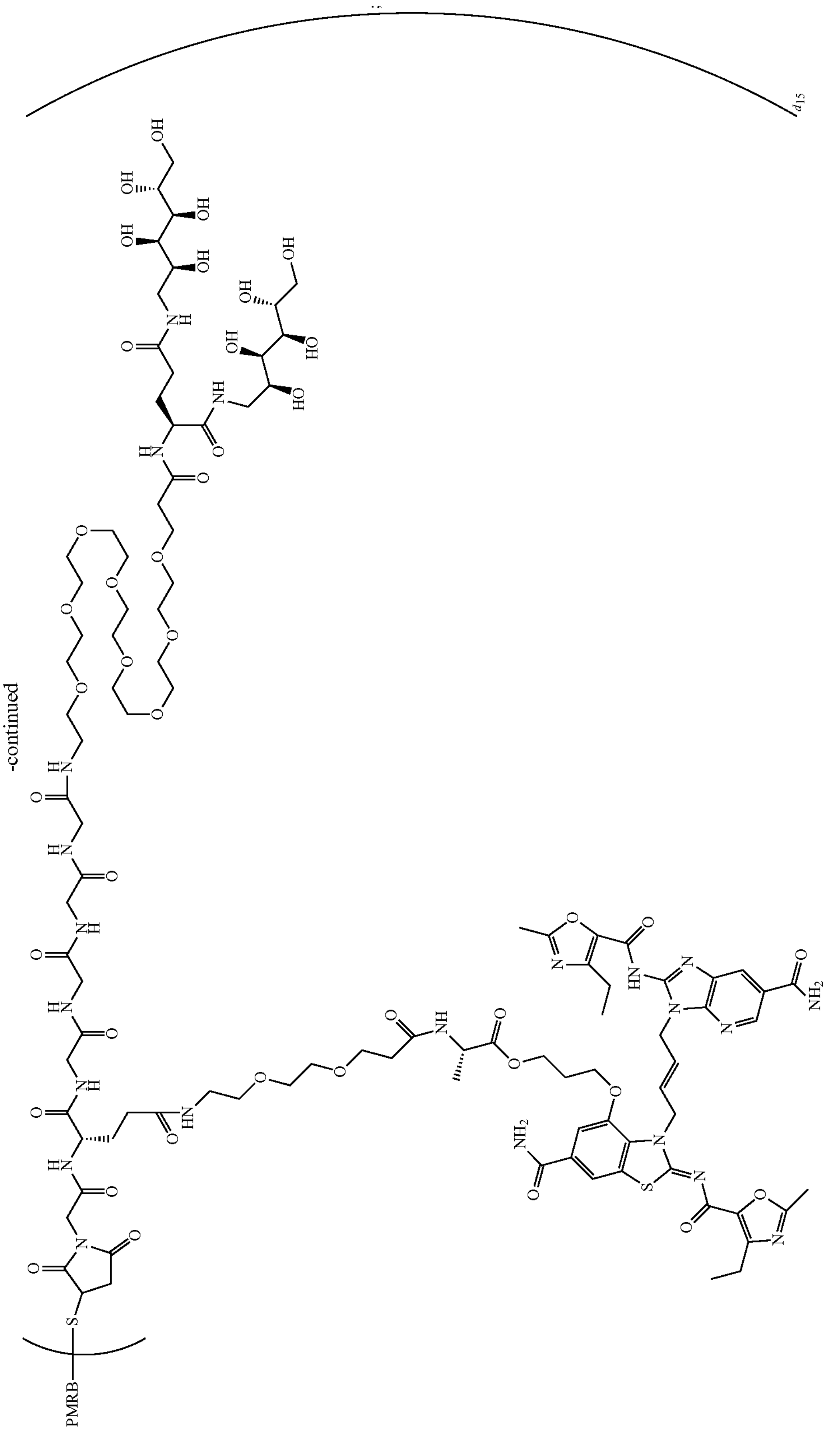

-continued
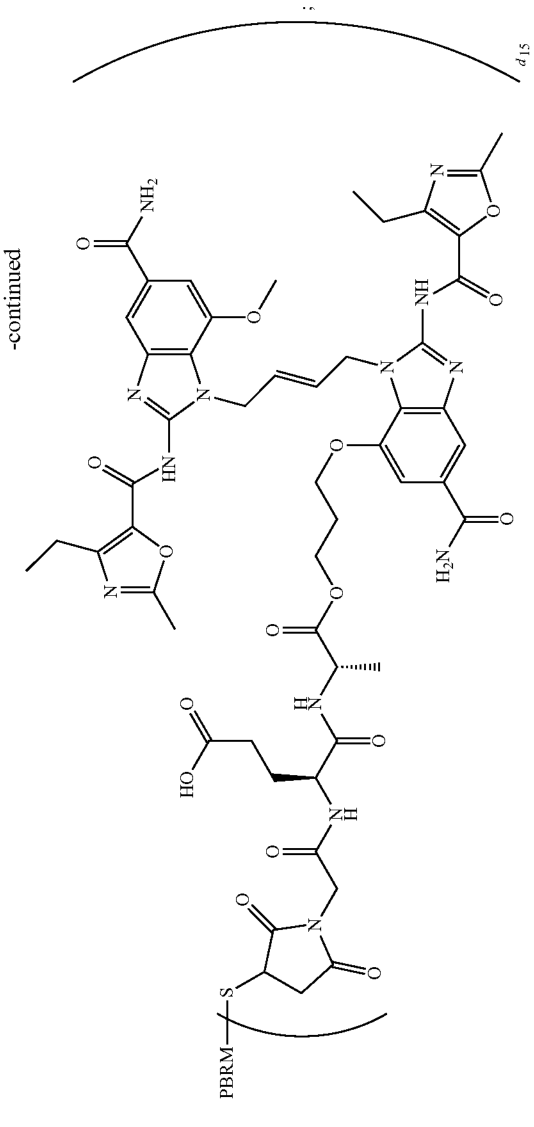
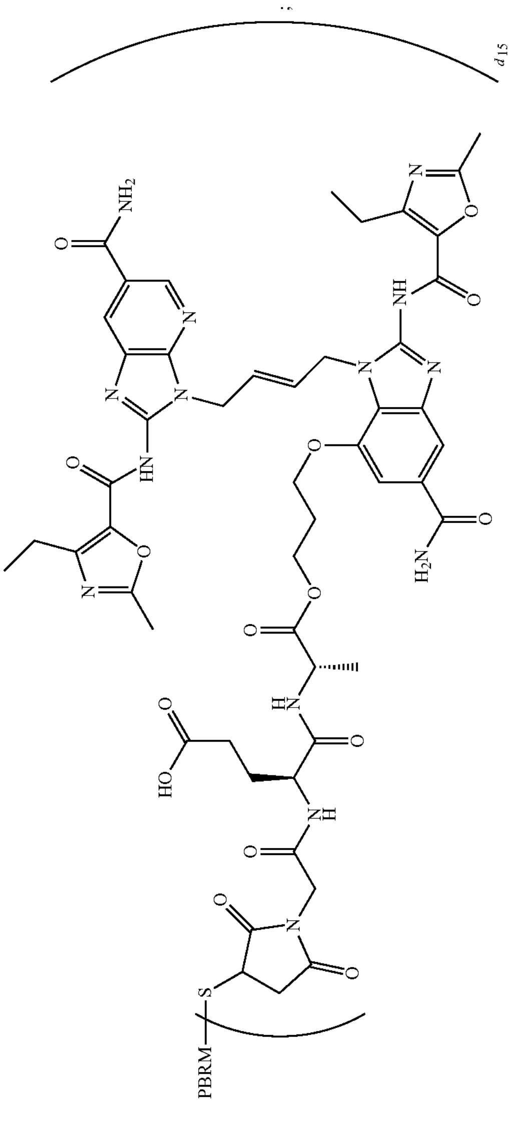

-continued
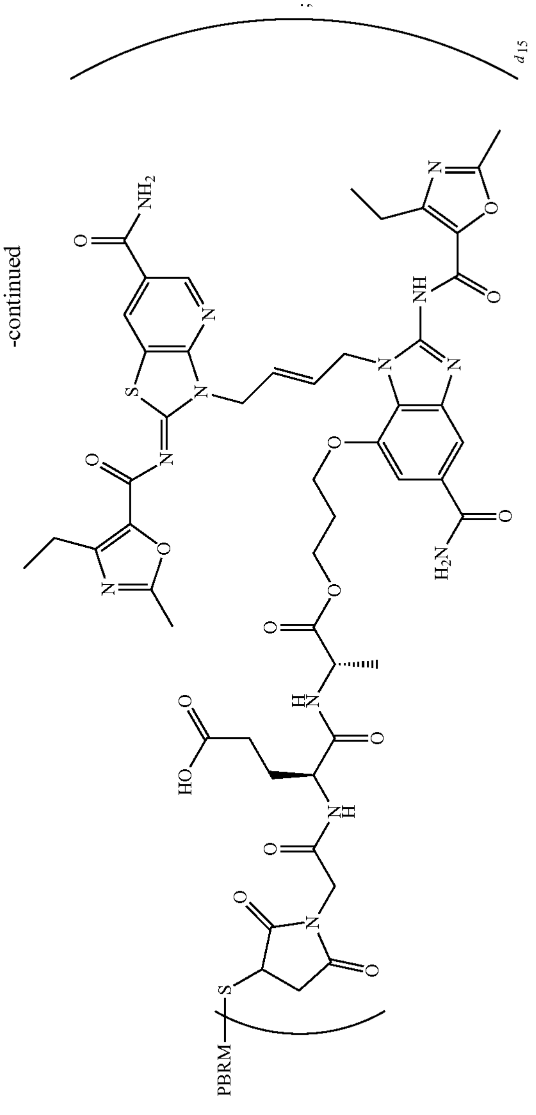
; or
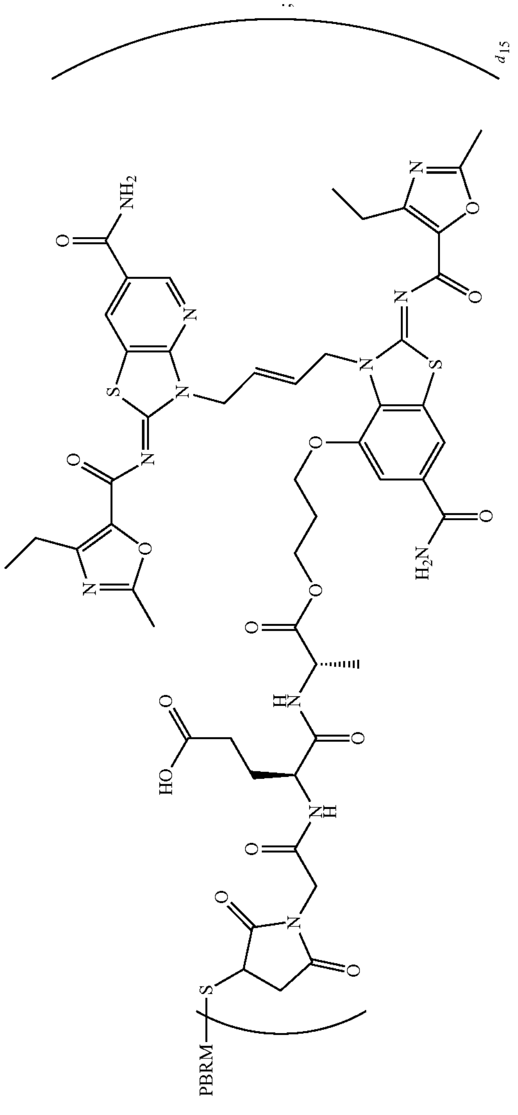
;

wherein $d_{15}$ is as defined herein.

Pharmaceutical Compositions

In some aspects, the present disclosure provides pharmaceutical compositions comprising a conjugate described herein and one or more pharmaceutically acceptable carriers or excipients.

The pharmaceutical compositions containing conjugates of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the conjugates into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the conjugates in the required amount in an appropriate solvent with one or a combination of ingredients enumerated above, as required, followed by filtered sterilization. Generally, dispersions are prepared by incorporating the conjugates into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the conjugates can be incorporated with excipients and used in the form of tablets, troches, or capsules. Oral compositions can also be prepared using a fluid carrier for use as a mouthwash, wherein conjugates in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the conjugates are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the conjugates are formulated into ointments, salves, gels, or creams as generally known in the art.

The conjugates can be prepared with pharmaceutically acceptable carriers that will protect the conjugates against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of conjugates can be calculated to produce the desired therapeutic effect in association with the required pharmaceutical carrier. The specification for the dosage unit forms of the disclosure are dictated by and directly dependent on the unique characteristics of the conjugates and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease.

It is understood that the pharmaceutical compositions can be included in a container, pack, or dispenser together with instructions for administration.

Methods of Use

In some embodiments, the present disclosure provides a method of treating or preventing a disease or disorder in a subject in need thereof, comprising administering to the subject a therapeutically effective amount of a conjugate disclosed herein.

In some embodiments, the present disclosure provides a method of treating a disease or disorder in a subject in need thereof, comprising administering to the subject a therapeutically effective amount of a conjugate disclosed herein.

In some embodiments, the present disclosure provides a method of activating or enhancing an activity of a STING in a subject, comprising administering to the subject a conjugate disclosed herein.

In some embodiments, the present disclosure relates to a method of treating a cancer in a subject in need thereof, comprising administering to the subject an effective amount of a conjugate disclosed herein.

In some embodiments, the present disclosure provides a conjugate disclosed herein for use in treating or preventing a disease or disorder in a subject in need thereof.

In some embodiments, the present disclosure provides a conjugate disclosed herein for use in treating a disease or disorder in a subject in need thereof.

In some embodiments, the present disclosure provides a conjugate disclosed herein for treating a STING-mediated disease or disorder in a subject.

In some embodiments, the present disclosure provides use of a conjugate disclosed herein for treating a cancer in a subject in need thereof.

In some embodiments, the present disclosure provides use of a conjugate disclosed herein in the manufacture of a medicament for treating a disease or disorder in a subject in need thereof.

In some embodiments, the present disclosure provides use of a conjugate disclosed herein in the manufacture of a medicament for treating or preventing a disease or disorder in a subject in need thereof.

In some embodiments, the present disclosure provides use of a conjugate disclosed herein in the manufacture of a medicament for treating a STING-mediated disease or disorder in a subject.

In some embodiments, the present disclosure provides use of a conjugate disclosed herein in the manufacture of a medicament for treating a cancer in a subject in need thereof.

In some embodiments, the present disclosure provides use of a conjugate disclosed herein for the treatment or prevention of a disease or disorder in a subject in need thereof.

In some embodiments, the present disclosure provides use of a conjugate disclosed herein for the treatment of a disease or disorder in a subject in need thereof.

In some embodiments, the present disclosure provides use of a conjugate disclosed herein for treating a STING-mediated disease or disorder in a subject.

In some embodiments, the present disclosure provides use of a conjugate disclosed herein for treatment of a cancer in a subject in need thereof.

In some embodiments, the conjugate disclosed herein is administered to the subject.

In some embodiments, the present disclosure provides a method of treating or preventing a disease or disorder in a subject in need thereof, comprising administering to the subject an efficient amount of at least one conjugate of the disclosure; wherein said conjugate releases one or more therapeutic agent upon biodegradation.

In some embodiments, the present disclosure provides a method of treating a disease or disorder in a subject in need thereof, comprising administering to the subject an efficient amount of at least one conjugate of the disclosure; wherein said conjugate releases one or more therapeutic agent upon biodegradation.

In some embodiments, the present disclosure the conjugate is an antibody-STING agonist conjugate. In some embodiments, the disease or disorder is cancer.

In some embodiments, the disclosure provides methods of treatment or prevention of STING mediated diseases and disorders. Exemplary diseases/disorders include, but are not limited to, cancer, infectious disease (e.g., HIV, HBV, HCV, HPV, and influenza), and vaccine adjuvant.

In some embodiments, the STING pathway may induce anti-tumor immunity by upregulating IFNβ and interferon (IFN)-stimulated genes (ISGs) in many cell types within tumors in response to agonistic, cytosolic nucleic acids.

In some embodiments, the present disclosure provides a conjugate disclosed herein for use as a vaccine adjuvant. There is also therefore provided an immunogenic composition or vaccine adjuvant comprising a conjugate disclosed herein.

In some embodiments, there is provided a composition comprising a conjugate disclosed herein, and one or more immunostimulatory agents.

In some embodiments, the present disclosure provides the use of a conjugate disclosed herein, in the manufacture of a vaccine. In some embodiments, the present disclosure provides use of a conjugate disclosed herein, for the manufacture of an immunogenic composition or a vaccine composition comprising an antigen or antigenic composition, for the treatment or prevention of disease.

In some embodiments, the disclosure is directed to a method of treating or preventing disease comprising the administration to a human subject suffering from or susceptible to disease, an immunogenic composition or a vaccine composition comprising an antigen or antigenic composition and a conjugate disclosed herein.

In some embodiments, the disease or disorder is inflammation, an autoimmune disease, an allergic disease, an infectious disease, an HIV infection, an AIDS infection, an HCV infection, influenza or a human papillomavirus (HPV) infection. The scope of the diseases would be readily recognized by a skilled artisan in the field. In some embodiments, these diseases are as described in PCT Application No. PCT/US2020/044538, the contents of which is hereby incorporated by reference in its entirety.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

In some embodiments, the disease or disorder is a precancerous syndrome.

The conjugate of the present disclosure may be used to treat inflammation of any tissue and organs of the body, including musculoskeletal inflammation, vascular inflammation, neural inflammation, digestive system inflammation, ocular inflammation, inflammation of the reproductive system, and other inflammation. The scope of the diseases would be readily recognized by a skilled artisan in the field. In some embodiments, these diseases are as described in PCT Application No. PCT/US2020/044538, the contents of which is hereby incorporated by reference in its entirety.

Examples of cancer diseases and conditions wherein the conjugate of the present disclosure may have potentially beneficial antitumor effects include, but are not limited to, cancers of the lung, bone, pancreas, skin, head, neck, uterus, ovaries, stomach, colon, breast, esophagus, biliary, small intestine, bowel, endocrine system, thyroid gland, parathyroid gland, adrenal gland, urethra, prostate, penis, testes, ureter or urothelial, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

In some embodiments, the disease or disorder is a solid tumor. In one aspect the tumor is selected from head and neck cancer, gastric cancer, melanoma, renal cell carcinoma (RCC), esophageal cancer, biliary cancer, non-small cell lung carcinoma (NSCLC), prostate cancer, colorectal cancer (CRC), colon cancer, ovarian cancer, endometrial cancer, urothelial cancer, cervical cancer, bladder cancer, papillary thyroid cancer, papillary renal cell cancer, cholangiocarcinoma, salivary duct cancer, kidney cancer, cervical cancer and pancreatic cancer. In some embodiments, the human has a liquid tumor such as diffuse large B cell lymphoma (DLBCL), multiple myeloma, chronic lymphoblastic leukemia (CLL), follicular lymphoma, acute myeloid leukemia, and chronic myelogenous leukemia. In some embodiments, the disease or disorder is a skin cancer (e.g., non-melanoma skin cancer, squamous cell carcinoma, basal cell carcinoma) or actinic keratosis. In addition to a field effect for clearing superficial skin cancers, the conjugate of the present disclosure may prevent the development of subsequent skin cancers and pre-malignant actinic keratosis in treated subjects.

In some embodiments, the disease or disorder is bladder cancer, breast cancer, colorectal cancer, colon cancer, endometrial cancer, gastric cancer, esophageal cancer, biliary cancer, urothelial cancer, head and neck squamous carcinoma, melanoma, non-small cell lung cancer, ovarian cancer, or pancreatic cancer. In some embodiments, the disease or disorder is breast cancer, gastric cancer, colorectal cancer, colon cancer, esophageal cancer, biliary cancer, endometrial cancer, urothelial cancer or non-small cell lung cancer.

In some embodiments the breast cancer is HER2 amplified/overexpressed breast cancer or HER2 low breast cancer.

In some embodiments, the endometrial cancer is serous endometrial cancer.

The conjugate of the present disclosure may also be useful in the treatment of one or more diseases afflicting mammals which are characterized by cellular proliferation in the area of disorders associated with neo-vascularization and/or vascular permeability, fibrotic disorders, and metabolic disorders. The scope of the diseases would be readily recognized by a skilled artisan in the field. In some embodiments, these diseases are as described in PCT Application No. PCT/US2020/044538, the contents of which is hereby incorporated by reference in its entirety.

In some embodiments, the disease or disorder is a neurodegenerative diseases. Exemplary neurodegenerative diseases includes, but are not limited to, multiple sclerosis, Huntington's disease, Alzheimer's disease, Parkinson's disease, amyotrophic lateral sclerosis (ALS). The scope of the diseases would be readily recognized by a skilled artisan in the field. In some embodiments, these diseases are as described in U.S. Provisional Application Nos. 62/882,081, 62/944,643, and 62/982,935, the contents of which are hereby incorporated by reference in their entirety.

In some embodiments, the disease or disorder is an infectious disease, which is any disease instigated by or coincident with an infection from a pathogen, derived from bacteria, derived from the DNA virus families, or RNA virus families. The scope of the diseases would be readily recognized by a skilled artisan in the field. In some embodiments, these diseases are as described in PCT Application No. PCT/US2020/044538, the contents of which is hereby incorporated by reference in its entirety.

The conjugates of the present disclosure may be employed alone or in combination with other therapeutic agents. As modulators of the immune response, the conjugates of the present disclosure may also be used in monotherapy or in combination with another therapeutic agent in the treatment of diseases and conditions wherein modulation of STING is beneficial. Combination therapies according to the present disclosure thus comprise the administration of a conjugate of the present disclosure or a pharmaceutically acceptable salt thereof, and at least one other therapeutically active agent. In some embodiments, combination therapies according to the present disclosure comprise the administration of at least one conjugate of the present disclosure or a pharmaceutically acceptable salt thereof, and at least one other therapeutic agent. The conjugate(s) of the present disclosure and pharmaceutically acceptable salts thereof, and the other therapeutic agent(s) may be administered together in a single pharmaceutical composition or separately and, when administered separately this may occur simultaneously or sequentially in any order. The amounts of the conjugate(s) of the present disclosure and pharmaceutically acceptable salts thereof, and the other therapeutic agent(s) and the relative timings of administration will be selected in order to achieve the desired combined therapeutic effect. Thus, in a further aspect, there is provided a combination comprising a conjugate of the present disclosure or a pharmaceutically acceptable salt thereof, together with one or more other therapeutic agents.

The conjugate of the present disclosure and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators, methotrexate, leukotriene modulators, monoclonal antibody therapy, receptor therapies, or antigen non-specific immunotherapies.

The conjugate of the present disclosure and pharmaceutically acceptable salts thereof may be used in combination with radiotherapy and/or surgery and/or at least one other therapeutic agent which may be useful in the treatment of cancer and pre-cancerous syndromes. Any anti-neoplastic agent, anti-microtubule, anti-mitotic agent, hormone, hormonal analogues signal transduction pathway inhibitor, protein tyrosine kinase, or anti-angiogenic therapeutic agent, may be utilized in the combination. The scope of the other therapeutic agents would be readily recognized by a skilled artisan in the field. In some embodiments, the other therapeutic agent is as described in PCT Application No. PCT/US2020/044538, the contents of which is hereby incorporated by reference in its entirety.

Agents used in immunotherapeutic regimens, therapeutic agents used in proapoptotic regimens, or cell cycle signaling inhibitors may also be useful in combination with the conjugate of the present disclosure.

In some embodiments, the combination of the present disclosure comprises a conjugate of the present disclosure or a salt, particularly a pharmaceutically acceptable salt thereof, and at least one anti-neoplastic agent, anti-microtubule, anti-mitotic agent, hormone, hormonal analogues signal transduction pathway inhibitor, protein tyrosine kinase, or anti-angiogenic therapeutic agent, or a combination thereof.

Additional examples of other therapeutic agents (e.g., anti-neoplastic agent) for use in combination or co-administered with a conjugate of the present disclosure or a pharmaceutically acceptable salt thereof are immuno-modulators.

In some embodiments, the combination of the present disclosure comprises a conjugate of the present disclosure or a salt, particularly a pharmaceutically acceptable salt thereof, and at least one immuno-modulator or at least one immunostimulatory agent.

As used herein "immuno-modulators" refer to any substance including monoclonal antibodies that affects the immune system. Immuno-modulators can be used as anti-neoplastic agents for the treatment of cancer. For example, immune-modulators include, but are not limited to, anti-CTLA-4 antibodies and anti-PD-1 antibodies. Other immuno-modulators include, but are not limited to, ICOS antibodies, OX-40 antibodies, PD-L1 antibodies, LAG3 antibodies, TIM-3 antibodies, 41BB antibodies and GITR antibodies.

Additional examples of other therapeutic agents (anti-neoplastic agent) for use in combination or co-administered with a conjugate of the present disclosure are anti-PD-L1 agents (i.e. anti-PD-L1 antibodies) or PD-1 antagonists.

Thus, in some embodiments, methods of treating a human in need thereof are provided comprising administering a conjugate of the present disclosure or a salt thereof and at least one immuno-modulator. In some embodiments, the immuno-modulator is selected from an ICOS agonist antibody, an OX-40 antibody, and a PD-1 antibody. In some embodiments, the human has cancer. Also provided herein is the use of a conjugate of the present disclosure or a salt thereof in combination with at least one immuno-modulator for the treatment of a human in need thereof.

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS. As used herein "immunostimulatory agent" refers to any agent that can stimulate the immune system. As used herein immunostimulatory agents include, but are not limited to, vaccine adjuvants.

The term "Toll-like receptor" (or "TLR") as used herein refers to a member of the Toll-like receptor family of proteins or a fragment thereof that senses a microbial product and/or initiates an adaptive immune response. In some embodiments, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity In some embodiments, the immunostimulatory agent for use in combination with the conjugate of the present disclosure is a TLR4 agonist.

Thus, in some embodiments, methods of treating a human in need thereof are provided comprising administering a conjugate of the present disclosure or a salt thereof and at least one immunostimulatory agent. In some embodiments, the immunostimulatory agent is a TLR4 agonist. In some embodiments, the immunostimulatory agent is an AGP. In some embodiments, the human has cancer. Also provided herein is the use a conjugate of the present disclosure or a salt thereof in combination with at least one immunostimulatory agent for the treatment of a human in need thereof.

In addition to the immunostimulatory agents described above, the compositions of the present disclosure may further comprise other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs).

Because of their adjuvant qualities, TLR agonists may be used in combinations with other vaccines, adjuvants and/or immune modulators, and may be combined in various combinations. In some embodiments, the conjugate of the present disclosure bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Further active ingredients (antineoplastic agents) for use in combination or co-administered with the conjugate of the present disclosure are IDO inhibitors.

In some embodiments, the conjugate of the disclosure may be employed in combination with at least one other therapeutic agent useful in the prevention or treatment of infectious diseases bacterial infections, viral infections, Kaposi's sarcoma-associated herpesvirus infections, TB infections, *Chlamydia, Plasmodium* infection, *staphylococcus* infections, amyotrophic lateral sclerosis (ALS), multiple sclerosis, systemic lupus erythematosus and related lupus disorders, psoriasis, or Sjogren's syndrome, The conjugates of the disclosure may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

In addition to the above described routes of administration suitable for treatment of oncology, the pharmaceutical compositions may be adapted for administration by intratumoral or peritumoral injection. The intratumorally or peritumoral injection of a conjugate of the present disclosure directly into or adjacent to a single solid tumor is expected to elicit an immune response that can attack and destroy cancer cells throughout the body, substantially reducing and in some cases permanently eliminating the tumor from the diseased subject. The activation of the immune system in this manner to kill tumors at a remote site is commonly known as the abscopal effect and has been demonstrated in animals with multiple therapeutic modalities. A further advantage of local or intratumoral or peritumoral administration is the ability to achieve equivalent efficacy at much lower doses, thus minimizing or eliminating adverse events that may be observed at much higher systemic doses The conjugates of the disclosure may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a conjugate of the disclosure depend on the pharmacokinetic properties of that conjugate, such as absorption, distribution, and half-life, which can be determined by the skilled artisan. In addition, suitable dosing regimens, including the duration such regimens are administered, for a conjugate of the disclosure depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg, preferably, total daily dosages range from 1 mg to 250 mg.

For use in therapy, the conjugates of the disclosure will be normally, but not necessarily, formulated into a pharmaceutical composition prior to administration to a patient. Accordingly, the disclosure also is directed to pharmaceutical compositions comprising a conjugate of the disclosure and at least one pharmaceutically acceptable excipient.

The pharmaceutical compositions of the disclosure may be prepared and packaged in bulk form or in unit dosage form. For oral application, for example, one or more tablets or capsules may be administered. A dose of the pharmaceutical composition contains at least a therapeutically effective amount of a conjugate of the present disclosure (i.e., a conjugate of the present disclosure or a salt, particularly a pharmaceutically acceptable salt, thereof). When prepared in unit dosage form, the pharmaceutical compositions may contain from 1 mg to 1000 mg of a conjugate of the present disclosure.

As provided herein, unit dosage forms (pharmaceutical compositions) comprising from 1 mg to 1000 mg of a conjugate of the disclosure may be administered one, two, three, or four times per day, preferably one, two, or three times per day, and more preferably, one or two times per day, to effect treatment of a STING-mediated disease or disorder.

The pharmaceutical compositions of the disclosure typically contain one conjugate of the disclosure. However, in certain embodiments, the pharmaceutical compositions of the disclosure contain more than one conjugate of the disclosure. In addition, the pharmaceutical compositions of the disclosure may optionally further comprise one or more additional therapeutic agents, (e.g., pharmaceutically active conjugates).

As used herein, "pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the conjugate of the disclosure when administered to a patient and interactions which would result in pharmaceutical compositions that are not pharmaceutically acceptable are avoided. In addition, each excipient must of course be of sufficiently high purity to render it pharmaceutically acceptable.

The conjugates of the disclosure and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the conjugate or conjugates of the disclosure once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the disclosure. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In one aspect, the disclosure is directed to a solid oral dosage form such as a tablet or capsule comprising an effective amount of a conjugate of the disclosure and a diluent or filler. The oral solid dosage form may further comprise a disintegrant or a lubricant.

It will be understood that the conjugates of the present disclosure may also be formulated with vaccines as adjuvants to modulate their activity. Such compositions may contain antibody (antibodies) or antibody fragment(s) or an antigenic component, optionally together with one or more other components with adjuvant activity.

Certain compounds and/or conjugates of the disclosure may be potent immunomodulators and accordingly, care should be exercised in their handling. The disclosure having been described, the following examples are offered by way of illustration and not limitation.

In some embodiments, the conjugate is Formula BB (BB)
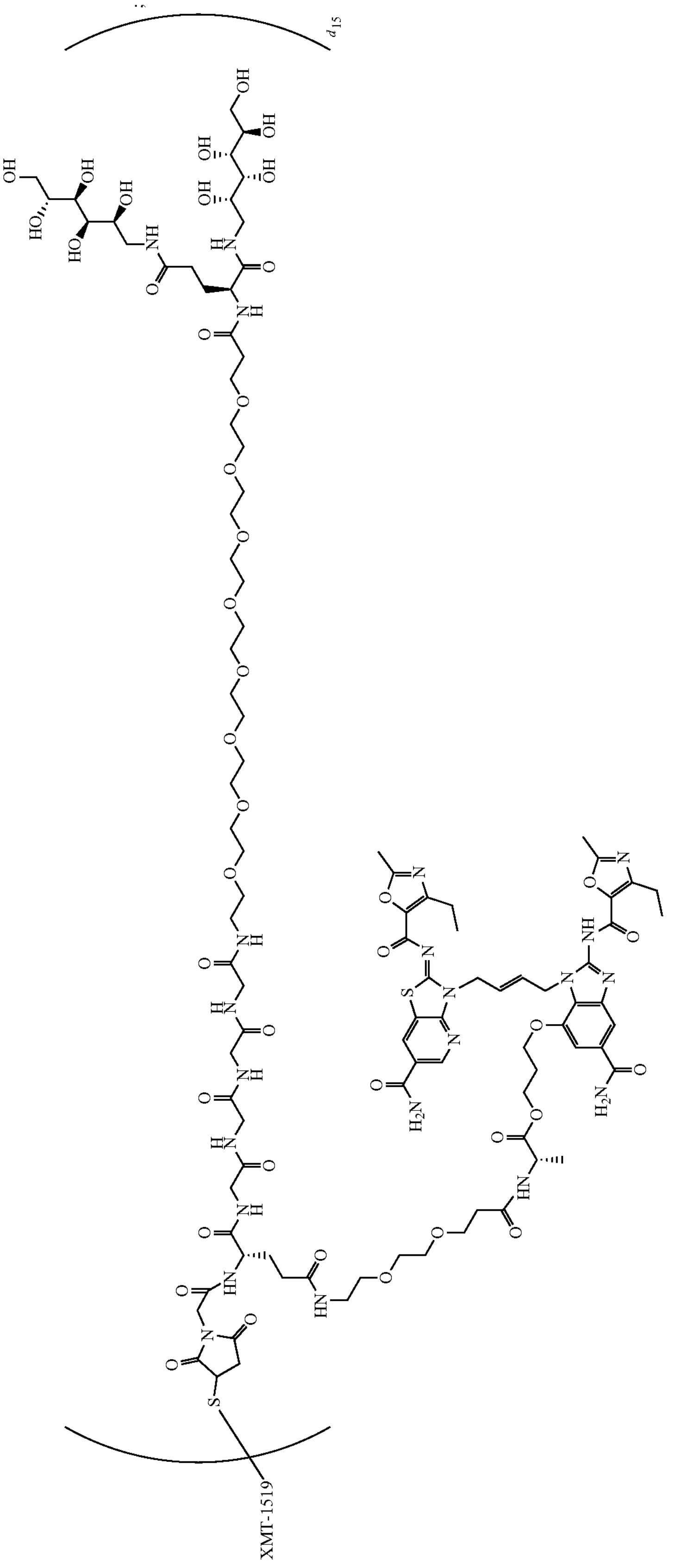

wherein the conjugate comprises the XMT-1519 antibody comprises a variable heavy chain complementarity determining region 1 (CDRH1) comprising the amino acid sequence FTFSSYSMN (SEQ ID NO: 20); a variable heavy chain complementarity determining region 2 (CDRH2) comprising the amino acid sequence YISSSSSTIYYADSVKG (SEQ ID NO: 21); a variable heavy chain complementarity determining region 3 (CDRH3) comprising the amino acid sequence GGHGYFDL (SEQ ID NO: 22); and a variable light chain complementarity determining region 1 (CDRL1) comprising the amino acid sequence RASQSVSSSYLA (SEQ ID NO: 27); a variable light chain complementarity determining region 2 (CDRL2) comprising the amino acid sequence GASSRAT (SEQ ID NO: 28); and a variable light chain complementarity determining region 3 (CDRL3) comprising the amino acid sequence QQYHHSPLT (SEQ ID NO: 29), and $d_{15}$ is about 8.

In some embodiments, the conjugate is Formula CC (CC)
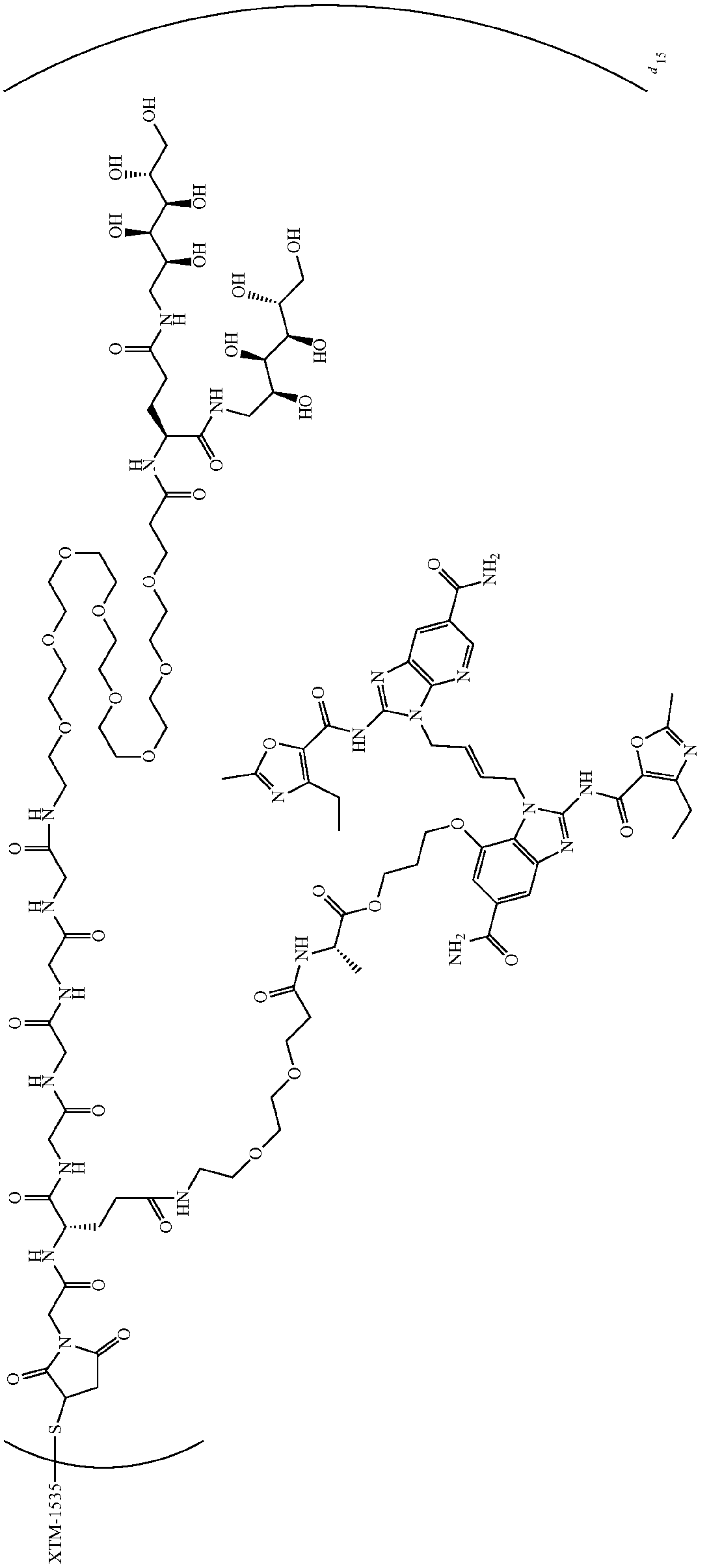

wherein the conjugate comprises the XMT-1535 antibody comprising: a CDRH1 comprising the amino acid sequence GYTFTGYNIH (SEQ ID NO: 5); a CDRH2 comprising the amino acid sequence AIYPGNGDTSYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); a CDRL3 comprising the amino acid sequence QQYSKLPLT (SEQ ID NO: 10) and $d_{15}$ is about 8.

In some embodiments, a conjugate of Formula BB or Formula CC is useful for treating a disease or disorder in a subject in need thereof, comprising administering to the subject a therapeutically effective amount of the conjugate of Formula BB or Formula CC. In some embodiments, the disease or disorder is cancer.

In some embodiments, for the conjugate of Formula BB, the cancer is breast cancer, gastric cancer, colorectal cancer, esophageal cancer, biliary cancer, endometrial cancer, urothelial cancer or non-small cell lung cancer. In some embodiments the breast cancer is HER2 amplified/overexpressed breast cancer or HER2 low breast cancer. In some embodiments, the endometrial cancer is serous endometrial cancer.

In some embodiments, for the conjugate of Formula CC, is useful for treating a NaPi2b-expressing tumor in a subject in need thereof. In some embodiments, the NaPi2b-expressing tumor is ovarian cancer, non-small cell lung cancer (NSCLC), papillary thyroid cancer, endometrial cancer, cholangiocarcinoma, papillary renal cell cancer, clear cell renal cancer, breast cancer, kidney cancer, cervical cancer or salivary duct cancer.

In some embodiments, the subject has epithelial ovarian cancer, fallopian tube cancer, primary peritoneal cancer, platinum resistant ovarian cancer, non-squamous NSCLC cancer, progressive, radioactive iodine-refractory, loco-regional recurrent or metastatic disease papillary thyroid cancer or epithelial endometrial cancer.

In some embodiments, the conjugate of Formula BB is useful for treating a disease or disorder in a subject in need thereof, comprising administering to the subject a therapeutically effective amount of the conjugate of Formula BB in combination with one or more therapeutic agents. In some embodiments, the therapeutic agent is an immuno-modulator agent or an immunostimulatory agent. In some embodiments, the immune-modulator agent is an anti-CTLA-4 antibody, an anti-PD-1 antibody, an ICOS antibody, an OX-40 antibody, a PD-L1 antibody, a LAG3 antibody, a TIM-3 antibody, a 41BB antibody or a GITR antibody.

In some embodiments the conjugate of Formula BB is useful for treating a disease or disorder in a subject in need thereof, comprising administering to the subject a therapeutically effective amount of the conjugate of Formula BB in combination with one or more HER2 antibodies that bind to a different epitope of HER2 than the HER2 antibody XMT-1519. In some embodiments the HER2 antibody that binds to a different of HER2 than the HER2 antibody XMT-1519 is trastuzumab, pertuzumab, Fab37, or chA21.

EXAMPLES

The following examples illustrate the disclosure. These examples are not intended to limit the scope of the present disclosure, but rather to provide guidance to the skilled artisan to prepare and use the Compounds, compositions, and methods of the present disclosure. While particular embodiments of the present disclosure are described, the skilled artisan will appreciate that various changes and modifications can be made without departing from the spirit and scope of the disclosure.

It will be understood that certain Compounds of the disclosure may be potent immunomodulators and accordingly, care should be exercised in their handling.

The reactions described herein are applicable for producing Compounds of the disclosure having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. Suitable protecting groups and the methods for protecting and de-protecting different substituents using such suitable protecting groups are well known to those skilled in the art; examples of which may be found in T. W. Greene 'Protective Groups in Organic Synthesis' (4th edition, J. Wiley and Sons, 2006). Unless otherwise noted, all starting materials were obtained from commercial suppliers and used without further purification.

ABBREVIATIONS

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

| | |
|---|---|
| ACN | Acetonitrile |
| CDI | 1,1'-Carbonyldiimidazole |
| DCC | N,N'-Dicyclohexylcarbodiimide |
| DCM | Dichloromethane |
| DIPEA | N,N-Diisopropylethylamine |
| DMA | Dimethylacetamide |
| DMF | Dimethylformamide |
| DMPA | Dimethylolpropionic acid |
| ESI | Electrospray ionization |
| HATU | 2-(1H-7-Azabenzotriazol-1-yl)-1,1,3,3-tetramethyluronoium hexafluorphosphate |
| HIC | Hydrophobic interaction chromatography |
| HOBt | Hydroxybenzotriazole |
| HPLC | High pressure liquid chromatography |
| MeOH | Methanol |
| SEC | Size exclusion chromatography |
| TFA | Trifluoroacetic acid |
| THF | Tetrahydrofuran |
| PyBOP | (Benzotriazole-1-yloxy)tripyrrolidinophosphonium hexafluorophosphate |

General Information

All reagents were purchased from relevant providers unless otherwise stated.

The diABZI STING agonist was prepared as described in Ramanjulu et al (Nature, 564(7736):439-443 (2018)).

XMT-1535 (anti-NaPi2b antibody) is disclosed in co-pending application U.S. Ser. No. 15/457,574, filed Mar. 13, 2017, the entire contents of which are incorporated herein by reference. XMT-1519 (anti-Her2 antibody) is disclosed in U.S. Pat. No. 9,555,112, issued Jan. 31, 2017 and U.S. Pat. No. 9,738,720, issued Aug. 22, 2017, the entire contents of which are incorporated herein by reference.

XMT-1535 AF-HPA ADC, DAR 5.9 and Rituximab AF-HPA ADC, DAR 5.5, were prepared as described in co-pending application U.S. 62/958,916, filed Jan. 9, 2020, and U.S. 63/040,735, filed Jun. 18, 2020, the entire contents of which are incorporated herein by reference.

HPLC purification was performed on a Phenomenex Gemini 5 μm C18 110 Å, 250×10 mm, semi-preparative column.

When applicable, the drug content of the conjugates was determined spectrophotometrically, otherwise RP-HPLC or $L^C$/MS as performed for quantitative determination of the drug content.

The protein content of the antibody-drug conjugates was determined spectrophotometrically or by ELISA.

Antibody-drug conjugates, drug carrying Scaffolds, or antibody Scaffolds were purified (i.e., removal of residual unreacted drug, unconjugated antibody, enzymes or starting materials) by extensive diafiltration, CHT chromatography or HIC, as required. If necessary, additional purification by SEC or HIC were conducted to remove aggregated antibody-drug conjugates. In general, the antibody-drug conjugates, as purified, contained <5% (w/w) (e.g., <2% (w/w)) aggregated antibody-drug conjugates as determined by SEC; <0.5% (w/w) (e.g., <0.1% (w/w)) free (unconjugated) drug as determined by RP-HPLC and/or LC-MS/MS; <1% (w/w) of free drug conjugate as determined by SEC and/or RP-HPLC; and <10% (w/w) (e.g., <1% (w/w)) unconjugated antibody or antibody fragments as determined by HIC-HPLC and/or RP-HPLC. Reduced or partially reduced antibodies were prepared using procedures described in the literature, see, for example, Francisco et al., Blood 102 (4): 1458-1465 (2003). The total drug (conjugated and unconjugated) concentration was determined by UV-Vis spectrophotometry or RP-HPLC.

To determine the concentration of the free drug in a biological sample, an acidified sample was treated with acetonitrile. The free drug was extracted, and the acetonitrile supernatant was analyzed. To determine the concentration of conjugated STING agonist in a non-clinical sample, the sample was subjected to immunocapture using anti-human Fc antibody magnetic beads followed by exhaustive basic hydrolysis. The acetonitrile supernatant containing the released drug was analyzed by LC-MS/MS. The total antibody in non-clinical samples was measured using an MSD ECL immunoassay.

Analysis of free drug was conducted by RP-HPLC using a C-4 column and an acetonitrile gradient. The MRM peak areas on the tandem mass spectrometry were integrated and compared to auristatin F (AF) and auristatin F hydroxypropyl amide (AF-HPA) standards. The method is quantitative for AF-HPA and AF in plasma and tissue homogenates and linear over the concentration ranges of 0.1 to 150 ng/mL. The total drug released after hydrolysis with NaOH was measured under the same condition with the dynamic range from 1 ng/mL to 5000 ng/mL. The total antibody standards range from 0.009 μg/mL to 20 μg/mL.

The drug to antibody ratio (DAR) was determined by measuring the absorption of the conjugates. The DAR value was calculated using the appropriate molar extinction coefficients of the antibody and the STING agonist payload.

Tumors were measured twice weekly using digital calipers and tumor volumes were calculated using the formula: tumor volume ($mm^3$)=($width^2$×length)/2. Body weights were recorded daily for the first week and twice weekly thereafter. Animals remained on study until individual tumor volume reached ≥1000 $mm^3$≥1500 $mm^3$ or as indicated. Percent change in body weight was calculated using the formula: body weight change (%)=(($weight^{study\ day\ x}$−$weight^{study\ day\ 1}$)/$weight^{study\ day\ 1}$)*100. Tumor volumes are reported as mean±standard error of the mean (SEM). Tumor growth inhibition (% TGI) was defined as the percent difference in mean tumor volumes (MTVs) between treated and control groups. Tumor size was measured throughout each efficacy study to determine tumor growth inhibition (TGI). Percent tumor regression was calculated using the formula: % regression=(1−(mean tumor $volume^{final}$)/(mean tumor $volume^{day\ 1}$))*100. A partial response (PR) is defined as a tumor volume of 50% or less for day 1 volume for three consecutive measurements and equal to or greater than 13.5 $mm^3$ for at least one of these three measurements. A complete response (CR) is defined as a tumor volume less than 13.5 $mm^3$ for three consecutive measurements. A tumor-free survivor (TFS) is classified as having a CR at the end of study.

Example 1: Synthesis of XMT-1519 Conjugate 8

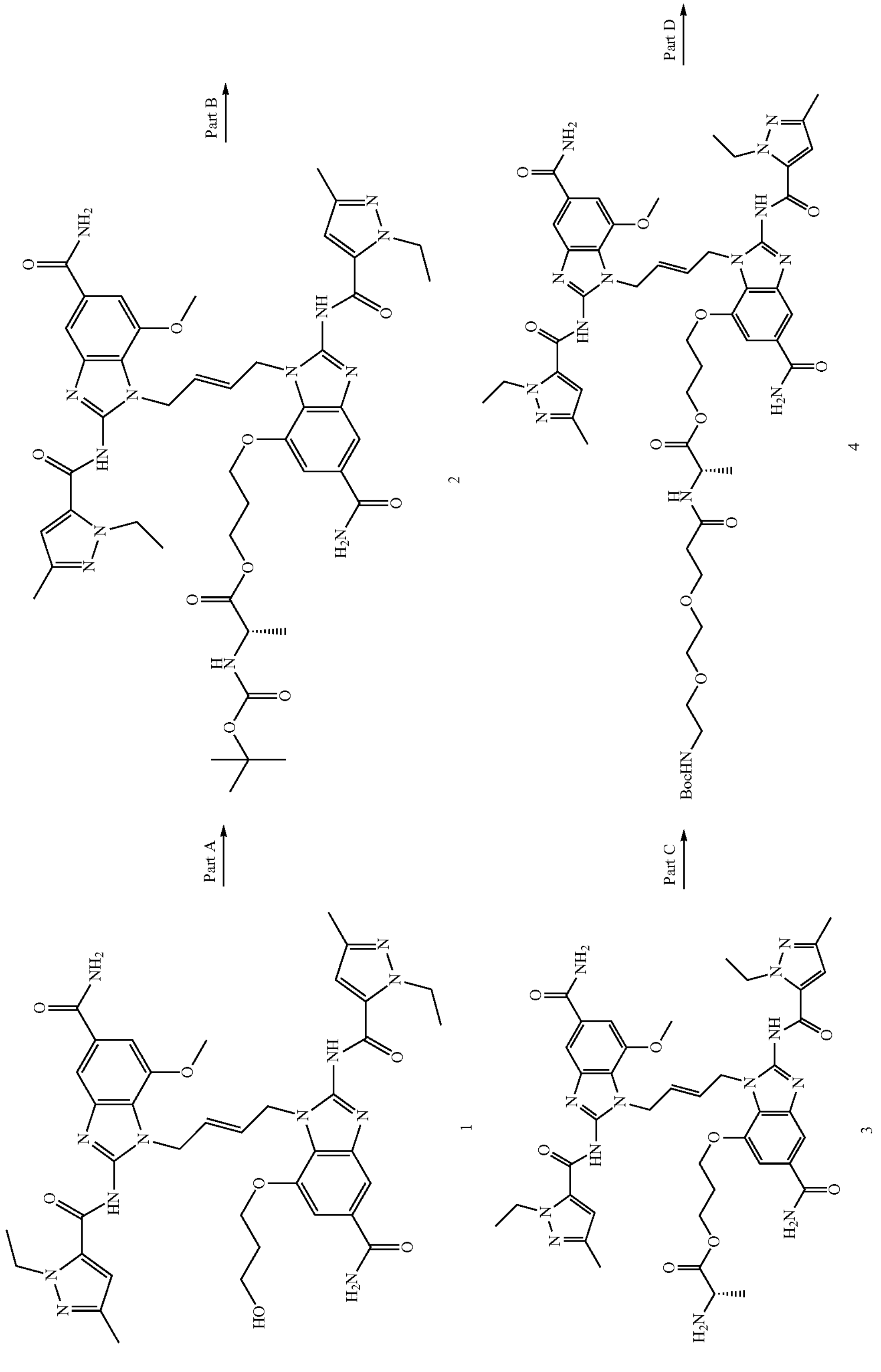
Part A
Part B
Part C
Part D
1
2
3
4

-continued
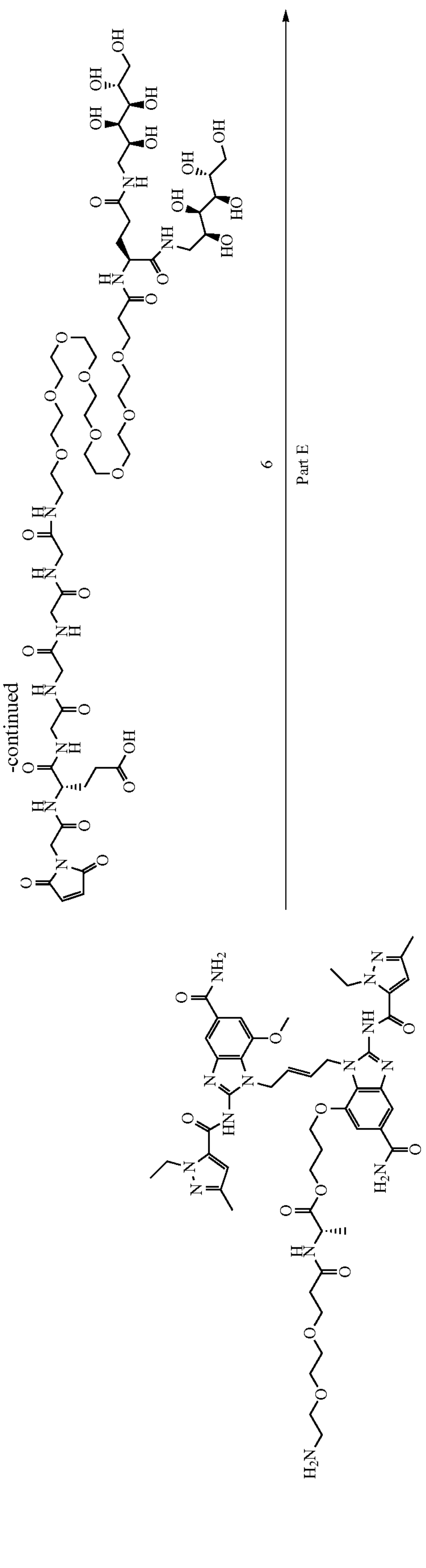
5

-continued
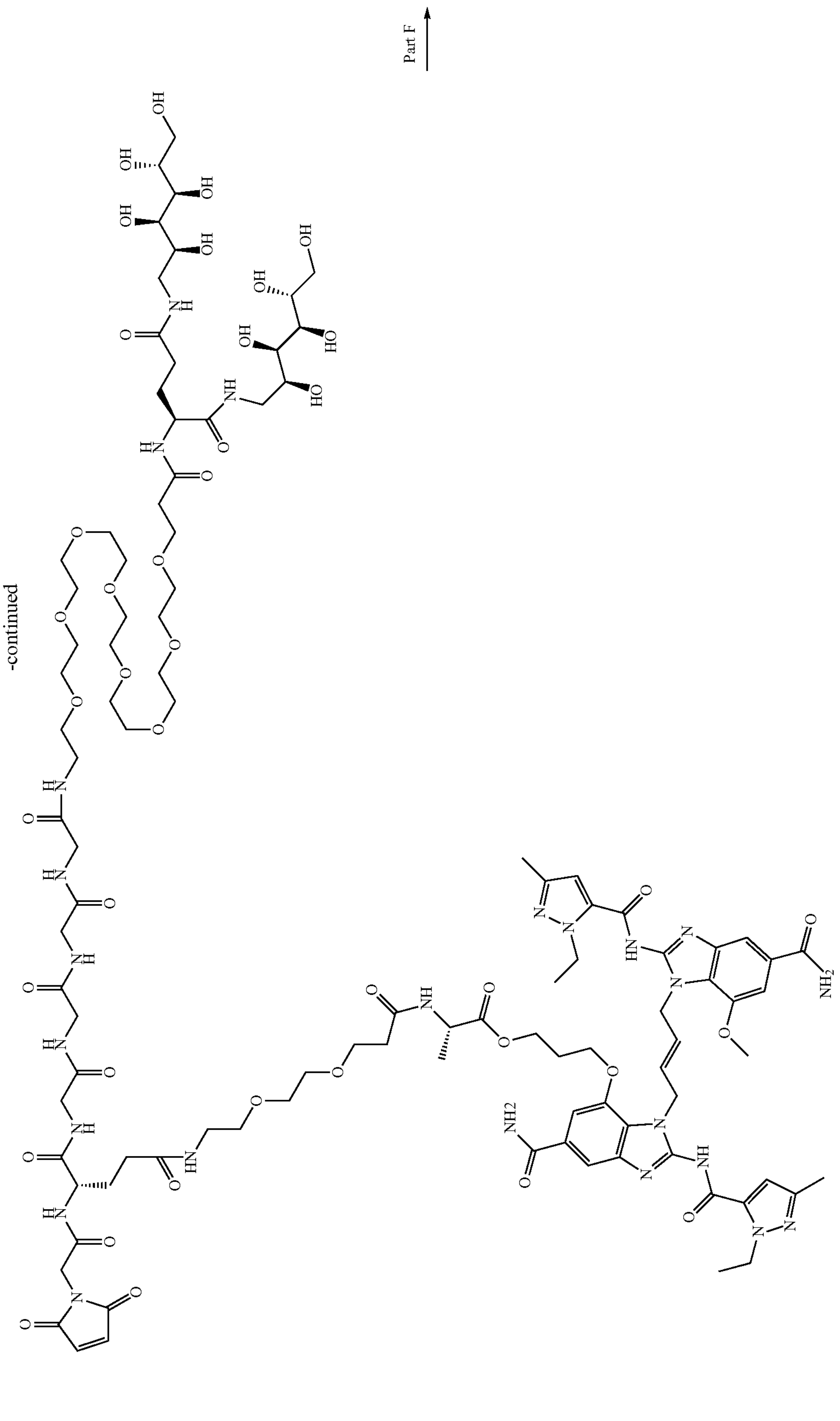
7

-continued
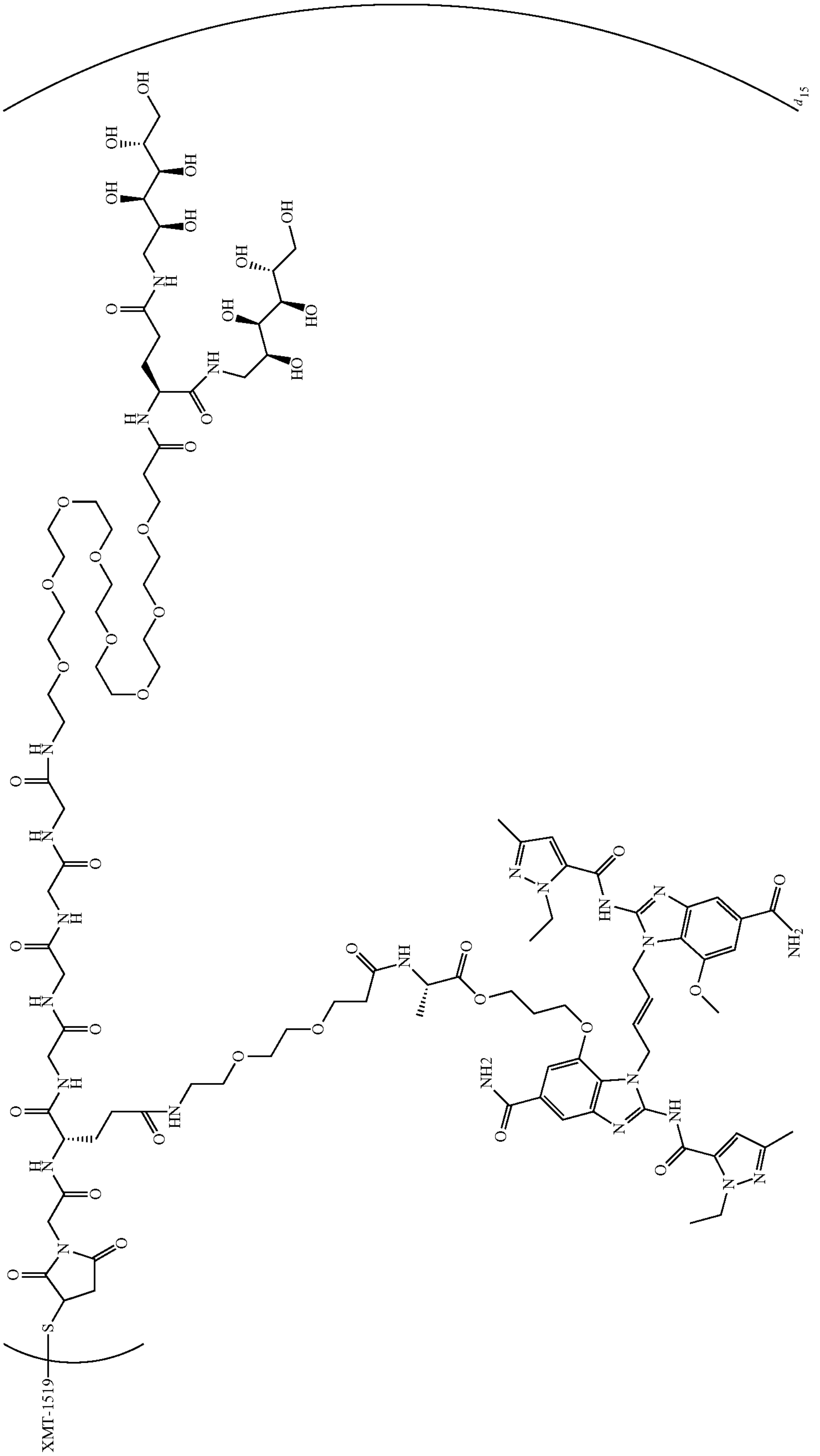
8

Part A: To a mixture of Compound 1 (prepared as described in WO2017175147A1, 0.5 g, 0.64 mmol), Boc-L-Alanine (0.242 g, 1.28 mmol), DMAP (7.8 mg, 0.064 mmol) and DCC (0.264 g, 1.28 mmol) was added DMF (2 mL). The suspension was stirred overnight at room temperature, then the solution was concentrated, and the residue was purified on silica gel (0-40% MeOH in DCM) to give Compound 2 as a light-yellow solid (0.52 g, 85% yield). ESI-MS m/z Calcd for $C_{46}H_{58}N_{13}O_{10}$ $[M+H]^+$: 952.4; found 952.4.

Part B: To a suspension of Compound 2 (0.52 g, 0.55 mmol) in dioxane (10 mL) was added 4 N HCl (2 mL, 8.19 mmol). The reaction mixture was stirred at room temperature for 2 h, then the suspension was concentrated and used without further purification in the next step. Compound 3 was obtained as a white solid. ESI-MS m/z Calcd for $C_{41}H_{50}N_{13}O_8$ [M+H]: 852.4; found 852.3.

Part C: To a solution of Compound 3 (0.586 g, 0.661 mmol) in DMF (5 mL) was added 2,2-dimethyl-4-oxo-3,8,11-trioxa-5-azatetradecan-14-oic acid (0.202 g, 0.727 mmol), followed by DIPEA (0.230 mL, 1.322 mmol). The reaction mixture was stirred at room temperature for 5 min, then HATU (0.376 g, 0.992 mmol) and HOBt (0.153 g, 0.992 mmol) were added. The reaction mixture was stirred at room temperature for 2 h. An additional aliquot of DIPEA (0.460 mL, 2.6 mmol) was added. After another 1 hour, the reaction mixture was concentrated to an oil. The residue was purified over silica gel (0-40% MeOH in DCM) to afford Compound 4 (0.9 g, >95% yield) as a white solid. ESI-MS m/z Calcd for $C_{53}H_{71}N_{14}O_{13}[M+H]^+$: 1111.5; found 1111.5.

Part D: To a suspension of Compound 4 (0.9 g, 0.810 mmol) in dioxane (10 mL) was added 4 N HCl (3.04 mL, 12.15 mmol). The reaction mixture was stirred at room temperature for 1.5 h. The suspension was concentrated to afford Compound 5 as a colorless solid (0.56 g, 66.0% yield). ESI-MS Calcd for $C_{48}H_{63}N_{14}O_{11}$ $[M+H]^+$: 1011.5; found 1011.4.

Part E: To a solution of Scaffold 6 (100 mg, 0.072 mmol, prepared as described in PCT/US2018/06719) and Compound 5 (72.7 mg, 0.072 mmol) in DMF (2 mL) were added PyBOP (37.5 mg, 0.072 mmol) and DIPEA (0.075 mL, 0.431 mmol). The reaction mixture was stirred at room temperature 2 h, then the solution was concentrated, and the residue was purified by preparative HPLC (0-80% ACN in water) to afford Compound 7 (109 mg, 64% yield). ESI-MS m/z Calcd for $C_{103}H_{156}N_{24}O_{41}$ $[M+2H]^{2+}$: 1192.5; found 1192.5.

Part F: To a solution of XMT-1519 (10 mg, 0.069 μmol) in 50 mM HEPES, 1 mM EDTA, pH 7 buffer was added TCEP (0.059 mg, 0.207 μmol) and the mixture was shaken at 37° C. for 90 minutes. To the reduced antibody was added Compound 7 (0.987 mg, 0.414 μmol in 200 μL DMA). The resulting mixture was shaken at 37° C. for 60 minutes. The reaction was quenched with cysteine (15 equivalents, 0.125 mg, 1.035 μmol in 125 μL of 50 mM HEPES, 1 mM EDTA, pH 7) and rotated at room temperature for 1 h. The resulting Conjugate 8 was purified by ultrafiltration or CHT chromatography. The details of the antibody-drug conjugates 8-1 and 8-2 are given below. Conjugates 8-1 and 8-2 were prepared as described except that a higher ratio of TCEP: mAb was used in the synthesis of 8-2 compared to 8-1 (4:1 vs 3:1) as well as a higher ratio of Compound 7 to mAb (8:1 vs 6:1).

| Conjugate | DAR |
|---|---|
| 8-1 | 6.1 |
| 8-2 | 6.8 |

Example 1a: Synthesis of Trastuzumab Conjugate 8a

8a
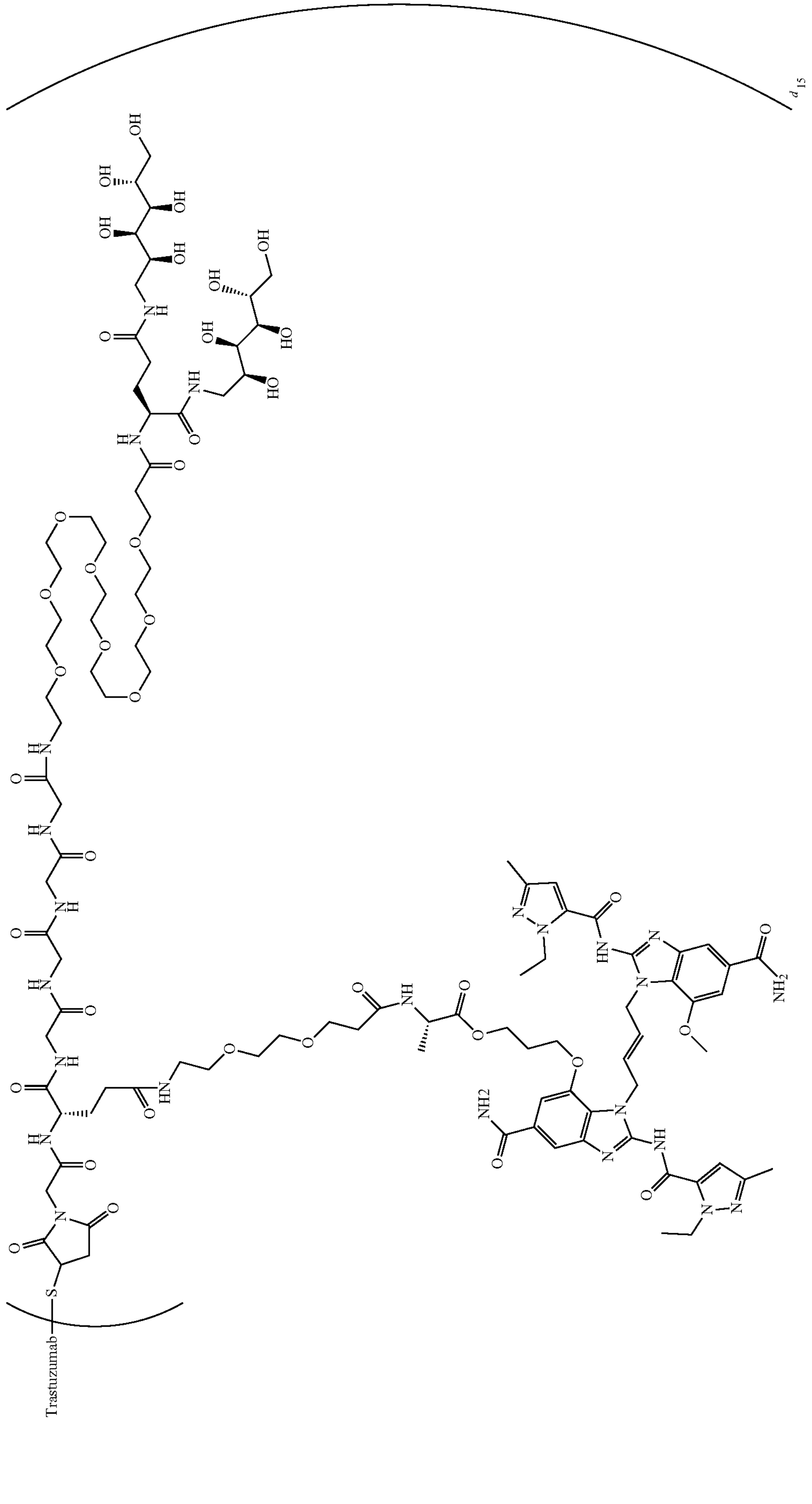

Conjugate 8a was prepared and characterized as described in Example 1 except that Trastuzumab was used instead of XMT-1519. The details of the antibody-drug conjugates 8a-1, 8a-2, and 8a-3 are given below.

| Conjugate | DAR |
|---|---|
| 8a-1 | 6.0 |
| 8a-2 | 7.0 |
| 8a-3 | 8.4 |

Example 1b: Synthesis of XMT-1535 Conjugate 8b, DAR 5.7

8b
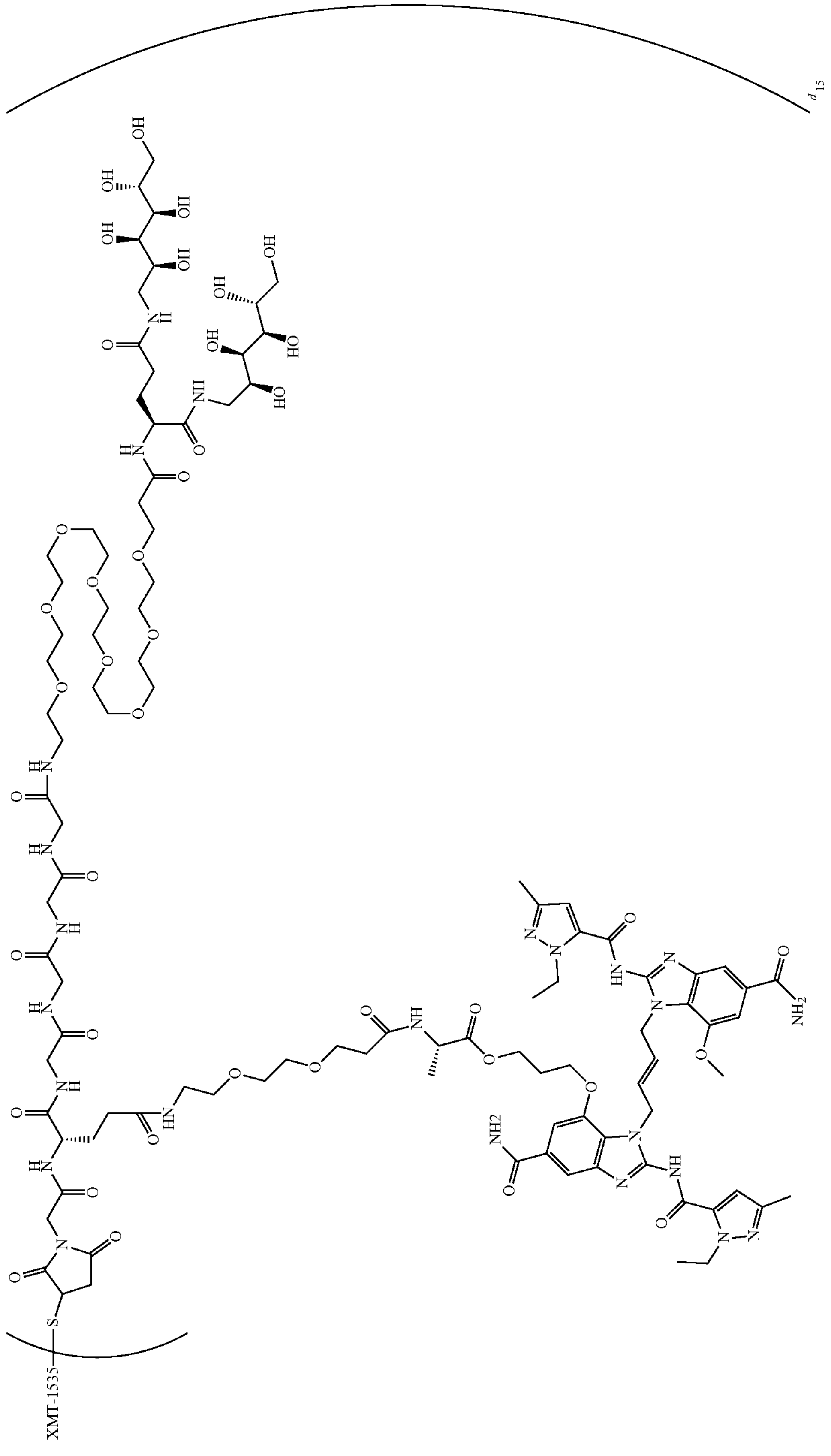

Conjugate 8b was prepared and characterized as described in Example 1 except that XMT-1535 was used instead of XMT-1519. The details of the antibody-drug conjugates 8b-1, 8b-2 and 8b-3 are given below.

| Conjugate | DAR |
|---|---|
| 8b-1 | 5.7 |
| 8b-2 | 6.6 |
| 8b-3 | 6.4 |

Example 1c: Synthesis of Palivizumab Conjugate 8c

8c
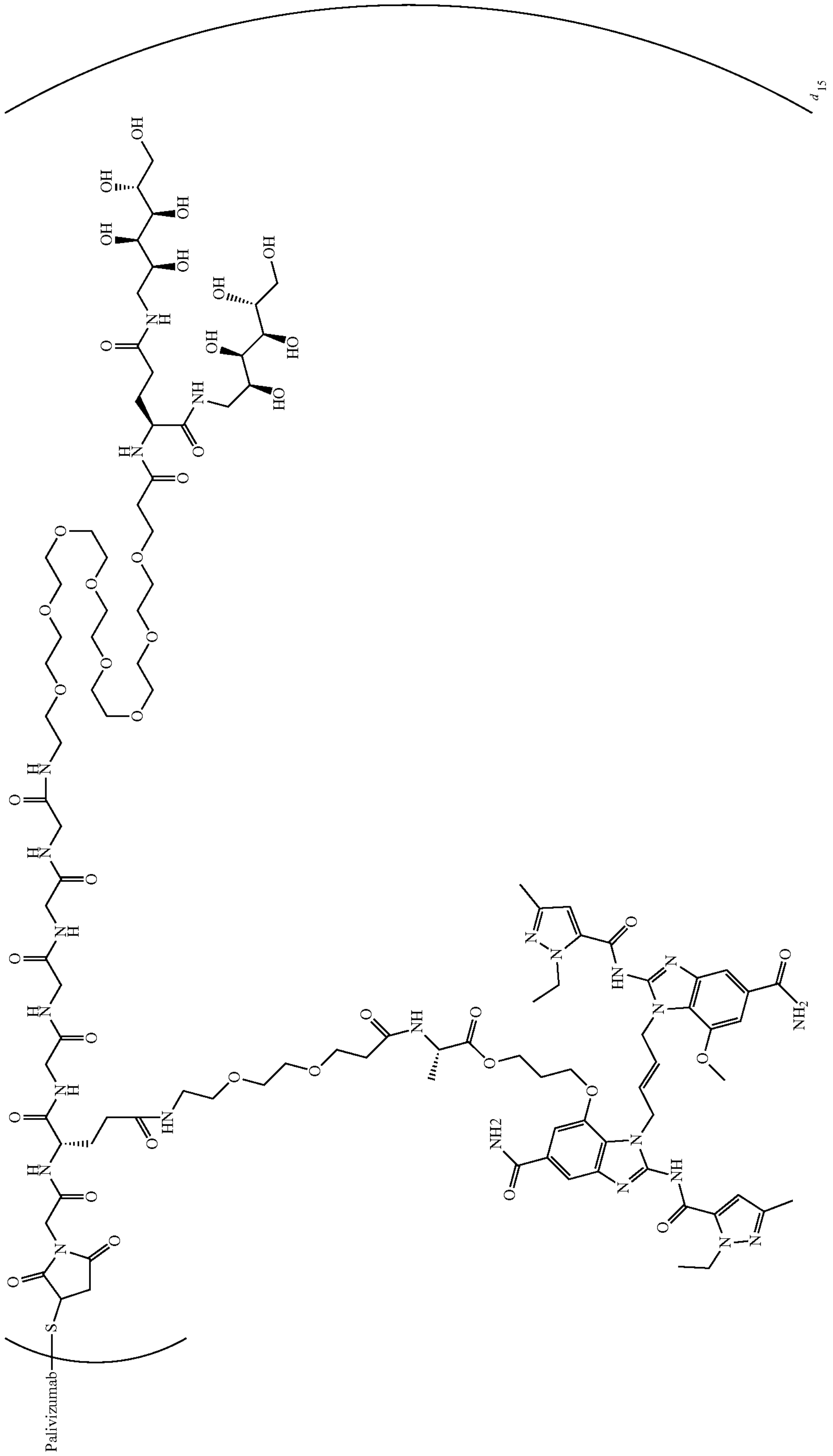

Conjugates 8c was prepared and characterized as described in Example 1 except that Palivizumab was used instead of XMT-1519. The details of the antibody-drug conjugates 8c-1 and 8c-2 are given below.

| Conjugate | DAR |
|---|---|
| 8c-1 | 7.5 |
| 8c-2 | 5.8 |

Example 1d: Synthesis of Palivizumab mIgG2a Conjugate 8d

8d
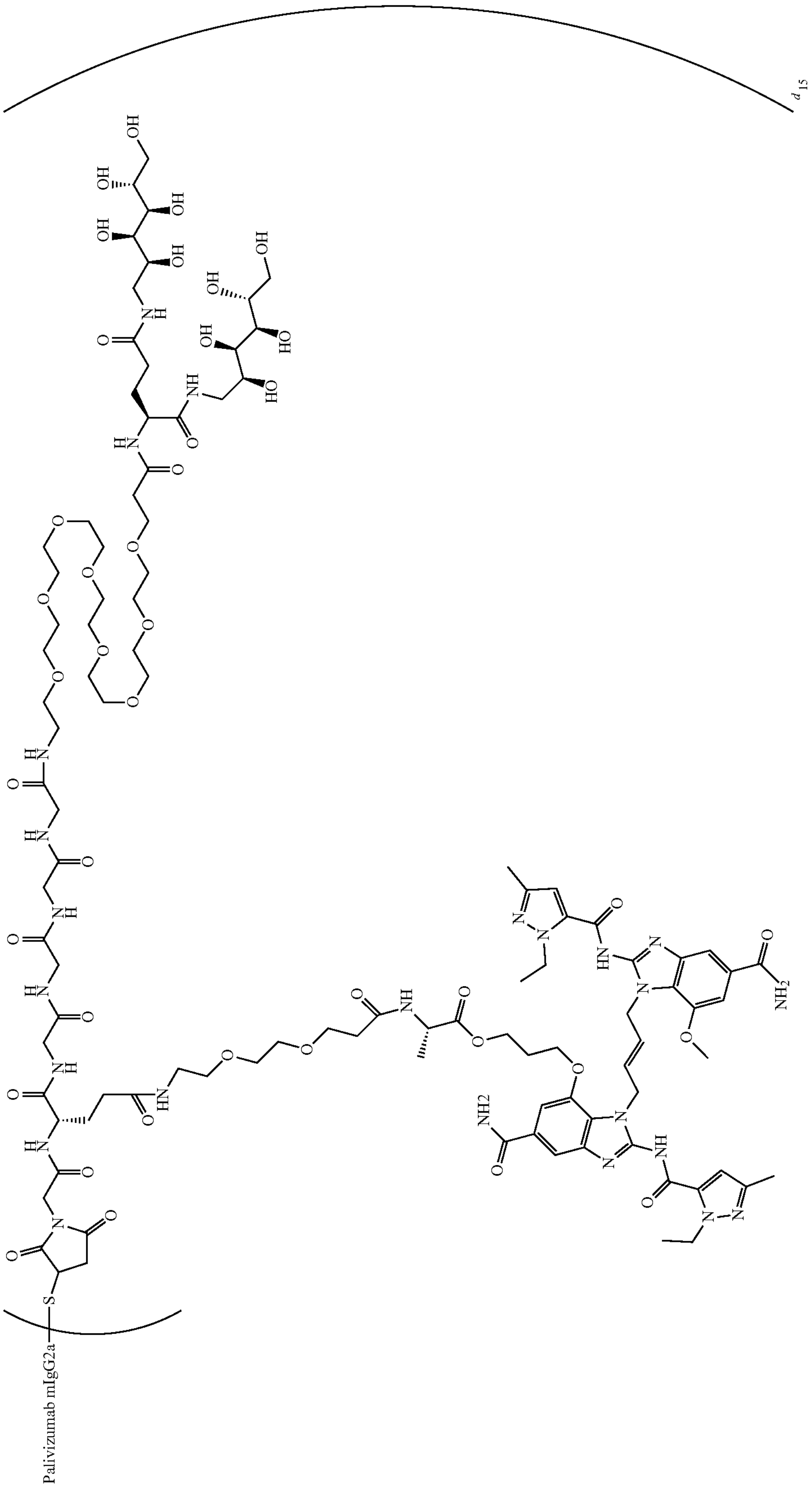

Conjugates 8d was prepared and characterized as described in Example 1 except that Palivizumab mIgG2a was used instead of XMT-1519. The details of the antibody-drug conjugates 8d-1, 8d-2 and 8d-3 are given below.

| Conjugate | DAR |
|---|---|
| 8d-1 | 6.8 |
| 8d-2 | 6.5 |
| 8d-3 | 6.0 |

Example 1e: Synthesis of XMT-1535 hIgG1-mIgG2a Conjugate 8e, DAR 7.0

8e
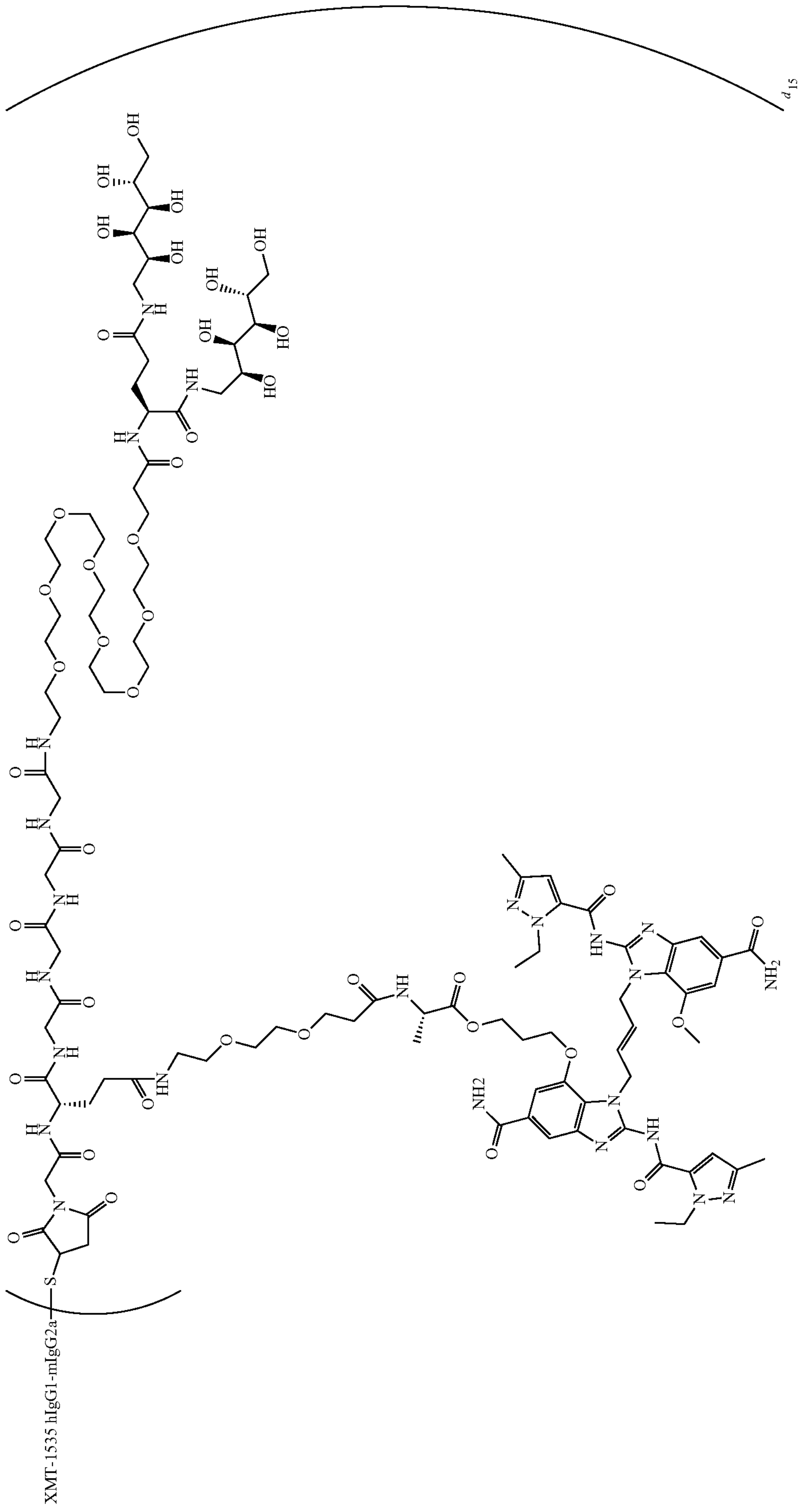

Conjugate 8e was prepared and characterized as described in Example 1 except that XMT-1535 mIgG2a was used instead of XMT-1519. The purified Conjugate 8e had a STING agonist to XMT-1535 hIgG1-mIgG2a ratio of 7.0.

Example 1f: Synthesis of XMT-1535 AAG Conjugate 8f, DAR 7.4

8f
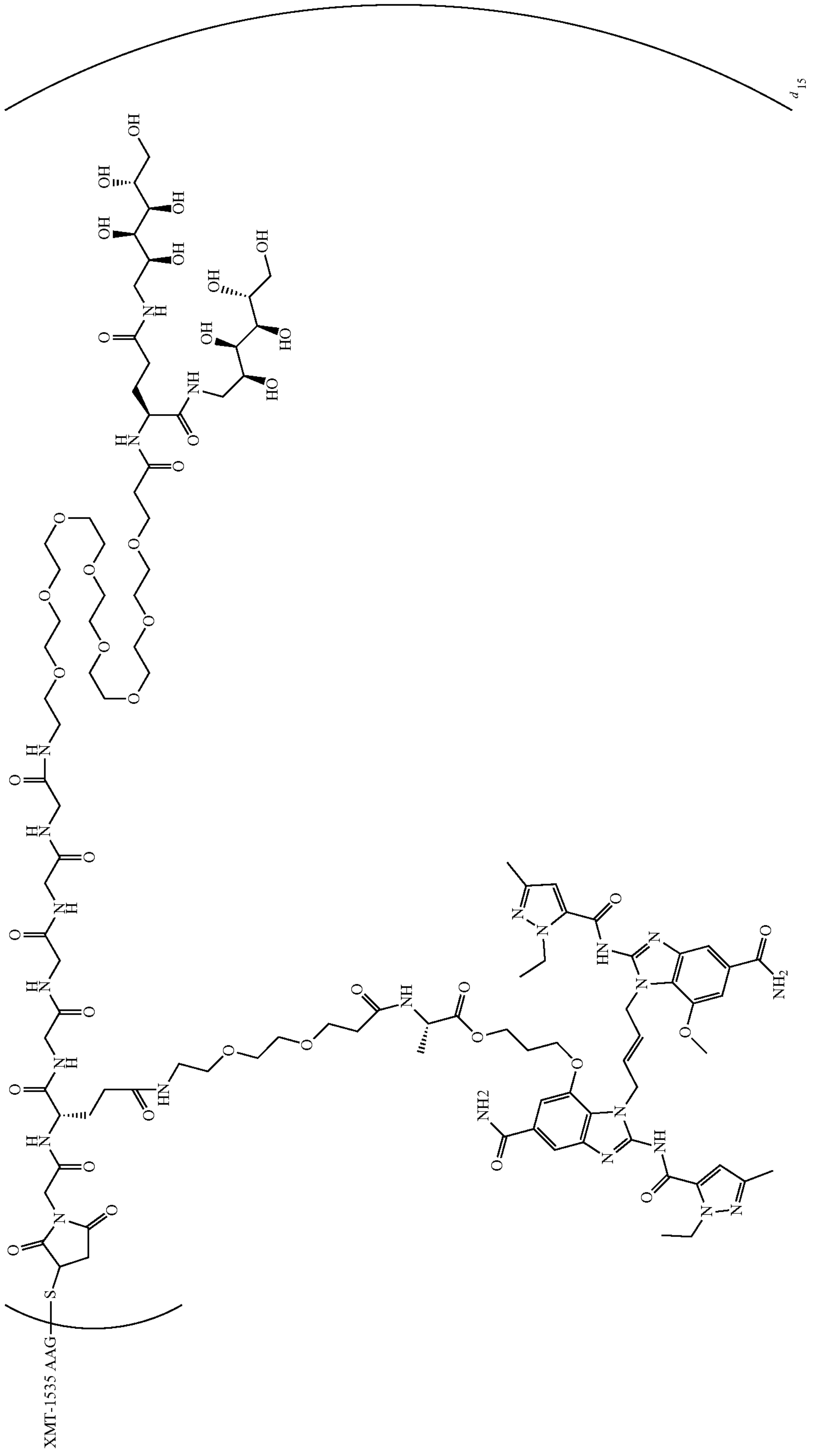

Conjugate 8f was prepared and characterized as described in Example 1 except that XMT-1535 AAG was used instead of XMT-1519. The purified Conjugate 8f had a STING agonist to XMT-1535 AAG ratio of 7.4.

Example 1g: Synthesis of Target D mIgG2a Conjugate 8g, DAR 7.4

8g
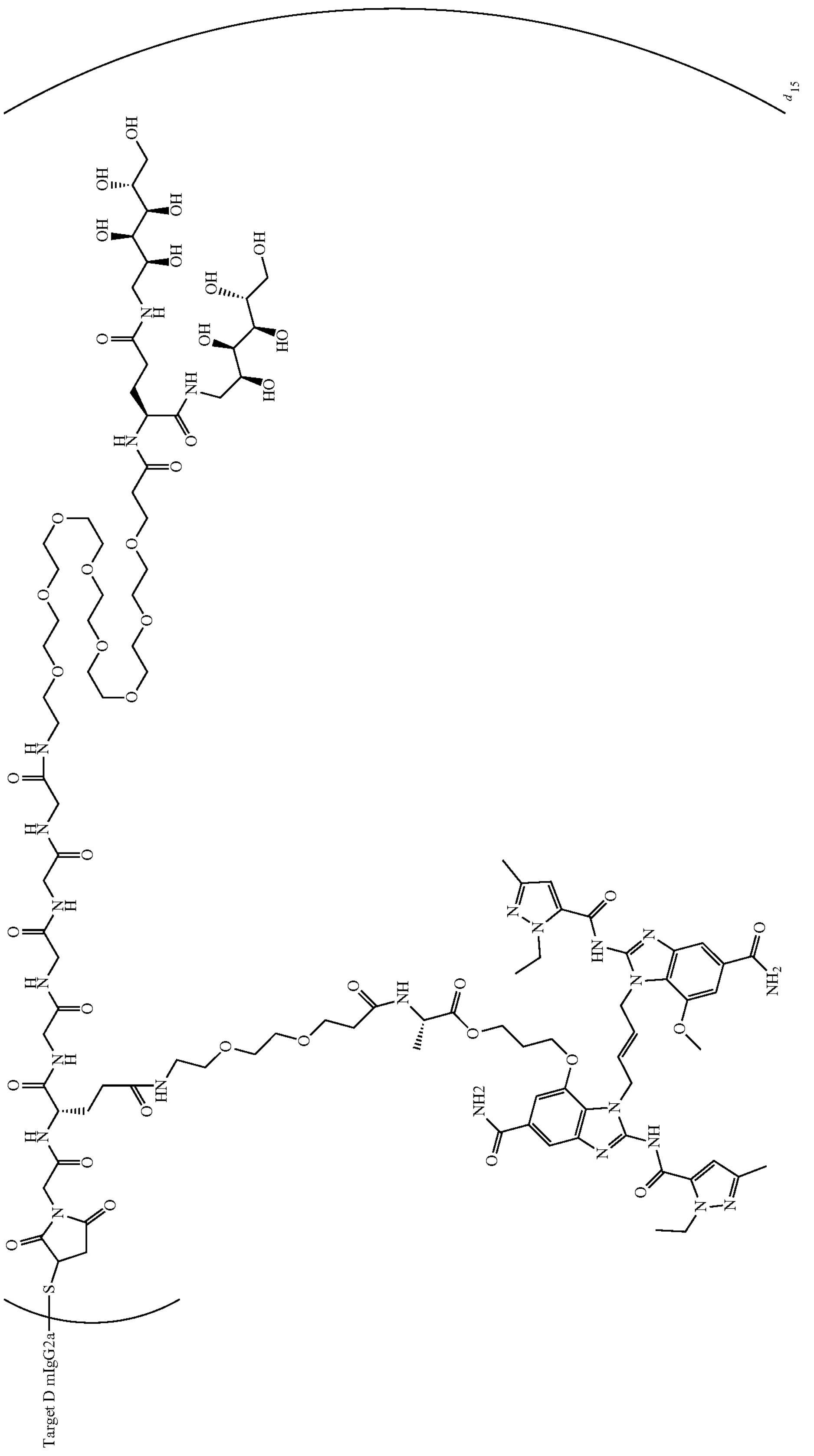

Conjugate 8g was prepared and characterized as described in Example 1 except that Target D mIgG2a was used instead of XMT-1519. The purified Conjugate 8g had a STING agonist to Target D_mIgG2a ratio of 7.4.

Example 1h: Synthesis of Target C hIgG1a Conjugate 8h, DAR 6.9

8h
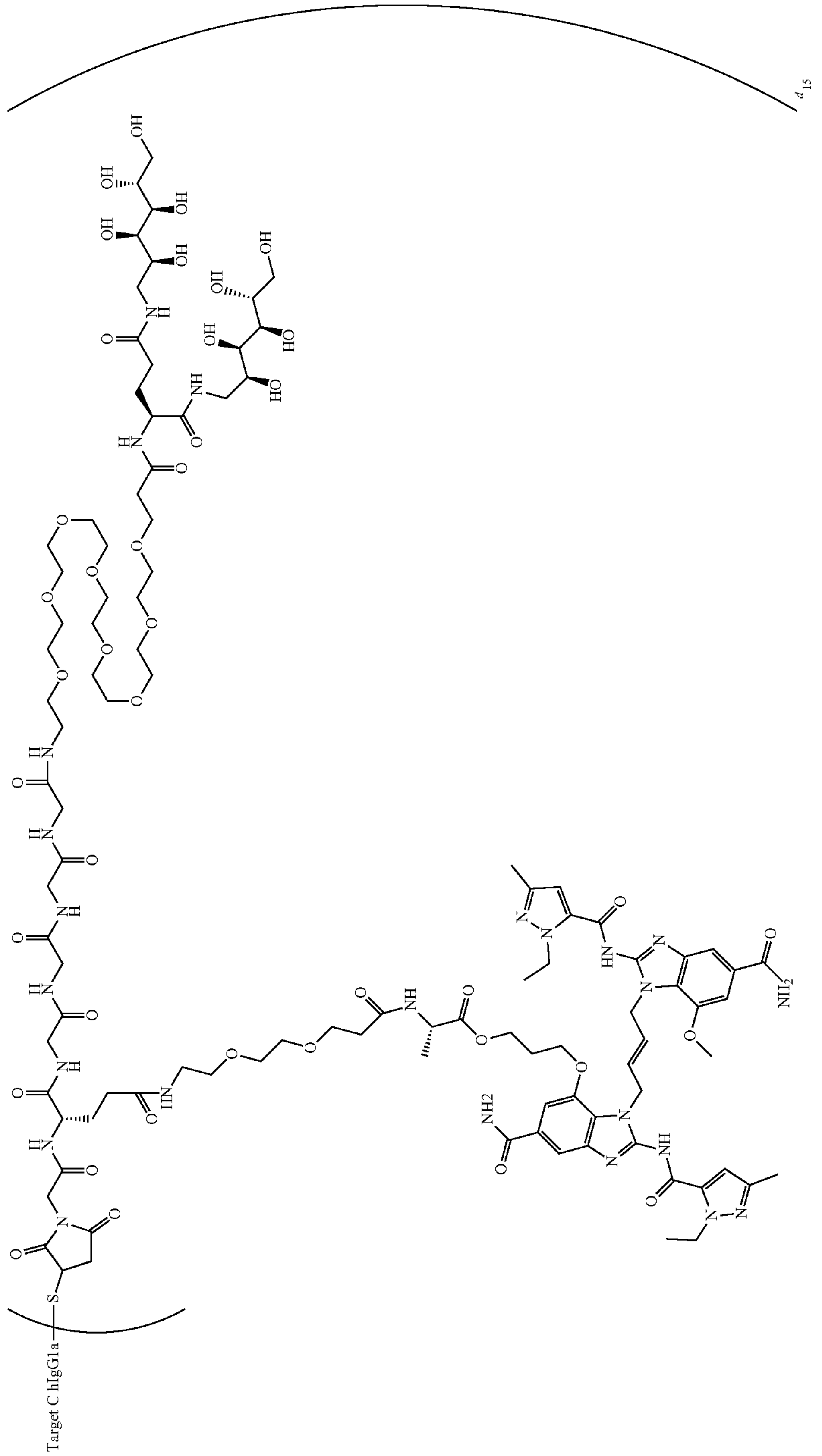

Conjugate 8h was prepared and characterized as described in Example 1 except that Target C hIgG1a was used instead of XMT-1519. The purified Conjugate 8g had a STING agonist to Target C hIgG1a ratio of 6.9.

Example 1i: Synthesis of Target E mIgG2a Conjugate 8i, DAR 10.0

8i
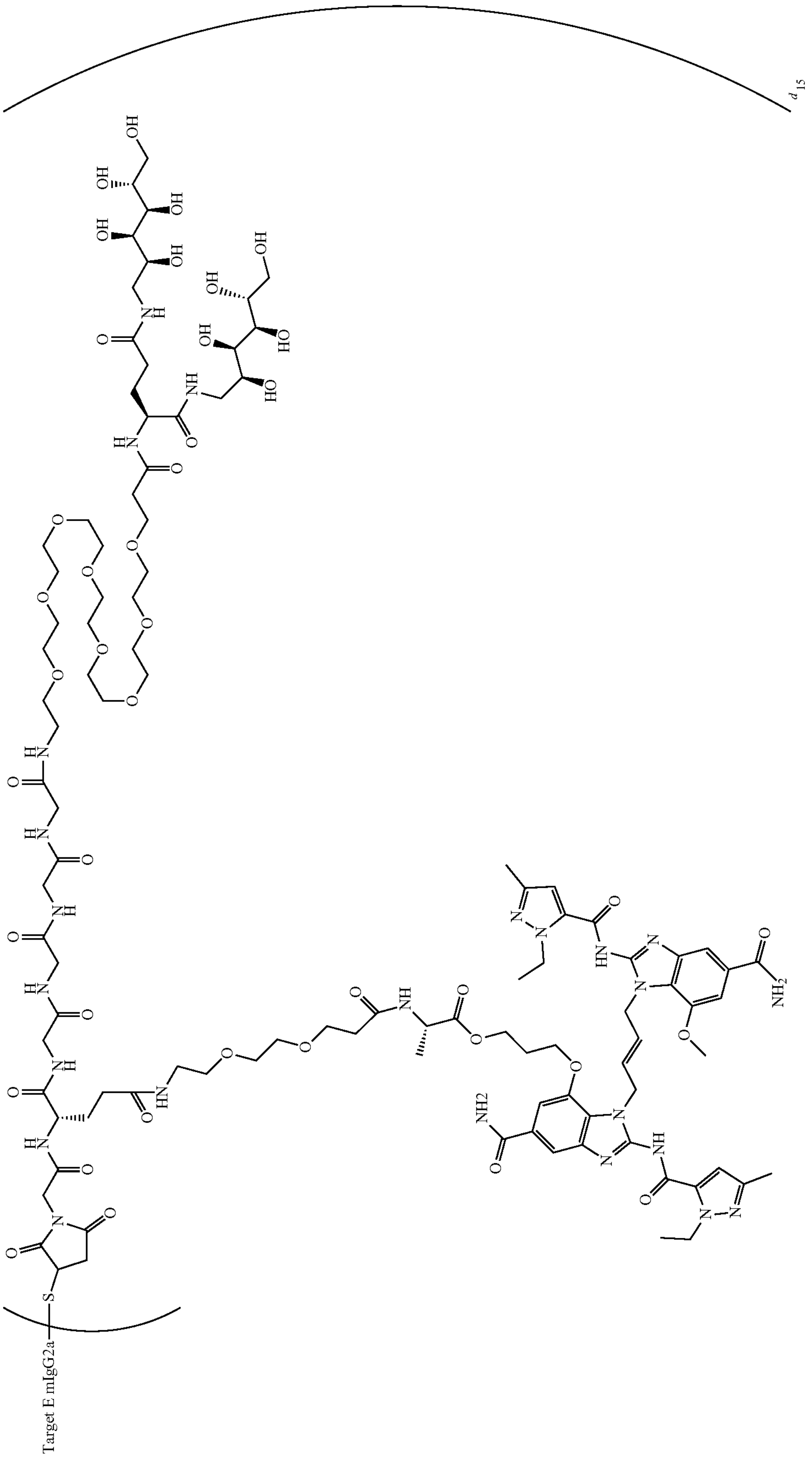

Conjugate 8i was prepared and characterized as described in Example 1 except that Target E mIgG2a was used instead of XM4T-1519. The purified Conjugate 8g had a STING agonist to Target E mIgG2a ratio of 10.0.

Example 1j: Synthesis of Trastuzumab AAG Conjugate 8j, DAR 7.0

8j
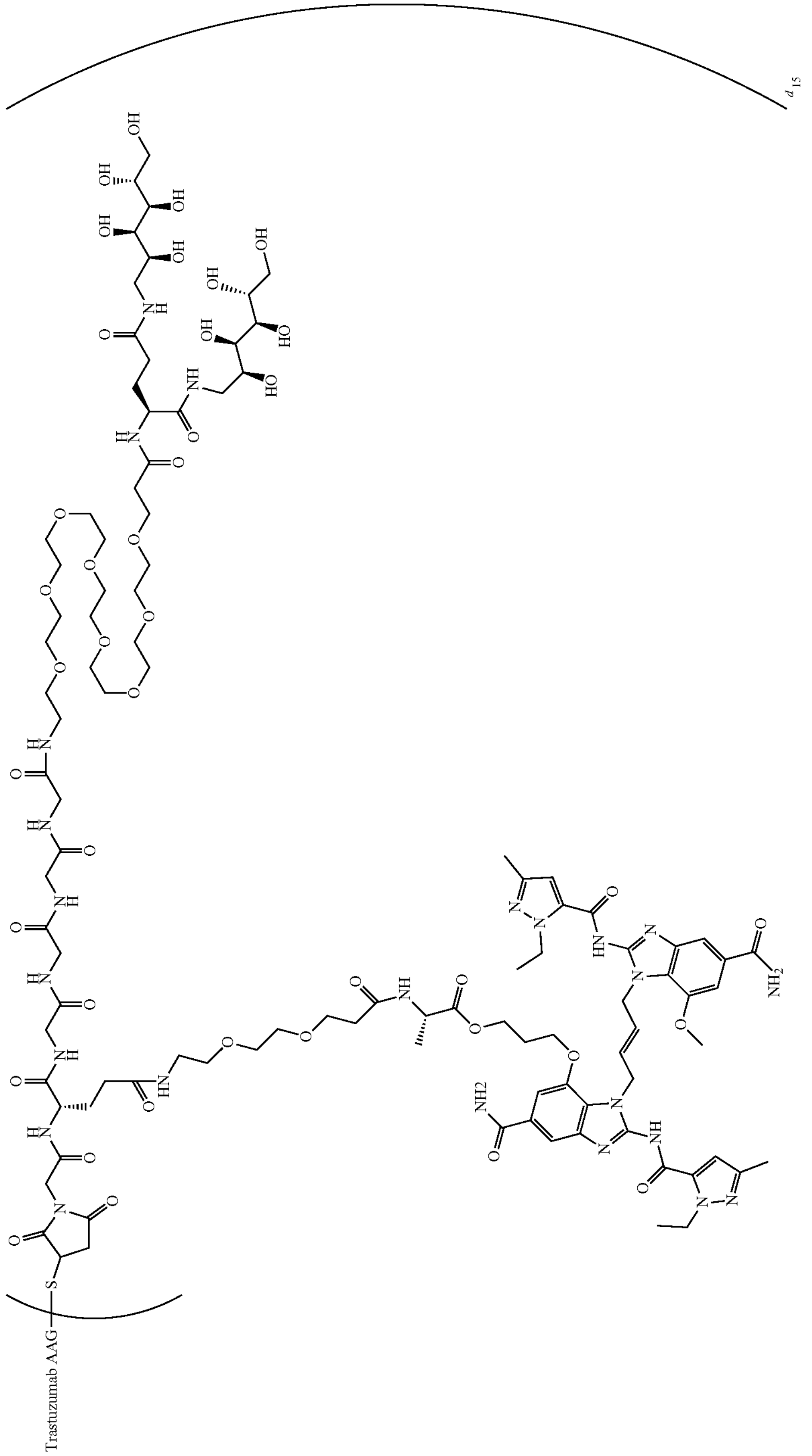

Conjugate 8j was prepared and characterized as described in Example 1 except that Trastuzumab AAG was used instead of XMT-1519.

The details of Conjugates 8j and 8j-1 are given below.

| Conjugate | DAR |
|---|---|
| 8j | 7.0 |
| 8j-1 | 4.2 |

Example 1k: Synthesis of Trastuzumab mIgG2a Conjugate 8k, DAR 8.1

8k
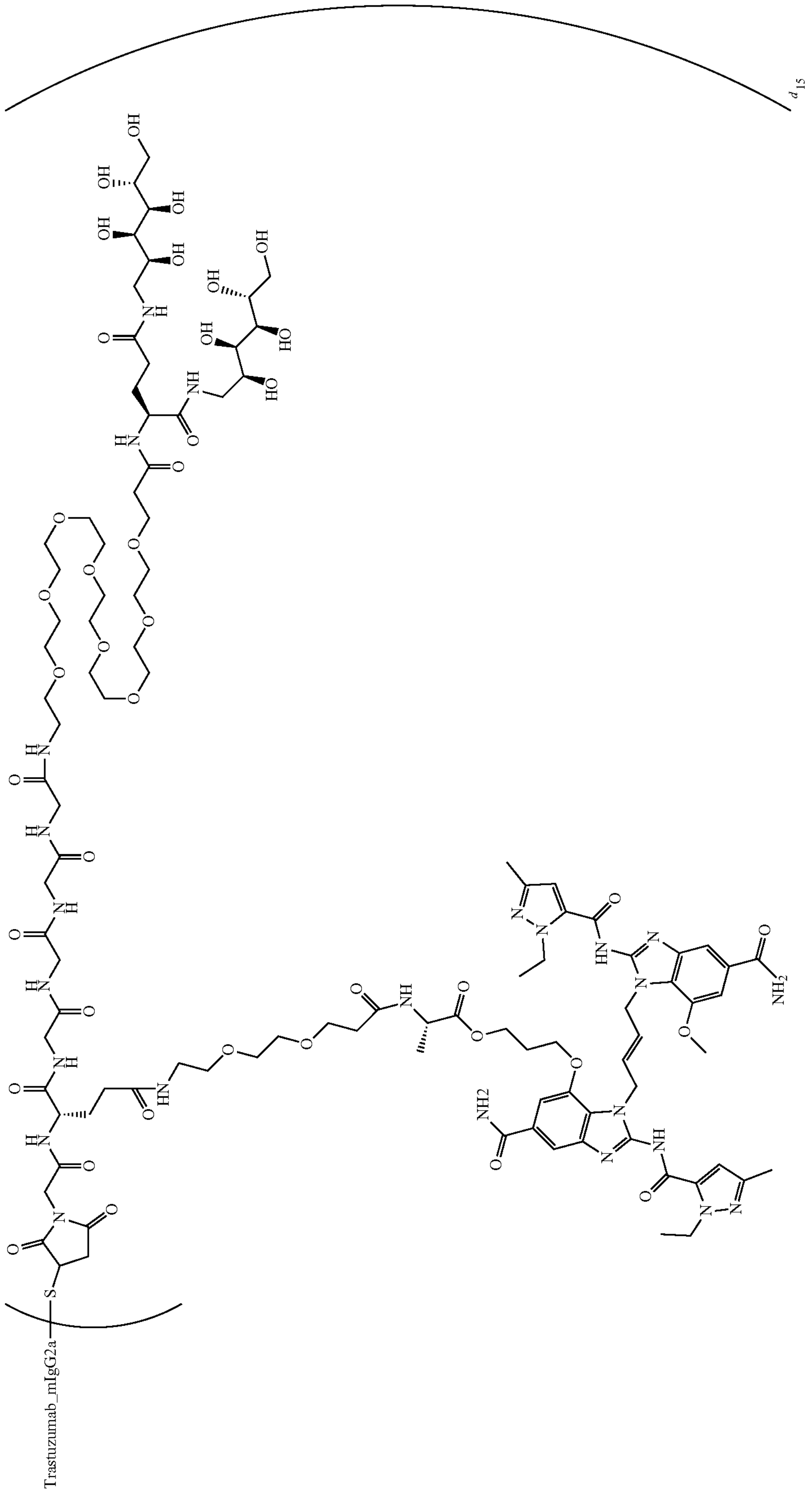

Conjugate 8k was prepared and characterized as described in Example 1 except that Trastuzumab mIgG2a was used instead of XMT-1519. The purified Conjugate 8k had a STING agonist to Trastuzumab mIgG2a ratio of 8.1.

Example 11: Synthesis of XMT-1535 Conjugate 81, DAR 4.7

18
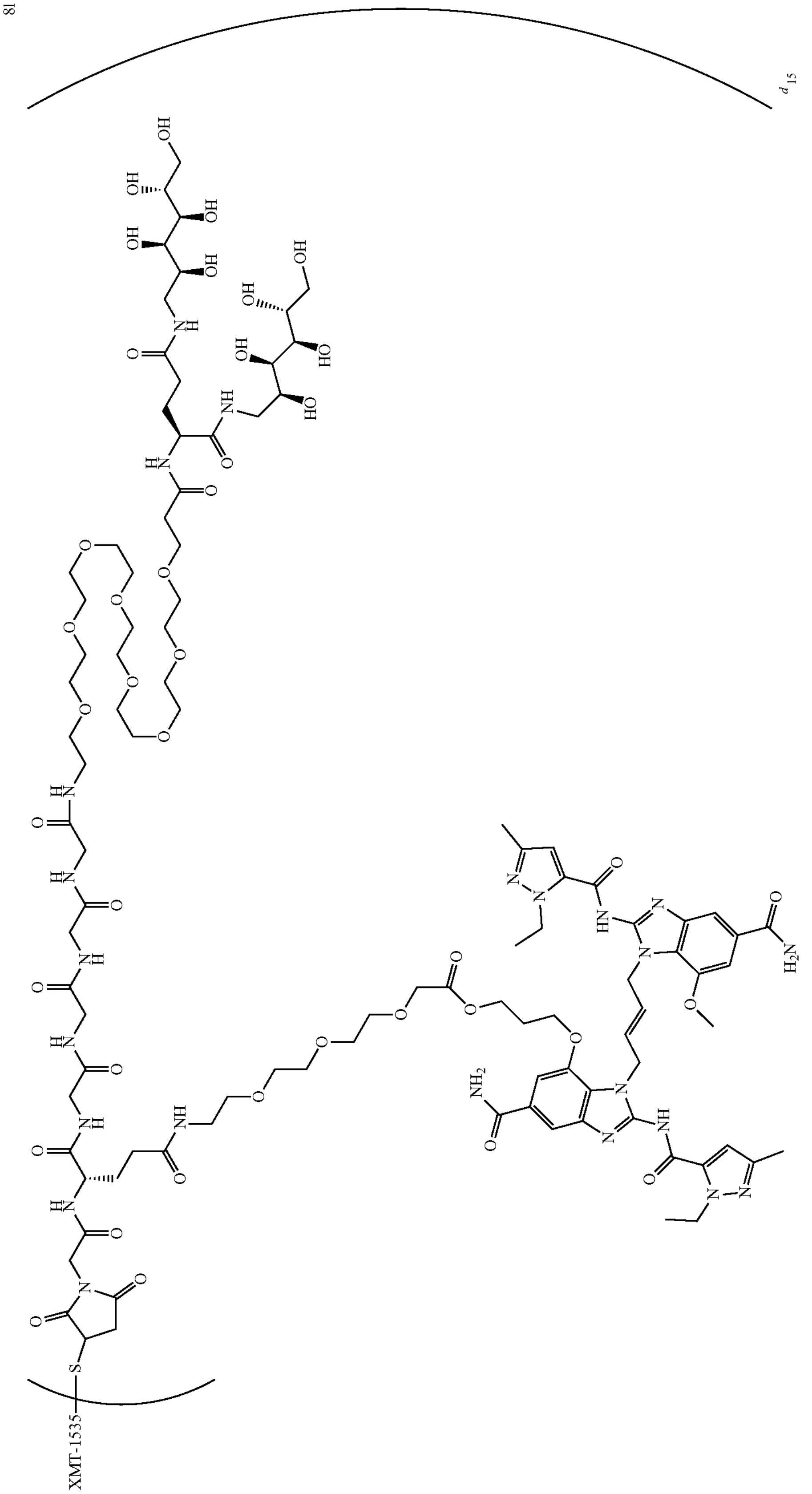

Conjugate 81 was prepared and characterized as described in Example 1 except that XMT-1535 was used instead of XMT-1519 and 2-(2-(2-(2-aminoethoxy)ethoxy)ethoxy)acetic acid was incorporated into the compound structure instead of (3-(2-(2-aminoethoxy)ethoxy)propanoyl)-L-alanine. The purified Conjugate 81 had a STING agonist to XM4T-1535 ratio of 4.7.

Example 1m: Synthesis of Palivizumab Conjugate 8m, DAR 4.5

8m
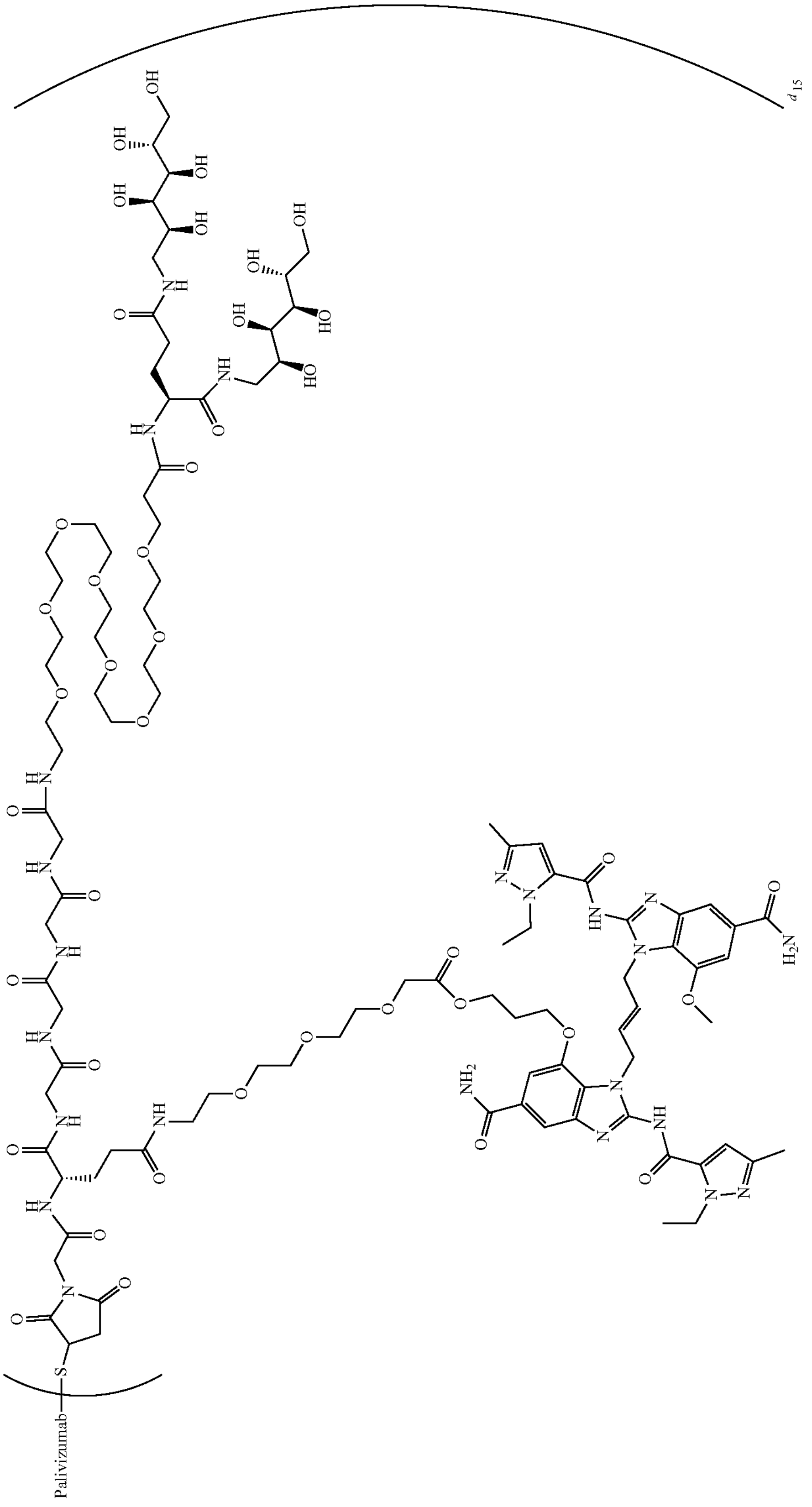

Conjugate 8m was prepared and characterized as described in Example 1 except that Palivizumab was used instead of XMT-1519 and 2-(2-(2-(2-aminoethoxy)ethoxy)ethoxy)acetic acid was incorporated into the compound structure instead of (3-(2-(2-aminoethoxy)ethoxy)propanoyl)-L-alanine. The purified Conjugate 8m had a STING agonist to Palivizumab ratio of 4.5.

Example 2: Synthesis of XMT-1519 Conjugate 16, DAR 5.3

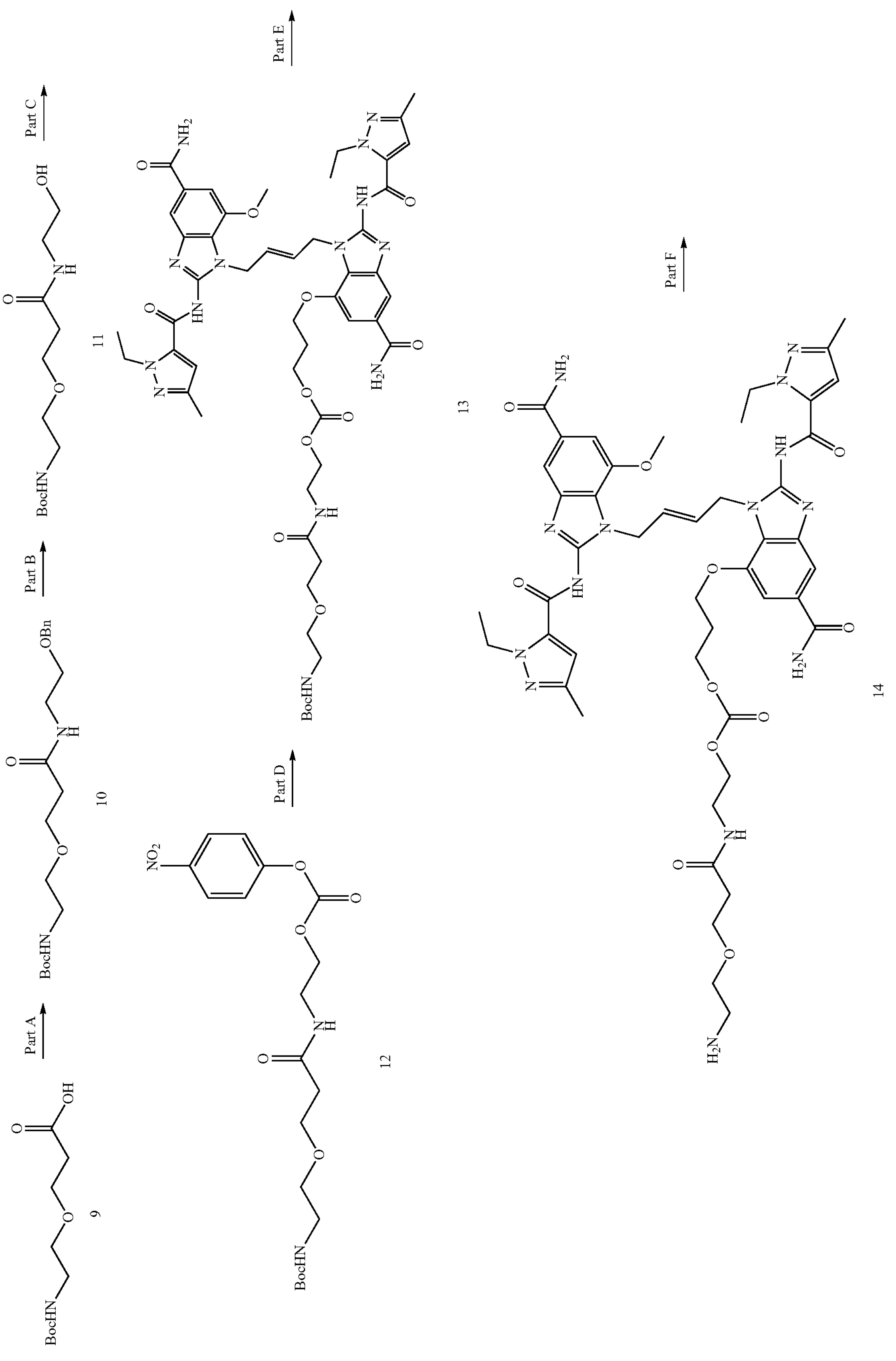
Part A
Part B
Part C
Part D
Part E
Part F
9
10
11
12
13
14

-continued
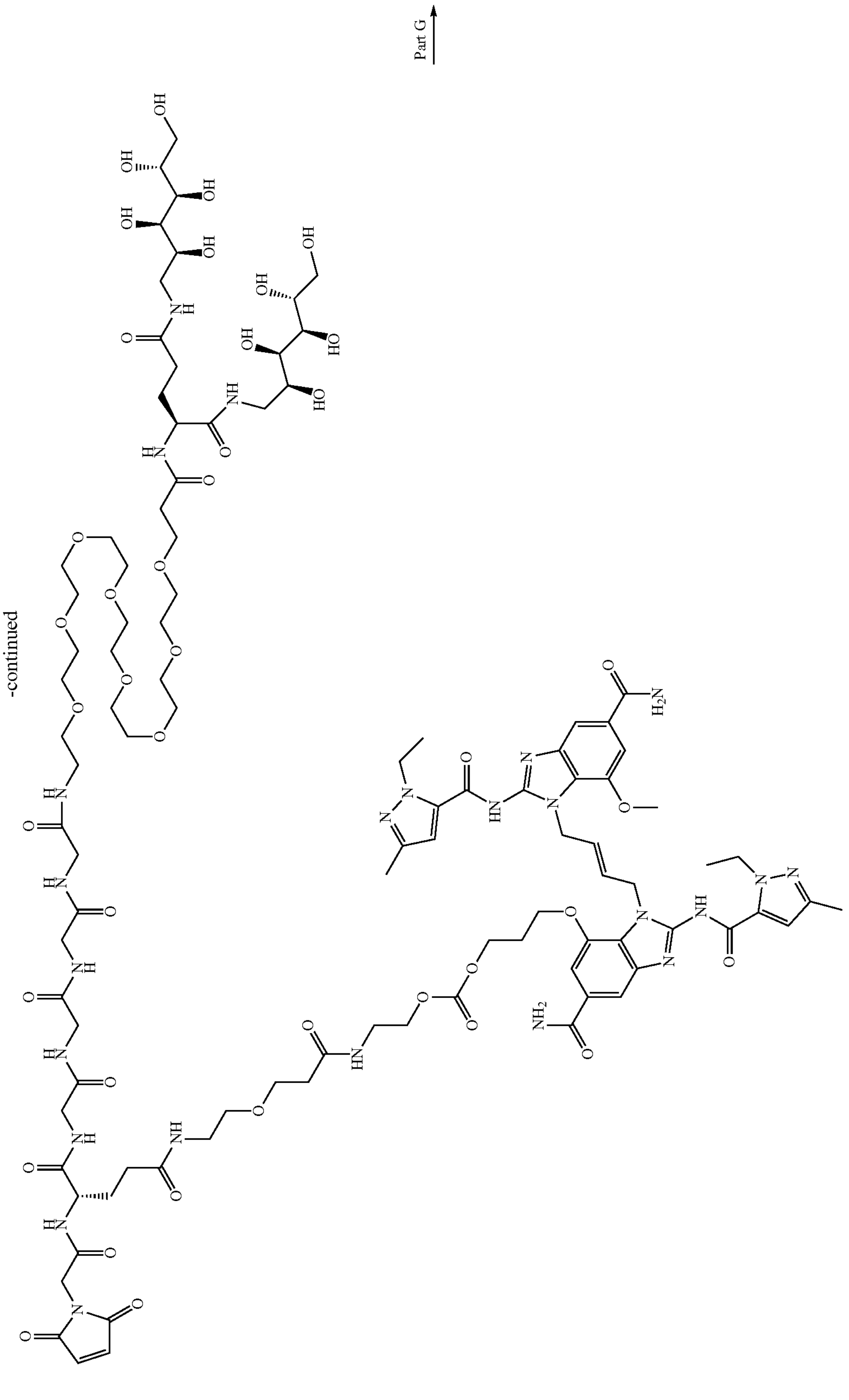

-continued
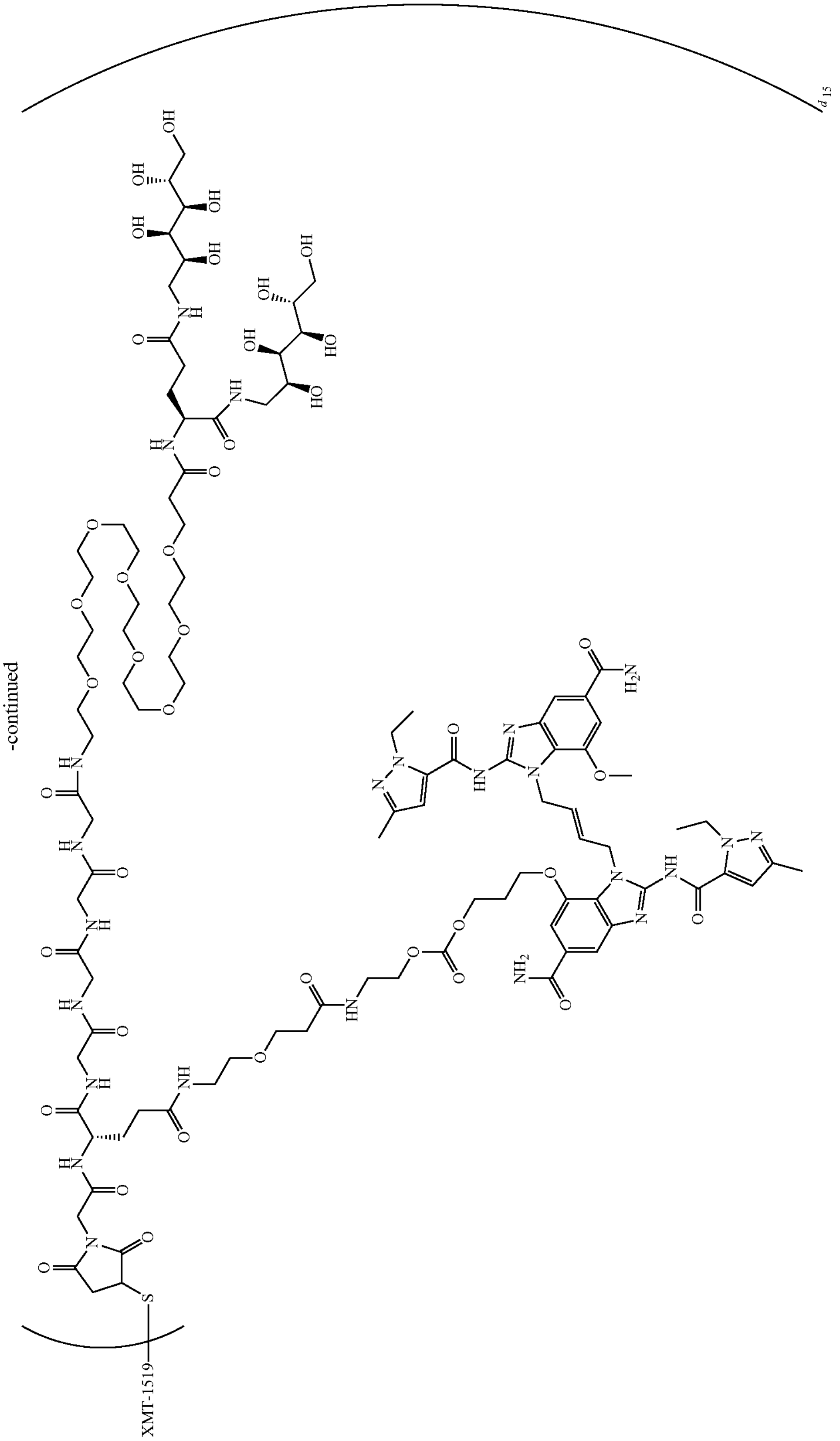
16

Part A: To a solution of Compound 9 (0.100 g, 0.429 mmol) in THF (5 mL) were added HATU (0.196 g, 0.514 mmol), and HOBt (0.079 g, 0.514 mmol), the reaction mixture stirred at 0° C. for 10 min, then 2-(benzyloxy)ethan-1-amine (0.0648 mg, 0.429 mmol) and DIPEA (0.112 mL, 0.643 mmol) were added. The reaction mixture was stirred at room temperature overnight, the solution was concentrated, and the residue was purified on silica gel (0-10% MeOH in DCM) to afford Compound 10 (0.2 g, 100% yield). ESI-MS m/z Calcd for: $C_{19}H_{30}N_2O_5Na$ $[(M+Na]^+)$: calc. 389.2; found 389.2.

Part B: A solution of Compound 10 (150 mg, 0.409 mmol) in EtOH (10 mL) was degassed with $N_2$ before Pd—C (43.6 mg, 0.409 mmol) was added. The mixture was then degassed with $H_2$. The reaction mixture stirred at room temperature under $H_2$ (1 atm) overnight. The solid was filtered off through a pad of Celite, and the filtrate was concentrated to afford Compound 11. Crude Compound 11 was used in the next step without further purification. ESI-MS m/z Calcd for $C_{12}H_{24}N_2O_5Na$ $[(M+Na]^+)$: calc. 299.2; found 299.2.

Part C: A 100 mL flask containing the residue of Compound 11 (128 mg, 0.463 mmol) and N,N-dimethylpyridin-4-amine (11.32 mg, 0.093 mmol) was flushed with argon, then triethylamine (129 μl, 0.926 mmol), acetonitrile (1.544 mL) and DMF (0.772 mL) were added. The reaction mixture was cooled to 0° C. and stirred for 5 min followed by the addition of 4-nitrophenyl carbonochloridate (140 mg, 0.695 mmol), and the resulting mixture was stirred at 20° C. for 2 h, then. concentrated to an oil. The residue was purified over silica gel (0-100% ethyl acetate in hexane) to afford Compound 12 (50 mg, 24% yield) as a white solid. ESI-MS m/z Calcd for: $C_{14}H_{19}N_3O_7$ $[(M\text{-}Boc+H]^+)$: calc. 342.2; found 342.1.

Part D: To a solution of Compound 12 (50 mg, 0.113 mmol) and Compound 1 (36.9 mg, 0.047 mmol) was added DMAP (1.153 mg, 9.44 μmol) in DMF (500 μL). The reaction mixture was heated at 80° C. for 3 h, then Compound 12 (50 mg, 0.113 mmol) was added. The reaction mixture was stirred for another 3 h and then cooled to room temperature. The mixture was concentrated, and the residue was purified over silica gel (0-30% MeOH in DCM) to afford Compound 13 (20 mg, 39% yield) as a white solid. ESI-MS m/z Calcd for: $C_{51}H_{67}N_{14}O_{13}$ $[(M+H)]^+$: calc. 1083.4; found 1083.5.

Part E: To a solution of Compound 13 (20 mg, 0.047 mmol) in DCM (0.5 mL) was added TFA (0.1 mL). The reaction mixture stirred at room temperature for 4 h then concentrated to afford Compound 14 (10 mg, 55% yield) as a solid. ESI-MS m/z Calcd for $C_{46}H_{59}N_{14}O_{11}$ $[M+H]^+$: calc. 983.4; found 983.5.

Part F: To a solution of Scaffold 6 (14.15 mg, 10.17 μmol) and Compound 14 (10 mg, 10.17 μmol) in DMF (1 mL) was added HATU (4.64 mg, 0.012 mmol), HOAt (1.881 mg, 0.012 mmol) and DIPEA (0.018 mL, 0.102 mmol). The reaction mixture stirred at room temperature 2 h then concentrated and the residue was purified on preparative RP HPLC (0-80% ACN in water) to afford Scaffold 15 (20 mg, 83% yield). ESI-MS m/z Calcd for: $C_{101}H_{152}N_{24}O_{41}$ $[(M+2H]^{2+})$: calc. 1178.7; found 1178.59.0.

Part G: A solution of XMT-1519 (10 mg, 0.069 μmol) was conjugated with Scaffold 15 ((0.823 mg, 0.347 μmol in 200 μL DMA) as described in Example 1. The purified Conjugate 16 had a STING agonist to XMT-1519 ratio of 5.3.

Example 3: Synthesis of Trastuzumab Conjugate 20

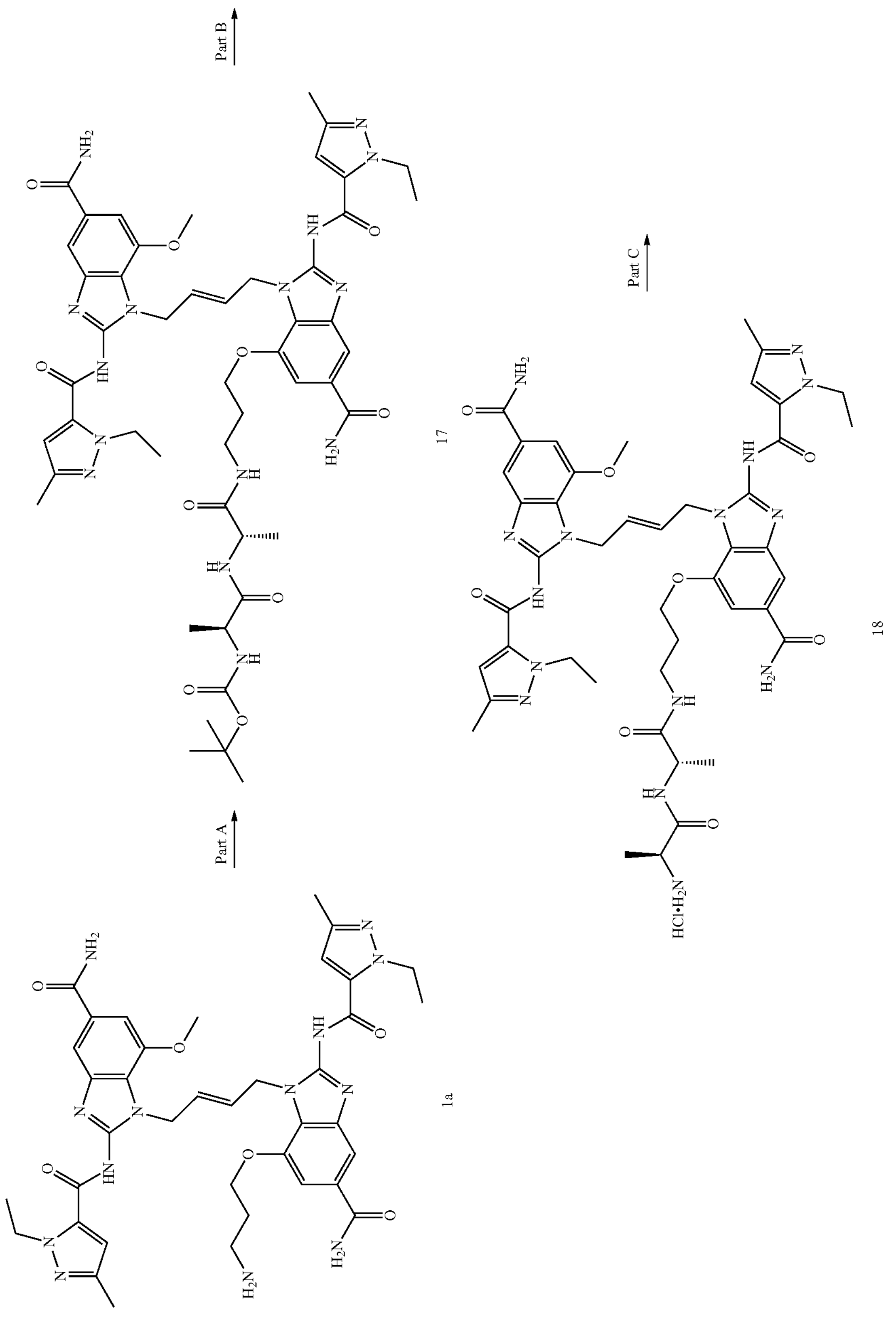
1a
17
18

-continued
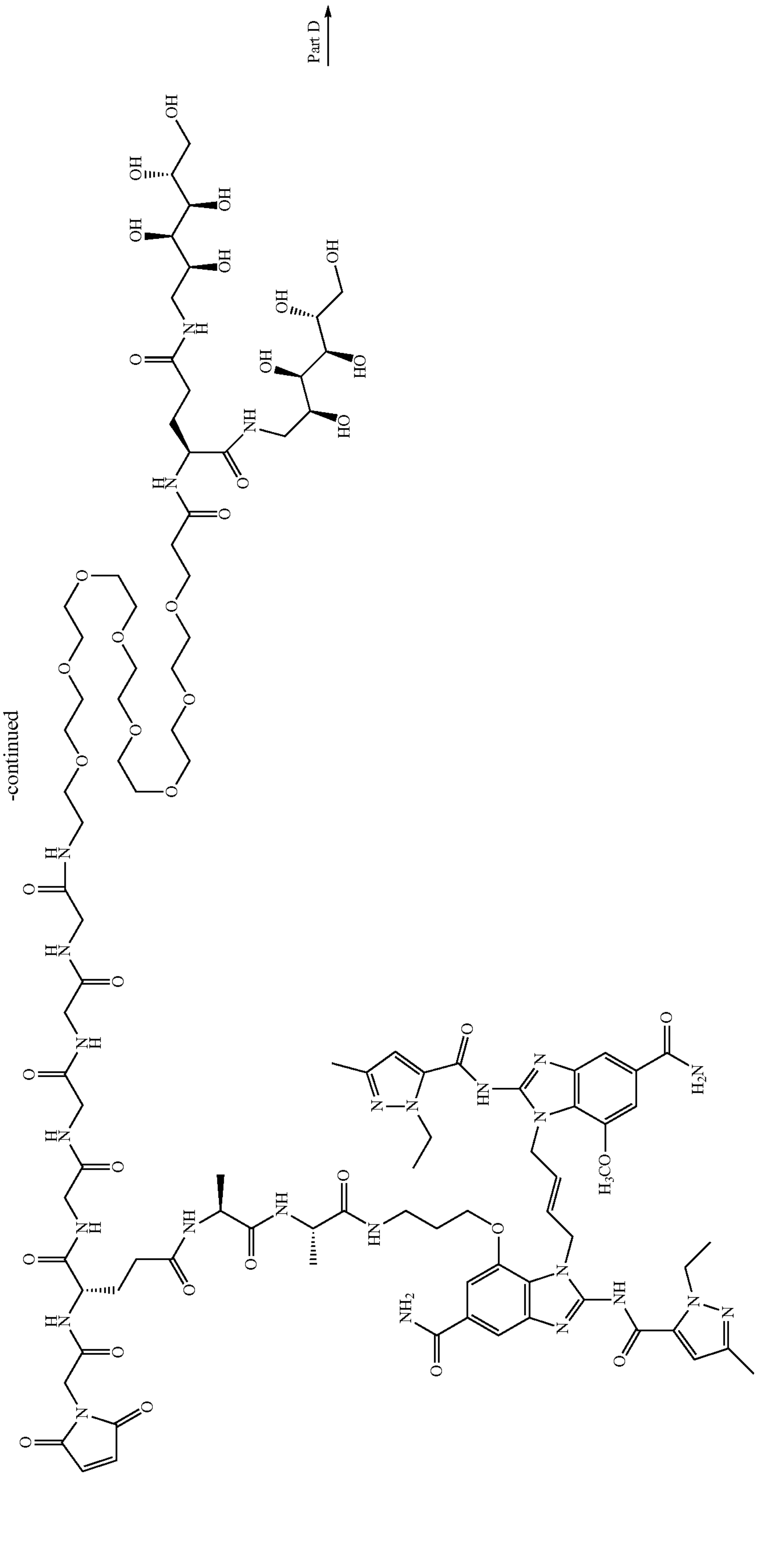
19

-continued
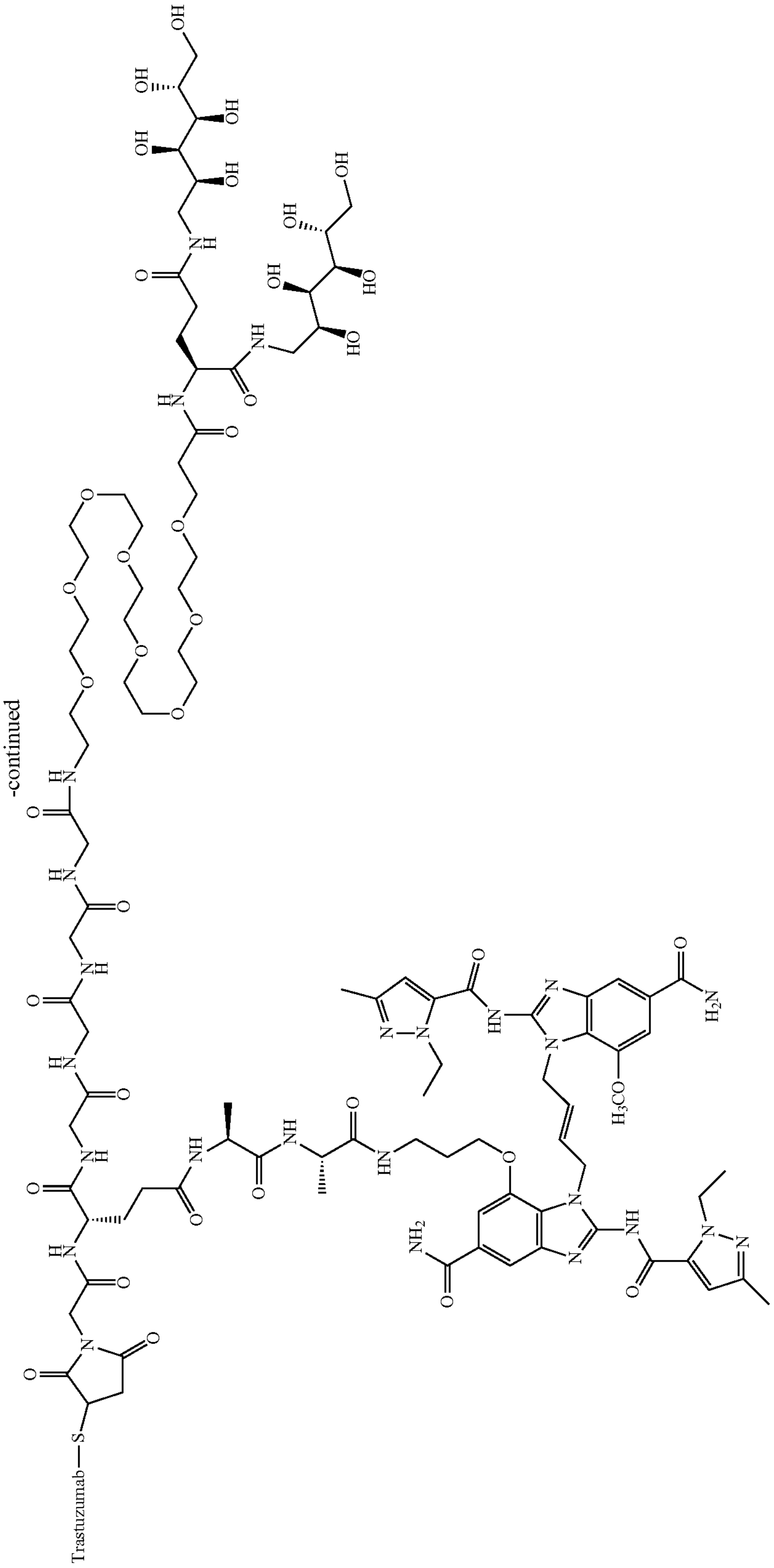

Part A: A solution of Boc-ala-ala-OH (67 mg, 256 μmol), CDI (70 mg, 435 μmol) and DMF (2 mL) was stirred at room temperature for 23 h. Then Compound 1a (prepared as described in WO2017175147A1, 100 mg, 128 μmol) and DIPEA (67 μL, 384 μmol) were added and the reaction stirred at room temperature for 23 h. The reaction mixture was concentrated, and the residue was chromatographed by silica gel (0-20% MeOH-DCM eluent). The product, Compound 17 was isolated as a yellow foam, (109 mg, 83% yield). ESI-MS m/zi Calcd for $C_{49}H_{64}N_{15}O_{10}$ $[M+H]^+$: 1022.5; found 1022.4.

Part B: A mixture of Compound 17 (108 mg, 106 μmol) and 2M HCl-dioxane (6 mL) was stirred at room temperature for 2 h. The reaction mixture was concentrated, and the residue was dried under high vacuum to afford Compound 18 is an off-white foam (103 mg, quant.). ESI-MS m/z Calcd for $C_{44}H_{56}N_{15}O_8$ [M+H]: 922.4; found 922.4.

Part C: A mixture of Compound 18 (80 mg, 84 μmol), Scaffold 6 (117 mg, 84 μmol), HOAt (12 mg, 84 μmol), DiPEA (59 μL, 336 μmol) and DMF (3 mL) was stirred at room temperature for 5 mins, then HATU (42 mg, 109 μmol) was added and the reaction mixture was stirred at room temperature for 20 h. The reaction mixture was then concentrated and chromatographed by reverse phase (10-100% ACN-water w/0.1% HCOOH eluent). Scaffold 19 was isolated as a white, fluffy solid, (35 mg, 18% yield). ESI-MS m/z Calcd for $C_{99}H_{149}N_{25}O_{38}$ $[M+2H]^{2+}$: calc. 1148.0; found 1148.4.

Part D: Trastuzumab (10 mg, 0.067 μmol) was conjugated with Scaffold 19 (1.237 mg, 0.539 μmol in 200 μL DMA) as described in Example 1 followed by purification using CHT type II chromatography to give Conjugate 20. The details of the antibody-drug conjugates 20-1 and 20-2 are given below.

| Conjugate | DAR |
|---|---|
| 20-1 | 6.0 |
| 20-2 | 6.1 |

Example 3a: Synthesis of Palivizumab Conjugate 20a, DAR 5.5

20a
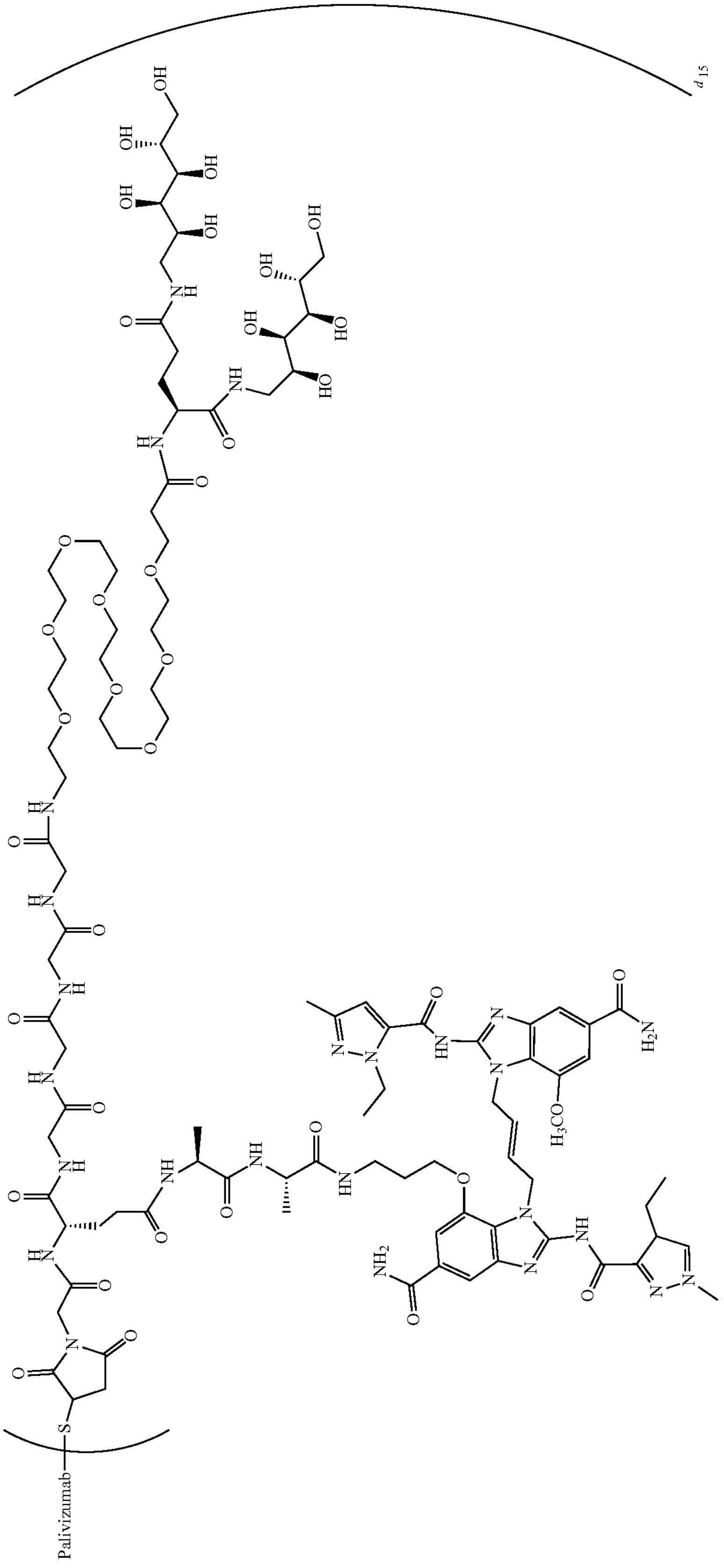

Conjugate 20a was prepared and characterized as described in Example 1 except that Palivizumab was used instead of XMT-1519. The purified Conjugate 20a had a STING agonist to Palivizumab ratio of 5.5.

Example 4: Synthesis of Trastuzumab Conjugate 25, DAR 6.6

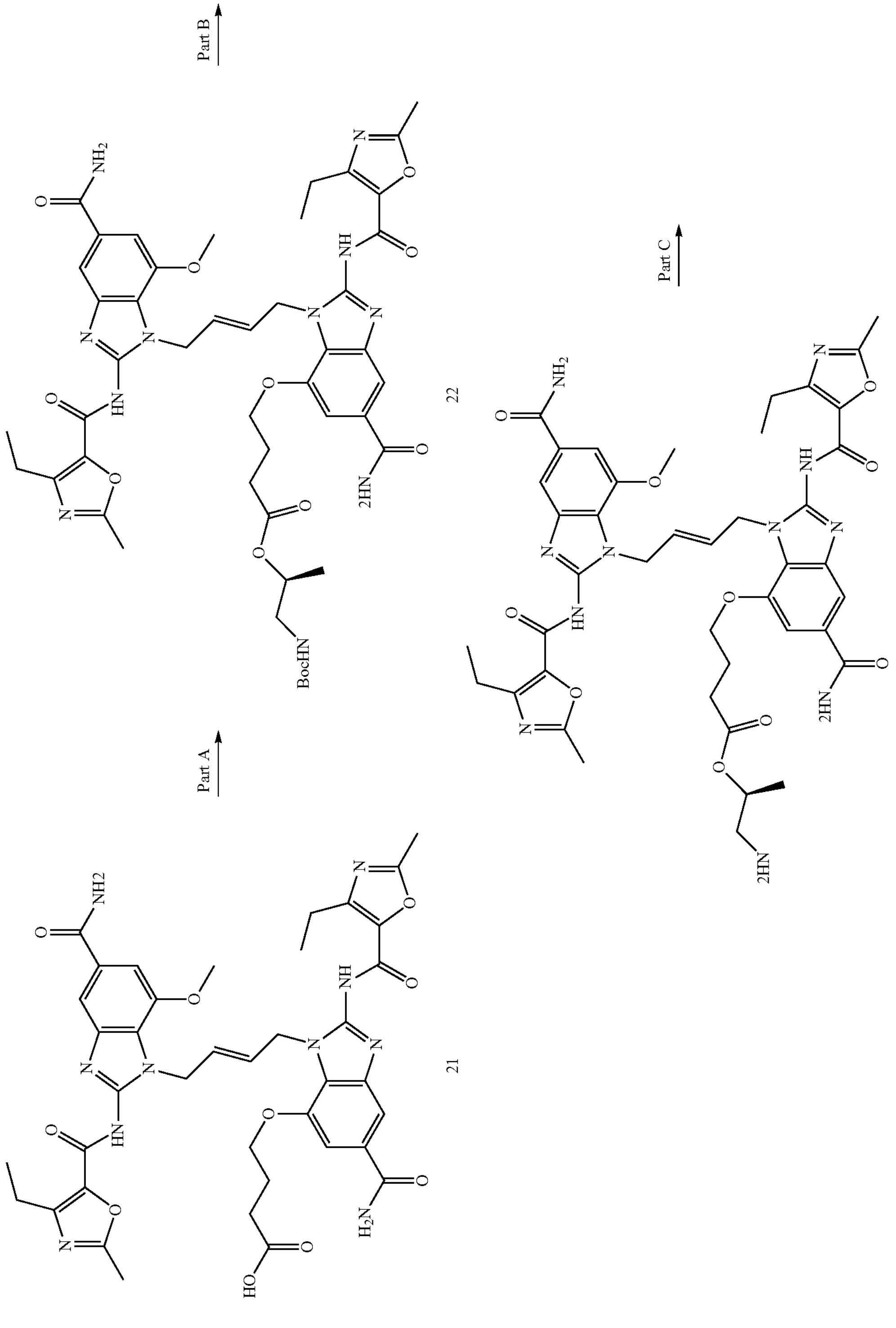
21
22
23

-continued
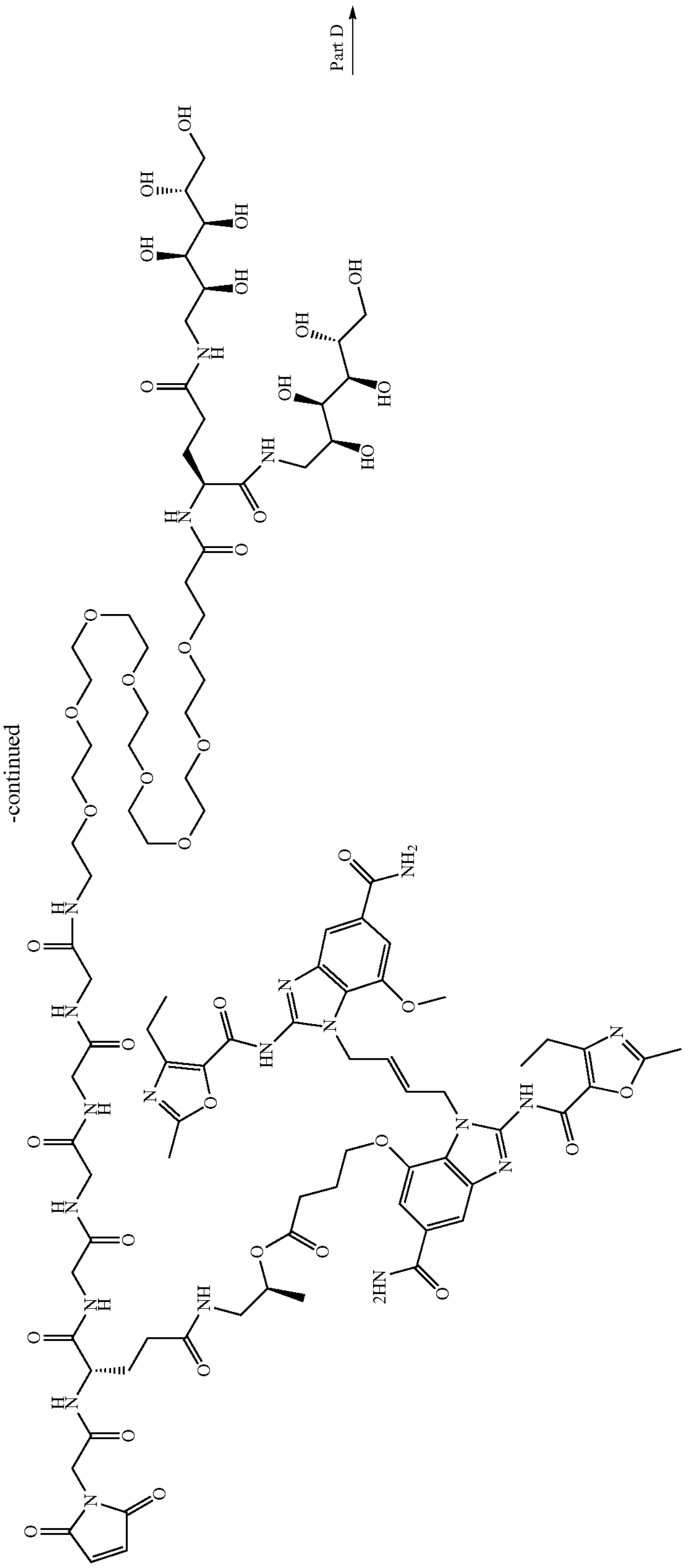
24

-continued
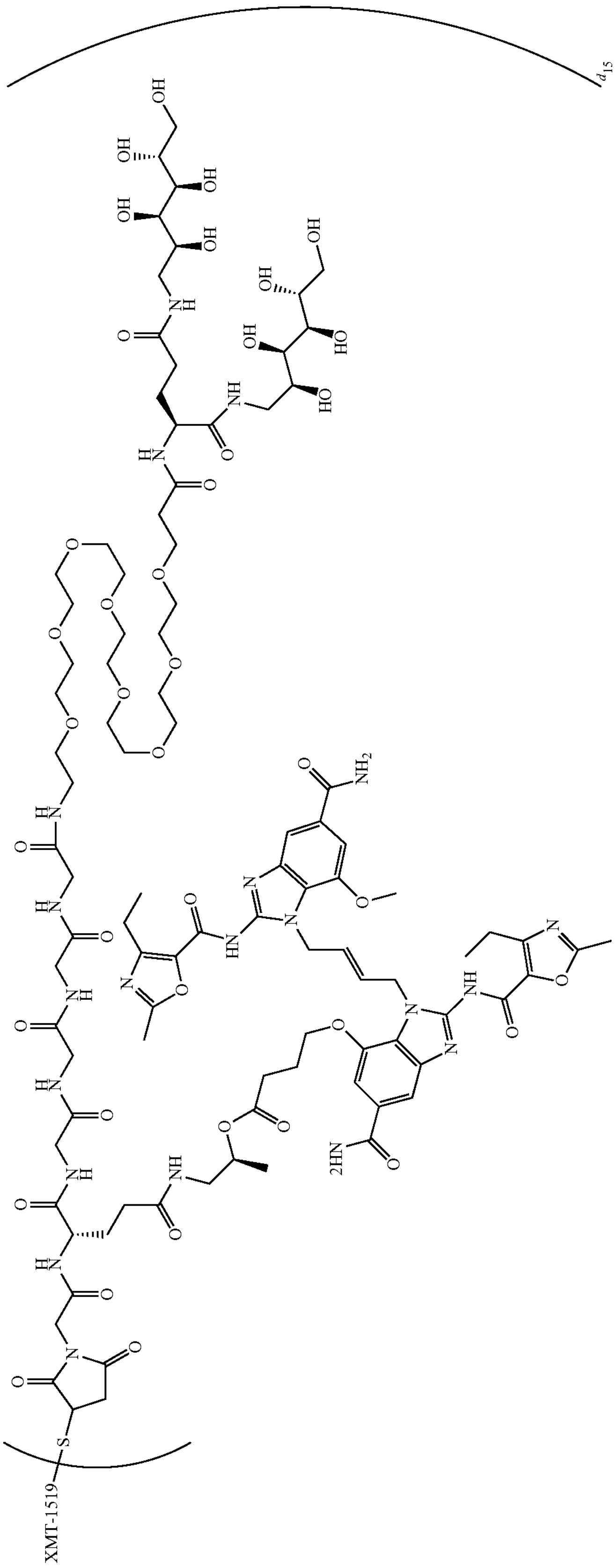

Part A: To a mixture of Compound 21 (prepared as described in U.S. 62/982,935, 38 mg, 0.047 mmol) and tert-butyl (S)-(2-hydroxypropyl)carbamate (9.85 mg, 0.056 mmol) in DMF (2 mL) were added 3-((ethylimino)methylene)amino)-N,N-dimethylpropan-1-amine hydrochloride (13.48 mg, 0.070 mmol), HOBt (10.77 mg, 0.070 mmol) DIPEA (0.016 mL, 0.094 mmol) and DMAP (5.73 mg, 0.047 mmol). The suspension was then stirred for 2 days at room temperature. The mixture was concentrated to afford a residue which was then purified on silica gel (0-30% MeOH in DCM) to give Compound 22 as light-yellow solid (20 mg, 44% yield). ESI-MS m/z Calcd for $C_{47}H_{58}N_{11}O_{12}$ $[M+H]^+$: calc. 968.4; found 968.3.

Part B: To a suspension of Compound 22 (20 mg, 0.021 mmol) in dioxane (4 mL) was added 4 N HCl (0.52 mL, 8.19 mmol). The reaction mixture was stirred at room temperature for 5 h, concentrated and used without purification in the next step. The product Compound 23 (17 mg, 95% yield) was a white solid. ESI-MS m/z Calcd for $C_{42}H_{50}N_{11}O_{10}$ $[M+H]^+$: 868.3; found 868.4.

Part C: To a solution of Compound 23 (17 mg, 0.020 mmol) and Scaffold 6 (32.1 mg, 0.023 mmol) in DMF (2 mL) were added PyBOP (15.3 mg, 0.03 mmol), and DIPEA (0.034 mL, 0.196 mmol). The reaction mixture stirred at room temperature 2 h, concentrated to afford a residue which was then purified on preparative RP HPLC (0-80% ACN in water) to afford Scaffold 24 (26 mg, 59% yield). ESI-MS m/z Calcd for $C_{97}H_{143}N_{21}O_{40}$ $[M+2H]^{2+}$: 1120.98; found 1121.06.

Part D: XMT-1519 antibody (5 mg, 0.0347 μmol) was conjugated with Scaffold 24 (0.622 mg, 0.278 μmol) As described in Example 1. The crude reaction mixture was purified by CHT column chromatography to give Conjugate 25 (3.19 mg, 64% yield). Purified Conjugate 25 had a STING agonist to XMT-1519 ratio of 6.6.

Example 5: Synthesis of XMT-1519 Conjugate 28, DAR 6.0

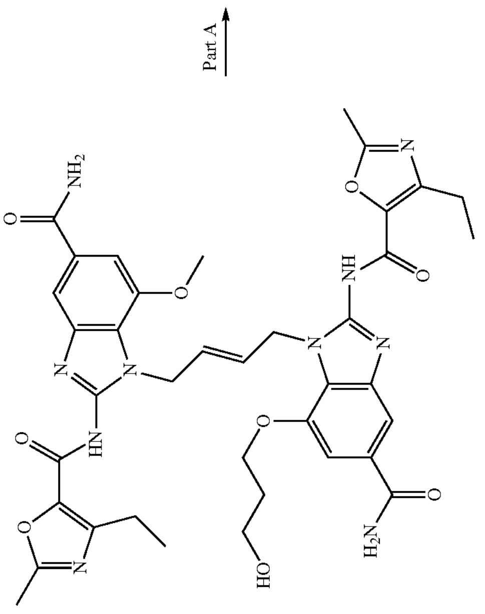
26

-continued
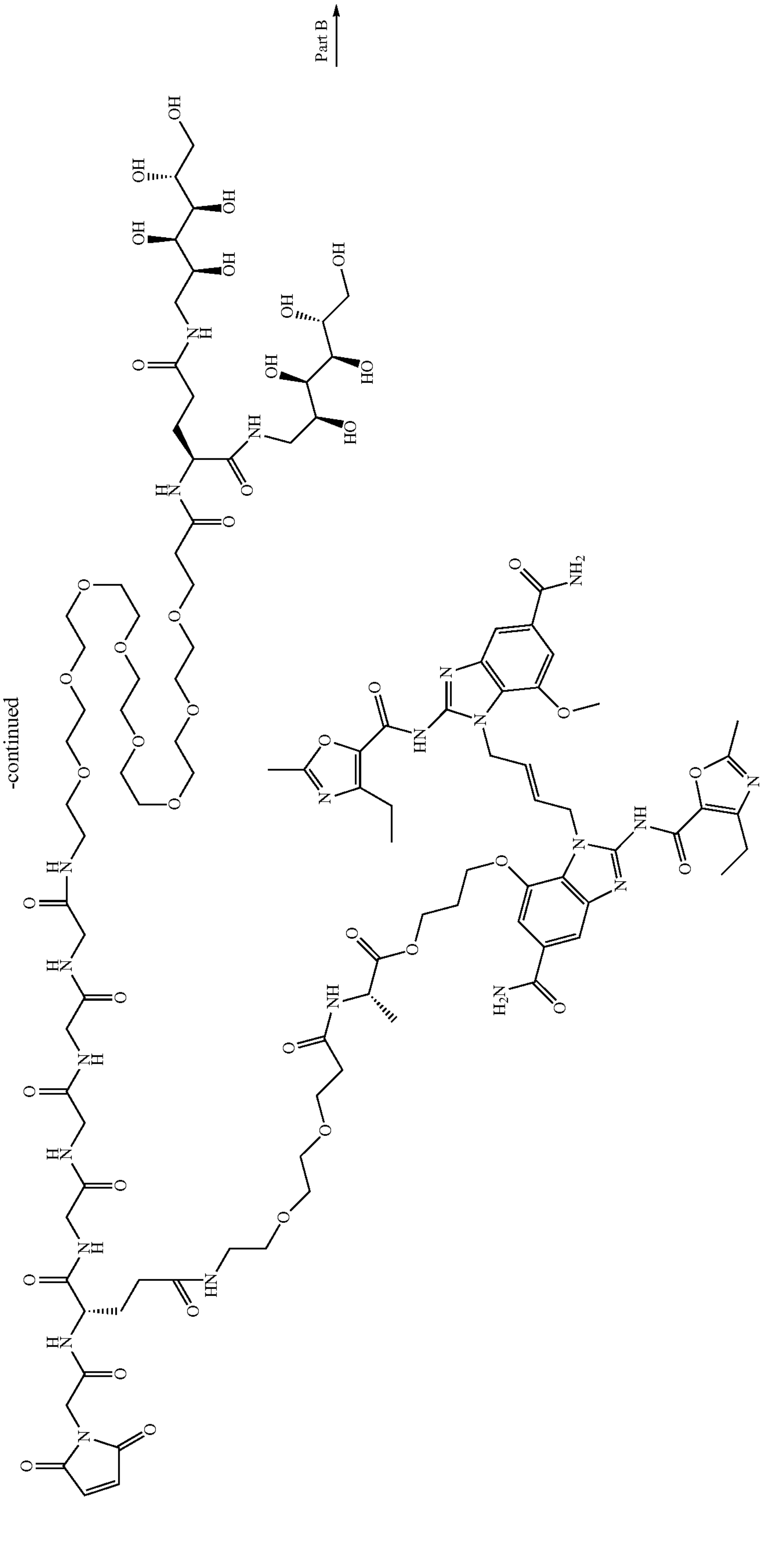
27

-continued
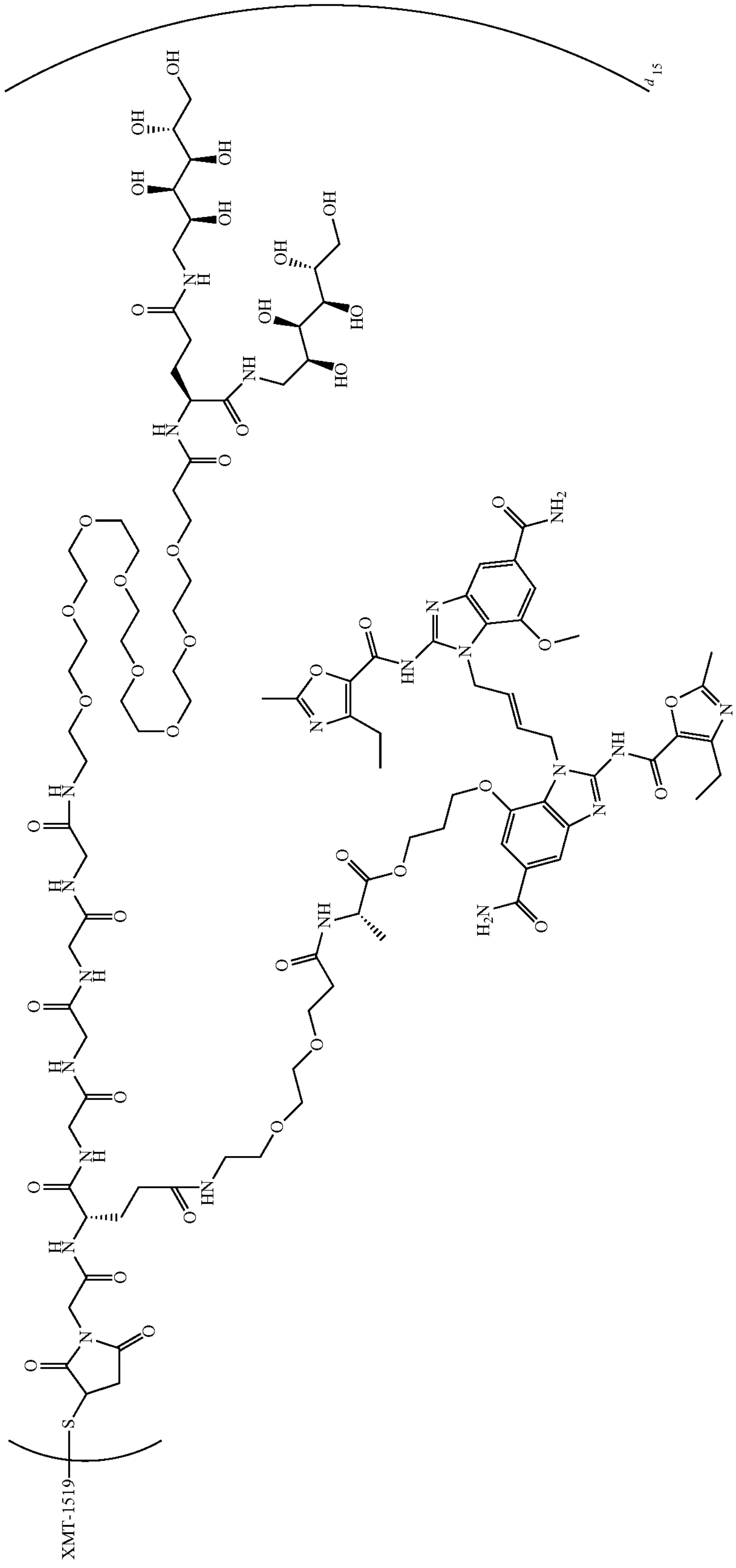
28

Part A: Compound 26 was prepared as described in Example 1 except that 26 (prepared as described in U.S. 62/982,935) was used instead of Compound 1. Compound 27 was obtained as a colorless solid (71.0 mg, 40% yield). ESI-MS m/z Calcd for $C_{103}H_{154}N_{22}O_{43}$ $[M+2H]^{2+}$: 1193.52; found 1193.48

Part B: Conjugate 28 was prepared as described in Example 1 to afford Conjugate 28. The purified Conjugate 28 had a STING agonist to XMT-1519 ratio of 6.0.

Example 6: Synthesis of XMT-1519 Conjugate 29, DAR 5.5

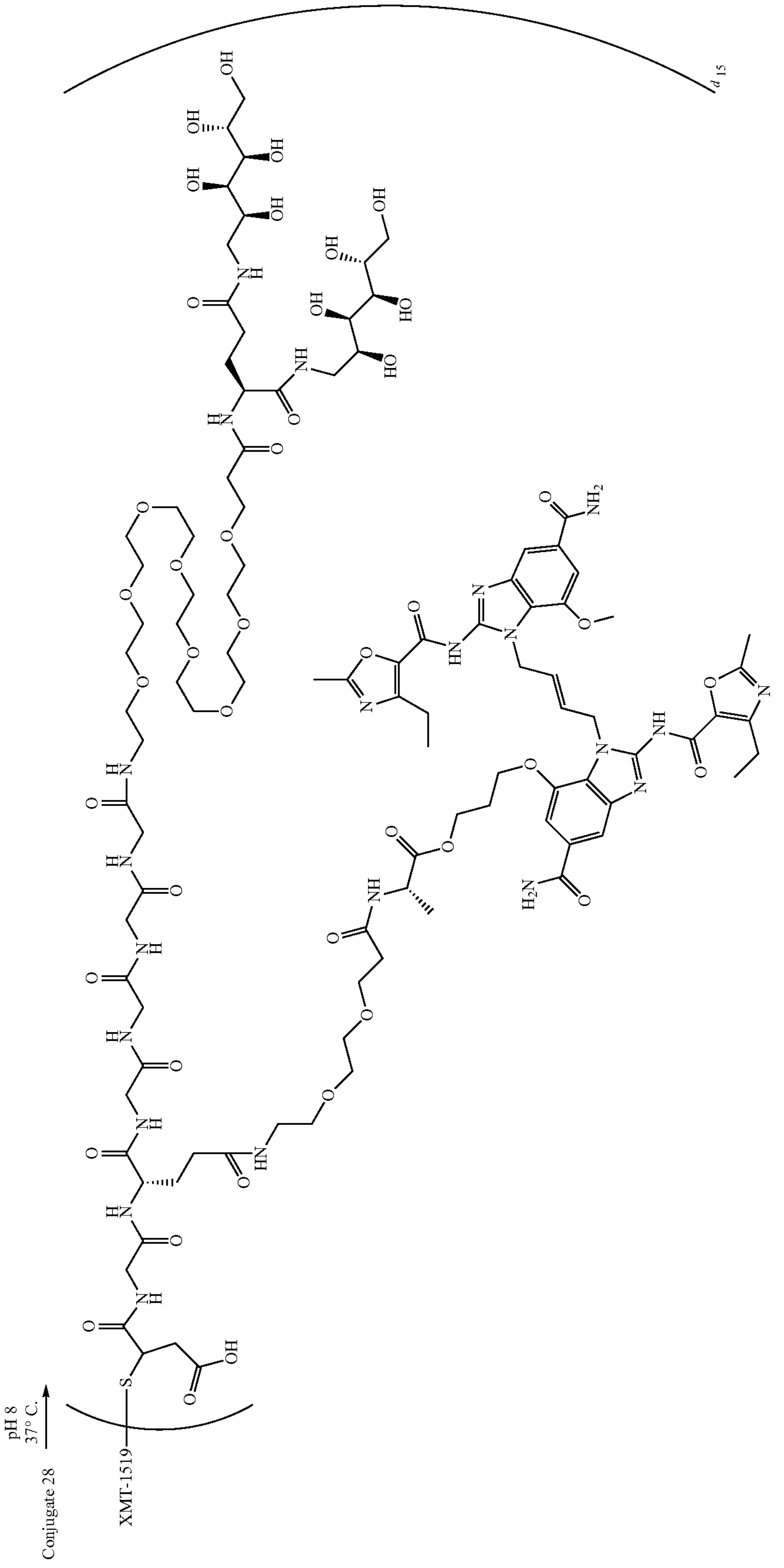
29

Conjugate 28 (6.5 mg) was formulated into PBS, pH 8 with 3 cycles of concentration and dilution using a 30 kDa MWCO ultrafiltration unit. The reformulated conjugate was then incubated at 37° C. for 24 h and then reformulated to trehalose buffer pH 5.5. Ring-opening was confirmed by LCMS analysis of heavy and light chain following antibody reduction. Good resolution was observed between various light chain species: unconjugated, conjugated with intact succinimide, and conjugated with ring-opened succinimide. Ring-opening could also be observed in the corresponding heavy chain species but resolution between the various species was poor. The degree of ring-opening was therefore estimated by focusing on the light chain species. Using this approach, the percentage of ring-opened product in Conjugate 29 relative to intact succinimide was estimated as 94%. Conjugate 29 had a STING agonist to XMT-1519 ratio of 5.5.

Example 7: Synthesis of XMT-1519 Conjugate 32-1, DAR 6.5

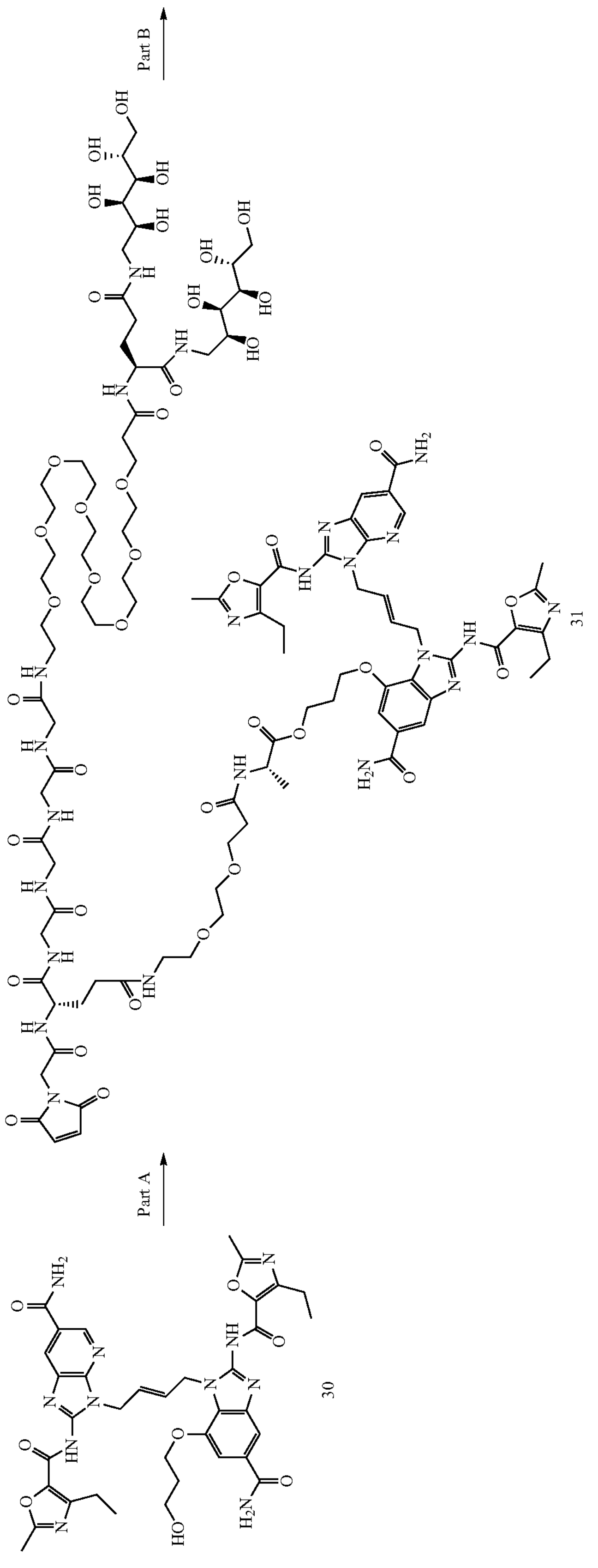
30
31

-continued
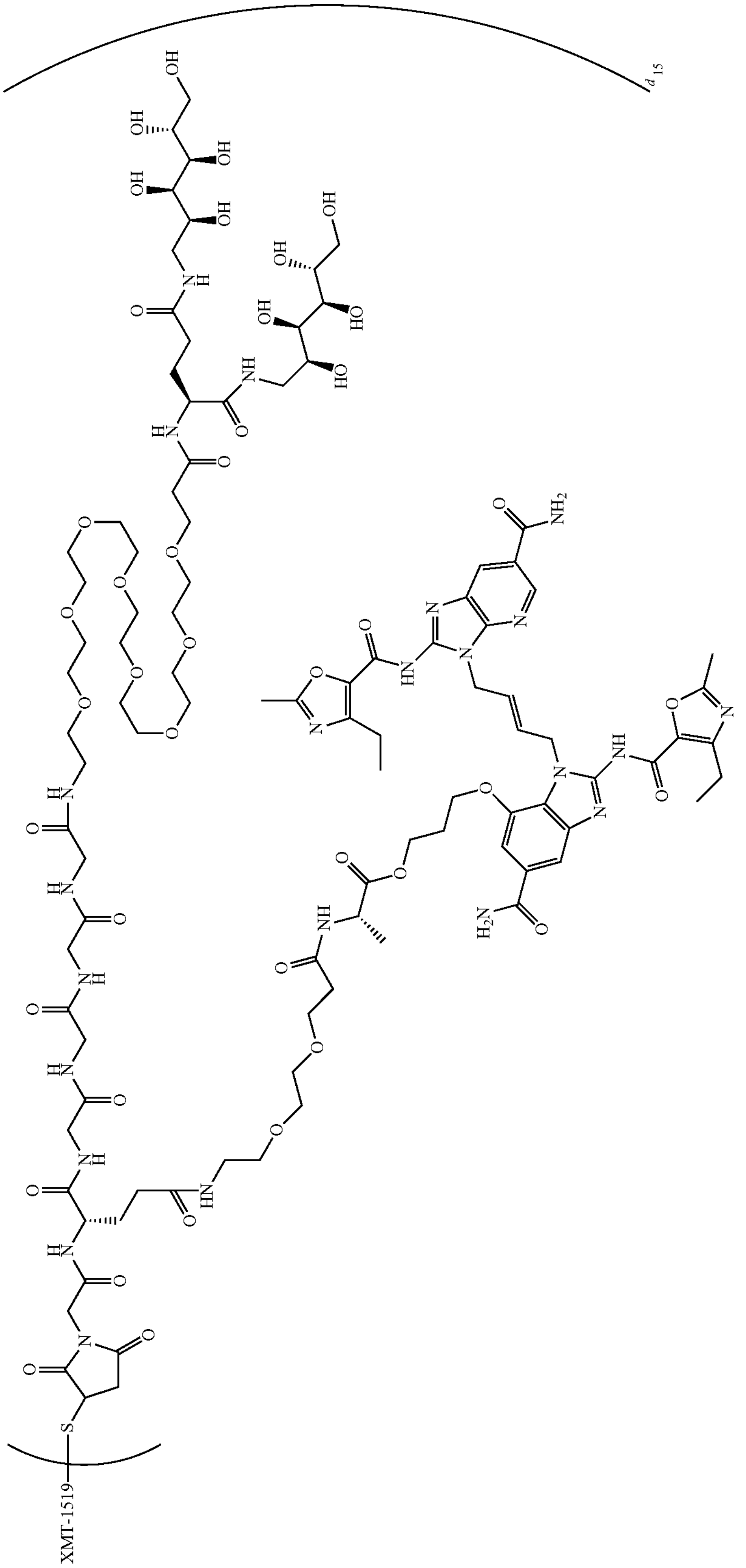
32-1

Part A: Scaffold 31 was prepared as described in Example 1 except that Compound 30 (prepared as described in U.S. 62/982,935) was used instead of Compound 1. Scaffold 31 was obtained as a colorless solid (9 mg, 8% yield). ESI-MS m/z Calcd for $C_{101}H_{151}N_{23}O_{42}$ $[M+2H]^{2+}$. 1179.02; found 1179.21.

Part B: Conjugates 32-1, 32-2, 32-3, and 32-4 were prepared as described in Example 1 to afford the title conjugate. The purified Conjugate 32-1, 32-2, 32-3, 32-4, and 32-5 had a STING agonist to XMT-1519 ratio as described in the table below. Conjugate 32-5 had a mAb concentration of >10 mg/mL, contained <1% of unconjugated mAb, and <1% high molecular weight species.

| Conjugate | DAR |
|---|---|
| 32-1 | 6.5 |
| 32-2 | 6.4 |
| 32-3 | 6.7 |
| 32-4 | 8.6 |
| 32-5 | 8.1 |

Example 7a: Synthesis of XMT-1535 Conjugate 32a, DAR 6.2

32a
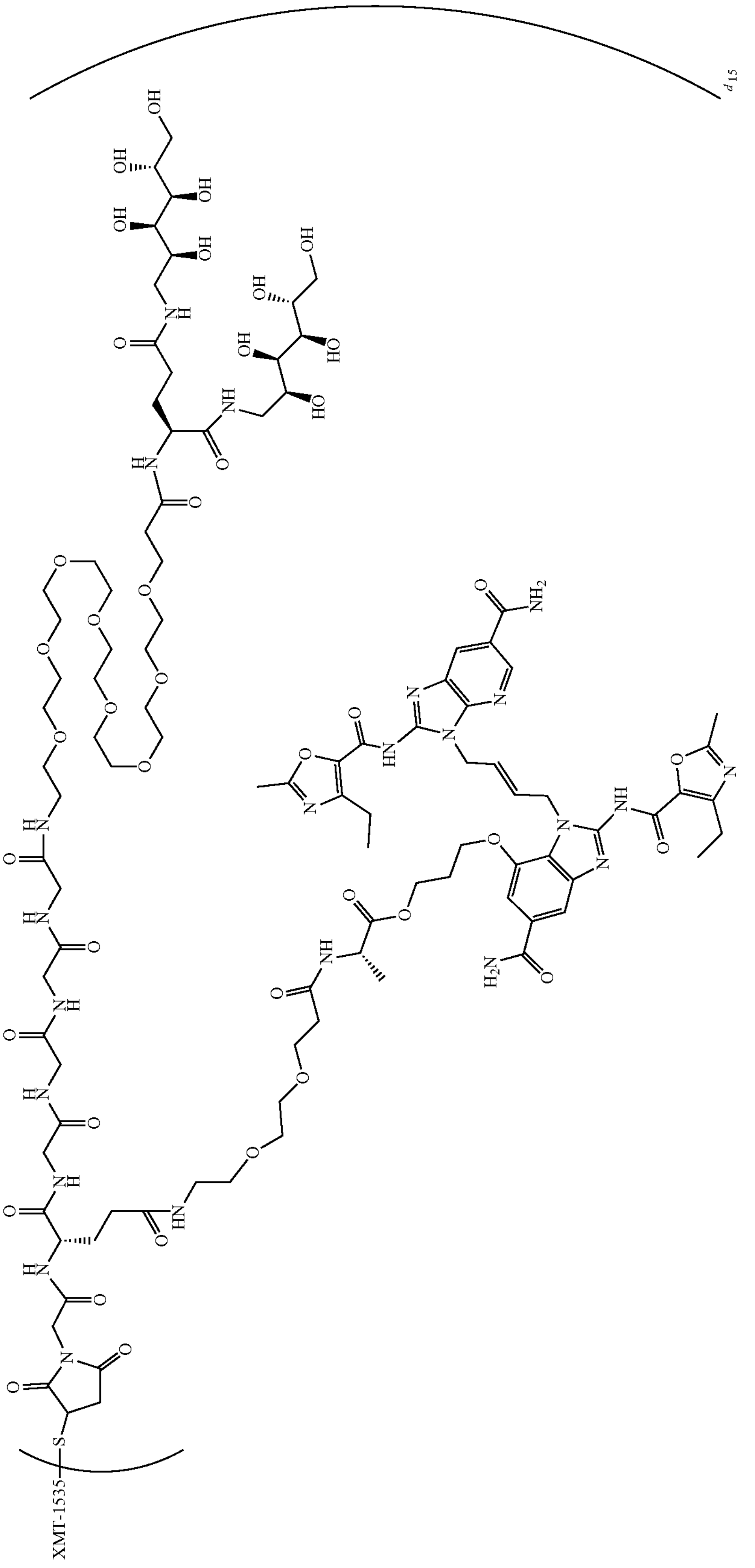

Conjugates 32a, 32a-1, 32a-2, 32a-3, and 32a-4 were prepared and characterized as described in Example 1 except that XMT-1535 was used instead of XMT-1519. The purified Conjugates 32a, 32a-1, 32a-2, 32a-3, and 32a-4 had a STING agonist to XMT-1535 ratio as described in the table below.

| Conjugate | DAR |
|---|---|
| 32a | 6.2 |
| 32a-1 | 7.4 |
| 32a-2 | 8.0 |
| 32a-3 | 7.5 |
| 32a-4 | 8.0 |

Example 7b: Synthesis of Palivizumab Conjugate 32b, DAR 6.8

32b
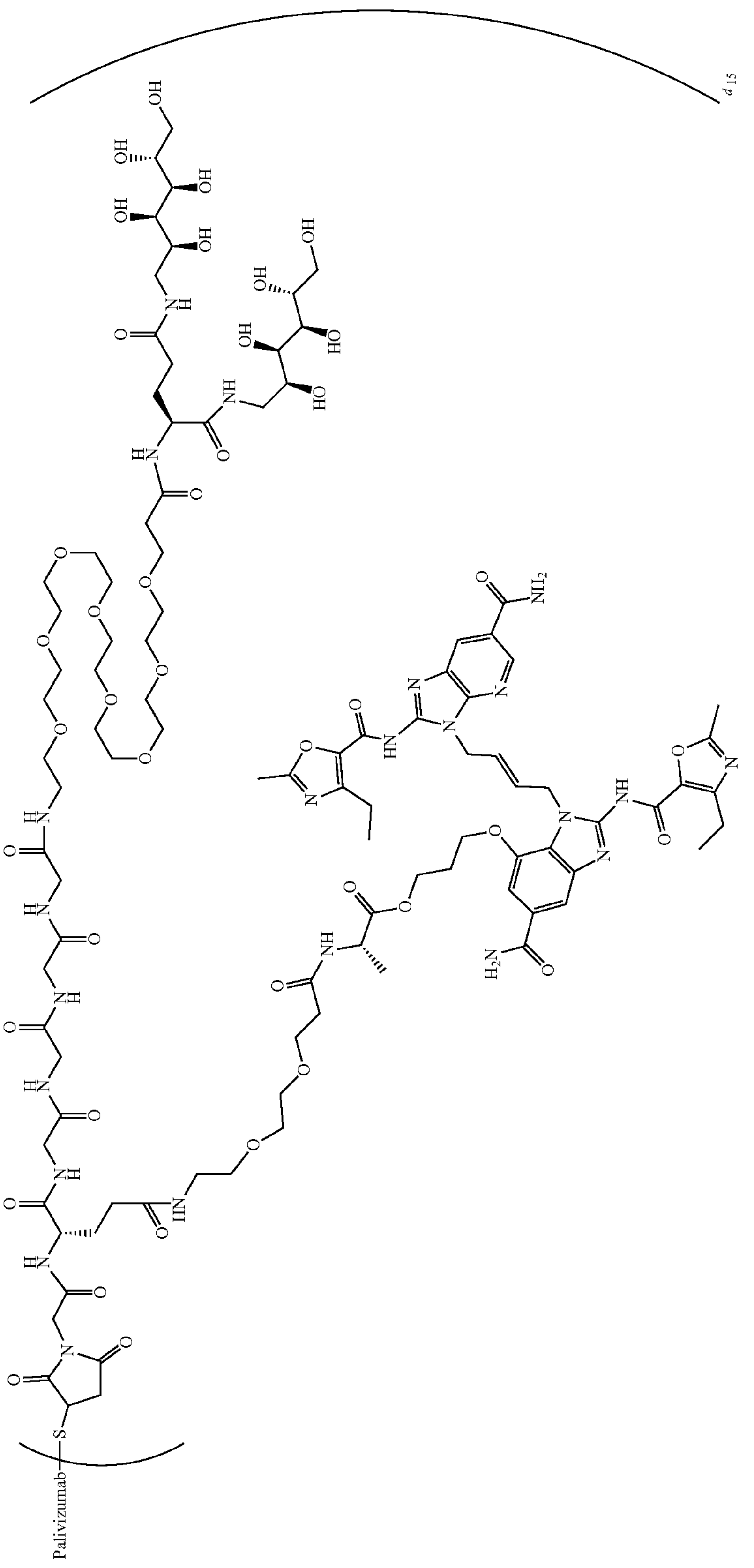

Conjugates 32b, 32b-1, and 32b-2 were prepared and characterized as described in Example 1 except that Palivizumab was used instead of XMT-1519. The purified Conjugates 32b, 32b-1, and 32b-2 had a STING agonist to Palivizumab ratio as described in the table below.

| Conjugate | DAR |
|---|---|
| 32b | 6.8 |
| 32b-1 | 5.7 |
| 32b-2 | 7.2 |

Example 7c: Synthesis of Palivizumab mIgG2a Conjugate 32c, DAR 9.1

32c
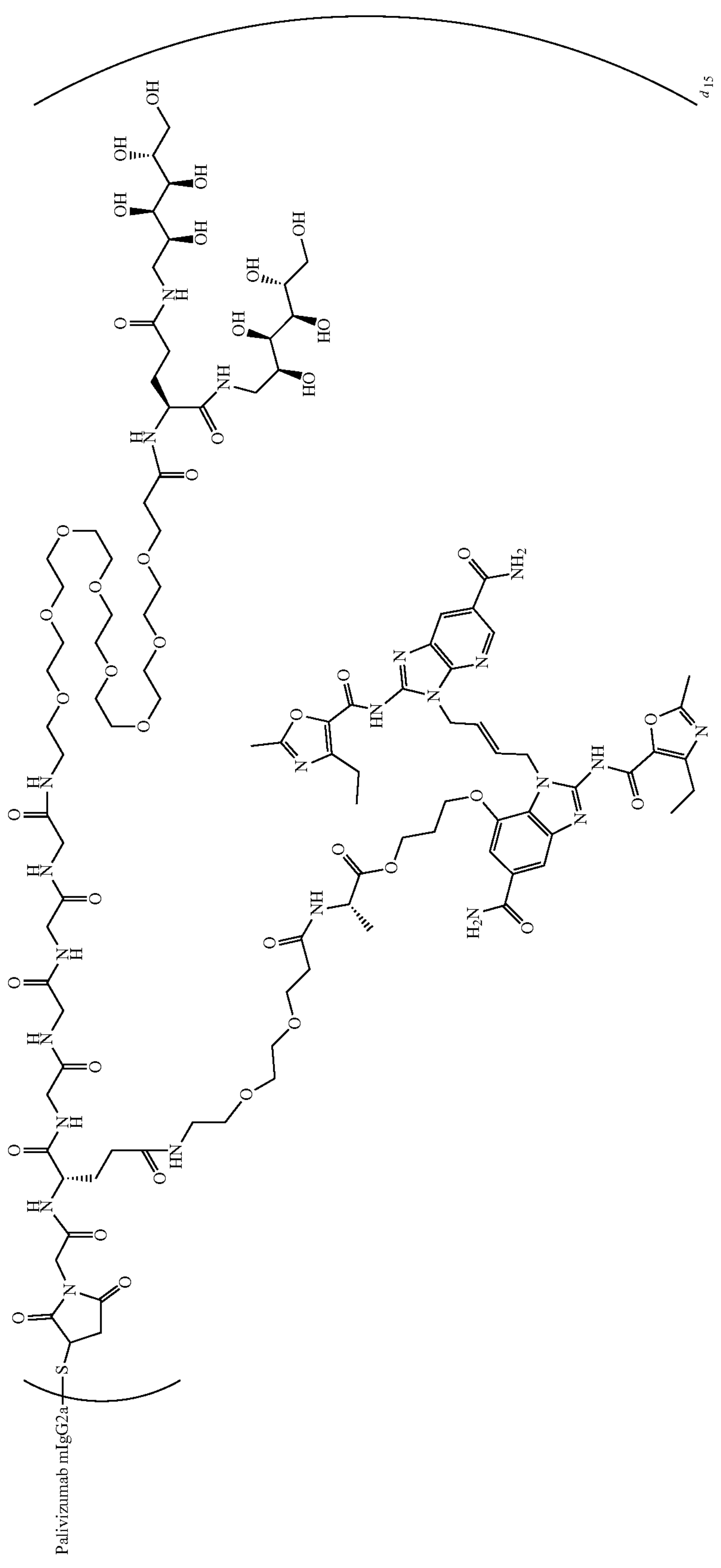

Conjugate 32c was prepared and characterized as described above in Example 1 except that Palivizumab mIgG2a was used instead of XMT-1519. The purified Conjugate 32c had a STING agonist to Palivizumab ratio of 9.1.

Example 7d: Synthesis of XMT-1535 mIgG2a Conjugate 32d, DAR 8.8

32d
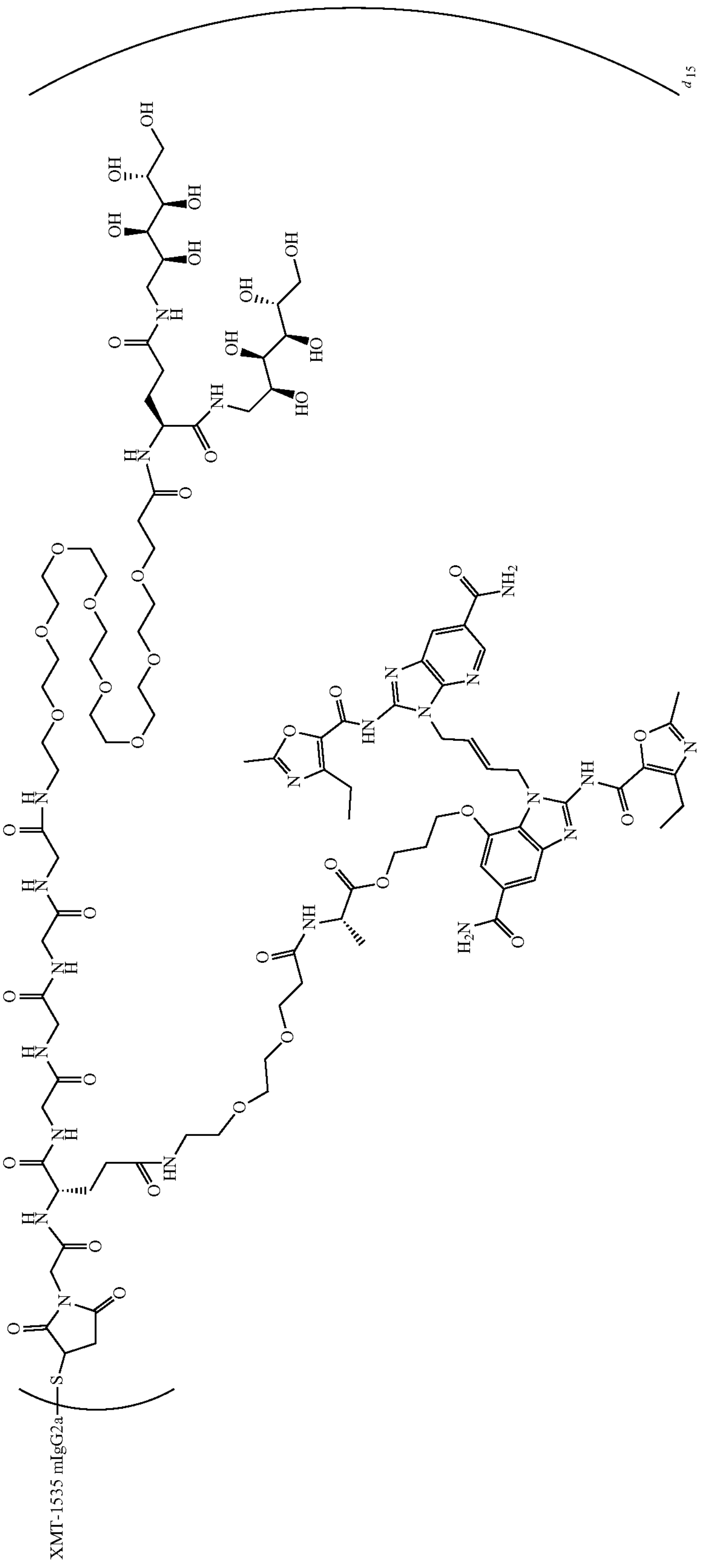

Conjugate 32d was prepared and characterized as described above in Example 1 except that XMT-1535 mIgG2a was used instead of XMT-1519. The purified Conjugate 32d had a STING agonist to XMT-1535 mIgG2a ratio of 8.8.

Example 7e: Synthesis of XMT-1519 AAG Conjugate 32e, DAR 7.4

32e
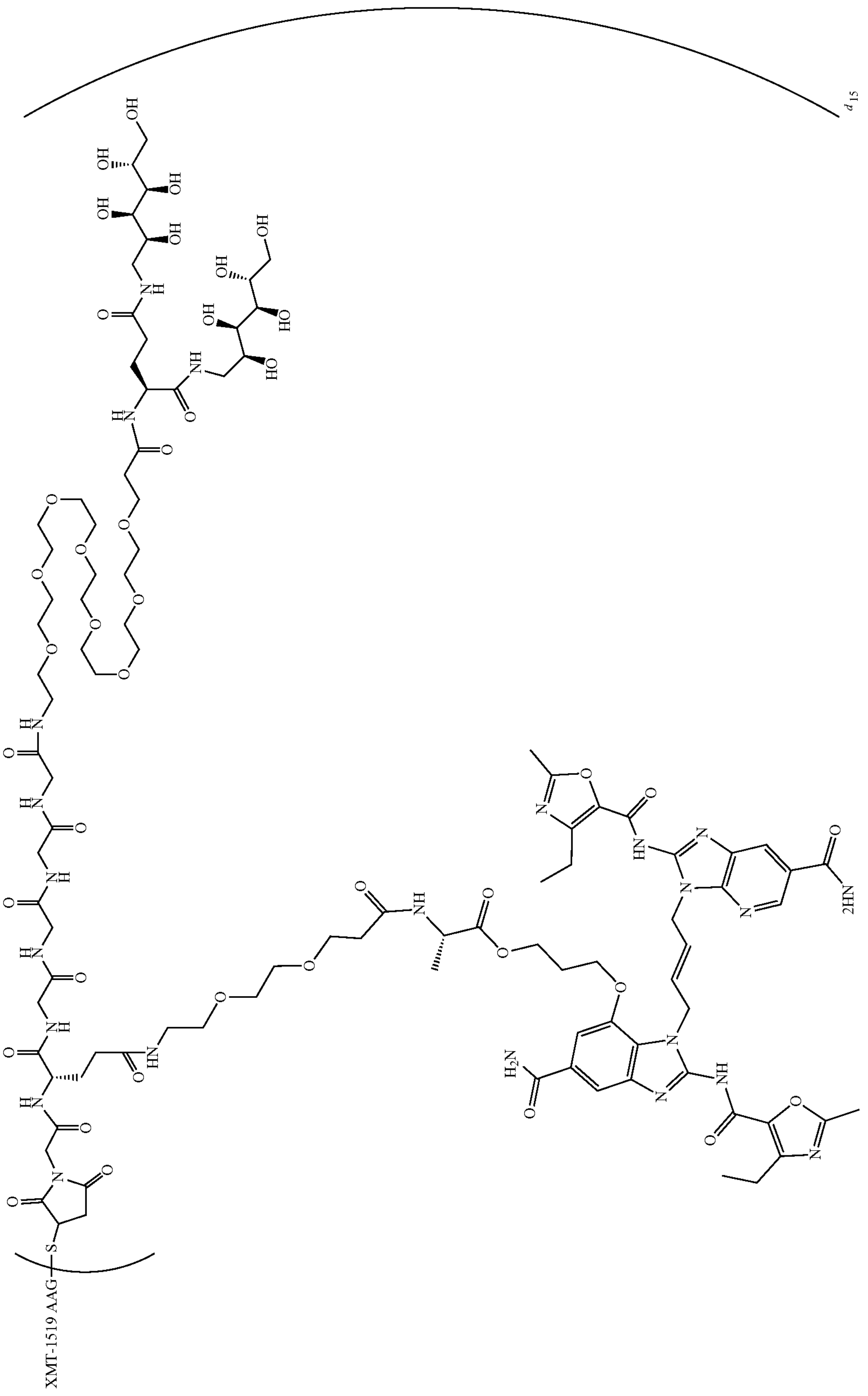

Conjugate 32e was prepared and characterized as described in Example 1 except that XMT-1519 AAG was used instead of XMT-1519. The purified Conjugate 32e had a STING agonist to XMT-1519 AAG ratio of 7.4.
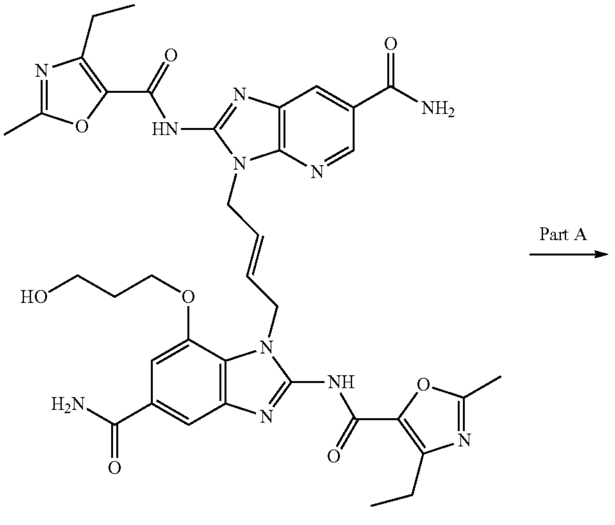
30
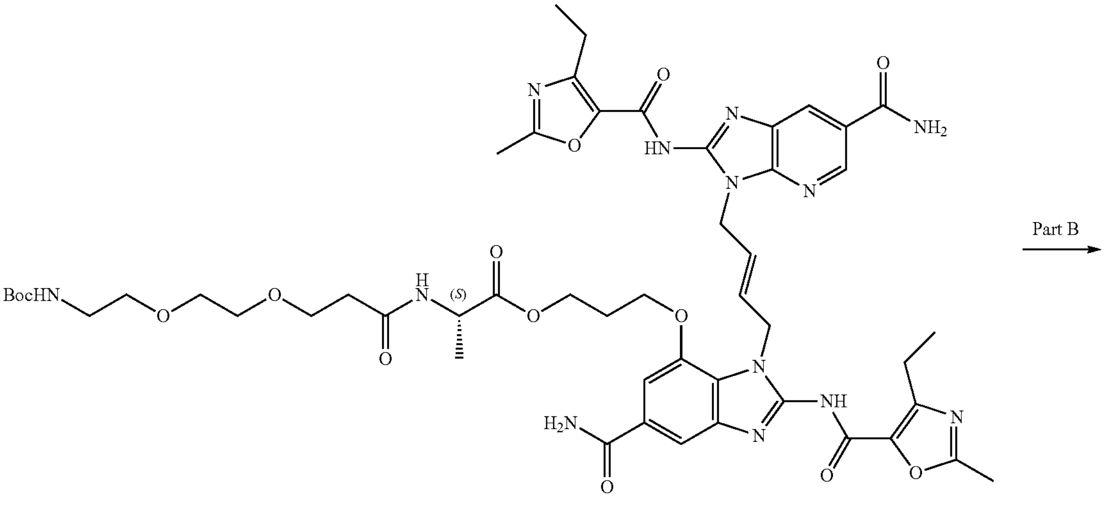
30a
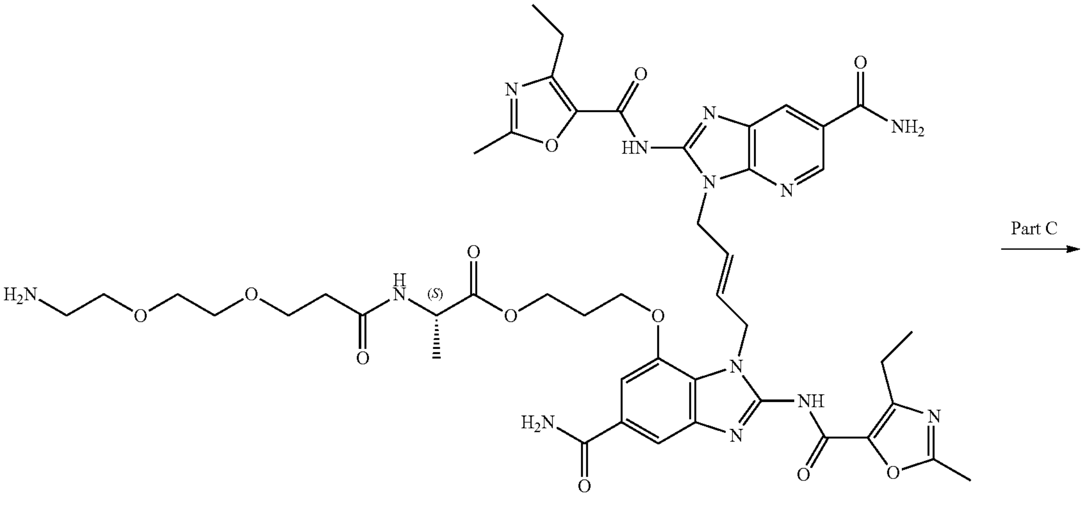
30b -continued

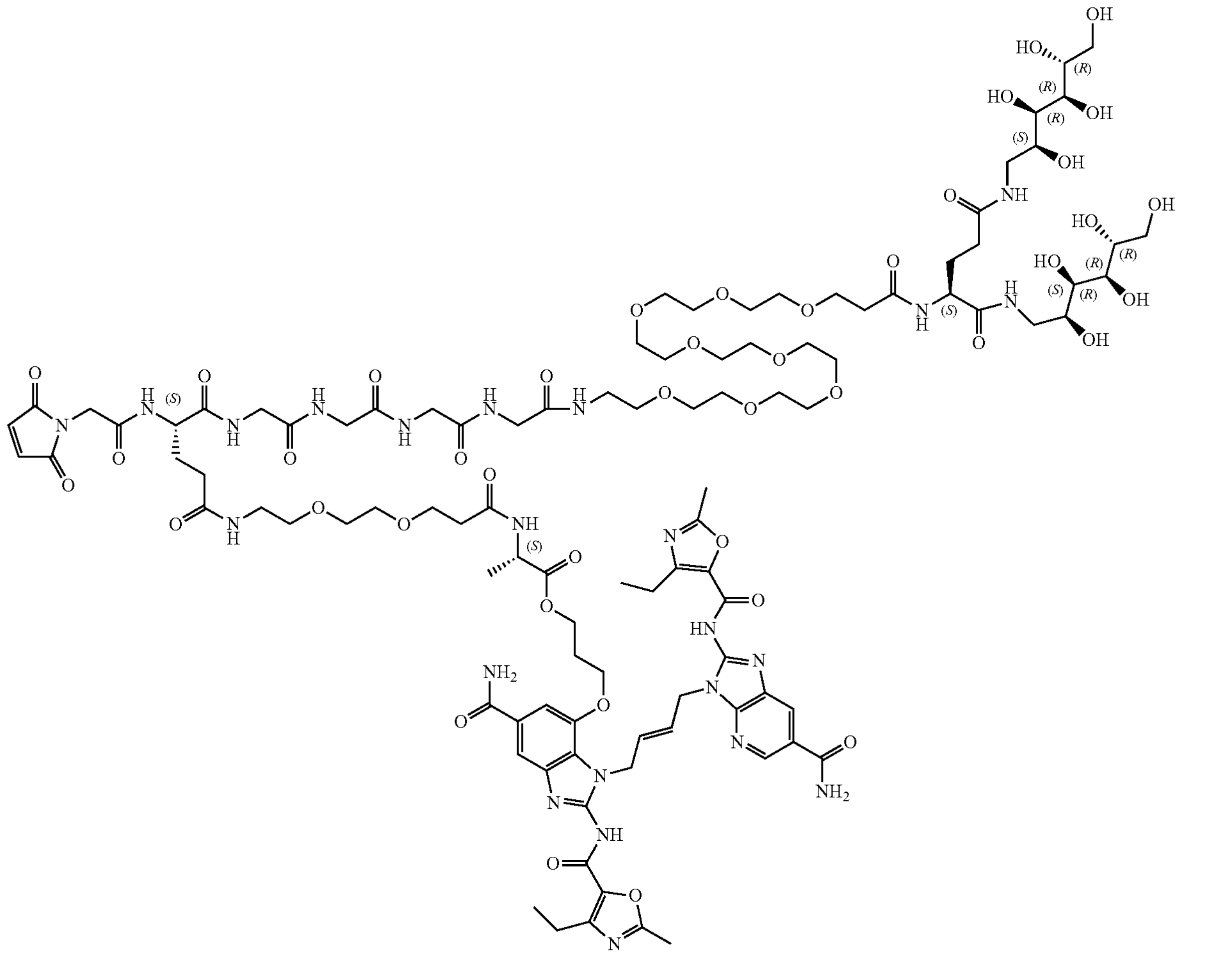

31

Example 7-1: Alternate Synthesis of Compound 31

Part A: Compound 30 (prepared as described in U.S. 62/982,935) (500 mg, 0.663 mmol, 1 eq), Boc-PEG2-Ala-OH (0.693 g, 1.99 mmol, 3 eq), EDC-HCl (381 mg, 1.99 mmol, 3 eq), and DMAP (243 mg, 1.99 mmol) were mixed in a vial under air in DMF (26.5 mL). Reaction was complete in 3 hours. Mixture was quenched with AcOH (0.76 mL, 10 eq), concentrated, and purified over silicagel (DCM:MeOH) to afford Compound 30a as a white solid. ESI-MS m/z Calcd for $C_{51}H_{66}N_{13}O_{14}$ $[M+H]^+$: 1084.5; found 1084.4.

Part B: Compound 30a (0.663 mmol) was suspended in dioxane (10 mL) in a flask under air. HCl (4M in dioxane, 6 mL) was added, and the mixture was stirred at room temperature for 1 hour. The mixture was concentrated to give a white solid. The solid was dissolved in pure water and purified by reverse phase chromatography (0-25% ACN in water) to afford Compound 30b (444 mg, 770) as a white solid. ESI-MS m/z Calcd for $C_{46}H_{58}N_{13}O_{12}$ $[M+H]^+$: 984.4; found 984.2.

Part C: To a solution of Scaffold 6 (450 mg, 0.32 mmol, prepared as described in PCT/US2018/06719) and Compound 30b (350 mg, 0.072 mmol) in DMF (6.5 mL) were added PyBOP (185 mg, 0.36 mmol) and triethylamine (0.23 mL, 1.62 mmol). The mixture was stirred at RT for 15 minutes and then quenched with AcOH (0.23 mL, 3.99 mmol) and purified by reverse phase purification (0-40% ACN in water w/0.1% acetic acid) to give Compound 31 (408 mg, 55% yield). ESI-MS m/z Calcd for $C_{101}H_{151}N_{23}O_{42}$ $[M+2H]^{2+}$: 1179.52; found 1179.27.

Example 8: Synthesis of Trastuzumab Conjugate 34, DAR 6.9
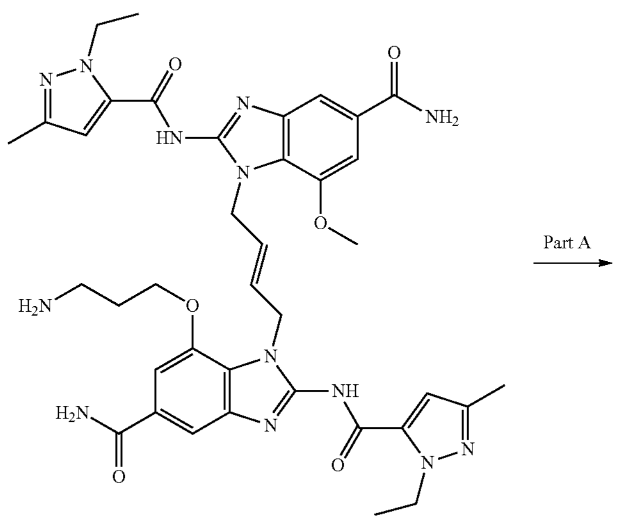
1a
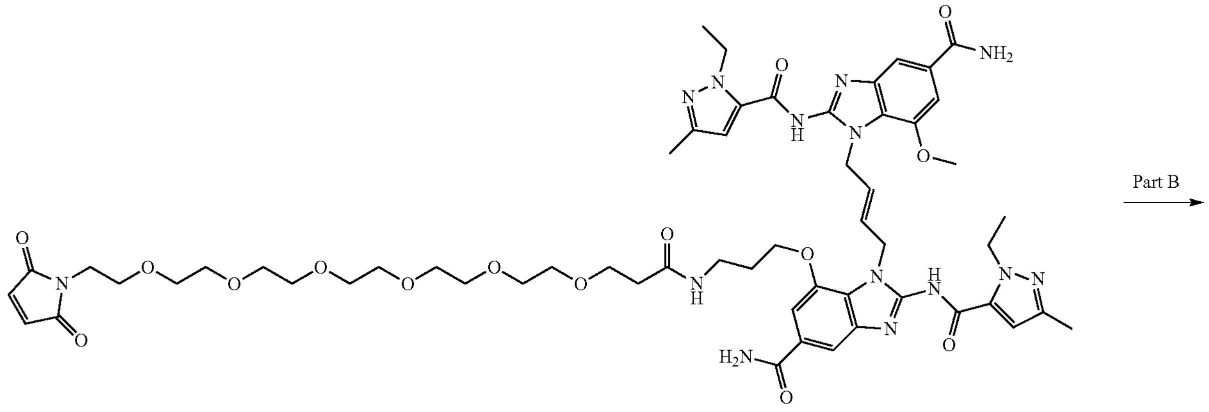
33
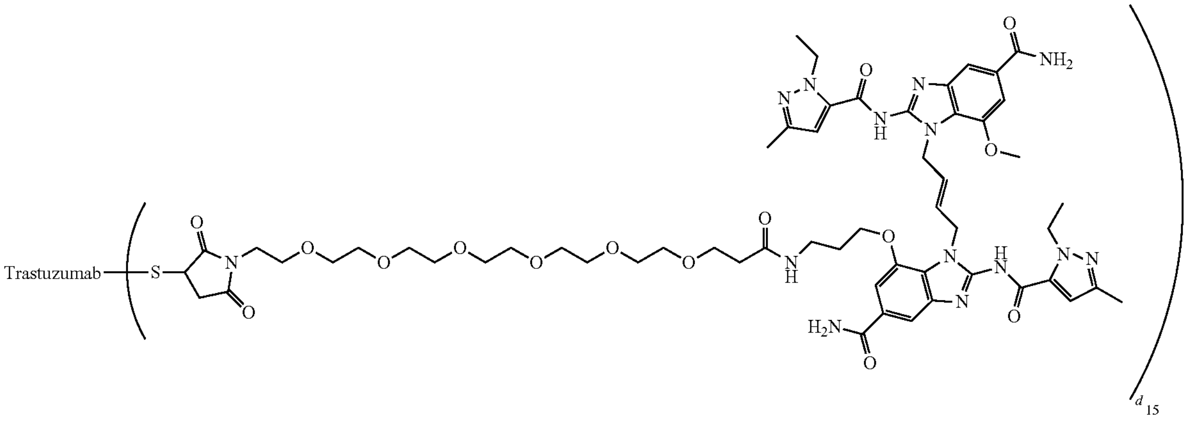
34

Part A: To a solution of Compound 1a (prepared as described in WO2017175147A1, 0.030 g, 0.038 mmol) in DMF (1.5 mL), was added N-ethyl-N-isopropylpropan-2-amine (0.067 mL, 0.385 mmol). The solution was stirred for 5 minutes at room temperature prior to the addition of 2,5-dioxopyrrolidin-1-yl 1-(2,5-dioxo-2,5-dihydro-1H-pyrrol-1-yl)-3,6,9,12,15,18-hexaoxahenicosan-21-oate (0.027 g, 0.050 mmol) in DMF (0.5 mL) and the reaction mixture was stirred at room temperature for 15 minutes. Then acetic acid (0.1 mL) was added followed by purification on a preparative HPLC column (C18, 21.2 mm×100 mm), 10-100% MeCN (0.1% HOAc) in $H_2O$ (0.1% HOAc, 20 min. gradient to give Scaffold 33 (0.006 g, 13.05% yield). ESI-MS m/z Calcd for $C_{57}H_{75}N_{14}O_{15}$ $[M+H]^+$: calc. 1195.55; found 1195.47.

Part B: Trastuzumab (10 mg, 0.069 μmol) was conjugated to Scaffold 33 (0.658 mg, 0.550 μmol in DMA) as described in Example 1. The crude Conjugate 34 was purified by CHT type II chromatography The purified Conjugate 34 had a STING agonist to Trastuzumab ratio of 6.9.

Example 8a: Synthesis of Palivizumab Conjugate 34a, DAR 7.0

34a

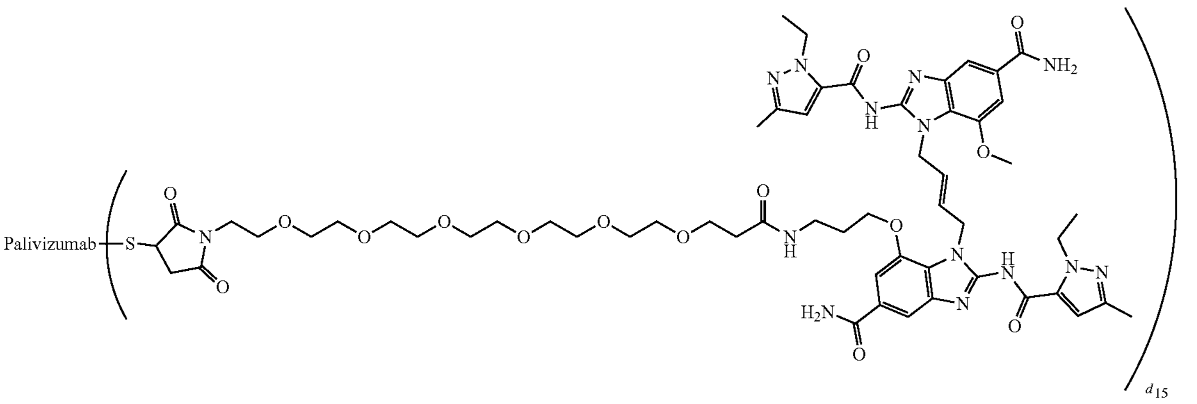

Conjugate 34a was prepared and characterized as described in Example 8 except that Palivizumab was used instead of Trastuzumab. The purified Conjugate 34a had a STING agonist to Palivizumab ratio of 7.0.

Example 9: Synthesis of XMT-1519 Conjugate 45, DAR 6.5

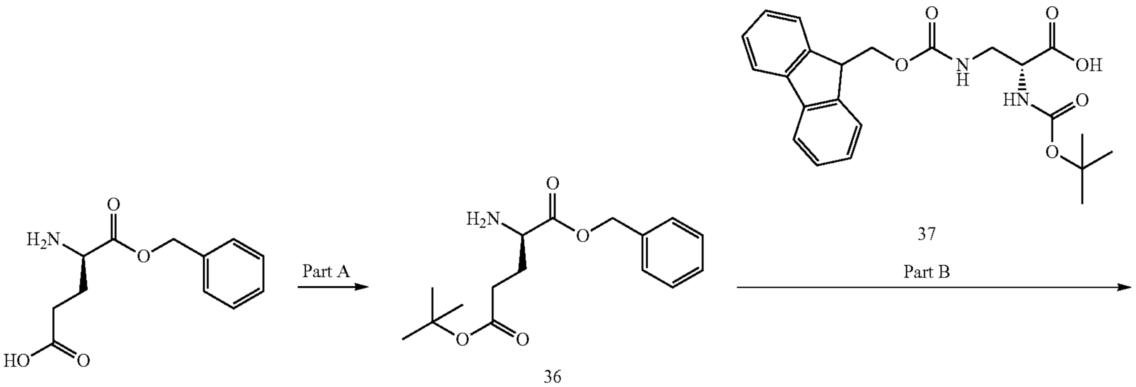

35 36 37

-continued
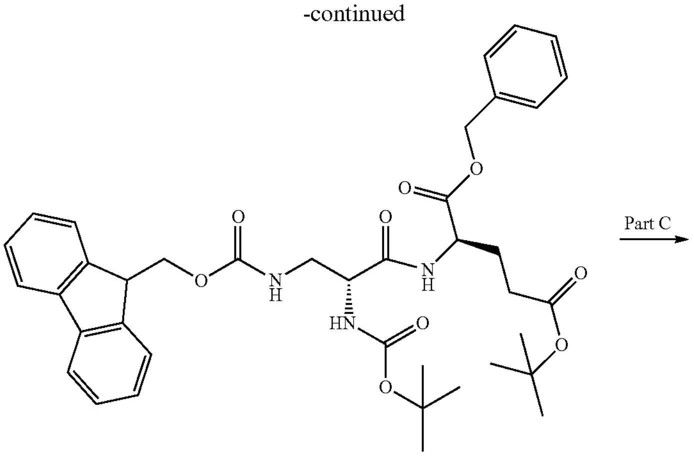
38
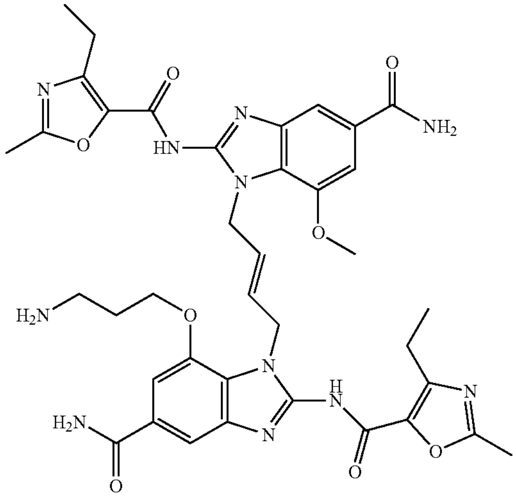
40
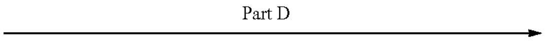
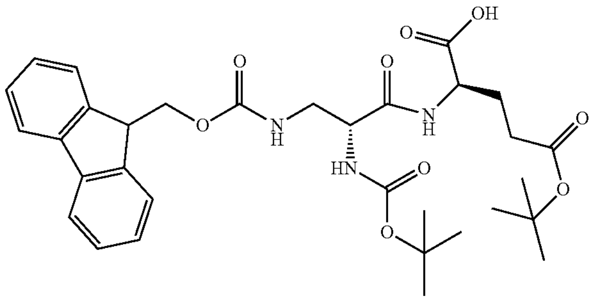
39
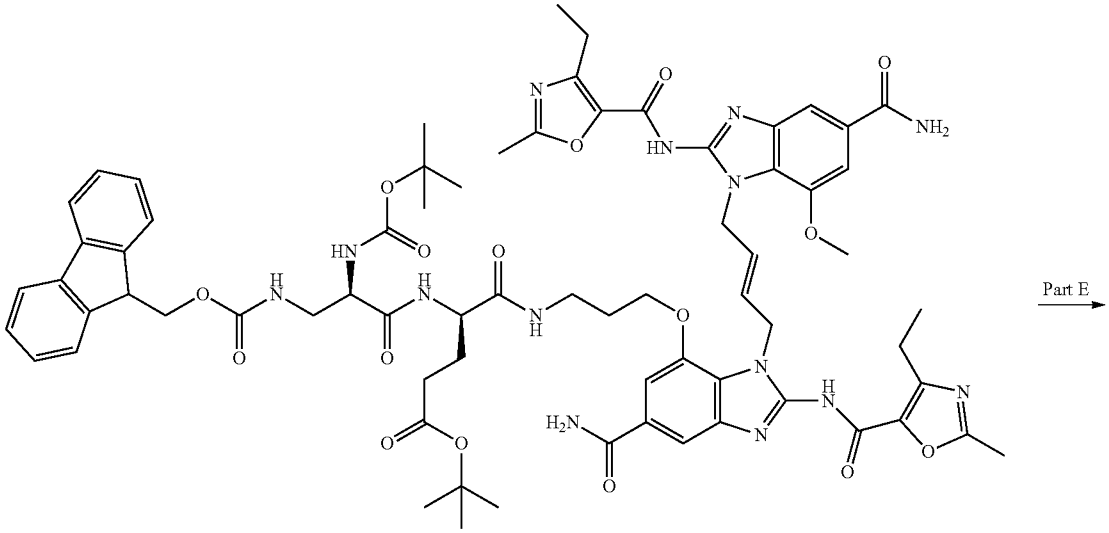
41

-continued
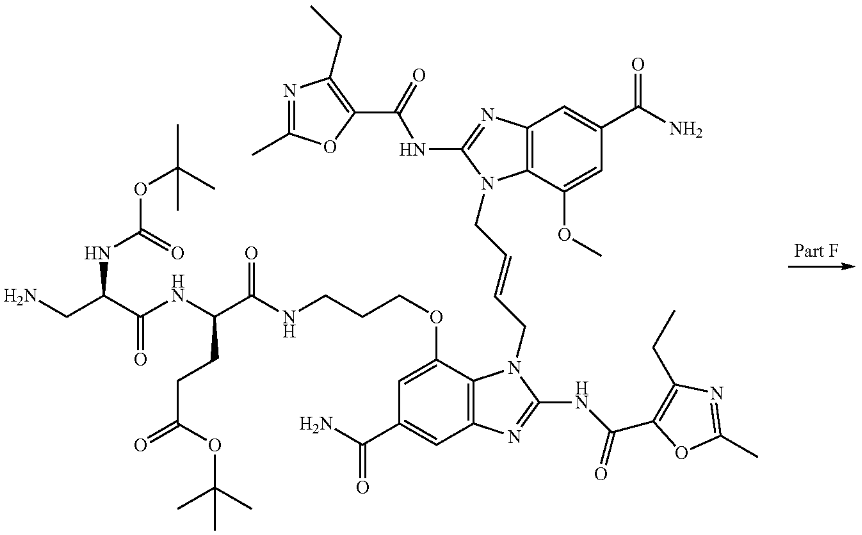
42
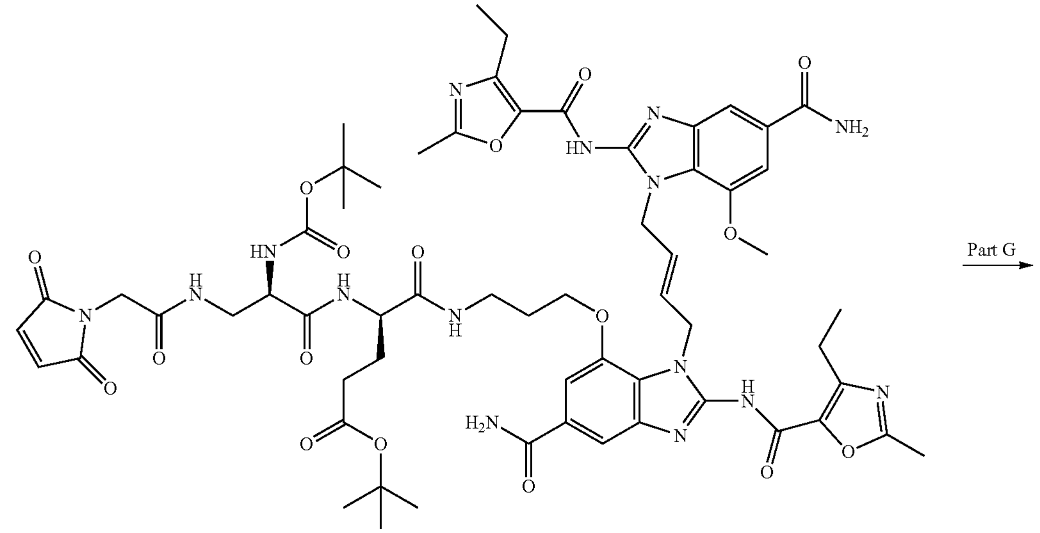
43
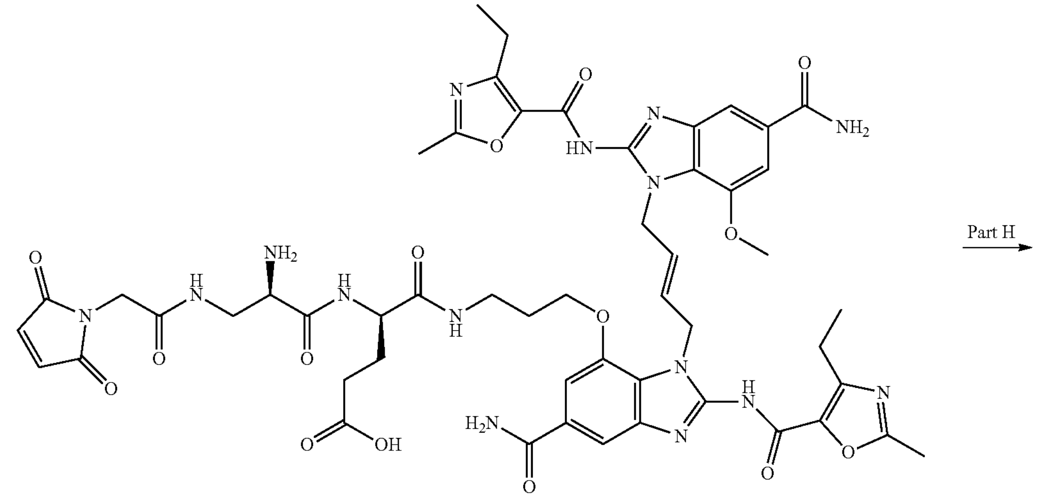
44

-continued

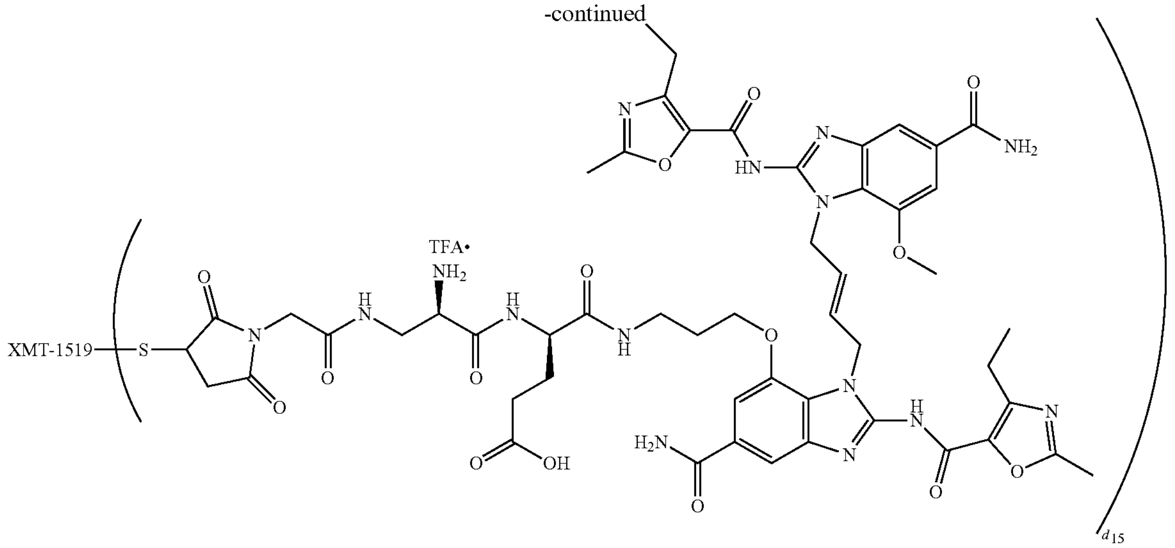

Part A: To a mixture of Compound 35 (400 mg, 1688 μmol) and t-butyl acetate (8 mL) was added 70% $HClO_4$ (302 mg, 2.11 mmol). The resulting solution was then stirred at room temperature for 21 h then neutralized with satd. $NaHCO_3$ solution. The aqueous phase was washed with EtOAc (2×) and the combined organics then washed with brine, dried ($Na_2SO_4$), filtered, and concentrated to give Compound 36 is an opaque oil (530 mg, quant.). ESI-MS m/z Calcd for $C_{16}H_{24}N_1O_4$ $[M+H]^+$: 294.2; found 294.2.

Part B: A mixture of Compound 36 (279 mg, 782 μmol), Compound 37 (370 mg, 938 μmol), HOAt (128 mg, 938 μmol), DIPEA (409 μL, 2.35 mmol) and DMF (4 mL) was stirred at room temperature for 5 mins, then HATU (416 mg, 1095 μmol) was added and the reaction stirred at room temperature for 2.5 h. The reaction mixture was then concentrated, and the residue chromatographed by silica gel (20-100% EtOAc/hexanes eluent). Compound 38 was isolated as a white fluffy solid (254 mg, 362 μmol, 46% yield). ESI-MS m/z Calcd for $C_{39}H_{48}N_2O_9$ $[M+H]^+$: 702.3; found 702.4.

Part C: A mixture of Compound 38 (254 mg, 362 μmol), MeOH (6 mL) and 10% Pd—C catalyst (50 mg) was stirred under a $H_2$ (1 atm) for 2 h at room temperature. The reaction mixture was then filtered, and the filtrate concentrated to give Compound 39 is a clear oil, (214 mg, 97% yield). ESI-MS m/z Calcd for $C_{32}H_{42}N_3O_9$ $[M+H]^+$: 612.3; found 612.3.

Part D: A mixture of Compound 39 (58 mg, 64 μmol), Compound 40 (prepared as described in U.S. 62/982,935, 47 mg, 77 μmol), HOAt (10 mg, 77 μmol), DiPEA (56 μL, 320 μL) and DMF (2 mL) was stirred at room temperature for 5 mins. Then HATU (36 mg, 96 μmol) was added and the reaction mixture stirred at room temperature for 16 h, then concentrated to give Compound 41 is a yellow oil, (90 mg, quant.). ESI-MS m/z Calcd for $C_{70}H_{83}N_{14}O_{16}$ $[M+H]^+$: 1375.6; found 1375.4.

Part E: A solution of Compound 41 (90 mg, 64 μmol) in 20% piperidine in DMF (2 mL) was stirred at room temperature for 1 h. The reaction mixture was then concentrated and chromatographed by silica gel (0-40% MeOH-DCM eluent) to give Compound 42 is a yellow oil, (30 mg, 41% yield). ESI-MS m/z Calcd for $C_{55}H_{73}N_{14}O_{14}$ [M+H]: 1153.5; found 1153.4.

Part F: A solution of Compound 42 (30 mg, 37 μmol), 2,5-dioxopyrrolidin-1-yl 2-(2,5-dioxo-2,5-dihydro-1H-pyrrol-1-yl)acetate (8 mg, 44 μmol), TEA (7 μL, 74 μmol) and DMF (1 mL) was stirred at room temperature for 17 h. The reaction mixture was then concentrated to give Scaffold 43 as a yellow oil (40 mg, quant.). ESI-MS m/z Calcd for $C_{61}H_{76}N_{15}O_{17}$ $[M+H]^+$: 1290.6; found 1290.3.

Part G: A solution of Scaffold 43 (30 mg, 26 μmol) in 10% TFA-DCM (2 mL) was stirred at room temperature for 1 h. The reaction mixture was then concentrated, and the residue chromatographed by HPLC (10-100% ACN-water w/0.1% HCOOH eluent). Scaffold 44 was isolated as an off-white fluffy solid (6 mg, 20% yield). ESI-MS m/z Calcd for $C_{52}H_{60}N_{15}O_{15}$ $[M+H]^+$: 1134.4; found 1134.2.

Part H: Conjugate 45 was prepared as described in Example 1 except that 4 equiv TCEP was used. The purified Conjugate 45 had a STING agonist to XMT-1519 ratio of 6.5.

Example 10: Synthesis of XMT-1519 Conjugate 50, DAR 8.2

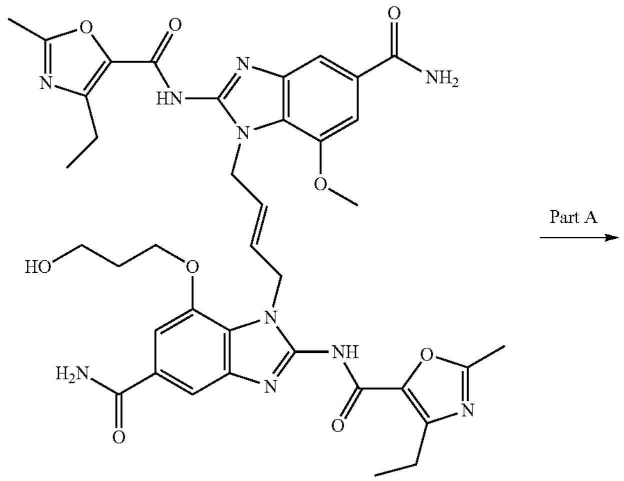
26
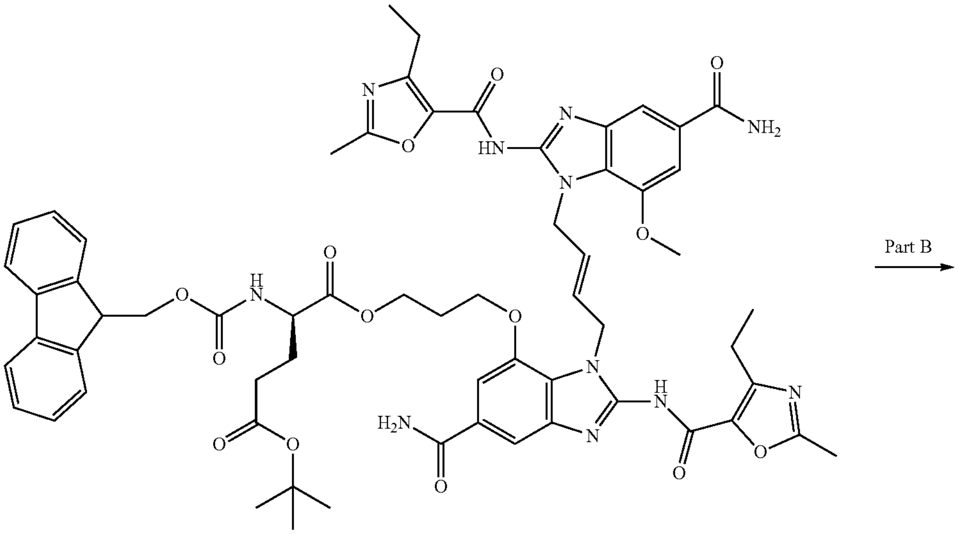
46
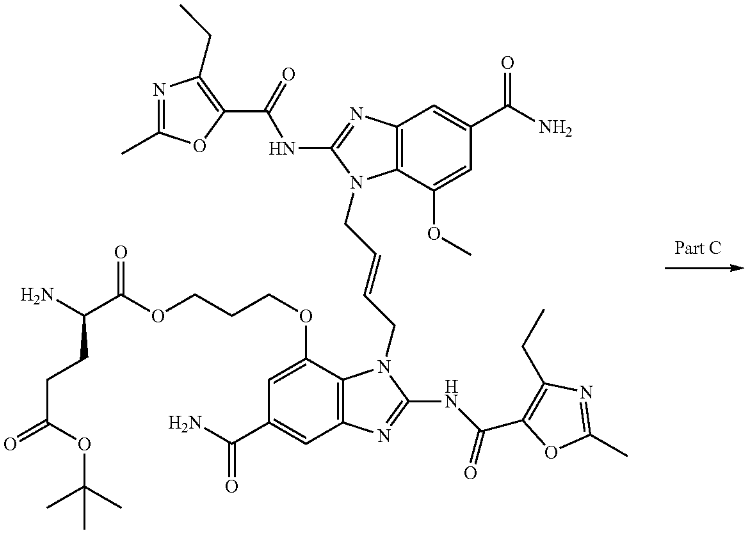
47

-continued
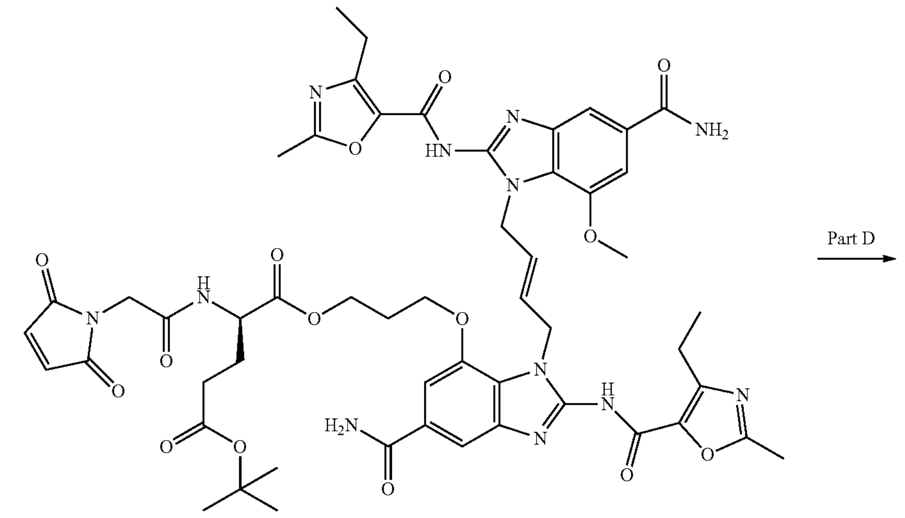
48
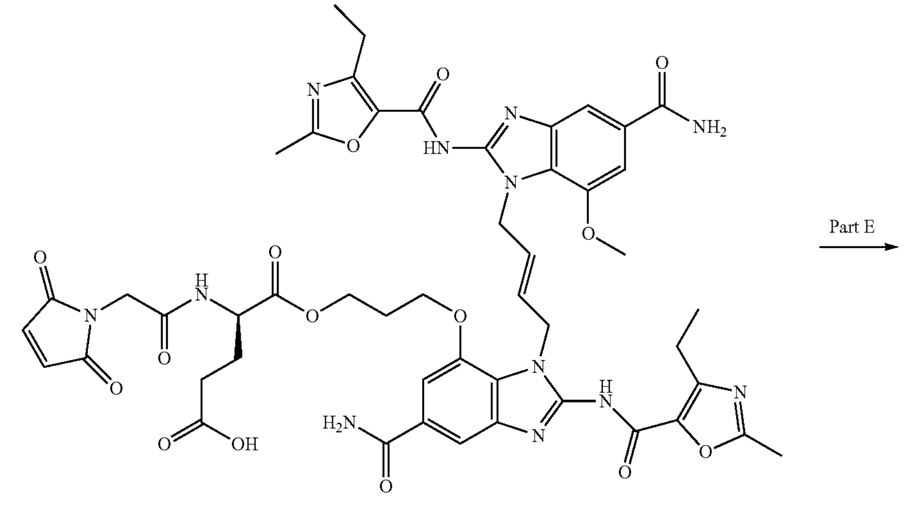
49
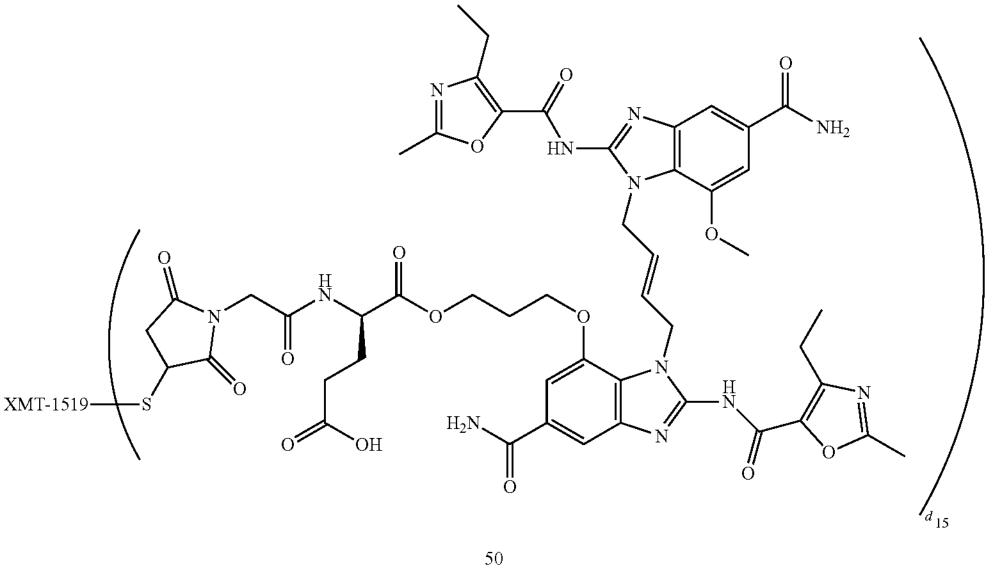
50

Part A: A mixture of Compound 26 (prepared as described in U.S. 62/982,935, 50 mg, 64 μmol), Fmoc-D-glutamic-O-tBu (54 mg, 128 μmol), DCC (26 mg, 128 μmol), DMAP (1 mg, 6 μmol) and DMF (2 mL) was stirred at room temperature for 17 h. The reaction mixture was concentrated and used in the next step without purification. Compound 46 was obtained as a yellow oil (135 mg). ESI-MS m/z Calcd for $C_{62}H_{68}N_{11}O_{14}$ $[M+H]^+$: 1190.5; found 1190.3.

Part B: A mixture of Compound 46 (135 mg, 64 μmol) and 33% TEA in DMF (2.4 mL) was stirred at room temperature for 4.5 h. The reaction mixture was concentrated, and the residue purified by chromatography by reverse-phase HPLC (10-100% ACN-water w/0.1% HCOOH eluent). Compound 47 was isolated as a yellow powder (27 mg, 44% yield). ESI-MS m/z Calcd for $C_{47}H_{58}N_{11}O_{12}$ $[M+H]^+$: 968.4; found 968.2.

Part C: A solution of Compound 47 (25 mg, 26 μmol), 2,5-dioxopyrrolidin-1-yl 2-(2,5-dioxo-2,5-dihydro-1H-pyrrol-1-yl)acetate (8 mg, 31 μmol), TEA (11 μL, 78 μmol) and DMF (1 mL) was stirred at room temperature for 1 h. The reaction mixture was concentrated and used in the next step without purification. Scaffold 48 is a yellow oil (40 mg, quant.). ESI-MS m/z Calcd for $C_{53}H_{61}N_{12}O_{15}$ $[M+H]^+$: 1105.4; found 1105.2.

Part D: A solution of Scaffold 48 (40 mg, 24 μmol) and 15% TFA in DCM (1 mL) was stirred at room temperature for 2 h. The reaction mixture was then concentrated and chromatographed by HPLC (10-100% ACN-water with 0.1% HCOOH eluent). Scaffold 49 was isolated as a white, fluffy solid (5 mg, 20% yield). ESI-MS m/z Calcd for $C_{49}H_{53}N_{12}O_{15}$ $[M+H]^+$: 1049.4; found 1049.2.

Part E: XMT-1519 (10 mg, 0.069 μmol) was conjugated with Scaffold 49 as described in Example 1. Conjugate 50 was purified by CHT type II chromatography. The purified Conjugate 50 had a STING agonist to XMT-1519 ratio of 8.2.

Example 11: Synthesis of XMT-1519 Conjugate 52, DAR 7.7

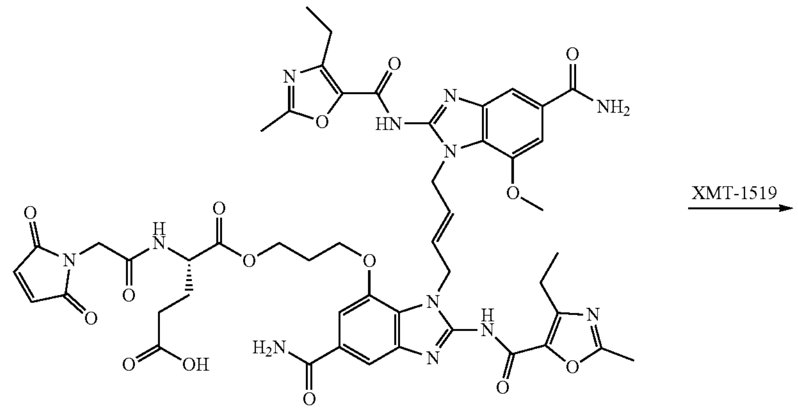

51

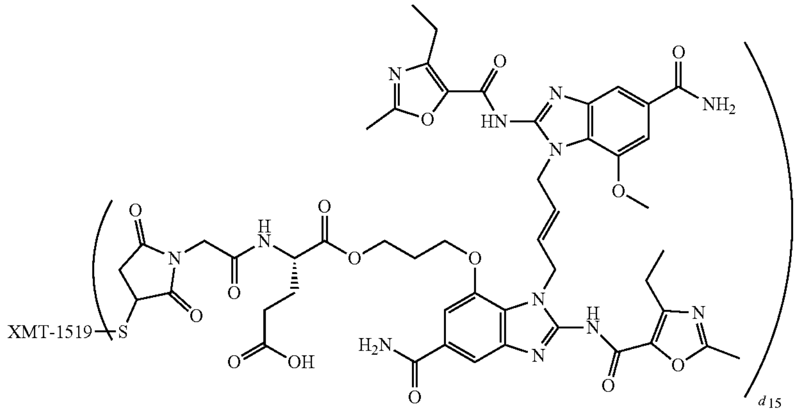

52

Conjugate 52 was prepared from Scaffold 51 as described in Example 10 except that Fmoc-L-Glu(O-tBu) was used instead of Fmoc-D-Glu(O-tBu). The purified Conjugate 52 had a STING agonist to XMT-1519 ratio of 7.7.
Example 12: Synthesis of XMT-1519 Conjugate 58, DAR 6.5
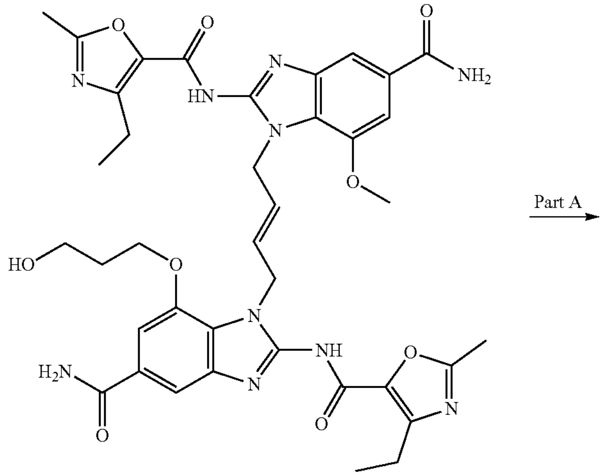
26
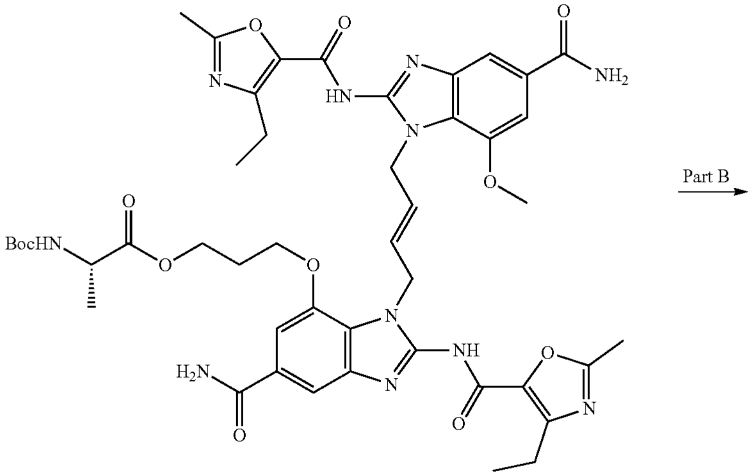
53
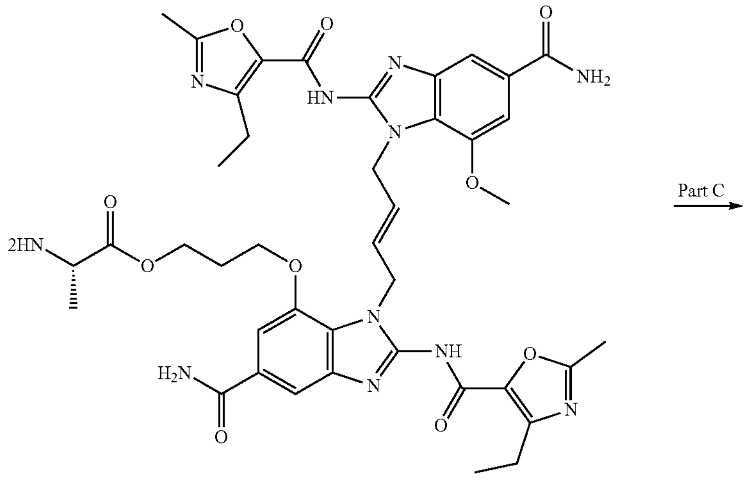
54

-continued
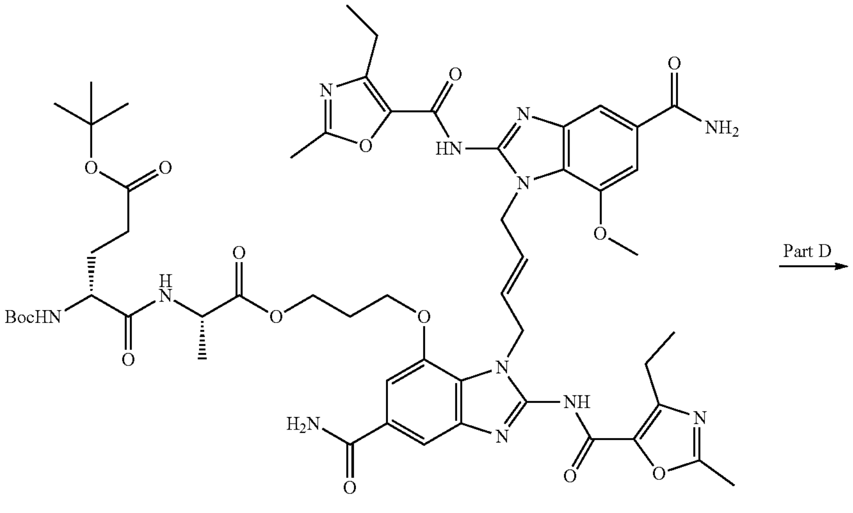
55
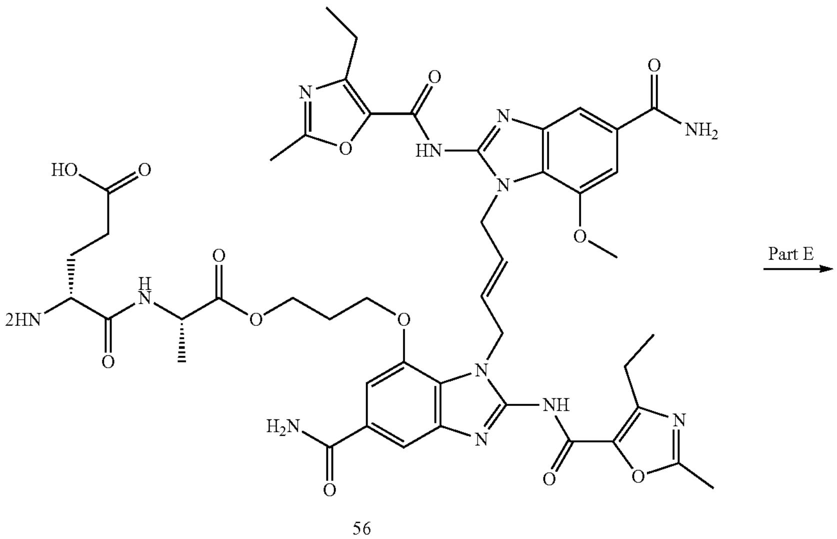
56

-continued

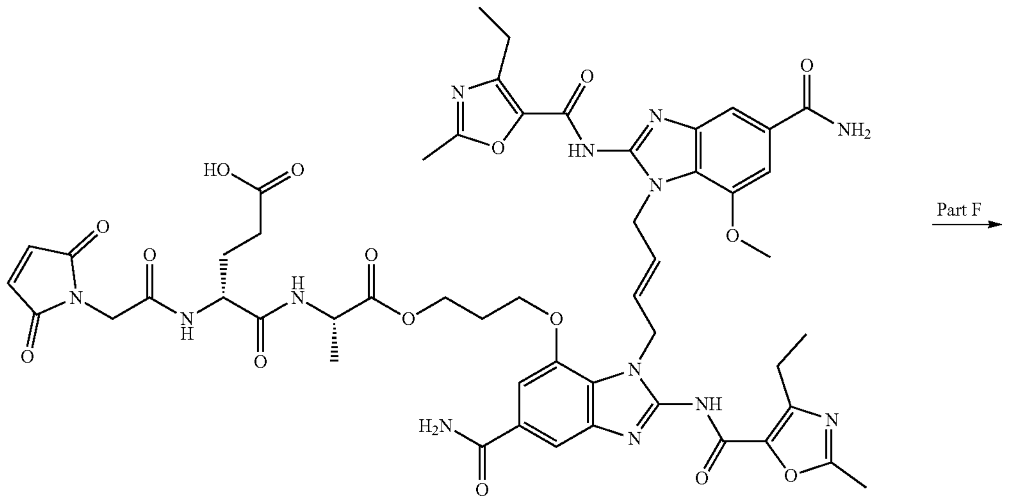

57

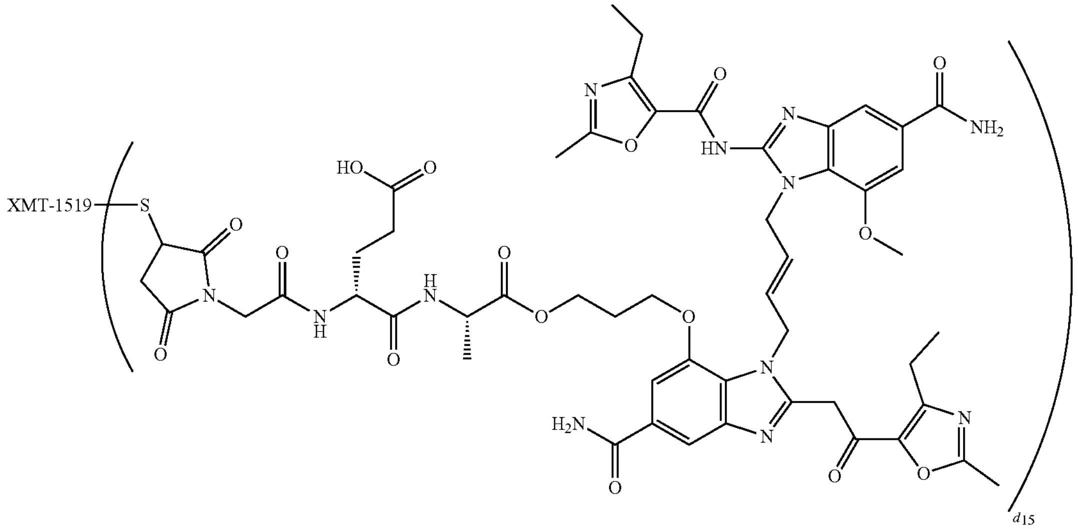

58

Part A: To a mixture of Compound 26 (prepared as described in U.S. 62/982,935, 0.105 g, 0.134 mmol), Boc-L-Alanine (50.8 mg, 0.268 mmol), DMAP (50.8 mg, 0.067 mmol) and DCC (0.111 g, 0.537 mmol) was added DMF (2 mL). The suspension was then stirred 2 days at room temperature. The mixture was concentrated and purified on silica gel (0-40% MeOH in DCM) to afford Compound 53 as a light-yellow solid (0.102 g, 80% yield). ESI-MS m/z Calcd for $C_{46}H_{56}N_{11}O_{12}$ $[M+H]^+$: 954.4; found 954.4.

Part B: To a suspension of Compound 53 (0.102 g, 0.107 mmol) in dioxane (10 mL) was added 4 N HCl (0.508 mL, 2.031 mmol). The reaction mixture was stirred at room temperature for 3 h. The suspension was then concentrated and used in the next step without purification. Compound 54 was obtained as a light-yellow solid. ESI-MS m/z Calcd for $C_{41}H_{48}N_{11}O_{10}$ $[M+H]^+$: 854.3; found 854.3.

Part C: To a solution of Compound 54 (0.015 g, 0.017 mmol) in DMF (1 mL) was added Boc-D-Glu (Otu)-OH (7.67 mg, 0.025 mmol), followed by DIPEA (0.026 mL, 0.152 mmol). The reaction mixture was stirred at room temperature for 5 min. Then PyBOP (13.15 mg, 0.025 mmol) was added, and the mixture was stirred at room temperature for 1 h, concentrated and the residue was purified over silica gel (0-30% MeOH in DCM) to afford Compound 55 (11 mg, 57.3% yield) as a white solid. ESI-MS m/z Calcd for $C_{55}H_{71}N_{12}O_{15}$ $[M+H]^+$: 1139.5; found 1139.5.

Part D: To a suspension of Compound 55 (11 mg, 0.00966 mmol) in dioxane (3 mL) was added 4 N HCl (0.241 mL, 0.966 mmol). The reaction mixture was stirred at room temperature for 2 h. The suspension was concentrated and used in the next step without purification. Compound 56 was a white solid. ESI-MS m/z Calcd for $C_{46}H_{55}N_{12}O_{13}$ [M+H]-: 983.4; found 983.4.

Part E: To a solution of Compound 56 (9.5 mg, 0.00966 mmol) in DMF (3 mL) were added DIEA (8.44 μL, 0.048 mmol) and 2,5-dioxopyrrolidin-1-yl 2-(2,5-dioxo-2,5-dihydro-1H-pyrrol-1-yl)acetate (3.17 mg, 0.013 mmol). The reaction mixture was stirred at room temperature for 1 h, neutralized to pH 6-7 with HOAc, then purified over preparative RP HPLC (0-75% ACN in water) to afford Scaffold 57 (3.3 mg, 31% yield) as a white solid. ESI-MS m/z Calcd for $C_{52}H_{58}N_{13}O_{16}$ $[M+H]^+$: 1120.4; found 1120.4.

Part F: XMT-1519 (10 mg, 0.069 μmol) was conjugated with Scaffold 57 (0.700 mg, 0.625 μmol in 200 μL DMA) as described in Example 1. Conjugate 58 was purified by CHT type II chromatography. The purified Conjugate 58 had a STING agonist to XMT-1519 ratio of 6.5.

Example 13: Synthesis of XMT-1519 Conjugate 60

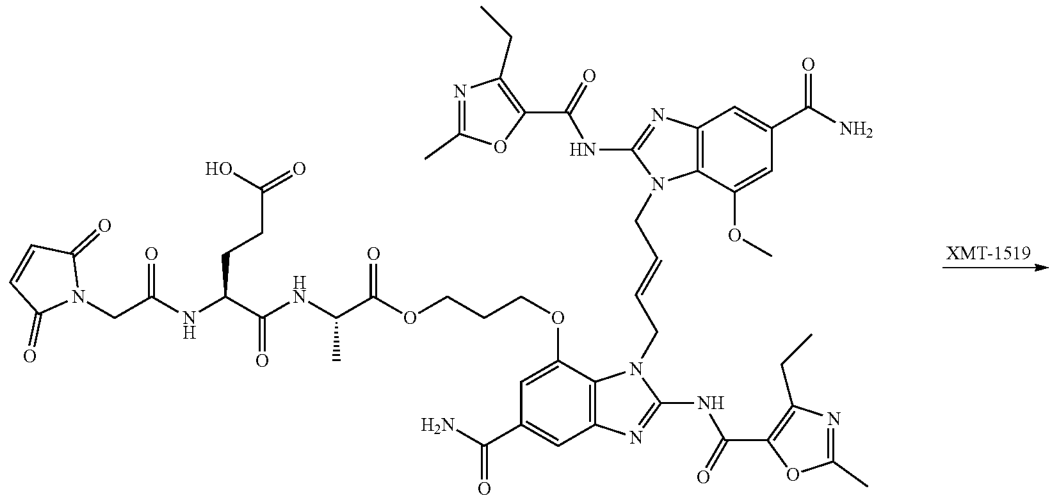

59

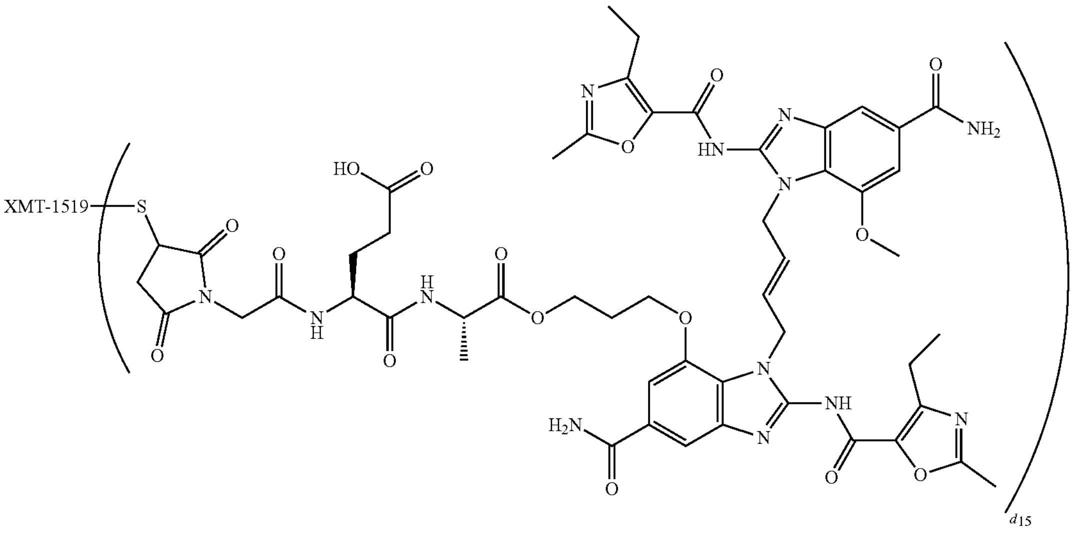

60

Conjugate 60 was prepared from 59 as described in Example 12 except that Boc-L-Glu (Otu)-OH was used instead of Boc-D-Glu-O-tBu. The details of the antibody-drug conjugates 60-1 and 60-2 are given below.

| Conjugate | DAR |
|---|---|
| 60-1 | 7.7 |
| 60-2 | 5.5 |

Example 14: Synthesis of XMT-1519 Conjugate 62, DAR 6.5

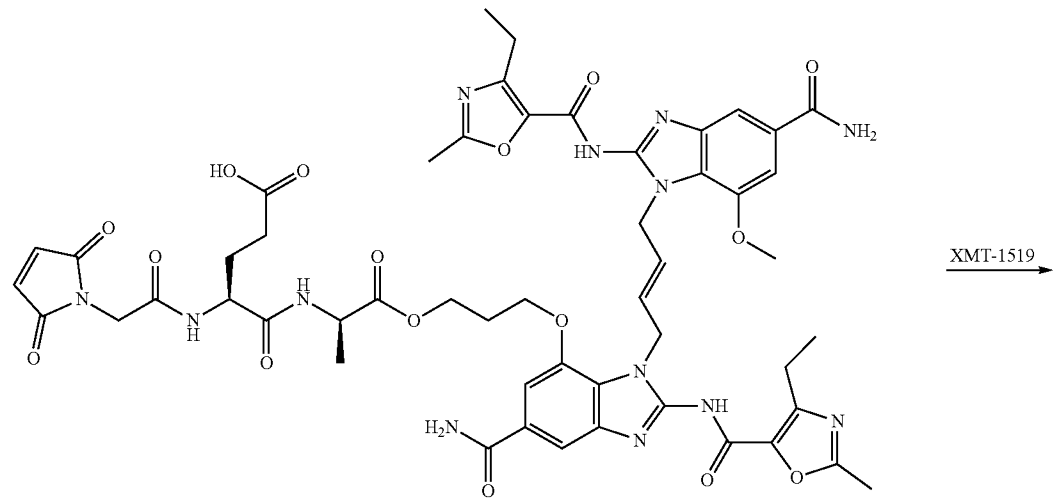

61

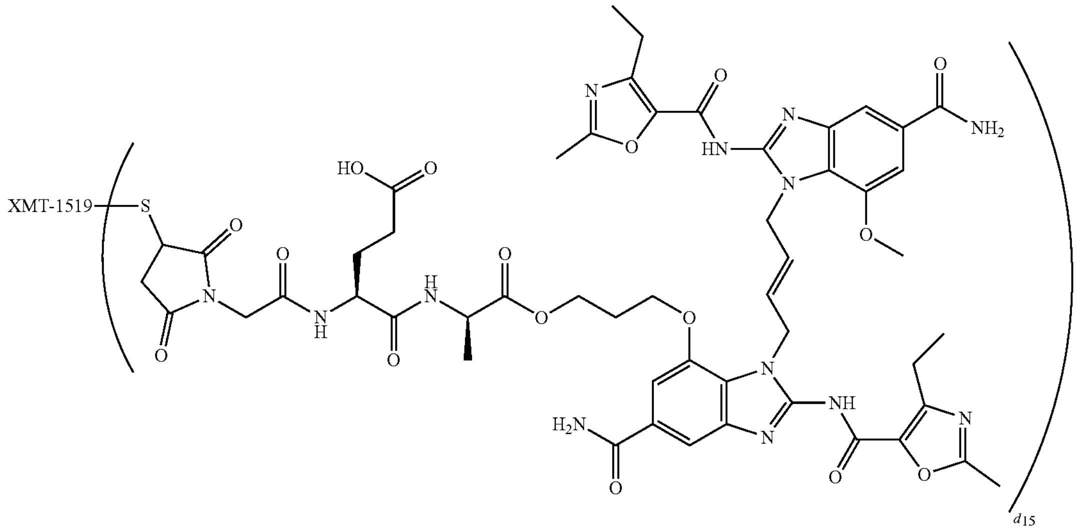

62

Conjugate 62 was prepared from Scaffold 61 as described Example 12 except that Boc-L-Glu (Otu)-OH was used instead of Boc-D-Glu-O-tBu and Boc-D-Ala was used instead of Boc-L-Ala. The purified Conjugate 62 had a STING agonist to XMT-1519 ratio of 6.5.

Example 15: Synthesis of XMT-1519 Conjugate 64, DAR 6.4
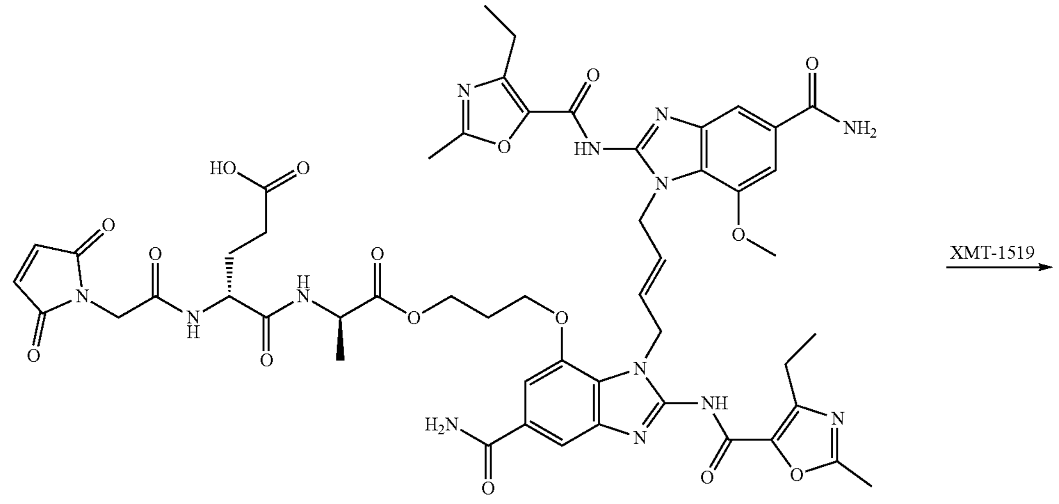
63
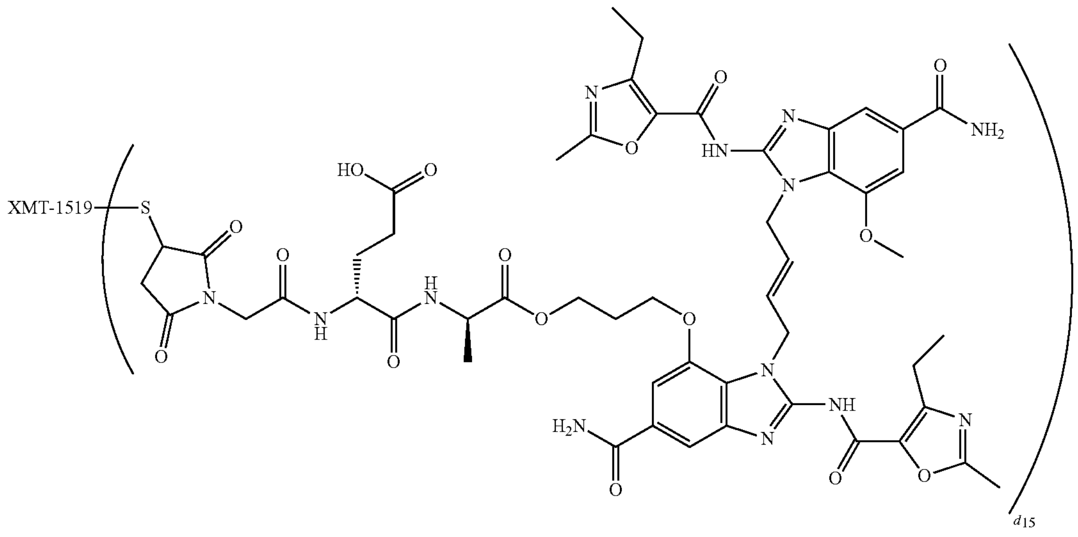
64
Conjugate 64 was prepared from Scaffold 63 as described in Example 12 except that Boc-D-Ala was used instead of Boc-L-Ala. The purified Conjugate 64 had a STING agonist to XMT-1519 ratio of 6.4.

Example 16: Synthesis of XMT-1519 Conjugate 66
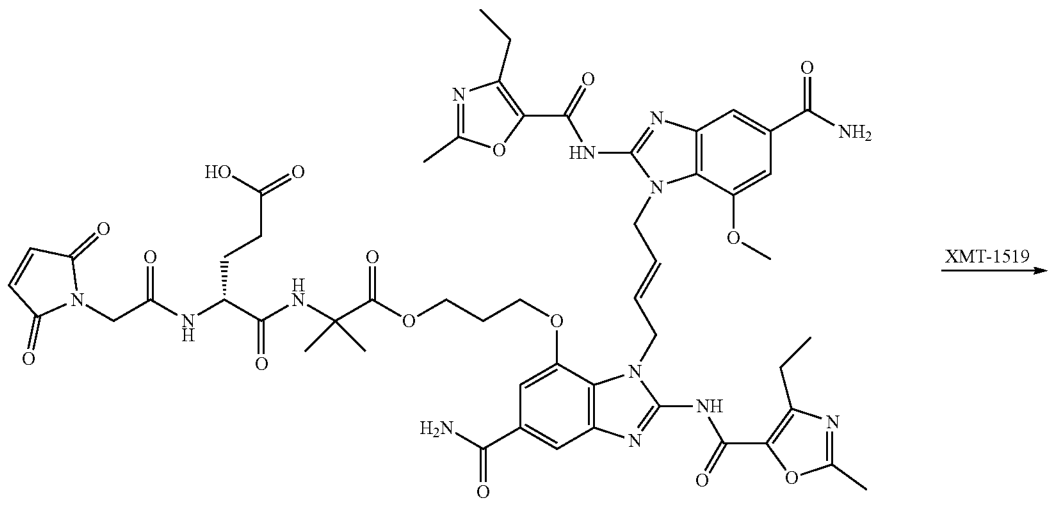
65
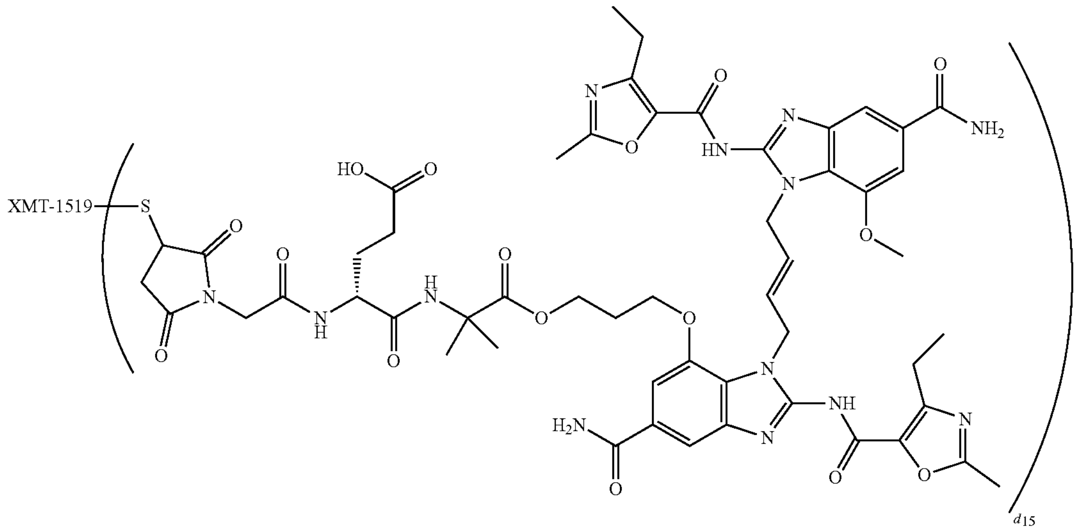
66
Conjugate 66 was prepared from Scaffold 65 as described in Example 12 except that Boc-2-amino-2-methylpropanoic acid was used instead of Boc-L-Ala. The details of the antibody-drug conjugates 66-1 and 66-2 are given below.
| Conjugate | DAR |
|---|---|
| 66-1 | 7.5 |
| 66-2 | 5.3 |

Example 17: Synthesis of XMT-1519 Conjugate 74, DAR 6.9
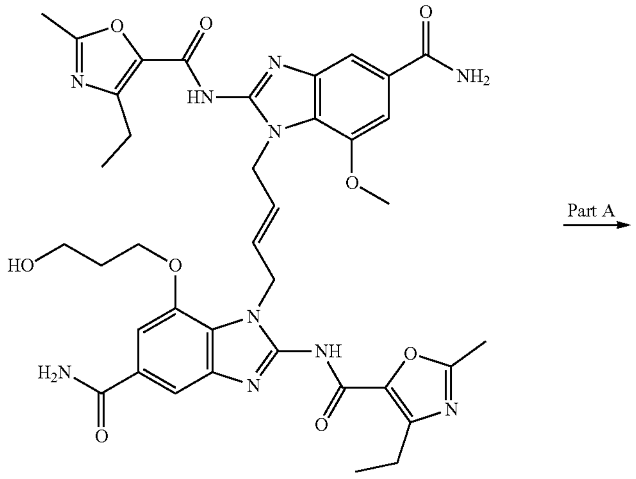
26
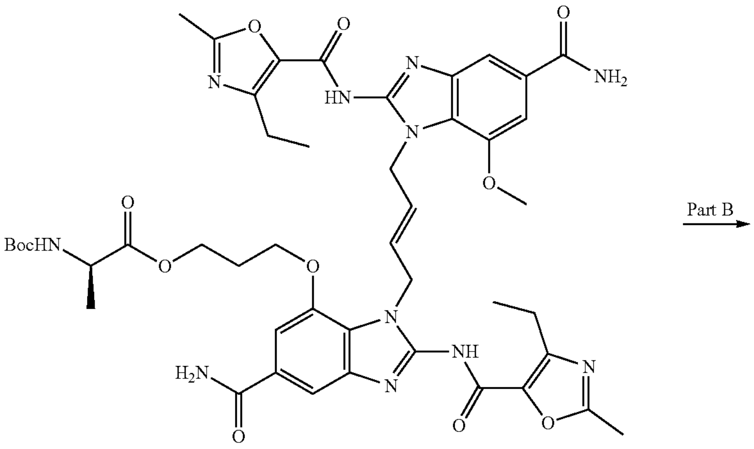
67
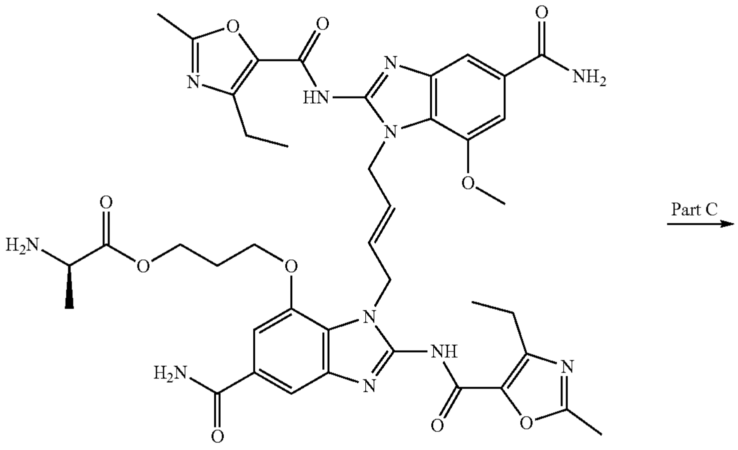
68

-continued
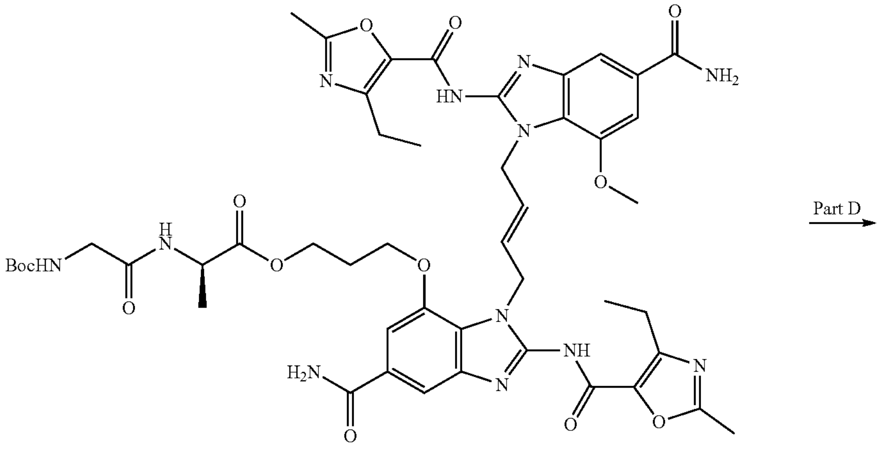
69
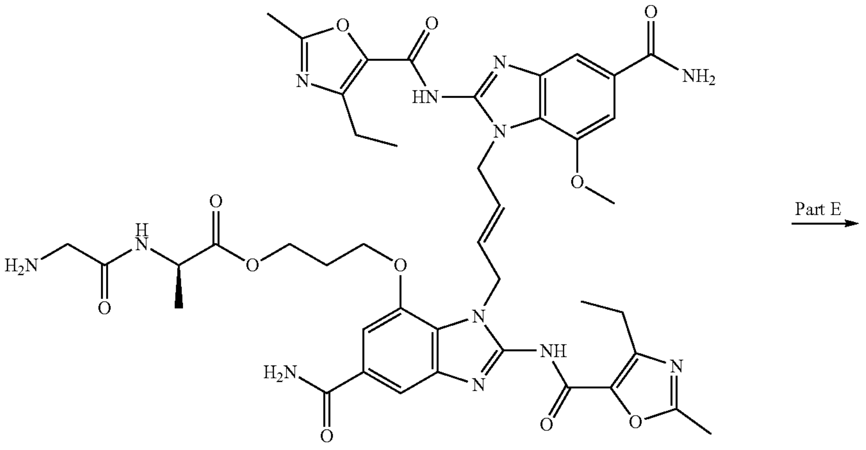
70
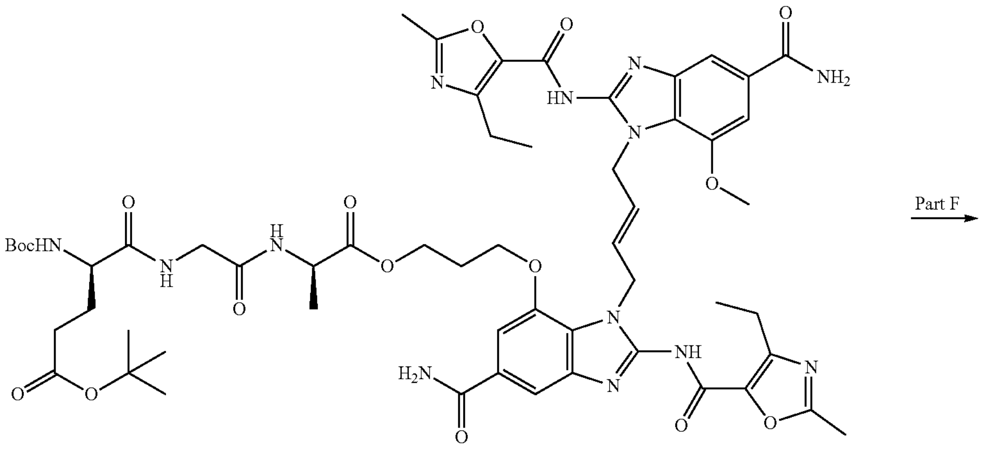
71

-continued
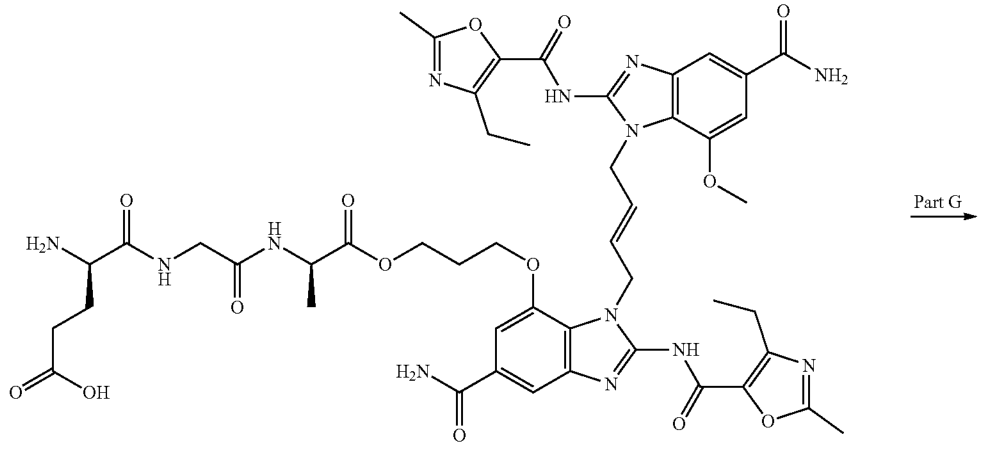
72
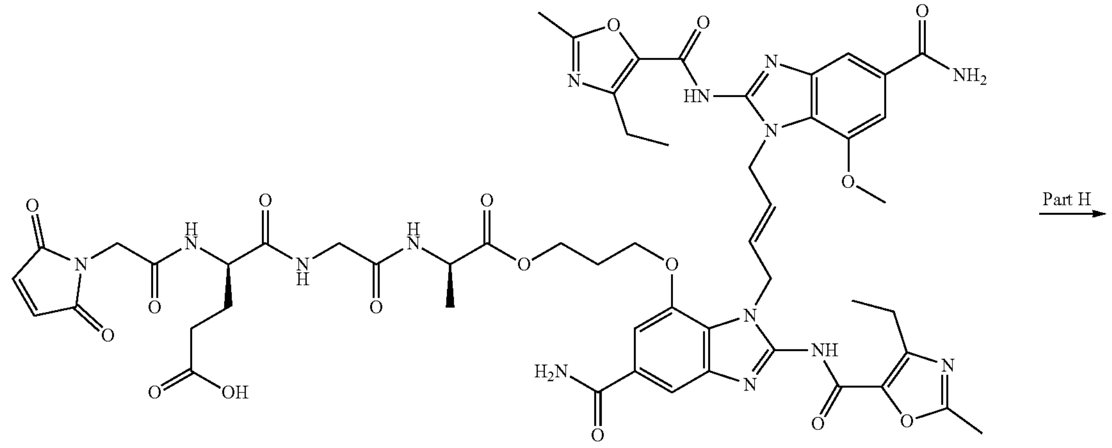
73
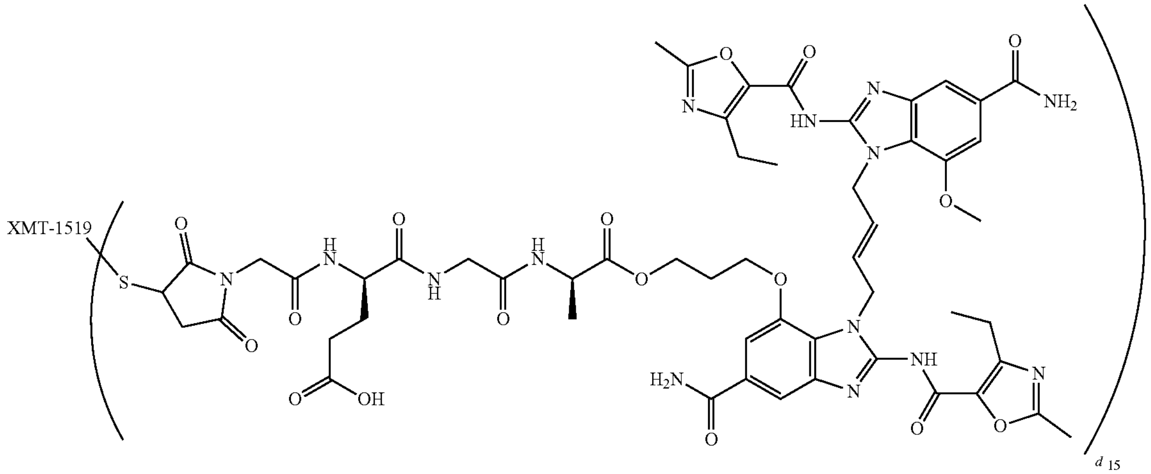
74

Part A: A mixture of Compound 26 (prepared as described in US 62/982,935, 75 mg, 0.096 mmol), N-Boc-(D)-Ala-OH (91 mg, 0.48 mmol), DCC (99 mg, 0.48 mmol), and DMAP (1.2 mg, 9.58 mol) in DMF (3 mL) was stirred at room temperature for 1 h, and then concentrated in vacuo. Purification over silica gel (DCM:MeOH 60:40 v/v) afforded Compound 67 (82 mg, 90% yield) as a light-yellow solid. ESI-MS m/z Calcd for $C_{46}H_{56}N_{11}O_{12}$ $[M+H]^+$: 954.40, found: 954.43

Part B: To a suspension of Compound 67 (80 mg, 0.084 mmol) in dioxane (5 mL) was added HCl (4M in dioxane, 0.42 mL, 1.68 mmol), and the mixture was stirred at room temperature for 4 h. The mixture was concentrated in vacuo to afford Compound 68 (72 mg, 100% yield) as a light-yellow solid. ESI-MS m/z Calcd for $C_{41}H_{48}N_{11}O_{10}$ $[M+H]^+$: 854.35, found: 854.38

Part C: To a stirred solution of Compound 68 (48 mg, 0.056 mmol), N-Boc-glycine (15 mg, 0.084 mmol) and PyBOP (44 mg, 0.084 mmol) in DMF (3 mL) was added DIPEA (0.088 mL, 0.51 mmol), and the mixture was stirred at room temperature for 2 h. The mixture was concentrated, and the residue was purified over silica gel (DCM:MeOH 60:40 v/v) to afford Compound 69 (53 mg, 93% yield) as a white solid. ESI-MS m/z Calcd for $C_{48}H_{59}N_{12}O_{13}$ $[M+H]^+$: 1011.42, found: 1011.45

Part D: To a suspension of Compound 69 (50 mg, 0.049 mmol) in dioxane (5 mL) was added HCl (4M in dioxane, 1 mL, 20% v/v), and the mixture was stirred at room temperature for 2 h then concentrated to afford Compound 70 (45 mg, 100% yield) as a white solid. ESI-MS m/z Calcd for $C_{43}H_{51}N_{12}O_{11}$ $[M+H]^+$: 911.37, found: 911.39

Part E: To a stirred solution of Compound 70 (20 mg, 0.022 mmol), N-Boc-(D)-Glu(OtBu)-OH (10 mg, 0.033 mmol) and PyBOP (17 mg, 0.033 mmol) in DMF (2 mL) was added DIPEA (0.03 mL, 0.22 mmol), and the mixture was stirred at room temperature for 2 h. The mixture was concentrated, and the residue was purified over silica gel (DCM:MeOH 60:40 v/v) to afford Compound 71 (24 mg, 90% yield) as a white solid. ESI-MS m/z Calcd for $C_{57}H_{74}N_{13}O_{16}$ $[M+H]^+$: 1196.53; found: 1196.55

Part F: To a suspension of Compound 71 (24 mg, 0.02 mmol) in DCM (5 mL) was added TFA (1 mL, 20% v/v), and the mixture was stirred at room temperature for 12 h. The mixture was concentrated to afford Compound 72 (21 mg, 100% yield) as a light-yellow solid. ESI-MS m/z Calcd for $C_{48}H_{58}N_{13}O_{14}$ $[M+H]^+$: 1040.41; found: 1040.23

Part G: To a stirred solution of Compound 72 (21 mg, 0.02 mmol), 2,5-dioxopyrrolidin-1-yl 2-(2,5-dioxo-2,5-dihydro-1H-pyrrol-1-yl)acetate (7.6 mg, 0.03 mmol) in DMF (2 mL) was added DIPEA (0.035 mL, 0.20 mmol), and the mixture was stirred at room temperature for 1 h. The mixture was concentrated, and the residue was purified over RP HPLC to afford Scaffold 73 (4.5 mg, 19% yield) as a white solid. ESI-MS m/z Calcd for $C_{54}H_{61}N_{14}O_{17}$ $[M+H]^+$: 1177.43; found: 1177.40

Part H: Conjugate 74 was prepared from Scaffold 73 as described in example 12. The purified Conjugate 74 had a STING agonist to XMT-1519 ratio of 6.9.

Example 18: Synthesis of XMT-1519 Conjugate 76, DAR 7.5

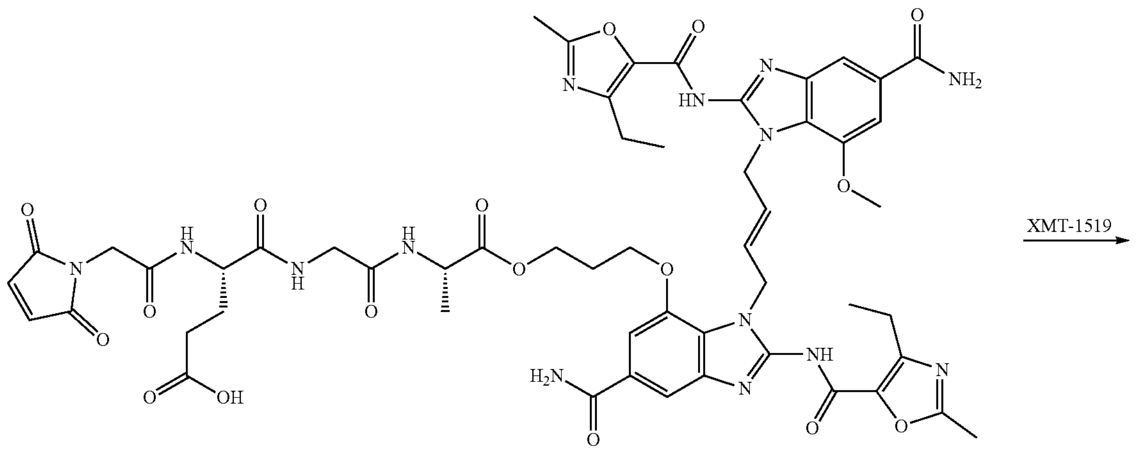

75

-continued
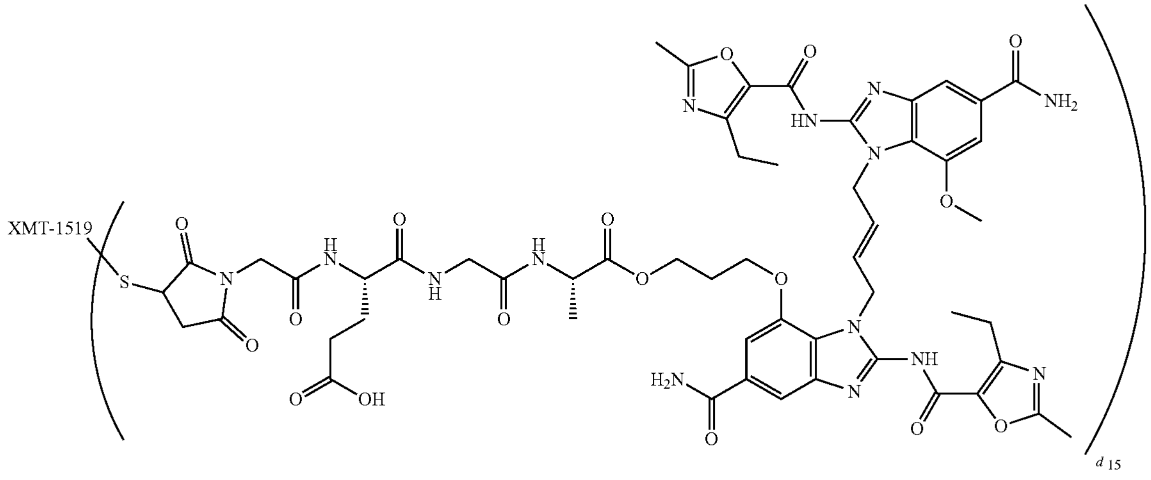
76
Conjugate 76 was prepared from Scaffold 75 as described in Example 17 except that N-Boc-(L)-Ala-OH was used instead of N-Boc-(D)-Ala-OH and N-Boc-(L)-Glu(OtBu)-OH was used instead of N-Boc-(D)-Glu(OtBu)-OH. The purified Conjugate 76 had a STING agonist to XMT-1519 ratio of 7.5.
Example 19: Synthesis of XMT-1519 Conjugate 78, DAR 7.4
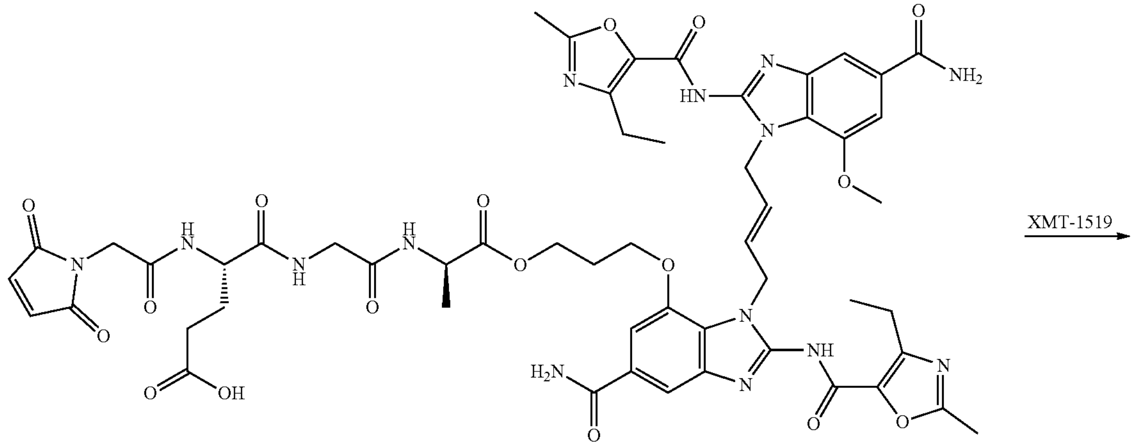
77

-continued
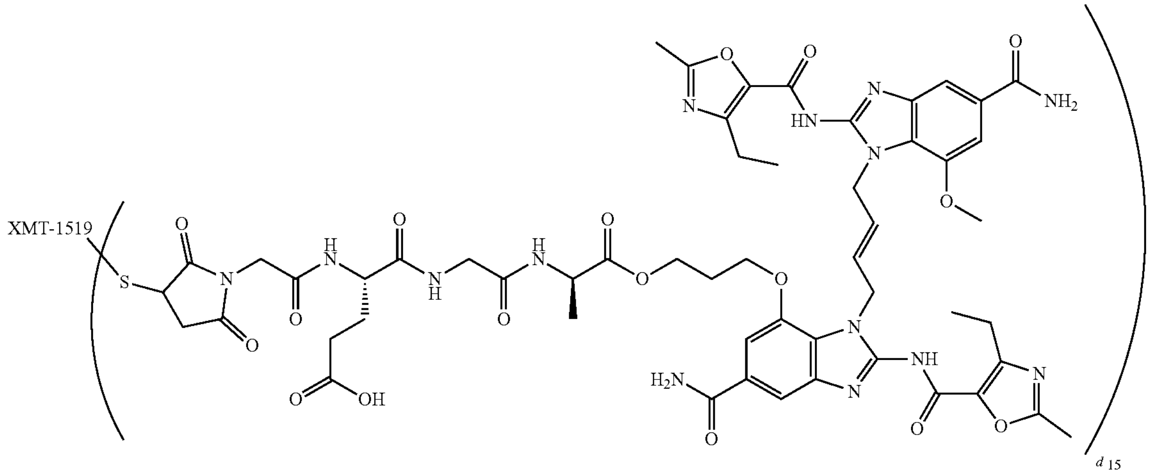
78
Conjugate 78 was prepared from Scaffold 70 as described in Example 17 except that N-Boc-(L)-Glu(OtBu)-OH was used instead of N-Boc-(D)-Glu(OtBu)-OH. The purified Conjugate 78 had a STING agonist to XMT-1519 ratio of 7.4.
Example 20: Synthesis of XMT-1519 Conjugate 80, DAR 7.5
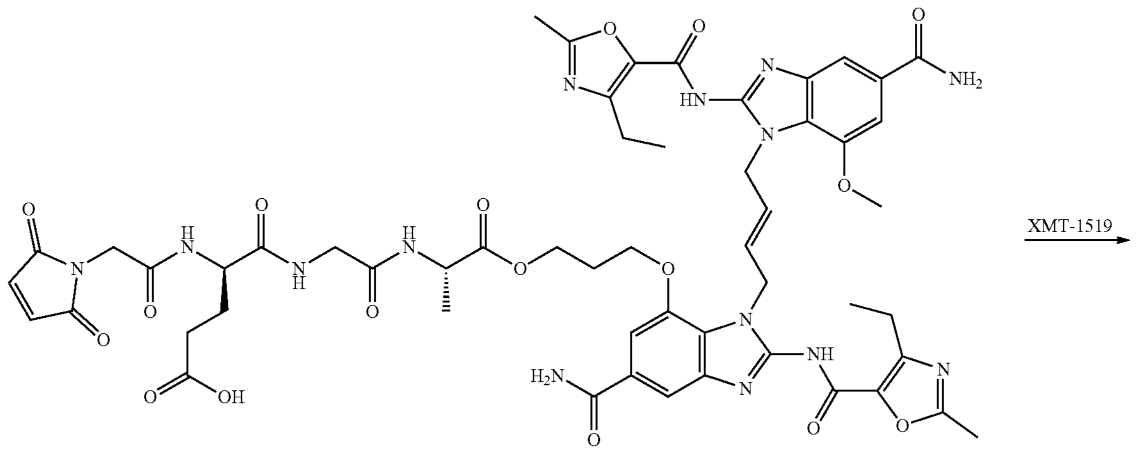
79

-continued
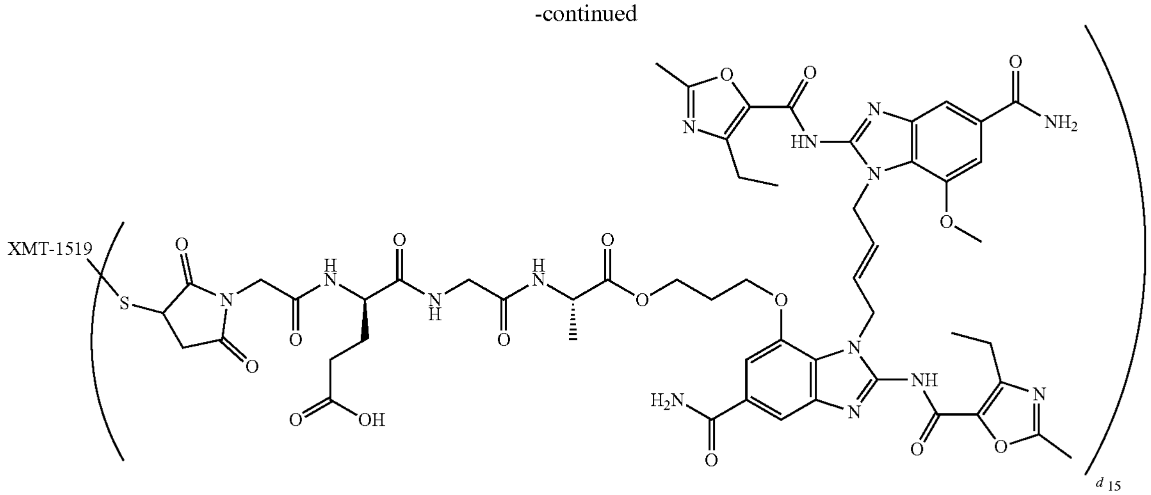
80
Conjugate 80 was prepared from Scaffold 79 as described in Example 17 except that N-Boc-(L)-Ala-OH was used instead of N-Boc-(D)-Ala-OH. The purified Conjugate 80 had a STING agonist to XMT-1519 ratio of 7.5.
Example 21: Synthesis of XMT-1519 Conjugate 82, DAR 5.7
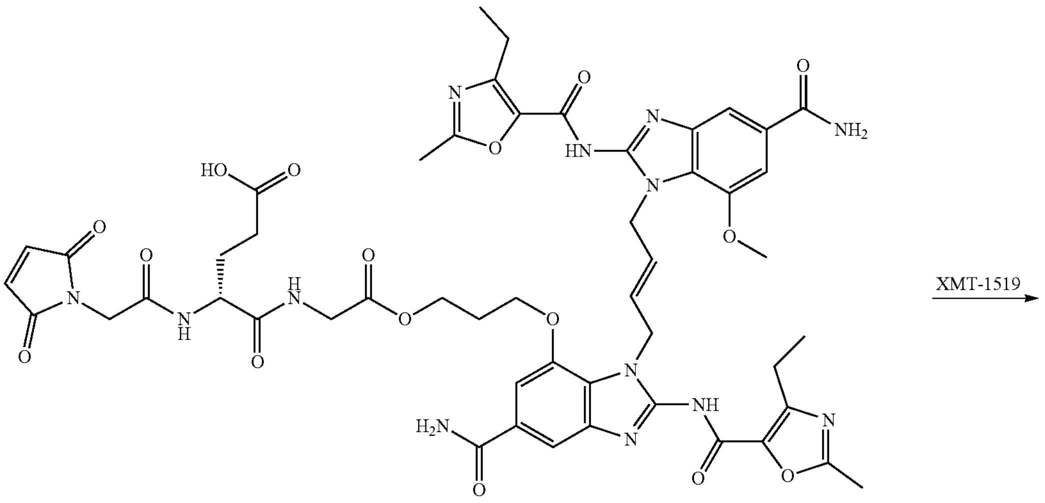
81

-continued
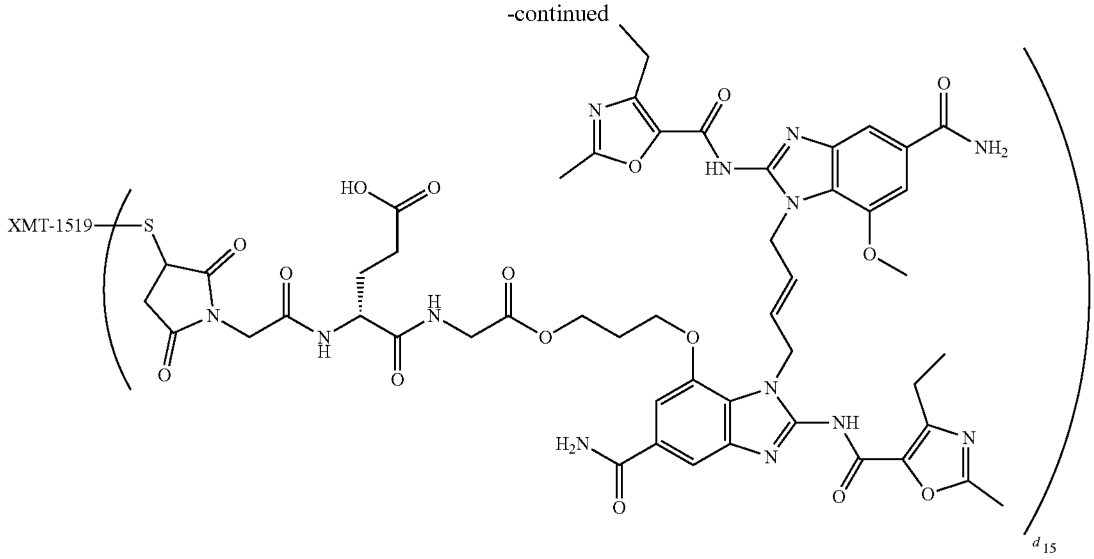
82
Conjugate 82 was prepared from Scaffold 81 as described in Example 12 except that Boc-Glycine was used instead of Boc-(L)-Ala-OH. The purified Conjugate 81 had a STING agonist to XMT-1519 ratio of 5.7.
Example 22: Synthesis of XMT-1519 Conjugate 85, DAR 6.5
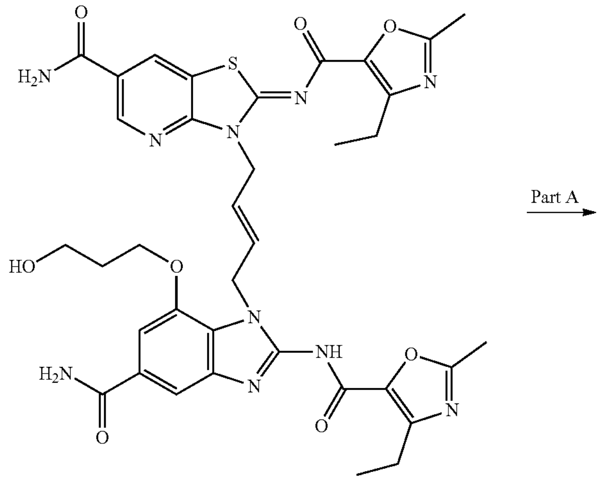
83

-continued

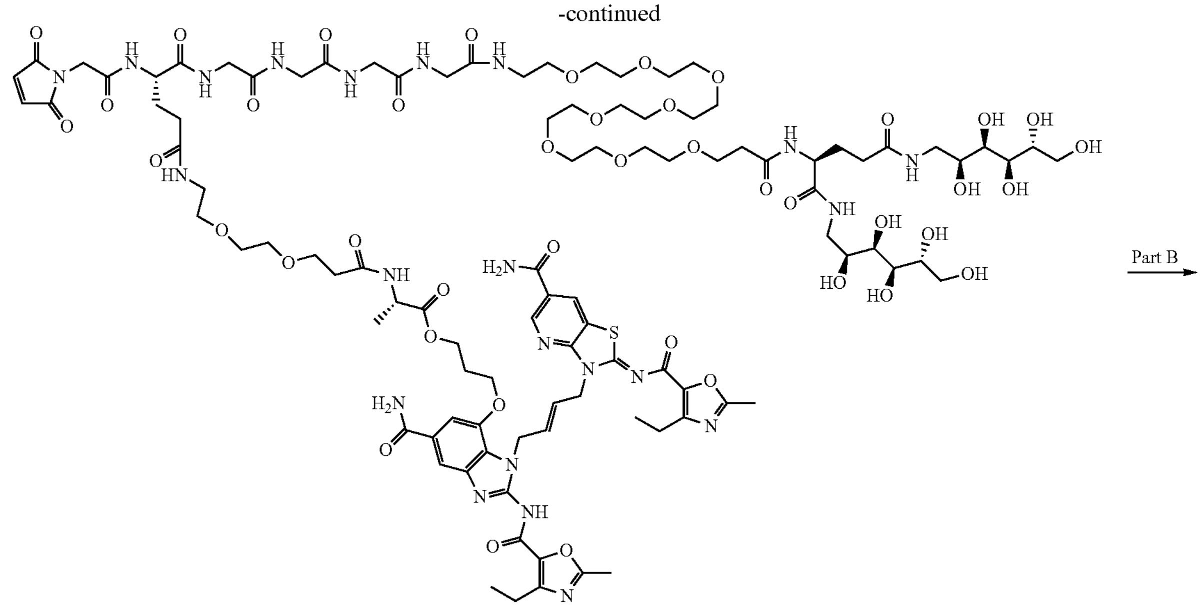

84

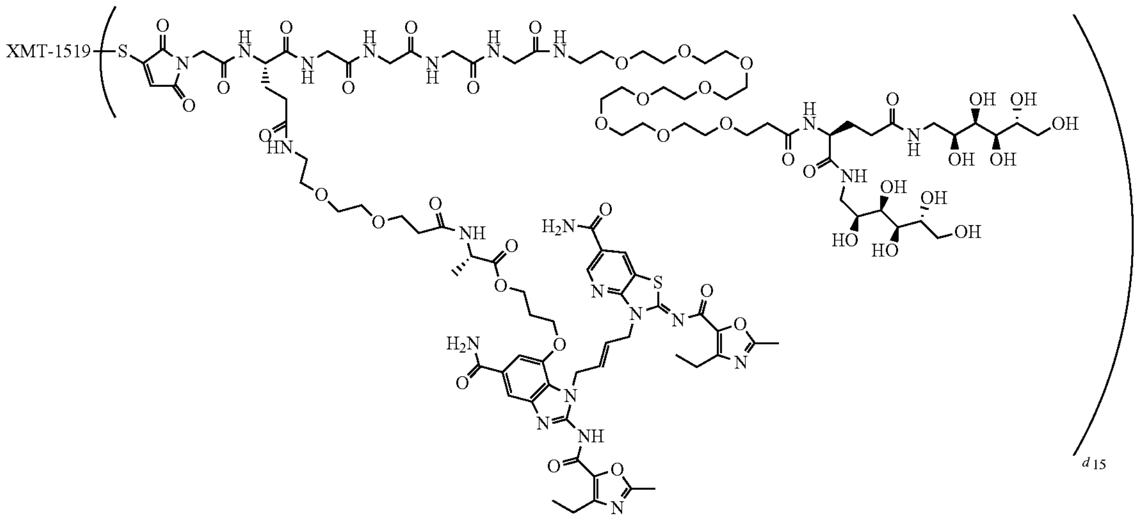

85

Part A: Scaffold 84 was prepared as described in Example 1 except that Compound 83 (prepared as described in U.S. 62/982,935) was used instead of Compound 1. Scaffold 84 was obtained as a white fluffy solid (3.3 mg, 0.500 yield over 5 steps). ESI-MS m/z Calcd for $C_{101}H_{148}N_{22}O_{42}S$ [M+2H]$^{2+}$: 1187.49; found 1187.78.

Part B: Conjugate 85 was prepared as described in Example 1 to afford the title conjugate. The purified Conjugate 85 had a STING agonist to XM4T-1519 ratio of 6.5.

Example 22a: Synthesis of Palivizumab Conjugate 85a, DAR 7.4

85a
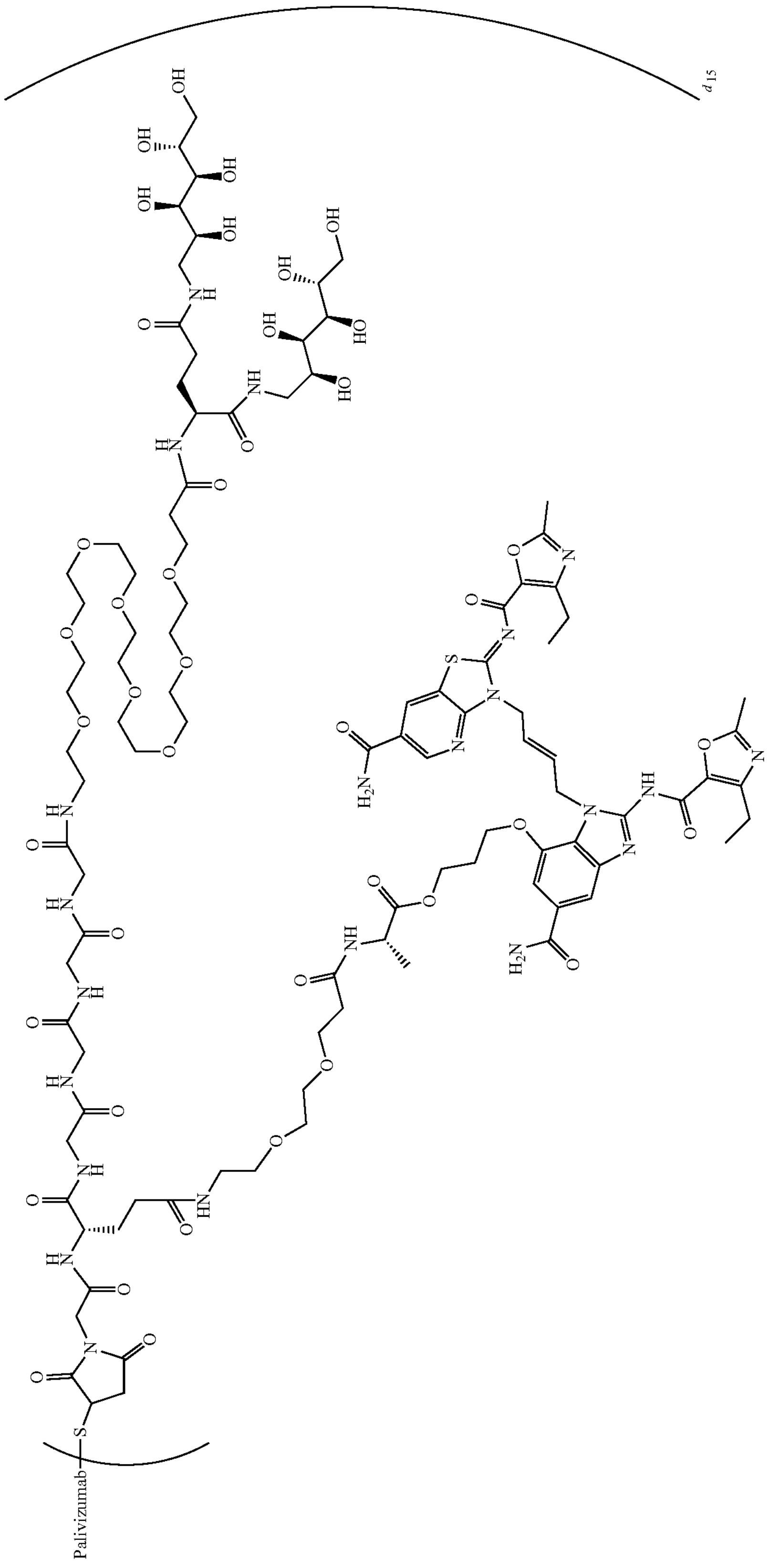

Conjugate 85a was prepared and characterized as described in Example 1 except that Palivizumab was used instead of XMT-1519. The purified Conjugate 85a had a STING agonist to Palivizumab ratio of 7.4.
Example 23: Synthesis of XMT-1519 Conjugate 88, DAR 6.6
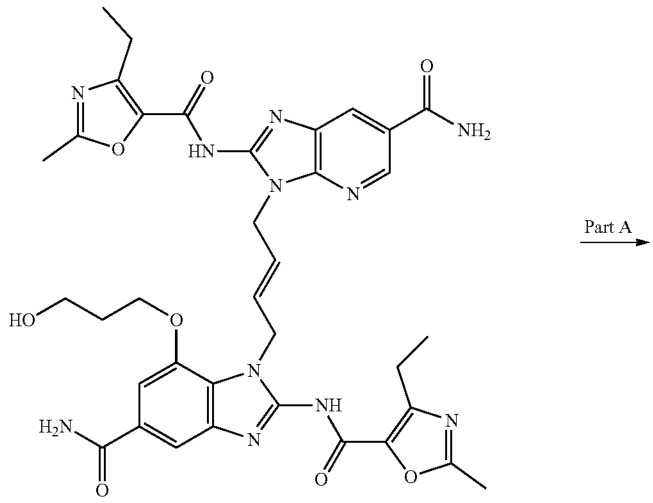
86
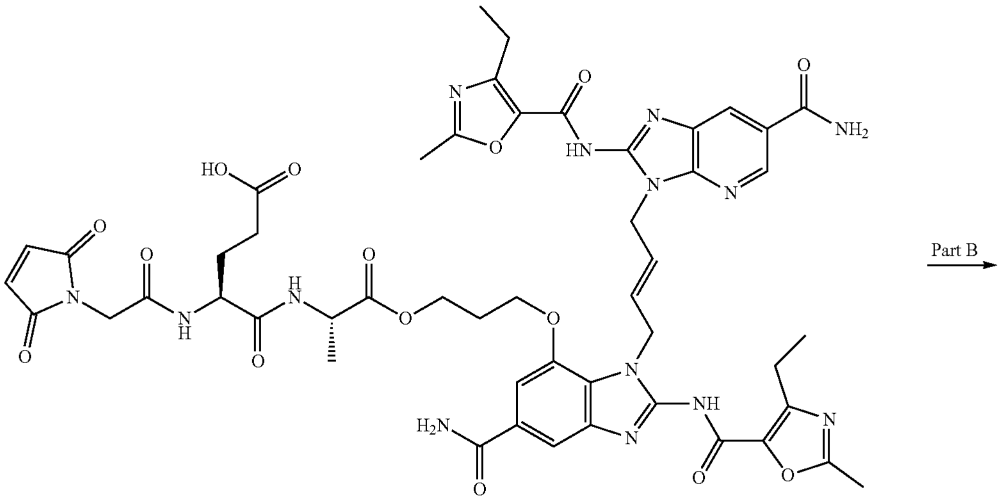
87

-continued

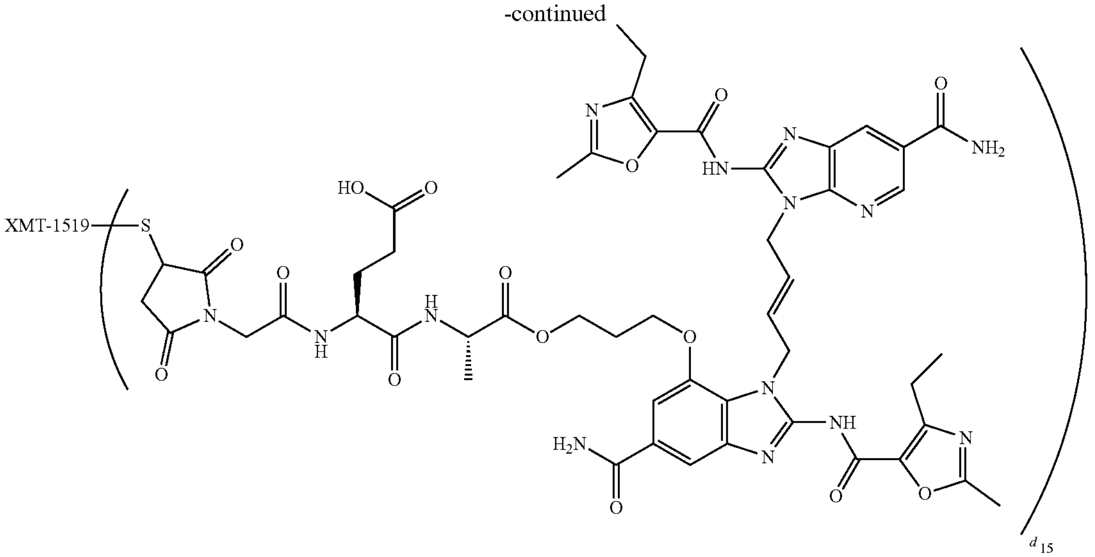

88

Part A: Scaffold 87 was prepared as described in Example 12 except that Compound 86 (prepared as described in U.S. 62/982,935) was used instead of Compound 26. ESI-MS m/z Calcd for $C_{50}H_{55}N_{14}O_{15}$ $[M+H]^+$: 1091.4; found 1091.2.

Part B: Conjugate 88 was prepared as described in Example 12 except that Scaffold 87 was used instead of Scaffold 57. The purified conjugate had a STING agonist to XMT-1519 ratio of 6.6.

Example 23a: Synthesis of Palivizumab Conjugate 89, DAR 5.9

89

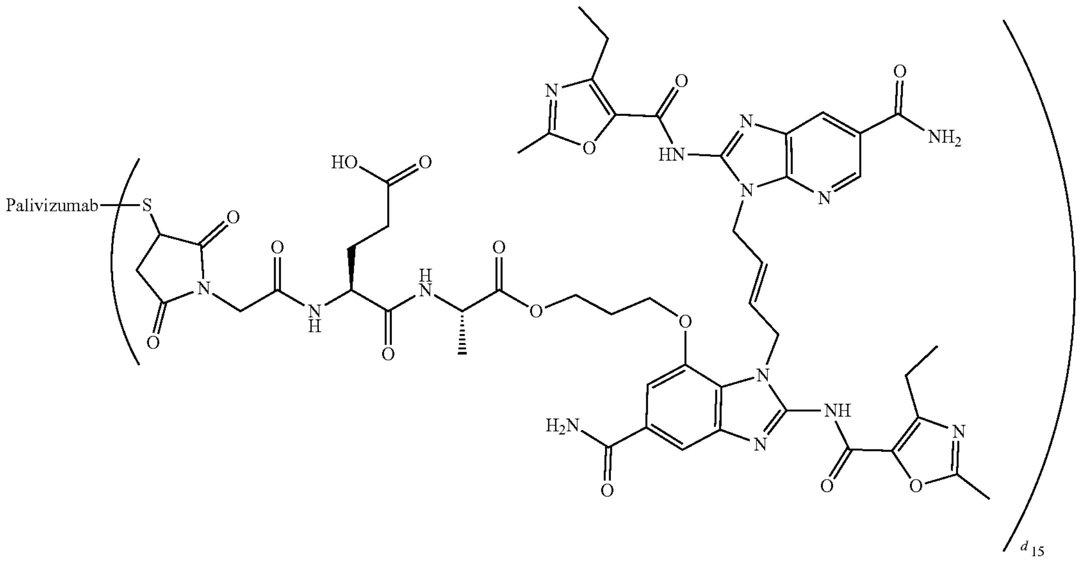

Conjugate 89 was prepared and characterized as described in Example 12 except that Palivizumab was used instead of XMT-1519. The purified Conjugate 89 had a STING agonist to Palivizumab ratio of 5.9.

Example 23b: Synthesis of CTL-48132_mIgG2a Conjugate 89a, DAR 8.8

89a

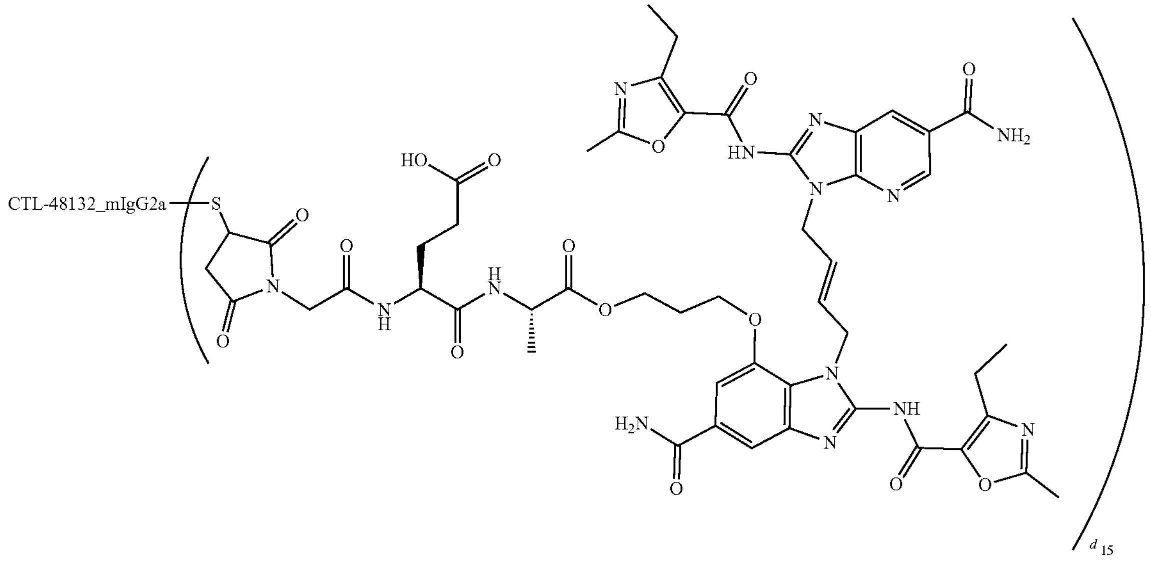

Conjugate 89a was prepared and characterized as described in Example 12 except that CTL-48132_mIgG2a was used instead of XMT-1519. The purified Conjugate 89a had a STING agonist to CTL-48132_mIgG2a ratio of 8.8.

Example 23c: Synthesis of MFP5_mIgG2a Conjugate 89b, DAR 9.0

89b

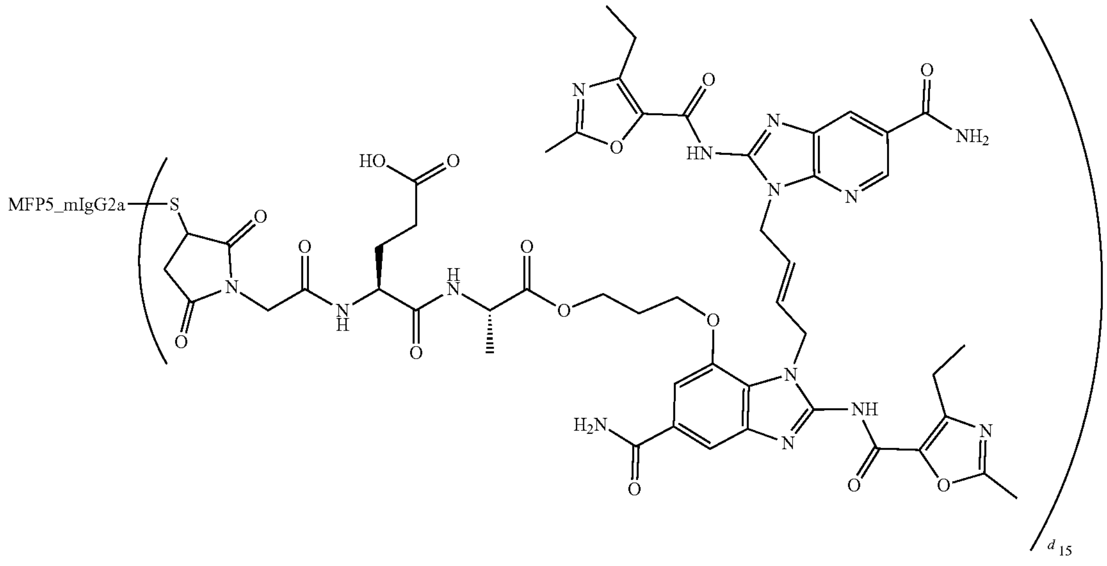

Conjugate 89b was prepared and characterized as described in Example 12 except that CTL-48132_mIgG2a was used instead of XMT-1519. The purified Conjugate 89b had a STING agonist to MFP5_mIgG2a ratio of 9.0.

Example 24: Synthesis of XMT-1519 Conjugate 92, DAR 7.6
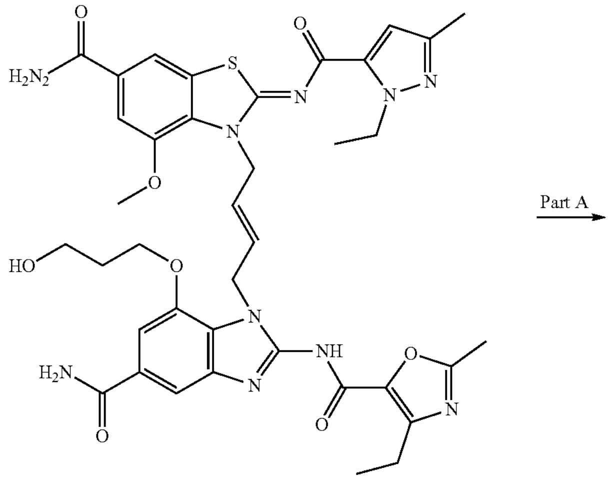
90
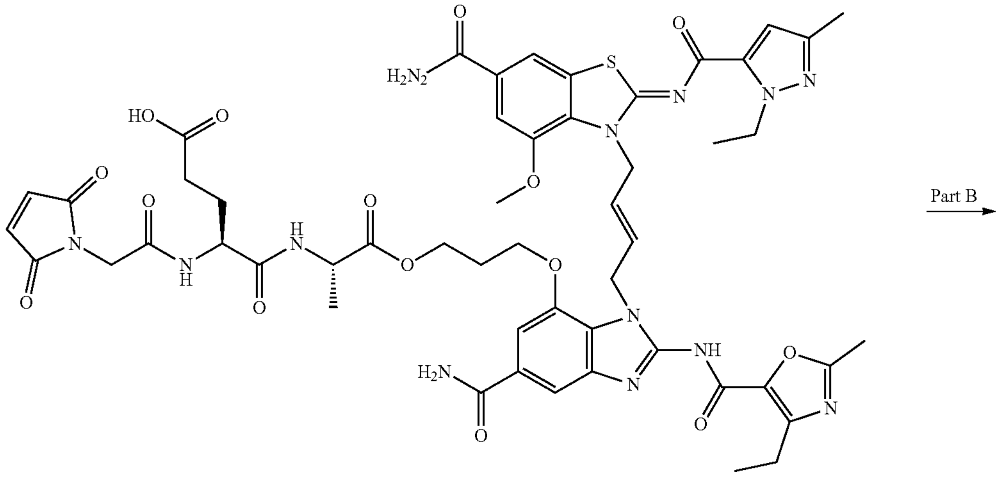
91
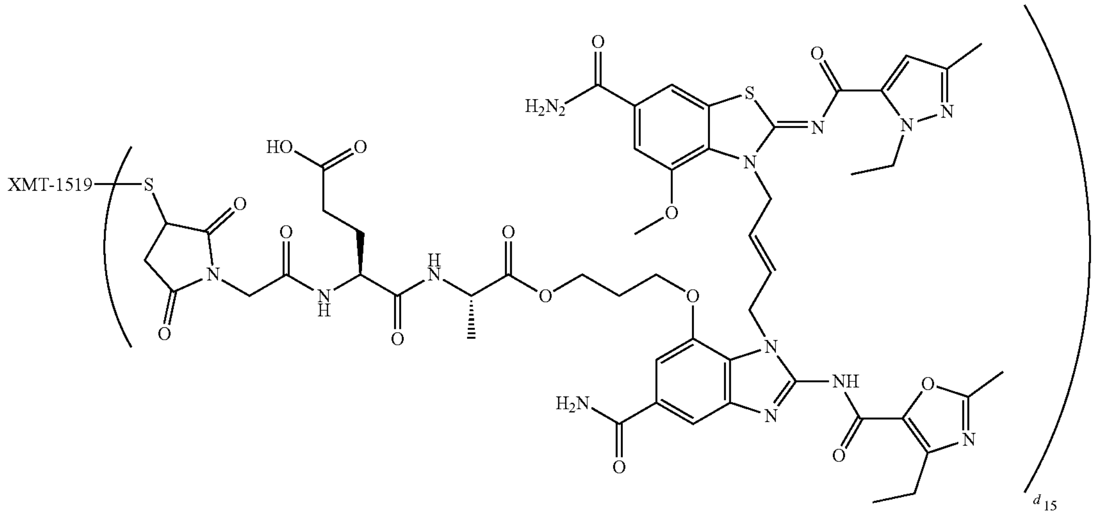
92

Part A: Scaffold 91 was prepared as described in Example 12 except that Compound 90 (prepared as described in U.S. 62/982,935) was used instead of Compound 26. ESI-MS m/z Calcd for $C_{52}H_{58}N_{13}O_{15}S$ [M+H]$^+$: 1136.4; found 1136.2.

Part B: Conjugate 88 was prepared as described in Example 12 except that Scaffold 87 was used instead of Scaffold 57. The purified conjugate had a STING agonist to XMT-1519 ratio of 7.6.

Example 24a: Synthesis of Palivizumab Conjugate 93, DAR 6.7

93

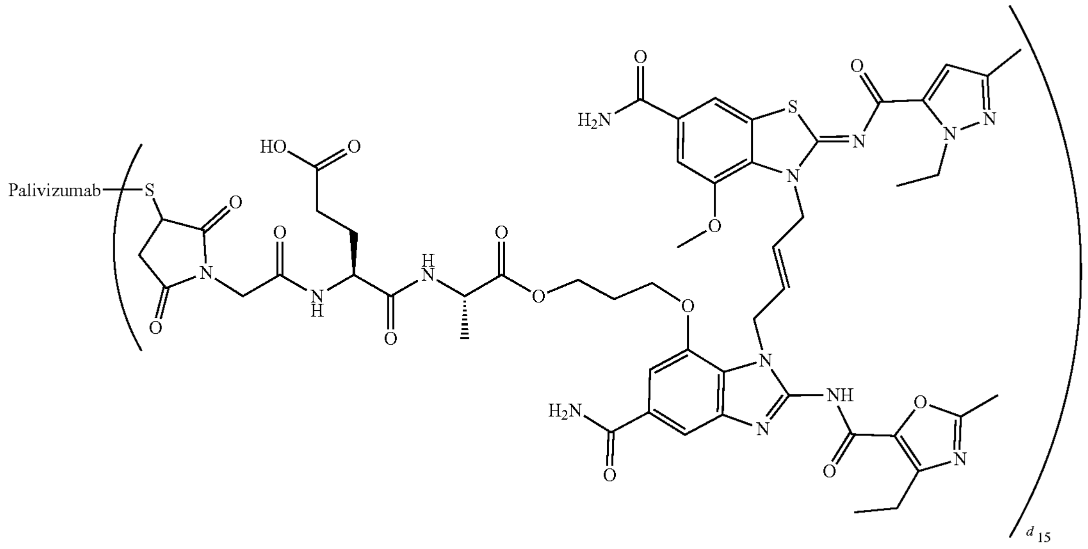

Conjugate 93 was prepared and characterized as described in Example 12 except that Palivizumab was used instead of XMT-1519. The purified Conjugate 93 had a STING agonist to Palivizumab ratio of 6.7.

Example 25: Synthesis of XMT-1519 Conjugate 100, DAR 7.8

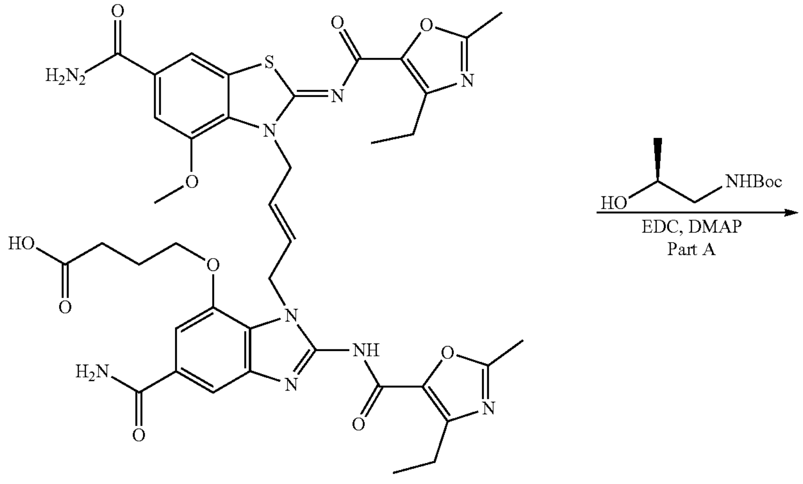

94

-continued
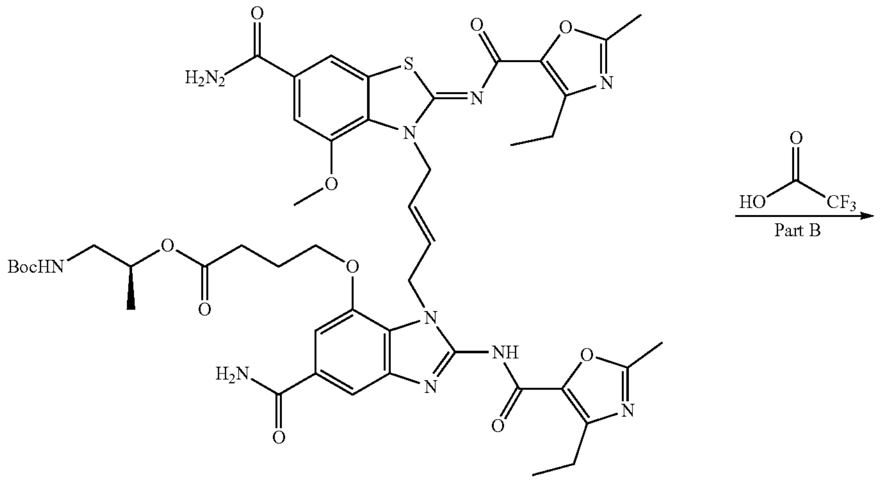
95
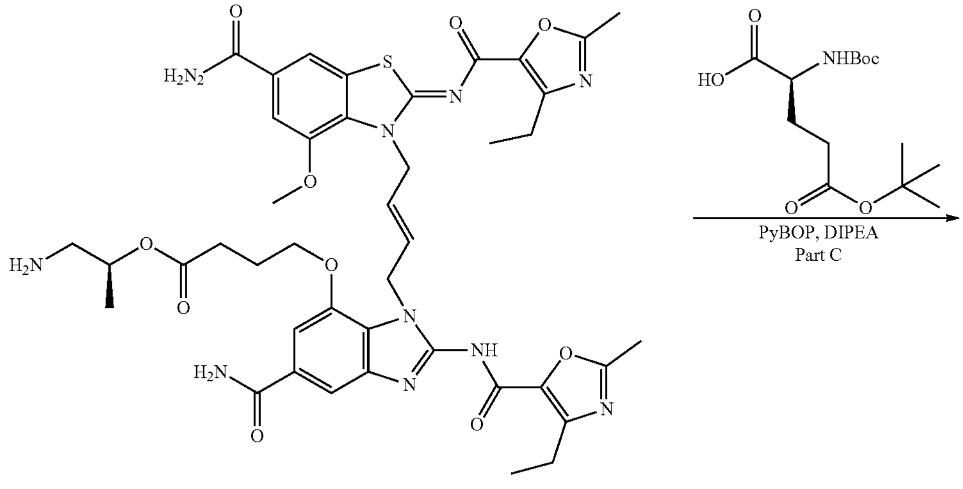
96
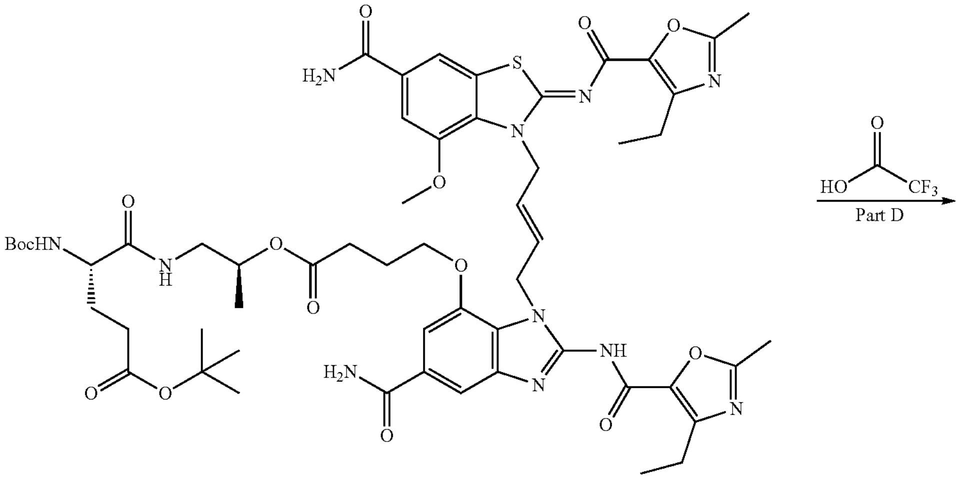
97

-continued

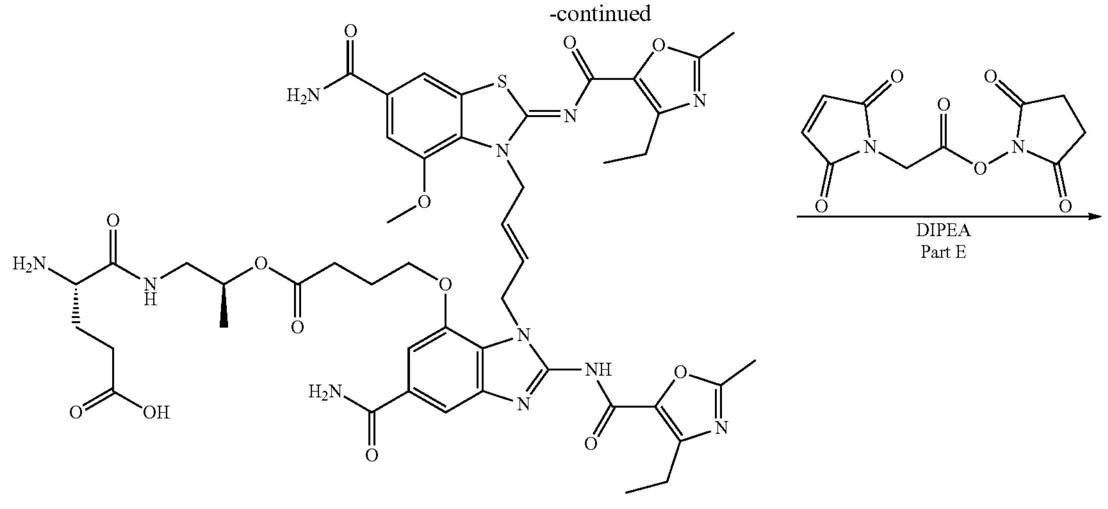

98

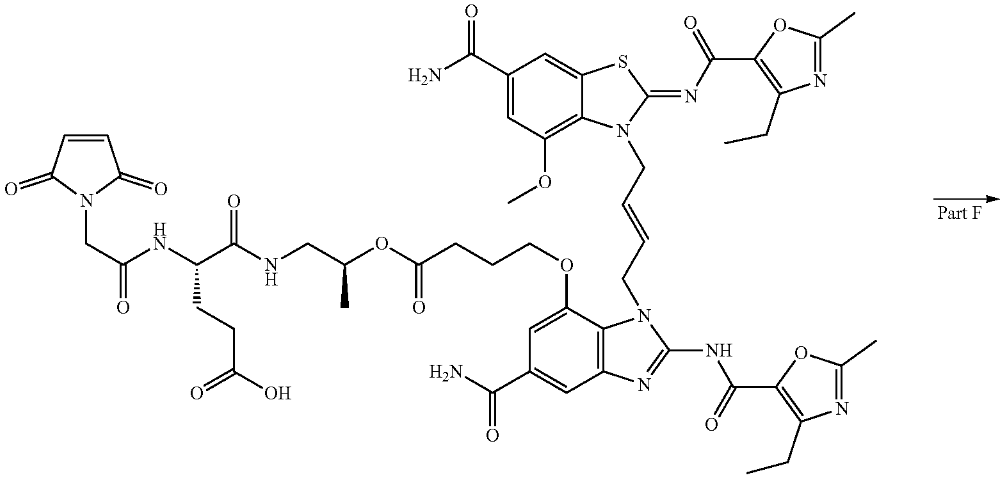

99

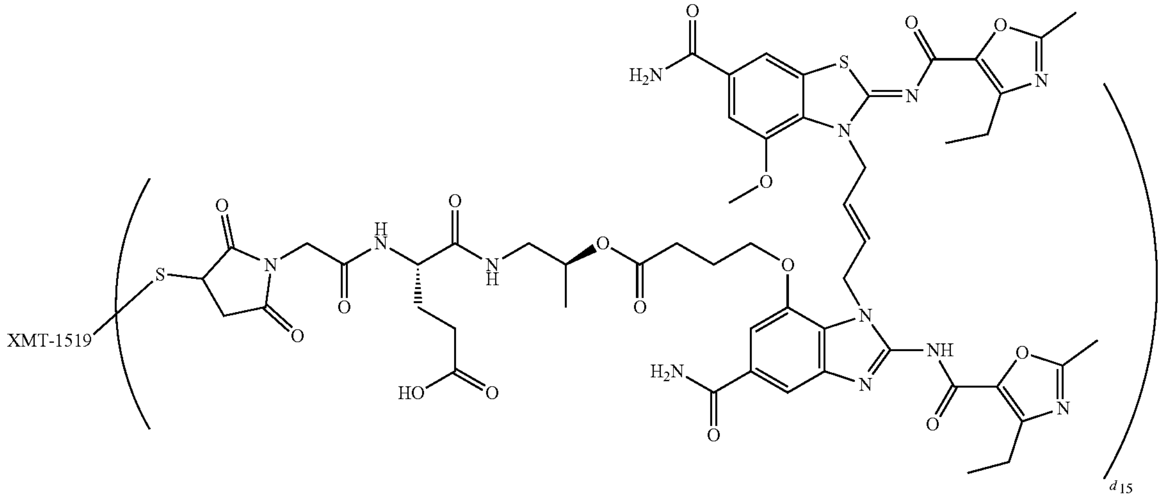

100

Part A: To a stirred solution of Compound 94 (prepared as described in U.S. 62/982,935, 45 mg, 0.054 mmol) in DMF (3 mL) was added (S)-1-(Boc-amino)propan-2-ol (19 mg, 0.11 mmol), EDC (17 mg, 0.109 mmol) and DMAP (3.3 mg, 0.027 mmol), and the mixture was stirred at room temperature for 12 hours. The reaction was concentrated in vacuo, and the residue was purified over silica gel (DCM:MeOH 60:40 v/v) to afford 95 (49 mg, 92% yield) as a white solid. ESI-MS: $C_{47}H_{57}N_{10}O_{12}S$ (M+H): calc. 985.38, found: 985.21.

Part B: To a stirred suspension of Compound 95 (49 mg, 0.05 mmol) in DCM (5 mL) was added TFA (1 mL, 20% v/v DCM), and the mixture was stirred at room temperature for 12 hours. The resulting mixture was concentrated to afford Compound 96 (44 mg, 100% yield) as a light yellow solid. ESI-MS: $C_{42}H_{49}N_{10}O_{10}S$ (M+H): calc. 885.33, found: 885.18.

Part C: To a stirred solution of Compound 96 (50 mg, 0.05 mmol) in DMF (2 mL) was added Boc-Glu-OtBu (86 mg, 0.28 mmol), PyBOP (118 mg, 0.23 mmol), and DIPEA (0.12 mL, 0.68 mmol), and the mixture was stirred at room temperature for 30 minutes. The mixture was concentrated in vacuo, and the residue was purified over silica gel (DCM:MeOH 60:40 v/v) to afford Compound 97 (45 mg, 77% yield) as a white solid. ESI-MS: $C_{56}H_{72}N_1O_{15}S$ (M+H): calc. 1170.49, found: 1170.29.

Part D: To a stirred suspension of Compound 97 (45 mg, 0.038 mmol) in DCM (5 mL) was added TFA (1 mL, 20% v/v DCM), and the mixture was stirred at room temperature for 12 hours. The mixture was concentrated in vacuo to afford Compound 98 (38 mg, 100% yield) as a light yellow solid. ESI-MS: $C_{47}H_{56}N_{11}O_{13}S$ (M+H): calc. 1014.37, found: 1014.20.

Part E: To a stirred solution of Compound 98 (20 mg, 0.02 mmol) in DMF (2 mL) was added 2,5-dioxopyrrolidin-1-yl 2-(2,5-dioxo-2,5-dihydro-1H-pyrrol-1-yl)acetate (5 mg, 0.02 mmol) and DIPEA (0.034 mL, 0.20 mmol), and the mixture was stirred at room temperature for 15 minutes. The reaction was quenched with acetic acid (0.034 mL, 1:1 v/v DIPEA) and directly purified via HPLC using a C18 stationary phase (water:ACN) to afford Scaffold 99 (4.7 mg, 20% yield) as a white solid. ESI-MS: $C_{53}H_{59}N_{12}O_{16}S$ (M+H): calc. 1151.38, found: 1151.18.

Part F: Conjugate 100 was prepared as described in Example 12 except that Scaffold 99 was used instead of Scaffold 57. The purified conjugate had a STING agonist to XMT-1519 ratio of 7.8.

Example 25a: Synthesis of Palivizumab Conjugate 101, DAR 6.5

Conjugate 101 was prepared as described in Example 25 except that Palivizumab was used instead of XMT-1519. The purified conjugate had a STING agonist to Palivizumab ratio of 6.5.

Example 26A: Cancer Cell-Targeted Wild Type or Fc Mutant STING-ADC Activity in Cancer Cell/THP1 Luciferase Reporter Cell Co-Cultures Generation of NaPi2b Fc silent antibodies: NaPi2b mAb with its Fc region engineered to abolish Fc effector function (anti-NaPi2b-(AAG)) was designed with three mutations in the heavy chain constant region L234A, L235A and P329G (AAG; Kabat Eu numbering) and generated through standard molecular biology procedure. The antibody was expressed and purified. Briefly, DNA encoding variable region of the heavy chain of NaPi2b antibody with constant region of human IgG1 carrying L234A, L235A and P329G mutations and variable region of light chain of anti-NaPi2b antibody with human kappa light chain were cloned into mammalian expression vectors. The heavy chain and light chain of NaPi2b-(AAG) were co-expressed in HEK293 cells, and the antibody was purified from cell supernatants by standard Protein A affinity chromatography.

Induction of STING pathway in immune cells: The induction of STING pathway in immune cells by NaPi2b-targeted STING ADC was evaluated by a cancer cell/THP1-IRF3-Luciferase reporter cell co-culture assay. OVCAR3 human ovarian carcinoma cells were seeded in 96-well CellBind surface tissue culture plates (15,000/well) and allowed to attach for 6 hours in RPMI-1640 medium with 10% FBS and 1% penicillin/streptomycin. A range of dilutions (0.4 nM to 100 nM based on payload; 3-fold serial dilutions in growth medium) of the test articles Conjugate 8b-1, Conjugate 8f, Conjugate 8d-1, and Compound 1 were added to each well and the plate was incubated for 20 min at 37° C. THP1-dual reporter cells (30,000) were then added to each well and the incubation continued for 20 hours at 37° C. in a humidified atmosphere of 5% $CO_2$. Cell culture supernatants (20 µl) from each incubated sample was added to resuspended QUANTI-Luc (50 l) and the luminescent signal was mea-

101

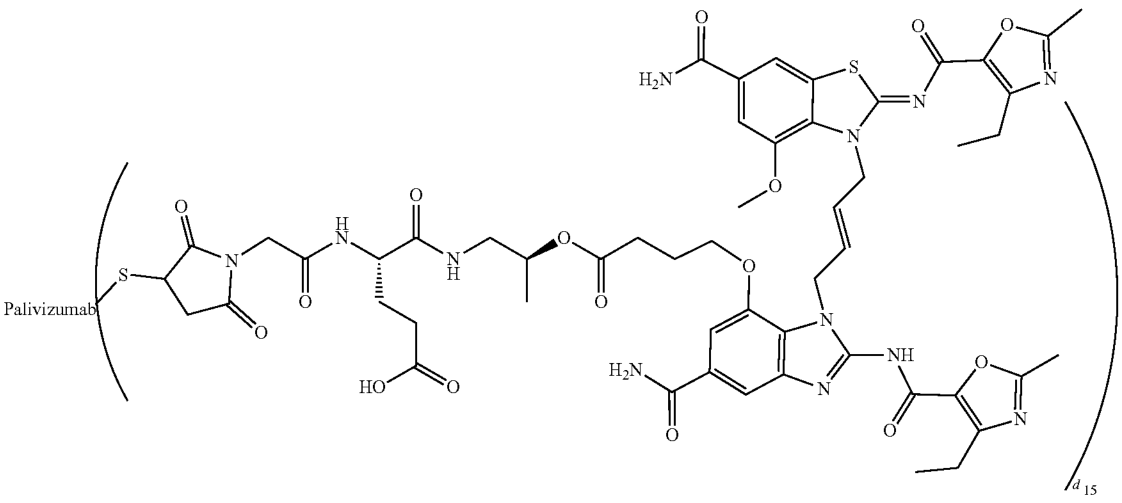

$d_{15}$ sured immediately using a SpectraMax M5 plate reader (Molecular Devices). The $EC_{50}$ value was determined from the dose response curve. Table 1A provides the $EC_{50}$ values in THP1-Dual cells co-cultured with OVCAR3 cancer cells.

TABLE 1A

| Test Article | Conjugate 8b-1 | Conjugate 8f | Conjugate 8d-1 | Compound 1 |
|---|---|---|---|---|
| $EC_{50}$ (nM) | <0.05 | 43.3 | 41.8 | 6.8 |

As shown in Table 1A, Conjugate 8b-1 with wild type Fc effector function exhibits greater than 100-fold increased activity compared to the free agonist, Compound 1, and ~1000-fold increased activity compared to Conjugate 8f and Conjugate 8d-1, confirming the role of the Fc receptor for activity. Results shown are $EC_{50}$ values of a representative experiment.

Example 26B: Cancer Cell-Targeted Wild Type or Fc Mutant STING-ADC Activity in Cancer Cell/THP1 Luciferase Reporter Cell Co-Cultures Generation of HER-2 Fc silent antibodies: Trastuzumab mAb with its Fc region engineered to abolish Fc effector function (anti-Her2-(AAG)) was designed with three mutations in the heavy chain constant region L234A, L235A, and P329G (AAG; Kabat Eu numbering) was generated as described in Example 26A.

Induction of STING pathway in immune cells: The induction of STING pathway in immune cells by Her2-targeted STING ADC was evaluated by a cancer cell/THP1-IRF3-Luciferase reporter cell co-culture assay using SKBR3 human breast carcinoma cells as described in Example 26A with test articles Conjugate 8a-2, Conjugate 8j, Conjugate 8c-2, and Compound 1) Table 1A provides the $EC_{50}$ values in THP1-Dual cells co-cultured with SKBR3 cancer cells.

TABLE 1B

| Test Article | Conjugate 8a-2 | Conjugate 8j | Conjugate 8c-2 | Compound 1 |
|---|---|---|---|---|
| $EC_{50}$ (nM) | 0.35 | >200 | >200 | 7.4 |

As shown in Table 1B, Conjugate 8a-2 with wild type Fe effector function exhibits ~50-fold increased activity compared to the free agonist, Compound 1, and ~1000-fold increased activity compared to Conjugate 8j and Conjugate 8c-2, confirming the role of the Fc receptor for activity. Results shown are $EC_{50}$ values of a representative experiment.

Example 27A: Cancer Cell-Targeted Wild Type or Fc Mutant STING ADC Activity in THP1 Luciferase Reporter Cells Cultured on Tumor Cell Antigen-Coated Plates Human NaPi2b-derived peptide (QINVTVPSTANCTSPSLCWTDGIQNWTMKN) was coated onto the surface of each well of a 96-well plate by incubation with the peptide (1p g/mL in PBS), overnight at 4° C. The wells were then washed 1× with PBS-T and blocked by incubation with BSA (3% in PBS-T) for 1 hour at room temperature. After washing with PBS-T (2×), PBS (1×), and growth medium (RPMI 1640, 10% FBS, 1% penicillin/streptomycin, lx), a range of dilutions (0.4 nM to 100 nM based on payload; 3-fold serial dilutions in growth medium) of the test articles, (Conjugate 8b-1, Conjugate 8f, Conjugate 8c-1, and Compound 1) were added to each well and the plate was incubated for 20 min at 37° C. THP1-dual reporter cells (50,000) were added into each well and incubated for 20 hours at 37° C. in a humidified atmosphere of 5% $CO_2$. Cell culture supernatants (20 μl) from each incubated sample was added to resuspended QUANTI-Luc (50 μl) and the luminescent signal was measured immediately using a SpectraMax M5 plate reader (Molecular Devices). The $EC_{50}$ value was determined from the dose response curve. Table 2A provides the $EC_{50}$ values in THP1-Dual cells cultured on NaPi2b recombinant peptide coated plates.

TABLE 2A

| Test Article | Conjugate 8b-1 | Conjugate 8f | Conjugate 8c-1 | Compound 1 |
|---|---|---|---|---|
| $EC_{50}$ (nM) | <0.022 | >100 | 18.99 | 5.18 |

As shown in Table 2, Conjugate 8b-1 with wild type Fc exhibits ~100-fold increased activity compared to Compound 1. Conjugate 8f has no activity and Conjugate 8c-1 has ~1000-fold lower activity compared to Conjugate 8b-1, confirming the role of the Fc receptor for activity. Results shown are $EC_{50}$ values of a representative experiment.

Example 27B: Cancer Cell-Targeted Wild Type or Fc Mutant STING ADC Activity in THP1 Luciferase Reporter Cells Cultured on Tumor Cell Antigen-Coated Plates Human HER2/ErbB2 protein (His-tagged, ECD, domain IV, 17.1 kDa) derived peptide was coated onto the surface of each well of a 96-well plate by incubation with the peptide (1 μg/mL in PBS), overnight at 4° C. and the assay was performed as described in Example 27A except that 3-fold serial dilutions (0.09 nM to 200 nM based on payload) of the test articles Conjugate 8a-3, Conjugate 8j, Conjugate 8c-2, and Compound 1 were used. Table 2B provides the $EC_{50}$ values in THP1-Dual cells cultured on Her2 recombinant protein coated plates.

TABLE 2B

| Test Article | Conjugate 8a-3 | Conjugate 8j | Conjugate 8c-2 | Compound 1 |
|---|---|---|---|---|
| $EC_{50}$ (nM) | 0.36 | >200 | >200 | 8.8 |

As shown in Table 2B, Conjugate 8a-3 with wild type Fc exhibits ~100-fold increased activity compared to Compound 1. Conjugates 8j and Conjugate 8c-2 have no activity, confirming the role of the Fc receptor for activity. Results shown are $EC_{50}$ values of a representative experiment.

Example 28A: Activity of Tumor Cell Targeted NaPi2b ADC in Cancer Cell/PBMC Co-Cultures OVCAR3 human ovarian carcinoma cells stably expressing nuclear restricted mKate fluorescent red protein were generated by transduction with IncuCyte© NucLight Red Lentivirus reagent. Stably transduced cells (designated as OVCAR3-NucRed cells) selected in puromycin-containing media (2 μg/mL) for two days, were seeded in 96-well tissue culture plates (8,000/well) and allowed to attach overnight in RPMI-1640 medium with 10% FBS and 1% penicillin/ streptomycin. Culture medium was replaced with fresh media (50 μL). Test articles (3× concentrated, Conjugate 8b-1 (100, 10, and 1 nM), Conjugate 8f (100, 10, and 1 nM), Conjugate 8c-1 (100 and 10 nM), and Compound 1 (100 and 10 nM); conjugate concentrations were based on the payload) were then added to each well in media (50 μL) and the plate was incubated for 20 min at 37° C. Frozen human peripheral blood mononuclear cells (PBMCs) were thawed according to the supplier's instructions and were added to each well (40,000 PBMCs in 50 μL media) and the plate was placed in an IncuCyte© live cell imaging instrument in an incubator (37° C., 5% 02) and scanned every 4 hours over 2 days. The number of red objects (cancer cells) were quantified using the IncuCyte© Zoom software. Red object confluency in each well was normalized to its own T=0 time point red object confluency.

FIG. 1A plots the red object confluency as a function of time and shows the robust induction of cancer cell killing by PBMCs in response to Conjugate 8b-1 at a 100× lower payload concentration compared to Compound 1. Conjugate 8f also exhibited activity although at reduced levels compared to Conjugate 8b. Conjugate 8c-1 had significantly lower activity compared to Conjugate 8b-1.

Example 28B: Activity of Tumor Cell Targeted NaPi2b ADC in Cancer Cell/PBMC Co-Cultures OVCAR3-NucRed cells were seeded in 96-well tissue culture plates (20,000/well) and allowed to attach 6 hours in RPMI-1640 medium with 10% FBS and 1% penicillin/streptomycin. Culture medium was replaced with fresh media (50 μL). Test articles (3× concentrated, Conjugate 8l and Compound 1 (each at 100, 10, and 1 nM) and Conjugate 8m (100 nM); conjugate concentrations were based on the payload) were then added to each well in media (50 μL). The assay was performed as described in Example 28A except that 30,000 PBMCs were used. The number of red objects (cancer cells) were quantified using the IncuCyte© Zoom software. Red object numbers in each well was normalized to its own T=0 time point red object numbers.

Figure 1B:
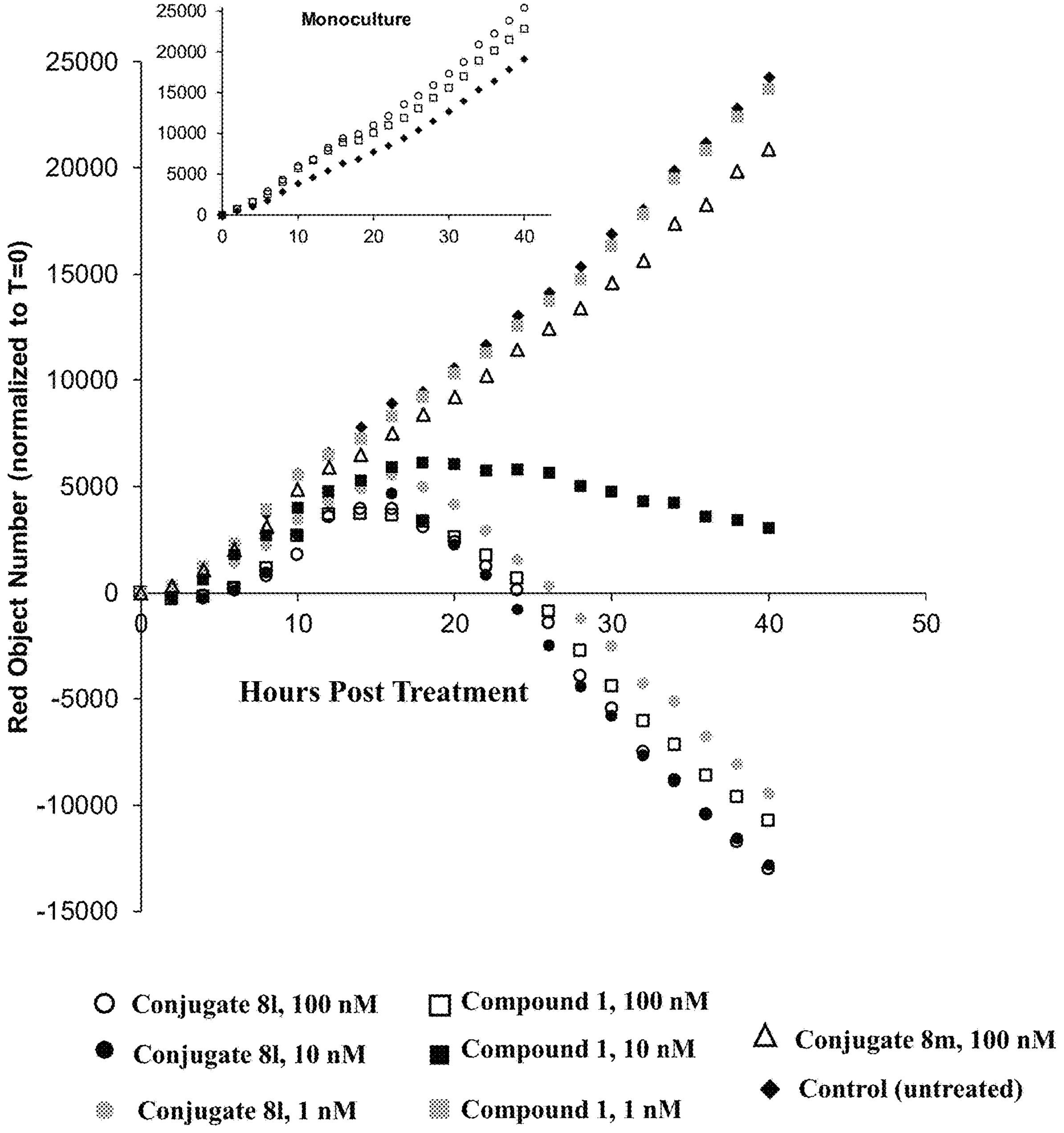
FIG. 1B plots the red object confluency as a function of time for Conjugate 8l and Compound 1 (each at 100, 10, and 1 nM) and Conjugate 8m (100 nM) (conjugate concentrations were based on the payload).

FIG. 1B plots the red object numbers as a function of time and shows the robust induction of cancer cell killing by PBMCs in response to Conjugate 8l at a 100×lower payload concentration compared to Compound 1. Conjugate 8m had no significant activity and the increase in red object number (cell growth) over time was similar to the untreated control. Inset shows that none of the test articles (100 nM) inhibited growth of OVCAR3-NucRed cells in monocultures.

Example 29: Flow Cytometry Analysis of CD14, Fcγ Receptors, and CD3 Expression in PBMCs and Isolated Monocyte Subpopulations Frozen human PBMCs ($1\times10^8$) were thawed and aliquoted into three tubes: one aliquot was subjected to human monocyte enrichment [StemCell Technologies] ("CD16 depleted monocytes"), one aliquot was subjected to human monocyte enrichment without CD16 depletion [StemCell Technologies] ("enriched monocytes"), and one aliquot was not subjected to enrichment ("PBMCs"). For flow cytometry, cells (50,000) from each group were transferred to a U-bottom 96-well plate in 4-replicates, washed with PBS and stained with live/dead fixable Aqua dead cell staining dye (Molecular Probes) followed by staining with fluorophore conjugated target specific (triplicates) or isotype control antibodies (Pacific Blue anti-human CD14, FITC anti-human CD3, APC/Cy7 CD16, PE anti-human CD32, PE/Cy7 anti-human CD64). Cells were fixed and surface expression of the proteins of interest was determined by flow cytometry analysis on a MACSQuant flow cytometer. Data analysis was performed by FlowJo software. Table 3 provides the frequency (% of single/live cells)) of CD14−/CD16+, CD14+/CD16+, CD14−/CD32+, CD14+/CD32+, CD14−/CD64+, CD14+/CD64+, and CD14−/CD3+ cells in PBMCs, enriched monocytes, and CD16-depleted monocyte populations

TABLE 3

| Population (%)* | CD14+ CD16+ | CD14− CD16+ | CD14+ CD32+ | CD14− CD32+ | CD14+ CD64+ | CD14− CD64+ | CD14− CD3+ |
|---|---|---|---|---|---|---|---|
| PBMCs | 1.8 ± 0.1 | 20.0 ± 0.8 | 15.5 ± 0.8 | 32.5 ± 0.5 | 15.5 ± 0.9 | 1.0 ± 0.3 | 47.5 ± 0.7 |
| Enriched Monocytes | 4.0 ± 0.4 | 23.6 ± 1.2 | 5.1 ± 1.2 | 20.7 ± 0.1 | 41.8 ± 0.1 | 2.7 ± 0.3 | 3.4 ± 0.5 |
| CD16 Depleted Monocytes | 2.0 ± 0.2 | 3.0 ± 0.9 | 5.8 ± 0.5 | 24.2 ± 1.1 | 46.8 ± 0.6 | 2.7 ± 0.1 | 2.5 ± 1.2 |

*Gated on single/live cells

Table 3 shows efficient depletion of CD3+ cells and enrichment of monocytes, and diminished levels of CD16 positive cells in the CD16-depleted monocytes post isolation. CD64 staining results indicate that all CD14 positive cells express CD64 (FcγRI) in PBMCs as well as in the enriched monocyte subpopulations.

Figure 2:
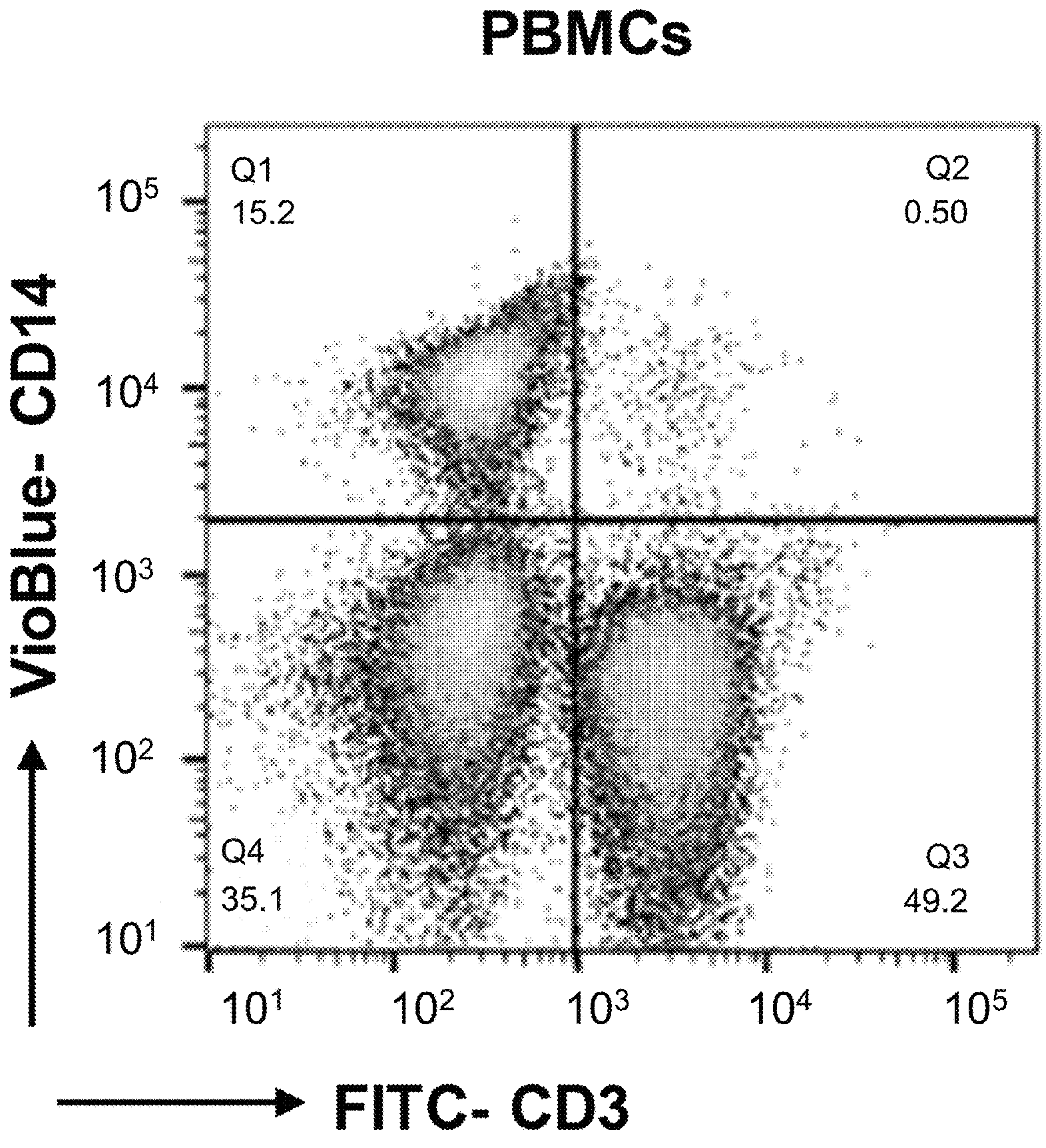
FIG. 2 shows CD14−/CD3+ cells in PBMCs, enriched monocytes, and CD16-depleted monocyte populations.
Figure 2:
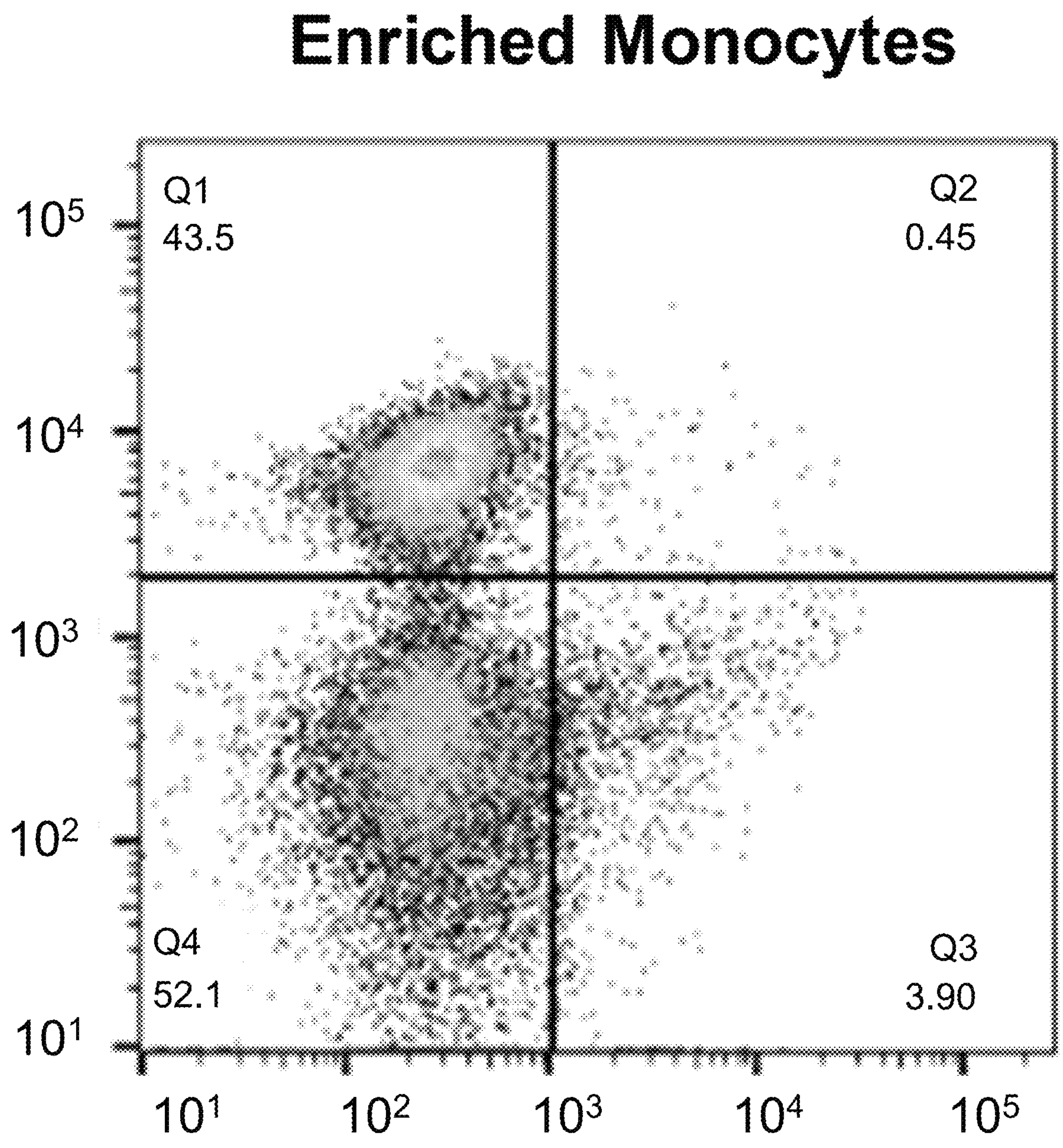
Figure 2:
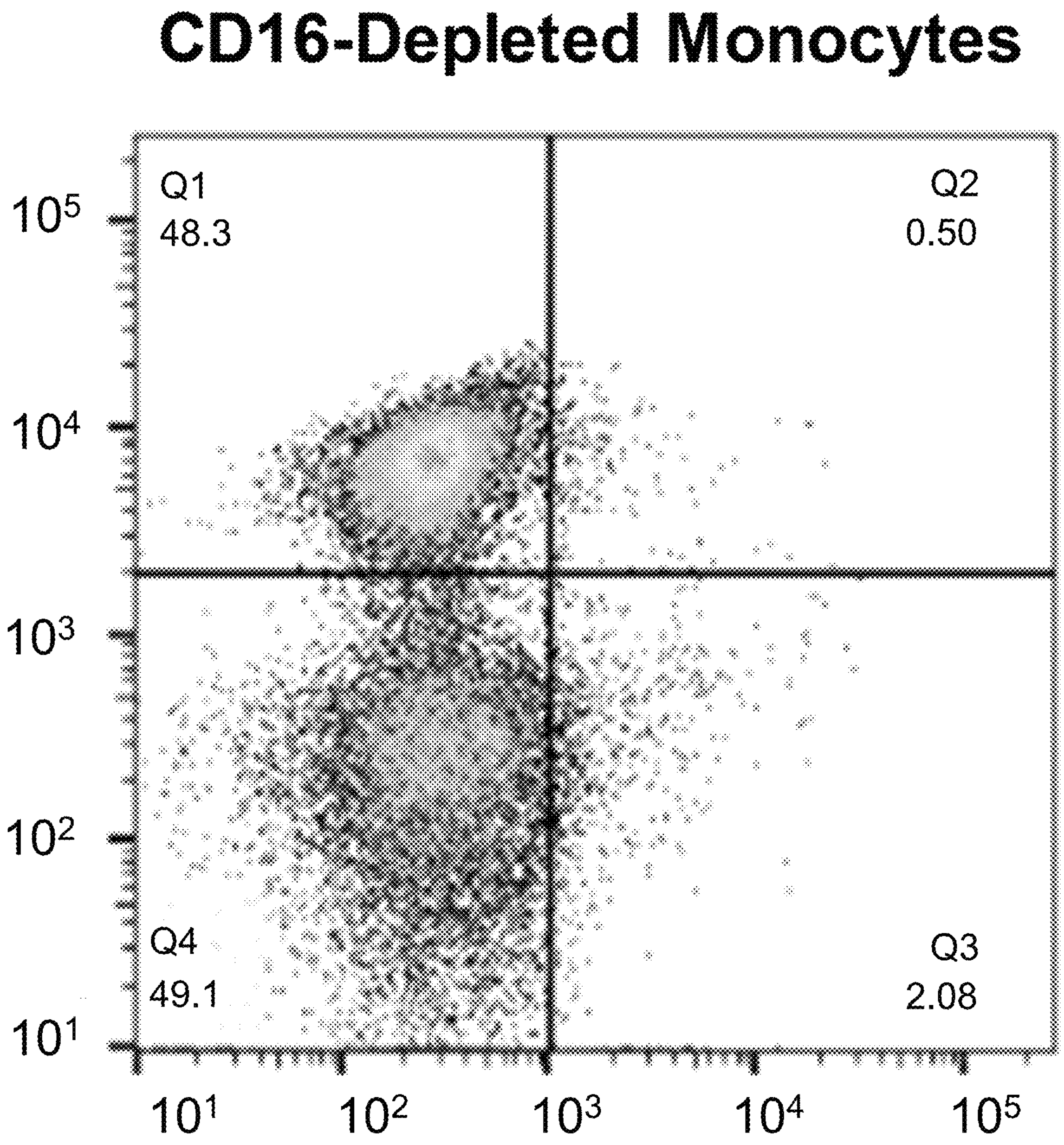

FIG. 2 demonstrates efficient depletion of CD3+ cells and enrichment of monocytes, and diminished levels of CD14 positive cells in the CD16-depleted monocytes post isolation.

Example 30: Cancer Cell-Killing Activity of the Fc-Mutant Tumor Cell Targeted Her2 ADC in In Vitro Co-Cultures of PBMCs and STING Wild Type or Knock Out SKBR3 Cells Generation of STING knock out single cell clones expressing nuclear restricted mKate fluorescent protein: SKBR3 cells were seeded in 24 well plates (50,000/well) and transfected with a non-targeting sgRNA and three different sgRNAs targeting the human STING gene using the TrueGuide™ Synthetic gRNA, TrueCut™ Cas9 Protein v2, and Lipofectamine™ CRISPMAX™ Transfection Reagent from Thermo Fisher according to the manufacturer's protocol. sgRNA sequences were: sgNT (non-targeting): AAAUGUGAGAUCAGAGUAAU; sg #3: TACTCCCTCCCAAATGCGGT; sg #4: CTCGCAGGCACTGAACATCC; and sg #5: GTTAAACGGGGTCTGCAGCC. Seven days post transfection, single cells were sorted in 96-well plates containing 100 μL of DMEM with 20% FBS and 1% penicillin/streptomycin and clones were formed in 2-3 weeks (media was refreshed once-twice a week). Multiple clones were trypsinized and expanded to analyze STING expression by Western blots using rabbit monoclonal anti-STING (Cell Signaling Technologies) and anti-β-Actin (Licor) antibodies. The clones with no STING protein expression (as determined by Western blots) were selected to stably express the nuclear restricted mKate fluorescent protein as described in Example 28.

Killing assay: STING wild type (sgNT-2: Non-targeting sgRNA, clone 2) and knock out (sg #3-2: sgRNA #3 clone 2) SKBR3 cells expressing NucRed were seeded in 96 well plates (15,000/well) in RPMI with 10% FBS and 1% penicillin/streptomycin and the PBMC killing assay was performed as described in Example 29 using Conjugate 8a-3, Conjugate 8j. Conjugate 8c-2, and Compound 1 each at 100, 25, 5 and 1 nM (conjugate concentrations were based on the payload).

Figure 3A:
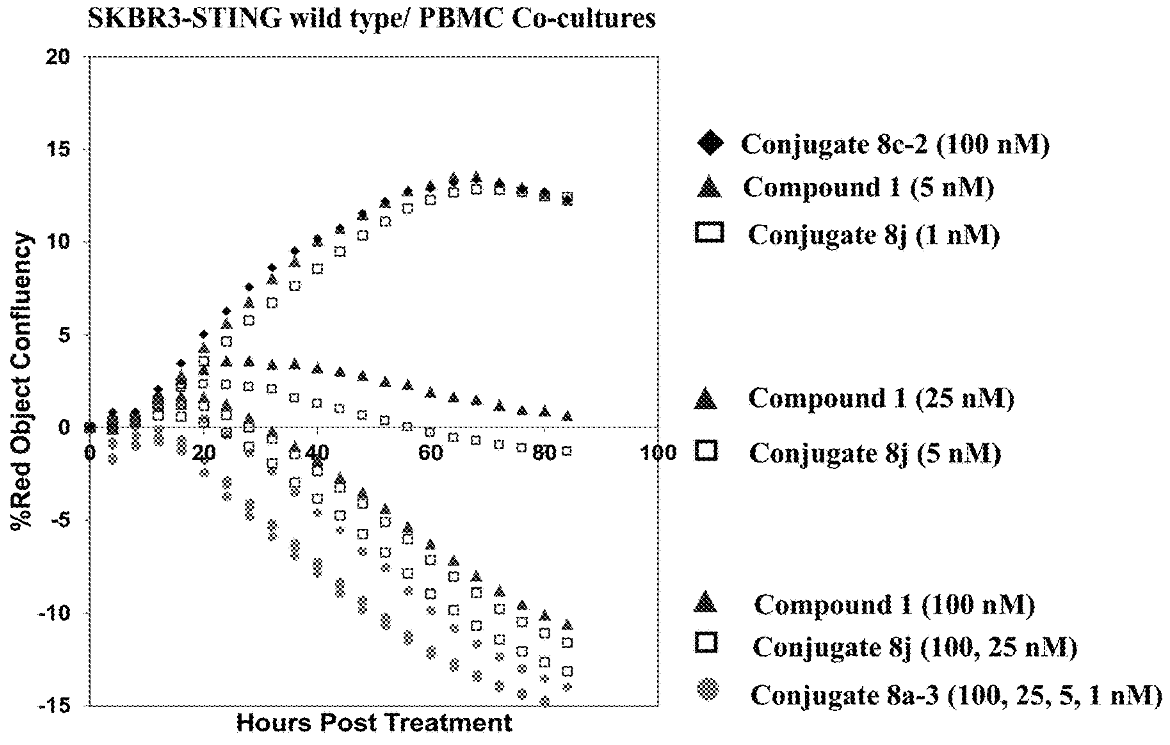
FIG. 3A and FIG. 3B plot the red object confluency as a function of time and show the killing of STING wild type (sgNT-2) and knock out (sg #3-2) SKBR3 NucRed cells respectively by PBMCs for Conjugate 8a-3, Conjugate 8j, Conjugate 8c-2, and Compound 1 each at 100, 25, 5 and 1 nM (conjugate concentrations were based on the payload).
Figure 3B:
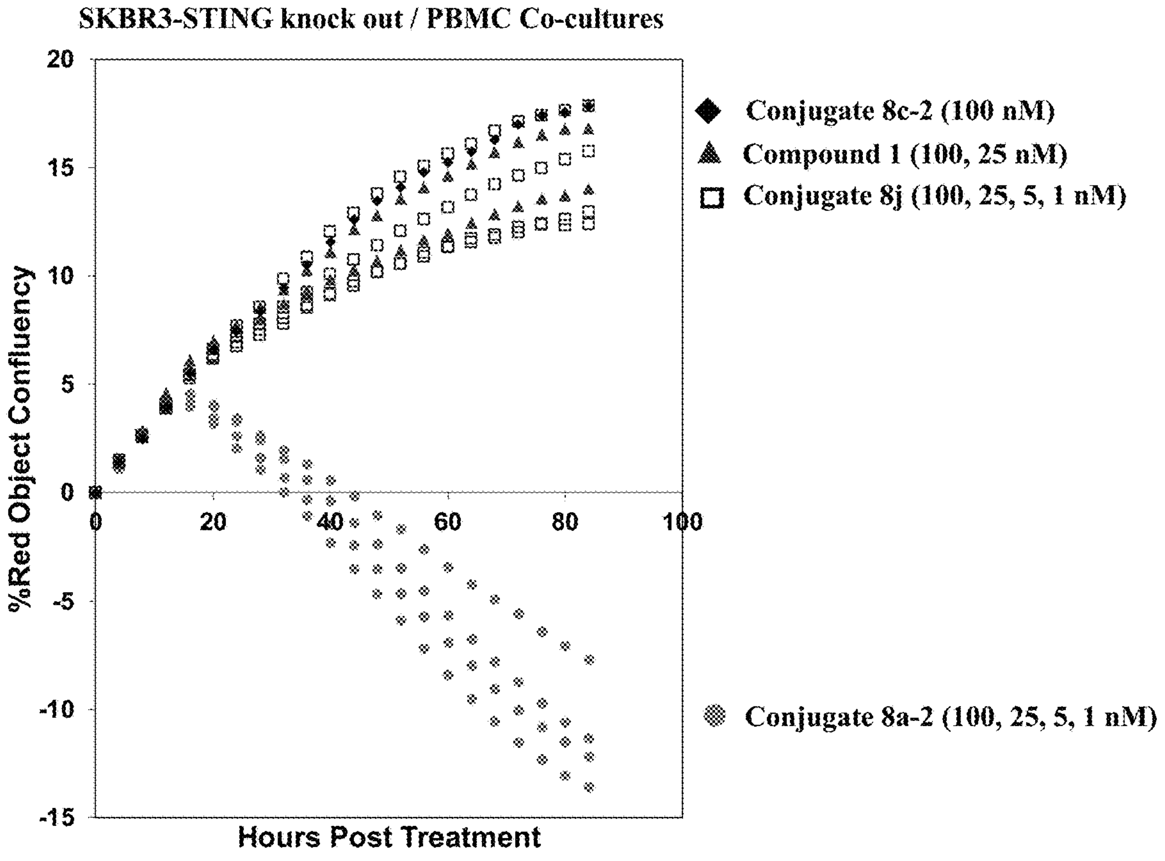

FIG. 3A and FIG. 3B plot the red object confluency as a function of time and shows the killing of STING wild type (sgNT-2) SKBR3 cells/PBMC co-cultures and knock out (sg #3-2) SKBR3 cells/PBMC co-cultures respectively. Conjugate 8a-3 induced robust killing of both STING wild type and knock out SKBR3 cells/PBMC cocultures at all doses tested. Conjugate 8j had high activity at 100, 25, and 5 nM in STING wild type (sgNT-2) SKBR3 cells/PBMC co-cultures and low activity in the STING knock out (sg #3-2) SKBR3 cells/PBMC co-cultures. Compound 1 showed activity in STING wild type (sgNT-2) SKBR3 cells/PBMC co-cultures at 100 nM only and no activity in the STING knock out (sg #3-2) SKBR3 cells/PBMC co-cultures at all doses. Conjugate 8c-2, did not have any activity in either STING wild type (sgNT-2) SKBR3 cells/PBMC co-cultures or STING knock out (sg #3-2) SKBR3 cells/PBMC co-cultures.

Figure 4A:
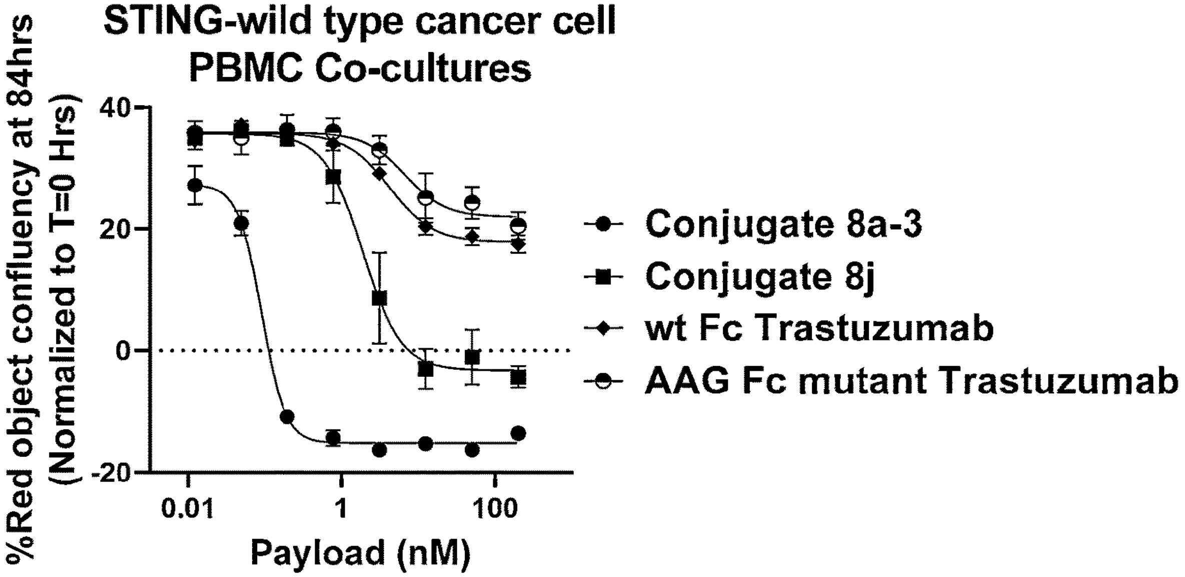
FIG. 4A plots the red object confluency as a function of the dose response of Conjugate 8a-3, Conjugate 8-j, wild type Fc Trastuzumab and AAG Fc mutant Trastuzumab for the STING wild type SKBR3 cancer cell killing activity in SKBR3 cancer cell/PBMC co-cultures.
Figure 4B:
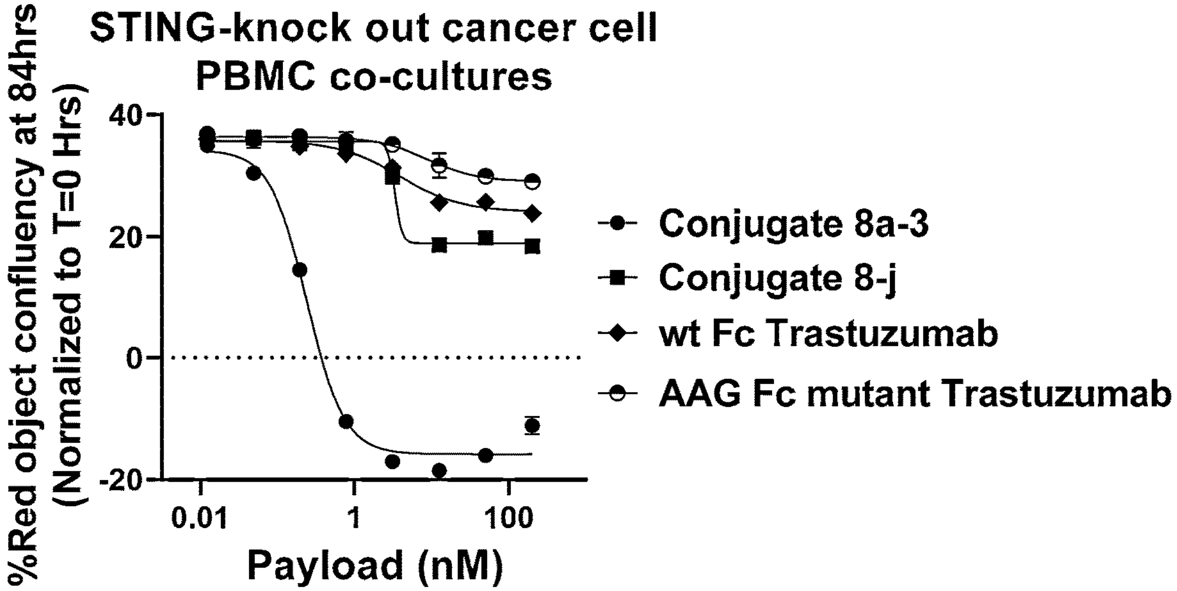
FIG. 4B plots the red object confluency as a function of the dose response Conjugate 8a-3, Conjugate 8-j, wild type Fe Trastuzumab and AAG Fe mutant Trastuzumab for the STING knock out SKBR3 cancer cell killing activity in SKBR3 cancer cell/PBMC co-cultures.

Example 30A: Activity of Tumor Cell Targeted Her2 ADC and Her2 Antibody in STING Wild Type or STING Knock Out SKBR3 Cancer Cell/PBMC Co-Cultures STING wild type (sgNT-2: non-targeting sgRNA, clone 2) and knock out (sg #3-2: sgRNA #3 clone 2) SKBR3 cells expressing NucRed were co-cultured with PBMCs and killing assay was performed as described in Example 30 using a dose range of Conjugate 8a-3, Conjugate 8-j (200 nM based on payload, 4×dilution). Unconjugated wild type Fc Trastuzumab and AAG Fc mutant Trastuzumab were dosed based on the antibody concentration corresponding to Conjugate 8a-3 antibody concentration. As shown in FIG. 4A and FIG. 4B Conjugate 8a-3 exhibited robust killing of both STING wild type and knock out SKBR3 cancer cells, whereas the Fc mutant Her2-targeted ADC, Conjugate 8-j showed killing activity only in the STING wild type SKBR3 co-cultures, which was nearly diminished in the STING knock out SKBR3 co-cultures. Both Fc wild type and AAG mutant unconjugated Trastuzumab antibodies showed low activity in both STING wildtype and knock out cancer cell co-cultures. These data demonstrates that the cancer cell killing activity of the Fc mutant cancer cell-targeted STING-ADC activity in immune cell co-cultures is contributed from the tumor cell-intrinsic STING activation.

Figure 5A:
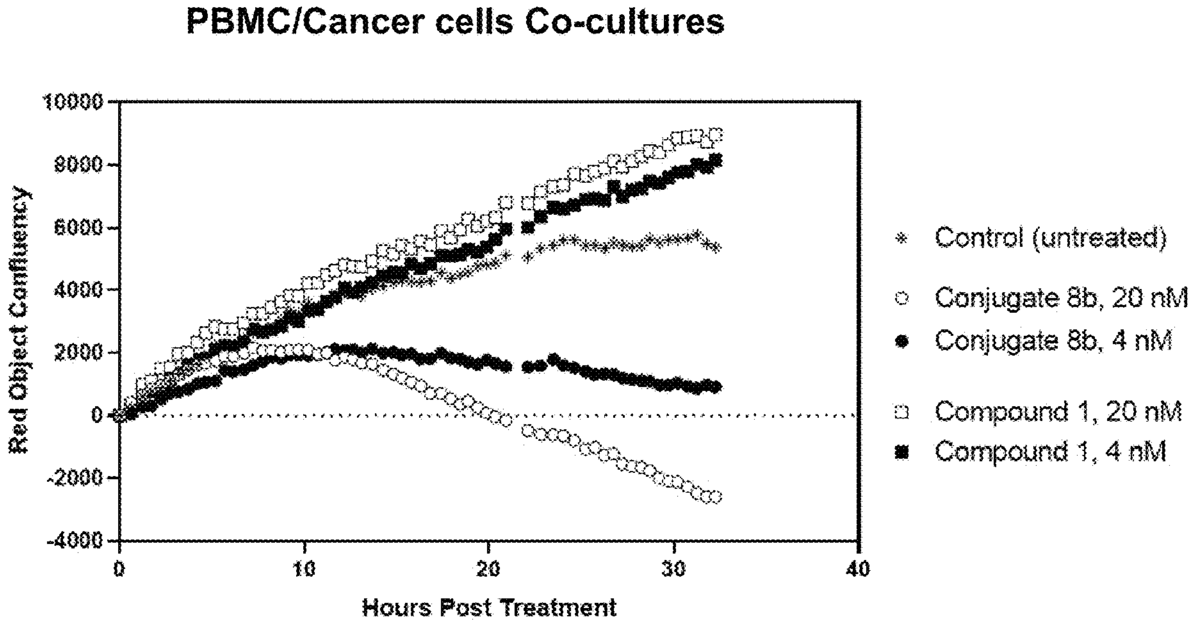
FIG. 5A plots the change of the red object confluency of OVCAR3-NucRed cancer cells as a function of time by PBMCs for Conjugate 8b-1 and Compound 1, both at 20 and 4 nM (conjugate concentration based on payload concentration).
Figure 5B:
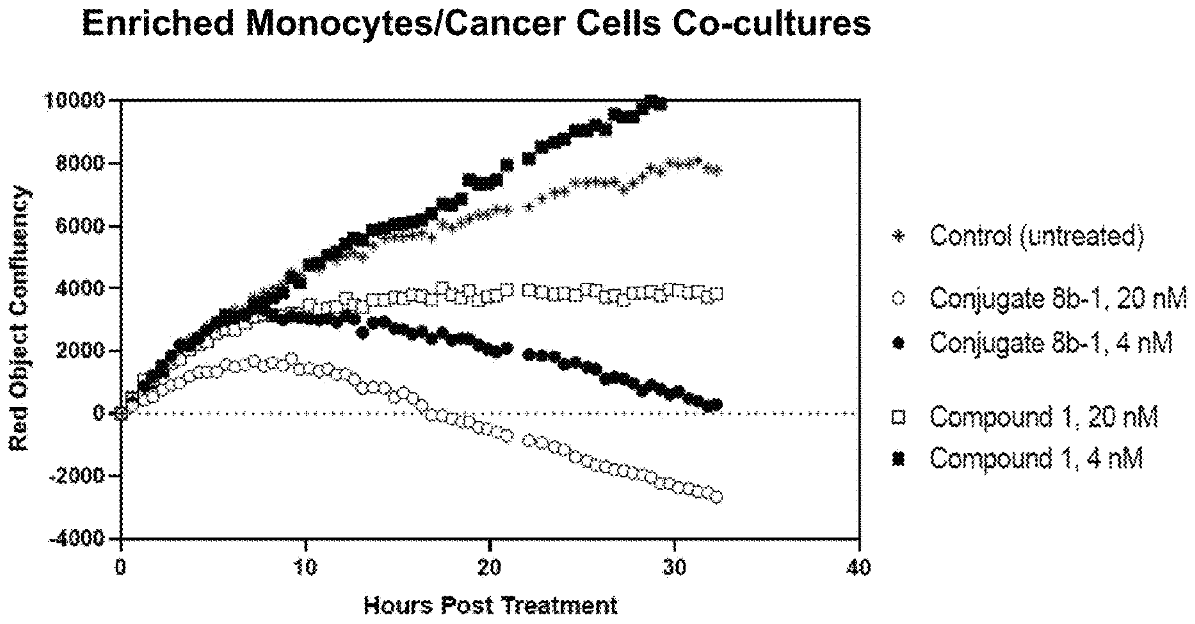
FIG. 5B plots the change of the red object confluency of OVCAR3-NucRed cancer cells as a function of time by enriched monocytes for Conjugate 8b-1 and Compound 1, both at 20 and 4 nM (conjugate concentration based on payload concentration).
Figure 5C:
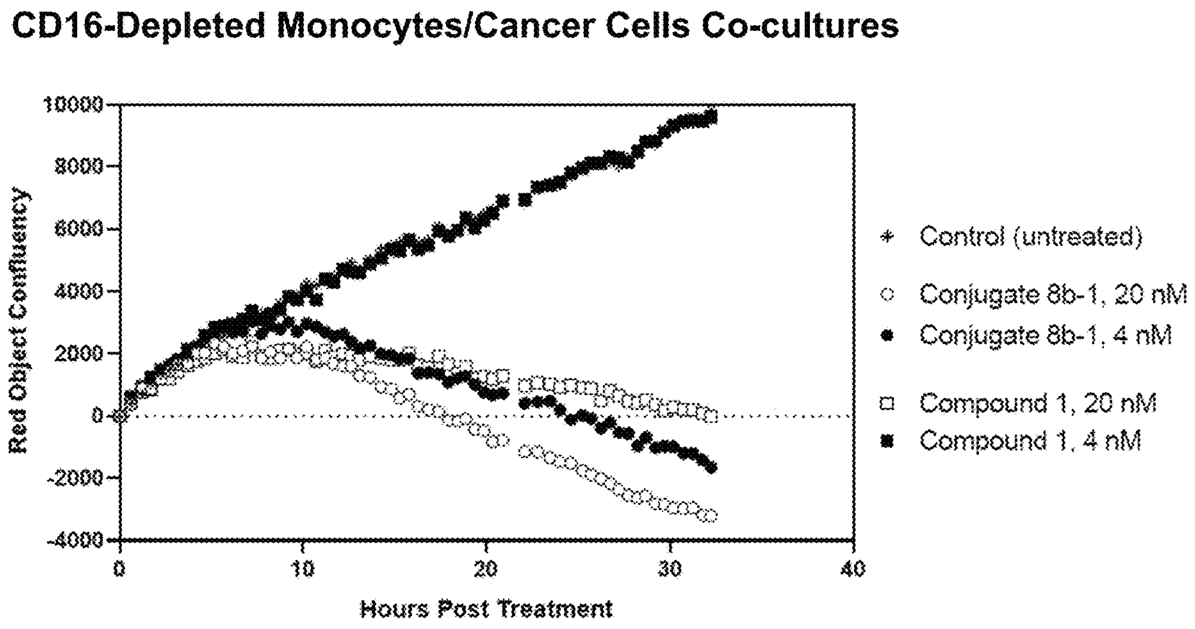
FIG. 5C plots the change of the red object confluency of OVCAR3-NucRed cancer cells as a function of time by CD16 depleted monocytes for Conjugate 8b-1 and Compound 1, both at 20 and 4 nM (conjugate concentration based on payload concentration).

Example 31: Activity of Tumor Cell Targeted NaPi2b ADC in Cancer Cell/Human Monocyte Co-Cultures in the Absence of T Cells OVCAR3-NucRed cells (generated as described in Example 28) were seeded (15,000/well) in 96-well CellBind surface tissue culture plates (Corning) and allowed to attach for 6 hours in RPMI-1640 medium with 10% FBS and 1% penicillin/streptomycin. Culture medium was replaced with fresh media (50 μL). Test articles (Conjugate 8b-1 and Compound 1, each at 20 and 4 nM, conjugate concentration based on payload concentration) were then added to each well in media (50 μL), and the plate was incubated for 20 min at 37° C. PBMCs, enriched monocytes, and CD16-depleted monocytes were prepared as described in Example 29. Live PBMCs (30,000/well), enriched monocytes (20,000/well), and CD16-depleted monocytes (20,000/well) were then added to the wells in culture medium (50 μL) and the plate was placed in an IncuCyte© live cell imaging instrument in an incubator (37° C., 5% 02) and scanned every 4 hours over 2 days. The number of red objects (cancer cells) were quantified using the IncuCyte© Zoom software. Red object confluency in each well was normalized to its own T=0 time point red object confluency. The red object confluency is plotted in FIGS. 5A to 5C as a function of time and shows that CD3+ T cell-depleted monocyte populations have comparable cancer cell killing activity in response to tumor cell-targeted ADC activity. Conjugate 8b-1, at 4 nM and 20 nM payload concentrations induced robust killing of OVCAR3-NucRed cancer cells by PBMCs (FIG. 5A), enriched monocytes (FIG. 5B), and CD16 depleted monocytes (FIG. 5C). Compound 1 at 20 nM induced cancer cell killing only in enriched monocyte and CD16-depleted monocyte co-cultures.

Example 32: In Vitro Measurements of Human CXCL10 and Cell Binding of HER2 Targeted Antibody Drug Conjugates to HCC1954 Human Breast Cancer Cell Line HCC1954 breast cancer cells were grown to ~80-95% confluency in RPMI 1640 medium supplemented with FBS (10%) and penicillin/streptomycin (1%). Cells were harvested and added to wells of a 96-well flat bottom plate (40,000/well) and incubated overnight at 37° C., 5% $CO_2$. Cells were then treated with test HER2 antibody-drug conjugates (20 μL) as indicated in Table 4, at concentrations ranging between 1 μM and 10 μM, and incubated for 24 hours at 37° C., 5% $CO_2$. Plates were centrifuged (300 g, 5 minutes), the supernatants were collected (100 mL) and subjected to ELISA analysis for human CXCL10 (Human CXCL10/IP-10). Developed plates were read at $OD_{450}$ on a SpectraMax M5 plate reader. The values for each treatment were plotted, and $EC_{50}$ values calculated with GraphPad Prism software using a four-parameter curve fitting.

For the determination of cell binding of HER2 antibody-drug conjugates to HCC1954 cells were grown to ~80-95% confluency in RPMI 1640 medium supplemented with FBS (10%) and penicillin/streptomycin (1%). Cells were harvested and added to wells of a 96-well V bottom plate (50,000/well). The cells were pelleted (300×g, 5 minutes) and resuspended in solutions of test HER2 antibody-drug conjugates as indicated in Table 4 at concentrations ranging between 0.01 nM and 100 nM and incubated on ice for 3 hours. Cells were then washed in ice cold PBS (3×), pelleted (300 g, 5 minutes), and incubated with detection antibody (Goat Anti Human IgG-Alexa-647 (H+L chain) for 1 hour at 4° C. Cell suspensions were pelleted (300 g, 5 minutes), washed 3 times in ice cold PBS, and fixed by resuspending in solution of paraformaldehyde (2%). Resuspended cells were then subjected to flow cytometry analysis on a MACS Quant Flow Cytometry. Single events (10,000) were collected for analysis. Population gating and Mean Fluorescent Intensity (MFI) analysis was performed with FlowJo Software.

Table 4 summarizes the mean $EC_{50}$ values for cell binding and CXCL10 induction in HCC1954.

TABLE 4

| Test Articles | DAR | CXCL10 ELISA $EC_{50}$ (nM) | Cell Binding $EC_{50}$ (nM) |
|---|---|---|---|
| Conjugate 25 | 6.6 | 0.13 | ND |
| Conjugate 45 | 6.5 | 0.17 | ND |
| Conjugate 8-2 | 6.8 | 0.51 | ND |
| Conjugate 28 | 6 | 0.16 | 1.0 |
| Conjugate 29 | 5.5 | 0.18 | ND |
| Conjugate 62 | 6.5 | 0.20 | ND |
| Conjugate 64 | 6.4 | 0.22 | ND |
| Conjugate 58 | 6.5 | 2.3 | ND |
| Conjugate 74 | 6.9 | 3.4 | ND |
| Conjugate 78 | 7.4 | 2.7 | ND |
| Conjugate 28 | 6 | 0.16 | 1.0 |
| Conjugate 82 | 5.7 | 0.17 | ND |
| Conjugate 52 | 7.7 | 0.12 | 2.3 |
| Conjugate 50-1 | 7.7 | 0.13 | ND |
| Conjugate 66-2 | 5.3 | 1.38 | ND |
| Conjugate 32-1 | 6.5 | 1.23 | 2.4 |

ND = Not Determined

As shown in Table 4, treatment of HCC1954 cells with Her2 targeted antibody-drug conjugates resulted in sub- to low nanomolar $EC_{50}$ values for induction of CXCL10. Where determined, $EC_{50}$ values for binding of Her2 targeted ADCs to HCC1954 cells were also in the low nanomolar range.

Example 33: Activity of Tumor Cell Targeted HER2 Antibody Drug Conjugates in Cancer Cell/PBMC Co-Cultures Cancer cell killing activity: SKBR3 human breast cancer cells stably expressing the nuclear-restricted mKate fluorescent protein were generated as described in Example 28A and designated as SKBR3 NucRed cells. 20,000 cells (per well) SKBR3 NucRed cells were seeded in 96-well tissue culture plates and allowed to attach 6 hours in 50 μL of RPMI-1640 medium with 10% FBS and 1% penicillin/streptomycin. A range of dilutions (0.0.1 nM to 200 nM based on payload; 4-fold serial dilutions in growth medium) of the 50 μL test articles (Conjugate 8a-2, Conjugate 8-j, Conjugate 8c-2 and Compound 1) were added to each well and the plate was incubated for 20 min at 37° C. PBMCs or primary human monocytes (isolated from PBMCs as described in Example 29) (50,000) were then added to each well and the assay was performed as described in Example 28. Table 5 shows the $IC_{50}$ values (killing activity) of the test articles in cancer cell/PBMC and isolated primary human monocyte co-cultures (cancer cell killing activity).

TABLE 5

| Test Article | Conjugate 8a-2 | Conjugate 8-j | Conjugate 8c-2 | Compound 1 |
|---|---|---|---|---|
| $IC_{50}$ (nM) - PBMC | 0.03 | 0.91 | NA | 9.51 |
| $IC_{50}$ (nM) - Monocyte | 0.05 | 1.6 | NA | 8.32 |

As shown in Table 5, Conjugate 8a-2 exhibited ~300× and ~150× greater potency compared to Compound 1 in PBMC and monocyte co-cultures, respectively. The potency of Conjugate 8-j was ~30× and 80× lower relative to Conjugate 8a-2 in PBMC and monocyte co-cultures respectively. Conjugate 8c-2 had minimal activity in both PBMC and monocyte co-cultures.

CXCL10 induction: Table 6 shows the $EC_{50}$ values of the test articles in cancer cell/PBMC and isolated primary human monocyte co-cultures for CXCL10 induction.

TABLE 6

| Test Article | Conjugate 8a-2 | Conjugate 8-j | Conjugate 8c-2 | Compound 1 |
|---|---|---|---|---|
| $EC_{50}$ (nM) - PBMC | 0.06 | 2.35 | NA | 26.13 |
| $EC_{50}$ (nM) - Monocyte | 0.04 | 2.05 | NA | 31.10 |

As shown in Table 6, Conjugate 8a-2 exhibited ~400× and ~700× greater potency for CXCL10 induction compared to the Compound 1 in PBMC and monocyte co-cultures, respectively. The potency of Conjugate 8-j was ~50× lower relative to Conjugate 8a-2 in both PBMC and monocyte co-cultures. Conjugate 8c-2 had minimal activity in both PBMC and monocyte co-cultures.

Type III IFN induction: Co-cultures of SKBR3 cells and PBMCs were setup as described above to analyze the induction of Type III Interferons in supernatants 24 hours post treatment using a human IL29/IL28b ELISA kit. Table 7 shows the $EC_{50}$ values of the test articles in cancer cell/PBMC co-cultures for IL29/IL28b induction (IFNλ1/λ3).

TABLE 7

| Test Article | Conjugate 8a-2 | Conjugate 8-j | Conjugate 8c-2 | Compound 1 |
|---|---|---|---|---|
| $EC_{50}$ (nM) - PBMC | 0.08 | 0.54 | NA | 28.30 |

As shown in Table 7, Conjugate 8a-2 exhibited ~400× greater potency for IL29/IL28b induction compared to the Compound 1 in PBMC co-cultures. The potency of Conjugate 8-j was ~6× lower relative to Conjugate 8a-2 in PBMC co-cultures. Conjugate 8c-2 had minimal activity in PBMC co-cultures The data in Tables 7-9, demonstrates that mutation in the Fc region of ADC that abrogates FcγR interactions reduces but does not eliminate the cancer cell killing activity of the targeted ADC thereby suggesting an Fc-independent contribution of the ADC.

Example 34: Induction of STING Pathway in Immune Cells

The induction of STING pathway in immune cells by Her2-targeted STING ADC was evaluated by a cancer cell/THP1-IRF3-Luciferase reporter cell co-culture assay. SKOV3 human ovarian adenocarcinoma cells were seeded in 96-well CellBind surface tissue culture plates (20,000/well) and allowed to attach for 6 hours in McCoy's 5a medium with 10% FBS and 1% penicillin/streptomycin. A range of dilutions (0.01 nM to 300 nM based on payload; 4-fold serial dilutions in growth medium) of the test articles Conjugate 32-5, Conjugate 32e and Compound 30 were added to each well and the plate was incubated for 20 min at 37° C. 50,000 THP1-dual reporter cells were then added to each well and the incubation continued for 20 hours at 37° C. in a humidified atmosphere of 5% $CO_2$. Cell culture supernatants (20 μL) from each incubated sample was added to resuspended QUANTI-Luc (50 μL) and the luminescent signal for IRF3 was measured immediately using a SpectraMax M5 plate reader (Molecular Devices). The $EC_{50}$ value was determined from the dose response curve. Table 8 provides the $EC_{50}$ values in THP1-Dual cells co-cultured with SKOV3 cancer cells.

TABLE 8

| Test Article | Conjugate 32-5 | Conjugate 32e | Compound 30 |
|---|---|---|---|
| $EC_{50}$ (nM) | 0.78 | NA | 38.51 |

As shown in Table 8, treatment of SKOV3 and THP-1 co-cultures with Her2-targeted ADCs resulted in subnanomolar to low nanomolar $EC_{50}$ values for induction of STING pathway in the THP-1 immune cells.

Example 35: Activity of Tumor Cell Targeted HER2 Antibody Drug Conjugates in Cancer Cell/PBMC Co-Cultures CXCL10 induction: Calu3 human lung adenocarcinoma cells were seeded in 96-well tissue culture plates and allowed to attach overnight at 37° C., 5% $CO_2$ in 100 µL of EMEM medium with 10% FBS and 1% penicillin/streptomycin. Culture medium was replaced with fresh media (100 µL). A range of dilutions (0.0.1 nM to 200 nM based on payload; 4-fold serial dilutions in growth medium) of the 50 µL test articles (Conjugate 32-4, Compound 30 and Conjugate 32b-1 were added to each well and the assay was performed as described in Example 33-CXCL10 induction. Table 9 shows the $EC_{50}$ values of the test articles in cancer cell/PBMC and cancer cell monocultures for CXCL10 induction.

TABLE 9

| Test Article | Conjugate 32-4 | Compound 30 | Conjugate 32b-1 |
|---|---|---|---|
| $EC_{50}$ (nM) - PBMC | 0.06 | 160.20 | NA |

As shown in Table 9, Conjugate 32-4 exhibited subnanomolar potency compared to Compound 30 in cancer cell/PBMC co-cultures and monocultures respectively. Conjugate 32b-1 had minimal activity in both cancer cell/PBMC co-cultures and monocultures.

Example 36: Activation of the STING Pathway in Cancer Cell Monocultures in the Presence of Conditioned Media from Untreated Immune Cell Cultures Conditioned media was prepared by culturing 1.5×10$^6$/mL PBMCs (two different donors), 1×10$^6$/mL primary monocytes (isolated from PBMCs from two different donors, as described in Example 29), or 1×10$^6$/mL THP1 cells in RPMI-1640 medium with 10% FBS and 1% penicillin/streptomycin for 24 hours at 37° C., 5% $O_2$, in an incubator. The supernatants were collected and spun down at 2000 rpm for 10 min to remove any cells. SKOV3 cells were seeded in 96 well plates (30,000/well) and allowed to attach overnight in RPMI-1640 medium with 10% FBS and 1% penicillin/streptomycin. Culture medium was replaced with either 100 µL/well of fresh media (control) or conditioned media from untreated immune cells followed by the addition of Compound 1 (50 µL/well, 100 nM final concentration) or control media (no treatment) to each well. After incubation for 24 hours at 37° C., 5% $O_2$ supernatants from the 96 well plates were analyzed for CXCL10 production using a human CXCL10 ELISA kit. Table 10 shows the O.D. 450 values for CXCL10 produced by the SKOV3 cancer cell monocultures.

TABLE 10

| Conditioned Media | O.D. 450 Control (No STING agonist treatment) | O.D. 450 + 100 nM Compound 1 |
|---|---|---|
| None | 0.02 +/− 0.028 | 0.16 +/− 0.038 |
| PBMC (Donor1) | 0.47 +/− 0.058 | 2.22 +/− 0.084 |
| PBMC (Donor2) | 0.13 +/− 0.019 | 0.83 +/− 0.086 |
| Monocyte (Donor1) | 0.04 +/− 0.010 | 1.62 +/− 0.050 |
| Monocyte (Donor2) | 0.21 +/− 0.018 | 0.97 +/− 0.142 |
| THP1 | 0.00 +/− 0.007 | 0.18 +/− 0.043 |

As shown in Table 10, SKOV3 cells responded to STING agonist treatment in monocultures only in the presence of conditioned media from PBMCs and primary human monocytes but not from THP1 cells, thereby suggesting that PBMCs or primary human monocytes secrete factors that can sensitize cancer cells to STING agonist treatment.

Example 37: Tumor Growth Response to Administration of HER2 Antibody-Drug Conjugate in SKOV3

Female CB.17 SCID mice were inoculated subcutaneously with SKOV3 human ovarian cancer cells (10×10$^6$ cells per mouse). Animals were randomized into treatment groups when tumor volumes were between 63-75 mm$^3$ (mean=65.4 mm$^3$/group) (n=10/group). Vehicle, Trastuzumab (3/0 mg/kg), diABZI STING agonist (0/5 mg/kg), Conjugate 8c-1 (1/0.04 mg/kg or 3/0.12 mg/kg), or Conjugate 8a-1 (1/0.03 mg/kg or 3/0.09 mg/kg) were dosed intravenously as a single dose on day 1 (all doses are given by antibody/payload). Transient body weight loss, within acceptable limits, was observed 2-3 days following treatment, with no additional clinical observations, for diABZI STING agonist (0/5 mg/kg) and Conjugate 8c-1 (3/0.12 mg/kg). Body weight loss at later time-points correlated with tumor progression, indicating tumor model-induced cachexia.

Figure 6:
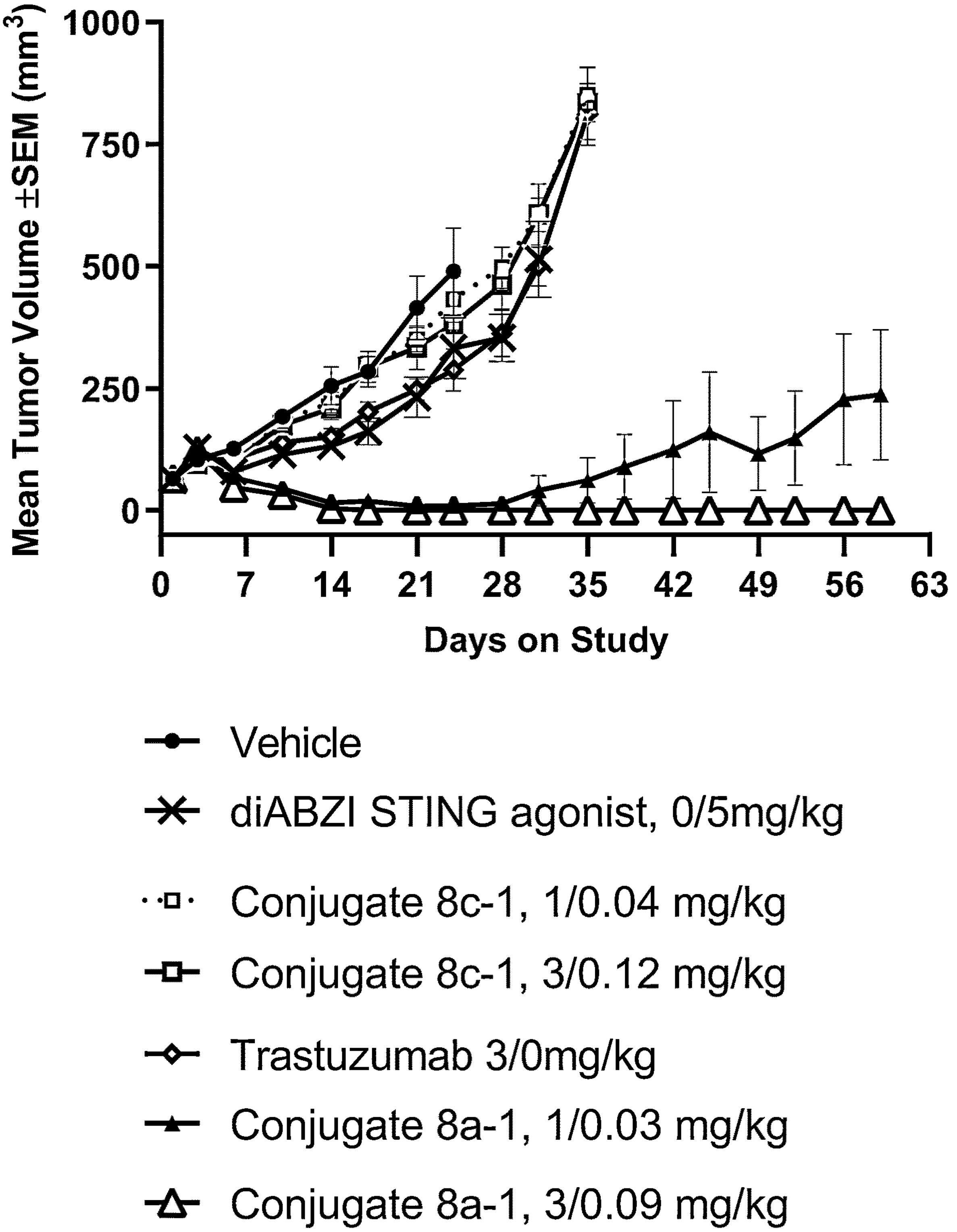
FIG. 6 is a graph showing the anti-tumor efficacy of Trastuzumab (3/0 mg/kg), diABZI STING agonist (0/5 mg/kg), Conjugate 8c-1 (1/0.04 mg/kg or 3/0.12 mg/kg), Conjugate 8a-1 (1/0.03 mg/kg or 3/0.09 mg/kg) (all doses are given by antibody/payload) in a SKOV3 xenograft model in mouse.
Figure 7A:
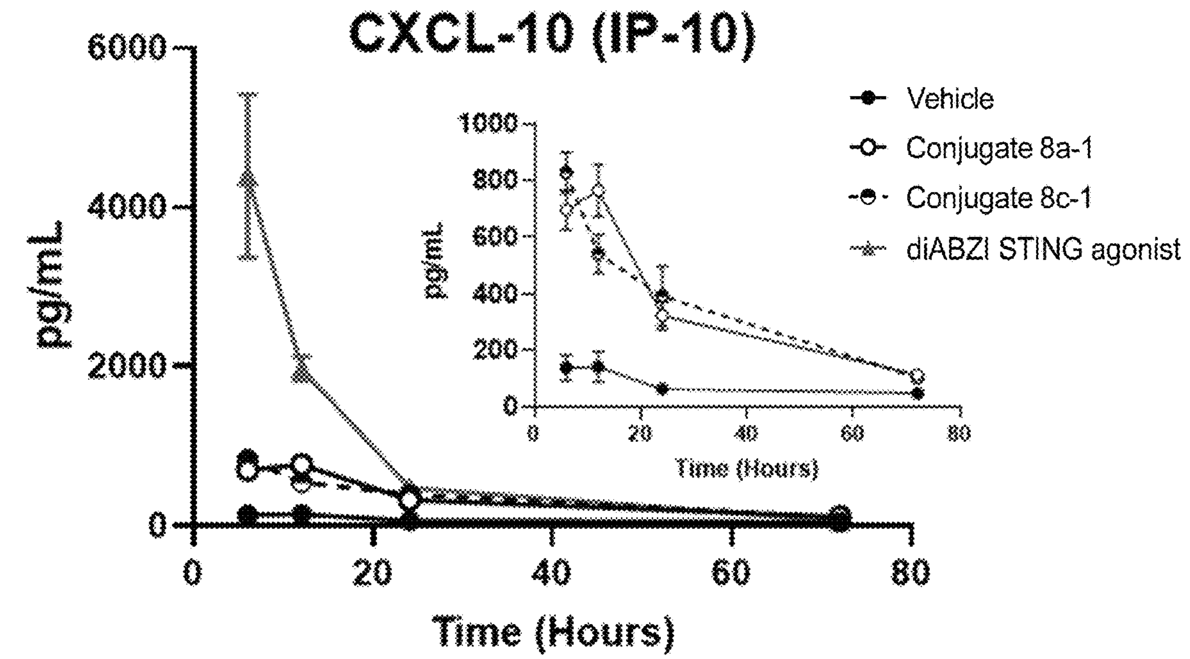
FIGS. 7A-7H show cytokines levels for murine CXCL-10 (IP-10.
Figure 7B:
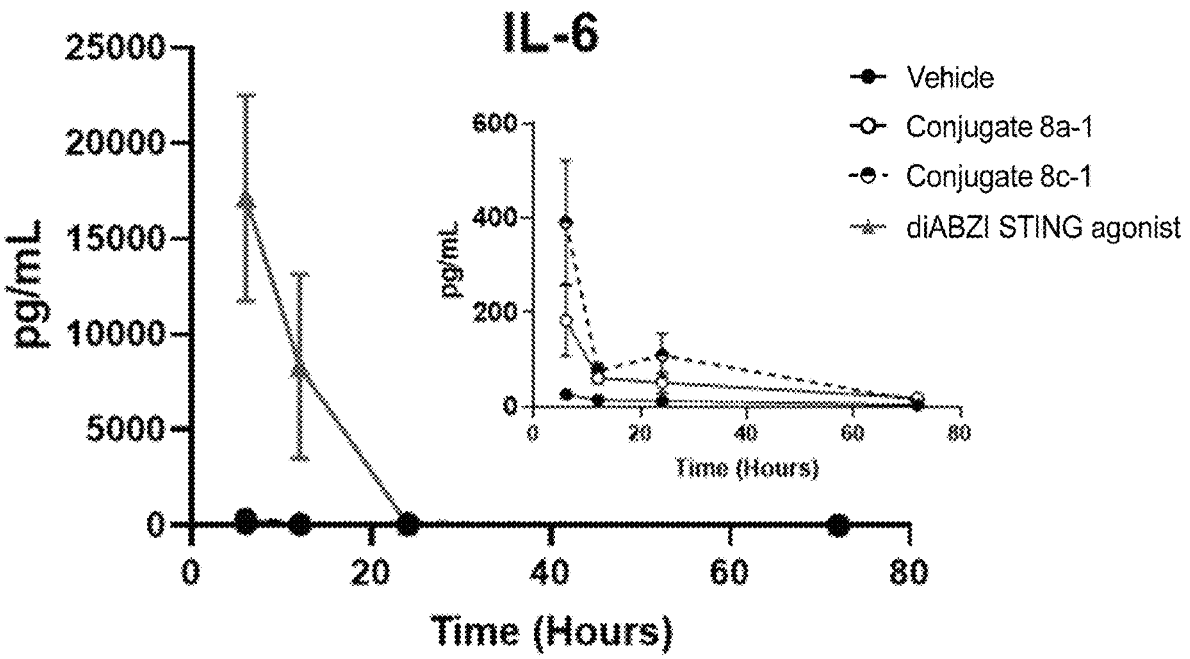
Figure 7C:
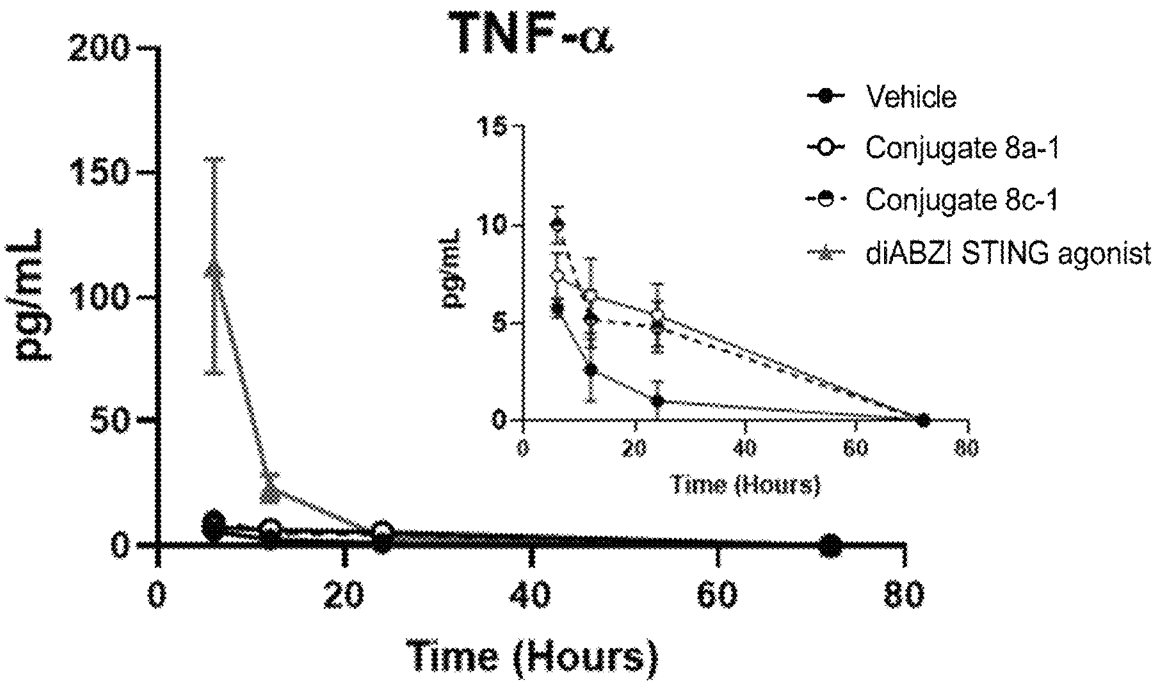
Figure 7D:
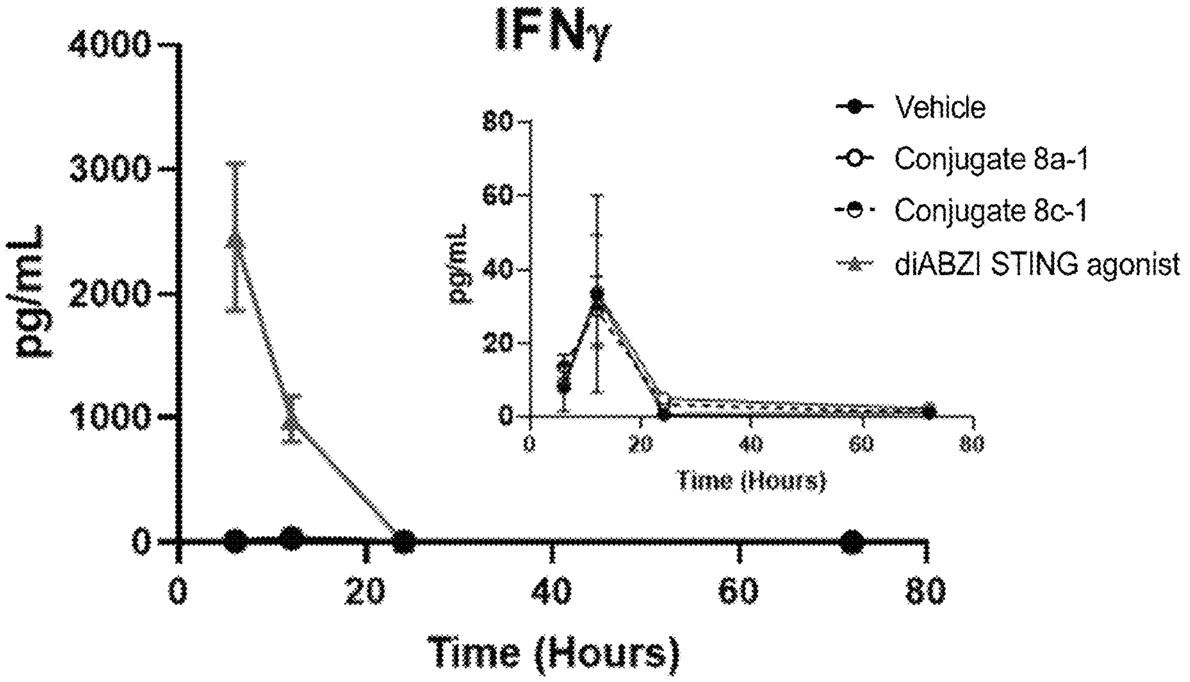
Figure 7E:
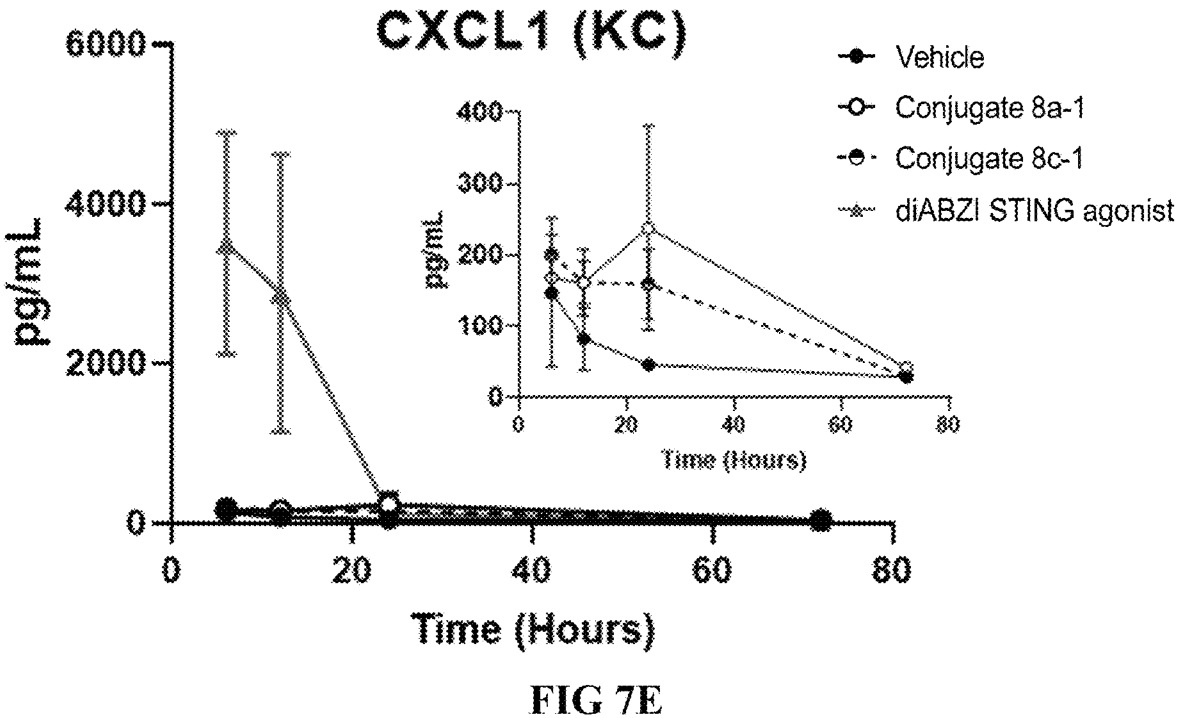
Figure 7F:
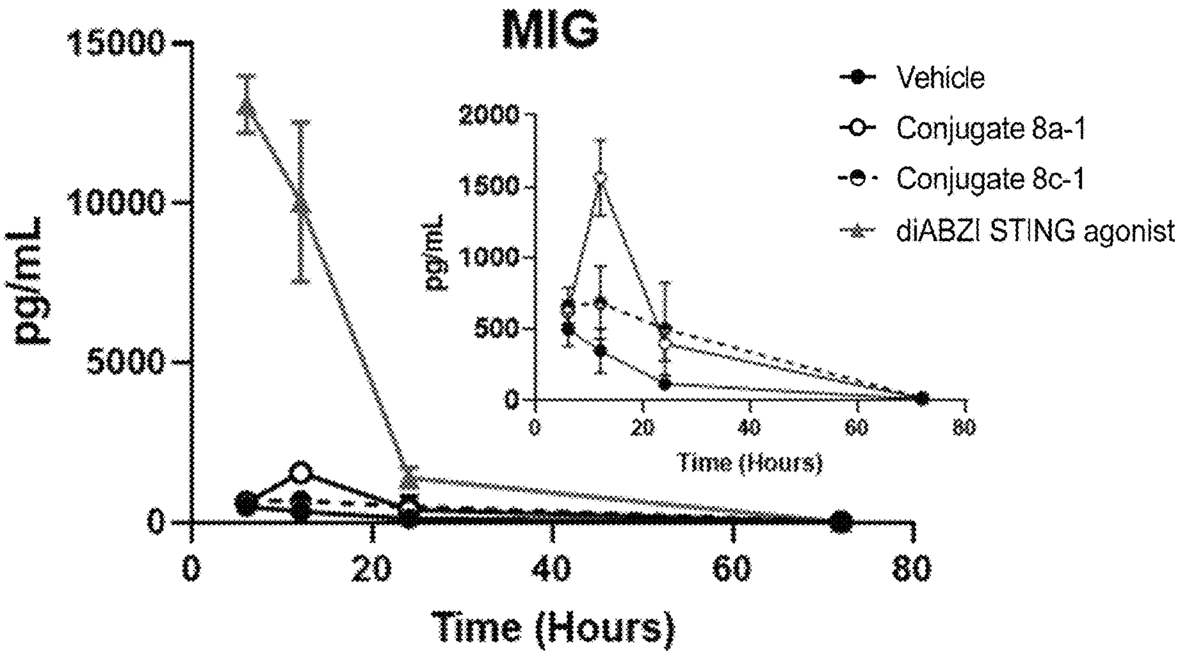
Figure 7G:
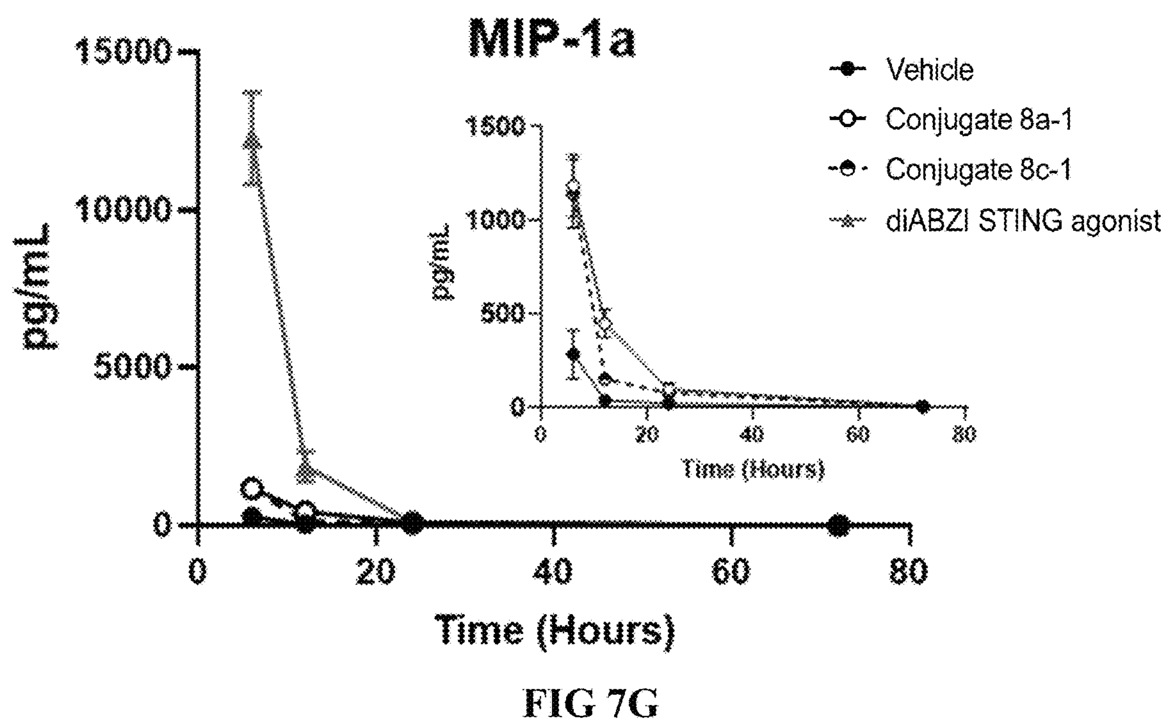
Figure 7H:
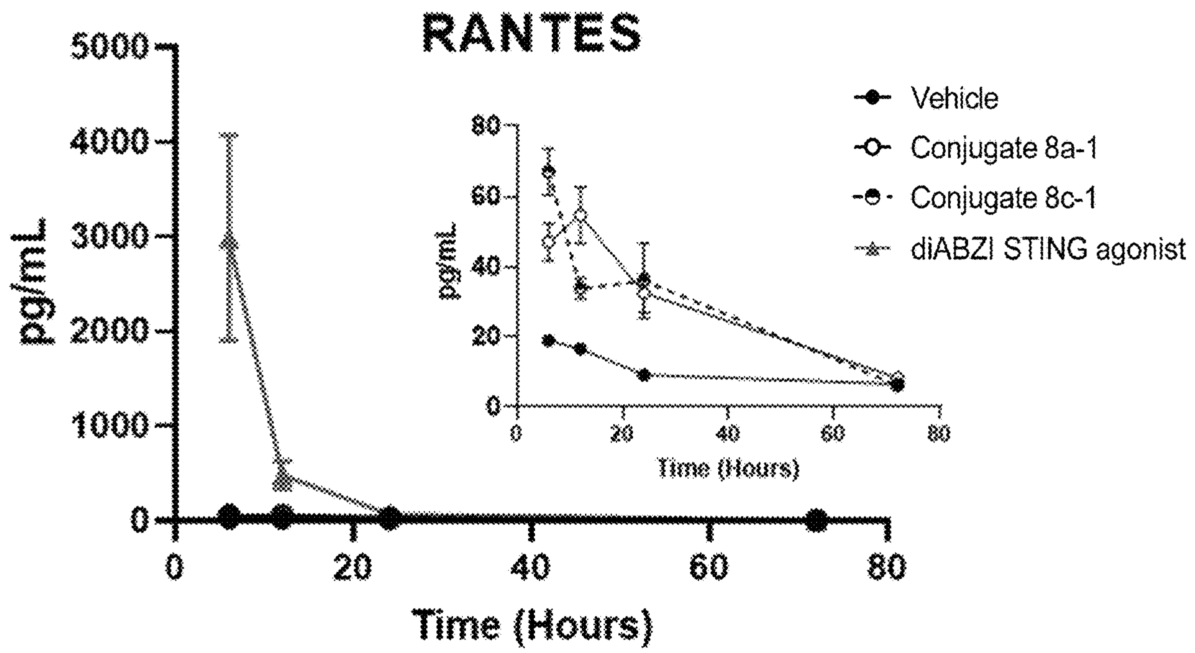

FIG. 6 provides the results for the tumor volumes of SKOV3 tumor-bearing mice treated with Trastuzumab, diABZI STING agonist, Conjugate 8c-1, Conjugate 8a-1 or vehicle. Treatment with Trastuzumab (3/0 mg/kg), diABZI STING agonist (0/5 mg/kg) or Conjugate 8c-1 (1/0.04 mg/kg or 3/0.12 mg/kg) resulted in 47.5, 36.9, 13.5 or 25.5% TGI, respectively. Treatment with Conjugate 8a-1 (1/0.03 mg/kg or 3/0.09 mg/kg) resulted in 86.5 and 100% tumor regression, respectively.

Example 38: Serum Cytokines Following Administration of HER2 Antibody-Drug Conjugate in SKOV3

Female CB.17 SCID mice were inoculated subcutaneously with SKOV3 human ovarian cancer cells (10×10$^6$ cells per mouse). Animals were randomized into treatment groups when tumor volumes were between 108-172 mm$^3$ (mean=128-131.6 mm$^3$). Vehicle, diABZI STING agonist (0/5 mg/kg), Conjugate 8c-1 (3/0.12 mg/kg) or Conjugate 8a-1 (3/0.09 mg/kg) were administered intravenously on day 1 (all doses are given as antibody/payload, n=10 for each group). Serum was collected at 6, 12, 24, and 72 hours post-dose (n=5 per group) and snap-frozen on dry ice for serum cytokine analysis. Tumors were collected at 12 and 72 hours post-dose (n=5 for each time point) and processed into formalin-fixed paraffin embedded (FFPE) blocks.

Serum cytokines (Eotaxin, G-CSF, GM-CSF, IFNγ, IL-1α, IL-1β, IL-2, IL-3, IL-4, IL-5, IL-6, IL-7, IL-9, IL-10, IL-12 (p40), IL-12 (p70), IL-13, IL-15, IL-17, CXCL10 (IP-10), CXCL1 (KC), LIF, LIX, MCP-1, M-CSF, MIG, MIP-1α, MIP-10, MIP-2, RANTES, TNFα, and VEGF) were analyzed using mouse cytokine/chemokine magnetic bead panel on a FlexMap3D Luminex instrument. Belysa Immunoassay Curve Fitting Software was used for data analysis.

FIGS. 7A-7H provide measured cytokines as a function of time. Only cytokines with a measurable increase relative to vehicle control are shown (CXCL-10 (IP-10), IL-6, TNFα, IFNγ, CXCL1 (KC), MIG, MIP-1α and RANTES). Inserts in each plot show cytokine levels induced by Conjugate 8a-1 and Conjugate 8c-1 relative to vehicle. The intravenously administered diABZI STING agonist induced significantly higher levels of serum cytokines than Conjugate 8a-1 or Conjugate 8c-1, with fold differences as high as 100 fold for IL6 and as low as 6 fold for CXCL10. For most cytokines, there was no significant difference between control and targeted ADCs, and few cytokines showed difference between the vehicle control and the ADCs. Y-axis scales in the main plot and insert emphasize the difference between diABZI STING agonist and the rest of the treatments in this study.

Example 39A: PD Responses Following Administration of HER2 Antibody-Drug Conjugate in SKOV3

Six-week-old female CB.17 SCID were inoculated subcutaneously with SKOV3 human ovarian cancer cells (10×$10^6$ cells per mouse). Animals were randomized into treatment groups when tumor volumes were between 75-126 $mm^3$ (mean=94.5-96.7 $mm^3$/group). Vehicle, Conjugate 8c-1 (3/0.12 mg/kg) or Conjugate 8a-1 (3/0.09 mg/kg), Conjugate 8c-1 (3/0.12 mg/kg) or Conjugate 8a-1 (3/0.09 mg/kg) were administered intravenously on day 1 (all doses are given as antibody/payload, n=12 for each group). Serum was collected at 6, 12, 24, and 72 hours post-dose (n=6 for each group) and snap-frozen on dry ice for serum cytokine analysis (data not shown). Tumors were collected at 12 and 72 hours (n=6 for each group) and fixed in FFPE blocks for further processing.

For Real Time qPCR Analysis, RNA was extracted from the FFPE blocks using the Qiagen Rneasy FFPE kit. Samples were equalized based on nanodrop reading and cDNA produced using the Thermofisher SuperScript IV VILO Master Mix with exDNase Enzyme Gene expression assays for mouse CXCL10, interferon-beta, and IL-6 were set up with the TaqMan Fast Advanced Master Mix. ABI assays for mouse Interferon-β (IFNb), IL-6 and CXCL10 were used with GAPDH, and RPL30 as housekeepers. Levels of mRNA relative to GAPDH were calculated using $2^{-\Delta\Delta CT}$ method.

Figure 8A:
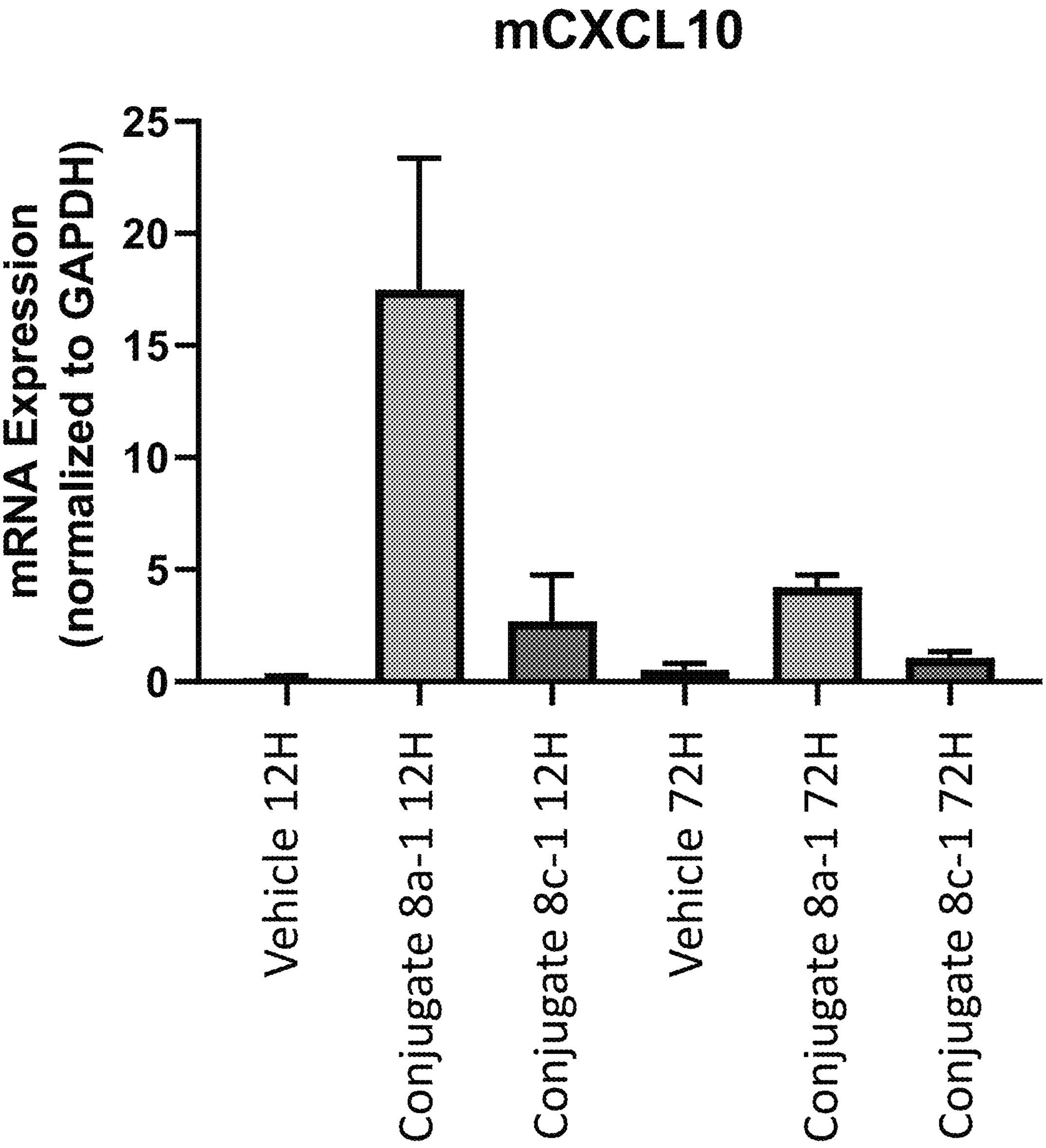
FIGS. 8A-8C show the levels of mouse CXCL10 (FIG. 8A), Interferon-β (FIG. 8B), and IL-6 (FIG. 8C) mRNA in a SKOV3 xenograft model in mouse at 12 h and 72 h following administration of Conjugate 8c-1 (3/0.12 mg/kg), Conjugate 8a-1 (3/0.09 mg/kg), Conjugate 8c-1 (3/0.12 mg/kg) or Conjugate 8a-1 (3/0.09 mg/kg) (all doses are written as antibody/payload).
Figure 8B:
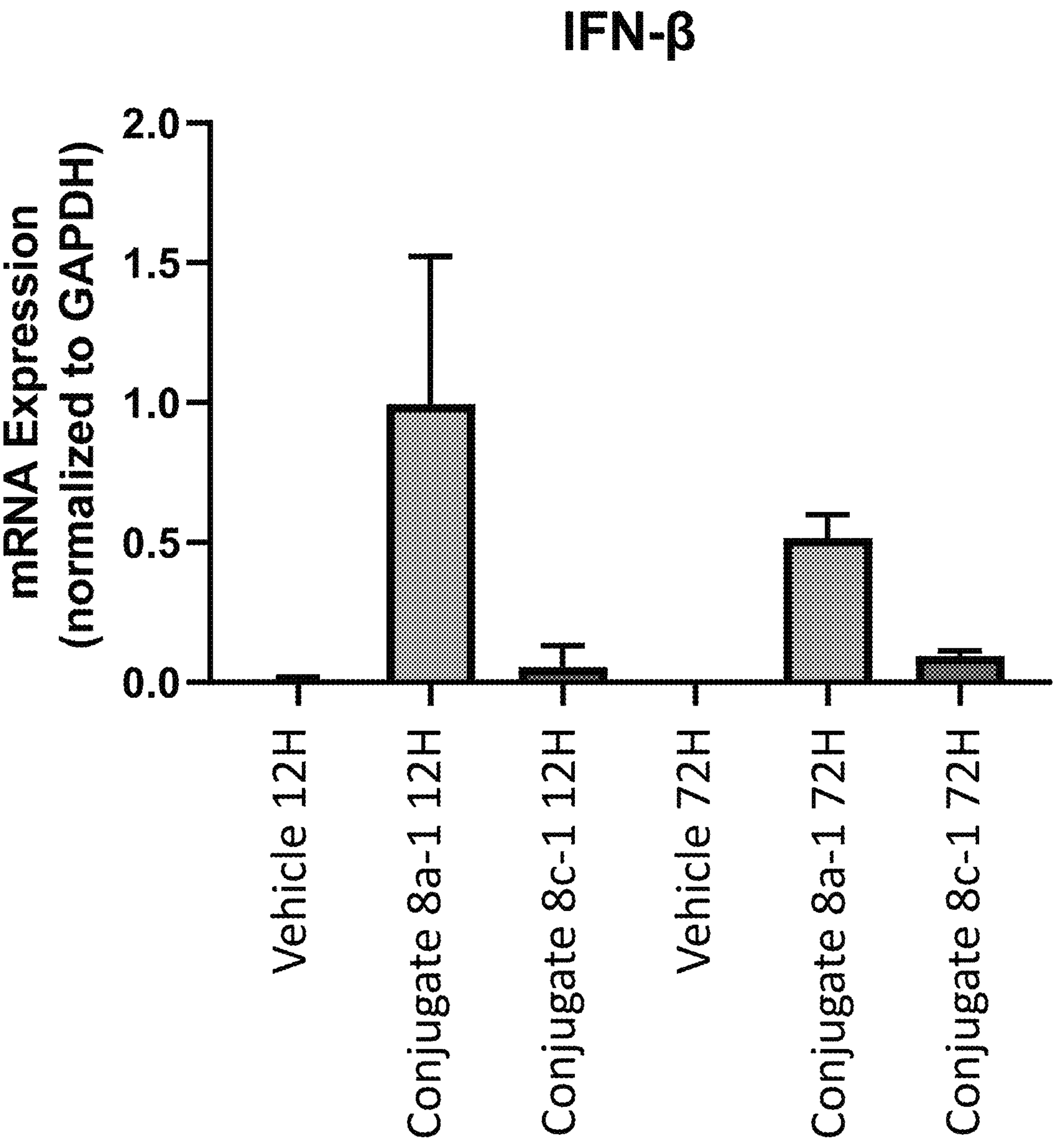
Figure 8C:
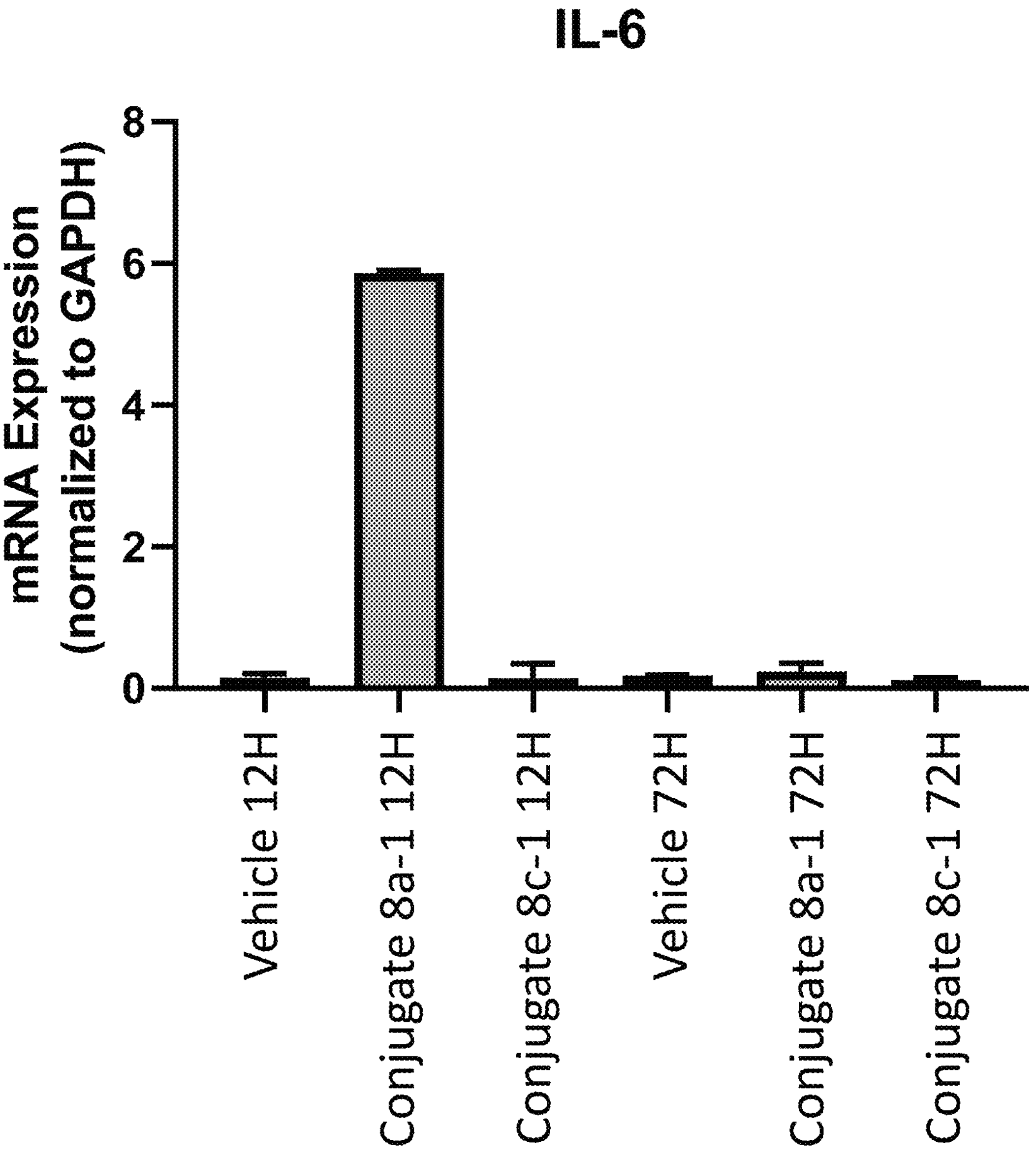

FIGS. 8A-8C provides levels of mouse CXCL10, Interferon-β, and IL-6 mRNA in SKOV3 tumors measured at 12 and 72 hours. Treatment with Conjugate 8a-1 resulted in the highest levels of CXCL10, Interferon-β, and IL-6 mRNA at 12 hours relative to the Vehicle or Conjugate 8c-1. For Conjugate 8a-1, CXCL10, Interferon-β, and IL-6 mRNA levels all decreased at 72 hours.

Figure 9:
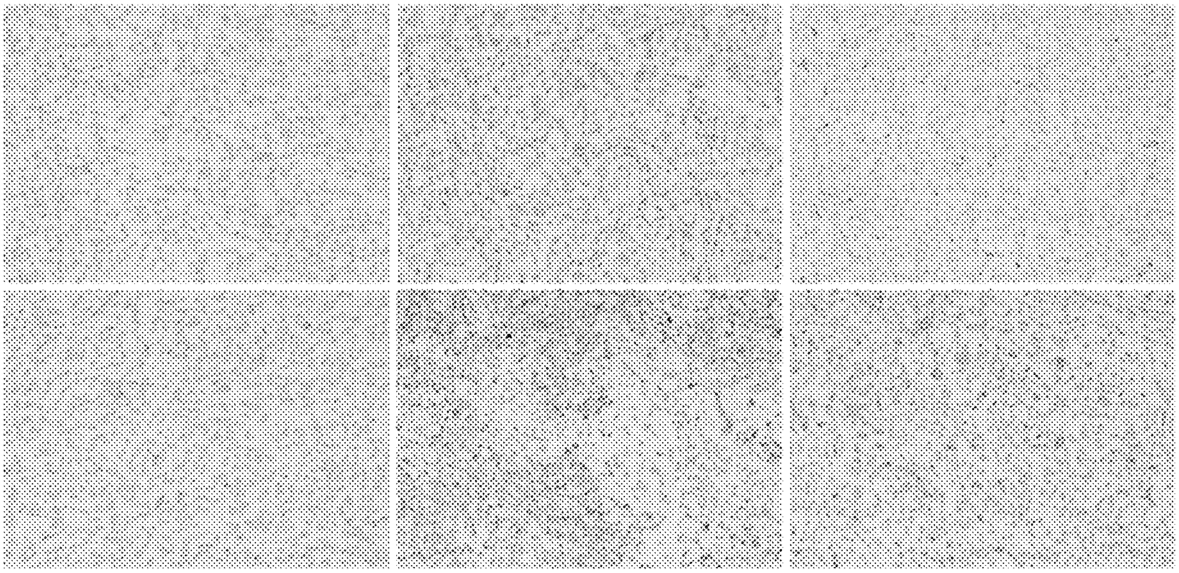
FIG. 9 is the CD45 immunohistochemistry (IHC) staining with rabbit anti-CD45 monoclonal antibody at 12 and 72 hours for Conjugate 8a-1 (3/0.09 mg/kg), Conjugate 8c-1 (3/0.12 mg/kg) or vehicle.

FIG. 9 provides CD45 immunohistochemistry (IHC) staining of FFPE tumor tissue sections with rabbit anti-CD45 monoclonal antibody at 12 and 72 hours for Conjugate 8a-1, Conjugate 8c-1 or vehicle. As shown, there was increased CD45-positive mouse immune cell infiltration into the SKOV3 tumors in SCID mice at 72 hours post treatment with Conjugate 8a-1.

Example 39B: Expression of STING Pathway Genes in SKOV3 Human Tumor Xenografts in SCID Mice in Response to HER2 Antibody-Drug Conjugate Female CB.17 SCID mice were inoculated subcutaneously with SKOV3 human ovarian cancer cells and treated with Conjugate 8a-1 (3/0.09 mg/kg) as described in Example 38. Tumors were harvested and processed into FFPE as described in Example 31. RNA was extracted using the Qiagen Rneasy FFPE kit according to kit instructions. 150 ng RNA per sample was analyzed on NanoString nCounter Max system using the nCounter pan-cancer human or mouse immune profiling panels and nCounter Standard Master Kit. Tables 11 shows the log 2 fold changes of selected STING pathway genes at 12 hours.

TABLE 11

| | Human | | Mouse | |
|---|---|---|---|---|
| Gene Name | Log2 fold Change | Std Error | Log2 fold Change | Std Error |
| CXCL10 | 11.7 | 1.11 | 8.02 | 0.482 |
| IFNβ1 | 9.26 | 1.02 | 4.82 | 1.13 |
| IFIT2 | 7.88 | 0.229 | 7.12 | 0.435 |
| IFIT1 | 6.96 | 0.31 | 5.81 | 0.396 |
| ISG15 | 6.67 | 0.36 | 5.79 | 0.382 |
| IL6 | 5.94 | 0.749 | 6.36 | 0.647 |
| IRF1 | 5.48 | 0.14 | 4.83 | 0.125 |
| MX1 | 5.4 | 0.324 | 6.68 | 0.542 |
| IFIH1 | 5.07 | 0.223 | 4.45 | 0.36 |
| IRF7 | 4.1 | 0.322 | 4.72 | 0.403 |
| IFNλ1 | 6.52 | 0.695 | Not Applicable | |
| IFNλ2 | 4.6 | 0.603 | Not Detected | |

As shown in Table 11, a single administration of Conjugate 8a-1 resulted in marked induction of both mouse and human STING pathway genes, suggesting that the tumor-targeted STING agonist ADCs may induce tumor-intrinsic STING pathway activation in tumors in vivo.

Example 40: Pharmacokinetic Analysis of her-2 Targeted ADC in CB.17 SCID Mice

Ten-week-old female CB.17 SCID mice were dosed intravenously as a single dose on day 1 with vehicle or Conjugate 8a-1 (3/0.1 mg/kg) (doses are given as antibody/payload, n=3 for each group). Blood was serially collected from all animals at 1, 24, 48, 72, 96, 168, 240, and 336 hours following treatment (n=3 for each group). Whole blood was immediately diluted 1:10 with acidic buffer (0.6% BSA (w/v), 5 mM EDTA in 100 mL PBS+15.34 ml 10 mg/mL citric acid), for a total volume of 0.1 mL. Diluted whole blood was snap-frozen on dry ice and stored at −80° C. until analysis for total antibody and conjugated drug.

Figure 10:
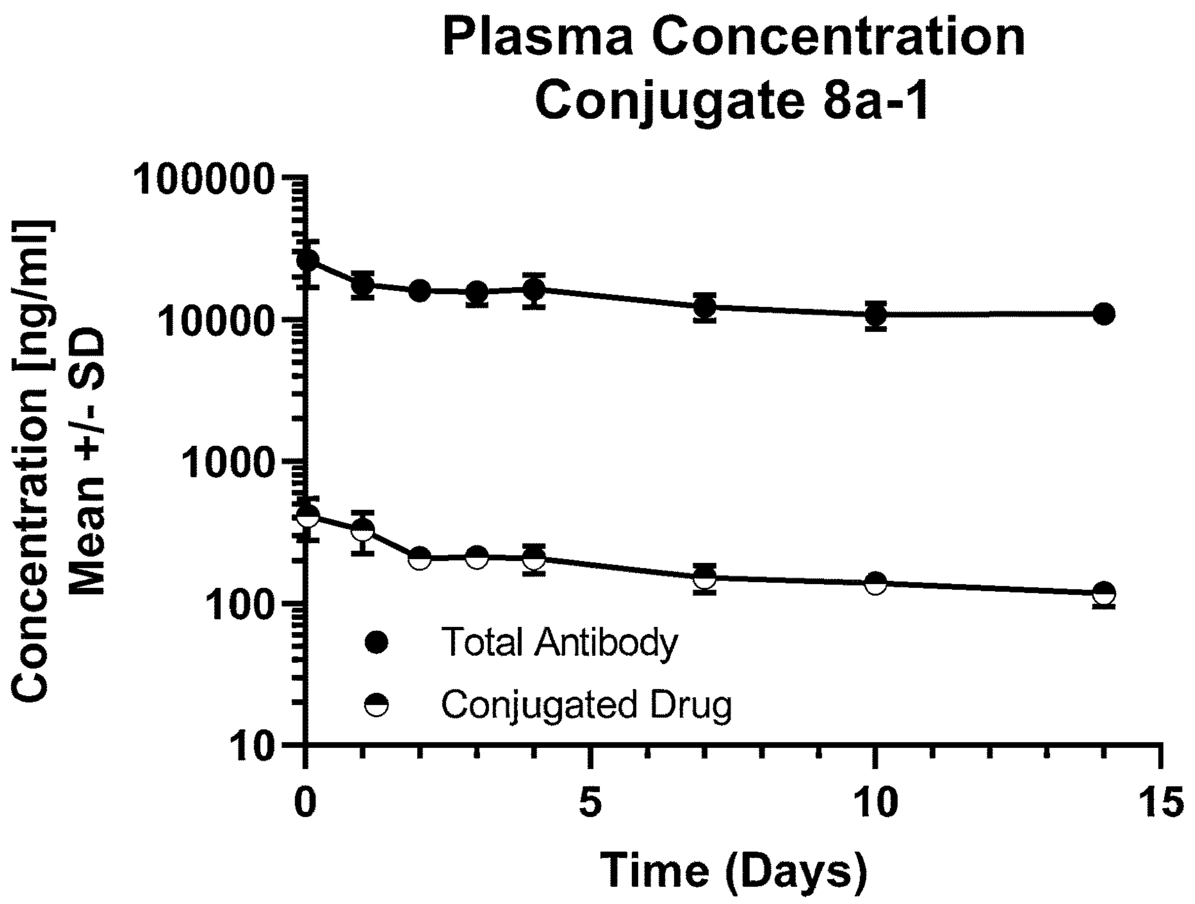
FIG. 10 is a graph showing the circulating plasma concentrations of total antibody and conjugated drug following administration of Conjugate 8a-1 (3/0.1 mg/kg) (dose is given as antibody/payload) to CB.17 SCID mice.

FIG. 10 provides the results for circulating plasma concentrations of total antibody and conjugated drug. Plasma concentrations of ~25.1 μg/mL and ~0.46 μg/mL were achieved for total antibody and conjugated drug, respectively, and a corresponding clearance rate of ~6.71 mL/day/kg for total antibody and ~20.2 mL/day/kg for conjugated drug.

Similarly, Conjugate 32-3 (1.14/0.04 mg/kg) was administered, and total antibody and conjugated drug was assessed at 0.25, 24, 72, 168, 240, and 336 hours. Data is reported in Table 12.

TABLE 12

| | Cmax (ng/mL) | Half-life (day) | AUC∞ (Day*ng/mL) | Cl_obs (mL/Day/Kg) |
|---|---|---|---|---|
| Conjugated Drug | 562 ± 16 | 6.43 ± 1.15 | 2880 ± 468 | 14.2 ± 2.51 |
| Total Antibody | 12200 ± 1160 | 8.69 ± 1.20 | 96300 ± 7190 | 11.9 ± 0.88 |

Example 41: Expression of STING Pathway Genes in SKBR3 Cancer Cell/PBMC Co-Cultures in Response to Her2-Targeted STING Agonist ADC Treatment Nanostring Analysis: Cancer cells were seeded (250,000 cells/well) in duplicates in 12 well plates in 0.75 mL culture medium (RPMI-1640 medium with 10% FBS and 1% penicillin/streptomycin) and allowed to attach at 37° C. in a 5% $CO_2$ incubator overnight. Culture medium was removed and Conjugate 8a-3 or vehicle was added into the wells in 0.5 mL culture medium at a final concentration of 50 nM (based on payload). 500,000 PBMCs per well were added to each well in 0.5 mL medium. After 5 hours of incubation at 37° C., the suspended cells were collected in an Eppendorf tube and spun down briefly. Supernatant was removed and the tube was placed on ice. The attached cells were lysed with the RNA lysis buffer and transferred onto the suspension cell pellet. RNA was extracted using the Qiagen Rneasy mini kit according to kit instructions. 150 ng RNA per sample was analyzed on NanoString nCounter Max system using the nCounter pan-cancer human immune profiling panel and nCounter Standard Master Kit.

Table 13 shows the log 2 fold changes of the selected STING pathway genes by Conjugate 8a-3 vs vehicle treatment (5 hours) in SKBR3 cancer cell and PBMC co-cultures in vitro. 50 nM Conjugate 8a-3 treatment led to marked induction of STING pathway genes and the type III Interferons (IFNλ1 and IFNλ2), confirming that the tumor-targeted STING agonist ADCs treatment induces STING pathway genes as well as Type III Interferons also in in vitro cancer/immune cell co-cultures.

TABLE 13

| Gene Name | Log2 fold Change | Std Error | P-value |
|---|---|---|---|
| IFNλ1 | 10.7 | 0.207 | 5.17E−08 |
| IFNλ2 | 12.5 | 0.318 | 2.04E−07 |
| CXCL10 | 7.86 | 0.0538 | 2.85E−10 |
| IFNβ1 | 9.76 | 0.0493 | 6.25E−11 |
| IFIT2 | 9.15 | 0.393 | 2.72E−06 |
| IFIT1 | 8.08 | 0.0854 | 2.49E−09 |

TABLE 13-continued

| Gene Name | Log2 fold Change | Std Error | P-value |
|---|---|---|---|
| ISG15 | 6.73 | 0.182 | 2.73E−07 |
| IL6 | 8.55 | 0.382 | 3.32E−06 |
| IRF1 | 6.99 | 0.171 | 1.65E−07 |
| MX1 | 4.48 | 0.0876 | 5.41E−08 |
| IFIH1 | 4.2 | 0.0853 | 6.49E−08 |
| IRF7 | 3.45 | 0.15 | 2.92E−06 |

qPCR Analysis of type III interferon genes: SKBR3/PBMC co-cultures were set up as described above and treated with 50 nM and 1 nM (based on payload) of Conjugate 8a-3 or Conjugate 8c-2 for 5 hours. Cells were harvested and RNA was extracted as described above. qPCR analysis was performed as described in Example 39A. ABI assays for human IFNλ1 (IL29), IFNλ2 (IL28a), and IFNλ3 (IL28b) were used with GAPDH, and ACTB as housekeepers. Levels of mRNA relative to GAPDH were calculated using $2^{-}$ΔΔCT method as shown in Table 14.

TABLE 14

| Treatment | Relative mRNA Expression IFNλ1 (IL29) | IFNλ2 (IL28a) | IFNλ3 (IL28b) |
|---|---|---|---|
| Conjugate 8a-3 - 50 nM | 190.5 ± 18.9 | 327 ± 2.5 | 27.7 ± 1.2 |
| Conjugate 8a-3 - 1 nM | 89 ± 1.2 | 201.6 ± 32.7 | 29.7 ± 2.0 |
| Conjugate 8c-2 - 50 nM | 1.8 ± 2.5 | 0 | 0 |
| Conjugate 8c-2 - 1 nM | 0 | 0 | 0 |

Table 14 shows the mRNA expression of type III interferons relative to the house keeping genes in response to targeted ADC and control ADC treatments of the cancer cell/PBMC co-cultures. Conjugate 8a-3 treatment at both 50 nM and 1 nM payload dose induced marked upregulation of type III interferon genes. Conjugate 8c-2 treatment did not induce type III interferons significantly at the doses used in this experiment.

Example 42: Induction of Type III Interferons in STING Wild Type or Knock Out SKBR3 Cancer Cell and PBMC Co-Cultures STING wild type or knock out cancer cell (as described in Example 30) and PBMC co-cultures were treated with Conjugate 8a-3, Conjugate 8j-1, Conjugate 8c-2 and Compound 1 (0.0.1 nM to 200 nM based on payload; 4-fold serial dilutions) and Type III Interferons IFNλ1/IFNλ3 (IL29/IL28b) cytokines were measured as described in Example 33—Type III Interferon Induction.

Table 15 shows the Type III Interferons IFNλ1/IFNλ3 (IL29/IL28b) cytokine production in STING wild type or STING knock out SKBR3 and PBMC co-cultures in response to Conjugate 8a-3, Conjugate 8j-1, Conjugate 8c-2 and Compound 1.

TABLE 15

| | Conjugate 8a-3 | | Conjugate 8j-1 | | Conjugate 8c-2 | | Compound 1 | |
|---|---|---|---|---|---|---|---|---|
| Cancer Cell Line | $EC_{50}$ (nM) | Bmax ($OD_{450}$) | $EC_{50}$ (nM) | Bmax ($OD_{450}$) | $EC_{50}$ (nM) | Bmax ($OD_{450}$) | $EC_{50}$ (nM) | Bmax ($OD_{450}$) |
| STING wild type | 0.13 | 2.6 | 0.89 | 2.6 | NA | 1.8 | 49.3 | 0.5 |
| STING knock out (sgRNA#3) | 0.19 | 0.7 | NA | 0.3 | NA | 0.2 | NA | 0 |
| STING knock out (sgRNA#4) | 0.27 | 0.7 | NA | 0.1 | NA | 0.1 | NA | 0 |

Both Conjugate 8a-3 and Conjugate 8j-1 induced robust Type III Interferons IFNλ1/IFNλ3 (IL29/IL28b) cytokine production in STING wild type SKBR3 cell co-cultures. Compound 1 also induced Type III Interferons IFNλ1/IFNλ3 (IL29/IL28b) production in this co-culture setting but with a ~400× lower $EC_{50}$ concentration whereas Conjugate 8c-2 had no significant activity. The amount of IFNλ1/IFNλ3 (IL29/28b) production in the STING knock out SKBR3 cell co-cultures was markedly reduced in response to all treatments as evident from the very low Bmax (OD450) levels.

Figure 11:
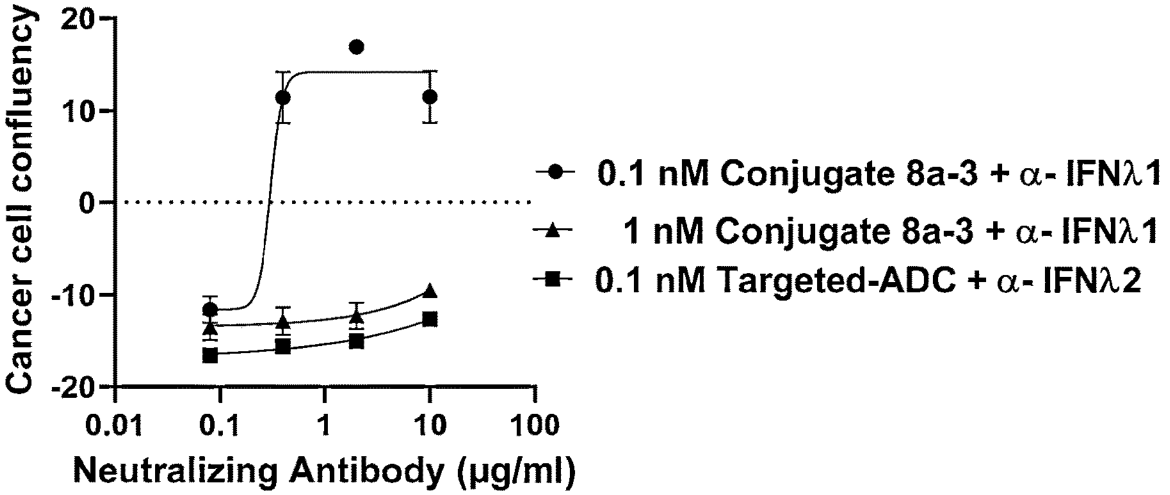
FIG. 11 shows the effect of IFNλ1 (IL29) or IFNλ2 (IL28A) neutralizing antibodies (10, 2, 0.4, 0.08 μg/mL) on the killing activity of Conjugate 8a-3 (1 nM or 0.1 nM, based on payload) in cancer cell and PBMC co-cultures.

Example 43A: Effect of IFNλ1 (IL29) or IFNλ2 (IL28A) Neutralizing Antibodies on the Killing Activity of the Her2-Targeted STING ADC in Cancer Cell and PBMC Co-Cultures Cancer cell killing activity: SKBR3 and PBMC co-cultures were conducted as described in Example 33—Type III Interferon Induction to assess the killing activity of Conjugate 8a-3 (1 nM or 0.1 nM based on payload) in the presence of IFNλ1 (IL29) or IFNλ2 (IL28b) neutralizing antibodies (10, 2, 0.4, 0.08 μg/mL). As shown in FIG. 11 the IFNλ1 neutralizing antibody at 10, 2, and 0.4 μg/mL inhibited the cancer cell killing activity Conjugate 8a-3 at 0.1 nM (based on payload) in PBMC co-cultures. No inhibition was observed with the IFNλ1 antibodies when Conjugate 8a-3 was used at the 1 nM (based on payload) IFNλ2 neutralizing antibodies did not inhibit cancer cell-killing activity even when Conjugate 8a-3 was dosed at 0.1 nM

Example 43B: IFNλ1/IFNλ3 (L29/28b) Cytokine Induction

Sister plates of the assay described in Example 43A were used to analyze IFNλ1/IFNλ3 (IL29/28b) in the supernatants 24 hours post treatment using a human IL29/28b ELISA kit as described in Example 33—Type III Interferon Induction. Table 16 shows the OD450 values obtained from each condition.

TABLE 16

| Conjugate 8a-2 (nM) | IFN λ1 mAb (μg/mL) | IFNλ1/IFNλ3 (IL29/28b) (OD450) |
|---|---|---|
| 1 nM | 0 | 2.996 ± 0.028 |
| | 10 | 1.470 ± 0.071 |
| | 2 | 1.584 ± 0.099 |
| | 0.4 | 1.491 ± 0.071 |
| | 0.08 | 1.464 ± 0.077 |

TABLE 16-continued

| Conjugate 8a-2 (nM) | IFN λ1 mAb (μg/mL) | IFNλ1/IFNλ3 (IL29/28b) (OD450) |
|---|---|---|
| 0.1 nM | 0 | 2.166 ± 0.023 |
| | 10 | 0.034 ± 0.014 |
| | 2 | 0.021 ± 0.008 |
| | 0.4 | 0.048 ± 0.011 |
| | 0.08 | 0.190 ± 0.014 |

Example 43C: CXCL10, IFNβ, IL6, and TNFα Cytokine Induction

Supernatants from Example 43B were used to analyze for CXCL10, IFNβ, IL6 and TNFα cytokine production using a human cytokine/chemokine magnetic bead panel on a FlexMap3D Luminex instrument. Belysa Immunoassay Curve Fitting Software was used for data analysis. Table 17 shows the CXCL10, IFNβ, IL6, and TNFα cytokines detected in the supernatants.

TABLE 17

| Conjugate 8a-2 (nM) | IFNλ1 mAb (μg/mL) | CXCL10 (pg/mL) | IFNβ (pg/mL) | IL6 (pg/mL) | TNFα (pg/mL) |
|---|---|---|---|---|---|
| 1 nM | 0 | 1187 ± 23.1 | 99 ± 9.5 | 4228 ± 292.0 | 469 ± 86.3 |
| | 10 | 827 ± 122.5 | 61 ± 5.9 | 2191 ± 194.3 | 43 ± 5.5 |
| | 2 | 1106 ± 167.9 | 71 ± 9.1 | 2831 ± 260.9 | 54 ± 2.9 |
| | 0.4 | 1128 ± 44.9 | 76 ± 7.7 | 3735 ± 456.2 | 71 ± 9.6 |
| | 0.08 | 1155 ± 34.4 | 104 ± 20.6 | 4475 ± 725.5 | 170 ± 27.2 |
| 0.1 nM | 0 | 1189 ± 7.5 | 32 ± 0.9 | 806 ± 117.9 | 52 ± 7.4 |
| | 10 | 306 ± 136.0 | 3 ± 1.5 | 77 ± 56.6 | 16 ± 3.8 |
| | 2 | 325 ± 98.2 | 2 ± 0.9 | 27 ± 15.4 | 12 ± 0.5 |
| | 0.4 | 435 ± 186.6 | 5 ± 2.2 | 42 ± 21.4 | 16 ± 0.5 |
| | 0.08 | 695 ± 173.0 | 15 ± 1.6 | 171 ± 14.1 | 22 ± 1.0 |

Together these data demonstrate that Type III Interferon production is important for the tumor cell-targeted STING-ADC activity, especially at the low concentrations.

Example 44: Tumor Growth Response to Administration of NaPi2b Antibody-Drug Conjugate in OVCAR-3

Five week-old female CB.17 SCID mice were inoculated subcutaneously with OVCAR-3 cells ($5\times10^6$ cells per mouse) Animals were randomized into treatment groups when tumor volumes were between 52-180 $mm^3$ (mean: 93-94 $mm^3$/group). Vehicle, diABZI STING agonist 0/5 mg/kg), Conjugate 8c-1 (3/0.12 mg/kg), Conjugate 8b-1 (3/0.09 mg/kg), or Conjugate 8f (3/0.12 mg/kg) were dosed intravenously as a single dose on day 1 (all doses are given by antibody/payload, n=8 for each group group). Transient body weight loss was observed 3-13 days following treatment with no additional clinical observations for diABZI STING agonist (0/5 mg/kg), Conjugate 8c-1, Conjugate 8b-1 and Conjugate 8f.

Figure 12:
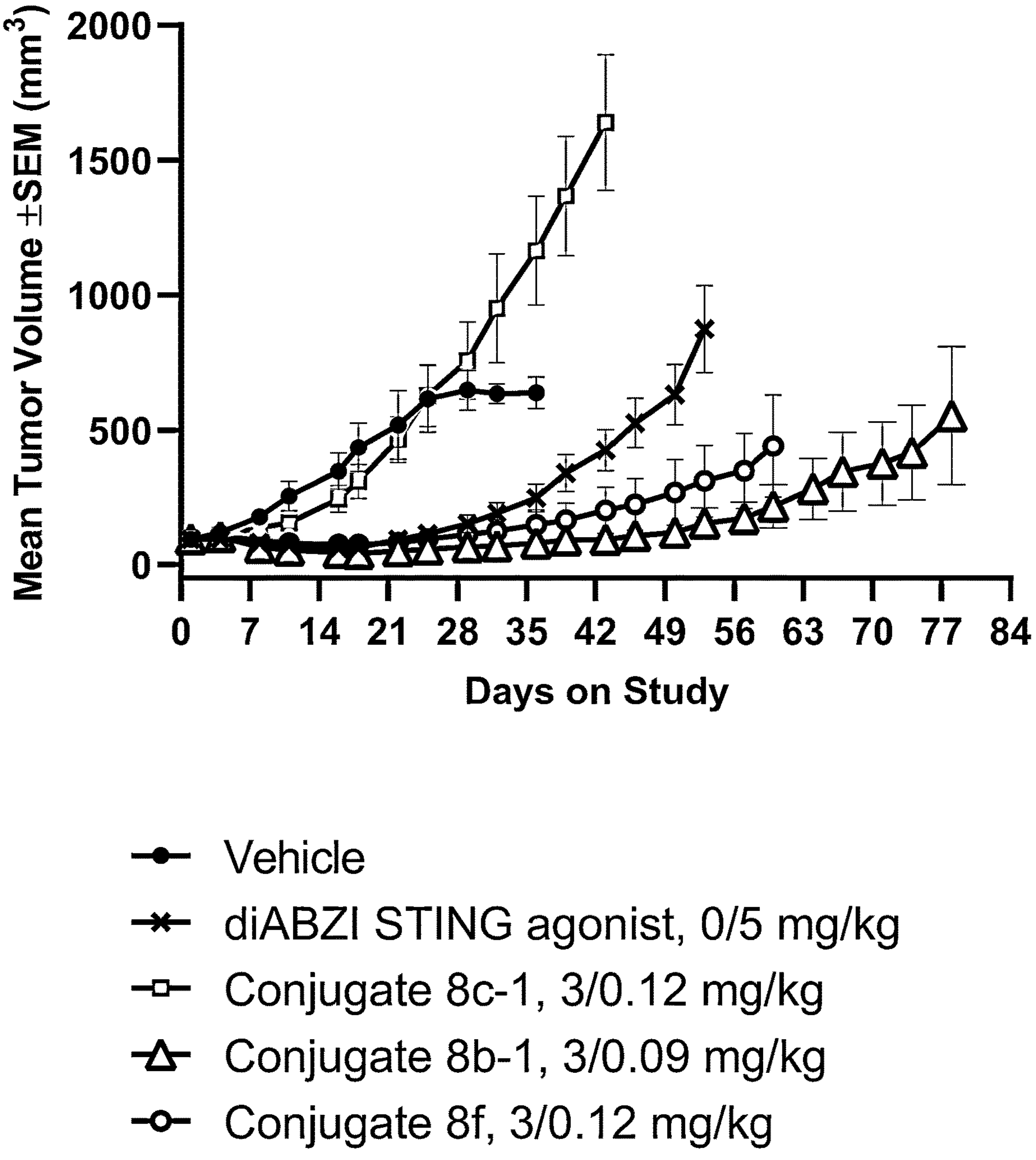
FIG. 12 is a graph showing the anti-tumor efficacy of diABZI STING agonist (0/5 mg/kg), Conjugate 8c-1 (3/0.12 mg/kg), Conjugate 8b-1 (3/0.09 mg/kg) or Conjugate 8f (3/0.12 mg/kg) (all doses are given by antibody/payload) in a OVCAR3 xenograft in mouse.

FIG. 12 provides the results for OVCAR-3 tumor-bearing mice treated with vehicle, diABZI STING agonist, Conjugate 8c-1, Conjugate 8b-1 or Conjugate 8f. When compared with vehicle control, treatment with Conjugate 8c-1 (3/0.12 mg/kg) resulted in a mean increase in tumor growth of 70.6%. Treatment with diABZI STING agonist (0/5 mg/kg) resulted in 42.7% TGI. Treatment with Conjugate 8b-1

(3/0.09 mg/kg) resulted in 98.4% TGI. Treatment with Conjugate 8f resulted in 83.1% TGI.

Example 45: Tumor Growth Response to Administration of Chimeric (hIgG1-mIgG2a) NaPi2b Antibody-Drug Conjugate in OVCAR-3

Female CB.17 SCID mice were inoculated subcutaneously with OVCAR-3 human ovarian cancer cells ($5\times10^6$ cells per mouse). Animals were randomized into treatment groups when tumor volumes were between 53-223 $mm^3$ (mean=112-122 $mm^3$/group). Vehicle, Conjugate 8d-2 (3/0.1 mg/kg), or Conjugate 8e (3/0.1 mg/kg) were administered intravenously on day 1 (all doses are given as antibody/payload, n=8 for each group). Transient body weight loss within acceptable limits was observed 3-15 days following treatment with no additional clinical observations for Conjugate 8d-2 (3/0.1 mg/kg) and Conjugate 8e (3/0.1 mg/kg).

Figure 13:
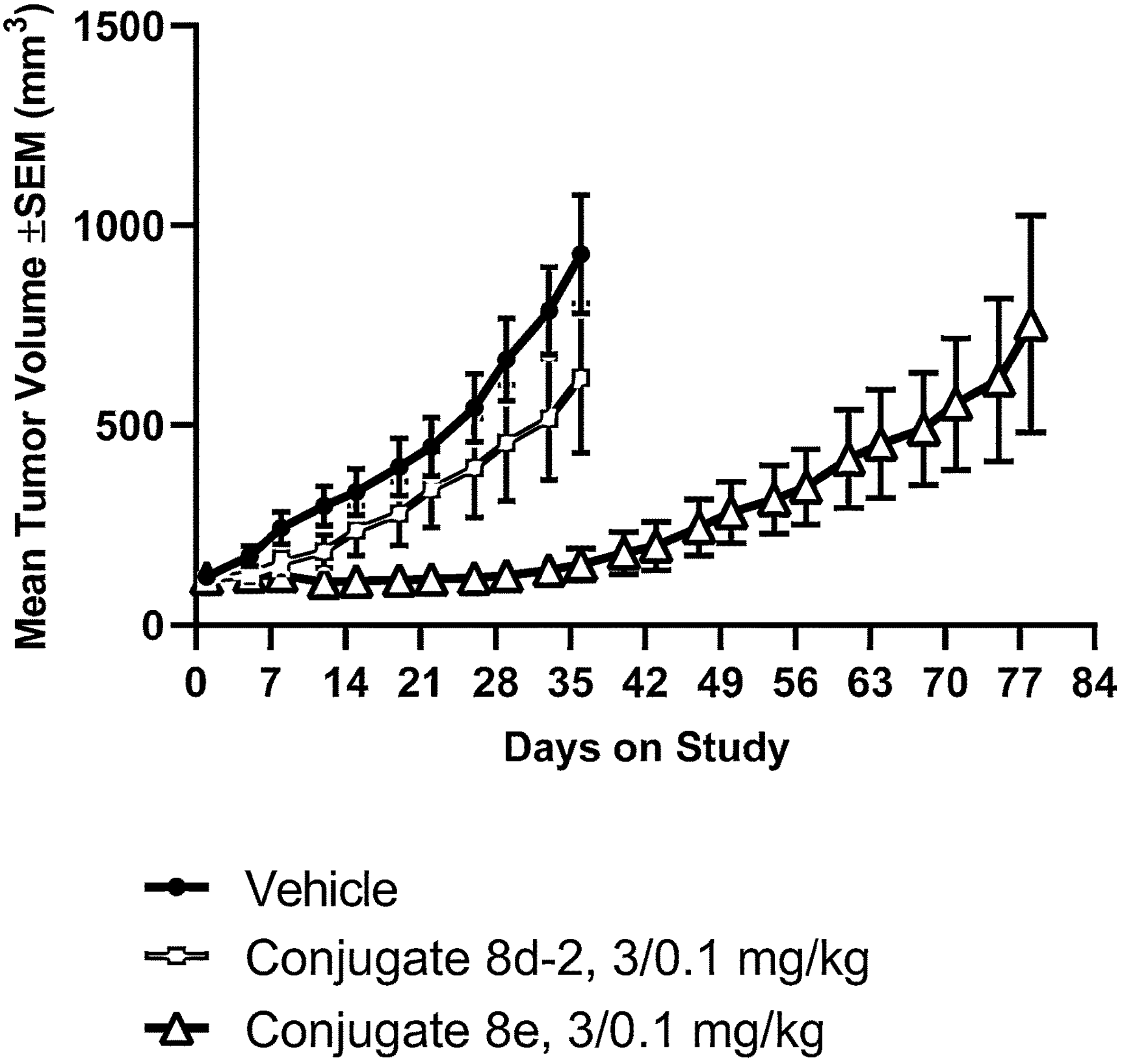
FIG. 13 is a graph showing the anti-tumor efficacy of Conjugate 8d-2 (3/0.1 mg/kg) or Conjugate 8e (3/0.1 mg/kg) (all doses are given as antibody/payload) in a OVCAR3 xenograft in mouse.

FIG. 13 provides the results for the tumor volumes of OVCAR-3 tumor-bearing mice treated with vehicle, Conjugate 8d-2 or Conjugate 8e. Treatment with Conjugate 8d-2 (3/0.1 mg/kg) resulted in 37.3% TGI. Treatment with Conjugate 8e (3/0.1 mg/kg) resulted in 95.8% TGI.

Example 46: Tumor Growth Response to Administration of Target C Antibody-Drug Conjugate in a Triple Negative Breast Cancer Xenograft Model Eight-week-old female NCr nu/nu mice (Charles River Laboratories) were implanted with human triple negative breast cancer (TNBC) tumor fragments (1 $mm^3$) expressing Target C. Animals were randomized into treatment groups when tumor volumes were between 63-108 $mm^3$ (mean=80.7-82 $mm^3$/group). Vehicle, diABZI STING agonist (0/5 mg/kg), Conjugate 8c-1 (1/0.04 mg/kg), or Conjugate 8h (1/0.04 mg/kg) were dosed intravenously as a single dose on day 1 (all doses are given as antibody/payload, n=9 for each group). Transient body weight loss within acceptable limits was observed 2 days following treatment with no additional clinical observations for diABZI STING agonist (0/5 mg/kg).

Figure 14:
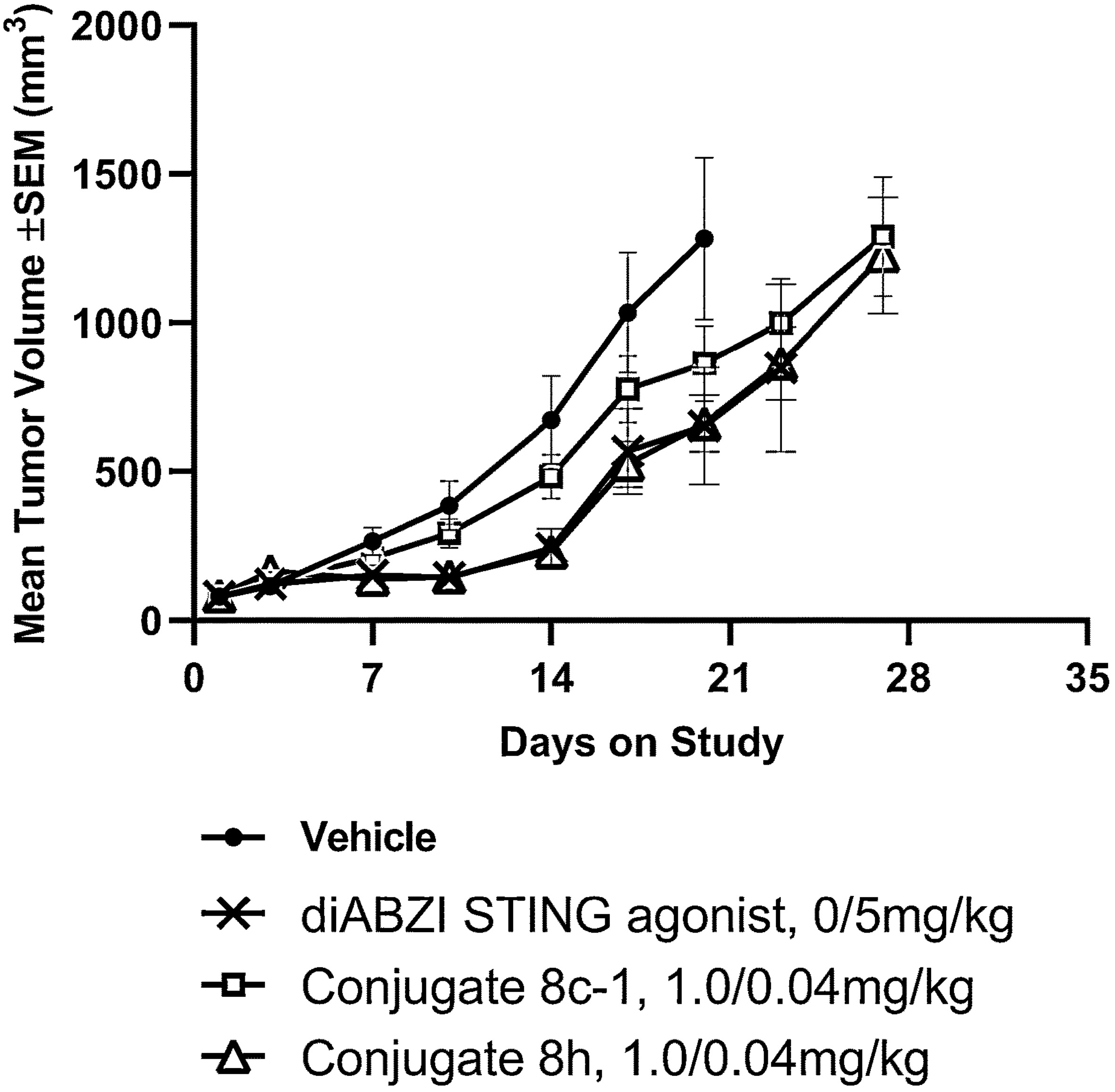
FIG. 14 is a graph showing the anti-tumor efficacy of diABZI STING agonist (0/5 mg/kg), Conjugate 8c-1 (1/0.04 mg/kg) or Conjugate 8h (1/0.04 mg/kg) (all doses are given as antibody/payload) in a triple negative breast cancer xenograft in mouse.

FIG. 14 provides the results for the tumor volumes of human TNBC tumor-bearing mice treated with vehicle, diABZI STING agonist, Conjugate 8c-1, or Conjugate 8h. Treatment with diABZI STING agonist (0/5 mg/kg) resulted in 52.4% TGI. Treatment with Conjugate 8c-1 resulted in 35.1% TGI. Treatment with Conjugate 8h (1.1/00.4 mg/kg) resulted in 51.8% TGI.

Example 47: Tumor Growth Response to Administration of Target D Antibody-Drug Conjugate in Colon Cancer Seven to eight-week-old female C57B1/6 mice were inoculated subcutaneously on the right flank with murine colon cancer cells ($5\times10^5$ cells per mouse). Animals were randomized into treatment groups 10 days following inoculation, when tumor volumes were between 63-108 $mm^3$ (mean=78 $mm^3$/group). Vehicle, Conjugate 8d-3 (1/0.04 mg/kg), or Conjugate 8g (0.09/0.04 mg/kg) were dosed intravenously as a single dose on day 1 (all doses represented as antibody/payload, n=10 for each group). Transient body weight loss within acceptable limits was observed 2 days following treatment with no additional clinical observations for Conjugate 8g (0.9/0.04 mg/kg).

Figure 15A:
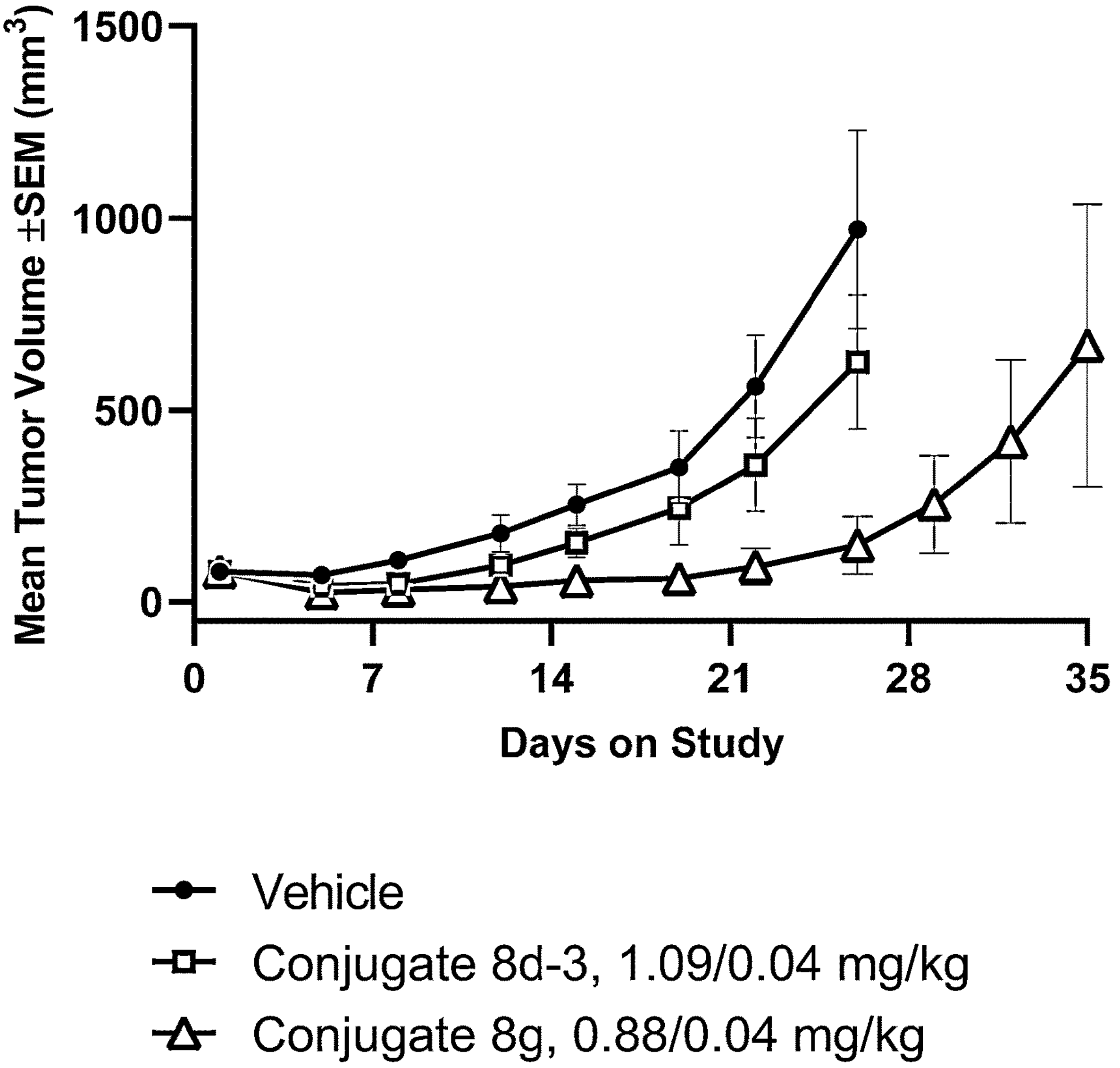
FIG. 15A is a graph showing the anti-tumor efficacy of Conjugate 8d-3 (1/0.04 mg/kg) or Conjugate 8g (0.88/0.04 mg/kg) (all doses are given as antibody/payload) in a colon cancer syngeneic mouse model.

FIG. 15A provides the results for the tumor volumes of murine colon cancer tumor-bearing mice treated with vehicle, Conjugate 8d-3 or Conjugate 8g. Treatment with Conjugate 8d-3 resulted in 42% TGI. whereas treatment with Conjugate 8g resulted in 92.5% TGI.

Figure 15B:
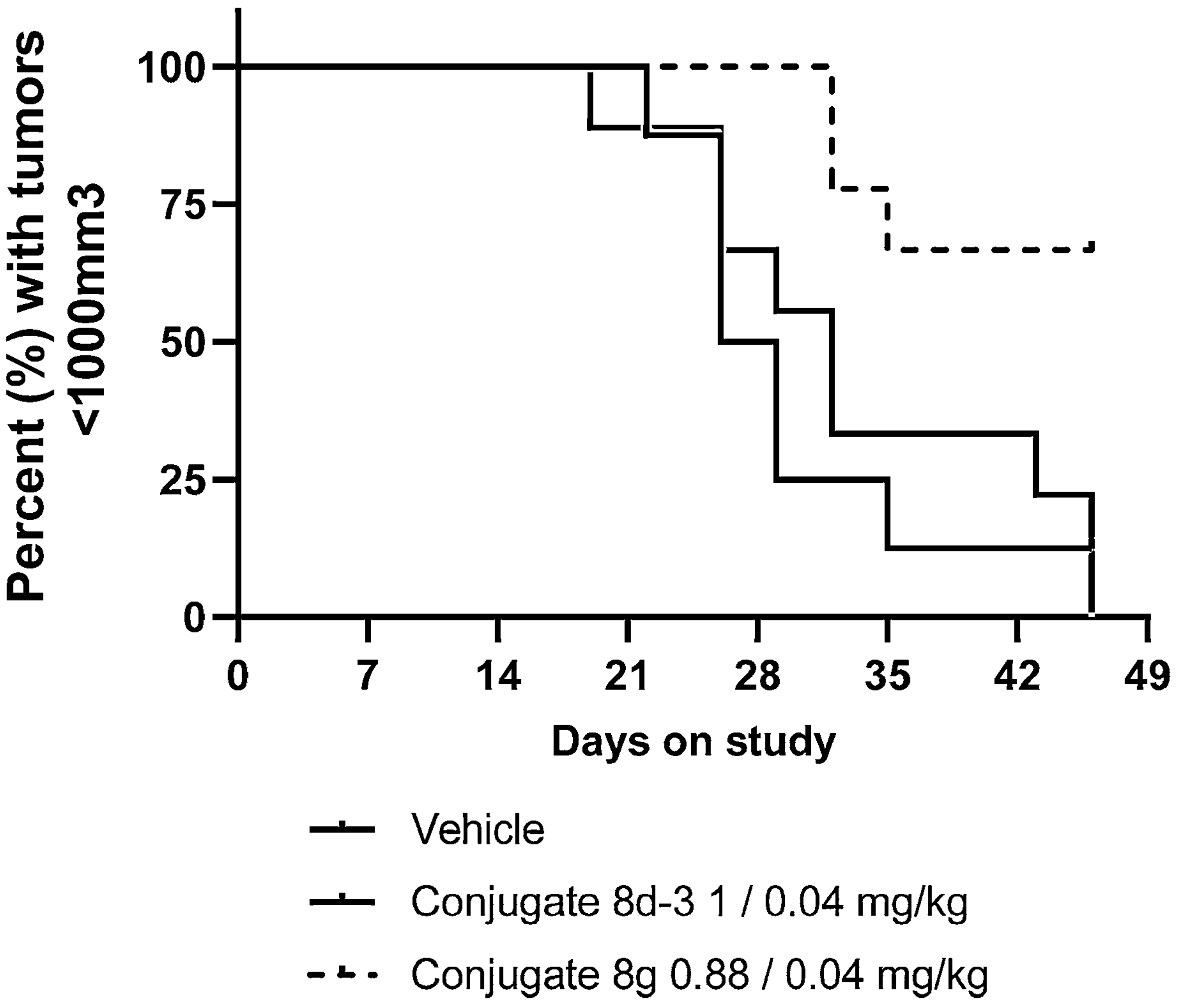
FIG. 15B shows the Kaplan Meier survival curves for Conjugate 8d-3 (1/0.04 mg/kg) or Conjugate 8g (0.88/0.04 mg/kg) (all doses are given as antibody/payload) in a colon cancer syngeneic mouse model.

FIG. 15B shows the Kaplan Meier survival curves for murine colon cancer tumor-bearing mice treated with vehicle, Conjugate 8d-3, or Conjugate 8g. Treatment with Conjugate 8d-3. Mice treated with Conjugate 8g had the longest survival.

Figure 16A:
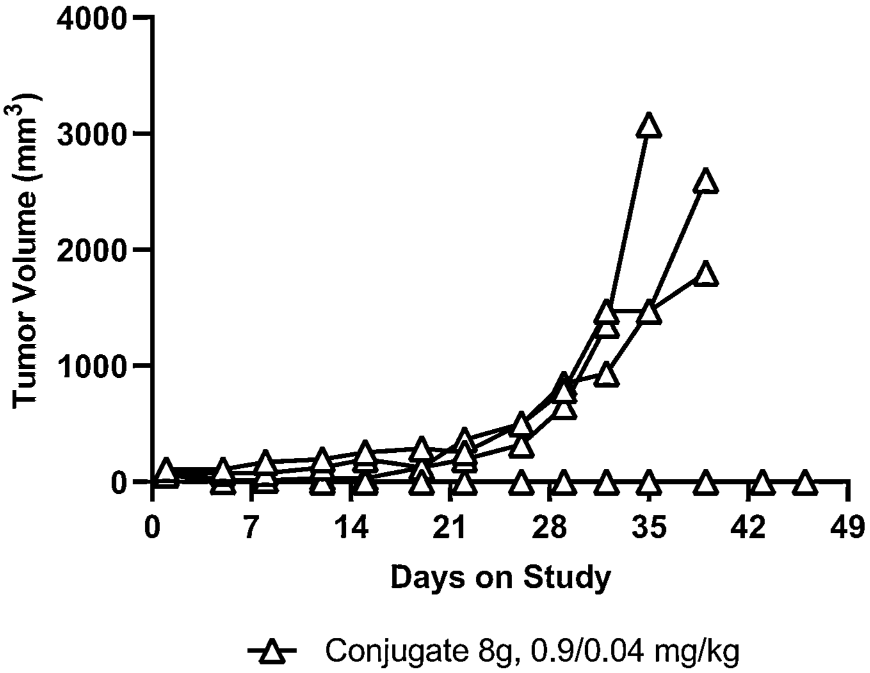
FIG. 16A is a graph showing anti-tumor efficacy of Conjugate 8g (0.9/0.04 mg/kg) (all doses are given as antibody/payload) for the individual mice in a colon cancer syngeneic mouse model.
Figure 16B:
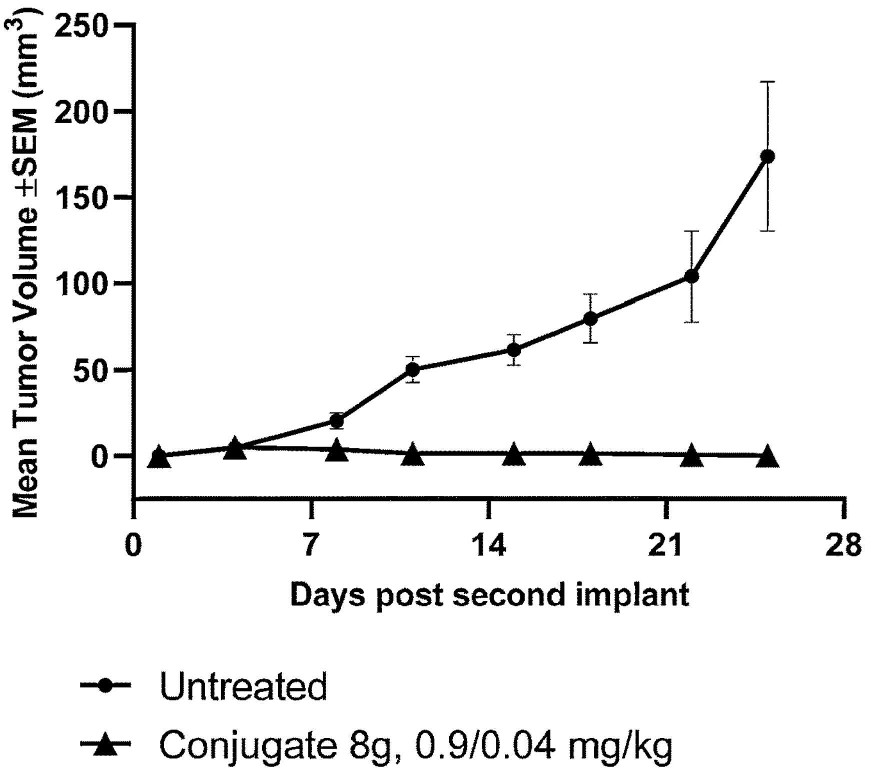
FIG. 16B is a graph showing the anti-tumor efficacy of Conjugate 8g (0.9/0.04 mg/kg) (all doses are given as antibody/payload) when re-challenged with syngeneic murine colon cancer cells.
Figure 16C:
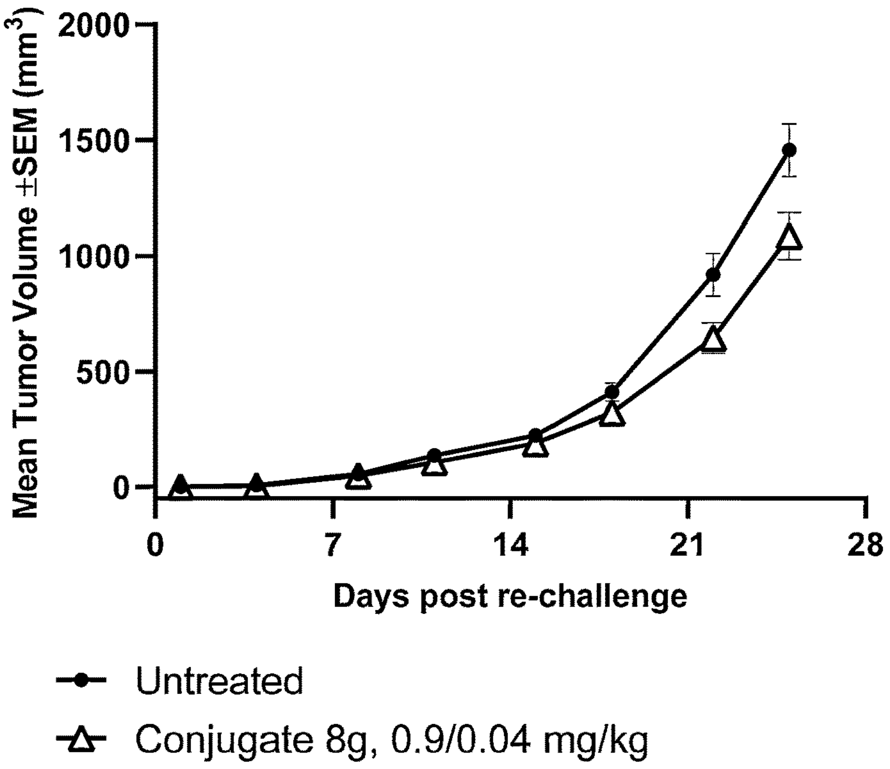
FIG. 16C is a graph showing the anti-tumor efficacy of Conjugate 8g (0.9/0.04 mg/kg) (all doses are given as antibody/payload) when re-challenged with syngeneic murine lung cancer cells.

Example 48: Re-Challenge Study for Tumor Growth Response to Administration of Target D Antibody-Drug Conjugate Tumor-free mice (6 out of 9) previously treated with Conjugate 8g (0.9/0.04 mg/kg) from Example 36 shown in FIG. 16A and age-matched untreated animals from Example 38 were inoculated subcutaneously on the left flank with murine colon cancer cells ($5\times10^5$ cells per mouse) and on the right flank with murine lung cancer cells ($1\times10^6$ cells per mouse) (n=6 and 12, respectively). The tumor growth of mice previously treated with Conjugate 8g (0.9/0.04 mg/kg) when re-challenged with murine colon cancer cells or murine lung cancer cells are shown in FIG. 16B and FIG. 16C, respectively. Previous treatment with Conjugate 8g resulted in 25.5% TGI of murine lung cancer model and 99.8% TGI of murine colon cancer model when compared with the respective untreated controls.

Example 49: Tumor Growth Response to Administration of Target E Antibody-Drug Conjugate in Embryonic Cancer Female Balb/C mice were inoculated subcutaneously with murine embryonic cancer cells ($5\times10^5$ cells per mouse). Animals were randomized into treatment groups when tumor volumes were between 56-108 $mm^3$ (mean=75.3-76.5 $mm^3$/group). Vehicle, diABZI STING agonist (0/5 mg/kg) Conjugate 8d-3 (5.5/0.18 mg/kg), or Conjugate 8i (3.2/0.18 mg/kg) were dosed intravenously as a single dose on day 1 (all doses are given as antibody/payload, n=10 for each group). Transient body weight loss within acceptable limits was observed 2 days following treatment with no additional clinical observations for diABZI STING agonist (0/5 mg/kg) and Conjugate 8i (3.2/0.18 mg/kg).

Figure 17:
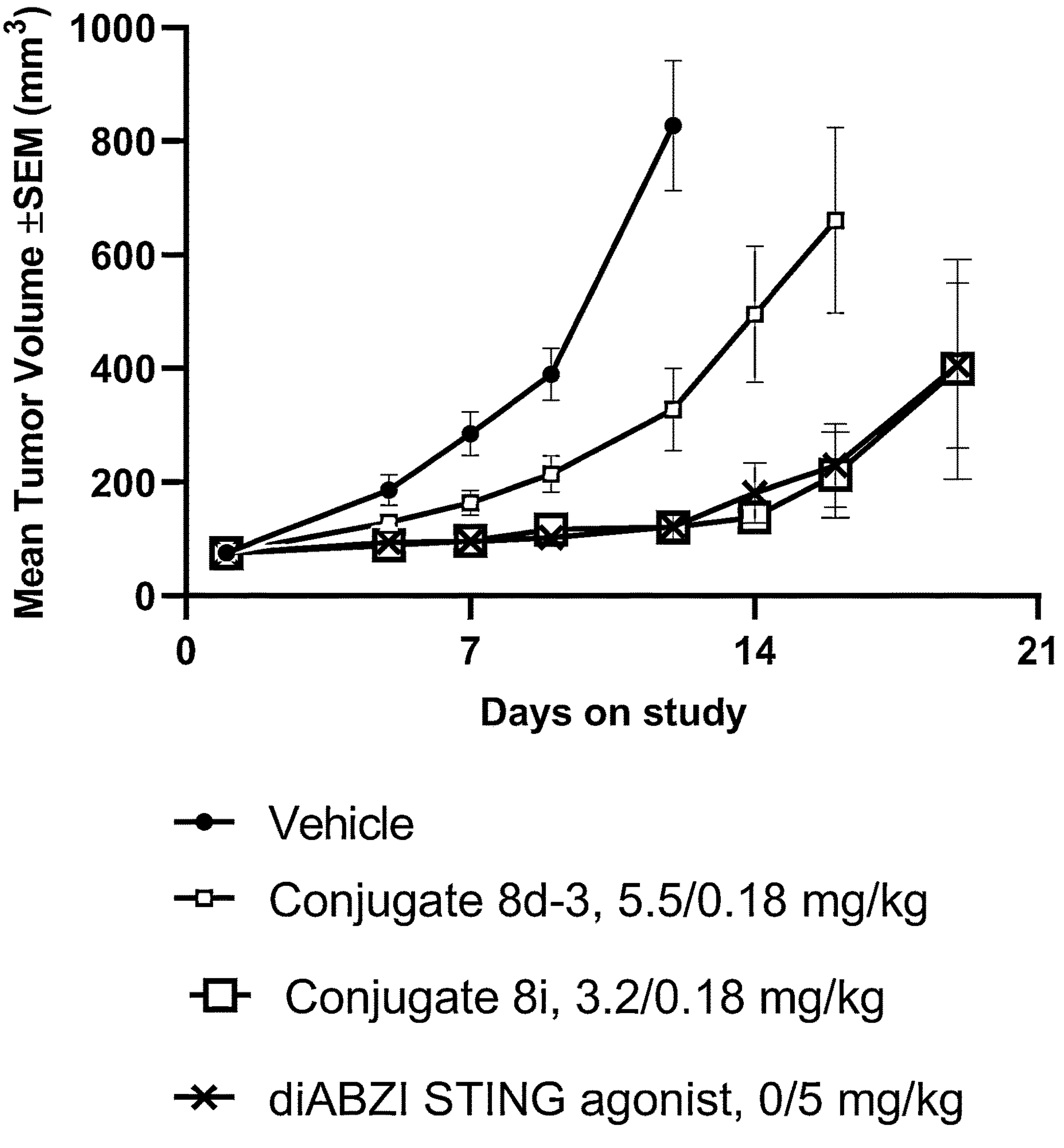
FIG. 17 is a graph showing the anti-tumor efficacy of diABZI STING agonist (0/5 mg/kg) Conjugate 8d-3 (5.5/0.18 mg/kg) or Conjugate 8i (3.2/0.18 mg/kg) (all doses are given as antibody/payload) in a syngeneic murine embryonic cancer model.

FIG. 17 provides the results for the tumor volumes of murine embryonic cancer tumor-bearing mice treated with vehicle, diABZI STING agonist, Conjugate 8d-3, or Conjugate 8i. Treatment with Conjugate 8d-3 (5.5/0.18 mg/kg) resulted in 27.5 and 66.5% TGI, respectively. Treatment with diABZI STING agonist (0/5 mg/kg) resulted in 93.8% TGI. Treatment with Conjugate 8i (3.2/0.18 mg/kg) resulted in 20.5 and 100% TGI, respectively.

Example 50: Tumor Growth Response to Administration of HER2 Antibody-Drug Conjugate in SKOV3 Ovarian Cancer Female CB.17 SCID mice were inoculated subcutaneously with SKOV3 human ovarian cancer cells ($10\times10^6$ cells per mouse). Animals were randomized into treatment groups when tumor volumes were between 63-75 $mm^3$ (mean=65.4 $mm^3$/group). Vehicle, Conjugate 34a (3/0.11 mg/kg), Conjugate 34 (3/0.11 mg/kg), Conjugate 20a (3/0.09 mg/kg), or Conjugate 20-1 (3/0.10 mg/kg) were dosed intravenously as a single dose on day 1 (all doses are given as antibody/ payload, n=10 for each group). Transient body weight loss within acceptable limits was observed 2-3 days following treatment with no additional clinical observations for Conjugate 34a, Conjugate 20a, Conjugate 34, and Conjugate 20-1. Body weight loss at later time-points correlated with tumor progression, indicating tumor model-induced cachexia.

Figure 18:
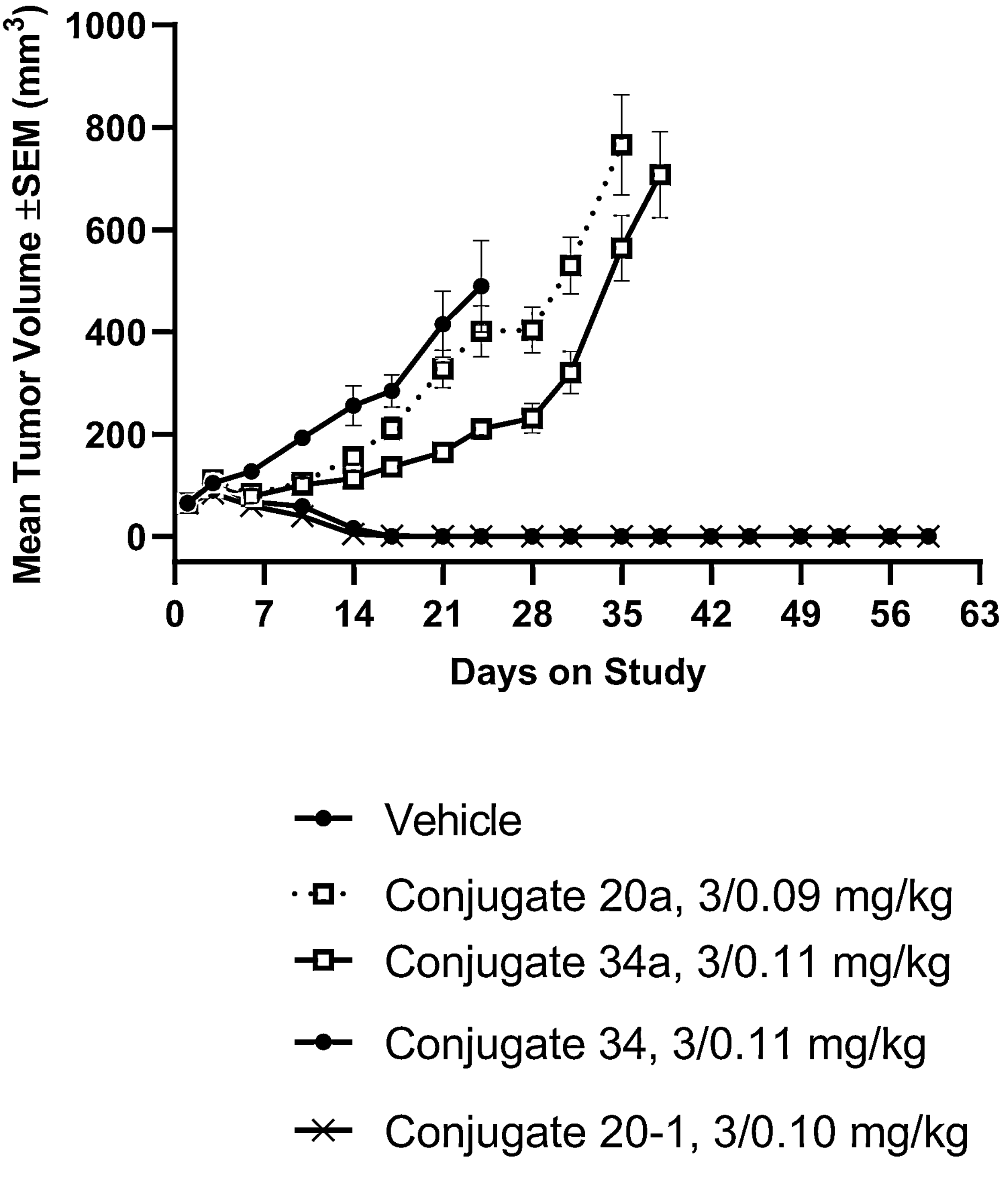
FIG. 18 is a graph showing the anti-tumor efficacy of Conjugate 20a (3/0.09 mg/kg), Conjugate 34a (3/0.11 mg/kg), Conjugate 34 (3/0.11 mg/kg), or Conjugate 20-1 (3/0.10 mg/kg) (all doses are given as antibody/payload) in a SKOV3 xenograft in mouse.

FIG. 18 provides the results for the tumor volumes of SKOV3 tumor-bearing mice treated with vehicle, Conjugate 34a, Conjugate 34, Conjugate 20a, or Conjugate 20-1 (3/0.09 mg/kg). Treatment with Conjugate 20a (3/0.09 mg/kg) or Conjugate 34a (3/0.11 mg/kg) resulted in 21 and 65.9% TGI, respectively. Treatment with Conjugate 34 (3/0.11 mg/kg) or Conjugate 20-1 (3/0.10 mg/kg) each resulted in 100% mean tumor regression.

Example 51: Tumor Growth Response to Administration of HER2 Antibody-Drug Conjugate in SKOV3 Ovarian Cancer Female CB.17 SCID mice were inoculated subcutaneously with SKOV3 human ovarian cancer cells ($10\times10^6$ cells per mouse). Animals were randomized into treatment groups when tumor volumes were between 88-126 $mm^3$ (mean=112.8-113.2 $mm^3$/group). Vehicle, Conjugate 28 (0.3/0.01 mg/kg or 1/0.03 mg/kg), Conjugate 29 (0.2/0.01 mg/kg or 0.8/0.02 mg/kg), Conjugate 8-2 (0.3/0.01 mg/kg or 1/0.04 mg/kg), Conjugate 25 (0.3/0.01 mg/kg or 1/0.04 mg/kg), or Conjugate 45 (0.3/0.01 mg/kg or 1/0.04 mg/kg) were dosed intravenously as a single dose on day 1 (all doses are given as antibody/payload, n=10 for each group). Transient body weight loss within acceptable limits was observed 3 days following treatment with no additional clinical observations for Conjugate 25 (1/0.04 mg/kg). Body weight loss at later timepoints correlated with tumor progression, indicating tumor model-induced cachexia.

Figure 19:
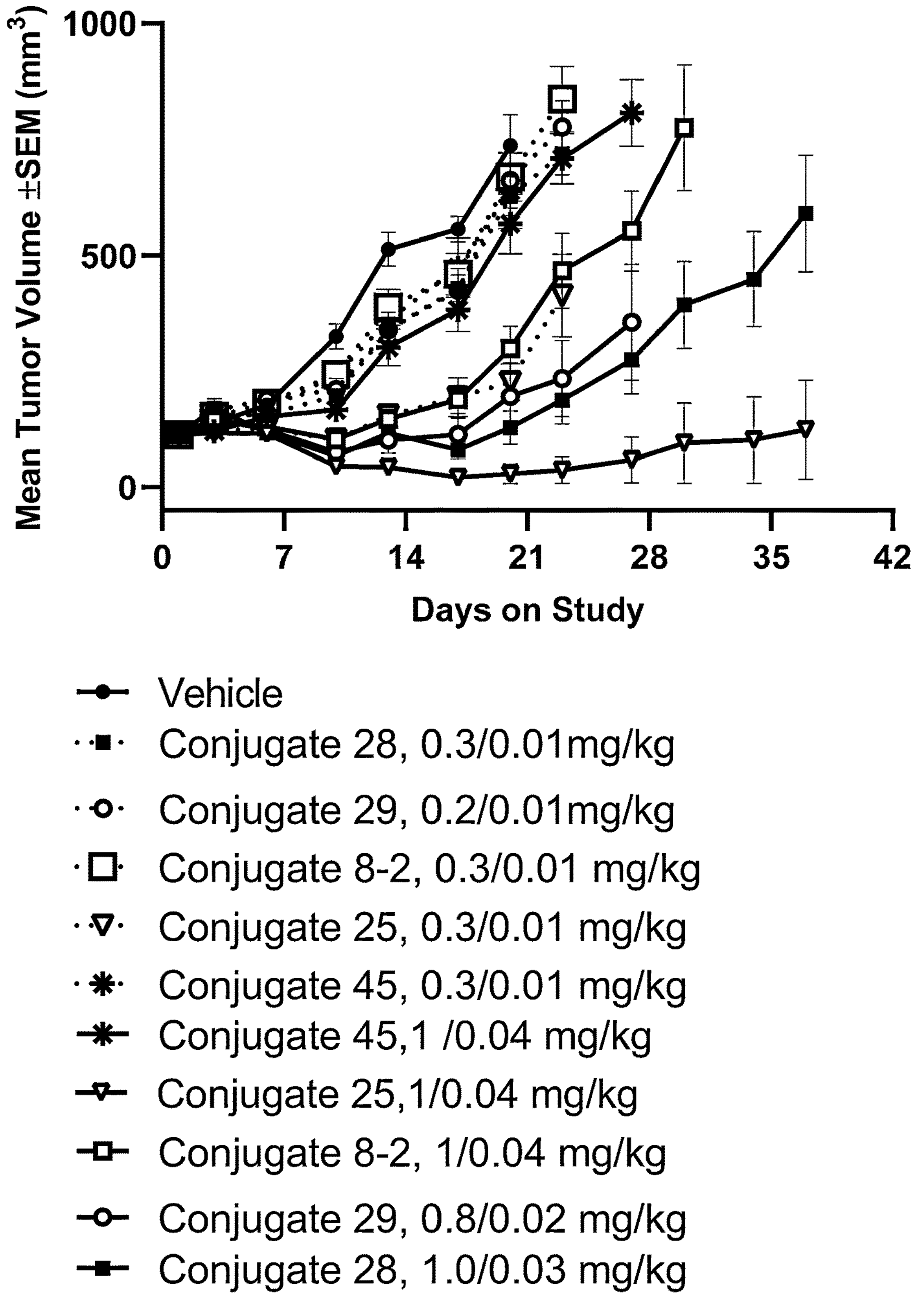
FIG. 19 is a graph showing the anti-tumor efficacy of Conjugate 28 (0.3/0.01 mg/kg or 1/0.03 mg/kg), Conjugate 29 (0.2/0.01 mg/kg or 0.8/0.02 mg/kg), Conjugate 8-2 (0.3/0.01 mg/kg or 1/0.04 mg/kg), Conjugate 25 (0.3/0.01 mg/kg or 1/0.04 mg/kg) or Conjugate 45 (0.3/0.01 mg/kg or 1/0.04 mg/kg) (all doses are given as antibody/payload) in a SKOV3 xenograft in mouse.

FIG. 19 provides tumor volumes of SKOV3 tumor-bearing mice treated with vehicle, Conjugate 28, Conjugate 29, Conjugate 8-2, Conjugate 25 or Conjugate 45. Treatment with Conjugate 28 (0.3/0.01 mg/kg or 1/0.03 mg/kg), Conjugate 29 (0.2/0.01 mg/kg or 0.8/0.02 mg/kg), Conjugate 8-2 (0.3/0.01 mg/kg or 1/0.04 mg/kg), Conjugate 25 (0.3/0.01 mg/kg), or Conjugate 45 (0.3/0.01 mg/kg or 1/0.04 mg/kg) resulted in 17.6, 97.6, 12.1, 86.9, 10.9, 70.3, 81.9, 15.8 and 27.2% TGI, respectively. Treatment with Conjugate 25 (1/0.04 mg/kg) resulted in 74.5% mean tumor regression.

Figure 20:
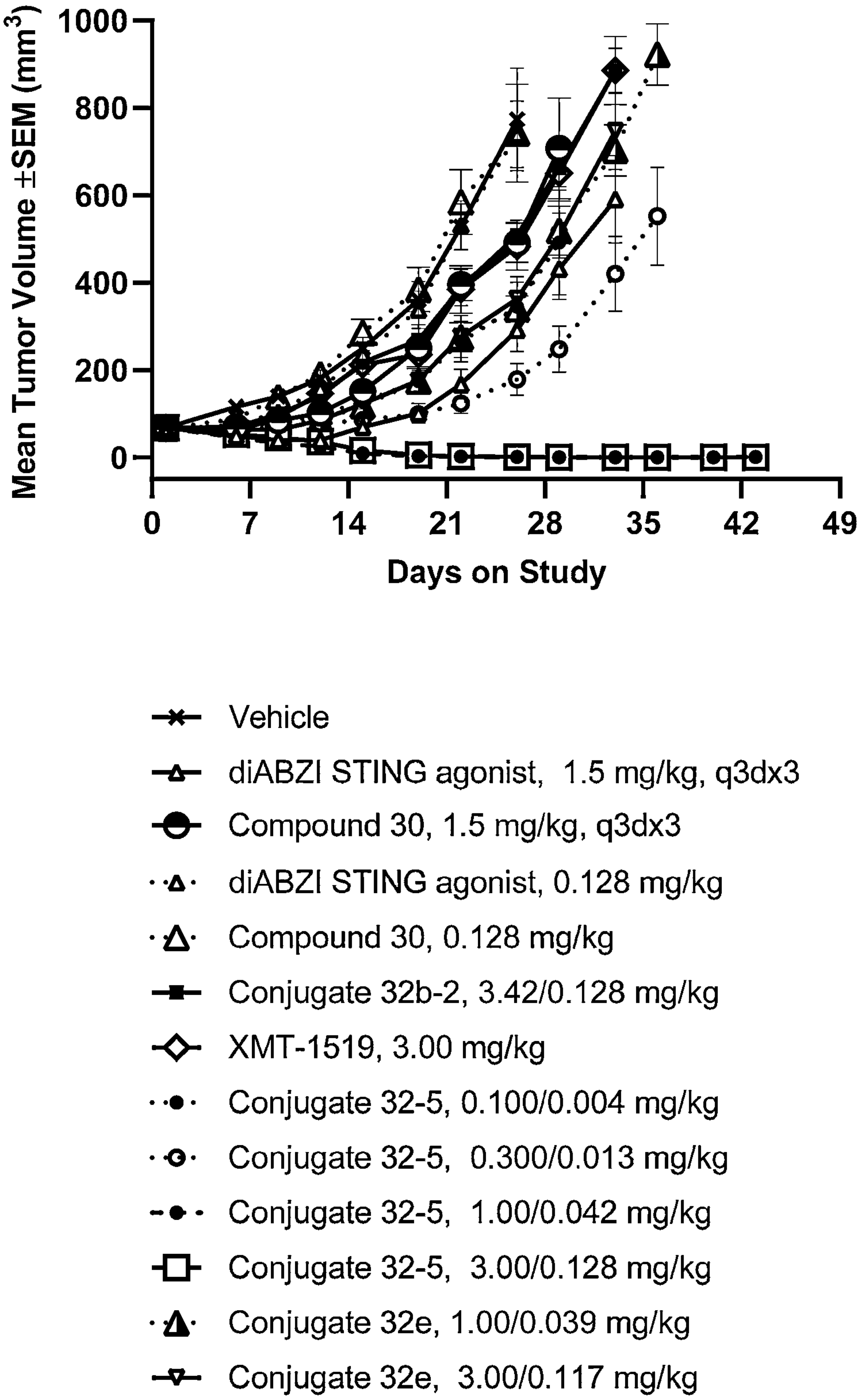
FIG. 20 graph showing the anti-tumor efficacy of diABZI STING agonist (1.5 mg/kg q3dx3 or 0.128 mg/kg qdx1), Compound 30 (1.5 mg/kg q3dx3 or 0.128 mg/kg qdx1), Conjugate 32b-2 (3.42/0.128 mg/kg qdx1), XMT-1519 (3.00 mg/kg qdx1), Conjugate 32-5 (0.100/0.004, 0.300/0.013, 1.00/0.042 or 3.00/0.128 mg/kg qdx1), Conjugate 32e (1.00/0.039 or 3.00/0.117 mg/kg qdx1)) (all doses are given as antibody/payload) in a SKOV3 xenograft in mouse.

Example 52: Tumor Growth Response to Administration of HER2 Antibody-Drug Conjugate in SKOV3 Ovarian Cancer Female CB.17 SCID mice were inoculated subcutaneously with SKOV3 human ovarian cancer cells ($10\times10^6$ cells/mouse+50% Matrigel). Animals were randomized into treatment groups when tumor volumes were between 63-75 $mm^3$ (mean=67.8 $mm^3$/group). Vehicle (saline, q3dx3 or q5dx5), diABZI STING agonist (1.5 mg/kg q3dx3 or 0.128 mg/kg qdx1), Compound 30 (1.5 mg/kg q3dx3 or 0.128 mg/kg qdx1), Conjugate 32b-2 (3.42/0.128 mg/kg qdx1), XMT-1519 (3.00 mg/kg qdx1), Conjugate 32-5 (0.100/0.004, 0.300/0.013, 1.00/0.042 or 3.00/0.128 mg/kg qdx1), Conjugate 32e (1.00/0.039 or 3.00/0.117 mg/kg qdx1) were all dosed intravenously starting on day 1 (all doses are given as antibody payload, n=10 for each group). FIG. 20 provides the tumor volumes of SKOV3 tumor-bearing mice treated with vehicle, diABZI STING agonist, Compound 30, Conjugate 32b-2, XMT-1519, Conjugate 32-5, or Conjugate 32e.

Treatment with Conjugate 32-5 at 1.00/0.042 or 3.00/0.117 mg/kg resulted in 10/10 complete responses.

Example 53: Tumor Growth Response to Administration of HER2 Antibody-Drug Conjugate in 4T1 Engineered to Express Human HER2

Female Balb/C mice were inoculated subcutaneously with 4T1 murine breast cancer cells engineered to express human HER2 (4T1-hHER2) ($2\times10^6$ cells per mouse). Animals were randomized into treatment groups when tumor volumes were between 75-88 $mm^3$ (mean=71.5-80.3 $mm^3$/group). Vehicle, Conjugate 8d-3 (1/0.04 mg/kg), or Conjugate 8k (0.9/0.04 mg/kg) were dosed intravenously as a single dose on day 1 (all doses are given as antibody/payload, n=10 for each group). Transient body weight loss within acceptable limits was observed 2 days following treatment with no additional clinical observations for Conjugate 8k (0.9/0.04 mg/kg)

Figure 21A:
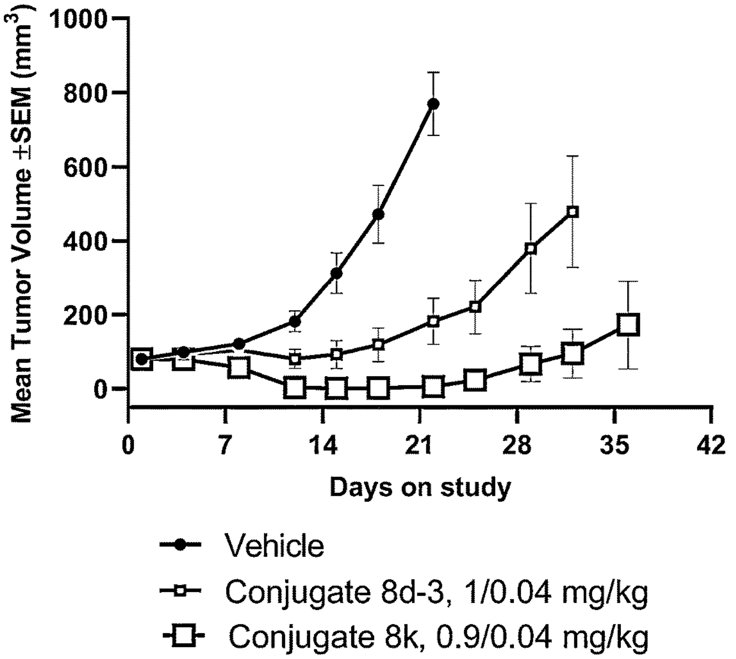
FIG. 21A is a graph showing the anti-tumor efficacy in a syngeneic mouse model of Conjugate 8d-3 (1/0.04 mg/kg) or Conjugate 8k (0.9/0.04 mg/kg).
Figure 21B:
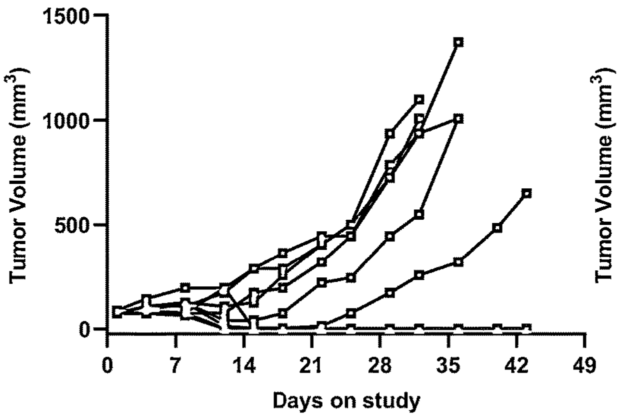
FIG. 21B shows the anti-tumor efficacy in a syngeneic mouse model of the individual mice for Conjugate 8d-3 (1/0.04 mg/kg).
Figure 21C:
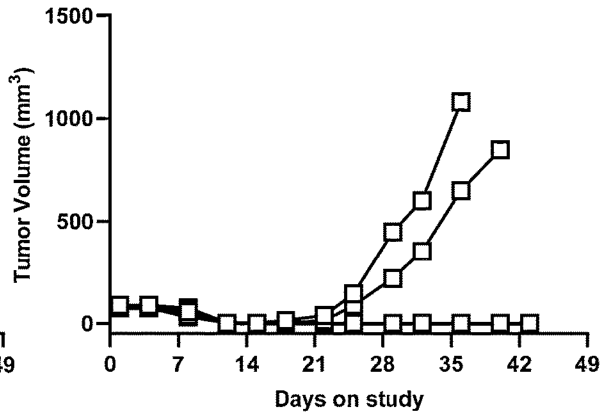
FIG. 21C shows the anti-tumor efficacy in a syngeneic mouse model of the individual mice for Conjugate 8k (0.9/0.04 mg/kg).

FIG. 21A provides tumor volumes of 4T1-hHER2 tumor-bearing mice treated with vehicle, Conjugate 8d-3 (1/0.04 mg/kg), or Conjugate 8k (0.9/0.04 mg/kg). Treatment with Conjugate 8d-3 (1/0.04 mg/kg) resulted in 85.4% TGI (FIG. 21B). Treatment with Conjugate 8k (0.9/0.04 mg/kg) resulted in 93.2% mean tumor regression, with 8 out of 10 animals tumor-free at the end of study (FIG. 21C).

Example 54: Tumor Growth Response to Administration of Fc Mutant HER2 Antibody-Drug Conjugates in SKOV3 Ovarian Cancer Female CB.17 SCID mice were inoculated subcutaneously with SKOV3 human ovarian cancer cells ($10\times10^6$ cells/mouse). Animals were randomized into treatment groups when tumor volumes were between 63-75 $mm^3$ (mean=72.6 $mm^3$/group). Vehicle, Conjugate 8c-2 (3.17/0.10 mg/kg), Conjugate 8a-2 (2.7/0.10 mg/kg or 0.81/0.03 mg/kg), Conjugate 8j (2.71/0.10 mg/kg or 0.81/0.03 mg/kg), or diABZI IV STING agonist (0/5 mg/kg) were dosed intravenously on day 1 (all doses are given as antibody/payload, n=10 for each group).

Figure 22:
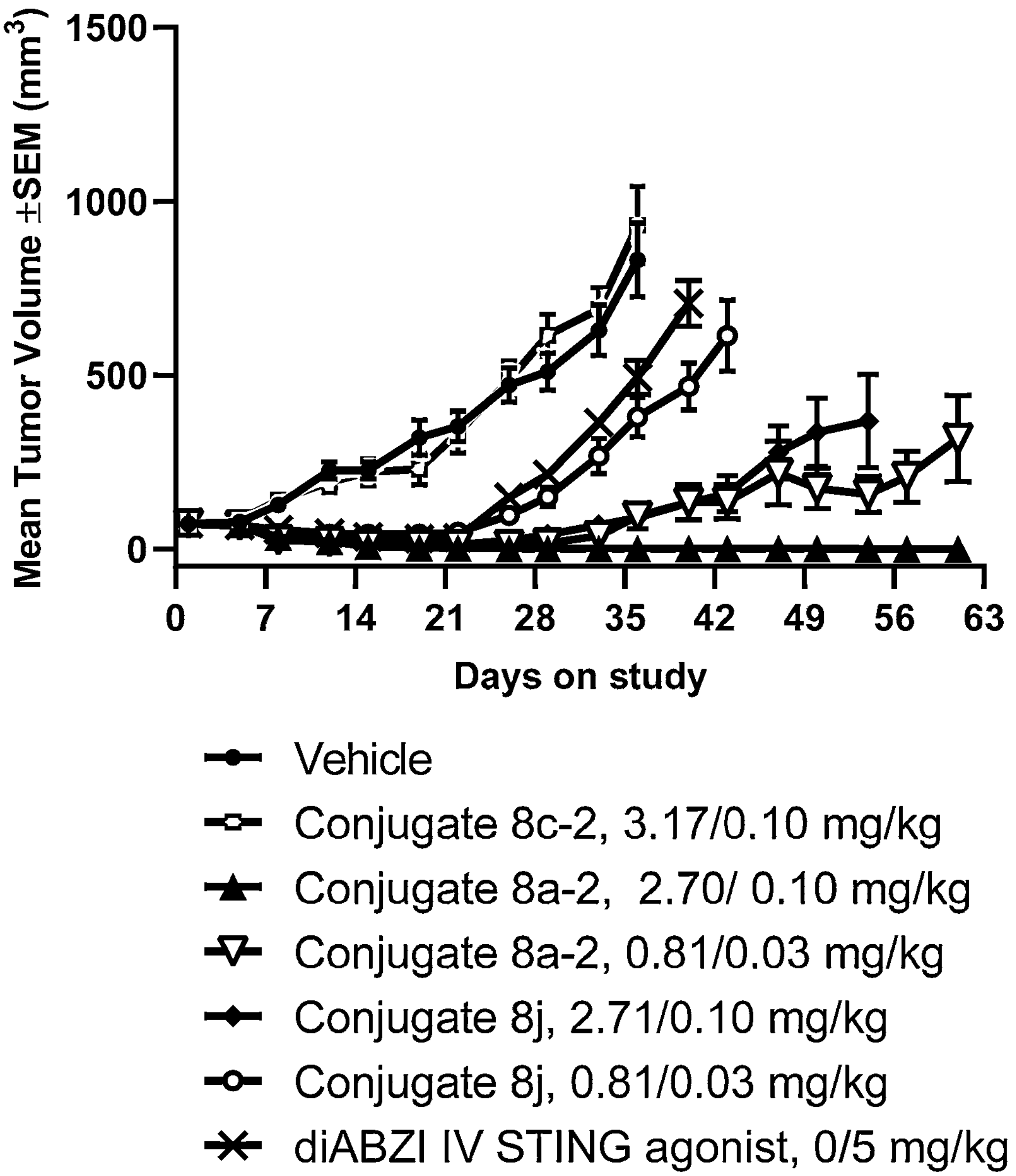
FIG. 22 is a graph showing the anti-tumor efficacy of Conjugate 8c-2 (3.17/0.10 mg/kg), Conjugate 8a-2 (2.7/0.10 mg/kg or 0.81/0.03 mg/kg), Conjugate 8j (2.71/0.10 mg/kg or 0.81/0.03 mg/kg), or diABZI IV STING agonist (0/5 mg/kg) (all doses are given as antibody/payload) in a SKOV3 xenograft in mouse.

FIG. 22 provides the tumor volumes of SKOV3 tumor-bearing mice treated with Conjugate 8c-2, Conjugate 8a-2, Conjugate 8j, or diABZI IV STING agonist. Treatment with Conjugate 8a-2 (2.70/0.10 mg/kg) resulted in 10 CR and 10 TFS. Treatment with Conjugate 8a-2 (0.81/0.030 mg/kg resulted in 2 PR, 8CR and 3 TFS. Treatment with Conjugate 8j (2.71/0.10 mg/kg) resulted in 2 PR and 6 CR. Treatment with Conjugate 8j (0.81/0.03 mg/kg) resulted in 3 PR and 1 CR. Treatment with diABZI IV STING agonist (0/5 mg/kg) resulted in 7 PR.

Example 55: In Vitro Binding of NaPi2b Antibody-Drug Conjugates to Human Ovarian Cancer Cells OVCAR3 cells were grown to ~80-95% confluency in RPMI 1640 medium supplemented with FBS (20%) and penicillin/streptomycin (1%). Cells were harvested and added to wells of a 96-well U bottom plate (50,000/well). The cells were pelleted (300× g, 5 minutes) and resuspended in solutions of test articles as indicated in Table 18 at concentrations ranging between 0.01 nM and 300 nM and incubated on ice for 1 hour. Cells were then washed in ice cold PBS (3×), pelleted (300 g, 5 minutes), and incubated with detection antibody (Goat Anti-Human IgG-Alexa-647 (H+L chain) for 1 hour at 4° C. Cell suspensions were pelleted (300 g, 5 minutes), washed 3 times in ice cold PBS, and fixed by resuspending in solution of paraformaldehyde (1%). Resuspended cells were then subjected to flow cytometry analysis on a MACS Quant Flow Cytometry. Single events (10,000) were collected for analysis. Population gating and Median Fluorescent Intensity (MFI) analysis was performed with MACS Quant Software. Table 18 summarizes the mean $EC_{50}$ values for cell binding.

TABLE 18

| Test Articles | DAR | Cell Binding $EC_{50}$ (nM) |
|---|---|---|
| Conjugate 60-1 | 6.2 | 3.33 |
| Conjugate 32d | 8.8 | 2.99 |
| Conjugate 32b-1 | 5.7 | ND |
| Conjugate 8b-3 | 6.4 | 8.13 |
| XMT-1535 | NA | 4.29 |
| XMT-1535 | NA | 3.74 |
| XMT-1535 mIgG2a | NA | 4.13 |
| Human IgG control | NA | ND |

ND = Not Determined; NA = Not Applicable

As shown in Table 18, $EC_{50}$ values for binding of NaPi2b ADCs to OVCAR3 cells were in the low nanomolar range whereas the isotype controls did not bind to OVCAR3 cells.

Example 56: Functional Activity of NaPi2b Bioconjugates in a Co-Culture Assay of OVCAR3 Human Ovarian Cancer and THP1 Reporter Cells The induction of STING pathway in immune cells by NaPi2b-targeted STING ADC was evaluated in a cancer cell/THP1-IRF3-Luciferase reporter cell co-culture assay. OVCAR3 human ovarian carcinoma cells were seeded in 96-well CellBind surface tissue culture plates (20,000/well) and allowed to attach for 6 hours in RPMI medium with 20% FBS and 1% penicillin/streptomycin. A range of dilutions (0.01 nM to 300 nM based on payload; 3-fold serial dilutions in growth medium) of the test articles were added to each well and the plate was incubated for 20 min at 37° C. 50,000 THP1-dual reporter cells were then added to each well and the incubation continued for 20 hours at 37° C., 5% $CO_2$. Cell culture supernatants (20 μl) from each incubated sample were added to resuspended QUANTI-Luc (50 μl) and the luminescent signal was measured immediately using a SpectraMax M5 plate reader (Molecular Devices). The $EC_{50}$ value was determined from the dose response curve. Table 19 provides the $EC_{50}$ values in THP1-Dual cells co-cultured with OVCAR3 cancer cells.

TABLE 19

| Test Article | Conjugate 32a | Conjugate 32d | Conjugate 32c | Conjugate 32b-1 | Conjugate 8b-3 |
|---|---|---|---|---|---|
| $EC_{50}$ (nM) | 0.29 | 0.47 | NA | NA | 0.21 |

As shown in Table 19, treatment of OVCAR3 and THP-1 co-cultures with NaPi2b-ADCs resulted in subnanomolar $EC_{50}$ values for induction of STING pathway in the THP-1 immune cells whereas the isotype controls had no activity.

Example 57: Tumor Growth Response to Administration of NaPi2b Antibody-Drug Conjugates in OVCAR-3

Female CB.17 SCID mice were inoculated subcutaneously with OVCAR-3 human ovarian cancer cells ($5\times10^6$ cells/mouse). Animals were randomized into treatment groups when tumor volumes were between 56-122 $mm^3$ (mean=83.9-84.7 $mm^3$/group) Vehicle, Conjugate 32b-1 (3.39/0.10 mg/kg), Conjugate 32a (0.93/0.03 or 3.12/0.10 mg/kg), Conjugate 32c (2.12/0.10 mg/kg), Conjugate 32d (2.20/0.10 mg/kg), or diABZI IV STING agonist (0/5 mg/kg) were dosed intravenously on day 1 (all doses are given as antibody/payload, n=10 for each group).

Figure 23:
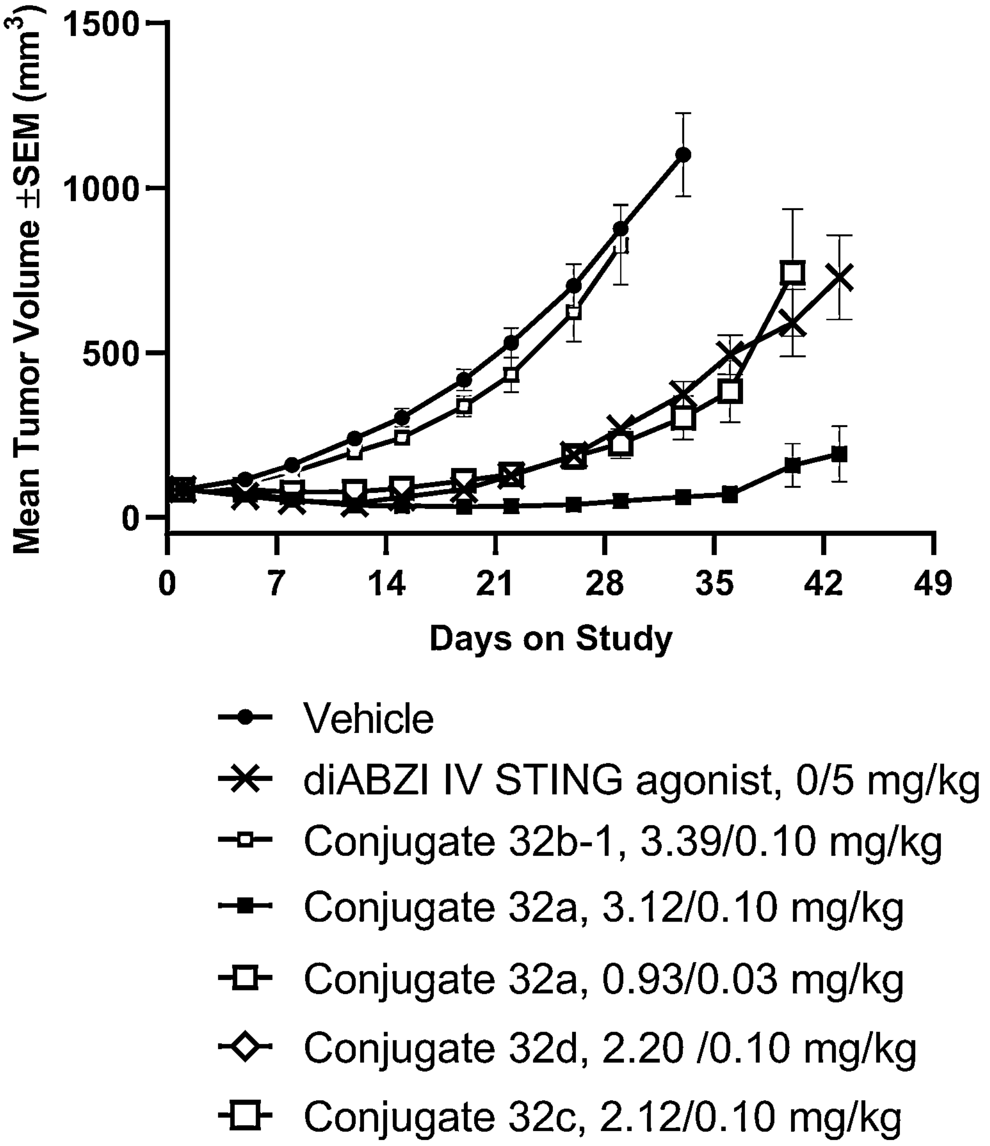
FIG. 23 is a graph showing the anti-tumor efficacy of Conjugate 32b-1 (3.39/0.10 mg/kg), Conjugate 32a (0.93/0.03 or 3.12/0.10 mg/kg), Conjugate 32c (2.12/0.10 mg/kg), Conjugate 32d (2.20/0.10 mg/kg) or diABZI IV STING agonist (0/5 mg/kg) (all doses are given as antibody/payload) in a OVCAR3 xenograft in mouse.

FIG. 23 provides the results for the tumor volumes of OVCAR-3 tumor-bearing mice treated with Conjugate 32b-1, Conjugate 32a, Conjugate 32c, Conjugate 32d, or diABZI IV STING agonist.

Example 58: Tumor Growth Response to Administration of NaPi2b STING Antibody-Drug Conjugate in Combination with a NaPi2b AF-HPA Antibody-Drug Conjugate in OVCAR-3

Female CB.17 SCID mice were inoculated subcutaneously with OVCAR-3 human ovarian cancer cells ($5\times10^6$ cells/mouse). Animals were randomized into treatment groups when tumor volumes were between 68-247 $mm^3$ (mean=148-148.2 $mm^3$/group) vehicle; a combination of Rituximab AF-HPA ADC (0.75/0.023 mg/kg) and Conjugate 8c-2 (4.0/0.126 mg/kg); XMT-1535 AF-HPA ADC (0.75/0.024 mg/kg); Conjugate 8b-2 (2.0/0.071 or 4.0/0.142 mg/kg); a combination of XMT-1535 AF-HPA ADC (0.75/0.024 mg/kg) and Conjugate 8c-2 (4.0/0.126 mg/kg); a combination of Rituximab AF-HPA ADC (0.75/0.023 mg/kg) and Conjugate 8b-2 (4.0/0.142 mg/kg); a combination of Rituximab AF-HPA ADC (0.75/0.023 mg/kg) and Conjugate 8b-2 (2.0/0.071 mg/kg); a combination of XMT-1535 AF-HPA ADC (0.75/0.024 mg/kg) and Conjugate 8b-2 (4.0/0.142 mg/kg); a combination of XMT-1535 AF-HPA ADC (0.75/0.024 mg/kg) and Conjugate 8b-2 (2.0/0.071 mg/kg); a combination of XMT-1535 AF-HPA ADC (0.75/0.024 mg/kg) and XMT-1535 (4.0/0 mg/kg); or XMT-1535 (4.75/0 mg/kg) were dosed intravenously on day 1 (all doses are given as antibody/payload, n=10 for each group).

Figure 24:
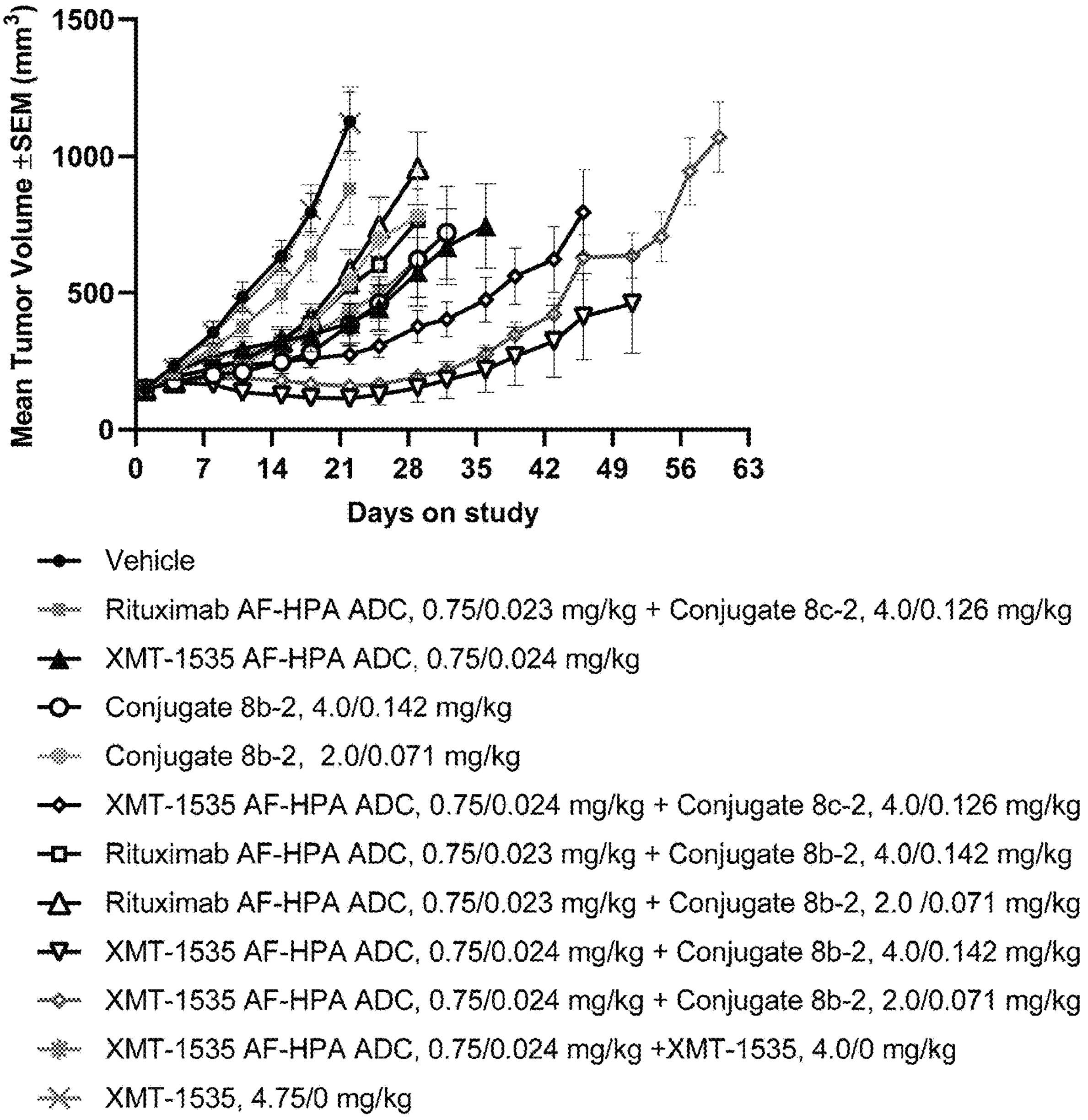
FIG. 24 is a graph showing the anti-tumor efficacy of a combination of Rituximab AF-HPA ADC (0.75/0.023 mg/kg) and Conjugate 8c-2 (4.0/0.126 mg/kg); XMT-1535 AF-HPA ADC (0.75/0.024 mg/kg); Conjugate 8b-2 (2.0/0.071 or 4.0/0.142 mg/kg); a combination of XMT-1535 AF-HPA ADC (0.75/0.024 mg/kg) and Conjugate 8c-2 (4.0/0.126 mg/kg); a combination of Rituximab AF-HPA ADC (0.75/0.023 mg/kg) and Conjugate 8b-2 (4.0/0.142 mg/kg); a combination of Rituximab AF-HPA ADC (0.75/0.023 mg/kg) and Conjugate 8b-2 (2.0/0.071 mg/kg); a combination of XMT-1535 AF-HPA ADC (0.75/0.024 mg/kg) and Conjugate 8b-2 (4.0/0.142 mg/kg); a combination of XMT-1535 AF-HPA ADC (0.75/0.024 mg/kg) and Conjugate 8b-2 (2.0/0.071 mg/kg); a combination of XMT-1535 AF-HPA ADC (0.75/0.024 mg/kg) and XMT-1535 (4.0/0 mg/kg); or XMT-1535 (4.75/0 mg/kg) in a OVCAR3 xenograft in mouse.

FIG. 24 provides the results for the tumor volumes of OVCAR-3 tumor-bearing mice treated with vehicle; a combination of Rituximab AF-HPA ADC and Conjugate 8c-2; XMT-1535 AF-HPA ADC; Conjugate 8b-2; a combination of XMT-1535 AF-HPA ADC and Conjugate 8c-2; a combination of Rituximab AF-HPA ADC and Conjugate 8b-2; a combination of Rituximab AF-HPA ADC and Conjugate 8b-2; a combination of XMT-1535 AF-HPA ADC and Conjugate 8b-2; a combination of XMT-1535 AF-HPA ADC and Conjugate 8b-2; a combination of XMT-1535 AF-HPA ADC and XMT-1535; or XMT-1535. All calculations were based on values on day 22. Treatment with a combination of Rituximab AF-HPA ADC (0.75/0.023 mg/kg) and Conjugate 8c-2 (4.0/0.126 mg/kg) resulted in TGI of 25.1% (n=10). Treatment with XMT-1535 AF-HPA ADC (0.75/0.024 mg/kg) resulted in a TGI of 71.6% (n=9) and a mean tumor shrinkage of 71.2% (n=1). Treatment with Conjugate 8b-2 (4.0/0.142 mg/kg) resulted in a TGI of 72.9% (n=9) and a mean tumor shrinkage of 48% (n=1). Treatment with Conjugate 8b-2 (2.0/0.071 mg/kg) resulted in a TGI of 59.8% (n=10). Treatment with a combination of XMT-1535 AF-HPA ADC (0.75/0.024 mg/kg) and Conjugate 8c-2 (4.0/0.126 mg/kg) resulted in a TGI of 85.1% (n=9) and a mean tumor shrinkage of 24.6% (n=1). Treatment with a combination of Rituximab AF-HPA ADC (0.75/0.023 mg/kg) and Conjugate 8b-2 (4.0/0.142 mg/kg) resulted in a TGI of 61.7% (n=10). Treatment with a combination of Rituximab AF-HPA ADC (0.74/0.023 mg/kg) and Conjugate 8b-2 (2.0/

0.071 mg/kg) resulted in a TGI of 55.7% (n=10). Treatment with a combination of XMT-1535 AF-HPA ADC (0.75/0.024 mg/kg) and Conjugate 8b-2 (4.0/0.142 mg/kg) resulted in a TGI of 95.2% (n=4) and a mean tumor shrinkage of 60.5% (n=6). Treatment with a combination of XMT-1535 AF-HPA ADC (0.75/0.024 mg/kg) and Conjugate 8b-2 (2.0/0.071 mg/kg) resulted in a TGI of 98.2% (n=8) and a mean tumor shrinkage of 17.8% (n=2). Treatment with a combination of XMT-1535 AF-HIPA ADC (0.75/0.024 mg/kg) and XMT-1535 (4.00/0 mg/kg) resulted in a TGI of 68.2% (n=9) and a mean tumor shrinkage of 23.7% (n=1). Treatment with XMT-1535 (4.75/0 mg/kg) resulted in a TGI of 0.6% (n=10).

Example 59: Tumor Growth Response to Administration of HER2 Antibody-Drug Conjugates in SKOV3 Ovarian Cancer Female CB.17 SCID mice were inoculated subcutaneously with SKOV3 human ovarian cancer cells ($10\times10^6$ cells/mouse). Animals were randomized into treatment groups when tumor volumes were between 75-100 $mm^3$ (mean=84-85 $mm^3$/group). Vehicle, Conjugate 32b (0.85/0.03 mg/kg), Conjugate 32-2 (0.90/0.03 mg/kg), Conjugate 88 (0.87/0.03 mg/kg), Conjugate 85 (2.87/0.10 mg/kg), Conjugate 92 (2.36/0.10 mg/kg), Conjugate 100 (2.23/0.10 mg/kg), Conjugate 89 (0.99/0.030 mg/kg), Conjugate 85a (2.59/0.10 mg/kg), Conjugate 93 (2.85/0.10 mg/kg), or Conjugate 101 (2.70/0.10 mg/kg) were dosed intravenously on day 1 (all doses are given as antibody/payload, n=10 for each group).

Figure 25:
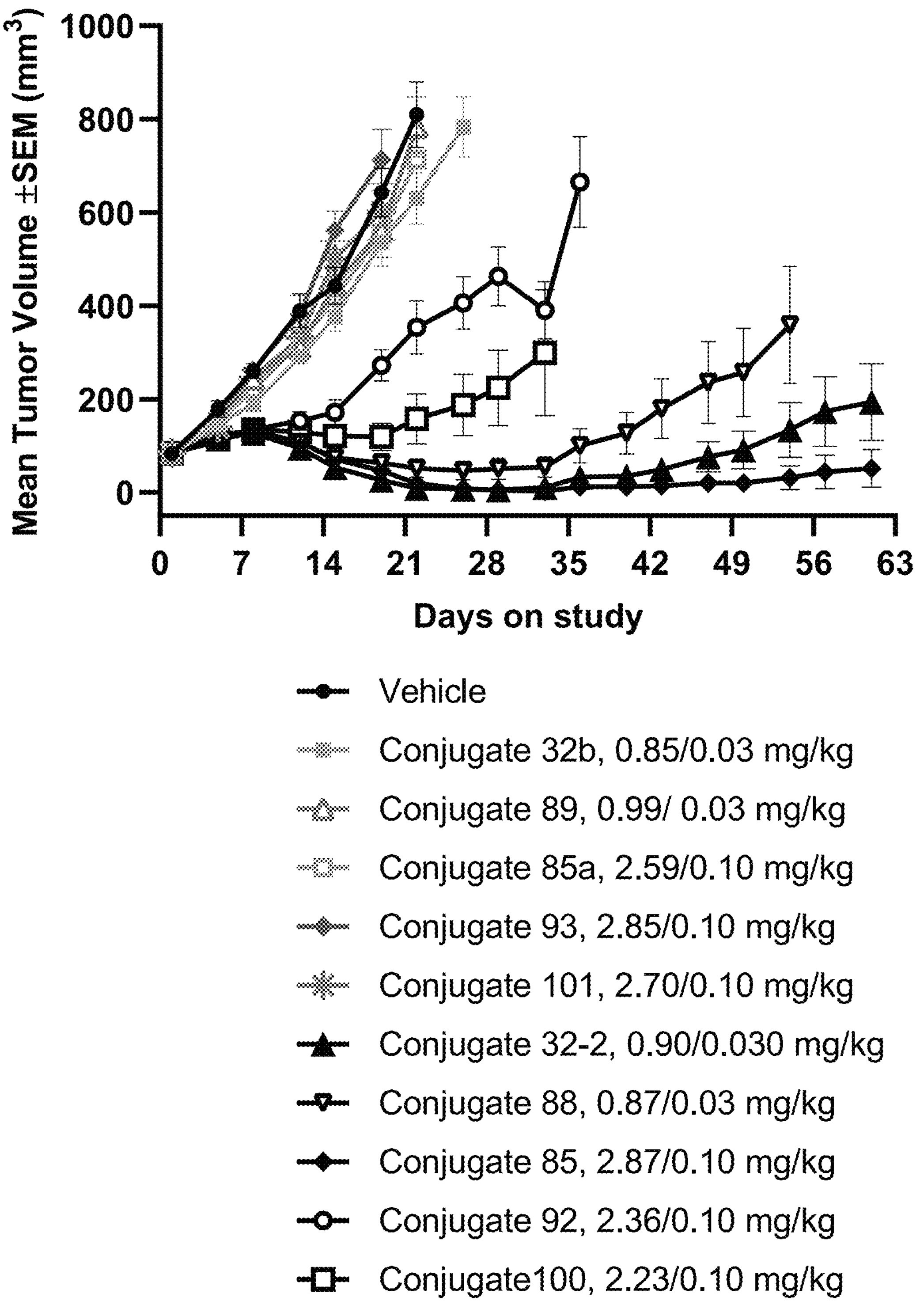
FIG. 25 is a graph showing the anti-tumor efficacy of Conjugate 32b (0.85/0.03 mg/kg), Conjugate 32-2 (0.90/0.03 mg/kg), Conjugate 88 (0.87/0.03 mg/kg), Conjugate 85 (2.87/0.10 mg/kg), Conjugate 92 (2.36/0.10 mg/kg), Conjugate 100 (2.23/0.10 mg/kg), Conjugate 89 (0.99/0.030 mg/kg), Conjugate 85a (2.59/0.10 mg/kg), Conjugate 93 (2.85/0.10 mg/kg), or Conjugate 101 (2.70/0.10 mg/kg) in a SKOV3 xenograft model in mouse.

FIG. 25 provides the results for the tumor volumes of SKOV3 tumor-bearing mice treated with Conjugate 32b, Conjugate 32-2, Conjugate 88, Conjugate 85, Conjugate 92, Conjugate 100, Conjugate 89, Conjugate 85a, Conjugate 93, or Conjugate 101. Treatment with Conjugate 32-2 (0.90/0.03 mg/kg) resulted in 1 PR and 9 CR and 5 TFS. Treatment with Conjugate 88 (0.87/0.03 mg/kg) resulted in 6 CR and 4 TFS. Treatment with Conjugate 85 (2.87/0.10 mg/kg) resulted in 9 CR and 8 TFS. Treatment with Conjugate 100 (2.23/0.10 mg/kg) resulted 1 PR.

Example 60: Tumor Growth Response to Administration of HER2 Antibody-Drug Conjugates in SKOV3

Female CB.17 SCID mice were inoculated subcutaneously with SKOV3 human ovarian cancer cells ($10\times10^6$ cells/mouse). Animals were randomized into treatment groups when tumor volumes were between 75-144 $mm^3$ (mean=112-114 $mm^3$/group) (n=10/group). Vehicle, Conjugate 28 (0.99/0.0325 mg/kg), or Conjugate 62 (0.9/0.0325 mg/kg) were dosed intravenously on day 1 (all doses are given as antibody/payload, n=10 for each group).

Figure 26:
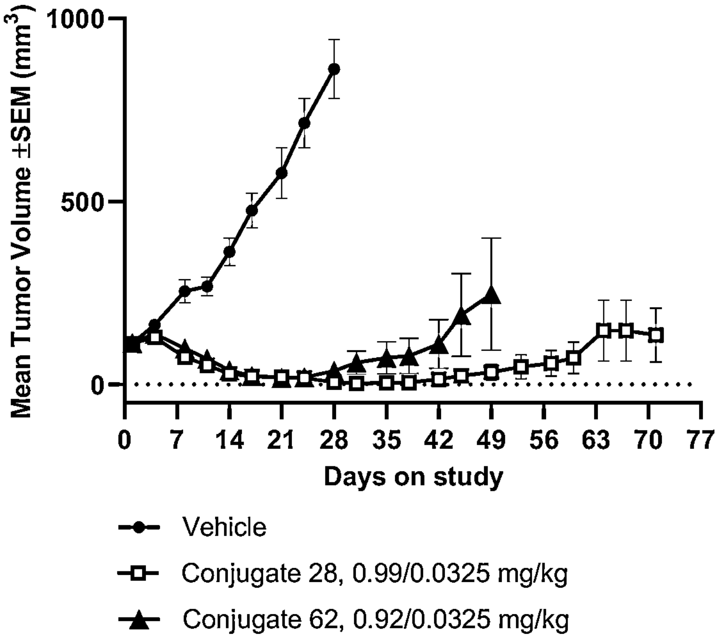
FIG. 26 is a graph showing the anti-tumor efficacy of with vehicle, Conjugate 28 (0.99/0.0325 mg/kg), or Conjugate 62 (0.92/0.0325 mg/kg) in a SKOV3 xenograft model in mouse.

FIG. 26 provides the results for the tumor volumes of SKOV3 tumor-bearing mice treated with vehicle, Conjugate 28, or Conjugate 62 (HER2-targeted). Treatment with Conjugate 28 (0.99/0.0325 mg/kg) resulted in 1 PR, 8 CR, and 5 TFS. Treatment with Conjugate 62 (0.92/0.0325 mg/kg) resulted in 2 PR, 7 CR and 4 TFS.

Example 61: Pharmacokinetics of HER2 Antibody-Drug Conjugates in SKOV3

Female CB.17 SCID mice were treated with a single, intravenous injection of vehicle, Conjugate 28 (3.0/0.10 mg/kg), or Conjugate 62 (2.84/0.10 mg/kg) (all doses are given as antibody/payload, n=4 for each group). Plasma was collected at 15 minutes, 1, 6, 24, 48, 72, 96, 168, and 336 hours following treatment. Plasma was diluted 1:10 in 1.33 mg/ml citric acid for a total volume of 0.1 ml. Diluted plasma was snap-frozen on dry ice and stored at −80° C. until PK analysis.

Figure 27:
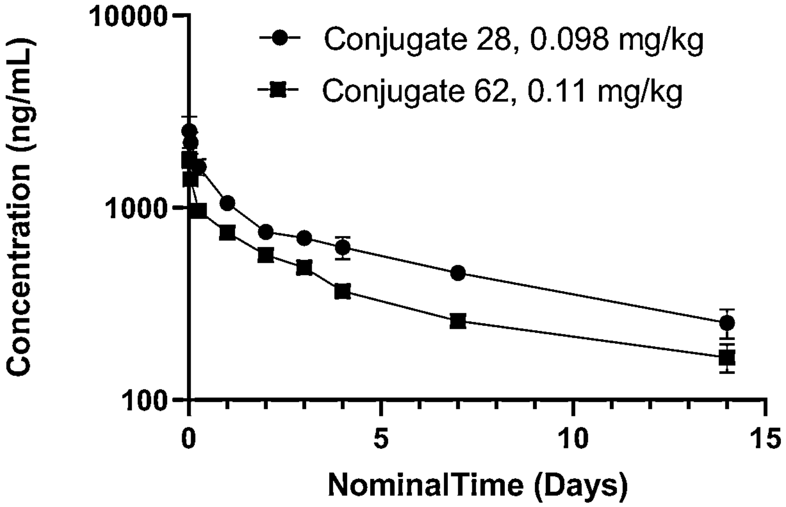
FIG. 27 is a graph showing the circulating plasma concentrations for conjugated drug following administration of Conjugate 28 (3.0/0.10 mg/kg) or Conjugate 62 (2.84/0.10 mg/kg) (dose is given as antibody/payload) to CB.17 SCID mice.

FIG. 27 provides the results for circulating plasma concentrations of conjugated drug. Plasma concentrations of ~2.5 µg/mL and ~1.8 µg/mL were achieved for Conjugate 28 and Conjugate 62, respectively, and a corresponding clearance rate of ~9.05 mL/day/kg and ~14.6 mL/day/kg respectively.

EQUIVALENTS

The details of one or more embodiments of the invention are set forth in the accompanying description above. Although any methods and materials similar or equivalent to those described herein can be used in the practice or testing of the present disclosure, the methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

What is claimed is:

1. An antibody-drug conjugate (ADC) being

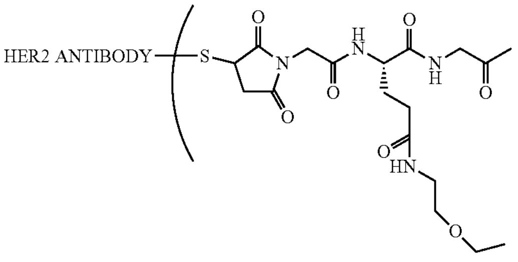

-continued

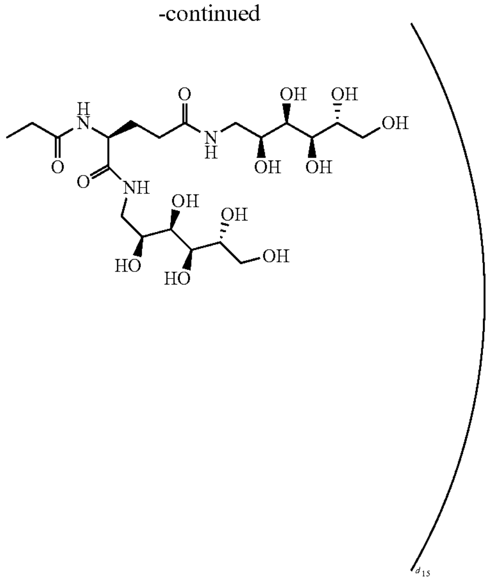

;

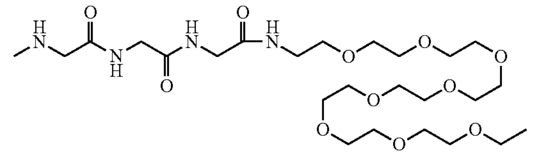

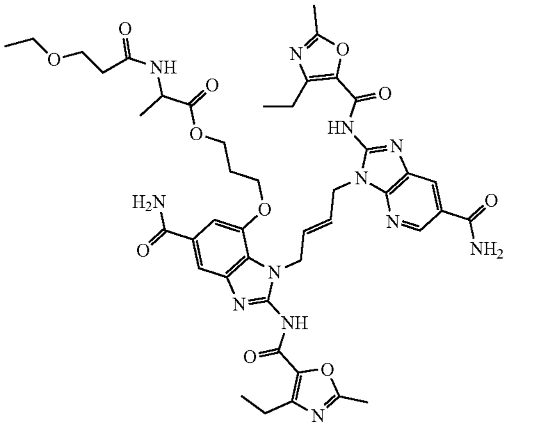

or a pharmaceutically acceptable salt or stereoisomer thereof, wherein the HER2 antibody comprises a variable heavy chain complementarity determining region 1 (CDRH1) comprising the amino acid sequence FTFSSYSMN (SEQ ID NO: 20); a variable heavy chain complementarity determining region 2 (CDRH2) comprising the amino acid sequence YISSSSSTIYYADSVKG (SEQ ID NO: 21); a variable heavy chain complementarity determining region 3 (CDRH3) comprising the amino acid sequence GGHGYFDL (SEQ ID NO: 22); a variable light chain complementarity determining region 1 (CDRL1) comprising the amino acid sequence RASQSVSSSYLA (SEQ ID NO: 27); a variable light chain complementarity determining region 2 (CDRL2) comprising the amino acid sequence GASSRAT (SEQ ID NO: 28); and a variable light chain complementarity determining region 3 (CDRL3) comprising the amino acid sequence QQYHHSPLT (SEQ ID NO: 29), and $d_{15}$ represents an integer ranging from about 1 to about 20.

2. The conjugate of claim 1, or a pharmaceutically acceptable salt or stereoisomer thereof, wherein the HER2 antibody comprises a heavy chain variable region comprising the amino acid sequence set forth in SEQ ID NO: 17 and a light chain variable region comprising the amino acid sequence set forth in SEQ ID NO: 24.

3. The conjugate of claim 1, or a pharmaceutically acceptable salt or stereoisomer thereof, wherein the HER2 antibody comprises a heavy chain comprising the amino acid sequence set forth in SEQ ID NO: 19 and a light chain comprising the amino acid sequence set forth in SEQ ID NO: 26.

4. The conjugate of claim 1, or a pharmaceutically acceptable salt or stereoisomer thereof, wherein $d_{15}$ represents an integer ranging from about 2 to about 14.

5. The conjugate of claim 1, or a pharmaceutically acceptable salt or stereoisomer thereof, wherein $d_{15}$ represents an integer ranging from about 2 to about 8.

6. The conjugate of claim 1, or a pharmaceutically acceptable salt or stereoisomer thereof, wherein $d_{15}$ is about 2, about 4, about 6, or about 8.

7. The conjugate of claim 1, or a pharmaceutically acceptable salt or stereoisomer thereof, wherein $d_{15}$ is an integer ranging from about 6 to about 10.

8. The conjugate of claim 1, or a pharmaceutically acceptable salt or stereoisomer thereof, wherein $d_{15}$ is about 6.

9. The conjugate of claim 1, or a pharmaceutically acceptable salt or stereoisomer thereof, wherein $d_{15}$ is about 7.

10. The conjugate of claim 1, or a pharmaceutically acceptable salt or stereoisomer thereof, wherein $d_{15}$ is about 8.

11. A pharmaceutical composition comprising the conjugate of claim 1, or a pharmaceutically acceptable salt or stereoisomer thereof, and one or more pharmaceutically acceptable carriers or excipients.

12. The pharmaceutical composition of claim 11, further comprising at least one immuno-modulator or at least one immunostimulatory agent.

13. A method of activating or enhancing an activity of a stimulator of interferon genes (STING) in a subject, comprising administering to the subject the conjugate of claim 1, or a pharmaceutically acceptable salt or stereoisomer thereof.

14. A method of treating a disease or disorder associated with the modulation of STING in a subject, comprising administering to the subject the conjugate of claim 1, or a pharmaceutically acceptable salt or stereoisomer thereof.

15. The method of claim 14, wherein the disease or disorder is cancer.

16. The method of claim 15, wherein the cancer is bladder cancer, breast cancer, colorectal cancer, colon cancer, endometrial cancer, gastric cancer, head and neck squamous carcinoma, melanoma, lung cancer, ovarian cancer, esophageal cancer, biliary cancer, urothelial cancer, cervical cancer, papillary thyroid cancer, papillary renal cell cancer, cholangiocarcinoma, salivary duct cancer, kidney cancer, or pancreatic cancer.

17. The method of claim 16, wherein the cancer is breast cancer, colorectal cancer, gastric cancer, or lung cancer.

18. An antibody-drug conjugate (ADC) being

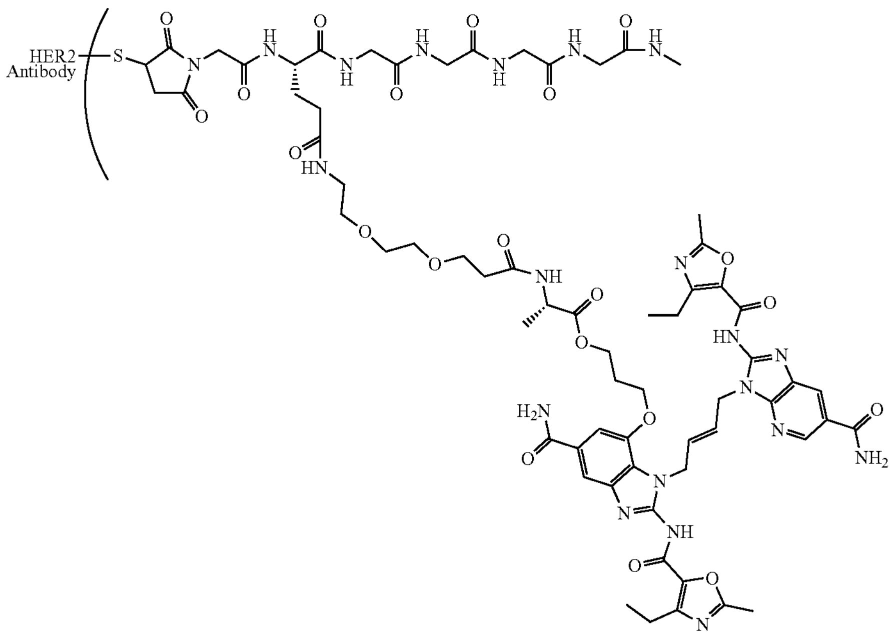

-continued

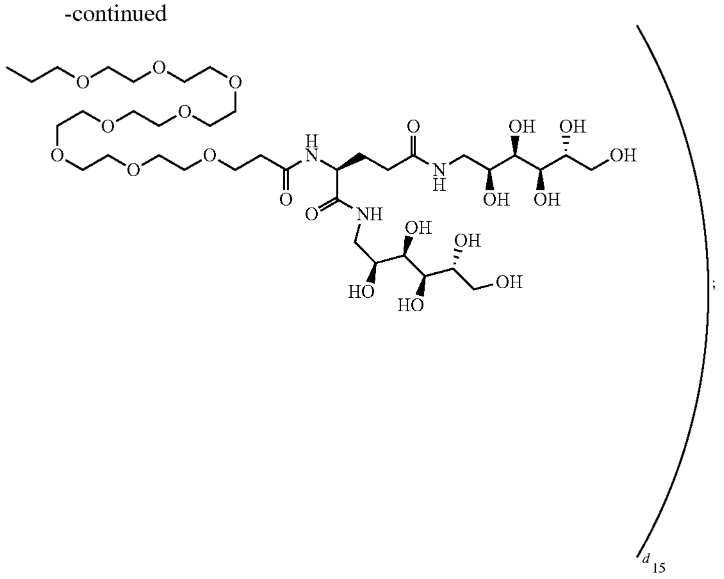

or a pharmaceutically acceptable salt or stereoisomer thereof, wherein the HER2 antibody comprises a variable heavy chain complementarity determining region 1 (CDRH1) comprising the amino acid sequence FTFSSYSMN (SEQ ID NO: 20); a variable heavy chain complementarity determining region 2 (CDRH2) comprising the amino acid sequence YISSSSSTIYYADSVKG (SEQ ID NO: 21); a variable heavy chain complementarity determining region 3 (CDRH3) comprising the amino acid sequence GGHGYFDL (SEQ ID NO: 22); a variable light chain complementarity determining region 1 (CDRL1) comprising the amino acid sequence RASQSVSSSYLA (SEQ ID NO: 27); a variable light chain complementarity determining region 2 (CDRL2) comprising the amino acid sequence GASSRAT (SEQ ID NO: 28); and a variable light chain complementarity determining region 3 (CDRL3) comprising the amino acid sequence QQYHHSPLT (SEQ ID NO: 29), and $d_{15}$ represents an integer ranging from about 1 to about 20.

19. An antibody-drug conjugate of Formula (I):

$$PBRM\text{-}[A^1\text{-}(L^C)\text{-}D]_{d15} \quad (I),$$

or a pharmaceutically acceptable salt or stereoisomer thereof, wherein:

$A^1$ is

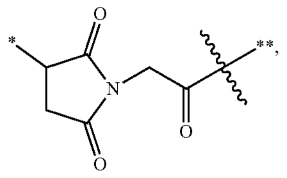

wherein * denotes attachment to PBRM and ** denotes attachment to $L^C$;

$L^C$ is

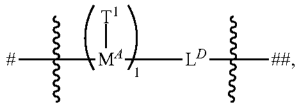

wherein # denotes attachment to $A^1$ and ## denotes attachment to D;

$M^A$ is

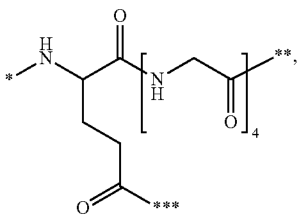

wherein * denotes attachment to $A^1$,  denotes attachment to $T^1$, and * denotes attachment to $L^D$;

$L^D$ is *—NH—$(CH_2CH_2O)_2$—$(CH_2)_2$—C(O)-(alanine)-**, wherein* denotes attachment to $M^A$ and **** denotes attachment to D;

$T^1$ is

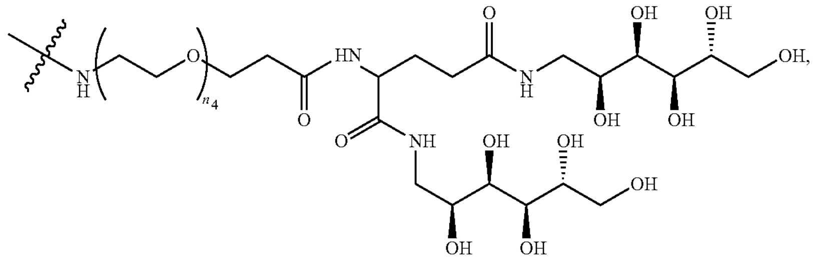

wherein $n_4$ is 8;

D is

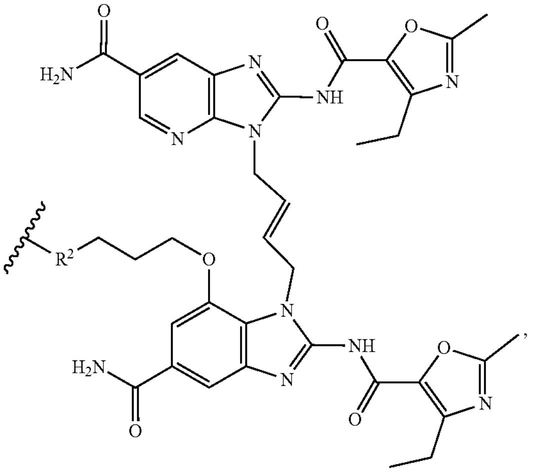

wherein $R^2$ is —O—, and

denotes attachment to $L^D$;

PBRM is a HER2 antibody comprising a variable heavy chain complementarity determining region 1 (CDRH1) comprising the amino acid sequence FTFSSYSMN (SEQ ID NO: 20); a variable heavy chain complementarity determining region 2 (CDRH2) comprising the amino acid sequence YISSSSSTIYYADSVKG (SEQ ID NO: 21); a variable heavy chain complementarity determining region 3 (CDRH3) comprising the amino acid sequence GGHGYFDL (SEQ ID NO: 22); a variable light chain complementarity determining region 1 (CDRL1) comprising the amino acid sequence RASQSVSSSYLA (SEQ ID NO: 27); a variable light chain complementarity determining region 2 (CDRL2) comprising the amino acid sequence GASSRAT (SEQ ID NO: 28); and a variable light chain complementarity determining region 3 (CDRL3) comprising the amino acid sequence QQYHHSPLT (SEQ ID NO: 29); and $d_{15}$ represents an integer ranging from about 1 to about 20.

20. The conjugate of claim 19, or a pharmaceutically acceptable salt or stereoisomer thereof, wherein $L^D$ is

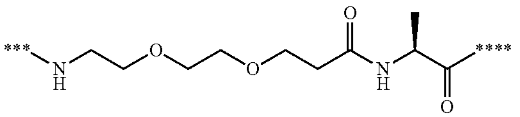

or

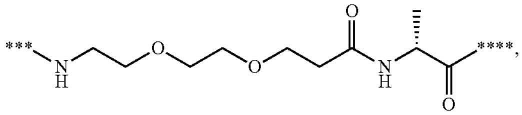

wherein:

* denotes attachment to $M^A$, and ** denotes attachment to D.

* * * * *

SEQUENCE LISTING

```
Sequence total quantity: 31
SEQ ID NO: 1           moltype = AA  length = 449
FEATURE                Location/Qualifiers
source                 1..449
                       mol_type = protein
                       organism = Homo sapiens
SEQUENCE: 1
QVQLVQSGAE VVKPGASVKM SCKASGYTFT GYNIHWVKQA PGQGLEWIGA IYPGNGDTSY  60
KQKFRGRATL TADTSTSTVY MELSSLRSED SAVYYCARGE TARATFAYWG QGTLVTVSSG  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449
```

```
SEQ ID NO: 2            moltype = AA  length = 215
FEATURE                 Location/Qualifiers
source                  1..215
                        mol_type = protein
                        organism = Homo sapiens
SEQUENCE: 2
DIQMTQSPSS LSASVGDRVT ITCSASQDIG NFLNWYQQKP GKTVKVLIYY TSSLYSGVPS  60
RFSGSGSGTD YTLTISSLQP EDFATYYCQQ YSKLPLTFGQ GTKLELKRRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 3            moltype = AA  length = 120
FEATURE                 Location/Qualifiers
source                  1..120
                        mol_type = protein
                        organism = Homo sapiens
SEQUENCE: 3
QVQLVQSGAE VVKPGASVKM SCKASGYTFT GYNIHWVKQA PGQGLEWIGA IYPGNGDTSY  60
KQKFRGRATL TADTSTSTVY MELSSLRSED SAVYYCARGE TARATFAYWG QGTLVTVSSG  120

SEQ ID NO: 4            moltype = AA  length = 108
FEATURE                 Location/Qualifiers
source                  1..108
                        mol_type = protein
                        organism = Homo sapiens
SEQUENCE: 4
DIQMTQSPSS LSASVGDRVT ITCSASQDIG NFLNWYQQKP GKTVKVLIYY TSSLYSGVPS  60
RFSGSGSGTD YTLTISSLQP EDFATYYCQQ YSKLPLTFGQ GTKLELKR              108

SEQ ID NO: 5            moltype = AA  length = 10
FEATURE                 Location/Qualifiers
source                  1..10
                        mol_type = protein
                        organism = Homo sapiens
SEQUENCE: 5
GYTFTGYNIH                                                        10

SEQ ID NO: 6            moltype = AA  length = 17
FEATURE                 Location/Qualifiers
source                  1..17
                        mol_type = protein
                        organism = Homo sapiens
SEQUENCE: 6
AIYPGNGDTS YKQKFRG                                                17

SEQ ID NO: 7            moltype = AA  length = 10
FEATURE                 Location/Qualifiers
source                  1..10
                        mol_type = protein
                        organism = Homo sapiens
SEQUENCE: 7
GETARATFAY                                                        10

SEQ ID NO: 8            moltype = AA  length = 11
FEATURE                 Location/Qualifiers
source                  1..11
                        mol_type = protein
                        organism = Homo sapiens
SEQUENCE: 8
SASQDIGNFL N                                                      11

SEQ ID NO: 9            moltype = AA  length = 7
FEATURE                 Location/Qualifiers
source                  1..7
                        mol_type = protein
                        organism = Homo sapiens
SEQUENCE: 9
YTSSLYS                                                           7

SEQ ID NO: 10           moltype = AA  length = 9
FEATURE                 Location/Qualifiers
source                  1..9
                        mol_type = protein
                        organism = Homo sapiens
SEQUENCE: 10
QQYSKLPLT                                                         9

SEQ ID NO: 11           moltype = AA  length = 329
```

-continued

```
FEATURE                Location/Qualifiers
source                 1..329
                       mol_type = protein
                       organism = Homo sapiens
SEQUENCE: 11
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                  329

SEQ ID NO: 12          moltype = AA  length = 107
FEATURE                Location/Qualifiers
source                 1..107
                       mol_type = protein
                       organism = Homo sapiens
SEQUENCE: 12
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 13          moltype = DNA  length = 357
FEATURE                Location/Qualifiers
source                 1..357
                       mol_type = genomic DNA
                       organism = Homo sapiens
SEQUENCE: 13
caagttcagc tggttcagtc tggcgccgag gttgtgaaac ctggcgcctc tgtgaagatg  60
agctgcaagg ccagcggcta caccttcacc ggctacaaca tccactgggt caagcaggcc  120
cctggacagg gactcgaatg gatcggagcc atctatcccg gcaacggcga caccagctac  180
aagcagaagt tccggggcag agccacactg accgccgata caagcaccag caccgtgtac  240
atggaactga gcagcctgag aagcgaggac agcgccgtgt actattgcgc cagaggcgaa  300
acagccagag ccacctttgc ctattggggc cagggaaccc tggtcaccgt tagctct     357

SEQ ID NO: 14          moltype = DNA  length = 321
FEATURE                Location/Qualifiers
source                 1..321
                       mol_type = genomic DNA
                       organism = Homo sapiens
SEQUENCE: 14
gatattcaga tgacacagag ccccagcagc ctgtctgcct ctgtgggaga cagagtgacc  60
atcacctgta gcgccagcca ggatatcggc aacttcctga actggtatca gcagaaaccc  120
ggcaagaccg tgaaggtgct gatctactac acctccagcc tgtacagcgg cgtgcccagc  180
agattttctg gcagcggctc tggcaccgac tacaccctga ccatatctag cctgcagcct  240
gaggacttcg ccacctacta ctgccagcag tacagcaagc tgcccctgac atttggccag  300
ggcaccaagc tggaactgaa g                                            321

SEQ ID NO: 15          moltype = AA  length = 690
FEATURE                Location/Qualifiers
source                 1..690
                       mol_type = protein
                       organism = Homo sapiens
SEQUENCE: 15
MAPWPELGDA QPNPDKYLEG AAGQQPTAPD KSKETNKTDN TEAPVTKIEL LPSYSTATLI  60
DEPTEVDDPW NLPTLQDSGI KWSERDTKGK ILCFFQGIGR LILLLGFLYF FVCSLDILSS  120
AFQLVGGKMA GQFFSNSSIM SNPLLGLVIG VLVTVLVQSS STSTSIVVSM VSSSLLTVRA  180
AIPIIMGANI GTSITNTIVA LMQVGDRSEF RRAFAGATVH DFFNWLSVLV LLPVEVATHY  240
LEIITQLIVE SFHFKNGEDA PDLLKVITKP FTKLIVQLDK KVISQIAMND EKAKNKSLVK  300
IWCKTFTNKT QINVTVPSTA NCTSPSLCWT DGIQNWTMKN VTYKENIAKC QHIFVNFHLP  360
DLAVGTILLI LSLLVLCGCL IMIVKILGSV LKGQVATVIK KTINTDFPFP FAWLTGYLAI  420
LVGAGMTFIV QSSSVFTSAL TPLIGIGVIT IERAYPLTLG SNIGTTTTAI LAALASPGNA  480
LRSSLQIALC HFFFNISGIL LWYPIPFTRL PIRMAKGLGN ISAKYRWFAV FYLIIFFFLI  540
PLTVFGLSLA GWRVLVGVGV PVVFIIILVL CLRLLQSRCP RVLPKKLQNW NFLPLWMRSL  600
KPWDAVVSKF TGCFQMRCCC CCRVCCRACC LLCDCPKCCR CSKCCEDLEE AQEGQDVPVK  660
APETFDNITI SREAQGEVPA SDSKTECTAL                                  690

SEQ ID NO: 16          moltype = AA  length = 1255
FEATURE                Location/Qualifiers
source                 1..1255
                       mol_type = protein
                       organism = Homo sapiens
SEQUENCE: 16
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
```

-continued

```
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255

SEQ ID NO: 17          moltype = AA  length = 117
FEATURE                Location/Qualifiers
source                 1..117
                       mol_type = protein
                       organism = Homo sapiens
SEQUENCE: 17
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCARGG HGYFDLWGRG TLVTVSS     117

SEQ ID NO: 18          moltype = AA  length = 329
FEATURE                Location/Qualifiers
source                 1..329
                       mol_type = protein
                       organism = Homo sapiens
SEQUENCE: 18
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                  329

SEQ ID NO: 19          moltype = AA  length = 446
FEATURE                Location/Qualifiers
source                 1..446
                       mol_type = protein
                       organism = Homo sapiens
SEQUENCE: 19
EVQLVESGGG LVQPGGSLRL SCAASGFTFS SYSMNWVRQA PGKGLEWVSY ISSSSSTIYY  60
ADSVKGRFTI SRDNAKNSLY LQMNSLRAED TAVYYCARGG HGYFDLWGRG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                     446

SEQ ID NO: 20          moltype = AA  length = 9
FEATURE                Location/Qualifiers
source                 1..9
                       mol_type = protein
                       organism = Homo sapiens
SEQUENCE: 20
FTFSSYSMN                                                        9

SEQ ID NO: 21          moltype = AA  length = 17
FEATURE                Location/Qualifiers
source                 1..17
                       mol_type = protein
                       organism = Homo sapiens
SEQUENCE: 21
YISSSSSTIY YADSVKG                                               17

SEQ ID NO: 22          moltype = AA  length = 8
FEATURE                Location/Qualifiers
source                 1..8
                       mol_type = protein
                       organism = Homo sapiens
SEQUENCE: 22
GGHGYFDL                                                         8

SEQ ID NO: 23          moltype = DNA  length = 351
FEATURE                Location/Qualifiers
source                 1..351
```

```
                       mol_type = genomic DNA
                       organism = Homo sapiens
SEQUENCE: 23
gaggtgcagc tggtggagtc tgggggaggc ttggtacagc ctgggggtc cctgagactc  60
tcctgtgcag cctctggatt caccttcagt agctatagca tgaactgggt ccgccaggct  120
ccagggaagg ggctggagtg ggtttcatac attagtagta gtagtagtac catatactac  180
gcagactctg tgaagggccg attcaccatc tccagagaca atgccaagaa ctcactgtat  240
ctgcaaatga acagcctgag agctgaggac acggcggtgt actactgcgc cagaggtgga  300
cacggatatt tcgacctatg gggagaggt accttggtca ccgtctcctc a           351

SEQ ID NO: 24          moltype = AA  length = 108
FEATURE                Location/Qualifiers
source                 1..108
                       mol_type = protein
                       organism = Homo sapiens
SEQUENCE: 24
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYHHSPLTFG GGTKVEIK              108

SEQ ID NO: 25          moltype = AA  length = 106
FEATURE                Location/Qualifiers
source                 1..106
                       mol_type = protein
                       organism = Homo sapiens
SEQUENCE: 25
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 26          moltype = AA  length = 215
FEATURE                Location/Qualifiers
source                 1..215
                       mol_type = protein
                       organism = Homo sapiens
SEQUENCE: 26
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYHHSPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 27          moltype = AA  length = 12
FEATURE                Location/Qualifiers
source                 1..12
                       mol_type = protein
                       organism = Homo sapiens
SEQUENCE: 27
RASQSVSSSY LA                                                     12

SEQ ID NO: 28          moltype = AA  length = 7
FEATURE                Location/Qualifiers
source                 1..7
                       mol_type = protein
                       organism = Homo sapiens
SEQUENCE: 28
GASSRAT                                                           7

SEQ ID NO: 29          moltype = AA  length = 9
FEATURE                Location/Qualifiers
source                 1..9
                       mol_type = protein
                       organism = Homo sapiens
SEQUENCE: 29
QQYHHSPLT                                                         9

SEQ ID NO: 30          moltype = DNA  length = 324
FEATURE                Location/Qualifiers
source                 1..324
                       mol_type = genomic DNA
                       organism = Homo sapiens
SEQUENCE: 30
gaaattgtgt tgacgcagtc tccaggcacc ctgtctttgt ctccagggga aagagccacc  60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtaccacc acagtcctct cacttttggc  300
ggagggacca aggttgagat caaa                                        324

SEQ ID NO: 31          moltype = AA  length = 630
FEATURE                Location/Qualifiers
source                 1..630
```

-continued

```
                      mol_type = protein
                      organism = Homo sapiens
SEQUENCE: 31
TQVCTGTDMK LRLPASPETH LDMLRHLYQG CQVVQGNLEL TYLPTNASLS FLQDIQEVQG  60
YVLIAHNQVR QVPLQRLRIV RGTQLFEDNY ALAVLDNGDP LNNTTPVTGA SPGGLRELQL 120
RSLTEILKGG VLIQRNPQLC YQDTILWKDI FHKNNQLALT LIDTNRSRAC HPCSPMCKGS 180
RCWGESSEDC QSLTRTVCAG GCARCKGPLP TDCCHEQCAA GCTGPKHSDC LACLHFNHSG 240
ICELHCPALV TYNTDTFESM PNPEGRYTFG ASCVTACPYN YLSTDVGSCT LVCPLHNQEV 300
TAEDGTQRCE KCSKPCARVC YGLGMEHLRE VRAVTSANIQ EFAGCKKIFG SLAFLPESFD 360
GDPASNTAPL QPEQLQVFET LEEITGYLYI SAWPDSLPDL SVFQNLQVIR GRILHNGAYS 420
LTLQGLGISW LGLRSLRELG SGLALIHHNT HLCFVHTVPW DQLFRNPHQA LLHTANRPED 480
ECVGEGLACH QLCARGHCWG PGPTQCVNCS QFLRGQECVE ECRVLQGLPR EYVNARHCLP 540
CHPECQPQNG SVTCFGPEAD QCVACAHYKD PPFCVARCPS GVKPDLSYMP IWKFPDEEGA 600
CQPCPINCTH SCVDLDDKGC PAEQRASPLT                                 630
```